United States Patent
Chen

(10) Patent No.: US 11,866,469 B2
(45) Date of Patent: Jan. 9, 2024

(54) DNA BINDING PROTEINS AND USES THEREOF

(71) Applicant: Klogenix LLC, Boston, MA (US)

(72) Inventor: Ci-Di Chen, Boston, MA (US)

(73) Assignee: Klogenix LLC, Boston, MA (US)

( * ) Notice: Subject to any disclaimer, the term of this patent is extended or adjusted under 35 U.S.C. 154(b) by 217 days.

(21) Appl. No.: 17/287,218

(22) PCT Filed: Dec. 16, 2019

(86) PCT No.: PCT/US2019/066535
§ 371 (c)(1),
(2) Date: Apr. 21, 2021

(87) PCT Pub. No.: WO2020/163017
PCT Pub. Date: Aug. 13, 2020

(65) Prior Publication Data
US 2021/0380648 A1    Dec. 9, 2021

Related U.S. Application Data

(60) Provisional application No. 62/860,407, filed on Jun. 12, 2019, provisional application No. 62/801,889, filed on Feb. 6, 2019.

(51) Int. Cl.
*C07K 14/47* (2006.01)
*A61K 48/00* (2006.01)
*A61K 38/00* (2006.01)

(52) U.S. Cl.
CPC ............ *C07K 14/47* (2013.01); *A61K 48/005* (2013.01); *A61K 38/00* (2013.01); *C07K 2319/81* (2013.01)

(58) Field of Classification Search
None
See application file for complete search history.

(56) References Cited

U.S. PATENT DOCUMENTS

| | | | |
|---|---|---|---|
| 4,186,183 A | 1/1980 | Alving et al. | |
| 4,217,344 A | 8/1980 | Vanlerberghe et al. | |
| 4,235,871 A | 11/1980 | Papahadjopoulos et al. | |
| 4,261,975 A | 4/1981 | Fullerton et al. | |
| 4,485,054 A | 11/1984 | Mezei et al. | |
| 4,501,728 A | 2/1985 | Geho et al. | |
| 4,774,085 A | 9/1988 | Fidler | |
| 4,837,028 A | 6/1989 | Allen | |
| 4,897,355 A | 1/1990 | Eppstein et al. | |
| 4,946,787 A | 8/1990 | Eppstein et al. | |
| 5,049,386 A | 9/1991 | Eppstein et al. | |
| 6,008,336 A | 12/1999 | Hanson et al. | |
| 6,453,242 B1 | 9/2002 | Eisenberg et al. | |
| 6,503,717 B2 | 1/2003 | Case et al. | |
| 6,534,261 B1 | 3/2003 | Cox, III et al. | |
| 6,599,692 B1 | 7/2003 | Case et al. | |
| 6,607,882 B1 | 8/2003 | Cox, III et al. | |
| 6,689,558 B2 | 2/2004 | Case | |
| 6,824,978 B1 | 11/2004 | Cox, III et al. | |
| 6,933,113 B2 | 8/2005 | Case et al. | |
| 6,979,539 B2 | 12/2005 | Cox, III et al. | |
| 7,013,219 B2 | 3/2006 | Case et al. | |
| 7,163,824 B2 | 1/2007 | Cox, III et al. | |
| 2006/0078880 A1 | 4/2006 | Barbas, III et al. | |
| 2011/0301073 A1 | 12/2011 | Gregory et al. | |

FOREIGN PATENT DOCUMENTS

| | | | |
|---|---|---|---|
| CN | 107916255 | 4/2018 | |
| WO | 9116024 A1 | 10/1991 | |
| WO | 9117424 A1 | 11/1991 | |
| WO | 0183692 A2 | 11/2001 | |
| WO | 2016050934 A1 | 4/2016 | |
| WO | 2018154096 A1 | 8/2018 | |
| WO | WO-2018154096 A1 * | 8/2018 | ........... C12N 15/102 |

OTHER PUBLICATIONS

GenBank (AB673445.1, Oct. 17, 2012) (Year: 2012).*
GenBank Accession No. AB673445, "*Homo sapiens* Klotho gene for Klotho protein, promoter and partial cds.", Oct. 17, 2012, Retrieved on May 5, 2020.
Chen et al., "A method to specifically activate the Klotho promoter by using zinc finger proteins constructed from modular building blocks and from naturally engineered Egr1 transcription factor backbone.", The FASEB Journal, Apr. 29, 2020.
International Search Report for International Patent Application No. PCT/US2019/066535, dated Jun. 22, 2020.
Written Opinion for International Patent Application No. PCT/US2019/066535, dated Jun. 22, 2020.
Ahmad et al., "Antibody-mediated Specific Binding and Cytotoxicity of Liposome entrapped Doxorubicin to Lung Cancer Cells in Vitro", Sep. 1, 1992, pp. 4817-4820.
Ansorge et al., "Development of a scalable process for high-yield lentiviral vector production by transient transfection of HEK293 suspension cultures", Jul. 20, 2009, pp. 868-876.
Blaese et al., "T Lymphocyte-Directed Gene Therapy for ADA SCID: Initial Trial Results After 4 Years", 1995.
Bloch et al., "Klotho is a substrate for $\alpha$-, $\beta$- and $\gamma$-secretase", 2009, pp. 3221-3224.
Bonas et al., "Genetic and structural characterization of the avirulence gene avrBs3 from Xanthomonas campestris pv. vesicatoria", 1989, pp. 127-136.
Chen et al., "Insulin stimulates the cleavage and release of the extracellular domain of Klotho by ADAM10 and ADAM17", Dec. 11, 2007, pp. 19796-19801, vol. 104, No. 50.

(Continued)

*Primary Examiner* — Sergio Coffa
(74) *Attorney, Agent, or Firm* — K&L Gates LLP

(57) ABSTRACT

The present disclosure relates to compositions and methods for modulating gene expression and in particular to DNA binding proteins and their use for increasing expression of Klotho. In some examples, the present disclosure provides an isolated or recombinant DNA binding protein comprising or attached to a transcriptional activation domain wherein the DNA binding protein binds to a target sequence within or near a Klotho gene.

6 Claims, 11 Drawing Sheets

Specification includes a Sequence Listing.

(56) References Cited

OTHER PUBLICATIONS

Chen et al., "Activation of the anti-aging and cognition-enhancing gene Klotho by CRISPR-dCas9 transcriptional effector complex", Feb. 2018, pp. 1-16.
Dubal et al., "Life Extension Factor Klotho Enhances Cognition", May 22, 2014, pp. 1065-1076.
Dubal et al., "Life Extension Factor Klotho Prevents Mortality and Enhances Cognition in hAPP Transgenic Mice", Feb. 11, 2015, pp. 2358-2371.
Elrod-Erickson et al., "Zif268 protein-DNA complex refined at 1.6 A: a model system for understanding zinc finger-DNA interactions", Oct. 1996, pp. 1171-1180, vol. 4, No. 10.
Furuno et al., "Role of Different Proteolytic Systems in the Degradation of Muscle Proteins during Denervation Atrophy", 1990, pp. 8550-8557.
Gashler et al., "A Novel Repression Module, an Extensive Activation Domain, and a Bipartite Nuclear Localization Signal Defined in the Immediate-Early Transcription Factor Egr-1", Aug. 1993, pp. 455-4571, vol. 13, No. 8.
Kay et al., "A Bacterial Effector Acts as a Plant Transcription Factor and Induces a Cell Size Regulator", 2007, pp. 648-651, vol. 318.
MacDiarmid et al., "Sequential treatment of drug-resistant tumors with targeted minicells containing siRNA or a cytotoxic drug", Jul. 2009, pp. 643-654, vol. 27, No. 7.
Mandell et al., "Zinc Finger Tools: custom DNA-binding domains for transcription factors and nucleases", 2006, pp. W516-W523, vol. 34.
Masso et al., "Secreted and Transmembrane αKlotho Isoforms Have Different Spatio-Temporal Profiles in the Brain during Aging and Alzheimer's Disease Progression", Nov. 2015, pp. 1-15.
Masuda et al., "Regulation of multiple ageing-like phenotypes by inducible klotho gene expression in klotho mutant mice", 2005, pp. 1274-1283.
Matsumura et al., "Identification of the Human Klotho Gene and Its Two Transcripts Encoding Membrane and Secreted Klotho Protein", 1998, pp. 626-630, vol. 242, No. 3.
Marzzotta et al., "Proangiogenic effects of soluble α-Klotho on systemic sclerosis dermal microvascular endothelial cells" 2017, pp. 1-14.
Moscou et al., "A Simple cipher governs DNA recognition by TAL Effectors", Dec. 11, 2009, p. 1501, vol. 326.
Patel et al., "Inhaled Nanoformulated mRNA Polyplexes for Protein Production in Lung Epithelium", 2019.
Pavletich et al., "Zinc Finger-DNA Recognition: Crystal Structure of a Zif268-DNA Complex at 2.1 Å", May 1991, pp. 809-817, vol. 252.
Peer et al., "Special delivery: targeted therapy with small RNAs", 2011, pp. 1127-1133.
Russo et al., "Transcriptional Activity of the Zinc Finger Protein NGFI-A Is Influenced by Its Interaction with a Cellular Factor", Nov. 1993, pp. 6858-6865, vol. 13, No. 11.
Witting et al., "Efficient Large Volume Lentiviral Vector Production Using Flow Electroporation", Feb. 2012, pp. 243-249.
Zeldich et al., "The Neuroprotective Effect of Klotho is Mediated via Regulation of Members of the Redox System", Aug. 29, 2014, pp. 24700-24715, vol. 289, No. 35.
Zeldich et al., "The Anti-Aging Protein Klotho Enhances Remyelination Following Cuprizone-Induced Demyelination", 2015, pp. 185-196.

* cited by examiner

Nucleotides 1-100 are located within SEQ ID NO: 23 and SEQ ID NO: 27
Nucleotides 101-200 are located within SEQ ID NO: 23 and SEQ ID NO: 27
Nucleotides 201-300 are located within SEQ ID NO: 23 and SEQ ID NO: 27

US 11,866,469 B2

DNA BINDING PROTEINS AND USES THEREOF

RELATED APPLICATIONS

This application claims the benefit of U.S. Provisional Application No. 62/801,889 filed Feb. 6, 2019 and U.S. Provisional Application No. 62/860,407 filed Jun. 12, 2019, both of which are incorporated herein in their entirety by reference.

STATEMENT REGARDING FEDERALLY FUNDED RESEARCH

This invention was made with Government support under contract No. 5 R44 AG053084 awarded by the National Institutes of Health. The government has certain rights in the invention.

FIELD OF THE DISCLOSURE

The present disclosure relates to compositions and methods for modulating gene expression and in particular to DNA binding proteins and their use for increasing expression of Klotho.

INCORPORATION BY REFERENCE OF SEQUENCE LISTING

This application contains a Sequence Listing in computer readable form (filename: 190350PCT sequence listing_ST25: 395,464 byes—ASCII text file; created Dec. 6, 2019), which is incorporated by reference in its entirety and forms part of the disclosure.

BACKGOUND OF THE DISCLOSURE

Any discussion of the prior art throughout the specification should in no way be considered as an admission that such prior art is widely known or forms part of the common general knowledge in the field.

The single copy gene Klotho plays important roles in ageing, cognition, anti-oxidative stress, neurological protection and development, and kidney health. Klotho is a Type I transmembrane protein which is mainly expressed in the brain, kidney and reproductive organs (Masuda et al., 2005. *Mech. Ageing Dev.* 126(21): 1274-1283). It is also shed by proteolytic cleavage resulting in a soluble form that is detectable in serum and cerebrospinal fluid (CSF) (Bloch et al., 2009. *FEBS Lett.* 583(19): 3221-3224; Chen et al., 2007. *Proc. Natl Acad. Sci. USA.* 104(50): 19796-19801; Matsumura et al., 1998. *Biochem. Biophys. Res. Commun.* 242(3): 626-630). A third form of Klotho, found mainly in the brain, results from differential mRNA splicing and is secreted from the cell into the blood and CSF (Masso et al., 2015. *PLoS One.* 10(11): e0143623). Both the transmembrane and soluble forms of Klotho have important functions in many homeostatic processes.

Klotho promotes oligodendrocyte maturation, and it protects neurons from oxidative stress by increasing expression of antioxidant factors. It also induces re-myelination in vivo in the cuprizone-induced demyelination model of multiple sclerosis (Zeldich et al., 2015. *J. Mol. Neurosci.* 57(2): 185-196). Studies have shown that Klotho overexpression reduces cognitive deficits in a mouse model of Alzheimer's disease, and that it enhances cognition in humans and mice (Dubal et al., 2014. *Cell Rep.* 7(4): 1065-1076; Dubal et al., 2015. *Off. J. Socr. Neuroscience.* 35(6): 2358-2371). Klotho has also been reported to have roles in the regulation of, or protection against, cancer, muscular disorders and kidney disorders.

In this context, there is a need for compositions and methods for modulating Klotho activity, and preferably for increasing Klotho activity.

SUMMARY OF THE DISCLOSURE

The present disclosure relates to compositions and methods for modulating gene expression and in particular to compositions and methods for increasing expression of Klotho. In work leading to the present disclosure, the inventors engineered DNA binding proteins that target sequences upstream of the Klotho translation start site. By fusing the DNA binding proteins to transcriptional activations domain, the inventors successfully increased the expression of Klotho.

In a first aspect, the present disclosure provides an isolated or recombinant DNA binding protein comprising or attached to a transcriptional activation domain wherein the DNA binding protein binds to a target sequence within or near a Klotho gene.

In some examples, the target sequence is located within a region between the Klotho gene translation start site and 4000 nucleotides upstream of the Klotho gene translation start site. The target sequence may be located within a region between the Klotho gene translation start site and 350 nucleotides upstream of the Klotho gene translation start site. The target sequence may be located within a region between 40 nucleotides and 300 nucleotides upstream of the Klotho gene translation start site.

In some examples, the target sequence comprises:
  the sequence set forth in SEQ ID NO. 60;
  the sequence set forth in SEQ ID NO. 61; or
  the sequence set forth in SEQ ID NO. 62.
In some example, the target sequence comprises at least 9 contiguous nucleotides from:
  the sequence set forth in SEQ ID NO. 63;
  the sequence set forth in SEQ ID NO. 64;
  the sequence set forth in SEQ ID NO. 65;
  the sequence set forth in SEQ ID NO. 66;
  the sequence set forth in SEQ ID NO. 67;
  the sequence set forth in SEQ ID NO. 68;
  the sequence set forth in SEQ ID NO. 69; or
  the sequence set forth in SEQ ID NO. 70.
In some examples, the target sequence comprises:
  the sequence set forth in SEQ ID NO. 63;
  the sequence set forth in SEQ ID NO. 64;
  the sequence set forth in SEQ ID NO. 65;
  the sequence set forth in SEQ ID NO. 66;
  the sequence set forth in SEQ ID NO. 67;
  the sequence set forth in SEQ ID NO. 68;
  the sequence set forth in SEQ ID NO. 69; or
  the sequence set forth in SEQ ID NO. 70.
In some examples, the target sequence comprises:
  the sequence set forth in SEQ ID NO. 64; or
  the sequence set forth in SEQ ID NO. 62.
In some examples, the DNA binding protein is a zinc finger protein.
In some examples, the zinc finger protein comprises:
  a zinc finger comprising the sequence set forth in SEQ ID NO. 17, a zinc finger comprising the sequence set forth in SEQ ID NO. 16 and a zinc finger comprising the sequence set forth in SEQ ID NO. 11;

a zinc finger comprising the sequence set forth in SEQ ID NO. 18, a zinc finger comprising the sequence set forth in SEQ ID NO. 16 and a zinc finger comprising the sequence set forth in SEQ ID NO. 11; or a zinc finger comprising the sequence set forth in SEQ ID NO. 18, a zinc finger comprising the sequence set forth in SEQ ID NO. 16 and a zinc finger comprising the sequence set forth in SEQ ID NO. 3.

In some examples, the zinc finger protein comprises:

a ZF1 zinc finger comprising the sequence set forth in SEQ ID NO. 1, a ZF2 zinc finger comprising the sequence set forth in SEQ ID NO. 2, a ZF3 zinc finger comprising the sequence set forth in SEQ ID NO. 3, a ZF4 zinc finger comprising the sequence set forth in SEQ ID NO. 4, a ZF5 zinc finger comprising the sequence set forth in SEQ ID NO. 5 and a ZF6 zinc finger comprising the sequence set forth in SEQ ID NO. 6;

a ZF1 zinc finger comprising the sequence set forth in SEQ ID NO. 7, a ZF2 zinc finger comprising the sequence set forth in SEQ ID NO. 8, a ZF3 zinc finger comprising the sequence set forth in SEQ ID NO. 9, a ZF4 zinc finger comprising the sequence set forth in SEQ ID NO. 7, a ZF5 zinc finger comprising the sequence set forth in SEQ ID NO. 10, a ZF6 zinc finger comprising the sequence set forth in SEQ ID NO. 11, a ZF7 zinc finger comprising the sequence set forth in SEQ ID NO. 12, a ZF8 zinc finger comprising the sequence set forth in SEQ ID NO. 13, a ZF9 zinc finger comprising the sequence set forth in SEQ ID NO. 14 and a ZF10 zinc finger comprising the sequence set forth in SEQ ID NO. 6;

a ZF1 zinc finger comprising the sequence set forth in SEQ ID NO. 15, a ZF2 zinc finger comprising the sequence set forth in SEQ ID NO. 16, a ZF3 zinc finger comprising the sequence set forth in SEQ ID NO. 17, a ZF4 zinc finger comprising the sequence set forth in SEQ ID NO. 16, a ZF5 zinc finger comprising the sequence set forth in SEQ ID NO. 11, a ZF6 zinc finger comprising the sequence set forth in SEQ ID NO. 11 and a ZF7 zinc finger comprising the sequence set forth in SEQ ID NO. 1;

a ZF1 zinc finger comprising the sequence set forth in SEQ ID NO. 11, a ZF2 zinc finger comprising the sequence set forth in SEQ ID NO. 1, a ZF3 zinc finger comprising the sequence set forth in SEQ ID NO. 18, a ZF4 zinc finger comprising the sequence set forth in SEQ ID NO. 16, a ZF5 zinc finger comprising the sequence set forth in SEQ ID NO. 11, a ZF6 zinc finger comprising the sequence set forth in SEQ ID NO. 19 and a ZF7 zinc finger comprising the sequence set forth in SEQ ID NO. 12;

a ZF1 zinc finger comprising the sequence set forth in SEQ ID NO. 8, a ZF2 zinc finger comprising the sequence set forth in SEQ ID NO. 16, a ZF3 zinc finger comprising the sequence set forth in SEQ ID NO. 18, a ZF4 zinc finger comprising the sequence set forth in SEQ ID NO. 16, a ZF5 zinc finger comprising the sequence set forth in SEQ ID NO. 3, a ZF6 zinc finger comprising the sequence set forth in SEQ ID NO. 8 and a ZF7 zinc finger comprising the sequence set forth in SEQ ID NO. 3;

a ZF1 zinc finger comprising the sequence set forth in SEQ ID NO. 17, a ZF2 zinc finger comprising the sequence set forth in SEQ ID NO. 13, a ZF3 zinc finger comprising the sequence set forth in SEQ ID NO. 13, a ZF4 zinc finger comprising the sequence set forth in SEQ ID NO. 9, a ZF5 zinc finger comprising the sequence set forth in SEQ ID NO. 17 and a ZF6 zinc finger comprising the sequence set forth in SEQ ID NO. 9;

a ZF1 zinc finger comprising the sequence set forth in SEQ ID NO. 20, a ZF2 zinc finger comprising the sequence set forth in SEQ ID NO. 21, a ZF3 zinc finger comprising the sequence set forth in SEQ ID NO. 22, a ZF4 zinc finger comprising the sequence set forth in SEQ ID NO. 19, a ZF5 zinc finger comprising the sequence set forth in SEQ ID NO. 12 and a ZF6 zinc finger comprising the sequence set forth in SEQ ID NO. 17; or a ZF1 zinc finger comprising the sequence set forth in SEQ ID NO. 20, a ZF2 zinc finger comprising the sequence set forth in SEQ ID NO. 21, a ZF3 zinc finger comprising the sequence set forth in SEQ ID NO. 22, a ZF4 zinc finger comprising the sequence set forth in SEQ ID NO. 8, a ZF5 zinc finger comprising the sequence set forth in SEQ ID NO. 3 and a ZF6 zinc finger comprising the sequence set forth in SEQ ID NO. 9.

In some examples, the zinc finger protein comprises:

a ZF1 zinc finger comprising the sequence set forth in SEQ ID NO. 7, a ZF2 zinc finger comprising the sequence set forth in SEQ ID NO. 8, a ZF3 zinc finger comprising the sequence set forth in SEQ ID NO. 9, a ZF4 zinc finger comprising the sequence set forth in SEQ ID NO. 7, a ZF5 zinc finger comprising the sequence set forth in SEQ ID NO. 10, a ZF6 zinc finger comprising the sequence set forth in SEQ ID NO. 11, a ZF7 zinc finger comprising the sequence set forth in SEQ ID NO. 12, a ZF8 zinc finger comprising the sequence set forth in SEQ ID NO. 13, a ZF9 zinc finger comprising the sequence set forth in SEQ ID NO. 14 and a ZF10 zinc finger comprising the sequence set forth in SEQ ID NO. 6;

a ZF1 zinc finger comprising the sequence set forth in SEQ ID NO. 8, a ZF2 zinc finger comprising the sequence set forth in SEQ ID NO. 16, a ZF3 zinc finger comprising the sequence set forth in SEQ ID NO. 18, a ZF4 zinc finger comprising the sequence set forth in SEQ ID NO. 16, a ZF5 zinc finger comprising the sequence set forth in SEQ ID NO. 3, a ZF6 zinc finger comprising the sequence set forth in SEQ ID NO. 8 and a ZF7 zinc finger comprising the sequence set forth in SEQ ID NO. 3;

a ZF1 zinc finger comprising the sequence set forth in SEQ ID NO. 20, a ZF2 zinc finger comprising the sequence set forth in SEQ ID NO. 21, a ZF3 zinc finger comprising the sequence set forth in SEQ ID NO. 22, a ZF4 zinc finger comprising the sequence set forth in SEQ ID NO. 19, a ZF5 zinc finger comprising the sequence set forth in SEQ ID NO. 12 and a ZF6 zinc finger comprising the sequence set forth in SEQ ID NO. 17; or a ZF1 zinc finger comprising the sequence set forth in SEQ ID NO. 20, a ZF2 zinc finger comprising the sequence set forth in SEQ ID NO. 21, a ZF3 zinc finger comprising the sequence set forth in SEQ ID NO. 22, a ZF4 zinc finger comprising the sequence set forth in SEQ ID NO. 8, a ZF5 zinc finger comprising the sequence set forth in SEQ ID NO. 3 and a ZF6 zinc finger comprising the sequence set forth in SEQ ID NO. 9.

In some examples, the zinc finger protein comprises:
  a zinc finger domain comprising the sequence set forth in SEQ ID NO. 41, or a sequence having at least about 80% identity to SEQ ID NO. 41;
  a zinc finger domain comprising the sequence set forth in SEQ ID NO. 42, or a sequence having at least about 80% identity to SEQ ID NO. 42;
  a zinc finger domain comprising the sequence set forth in SEQ ID NO. 43, or a sequence having at least about 80% identity to SEQ ID NO. 43;
  a zinc finger domain comprising the sequence set forth in SEQ ID NO. 44, or a sequence having at least about 80% identity to SEQ ID NO. 44;
  a zinc finger domain comprising the sequence set forth in SEQ ID NO. 45, or a sequence having at least about 80% identity to SEQ ID NO. 45; or
  a zinc finger domain comprising the sequence set forth in SEQ ID NO. 46, or a sequence having at least about 80% identity to SEQ ID NO. 46.

In some examples, the DNA binding protein competes for binding to the target sequence with a zinc finger protein comprising:
  a zinc finger domain comprising the sequence set forth in SEQ ID NO. 41;
  a zinc finger domain comprising the sequence set forth in SEQ ID NO. 42;
  a zinc finger domain comprising the sequence set forth in SEQ ID NO. 43;
  a zinc finger domain comprising the sequence set forth in SEQ ID NO. 44;
  a zinc finger domain comprising the sequence set forth in SEQ ID NO. 45; or
  a zinc finger domain comprising the sequence set forth in SEQ ID NO. 46.

In some examples, the DNA binding protein competes for binding to the target sequence with a zinc finger protein comprising or consisting of:
  the sequence set forth in SEQ ID NO. 29;
  the sequence set forth in SEQ ID NO. 30;
  the sequence set forth in SEQ ID NO. 32;
  the sequence set forth in SEQ ID NO. 33;
  the sequence set forth in SEQ ID NO. 34;
  the sequence set forth in SEQ ID NO. 36;
  the sequence set forth in SEQ ID NO. 37; or
  the sequence set forth in SEQ ID NO. 39.

In some examples, the transcriptional activation domain is selected from the group consisting of VP16, or a plurality thereof, VP64, VP160, p65, MyoD1, HSF1, RTA, TET3CD, p300 and SET7/9. The DNA binding protein may comprise or be attached to more than one transcriptional activation domain. The more than one transcriptional activation domain may comprise VP64, p65 and RTA.

In some examples, the Klotho gene is a human Klotho gene.

In some examples, the DNA binding protein comprises a nuclear localisation signal.

In a second aspect, the present disclosure provides an isolated or recombinant nucleic acid encoding the DNA binding protein of the first aspect.

In a third aspect, the present disclosure provides a vector comprising the nucleic acid of the second aspect.

In some examples, the vector is an adeno-associated virus (AAV) vector.

In a fourth aspect, the present disclosure provides a cell comprising the DNA binding protein of the first aspect, the nucleic acid of the second aspect or the vector of the third aspect.

In a fifth aspect, the present disclosure provides a method of increasing expression of a Klotho gene in a cell the method comprising administering to the cell a DNA binding protein comprising or attached to a transcriptional activation domain wherein the DNA binding protein binds to a target sequence within or near the Klotho gene and thereby increases expression of the Klotho gene.

In some examples, the target sequence is located within a region between the Klotho gene translation start site and 4000 nucleotides upstream of the Klotho gene translation start site. The target sequence may be located within a region between the Klotho gene translation start site and 350 nucleotides upstream of the Klotho gene translation start site. The target sequence may be located within a region between 40 nucleotides and 300 nucleotides upstream of the Klotho gene translation start site.

In some examples, the target sequence comprises:
  the sequence set forth in SEQ ID NO. 60;
  the sequence set forth in SEQ ID NO. 61; or
  the sequence set forth in SEQ ID NO. 62.

In some examples, the target sequence comprises at least 9 contiguous nucleotides from:
  the sequence set forth in SEQ ID NO. 63;
  the sequence set forth in SEQ ID NO. 64;
  the sequence set forth in SEQ ID NO. 65;
  the sequence set forth in SEQ ID NO. 66;
  the sequence set forth in SEQ ID NO. 67;
  the sequence set forth in SEQ ID NO. 68;
  the sequence set forth in SEQ ID NO. 69; or
  the sequence set forth in SEQ ID NO. 70.

In some examples, the target sequence comprises:
  the sequence set forth in SEQ ID NO. 63;
  the sequence set forth in SEQ ID NO. 64;
  the sequence set forth in SEQ ID NO. 65;
  the sequence set forth in SEQ ID NO. 66;
  the sequence set forth in SEQ ID NO. 67;
  the sequence set forth in SEQ ID NO. 68;
  the sequence set forth in SEQ ID NO. 69; or
  the sequence set forth in SEQ ID NO. 70.

In some examples, the target sequence comprises:
  the sequence set forth in SEQ ID NO. 64; or
  the sequence set forth in SEQ ID NO. 62.

In some examples, the DNA binding protein is a zinc finger protein.

In some examples, the zinc finger protein comprises:
  a zinc finger comprising the sequence set forth in SEQ ID NO. 17, a zinc finger comprising the sequence set forth in SEQ ID NO. 16 and a zinc finger comprising the sequence set forth in SEQ ID NO. 11;
  a zinc finger comprising the sequence set forth in SEQ ID NO. 18, a zinc finger comprising the sequence set forth in SEQ ID NO. 16 and a zinc finger comprising the sequence set forth in SEQ ID NO. 11; or
  a zinc finger comprising the sequence set forth in SEQ ID NO. 18, a zinc finger comprising the sequence set forth in SEQ ID NO. 16 and a zinc finger comprising the sequence set forth in SEQ ID NO. 3.

In some examples, the zinc finger protein comprises:
  a ZF1 zinc finger comprising the sequence set forth in SEQ ID NO. 1, a ZF2 zinc finger comprising the sequence set forth in SEQ ID NO. 2, a ZF3 zinc finger comprising the sequence set forth in SEQ ID NO. 3, a ZF4 zinc finger comprising the sequence set forth in SEQ ID NO. 4, a ZF5 zinc finger comprising the sequence set forth in SEQ ID NO. 5 and a ZF6 zinc finger comprising the sequence set forth in SEQ ID NO. 6;

a ZF1 zinc finger comprising the sequence set forth in SEQ ID NO. 7, a ZF2 zinc finger comprising the sequence set forth in SEQ ID NO. 8, a ZF3 zinc finger comprising the sequence set forth in SEQ ID NO. 9, a ZF4 zinc finger comprising the sequence set forth in SEQ ID NO. 7, a ZF5 zinc finger comprising the sequence set forth in SEQ ID NO. 10, a ZF6 zinc finger comprising the sequence set forth in SEQ ID NO. 11, a ZF7 zinc finger comprising the sequence set forth in SEQ ID NO. 12, a ZF8 zinc finger comprising the sequence set forth in SEQ ID NO. 13, a ZF9 zinc finger comprising the sequence set forth in SEQ ID NO. 14 and a ZF10 zinc finger comprising the sequence set forth in SEQ ID NO. 6;

a ZF1 zinc finger comprising the sequence set forth in SEQ ID NO. 15, a ZF2 zinc finger comprising the sequence set forth in SEQ ID NO. 16, a ZF3 zinc finger comprising the sequence set forth in SEQ ID NO. 17, a ZF4 zinc finger comprising the sequence set forth in SEQ ID NO. 16, a ZF5 zinc finger comprising the sequence set forth in SEQ ID NO. 11, a ZF6 zinc finger comprising the sequence set forth in SEQ ID NO. 11 and a ZF7 zinc finger comprising the sequence set forth in SEQ ID NO. 1;

a ZF1 zinc finger comprising the sequence set forth in SEQ ID NO. 11, a ZF2 zinc finger comprising the sequence set forth in SEQ ID NO. 1, a ZF3 zinc finger comprising the sequence set forth in SEQ ID NO. 18, a ZF4 zinc finger comprising the sequence set forth in SEQ ID NO. 16, a ZF5 zinc finger comprising the sequence set forth in SEQ ID NO. 11, a ZF6 zinc finger comprising the sequence set forth in SEQ ID NO. 19 and a ZF7 zinc finger comprising the sequence set forth in SEQ ID NO. 12;

a ZF1 zinc finger comprising the sequence set forth in SEQ ID NO. 8, a ZF2 zinc finger comprising the sequence set forth in SEQ ID NO. 16, a ZF3 zinc finger comprising the sequence set forth in SEQ ID NO. 18, a ZF4 zinc finger comprising the sequence set forth in SEQ ID NO. 16, a ZF5 zinc finger comprising the sequence set forth in SEQ ID NO. 3, a ZF6 zinc finger comprising the sequence set forth in SEQ ID NO. 8 and a ZF7 zinc finger comprising the sequence set forth in SEQ ID NO. 3;

a ZF1 zinc finger comprising the sequence set forth in SEQ ID NO. 17, a ZF2 zinc finger comprising the sequence set forth in SEQ ID NO. 13, a ZF3 zinc finger comprising the sequence set forth in SEQ ID NO. 13, a ZF4 zinc finger comprising the sequence set forth in SEQ ID NO. 9, a ZF5 zinc finger comprising the sequence set forth in SEQ ID NO. 17 and a ZF6 zinc finger comprising the sequence set forth in SEQ ID NO. 9;

a ZF1 zinc finger comprising the sequence set forth in SEQ ID NO. 20, a ZF2 zinc finger comprising the sequence set forth in SEQ ID NO. 21, a ZF3 zinc finger comprising the sequence set forth in SEQ ID NO. 22, a ZF4 zinc finger comprising the sequence set forth in SEQ ID NO. 19, a ZF5 zinc finger comprising the sequence set forth in SEQ ID NO. 12 and a ZF6 zinc finger comprising the sequence set forth in SEQ ID NO. 17; or a ZF1 zinc finger comprising the sequence set forth in SEQ ID NO. 20, a ZF2 zinc finger comprising the sequence set forth in SEQ ID NO. 21, a ZF3 zinc finger comprising the sequence set forth in SEQ ID NO. 22, a ZF4 zinc finger comprising the sequence set forth in SEQ ID NO. 8, a ZF5 zinc finger comprising the sequence set forth in SEQ ID NO. 3 and a ZF6 zinc finger comprising the sequence set forth in SEQ ID NO. 9.

In some examples, the zinc finger protein comprises:

a ZF1 zinc finger comprising the sequence set forth in SEQ ID NO. 7, a ZF2 zinc finger comprising the sequence set forth in SEQ ID NO. 8, a ZF3 zinc finger comprising the sequence set forth in SEQ ID NO. 9, a ZF4 zinc finger comprising the sequence set forth in SEQ ID NO. 7, a ZF5 zinc finger comprising the sequence set forth in SEQ ID NO. 10, a ZF6 zinc finger comprising the sequence set forth in SEQ ID NO. 11, a ZF7 zinc finger comprising the sequence set forth in SEQ ID NO. 12, a ZF8 zinc finger comprising the sequence set forth in SEQ ID NO. 13, a ZF9 zinc finger comprising the sequence set forth in SEQ ID NO. 14 and a ZF10 zinc finger comprising the sequence set forth in SEQ ID NO. 6;

a ZF1 zinc finger comprising the sequence set forth in SEQ ID NO. 8, a ZF2 zinc finger comprising the sequence set forth in SEQ ID NO. 16, a ZF3 zinc finger comprising the sequence set forth in SEQ ID NO. 18, a ZF4 zinc finger comprising the sequence set forth in SEQ ID NO. 16, a ZF5 zinc finger comprising the sequence set forth in SEQ ID NO. 3, a ZF6 zinc finger comprising the sequence set forth in SEQ ID NO. 8 and a ZF7 zinc finger comprising the sequence set forth in SEQ ID NO. 3;

a ZF1 zinc finger comprising the sequence set forth in SEQ ID NO. 20, a ZF2 zinc finger comprising the sequence set forth in SEQ ID NO. 21, a ZF3 zinc finger comprising the sequence set forth in SEQ ID NO. 22, a ZF4 zinc finger comprising the sequence set forth in SEQ ID NO. 19, a ZF5 zinc finger comprising the sequence set forth in SEQ ID NO. 12 and a ZF6 zinc finger comprising the sequence set forth in SEQ ID NO. 17; or a ZF1 zinc finger comprising the sequence set forth in SEQ ID NO. 20, a ZF2 zinc finger comprising the sequence set forth in SEQ ID NO. 21, a ZF3 zinc finger comprising the sequence set forth in SEQ ID NO. 22, a ZF4 zinc finger comprising the sequence set forth in SEQ ID NO. 8, a ZF5 zinc finger comprising the sequence set forth in SEQ ID NO. 3 and a ZF6 zinc finger comprising the sequence set forth in SEQ ID NO. 9.

In some examples, the zinc finger protein comprises:

a zinc finger domain comprising the sequence set forth in SEQ ID NO. 41, or a sequence having at least about 80% identity to SEQ ID NO. 41;

a zinc finger domain comprising the sequence set forth in SEQ ID NO. 42, or a sequence having at least about 80% identity to SEQ ID NO. 42;

a zinc finger domain comprising the sequence set forth in SEQ ID NO. 43, or a sequence having at least about 80% identity to SEQ ID NO. 43;

a zinc finger domain comprising the sequence set forth in SEQ ID NO. 44, or a sequence having at least about 80% identity to SEQ ID NO. 44;

a zinc finger domain comprising the sequence set forth in SEQ ID NO. 45, or a sequence having at least about 80% identity to SEQ ID NO. 45; or a zinc finger domain comprising the sequence set forth in SEQ ID NO. 46, or a sequence having at least about 80% identity to SEQ ID NO. 46.

In some examples, the DNA binding protein competes for binding to the target sequence with a zinc finger protein comprising:
- a zinc finger domain comprising the sequence set forth in SEQ ID NO. 41;
- a zinc finger domain comprising the sequence set forth in SEQ ID NO. 42;
- a zinc finger domain comprising the sequence set forth in SEQ ID NO. 43;
- a zinc finger domain comprising the sequence set forth in SEQ ID NO. 44;
- a zinc finger domain comprising the sequence set forth in SEQ ID NO. 45; or
- a zinc finger domain comprising the sequence set forth in SEQ ID NO. 46.

In some examples, the DNA binding protein competes for binding to the target sequence with a zinc finger protein comprising or consisting of:
- the sequence set forth in SEQ ID NO. 29;
- the sequence set forth in SEQ ID NO. 30;
- the sequence set forth in SEQ ID NO. 32;
- the sequence set forth in SEQ ID NO. 33;
- the sequence set forth in SEQ ID NO. 34;
- the sequence set forth in SEQ ID NO. 36;
- the sequence set forth in SEQ ID NO. 37; or
- the sequence set forth in SEQ ID NO. 39.

In some examples, the transcriptional activation domain is selected from the group consisting of VP16, or a plurality thereof, VP64, VP160, p65, MyoD1, HSF1, RTA, TET3CD, p300 and SET7/9. The DNA binding protein may comprise or be attached to more than one transcriptional activation domain. The more than one transcriptional activation domain may comprise VP64, p65 and RTA.

In some examples, the DNA binding protein is administered to the cell directly as a protein.

In some examples, the DNA binding protein is administered to the cell in the form of a nucleic acid.

In some examples, the DNA binding protein is administered to the cell in the form of an AAV vector.

In some examples, the method comprises administering to the cell more than one DNA binding protein and wherein each DNA binding protein is independently selected from the DNA binding protein defined in the first aspect.

In some examples, the cell is a human cell.

In some examples, the DNA binding protein comprises a nuclear localisation signal.

In a sixth aspect, the present disclosure provides a method of treating cancer in a subject the method comprising administering to the subject a therapeutically effective amount of a DNA binding protein comprising or attached to a transcriptional activation domain wherein the DNA binding protein binds to a target sequence within or near a Klotho gene in the subject and thereby increases expression of the Klotho gene.

In some examples, the cancer is selected from the group consisting of colon cancer, prostate cancer, lung cancer, cervical cancer, pancreatic cancer, ovarian cancer and breast cancer.

In a seventh aspect, the present disclosure provides a method of treating a muscle disorder in a subject the method comprising administering to the subject a therapeutically effective amount of a DNA binding protein comprising or attached to a transcriptional activation domain wherein the DNA binding protein binds to a target sequence within or near a Klotho gene in the subject and thereby increases expression of the Klotho gene.

In some examples, the muscle disorder is selected from the group consisting of muscle atrophy and muscular dystrophy.

In an eighth aspect, the present disclosure provides a method of treating a kidney disorder in a subject the method comprising administering to the subject a therapeutically effective amount of a DNA binding protein comprising or attached to a transcriptional activation domain wherein the DNA binding protein binds to a target sequence within or near a Klotho gene in the subject and thereby increases expression of the Klotho gene.

In some examples, the kidney disorder is selected from the group consisting of renal dysfunction, acute kidney injury and kidney disease.

In a ninth aspect, the present disclosure provides a method of enhancing cognition in a subject the method comprising administering to the subject a therapeutically effective amount of a DNA binding protein comprising or attached to a transcriptional activation domain wherein the DNA binding protein binds to a target sequence within or near a Klotho gene in the subject and thereby increases expression of the Klotho gene.

In a tenth aspect, the present disclosure provides a method of treating a neurological disorder in a subject the method comprising administering to the subject a therapeutically effective amount of a DNA binding protein comprising or attached to a transcriptional activation domain wherein the DNA binding protein binds to a target sequence within or near a Klotho gene in the subject and thereby increases expression of the Klotho gene.

In some examples, the neurological disorder is selected from the group consisting of memory loss, stress, biopolar disorder, epilepsy, dementia, Alzheimer's disease, Parkinson's disease, Huntington's disease, Creutzfeldt-Jakob disease, ataxia telangiectasia, craniocerebral trauma, amyotrophic lateral sclerosis, depression, schizophrenia, multiple sclerosis, myelin-related disease, oxidative stress and neurodegeneration.

In an eleventh aspect, the present disclosure provides a method of promoting angiogenesis in a subject the method comprising administering to the subject a therapeutically effective amount of a DNA binding protein comprising or attached to a transcriptional activation domain wherein the DNA binding protein binds to a target sequence within or near a Klotho gene in the subject and thereby increases expression of the Klotho gene.

In a twelfth aspect, the present disclosure provides a method of treating a wound or a skin disorder in a subject the method comprising administering to the subject a therapeutically effective amount of a DNA binding protein comprising or attached to a transcriptional activation domain wherein the DNA binding protein binds to a target sequence within or near a Klotho gene in the subject and thereby increases expression of the Klotho gene.

In some examples, the target sequence is located within a region between the Klotho gene translation start site and 4000 nucleotides upstream of the Klotho gene translation start site. The target sequence may be located within a region between the Klotho gene translation start site and 350 nucleotides upstream of the Klotho gene translation start site. The target sequence may be located within a region between 40 nucleotides and 300 nucleotides upstream of the Klotho gene translation start site.

In some examples, the target sequence comprises:
- the sequence set forth in SEQ ID NO. 60;
- the sequence set forth in SEQ ID NO. 61; or
- the sequence set forth in SEQ ID NO. 62.

In some examples, the target sequence comprises at least 9 contiguous nucleotides from:
the sequence set forth in SEQ ID NO. 63;
the sequence set forth in SEQ ID NO. 64;
the sequence set forth in SEQ ID NO. 65;
the sequence set forth in SEQ ID NO. 66;
the sequence set forth in SEQ ID NO. 67;
the sequence set forth in SEQ ID NO. 68;
the sequence set forth in SEQ ID NO. 69; or
the sequence set forth in SEQ ID NO. 70.

In some examples, the target sequence comprises:
the sequence set forth in SEQ ID NO. 63;
the sequence set forth in SEQ ID NO. 64;
the sequence set forth in SEQ ID NO. 65;
the sequence set forth in SEQ ID NO. 66;
the sequence set forth in SEQ ID NO. 67;
the sequence set forth in SEQ ID NO. 68;
the sequence set forth in SEQ ID NO. 69; or
the sequence set forth in SEQ ID NO. 70.

In some examples, the target sequence comprises:
the sequence set forth in SEQ ID NO. 64; or
the sequence set forth in SEQ ID NO. 62.

In some examples, the DNA binding protein is a zinc finger protein.

In some examples, the zinc finger protein comprises:
a zinc finger comprising the sequence set forth in SEQ ID NO. 17, a zinc finger comprising the sequence set forth in SEQ ID NO. 16 and a zinc finger comprising the sequence set forth in SEQ ID NO. 11;
a zinc finger comprising the sequence set forth in SEQ ID NO. 18, a zinc finger comprising the sequence set forth in SEQ ID NO. 16 and a zinc finger comprising the sequence set forth in SEQ ID NO. 11; or
a zinc finger comprising the sequence set forth in SEQ ID NO. 18, a zinc finger comprising the sequence set forth in SEQ ID NO. 16 and a zinc finger comprising the sequence set forth in SEQ ID NO. 3.

In some examples, the zinc finger protein comprises:
a ZF1 zinc finger comprising the sequence set forth in SEQ ID NO. 1, a ZF2 zinc finger comprising the sequence set forth in SEQ ID NO. 2, a ZF3 zinc finger comprising the sequence set forth in SEQ ID NO. 3, a ZF4 zinc finger comprising the sequence set forth in SEQ ID NO. 4, a ZF5 zinc finger comprising the sequence set forth in SEQ ID NO. 5 and a ZF6 zinc finger comprising the sequence set forth in SEQ ID NO. 6;
a ZF1 zinc finger comprising the sequence set forth in SEQ ID NO. 7, a ZF2 zinc finger comprising the sequence set forth in SEQ ID NO. 8, a ZF3 zinc finger comprising the sequence set forth in SEQ ID NO. 9, a ZF4 zinc finger comprising the sequence set forth in SEQ ID NO. 7, a ZF5 zinc finger comprising the sequence set forth in SEQ ID NO. 10, a ZF6 zinc finger comprising the sequence set forth in SEQ ID NO. 11, a ZF7 zinc finger comprising the sequence set forth in SEQ ID NO. 12, a ZF8 zinc finger comprising the sequence set forth in SEQ ID NO. 13, a ZF9 zinc finger comprising the sequence set forth in SEQ ID NO. 14 and a ZF10 zinc finger comprising the sequence set forth in SEQ ID NO. 6;
a ZF1 zinc finger comprising the sequence set forth in SEQ ID NO. 15, a ZF2 zinc finger comprising the sequence set forth in SEQ ID NO. 16, a ZF3 zinc finger comprising the sequence set forth in SEQ ID NO. 17, a ZF4 zinc finger comprising the sequence set forth in SEQ ID NO. 16, a ZF5 zinc finger comprising the sequence set forth in SEQ ID NO. 11, a ZF6 zinc finger comprising the sequence set forth in SEQ ID NO. 11 and a ZF7 zinc finger comprising the sequence set forth in SEQ ID NO. 1;
a ZF1 zinc finger comprising the sequence set forth in SEQ ID NO. 11, a ZF2 zinc finger comprising the sequence set forth in SEQ ID NO. 1, a ZF3 zinc finger comprising the sequence set forth in SEQ ID NO. 18, a ZF4 zinc finger comprising the sequence set forth in SEQ ID NO. 16, a ZF5 zinc finger comprising the sequence set forth in SEQ ID NO. 11, a ZF6 zinc finger comprising the sequence set forth in SEQ ID NO. 19 and a ZF7 zinc finger comprising the sequence set forth in SEQ ID NO. 12;
a ZF1 zinc finger comprising the sequence set forth in SEQ ID NO. 8, a ZF2 zinc finger comprising the sequence set forth in SEQ ID NO. 16, a ZF3 zinc finger comprising the sequence set forth in SEQ ID NO. 18, a ZF4 zinc finger comprising the sequence set forth in SEQ ID NO. 16, a ZF5 zinc finger comprising the sequence set forth in SEQ ID NO. 3, a ZF6 zinc finger comprising the sequence set forth in SEQ ID NO. 8 and a ZF7 zinc finger comprising the sequence set forth in SEQ ID NO. 3;
a ZF1 zinc finger comprising the sequence set forth in SEQ ID NO. 17, a ZF2 zinc finger comprising the sequence set forth in SEQ ID NO. 13, a ZF3 zinc finger comprising the sequence set forth in SEQ ID NO. 13, a ZF4 zinc finger comprising the sequence set forth in SEQ ID NO. 9, a ZF5 zinc finger comprising the sequence set forth in SEQ ID NO. 17 and a ZF6 zinc finger comprising the sequence set forth in SEQ ID NO. 9;
a ZF1 zinc finger comprising the sequence set forth in SEQ ID NO. 20, a ZF2 zinc finger comprising the sequence set forth in SEQ ID NO. 21, a ZF3 zinc finger comprising the sequence set forth in SEQ ID NO. 22, a ZF4 zinc finger comprising the sequence set forth in SEQ ID NO. 19, a ZF5 zinc finger comprising the sequence set forth in SEQ ID NO. 12 and a ZF6 zinc finger comprising the sequence set forth in SEQ ID NO. 17; or
a ZF1 zinc finger comprising the sequence set forth in SEQ ID NO. 20, a ZF2 zinc finger comprising the sequence set forth in SEQ ID NO. 21, a ZF3 zinc finger comprising the sequence set forth in SEQ ID NO. 22, a ZF4 zinc finger comprising the sequence set forth in SEQ ID NO. 8, a ZF5 zinc finger comprising the sequence set forth in SEQ ID NO. 3 and a ZF6 zinc finger comprising the sequence set forth in SEQ ID NO. 9.

In some examples, the zinc finger protein comprises:
a ZF1 zinc finger comprising the sequence set forth in SEQ ID NO. 7, a ZF2 zinc finger comprising the sequence set forth in SEQ ID NO. 8, a ZF3 zinc finger comprising the sequence set forth in SEQ ID NO. 9, a ZF4 zinc finger comprising the sequence set forth in SEQ ID NO. 7, a ZF5 zinc finger comprising the sequence set forth in SEQ ID NO. 10, a ZF6 zinc finger comprising the sequence set forth in SEQ ID NO. 11, a ZF7 zinc finger comprising the sequence set forth in SEQ ID NO. 12, a ZF8 zinc finger comprising the sequence set forth in SEQ ID NO. 13, a ZF9 zinc finger comprising the sequence set forth in SEQ ID NO. 14 and a ZF10 zinc finger comprising the sequence set forth in SEQ ID NO. 6;

a ZF1 zinc finger comprising the sequence set forth in SEQ ID NO. 8, a ZF2 zinc finger comprising the sequence set forth in SEQ ID NO. 16, a ZF3 zinc finger comprising the sequence set forth in SEQ ID NO. 18, a ZF4 zinc finger comprising the sequence set forth in SEQ ID NO. 16, a ZF5 zinc finger comprising the sequence set forth in SEQ ID NO. 3, a ZF6 zinc finger comprising the sequence set forth in SEQ ID NO. 8 and a ZF7 zinc finger comprising the sequence set forth in SEQ ID NO. 3;

a ZF1 zinc finger comprising the sequence set forth in SEQ ID NO. 20, a ZF2 zinc finger comprising the sequence set forth in SEQ ID NO. 21, a ZF3 zinc finger comprising the sequence set forth in SEQ ID NO. 22, a ZF4 zinc finger comprising the sequence set forth in SEQ ID NO. 19, a ZF5 zinc finger comprising the sequence set forth in SEQ ID NO. 12 and a ZF6 zinc finger comprising the sequence set forth in SEQ ID NO. 17; or a ZF1 zinc finger comprising the sequence set forth in SEQ ID NO. 20, a ZF2 zinc finger comprising the sequence set forth in SEQ ID NO. 21, a ZF3 zinc finger comprising the sequence set forth in SEQ ID NO. 22, a ZF4 zinc finger comprising the sequence set forth in SEQ ID NO. 8, a ZF5 zinc finger comprising the sequence set forth in SEQ ID NO. 3 and a ZF6 zinc finger comprising the sequence set forth in SEQ ID NO. 9.

In some examples, the zinc finger protein comprises:

a zinc finger domain comprising the sequence set forth in SEQ ID NO. 41, or a sequence having at least about 80% identity to SEQ ID NO. 41;

a zinc finger domain comprising the sequence set forth in SEQ ID NO. 42, or a sequence having at least about 80% identity to SEQ ID NO. 42;

a zinc finger domain comprising the sequence set forth in SEQ ID NO. 43, or a sequence having at least about 80% identity to SEQ ID NO. 43;

a zinc finger domain comprising the sequence set forth in SEQ ID NO. 44, or a sequence having at least about 80% identity to SEQ ID NO. 44;

a zinc finger domain comprising the sequence set forth in SEQ ID NO. 45, or a sequence having at least about 80% identity to SEQ ID NO. 45; or a zinc finger domain comprising the sequence set forth in SEQ ID NO. 46, or a sequence having at least about 80% identity to SEQ ID NO. 46.

In some examples, the DNA binding protein competes for binding to the target sequence with a zinc finger protein comprising:

a zinc finger domain comprising the sequence set forth in SEQ ID NO. 41;

a zinc finger domain comprising the sequence set forth in SEQ ID NO. 42;

a zinc finger domain comprising the sequence set forth in SEQ ID NO. 43;

a zinc finger domain comprising the sequence set forth in SEQ ID NO. 44;

a zinc finger domain comprising the sequence set forth in SEQ ID NO. 45; or a zinc finger domain comprising the sequence set forth in SEQ ID NO. 46.

In some examples, the DNA binding protein competes for binding to the target sequence with a zinc finger protein comprising or consisting of:

the sequence set forth in SEQ ID NO. 29;

the sequence set forth in SEQ ID NO. 30;

the sequence set forth in SEQ ID NO. 32;

the sequence set forth in SEQ ID NO. 33;

the sequence set forth in SEQ ID NO. 34;

the sequence set forth in SEQ ID NO. 36;

the sequence set forth in SEQ ID NO. 37; or the sequence set forth in SEQ ID NO. 39.

In some examples, the transcriptional activation domain is selected from the group consisting of VP16, or a plurality thereof, VP64, VP160, p65, MyoD1, HSF1, RTA, TET3CD, p300 and SET7/9. The DNA binding protein may comprise or be attached to more than one transcriptional activation domain. The more than one transcriptional activation domain may comprise VP64, p65 and RTA.

In some examples, the DNA binding protein is administered to the subject directly as a protein.

In some examples, the DNA binding protein is administered to the subject in the form of a nucleic acid.

In some examples, the DNA binding protein is administered to the subject in the form of an AAV vector.

In some examples, the method comprises administering to the subject more than one DNA binding protein and wherein each DNA binding protein is independently selected from the DNA binding protein defined in the first aspect.

In some examples, the subject is a human.

In some examples, the DNA binding protein comprises a nuclear localisation signal.

In a thirteenth aspect, the present disclosure provides use of a DNA binding protein comprising or attached to a transcriptional activation domain in the manufacture of a medicament for increasing expression of a Klotho gene in a cell, wherein the DNA binding protein binds to a target sequence within or near the Klotho gene and thereby increases expression of the Klotho gene.

In a fourteenth aspect, the present disclosure provides use of a DNA binding protein comprising or attached to a transcriptional activation domain in the manufacture of a medicament for the treatment of cancer in a subject, wherein the DNA binding protein binds to a target sequence within or near a Klotho gene in the subject and thereby increases expression of the Klotho gene.

In a fifteenth aspect, the present disclosure provides use of a DNA binding protein comprising or attached to a transcriptional activation domain in the manufacture of a medicament for the treatment of a muscle disorder in a subject, wherein the DNA binding protein binds to a target sequence within or near a Klotho gene in the subject and thereby increases expression of the Klotho gene.

In a sixteenth aspect, the present disclosure provides use of a DNA binding protein comprising or attached to a transcriptional activation domain in the manufacture of a medicament for the treatment of a kidney disorder in a subject, wherein the DNA binding protein binds to a target sequence within or near a Klotho gene in the subject and thereby increases expression of the Klotho gene.

In a seventeenth aspect, the present disclosure provides use of a DNA binding protein comprising or attached to a transcriptional activation domain in the manufacture of a medicament for enhancing cognition in a subject, wherein the DNA binding protein binds to a target sequence within or near a Klotho gene in the subject and thereby increases expression of the Klotho gene.

In an eighteenth aspect, the present disclosure provides use of a DNA binding protein comprising or attached to a transcriptional activation domain in the manufacture of a medicament for the treatment of a neurological disorder in a subject, wherein the DNA binding protein binds to a target sequence within or near a Klotho gene in the subject and thereby increases expression of the Klotho gene.

In a nineteenth aspect, the present disclosure provides use of a DNA binding protein comprising or attached to a transcriptional activation domain in the manufacture of a medicament for promoting angiogenesis in a subject, wherein the DNA binding protein binds to a target sequence within or near a Klotho gene in the subject and thereby increases expression of the Klotho gene.

In a twentieth aspect, the present disclosure provides use of a DNA binding protein comprising or attached to a transcriptional activation domain in the manufacture of a medicament for the treatment of a wound or a skin disorder in a subject, wherein the DNA binding protein binds to a target sequence within or near a Klotho gene in the subject and thereby increases expression of the Klotho gene.

DETAILED DESCRIPTION

Definitions

Figure 1:
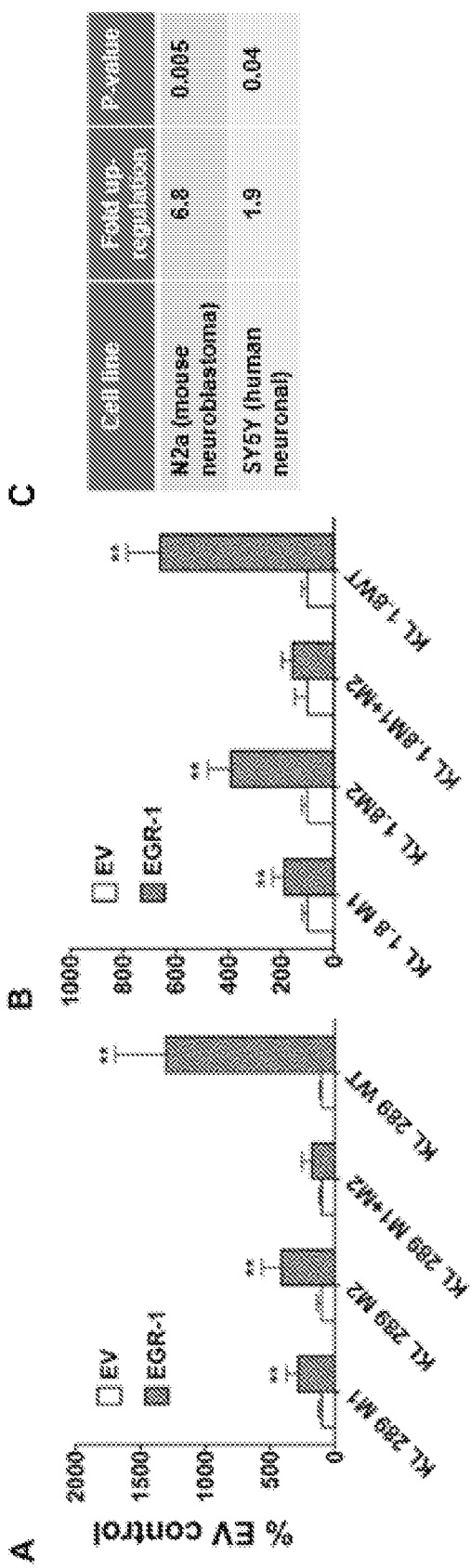
FIG. 1. Mutations in Egr1 binding sites of the Klotho promoter fragments −289 bp (A) and −1800 bp (B) from the translation start site decreased Klotho transcription in Egr1-transfected cells. Mutating both sites abrogates upregulation by Egr1. *, p<0.05. **, p<0.01 (transfected with empty vector (EV) or Egr1; mutated vs. WT). (C) qPCR analysis of Klotho expression in two neuronal cell lines 48 hours after transfection with the Egr1 transcription factor.

In the context of this specification, the terms "a" and "an" are used herein to refer to one or to more than one (ie, to at least one) of the grammatical object of the article. By way of example, "an element" means one element or more than one element.

The term "about" is understood to refer to a range of +/−10%, preferably +/−5% or +/−1% or, more preferably, +/−0.1%.

The terms "administration concurrently" or "administering concurrently" or "co-administering" and the like refer to the administration of a single composition containing two or more actives, or the administration of each active as separate compositions and/or delivered by separate routes either contemporaneously or simultaneously or sequentially within a short enough period of time that the effective result is equivalent to that obtained when all such actives are administered as a single composition. By "simultaneously" is meant that the active agents are administered at substantially the same time, and preferably together in the same formulation.

The terms "comprise", "comprises", "comprised" or "comprising", "including" or "having" and the like in the present specification and claims are used in an inclusive sense, ie, to specify the presence of the stated features but not preclude the presence of additional or further features.

The term "isolated" as used herein refers to material that is substantially or essentially free from components that normally accompany it in its native state. For example, an "isolated polynucleotide" or "isolated nucleic acid" as used herein refers to a polynucleotide which has been purified from the sequences which flank it in a naturally-occurring state, eg, a DNA fragment which has been removed from the sequences that are normally adjacent to the fragment. Alternatively, an "isolated peptide", an "isolated polypeptide", and "isolated protein" and the like, as used herein, refer to in vitro isolation and/or purification of a peptide or polypeptide molecule from its natural cellular environment, and from association with other components of the cell, ie, it is not associated with in vivo substances.

The term "operably connected" or "operably linked" as used herein refers to the functional relationship between two or more nucleic acid segments such as a gene and a regulatory element including but not limited to a promoter, which then regulates the expression of the gene.

The term "pharmaceutically acceptable" as used herein refers to substances that do not cause substantial adverse allergic or immunological reactions when administered to a subject. A "pharmaceutically acceptable carrier" includes, but is not limited to, solvents, coatings, dispersion agents, wetting agents, isotonic and absorption delaying agents and disintegrants.

"Prevention" includes reduction of risk, incidence and/or severity of a condition or disorder. The terms "treatment" and "treat" include both prophylactic or preventive treatment (that prevent and/or slow the development of a targeted pathologic condition or disorder) and curative, therapeutic or disease-modifying treatment, including therapeutic measures that cure, slow down, lessen symptoms of, and/or halt progression of a pathologic condition or disorder; and treatment of patients at risk of contracting a disease or suspected to have contracted a disease, as well as patients who are ill or have been diagnosed as suffering from a disease or medical condition. The terms "treatment" and "treat" do not necessarily imply that a subject is treated until total recovery. The terms "treatment" and "treat" also refer to the maintenance and/or promotion of health in an individual not suffering from a disease but who may be susceptible to the development of an unhealthy condition. The terms "treatment" and "treat" are also intended to include the potentiation or otherwise enhancement of one or more primary prophylactic or therapeutic measures. As non-limiting examples, a treatment can be performed by a patient, a caregiver, a doctor, a nurse, or another healthcare professional.

The term "recombinant nucleic acid" as used herein refers to a nucleic acid formed in vitro by the manipulation of nucleic acid into a form not normally found in nature. For example, the recombinant polynucleotide may be in the form of an expression vector. Generally, such expression vectors include transcriptional and translational regulatory nucleic acid operably linked to the nucleotide sequence.

The term "recombinant protein" as used herein refers to a protein made using recombinant techniques, ie, through the expression of a recombinant polynucleotide.

A "therapeutically effective amount" is at least the minimum concentration or amount required to effect a measurable improvement of a particular disease or condition. A therapeutically effective amount herein may vary according to factors such as the disease state, age, sex and weight of the patient. A therapeutically effective amount is also one in which any toxic or detrimental effects are outweighed by the therapeutically beneficial effects.

Klotho

Klotho plays important regulatory and protective roles in, inter alia, memory loss, stress, synaptic plasticity, biopolar disorder, epilepsy, Alzheimer's disease, Parkinson's disease, multiple sclerosis, myelin-related disease, neurogenic decline, neurodegeneration and kidney dysfunction (Vo et al., 2018. *Brain Plast.* 3: 183-194).

The human Klotho gene is located on chromosome 13 and comprises five exons. The Klotho protein primarily exists in one of three forms. Transmembrane Klotho is an approximately 130 kDa, glycosylated, Type I transmembrane protein. The transmembrane Klotho can be shed from the cell surface by ADAM10/17 metalloproteinases into a soluble form that is detectable in serum and CSF (Bloch et al., 2009. *FEBS Lett.* 583(19): 3221-3224; Chen et al., 2007. *Proc. Natl Acad. Sci. USA.* 104(50): 19796-19801; Matsumura et al., 1998. *Biochem. Biophys. Res. Commun.* 242(3): 626-630). A third, secreted form of Klotho is generated by alternative splicing of exon 3 to produce a 70 kDa protein which is detectable in blood and CSF (Masso et al., 2015. *PLoS One.* 10(11): e0143623). Both the transmembrane and soluble forms of Klotho have important functions in many homeostatic processes.

Sequences

Table 1 lists various sequences relevant to the present disclosure. However, those skilled in the art will understand that several Klotho alleles exist, and the present disclosure is not limited to any particular allele. Skilled persons will also understand that greater levels of sequence variation may exist in genomic regions which do not directly encode amino acids compared to those regions which do encode amino acids.

TABLE 1

Klotho sequences

| SEQ ID NO. | Description |
| --- | --- |
| 23 | 4,000 nt genomic region extending upstream of human Klotho translation start site (sense) |
| 24 | 4,000 nt genomic region extending upstream of human Klotho translation start site (antisense) |
| 25 | Genomic sequence of human Klotho from translation start site to translation stop site (sense) |
| 26 | Genomic sequence of human Klotho from translation start site to translation stop site (antisense) |
| 27 | Genomic region extending from 4,000 nt upstream of human Klotho translation start site to Klotho translation stop site (sense) |
| 28 | Genomic region extending from 4,000 nt upstream of human Klotho translation start site to Klotho translation stop site (antisense) |

Set forth below is a 4,000 nt genomic region extending upstream of the human Klotho translation start site (SEQ ID NO. 23). ZFP1 target sequence is in lower case, ZFP52 target sequence is underlined and in lower case, site 1 target sequence is bold and underlined, site 2 target sequence is underlined and site 3 target sequence (antisense) is bold.

ACAATATATTGTATTTTTGAAAATCTCAGAGTAGATTTTAAGTATTCTT

CTTTTTCTTTCTTTTCTTCTTTTCTTTTCTTTTTTCTTTTTTGAAACAG

ACTCTTGCTCTGTTGCCAAAGCTGGAGTACAGTGGTGTGATCTCAGCTC

ACTGCAACCTCCGCCTCCCGGGTTCAAGTGATTCTCCTGCCTCAGCCTC

CTGAGTAGCTGGGATTACAGGTGCCTGCCACCATGTTGGTGAATTTTTG

TATTTTTAGTAGAGACAGGAGTTTCACCATGTTGGCCAGGCTGGTCTCG

AACTCCTGACCTTAGGTGGTCCACCTGCCTCGGCCTCTCAAAGTGCTGG

GATTACAGGTGTGAGCCACCACGCCCGGCCAGATTTTAAGTCTTCTTAC

CACAAAAAAATAAGTATGTGAGGTAATACATACGTTTATTAGCTCAAT

TTAGCCACTCTACAAATGTGTATATATTTTAAAATAACATGCTGTACAT

GAAAATATATATAATTTTTTGTCTGTTAAAAATTAATTAATTAATTAAT

TTTAAAAGAGGAGGGCAGGGAATACTTGTGTATTTTGTTAACTGGACA

AATGAAACTCTACTTTCATTTGCTCATTAAACAAATACTTGTTTTGTGC

TCAGCATGATTCTAGGCACTGGGACTACTGCATTTTGGTCCATTACTTC

CTTGCGCACAAAAACCCTTTCTTTTCACCACGAATACACTATGAACATG

TTTTTTTCTTCAGTGTTGGCATCTCTTGATTCCTTCCCTCCAGGTCTTT

GTGCGAGTTTTACTCTTTAAACCCCAGATATTGTCATATTTTTCTCTGT

TAAACTTTTCCAAACAACTCAAAATAGGGTAATTTCTTCTTCTTCTGAA

TTTCTCTGACAATTATTCTATGGGTCATTTATTAACACAGCATAATCAA

-continued
ACAACTTATTTATTTTCATCTTTCTTGATCCTTTCTTCAGTTGGATGTT

GTCTTTGAGGGCAGAGGTTGTCCTCTATGTTTTGAAGTCTCCACACAGC

TCATCGTTGCCTTGCCCGTAGTTGTAGCTCAGTGAAATAAAAATATGTC

CGTAGAAGGTGATGTCTGTGACTGGTGAGCCGAGAGCTTGTGGGGTTGG

TGTTGTATTTGAGTGCATGTGAATCAGTGCATCTCCTGCTCCATTGGTG

TTAAAAGGCTCCCATCGTCCTGGGAACACAATAGGAAAGAGAACAGGTG

GGAAGGCACTGGATGAAGGAATGTGGAGAATGGAGGAAAAGTTGATCAG

ATTGTTGACAACTTTCAGTGTTGAAATTGTCACCAAAATCAAAGTCAGT

AAATAAATTTACAATGTCCTTTTCTTCAATGCATCAATAACTTCACCTT

CCTGTTCAAAGCACAGCAAGTAATTAATCTCTTATTTGCATTTGAAACC

CAAGTTTCAGATGTTTGAAGGTGGTTGTAAAAAATAAAAACCAAAATAA

AGCCAAAATAAATAAGCAGCAGCACTAGGCCGGGCACAGTGTCTCACAC

CTGTAATCCCAGCATTTTAGGAGACCGAGGTGGGTGGATCACAGGAGAT

CAGGAGTTTGAGACCAGCCTGGTCAGCATGGTGAAACCCTGTCTCTACT

AAAAATACAAAAATTAGCCAGGTGTGGTGGTGTGCCCTTATAATCCCAG

CTACTGGGGGCTGAGACAGGAGAATTGCTTGAACCTGGGAGGCAGAGG

TTGCAGTGAGCAGAGACCATGCCACTGCACTCCAGCCTGGGCGACAGAG

TGAGACTCCGTCTCACACTTGTGGAACCCAGAACTTAGTAACCATGAAC

AGAACCTTAATAAACAGAAAGTTCTGGAAATAAAGTTTAATCATCATGC

AATCTTTATCACTGGGTTAAATGAACAATCATCTGGGAACATGTCTTGG

AATGCTTAAAGCTTTGAGATGCATGTGCCTATGTGGCAGACAAATTTCA

AATGTGAAACGTTTAGTTAACTTGGTCTTGCTTTTTAATCACTGCTTTA

AAATTTAAAAAATGCTGCTGGTCAAGTAAAAATAGCAATAGATAAAATC

TGCCCTGAGCAAACAGACCATACATCAATAAATGAATACTTAGCTTAAG

CGATTTTCCATGAGACCCATGAAGCATTTCTAATTGAAACTTAACAAGC

TACAACCCAACAGACACTCCAATCTTCACTTCTAGAAGGGAAATGTGAT

ACTCCATGTAGACGTAGCTTTTTAAATTTAGCTGGAAGACAGCGTGACA

GTGAAGTTGTGTGCTGTAATTTTTTAAAATTGCTGAAGTGTCATGGTTT

GCTATTTCGTATTTATTGAAAAAATGTAAATGCTATATTTAACAGAATG

GCAGTAACTCTGTTTCAATCTGAAGACTTAATCTTACTAATCATGGTAA

TATATGCTGGCTGGAGTTGGGAATATTTCATAAAATACTGGAATAAATT

TGTGCTTATATTTCAGGGGAATTAATAAAAGCACCTTCATCTGCAACAT

TTAAAATGTTATTGCCTTTAAATTTGTATTAAATAATGCAGGGAGGATA

GATCACTGGGGGAGAATGGATGCACCTCTGTGAGGATCTTGGTCATTCA

ACACACGTGTACGGGTGAGGAAACTAAGGCACGACTTACTGGGTAGGGA

GGTAGGGATATTAGCAAGATCCTTCACTTGTCTGGGCTTTCTGTCTTTG

AGTCACCTTTGCGCAGTTTTTCACTGGACTTCACAAGCCTCTGAGGCGG

CAGGGCAGACAGGACATCCTTATTTTATAGAGGAAAAAACTTAGGCTTA

CAGAGGTTTCCTGCCCCAAATCACAAAGGTGGAGCCTAGACCTTCTCAG

TCTCCACCAACTGTATTTCGGTTAGCCACAATCCTATCTACCCACATCC

AAATGGACACCGTGGCTCTGCAACTTCTGTCAAAAGGGCTCTTTGGCAA

-continued
CAGGAAAAACGTCATGGCTCCATTGTATTGTAGAGGATGGGAATGGGTG

TTCCGGCTAAATTCTCCCTCCCCTTTCCCTCCACAGCTCAGATGGCAAA

TGTGCGACCCAGGGACCTCCCGCTCCAGCAGACCTGTGCGCACAACTTT

GCACAGATTACCTGCTAAGTCAGAGCCGAAAGGTAACACAGATGCCAAA

GGATAATAAAGGTGAATGAGATTTACTCAAAATTGGAAACTTGGTGTTT

GGTTTTTCAGGAGAACAATCAACGACTGTGATTTGAAGTTCACCAGGGT

ATTCTGAGAGATCTAATCAAAGATAGAGTGCTGGTTTGAAATTATTAAA

AGGTAACAGTAAAAGGGAGAGCAAAACCCCAGTCCCAACGCAACCCATA

AATCTACTTTGTCTTCCTCGAAAGAGGGGCGCGGGTGGGCGCGTCTCCC

CGCGAGCATCTCACCTAAGGGGGAATCCCTTTCAGCGCACGGCGAAGTT

CCCCCTCGGCTGTCCCACCTGGCAGTCCCTCTAGGATTTCGGCCAGTCC

CTAATTGGCTCCAGCAATGTCCAGCCGGAGCTTCTTTGGGCCTCCGAGT

GGGAGAAAAGTGAGAGCAGGTGCTTCCCCAGCGGCGCGCTCCGCTAGGG

CCCGGCAGGATCCCGCCCCCAAGTCGGGGAAAGTTGGTCGGCGCCTTTT

CTCCCCGACGAAGCCGCTCCAGGGCTGCTCTCAGAGGACGCGCGGCAGG

CAAAGAGAATGAACCTGAGCGTCCAcgaaacgtcctgcacggcTCCCGG

GAGCTGGGAGGAACAGGTGCCTTTCTccgacgtccgcgggcgacgcctg ccgcacctTGCCCGCTGCCGCGCCCCTCCCGGGCACCCCTCGCCCTCGG

CGCCCCTGCCCCCACCCCCAGTGCCAGGGCGGAGGCAGTCCCGGCTCGC

AGGTAATTATTGCCAGCGGAGCCCGCCGGGGAGCGGGGGTGGGCGCGCC

GGCGGTGGGCGGGCGGGCGCGCGGGGCGCGGGCATAAAGGGGCGCGGC

GCGGGCCCCGGAGCCTGGCTCCCGCGCAGC

DNA Binding Proteins

In some examples, the present disclosure provides an isolated or recombinant DNA binding protein comprising or attached to a transcriptional activation domain wherein the DNA binding protein binds to a target sequence within or near a Klotho gene. It will be understood that in such examples, the DNA binding protein is capable of binding to the target sequence even if it is not bound to that sequence.

A DNA binding protein is a protein that comprises a plurality of amino acids which interact with DNA, and thereby enable the protein to bind to the DNA. The amino acids may interact with a defined sequence of nucleotides such that the DNA binding protein will bind at specific loci along a long polynucleotide such as a chromosome.

Zinc finger DNA binding proteins are proteins which bind to DNA in a sequence-specific manner through one or more zinc fingers. The term zinc finger DNA binding protein is often abbreviated as zinc finger protein or ZFP. Each zinc finger typically comprises a recognition helix which interacts with DNA; typically a trinucleotide whose sequence will depend on the primary sequence of the recognition helix. $Cys_2$-$His_2$ zinc fingers generally comprise about 30 amino acids (although the precise length can vary) with a ββα fold stabilised by hydrophobic interactions and the coordination of a zinc ion.

A ZFP may comprise (or may be engineered to comprise) tandem zinc fingers such that longer stretches of DNA can be recognised. For example, a ZFP may comprise three zinc fingers, and may recognise a nine-nucleotide stretch of DNA. In such cases, the zinc fingers are often referred to sequentially as ZF1, ZF2 and ZF3.

Structural studies have indicated that each zinc finger contacts the target sequence in an antiparallel manner (Pavletich and Pabo. 1991. Science. 252: 809-817; Elrod-Erickson et al. 1996. Structure. 4: 1171-1180). For example, in the case of a zinc finger domain comprising three zinc fingers, ZF1 would typically recognise the 3'-most trinucleotide, ZF2 would recognise the second trinucleotide, and ZF3 would recognise the 5'-most trinucleotide.

The zinc finger proteins of the present disclosure may comprise more than one zinc finger such as 2, 3, 4, 5, 6, 7, 8, 9, 10 or more zinc fingers, each zinc finger having a recognition helix that binds to a defined sequence within a target sequence. In some examples, the zinc finger protein of the present disclosure comprises at least 2, such as at least 3, or at least 4, or at least 5 or 6 zinc fingers selected from a zinc finger comprising the sequence set forth in SEQ ID NO. 1, a zinc finger comprising the sequence set forth in SEQ ID NO. 2, a zinc finger comprising the sequence set forth in SEQ ID NO. 3, a zinc finger comprising the sequence set forth in SEQ ID NO. 4, a zinc finger comprising the sequence set forth in SEQ ID NO. 5 and a zinc finger comprising the sequence set forth in SEQ ID NO. 6. For example, the zinc finger protein may comprise a ZF1 zinc finger comprising the sequence set forth in SEQ ID NO. 1, a ZF2 zinc finger comprising the sequence set forth in SEQ ID NO. 2, a ZF3 zinc finger comprising the sequence set forth in SEQ ID NO. 3, a ZF4 zinc finger comprising the sequence set forth in SEQ ID NO. 4, a ZF5 zinc finger comprising the sequence set forth in SEQ ID NO. 5 and a ZF6 zinc finger comprising the sequence set forth in SEQ ID NO. 6.

In some examples, the zinc finger protein of the present disclosure comprises at least 2, such as at least 3, or at least 4, or at least 5, or at least 6, or at least 7, or at least 8, or at least 9 or 10 zinc fingers selected from a zinc finger comprising the sequence set forth in SEQ ID NO. 7, a zinc finger comprising the sequence set forth in SEQ ID NO. 8, a zinc finger comprising the sequence set forth in SEQ ID NO. 9, a zinc finger comprising the sequence set forth in SEQ ID NO. 10, a zinc finger comprising the sequence set forth in SEQ ID NO. 11, a zinc finger comprising the sequence set forth in SEQ ID NO. 12, a zinc finger comprising the sequence set forth in SEQ ID NO. 13, a zinc finger comprising the sequence set forth in SEQ ID NO. 14 and a zinc finger comprising the sequence set forth in SEQ ID NO. 6. For example, the zinc finger protein may comprise a ZF1 zinc finger comprising the sequence set forth in SEQ ID NO. 7, a ZF2 zinc finger comprising the sequence set forth in SEQ ID NO. 8, a ZF3 zinc finger comprising the sequence set forth in SEQ ID NO. 9, a ZF4 zinc finger comprising the sequence set forth in SEQ ID NO. 7, a ZF5 zinc finger comprising the sequence set forth in SEQ ID NO. 10, a ZF6 zinc finger comprising the sequence set forth in SEQ ID NO. 11, a ZF7 zinc finger comprising the sequence set forth in SEQ ID NO. 12, a ZF8 zinc finger comprising the sequence set forth in SEQ ID NO. 13, a ZF9 zinc finger comprising the sequence set forth in SEQ ID NO. 14 and a ZF10 zinc finger comprising the sequence set forth in SEQ ID NO. 6.

In some examples, the zinc finger protein of the present disclosure comprises at least 2, such as at least 3, or at least 4, or at least 5, or at least 6 or 7 zinc fingers selected from a zinc finger comprising the sequence set forth in SEQ ID NO. 15, a zinc finger comprising the sequence set forth in SEQ ID NO. 16, a zinc finger comprising the sequence set forth in SEQ ID NO. 17, a zinc finger comprising the sequence set forth in SEQ ID NO. 11 and a zinc finger comprising the sequence set forth in SEQ ID NO. 1. For example, the zinc finger protein may comprise a ZF1 zinc finger comprising the sequence set forth in SEQ ID NO. 15, a ZF2 zinc finger comprising the sequence set forth in SEQ ID NO. 16, a ZF3 zinc finger comprising the sequence set forth in SEQ ID NO. 17, a ZF4 zinc finger comprising the sequence set forth in SEQ ID NO. 16, a ZF5 zinc finger comprising the sequence set forth in SEQ ID NO. 11, a ZF6 zinc finger comprising the sequence set forth in SEQ ID NO. 11 and a ZF7 zinc finger comprising the sequence set forth in SEQ ID NO. 1.

In some examples, the zinc finger protein of the present disclosure comprises at least 2, such as at least 3, or at least 4, or at least 5, or at least 6 or 7 zinc fingers selected from a zinc finger comprising the sequence set forth in SEQ ID NO. 11, a zinc finger comprising the sequence set forth in SEQ ID NO. 1, a zinc finger comprising the sequence set forth in SEQ ID NO. 18, a zinc finger comprising the sequence set forth in SEQ ID NO. 16, a zinc finger comprising the sequence set forth in SEQ ID NO. 19 and a zinc finger comprising the sequence set forth in SEQ ID NO. 12. For example, the zinc finger protein may comprise a ZF1 zinc finger comprising the sequence set forth in SEQ ID NO. 11, a ZF2 zinc finger comprising the sequence set forth in SEQ ID NO. 1, a ZF3 zinc finger comprising the sequence set forth in SEQ ID NO. 18, a ZF4 zinc finger comprising the sequence set forth in SEQ ID NO. 16, a ZF5 zinc finger comprising the sequence set forth in SEQ ID NO. 11, a ZF6 zinc finger comprising the sequence set forth in SEQ ID NO. 19 and a ZF7 zinc finger comprising the sequence set forth in SEQ ID NO. 12.

In some examples, the zinc finger protein of the present disclosure comprises at least 2, such as at least 3, or at least 4, or at least 5, or at least 6 or 7 zinc fingers selected from a zinc finger comprising the sequence set forth in SEQ ID NO. 8, a zinc finger comprising the sequence set forth in SEQ ID NO. 16, a zinc finger comprising the sequence set forth in SEQ ID NO. 18, a zinc finger comprising the sequence set forth in SEQ ID NO. 8 and a zinc finger comprising the sequence set forth in SEQ ID NO. 3. For example, the zinc finger protein may comprise a ZF1 zinc finger comprising the sequence set forth in SEQ ID NO. 8, a ZF2 zinc finger comprising the sequence set forth in SEQ ID NO. 16, a ZF3 zinc finger comprising the sequence set forth in SEQ ID NO. 18, a ZF4 zinc finger comprising the sequence set forth in SEQ ID NO. 16, a ZF5 zinc finger comprising the sequence set forth in SEQ ID NO. 3, a ZF6 zinc finger comprising the sequence set forth in SEQ ID NO. 8 and a ZF7 zinc finger comprising the sequence set forth in SEQ ID NO. 3.

In some examples, the zinc finger protein of the present disclosure comprises at least 2, such as at least 3, or at least 4, or at least 5 or 6 zinc fingers selected from a zinc finger comprising the sequence set forth in SEQ ID NO. 17, a zinc finger comprising the sequence set forth in SEQ ID NO. 13 and a zinc finger comprising the sequence set forth in SEQ ID NO. 9. For example, the zinc finger protein may comprise a ZF1 zinc finger comprising the sequence set forth in SEQ ID NO. 17, a ZF2 zinc finger comprising the sequence set forth in SEQ ID NO. 13, a ZF3 zinc finger comprising the sequence set forth in SEQ ID NO. 13, a ZF4 zinc finger comprising the sequence set forth in SEQ ID NO. 9, a ZF5 zinc finger comprising the sequence set forth in SEQ ID NO. 17 and a ZF6 zinc finger comprising the sequence set forth in SEQ ID NO. 9.

In some examples, the zinc finger protein of the present disclosure comprises at least 2, such as at least 3, or at least 4, or at least 5 or 6 zinc fingers selected from a zinc finger comprising the sequence set forth in SEQ ID NO. 20, a zinc finger comprising the sequence set forth in SEQ ID NO. 21, a zinc finger comprising the sequence set forth in SEQ ID NO. 22, a zinc finger comprising the sequence set forth in SEQ ID NO. 19, a zinc finger comprising the sequence set forth in SEQ ID NO. 12 and a zinc finger comprising the sequence set forth in SEQ ID NO. 17. For example, the zinc finger protein may comprise a ZF1 zinc finger comprising the sequence set forth in SEQ ID NO. 20, a ZF2 zinc finger comprising the sequence set forth in SEQ ID NO. 21, a ZF3 zinc finger comprising the sequence set forth in SEQ ID NO. 22, a ZF4 zinc finger comprising the sequence set forth in SEQ ID NO. 19, a ZF5 zinc finger comprising the sequence set forth in SEQ ID NO. 12 and a ZF6 zinc finger comprising the sequence set forth in SEQ ID NO. 17.

In some examples, the zinc finger protein of the present disclosure comprises at least 2, such as at least 3, or at least 4, or at least 5 or 6 zinc fingers selected from a zinc finger comprising the sequence set forth in SEQ ID NO. 20, a zinc finger comprising the sequence set forth in SEQ ID NO. 21, a zinc finger comprising the sequence set forth in SEQ ID NO. 22, a zinc finger comprising the sequence set forth in SEQ ID NO. 8, a zinc finger comprising the sequence set forth in SEQ ID NO. 3 and a zinc finger comprising the sequence set forth in SEQ ID NO. 9. For example, the zinc finger protein may comprise a ZF1 zinc finger comprising the sequence set forth in SEQ ID NO. 20, a ZF2 zinc finger comprising the sequence set forth in SEQ ID NO. 21, a ZF3 zinc finger comprising the sequence set forth in SEQ ID NO. 22, a ZF4 zinc finger comprising the sequence set forth in SEQ ID NO. 8, a ZF5 zinc finger comprising the sequence set forth in SEQ ID NO. 3 and a ZF6 zinc finger comprising the sequence set forth in SEQ ID NO. 9.

In some examples, the zinc finger protein of the present disclosure comprises:
- a ZF1 zinc finger comprising the sequence set forth in SEQ ID NO. 1, a ZF2 zinc finger comprising the sequence set forth in SEQ ID NO. 2, a ZF3 zinc finger comprising the sequence set forth in SEQ ID NO. 3, a ZF4 zinc finger comprising the sequence set forth in SEQ ID NO. 4, a ZF5 zinc finger comprising the sequence set forth in SEQ ID NO. 5 and a ZF6 zinc finger comprising the sequence set forth in SEQ ID NO. 6;
- a ZF1 zinc finger comprising the sequence set forth in SEQ ID NO. 7, a ZF2 zinc finger comprising the sequence set forth in SEQ ID NO. 8, a ZF3 zinc finger comprising the sequence set forth in SEQ ID NO. 9, a ZF4 zinc finger comprising the sequence set forth in SEQ ID NO. 7, a ZF5 zinc finger comprising the sequence set forth in SEQ ID NO. 10, a ZF6 zinc finger comprising the sequence set forth in SEQ ID NO. 11, a ZF7 zinc finger comprising the sequence set forth in SEQ ID NO. 12, a ZF8 zinc finger comprising the sequence set forth in SEQ ID NO. 13, a ZF9 zinc finger comprising the sequence set forth in SEQ ID NO. 14 and a ZF10 zinc finger comprising the sequence set forth in SEQ ID NO. 6;
- a ZF1 zinc finger comprising the sequence set forth in SEQ ID NO. 15, a ZF2 zinc finger comprising the sequence set forth in SEQ ID NO. 16, a ZF3 zinc finger comprising the sequence set forth in SEQ ID NO. 17, a ZF4 zinc finger comprising the sequence set forth in SEQ ID NO. 16, a ZF5 zinc finger comprising the sequence set forth in SEQ ID NO. 11, a ZF6 zinc finger comprising the sequence set forth in SEQ ID NO. 11 and a ZF7 zinc finger comprising the sequence set forth in SEQ ID NO. 1;
- a ZF1 zinc finger comprising the sequence set forth in SEQ ID NO. 11, a ZF2 zinc finger comprising the sequence set forth in SEQ ID NO. 1, a ZF3 zinc finger comprising the sequence set forth in SEQ ID NO. 18, a ZF4 zinc finger comprising the sequence set forth in SEQ ID NO. 16, a ZF5 zinc finger comprising the sequence set forth in SEQ ID NO. 11, a ZF6 zinc finger comprising the sequence set forth in SEQ ID NO. 19 and a ZF7 zinc finger comprising the sequence set forth in SEQ ID NO. 12;
- a ZF1 zinc finger comprising the sequence set forth in SEQ ID NO. 8, a ZF2 zinc finger comprising the sequence set forth in SEQ ID NO. 16, a ZF3 zinc finger comprising the sequence set forth in SEQ ID NO. 18, a ZF4 zinc finger comprising the sequence set forth in SEQ ID NO. 16, a ZF5 zinc finger comprising the sequence set forth in SEQ ID NO. 3, a ZF6 zinc finger comprising the sequence set forth in SEQ ID NO. 8 and a ZF7 zinc finger comprising the sequence set forth in SEQ ID NO. 3;
- a ZF1 zinc finger comprising the sequence set forth in SEQ ID NO. 17, a ZF2 zinc finger comprising the sequence set forth in SEQ ID NO. 13, a ZF3 zinc finger comprising the sequence set forth in SEQ ID NO. 13, a ZF4 zinc finger comprising the sequence set forth in SEQ ID NO. 9, a ZF5 zinc finger comprising the sequence set forth in SEQ ID NO. 17 and a ZF6 zinc finger comprising the sequence set forth in SEQ ID NO. 9;
- a ZF1 zinc finger comprising the sequence set forth in SEQ ID NO. 20, a ZF2 zinc finger comprising the sequence set forth in SEQ ID NO. 21, a ZF3 zinc finger comprising the sequence set forth in SEQ ID NO. 22, a ZF4 zinc finger comprising the sequence set forth in SEQ ID NO. 19, a ZF5 zinc finger comprising the sequence set forth in SEQ ID NO. 12 and a ZF6 zinc finger comprising the sequence set forth in SEQ ID NO. 17; or
- a ZF1 zinc finger comprising the sequence set forth in SEQ ID NO. 20, a ZF2 zinc finger comprising the sequence set forth in SEQ ID NO. 21, a ZF3 zinc finger comprising the sequence set forth in SEQ ID NO. 22, a ZF4 zinc finger comprising the sequence set forth in SEQ ID NO. 8, a ZF5 zinc finger comprising the sequence set forth in SEQ ID NO. 3 and a ZF6 zinc finger comprising the sequence set forth in SEQ ID NO. 9.

In some examples, the zinc finger protein of the present disclosure comprises:
- a zinc finger domain comprising the sequence set forth in SEQ ID NO. 41, or a sequence having at least about 70% identity, or at least about 75% identity, or at least about 80% identity, or at least about 85% identity, or at least about 90% identity, or at least about 95% identity or at least about 99% identity or 100% identity to SEQ ID NO. 41;
- a zinc finger domain comprising the sequence set forth in SEQ ID NO. 42, or a sequence having at least about 70% identity, or at least about 75% identity, or at least about 80% identity, or at least about 85% identity, or at least about 90% identity, or at least about 95% identity or at least about 99% identity or 100% identity to SEQ ID NO. 42;

a zinc finger domain comprising the sequence set forth in SEQ ID NO. 43, or a sequence having at least about 70% identity, or at least about 75% identity, or at least about 80% identity, or at least about 85% identity, or at least about 90% identity, or at least about 95% identity or at least about 99% identity or 100% identity to SEQ ID NO. 43;

a zinc finger domain comprising the sequence set forth in SEQ ID NO. 44, or a sequence having at least about 70% identity, or at least about 75% identity, or at least about 80% identity, or at least about 85% identity, or at least about 90% identity, or at least about 95% identity or at least about 99% identity or 100% identity to SEQ ID NO. 44;

a zinc finger domain comprising the sequence set forth in SEQ ID NO. 45, or a sequence having at least about 70% identity, or at least about 75% identity, or at least about 80% identity, or at least about 85% identity, or at least about 90% identity, or at least about 95% identity or at least about 99% identity or 100% identity to SEQ ID NO. 45; or a zinc finger domain comprising the sequence set forth in SEQ ID NO. 46, or a sequence having at least about 70% identity, or at least about 75% identity, or at least about 80% identity, or at least about 85% identity, or at least about 90% identity, or at least about 95% identity or at least about 99% identity or 100% identity to SEQ ID NO. 46.

"Two handed" zinc finger proteins are those proteins in which two clusters of zinc fingers are separated by intervening amino acids so that the two zinc finger domains bind to two respective target sites. An example of a two handed zinc finger binding protein is SIP1, which comprises an N-terminal cluster of zinc fingers and a C-terminal cluster (Remacle et al. 1999. EMBO J.15(18): 5073-5084). In some examples, the DNA binding protein of the present disclosure comprises two or more zinc finger domains. The domains may be linked by an extendable flexible linker. Each zinc finger domain may independently comprise, for example, 1, 2, 3, 4, 5, 6, 7, 8, 9, 10 or more zinc fingers.

In some examples, the present disclosure provides a zinc finger protein comprising at least two zinc finger domains independently selected from:

a zinc finger domain comprising a ZF1 zinc finger comprising the sequence set forth in SEQ ID NO. 1, a ZF2 zinc finger comprising the sequence set forth in SEQ ID NO. 2, a ZF3 zinc finger comprising the sequence set forth in SEQ ID NO. 3, a ZF4 zinc finger comprising the sequence set forth in SEQ ID NO. 4, a ZF5 zinc finger comprising the sequence set forth in SEQ ID NO. 5 and a ZF6 zinc finger comprising the sequence set forth in SEQ ID NO. 6;

a zinc finger domain comprising a ZF1 zinc finger comprising the sequence set forth in SEQ ID NO. 7, a ZF2 zinc finger comprising the sequence set forth in SEQ ID NO. 8, a ZF3 zinc finger comprising the sequence set forth in SEQ ID NO. 9, a ZF4 zinc finger comprising the sequence set forth in SEQ ID NO. 7, a ZF5 zinc finger comprising the sequence set forth in SEQ ID NO. 10, a ZF6 zinc finger comprising the sequence set forth in SEQ ID NO. 11, a ZF7 zinc finger comprising the sequence set forth in SEQ ID NO. 12, a ZF8 zinc finger comprising the sequence set forth in SEQ ID NO. 13, a ZF9 zinc finger comprising the sequence set forth in SEQ ID NO. 14 and a ZF10 zinc finger comprising the sequence set forth in SEQ ID NO. 6;

a zinc finger domain comprising a ZF1 zinc finger comprising the sequence set forth in SEQ ID NO. 15, a ZF2 zinc finger comprising the sequence set forth in SEQ ID NO. 16, a ZF3 zinc finger comprising the sequence set forth in SEQ ID NO. 17, a ZF4 zinc finger comprising the sequence set forth in SEQ ID NO. 16, a ZF5 zinc finger comprising the sequence set forth in SEQ ID NO. 11, a ZF6 zinc finger comprising the sequence set forth in SEQ ID NO. 11 and a ZF7 zinc finger comprising the sequence set forth in SEQ ID NO. 1;

a zinc finger domain comprising a ZF1 zinc finger comprising the sequence set forth in SEQ ID NO. 11, a ZF2 zinc finger comprising the sequence set forth in SEQ ID NO. 1, a ZF3 zinc finger comprising the sequence set forth in SEQ ID NO. 18, a ZF4 zinc finger comprising the sequence set forth in SEQ ID NO. 16, a ZF5 zinc finger comprising the sequence set forth in SEQ ID NO. 11, a ZF6 zinc finger comprising the sequence set forth in SEQ ID NO. 19 and a ZF7 zinc finger comprising the sequence set forth in SEQ ID NO. 12;

a zinc finger domain comprising a ZF1 zinc finger comprising the sequence set forth in SEQ ID NO. 8, a ZF2 zinc finger comprising the sequence set forth in SEQ ID NO. 16, a ZF3 zinc finger comprising the sequence set forth in SEQ ID NO. 18, a ZF4 zinc finger comprising the sequence set forth in SEQ ID NO. 16, a ZF5 zinc finger comprising the sequence set forth in SEQ ID NO. 3, a ZF6 zinc finger comprising the sequence set forth in SEQ ID NO. 8 and a ZF7 zinc finger comprising the sequence set forth in SEQ ID NO. 3;

a zinc finger domain comprising a ZF1 zinc finger comprising the sequence set forth in SEQ ID NO. 17, a ZF2 zinc finger comprising the sequence set forth in SEQ ID NO. 13, a ZF3 zinc finger comprising the sequence set forth in SEQ ID NO. 13, a ZF4 zinc finger comprising the sequence set forth in SEQ ID NO. 9, a ZF5 zinc finger comprising the sequence set forth in SEQ ID NO. 17 and a ZF6 zinc finger comprising the sequence set forth in SEQ ID NO. 9;

a zinc finger domain comprising a ZF1 zinc finger comprising the sequence set forth in SEQ ID NO. 20, a ZF2 zinc finger comprising the sequence set forth in SEQ ID NO. 21, a ZF3 zinc finger comprising the sequence set forth in SEQ ID NO. 22, a ZF4 zinc finger comprising the sequence set forth in SEQ ID NO. 19, a ZF5 zinc finger comprising the sequence set forth in SEQ ID NO. 12 and a ZF6 zinc finger comprising the sequence set forth in SEQ ID NO. 17; and a zinc finger domain comprising a ZF1 zinc finger comprising the sequence set forth in SEQ ID NO. 20, a ZF2 zinc finger comprising the sequence set forth in SEQ ID NO. 21, a ZF3 zinc finger comprising the sequence set forth in SEQ ID NO. 22, a ZF4 zinc finger comprising the sequence set forth in SEQ ID NO. 8, a ZF5 zinc finger comprising the sequence set forth in SEQ ID NO. 3 and a ZF6 zinc finger comprising the sequence set forth in SEQ ID NO. 9.

In some examples, the DNA binding protein is a modified Early growth response protein 1 (EGR1). EGR1 is a $Cys_2$-$His_2$ zinc finger protein which generally comprises three zinc fingers. In some examples, the modified EGR1 of the present disclosure may be engineered to comprise additional zinc fingers. In some examples, the modified EGR1 comprises more than 3 zinc fingers, such as more than 4 zinc fingers or more than 5 zinc fingers such as 6 zinc fingers. In some examples, the modified EGR1 of the present disclosure may be engineered such that it lacks a functional repressor domain.

Another class of DNA binding proteins is the transcription activator-like effectors (TALE) proteins, which mimic plant transcriptional activators (see Kay et al. 2007. Science 318:648-651). TALEs typically comprise a DNA binding domain and a transcriptional activation domain. One of the most well characterized TALEs is AvrBs3 from *Xanthomonas campestris* pv. *Vesicatoria* (see Bonas et al. 1989. Mol. Gen. Genet. 218: 127-136). TALEs comprise a centralized domain of tandem repeats, each repeat containing approximately 34 amino acids, which are important to the DNA binding specificity of these proteins. In addition, they can contain a nuclear localization sequence and an acidic transcriptional activation domain.

Specificity of these TALEs typically depends on the sequences found in the tandem repeats (see Bonas et al. 1989. Mol. Gen. Genet. 218: 127-136). Polymorphism of the repeats is usually located at positions 12 and 13 and there appears to be a one-to-one correspondence between the identity of the hypervariable diresidues at positions 12 and 13 with the identity of the contiguous nucleotides in the TALE's target sequence (see Moscou and Bogdanove. 2009. Science 326:1501). The code for DNA recognition of these TALEs has been reported such that, in most cases, an HD sequence at positions 12 and 13 leads to a binding to C, NG binds to T, NI binds to A, NN binds to A or G, and NG binds to T. The DNA binding repeats can be engineered into proteins to make artificial transcription factors.

DNA binding proteins such as ZFPs and TALEs can be designed or engineered to possess DNA sequence-specific binding. Many computational tools are available to predict and design ZFPs that bind to specific target sequences. Zinc Finger Tools, for example, employs a non-redundant set of helices that target defined DNA trinucleotides (Mandell and Barbas. 2006. Nucleic Acids Res. 34(Web Server issue): W516-23). Rational design of TALEs can also be performed (see, eg, US Publication No. 20110301073). Selection of DNA binding proteins such as ZFPs and TALEs typically comprises an empirical process such as phage display, interaction trap or hybrid selection. Those skilled in the art will be aware of other classes of DNA binding proteins that may be used in accordance with the present disclosure.

As described herein, the DNA binding proteins of the present disclosure comprise, or are attached to, a transcriptional activation domain and may be administered to a cell or to a subject to increase expression of Klotho. It will be understood that the DNA binding proteins (and the transcriptional activation domains) of the present disclosure can be administered to the cell or to the subject directly as a protein or indirectly as a nucleic acid. In either case, the DNA binding protein is considered to be administered to the cell or the subject. When administered in the form of a nucleic acid, the nucleic acid may be a RNA which is translated in the cell or the subject, or the nucleic acid may be a DNA which is transcribed and then translated in the cell or the subject. In preferred examples, the nucleic acid is carried on a viral vector such as an adeno-associated virus (AAV) vector.

The DNA binding proteins of the present disclosure bind to a target sequence within or near a Klotho gene and promote expression of the Klotho gene by way of its transcriptional activation domain. A target sequence will be considered "near" the Klotho gene if, despite not being located within the Klotho gene, the target sequence is sufficiently close to the Klotho gene such that when the target sequence is bound by a DNA binding protein of the present disclosure (including a transcriptional activation domain), expression of the Klotho gene is increased relative to an absence of such binding.

The target sequence may be located anywhere within or near the Klotho gene such that binding of a DNA binding protein comprising or attached to a transcriptional activation domain enhances transcription of Klotho. In some examples, the target sequence is located within a region between about 5 kb upstream of the Klotho translation start site and about 1 kb downstream of the Klotho translation start site (ie, a region of about 6 kb in length), or between about 5 kb upstream of the Klotho translation start site and about 500 nucleotides downstream of the Klotho translation start site. In certain examples, the target sequence is located within a region between the Klotho gene translation start site and about 5 kb upstream of the Klotho translation start site. In other words, the target sequence may be located within a window starting from the translation initiation site and extending 5 kb upstream. It will be understood that the target sequence may be located on either stand of DNA within this region. In some examples, the target sequence may be located within a region extending about 4.5 kb upstream of the Klotho translation start site, or about 4 kb upstream of the Klotho translation start site, or about 3.5 kb upstream of the Klotho translation start site, or about 3 kb upstream of the Klotho translation start site, or about 2.5 kb upstream of the Klotho translation start site, or about 2 kb upstream of the Klotho translation start site, or about 1.5 kb upstream of the Klotho translation start site, or about 1 kb upstream of the Klotho translation start site, or about 0.5 kb upstream of the Klotho translation start site. In certain examples, the target sequence is located within a region between about 10 nucleotides and 5000 nucleotides upstream of the Klotho translation start site; that is, the target sequence may be located within a window which starts about 10 nucleotides upstream of the Klotho gene translation start site and extends to a point about 5000 nucleotides upstream of the Klotho gene translation start site. In some examples, the target sequence is located within a region between about 15 nucleotides and 5000 nucleotides upstream of the Klotho translation start site, or within a region between about 20 nucleotides and 5000 nucleotides upstream of the Klotho translation start site, or within a region between about 20 nucleotides and 4500 nucleotides upstream of the Klotho translation start site, or within a region between about 20 nucleotides and 4000 nucleotides upstream of the Klotho translation start site, or within a region between about 20 nucleotides and 3500 nucleotides upstream of the Klotho translation start site, or within a region between about 20 nucleotides and 3000 nucleotides upstream of the Klotho translation start site, or within a region between about 20 nucleotides and 2500 nucleotides upstream of the Klotho translation start site, or within a region between about 20 nucleotides and 2000 nucleotides upstream of the Klotho translation start site, or within a region between about 20 nucleotides and 1500 nucleotides upstream of the Klotho translation start site, or within a region between about 20 nucleotides and 1000 nucleotides upstream of the Klotho translation start site, or within a region between about 20 nucleotides and 500 nucleotides upstream of the Klotho translation start site, within a region between about 20 nucleotides and 300 nucleotides upstream of the Klotho translation start site, within a region between about 30 nucleotides and 300 nucleotides upstream of the Klotho translation start site, within a region between about 40 nucleotides and 300 nucleotides upstream of the Klotho translation start site, or within a region between about 50 nucleotides and 300 nucleotides upstream of the Klotho translation start site.

In certain examples, the target sequence is located within a regulatory element of the Klotho gene such as a promoter or an enhancer. Expression of eukaryotic protein-coding genes generally is regulated through multiple cis-acting transcription-control regions. Some control elements are located close to the start site (promoter-proximal elements), whereas others lie more distal (enhancers and silencers). Promoters determine the site of transcription initiation and direct binding of RNA polymerase II. They may extend a few hundred base pairs to several kilobases upstream of a transcription start site. Enhancers may be 100 to 200 base pairs in length and may be located a hundred base pairs up to tens of kilobases upstream or down stream of a promoter. Promoters of highly expressed genes often comprise a TATA box. CpG islands are characteristic of transcribed genes.

For the purposes of the present disclosure, a target sequence will be considered "within" a region if it is entirely within that region or partially within that region. For example, the target sequence may be located entirely within a region between 40 nucleotides and 300 nucleotides upstream of the Klotho gene translation start site, or alternatively, only a part of the target sequence may be located within that region. In either case, the target sequence is deemed to be "within" a region between 40 nucleotides and 300 nucleotides upstream of the Klotho gene translation start site.

The target sequence is preferably less than about 100 nucleotides in length such as less than about 75 nucleotides in length such as between about 6 nucleotides and 60 nucleotides, or between about 6 nucleotides and 54 nucleotides, or between about 6 nucleotides and 45 nucleotides, or between about 6 nucleotides and 42 nucleotides, or between about 6 nucleotides and 39 nucleotides, or between about 6 nucleotides and 36 nucleotides, or between about 6 nucleotides and 33 nucleotides, or between about 6 nucleotides and 30 nucleotides, or between about 9 nucleotides and 30 nucleotides, such as about 9 nucleotides, or about 12 nucleotides, or about 15 nucleotides, or about 18 nucleotides, or about 21 nucleotides, or about 24 nucleotides, or about 27 nucleotides, or about 30 nucleotides.

In some examples, the DNA binding protein of the present disclosure binds to a target sequence comprising: the sequence set forth in SEQ ID NO. 60; the sequence set forth in SEQ ID NO. 61; or the sequence set forth in SEQ ID NO. 62. In some examples, the DNA binding protein of the present disclosure binds to a target sequence comprising at least 6 contiguous nucleotides, at least 7 contiguous nucleotides, at least 8 contiguous nucleotides, at least 9 contiguous nucleotides, at least 10 contiguous nucleotides, at least 11 contiguous nucleotides, at least 12 contiguous nucleotides, at least 13 contiguous nucleotides, at least 14 contiguous nucleotides, at least 15 contiguous nucleotides, at least 16 contiguous nucleotides, at least 17 contiguous nucleotides, or at least 18 contiguous nucleotides from: a sequence set forth in SEQ ID NO. 63; a sequence set forth in SEQ ID NO. 64; a sequence set forth in SEQ ID NO. 65; a sequence set forth in SEQ ID NO. 66; a sequence set forth in SEQ ID NO. 67; a sequence set forth in SEQ ID NO. 68; a sequence set forth in SEQ ID NO. 69; or a sequence set forth in SEQ ID NO. 70. Preferably, the target sequence comprises: a sequence set forth in SEQ ID NO. 63 or a sequence having at least about 70% identity, or at least about 75% identity, or at least about 80% identity, or at least about 85% identity, or at least about 90% identity, or at least about 95% identity or at least about 99% identity to SEQ ID NO. 63; a sequence set forth in SEQ ID NO. 64 or a sequence having at least about 70% identity, or at least about 75% identity, or at least about 80% identity, or at least about 85% identity, or at least about 90% identity, or at least about 95% identity or at least about 99% identity to SEQ ID NO. 64; a sequence set forth in SEQ ID NO. 65, or a sequence having at least about 70% identity, or at least about 75% identity, or at least about 80% identity, or at least about 85% identity, or at least about 90% identity, or at least about 95% identity or at least about 99% identity to SEQ ID NO. 65; a sequence set forth in SEQ ID NO. 66, or a sequence having at least about 70% identity, or at least about 75% identity, or at least about 80% identity, or at least about 85% identity, or at least about 90% identity, or at least about 95% identity or at least about 99% identity to SEQ ID NO. 66; a sequence set forth in SEQ ID NO. 67, or a sequence having at least about 70% identity, or at least about 75% identity, or at least about 80% identity, or at least about 85% identity, or at least about 90% identity, or at least about 95% identity or at least about 99% identity to SEQ ID NO. 67; a sequence set forth in SEQ ID NO. 68, or a sequence having at least about 70% identity, or at least about 75% identity, or at least about 80% identity, or at least about 85% identity, or at least about 90% identity, or at least about 95% identity or at least about 99% identity to SEQ ID NO. 68; a sequence set forth in SEQ ID NO. 69, or a sequence having at least about 70% identity, or at least about 75% identity, or at least about 80% identity, or at least about 85% identity, or at least about 90% identity, or at least about 95% identity or at least about 99% identity to SEQ ID NO. 69; or a sequence set forth in SEQ ID NO. 70, or a sequence having at least about 70% identity, or at least about 75% identity, or at least about 80% identity, or at least about 85% identity, or at least about 90% identity, or at least about 95% identity or at least about 99% identity to SEQ ID NO. 70.

The frequency of off-target activity can be assessed relative to the frequency of on-target activity. In some cases, cells that have been correctly targeted at the desired locus can have a selective advantage relative to other cells. Illustrative, but non-limiting, examples of a selective advantage include the acquisition of attributes such as enhanced rates of replication, persistence, resistance to certain conditions, enhanced rates of successful engraftment or persistence in vivo following introduction into a patient, and other attributes associated with the maintenance or increased numbers or viability of such cells. In other cases, cells that have been correctly targeted at the desired locus can be positively selected for by one or more screening methods used to identify, sort or otherwise select for cells that have been correctly targeted.

In some examples, the present disclosure provides a method of increasing expression of a Klotho gene in a cell the method comprising administering to the cell a zinc finger protein comprising or attached to a transcriptional activation domain wherein the zinc finger protein binds to a target sequence within or near the Klotho gene and thereby increases expression of the Klotho gene, and wherein the zinc finger protein comprises: at least 2, such as at least 3, or at least 4, or at least 5 or 6 zinc fingers independently selected from a zinc finger comprising the sequence set forth in SEQ ID NO. 1, a zinc finger comprising the sequence set forth in SEQ ID NO. 2, a zinc finger comprising the sequence set forth in SEQ ID NO. 3, a zinc finger comprising the sequence set forth in SEQ ID NO. 4, a zinc finger comprising the sequence set forth in SEQ ID NO. 5 and a zinc finger comprising the sequence set forth in SEQ ID NO. 6; at least 2, such as at least 3, or at least 4, or at least 5, or at least 6, or at least 7, or at least 8, or at least 9 or 10 zinc fingers independently selected from a zinc finger comprising the sequence set forth in SEQ ID NO. 7, a zinc finger comprising the sequence set forth in SEQ ID NO. 8, a zinc finger comprising the sequence set forth in SEQ ID NO. 9, a zinc finger comprising the sequence set forth in SEQ ID NO. 10, a zinc finger comprising the sequence set forth in SEQ ID NO. 11, a zinc finger comprising the sequence set forth in SEQ ID NO. 12, a zinc finger comprising the sequence set forth in SEQ ID NO. 13, a zinc finger comprising the sequence set forth in SEQ ID NO. 14 and a zinc finger comprising the sequence set forth in SEQ ID NO. 6; at least 2, such as at least 3, or at least 4, or at least 5, or at least 6 or 7 zinc fingers independently selected from a zinc finger comprising the sequence set forth in SEQ ID NO. 15, a zinc finger comprising the sequence set forth in SEQ ID NO. 16, a zinc finger comprising the sequence set forth in SEQ ID NO. 17, a zinc finger comprising the sequence set forth in SEQ ID NO. 11 and a zinc finger comprising the sequence set forth in SEQ ID NO. 1; at least 2, such as at least 3, or at least 4, or at least 5, or at least 6 or 7 zinc fingers independently selected from a zinc finger comprising the sequence set forth in SEQ ID NO. 11, a zinc finger comprising the sequence set forth in SEQ ID NO. 1, a zinc finger comprising the sequence set forth in SEQ ID NO. 18, a zinc finger comprising the sequence set forth in SEQ ID NO. 16, a zinc finger comprising the sequence set forth in SEQ ID NO. 19 and a zinc finger comprising the sequence set forth in SEQ ID NO. 12; at least 2, such as at least 3, or at least 4, or at least 5, or at least 6 or 7 zinc fingers independently selected from a zinc finger comprising the sequence set forth in SEQ ID NO. 8, a zinc finger comprising the sequence set forth in SEQ ID NO. 16, a zinc finger comprising the sequence set forth in SEQ ID NO. 18, a zinc finger comprising the sequence set forth in SEQ ID NO. 8 and a zinc finger comprising the sequence set forth in SEQ ID NO. 3; at least 2, such as at least 3, or at least 4, or at least 5 or 6 zinc fingers independently selected from a zinc finger comprising the sequence set forth in SEQ ID NO. 17, a zinc finger comprising the sequence set forth in SEQ ID NO. 13 and a zinc finger comprising the sequence set forth in SEQ ID NO. 9; at least 2, such as at least 3, or at least 4, or at least 5 or 6 zinc fingers independently selected from a zinc finger comprising the sequence set forth in SEQ ID NO. 20, a zinc finger comprising the sequence set forth in SEQ ID NO. 21, a zinc finger comprising the sequence set forth in SEQ ID NO. 22, a zinc finger comprising the sequence set forth in SEQ ID NO. 19, a zinc finger comprising the sequence set forth in SEQ ID NO. 12 and a zinc finger comprising the sequence set forth in SEQ ID NO. 17; and/or at least 2, such as at least 3, or at least 4, or at least 5 or 6 zinc fingers independently selected from a zinc finger comprising the sequence set forth in SEQ ID NO. 20, a zinc finger comprising the sequence set forth in SEQ ID NO. 21, a zinc finger comprising the sequence set forth in SEQ ID NO. 22, a zinc finger comprising the sequence set forth in SEQ ID NO. 8, a zinc finger comprising the sequence set forth in SEQ ID NO. 3 and a zinc finger comprising the sequence set forth in SEQ ID NO. 9.

In some examples, the present disclosure provides a method of increasing expression of a Klotho gene in a cell the method comprising administering to the cell a zinc finger protein comprising or attached to a transcriptional activation domain wherein the zinc finger protein binds to a target sequence within or near the Klotho gene and thereby increases expression of the Klotho gene, and wherein the zinc finger protein comprises:

a ZF1 zinc finger comprising the sequence set forth in SEQ ID NO. 1, a ZF2 zinc finger comprising the sequence set forth in SEQ ID NO. 2, a ZF3 zinc finger comprising the sequence set forth in SEQ ID NO. 3, a ZF4 zinc finger comprising the sequence set forth in SEQ ID NO. 4, a ZF5 zinc finger comprising the sequence set forth in SEQ ID NO. 5 and a ZF6 zinc finger comprising the sequence set forth in SEQ ID NO. 6;

a ZF1 zinc finger comprising the sequence set forth in SEQ ID NO. 7, a ZF2 zinc finger comprising the sequence set forth in SEQ ID NO. 8, a ZF3 zinc finger comprising the sequence set forth in SEQ ID NO. 9, a ZF4 zinc finger comprising the sequence set forth in SEQ ID NO. 7, a ZF5 zinc finger comprising the sequence set forth in SEQ ID NO. 10, a ZF6 zinc finger comprising the sequence set forth in SEQ ID NO. 11, a ZF7 zinc finger comprising the sequence set forth in SEQ ID NO. 12, a ZF8 zinc finger comprising the sequence set forth in SEQ ID NO. 13, a ZF9 zinc finger comprising the sequence set forth in SEQ ID NO. 14 and a ZF10 zinc finger comprising the sequence set forth in SEQ ID NO. 6;

a ZF1 zinc finger comprising the sequence set forth in SEQ ID NO. 15, a ZF2 zinc finger comprising the sequence set forth in SEQ ID NO. 16, a ZF3 zinc finger comprising the sequence set forth in SEQ ID NO. 17, a ZF4 zinc finger comprising the sequence set forth in SEQ ID NO. 16, a ZF5 zinc finger comprising the sequence set forth in SEQ ID NO. 11, a ZF6 zinc finger comprising the sequence set forth in SEQ ID NO. 11 and a ZF7 zinc finger comprising the sequence set forth in SEQ ID NO. 1;

a ZF1 zinc finger comprising the sequence set forth in SEQ ID NO. 11, a ZF2 zinc finger comprising the sequence set forth in SEQ ID NO. 1, a ZF3 zinc finger comprising the sequence set forth in SEQ ID NO. 18, a ZF4 zinc finger comprising the sequence set forth in SEQ ID NO. 16, a ZF5 zinc finger comprising the sequence set forth in SEQ ID NO. 11, a ZF6 zinc finger comprising the sequence set forth in SEQ ID NO. 19 and a ZF7 zinc finger comprising the sequence set forth in SEQ ID NO. 12;

a ZF1 zinc finger comprising the sequence set forth in SEQ ID NO. 8, a ZF2 zinc finger comprising the sequence set forth in SEQ ID NO. 16, a ZF3 zinc finger comprising the sequence set forth in SEQ ID NO. 18, a ZF4 zinc finger comprising the sequence set forth in SEQ ID NO. 16, a ZF5 zinc finger comprising the sequence set forth in SEQ ID NO. 3, a ZF6 zinc finger comprising the sequence set forth in SEQ ID NO. 8 and a ZF7 zinc finger comprising the sequence set forth in SEQ ID NO. 3;

a ZF1 zinc finger comprising the sequence set forth in SEQ ID NO. 17, a ZF2 zinc finger comprising the sequence set forth in SEQ ID NO. 13, a ZF3 zinc finger comprising the sequence set forth in SEQ ID NO. 13, a ZF4 zinc finger comprising the sequence set forth in SEQ ID NO. 9, a ZF5 zinc finger comprising the sequence set forth in SEQ ID NO. 17 and a ZF6 zinc finger comprising the sequence set forth in SEQ ID NO. 9;

a ZF1 zinc finger comprising the sequence set forth in SEQ ID NO. 20, a ZF2 zinc finger comprising the sequence set forth in SEQ ID NO. 21, a ZF3 zinc finger comprising the sequence set forth in SEQ ID NO. 22, a ZF4 zinc finger comprising the sequence set forth in SEQ ID NO. 19, a ZF5 zinc finger comprising the sequence set forth in SEQ ID NO. 12 and a ZF6 zinc finger comprising the sequence set forth in SEQ ID NO. 17; or a ZF1 zinc finger comprising the sequence set forth in SEQ ID NO. 20, a ZF2 zinc finger comprising the sequence set forth in SEQ ID NO. 21, a ZF3 zinc finger comprising the sequence set forth in SEQ ID NO. 22, a ZF4 zinc finger comprising the sequence set forth in SEQ ID NO. 8, a ZF5 zinc finger comprising the sequence set forth in SEQ ID NO. 3 and a ZF6 zinc finger comprising the sequence set forth in SEQ ID NO. 9.

In some examples, the present disclosure provides a method of increasing expression of a Klotho gene in a cell the method comprising administering to the cell a zinc finger protein comprising or attached to a transcriptional activation domain wherein the zinc finger protein binds to a target sequence within or near the Klotho gene and thereby increases expression of the Klotho gene, and wherein the target sequence is located within a region between the Klotho gene translation start site and 4000 nucleotides upstream of the Klotho gene translation start site, such as within a region between 40 nucleotides and 300 nucleotides upstream of the Klotho gene translation start site. In some examples, the present disclosure provides a method of increasing expression of a Klotho gene in a cell the method comprising administering to the cell a zinc finger protein comprising or attached to a transcriptional activation domain wherein the zinc finger protein binds to a target sequence within or near the Klotho gene and thereby increases expression of the Klotho gene, and wherein the target sequence comprises at least 9 contiguous nucleotides from: a sequence set forth in SEQ ID NO. 63; a sequence set forth in SEQ ID NO. 64; a sequence set forth in SEQ ID NO. 65; a sequence set forth in SEQ ID NO. 66; a sequence set forth in SEQ ID NO. 67; a sequence set forth in SEQ ID NO. 68; a sequence set forth in SEQ ID NO. 69; or a sequence set forth in SEQ ID NO. 70.

In some examples, the present disclosure provides a DNA binding protein which competes for binding to a target sequence with a DNA binding protein described herein.

Those skilled in the art will understand that it is possible to determine, without undue burden or experimentation, if a DNA binding protein has the same or similar target sequence specificity as a DNA binding protein described herein by ascertaining whether the former prevents the latter from binding to the target sequence. If the DNA binding protein being tested competes with a DNA binding protein described herein, then the two DNA binding proteins bind to the same, similar, overlapping or adjacent target sequences. In some examples, the DNA binding protein competes for binding to a target sequence with a DNA binding protein described herein by 10%, 20%, 30%, 40%, 50%, 60%, 70%, 80%, 90%, 99% or more. In some examples, the DNA binding protein of the present disclosure competes for binding with a zinc finger protein comprising or consisting of the sequence set forth in SEQ ID NO. 29; SEQ ID NO. 30; SEQ ID NO. 32; SEQ ID NO. 33; SEQ ID NO. 34; SEQ ID NO. 36; SEQ ID NO. 37; or SEQ ID NO. 39. DNA binding may be assayed, for example, by filter-binding, chemiluminescent, electrophoretic mobility-shift, immunoprecipitation or DNA-binding enzyme-linked immunosorbent assays. Those skilled in the art will be aware of other methods by which competitive DNA binding can be assayed.

In some examples, the present disclosure provides a method of increasing expression of a Kotho gene in a cell the method comprising administering to the cell a DNA binding protein of the present disclosure wherein the DNA binding protein binds to a target sequence within or near the Klotho gene and thereby increases expression of the Klotho gene, wherein the DNA binding protein competes for binding to the target sequence with a zinc finger protein comprising or consisting of the sequence set forth in SEQ ID NO. 29; SEQ ID NO. 30; SEQ ID NO. 32; SEQ ID NO. 33; SEQ ID NO. 34; SEQ ID NO. 36; SEQ ID NO. 37; or SEQ ID NO. 39. It will be understood that in such examples, although the DNA binding protein and the zinc finger protein would compete for binding to the target sequence when both proteins are present together with the target sequence, the method need not include active competition between the DNA binding protein and the zinc finger protein.

Sequences

Table 2 sets forth DNA recognition sequences of zinc fingers that are relevant to the present disclosure.

TABLE 2

Zinc finger DNA recognition sequences.

| ZFP ID | ZF1 | ZF2 | ZF3 | ZF4 | ZF5 |
| --- | --- | --- | --- | --- | --- |
| ZFP1 | DPGHLVR (SEQ ID NO. 1) | SKKALTE (SEQ ID NO. 2) | RNDALTE (SEQ ID NO. 3) | DPGALVR (SEQ ID NO. 4) | DSGNLRV (SEQ ID NO. 5) |
| ZFP52 | TKNSLTE (SEQ ID NO. 7) | QSGDLRR (SEQ ID NO. 8) | DCRDLAR (SEQ ID NO. 9) | TKNSLTE (SEQ ID NO. 7) | RTDTLRD (SEQ ID NO. 10) |
| ZFP1-Egr1-site1-sense | TSGNLTE (SEQ ID NO. 15) | RSDKLVR (SEQ ID NO. 16) | HTGHLLE (SEQ ID NO. 17) | RSDKLVR (SEQ ID NO. 16) | RSDDLVR (SEQ ID NO. 11) |
| ZFP2-Egr1-site2-sense | RSDDLVR (SEQ ID NO. 11) | DPGHLVR (SEQ ID NO. 1) | RSDELVR (SEQ ID NO. 18) | RSDKLVR (SEQ ID NO. 16) | RSDDLVR (SEQ ID NO. 11) |
| ZFP3-Egr1-site3-antisense | QSGDLRR (SEQ ID NO. 8) | RSDKLVR (SEQ ID NO. 16) | RSDELVR (SEQ ID NO. 18) | RSDKLVR (SEQ ID NO. 16) | RNDALTE (SEQ ID NO. 3) |
| ZFP4-Egr1-site1-antisense | HTGHLLE (SEQ ID NO. 17) | RNDTLTE (SEQ ID NO. 13) | RNDTLTE (SEQ ID NO. 13) | DCRDLAR (SEQ ID NO. 9) | HTGHLLE (SEQ ID NO. 17) |

TABLE 2-continued

Zinc finger DNA recognition sequences.

| | | | | | |
|---|---|---|---|---|---|
| Egr1-insert-site2 | RSDELTR (SEQ ID NO. 20) | RSDHLTT (SEQ ID NO. 21) | RSDERKR (SEQ ID NO. 22) | QRAHLER (SEQ ID NO. 19) | RSDKLTE (SEQ ID NO. 12) |
| Egr1-insert-site3 | RSDELTR (SEQ ID NO. 20) | RSDHLTT (SEQ ID NO. 21) | RSDERKR (SEQ ID NO. 22) | QSGDLRR (SEQ ID NO. 8) | RNDALTE (SEQ ID NO. 3) |

| ZFP ID | ZF6 | ZF7 | ZF8 | ZF9 | ZF10 |
|---|---|---|---|---|---|
| ZFP1 | QSGHLTE (SEQ ID NO. 6) | | | | |
| ZFP52 | RSDDLVR (SEQ ID NO. 11) | RSDKLTE (SEQ ID NO. 12) | RNDTLTE (SEQ ID NO. 13) | SRRTCRA (SEQ ID NO. 14) | QSGHLTE (SEQ ID NO. 6) |
| ZFP1-Egr1-site1-sense | RSDDLVR (SEQ ID NO. 11) | DPGHLVR (SEQ ID NO. 1) | | | |
| ZFP2-Egr1-site2-sense | QRAHLER (SEQ ID NO. 19) | RSDKLTE (SEQ ID NO. 12) | | | |
| ZFP3-Egr1-site3-antisense | QSGDLRR (SEQ ID NO. 8) | RNDALTE (SEQ ID NO. 3) | | | |
| ZFP4-Egr1-site1-antisense | DCRDLAR (SEQ ID NO. 9) | | | | |
| Egr1-insert-site2 | HTGHLLE (SEQ ID NO. 17) | | | | |
| Egr1-insert-site3 | DCRDLAR (SEQ ID NO. 9) | | | | |

Table 3 lists sequences of zinc finger proteins and related sequences that are relevant to the present disclosure.

TABLE 3

Zinc finger proteins and related sequences.

| SEQ ID NO. | Description | Sequence |
|---|---|---|
| 29 | ZFP1<br>•Zinc finger DNA recognition sequences underlined<br>•NLS lower case<br>•VP64 bold<br>•HA tag italics | MAQAALEPGEKPYKCPECGKSFSDPGHLVRHQRTHTGEKPYKCPECGKSFSS KKALTEHQRTHTGEKPYKCPECGKSFSRNDALTEHQRTHTGEKPYKCPECGK SFSDPGALVRHQRTHTGEKPYKCPECGKSFSDSGHLRVHQRTHTGEKPYKCP ECGKSFSQSGHLTEHQRTHTGKKTSQAGQASpkkrkvGRADALDDFDLDML GSDALDDFDLDMLGSDALDDFDLDMLGSDALDDFDLDMLINYPYDVPDYAS |
| 30 | ZFP52<br>•Zinc finger DNA recognition sequences underlined<br>•NLS lower case<br>•VP64 bold<br>•HA tag italics | MAQAALEPGEKPYKCPECGKSFSTKNSLTEHQRTHTGEKPYKCPECGKSFSQ SGDLRRHQRTHTGEKPYKCPECGKSFSDCRDLARHQRTHTGEKPYKCPECG KSFSTKNSLTEHQRTHTGEKPYKCPECGKSFSRTDFLRDHQRTHTGEKPYKC PECGKSFSRSDDLVRHQRTHTGEKPYKCPECGKSFSRSDKLTEHQRTHTGEK PYKCPECGKSFSRNDTLTEHQRTHTGEKPYKCPECGKSFSSRRTCRAHQRTH TGEKPYKCPECGKSFSQSGHLTEHQRTHTGKKTSQAGQASpkkrkvGRADA LDDFDLDMLGSDALDDFDLDMLGSDALDDFDLDMLGSDALDDFDLDMLINYP YDVPDYAS |
| 31 | ZFP52_VPR<br>•Zinc finger DNA recognition sequences underlined<br>•NLS lower case and underlined<br>•HA tag italics<br>•VP64 bold<br>•p65 lower case<br>•Rta italics and underlined<br>•V5 lower case and bold<br>•His tag italics and bold | MAQAALEPGEKPYKCPECGKSFSTKNSLTEHQRTHTGEKPYKCPECGKSFSQ SGDLRRHQRTHTGEKPYKCPECGKSFSDCRDLARHQRTHTGEKPYKCPECG KSFSTKNSLTEHQRTHTGEKPYKCPECGKSFSRTDFLRDHQRTHTGEKPYKC PECGKSFSRSDDLVRHQRTHTGEKPYKCPECGKSFSRSDKLTEHQRTHTGEK PYKCPECGKSFSRNDTLTEHQRTHTGEKPYKCPECGKSFSSRRTCRAHQRTH TGEKPYKCPECGKSFSQSGHLTEHQRTHTGKKTSQAGQASpkkrkvGRADA LDDFDLDMLGSDALDDFDLDMLGSDALDDFDLDMLGSDALDDFDLDMLINYP YDVPDYASssGspkkkrkvGsgylpdtddrhrieekrkrtyetfksimkspfsgptdprppprriavpsr ssasvpkapqpypftsslstinydefptmvfpsgqisqaaalapappvlpqapapamvsalaqap apvpvlapgppqavappkptqagegtlseallqfdededigallgnstdpavftdlasvdnsefqqllnqgip vaphttepmlmeypeaitrlrvtgaqrppdpapapigapglpngllsgdedfssiadmdfsallGSGSGSR *DSREGMFLPKPEAGSAISDVFEGREVCQPKRIRPFHPPGSPWANRPLPASLAP* *TPTGPVHEPVGSLTPAPVPQPLDPAPAVTPEASHLLEDPDEETSQAVKALREM* *ADTVIPQKEEAAICGQMDLSHPPPRGHLDELTTTLESMTEDLNLDSPLTPELNEI* *LDTFLNDECLLHAMHISTGLSIFDTSLFDSSLEGPRPFE*gkpipnpllgldstRTG***HHH* *HHH* |
| 32 | ZFP1_Egr1_site1_sense<br>•Zinc finger DNA recognition sequences underlined<br>•NLS lower case<br>•VP64 bold<br>•HA tag italics | MAQAALEPGEKPYKCPECGKSFSTGHLTEHQRTHTGEKPYKCPECGKSFSR SDKLVRHQRTHTGEKPYKCPECGKSFSHTGHLLEHQRTHTGEKPYKCPECGK SFSRSDLVRHQRTHTGEKPYKCPECGKSFSRSDDLVRHQRTHTGEKPYKCP ECGKSFSRSDKLVRHQRTHTGEKPYKCPECGKSFSDPGHLVRHQRTHTGKKT SGQAGQASpkkrkvGRADALDDFDLDMLGSDALDDFDLDMLGSDALDDFDLD MLGSDALDDFDLDMLINYPYDVPDYAS |
| 33 | ZFP2_Egr1_site2_sense<br>•Zinc finger DNA recognition sequences | MAQAALEPGEKPYKCPECGKSFSDPGHLVRHQRTHTGEKPYKCPECGKSFSD PGHLVRHQRTHTGEKPYKCPECGKSFSRSDELVRHQRTHTGEKPYKCPECGK SFSRSDKLVRHQRTHTGEKPYKCPECGKSFSRSDDLVRHQRTHTGEKPYKCP |

TABLE 3-continued

Zinc finger proteins and related sequences.

| SEQ ID NO. | Description | Sequence |
|---|---|---|
| 34 | ZFP3_Egr1_site3_antisense<br>•Zinc finger DNA recognition sequences underlined<br>•NLS lower case<br>•VP64 bold<br>•HA tag italics | MAQAALEPGEKPYKCPECGKSFSQSGDLRRHQRTHTGEKPYKCPECGKSFS<br>RSDKLVRHQRTHTGEKPYKCPECGKSFSQSGDLRRHQRTHTGEKPYKCPECG<br>KSFSRSDKLVRHQRTHTGEKPYKCPECGKSFSRNDALTEHQRTHTGEKPYKC<br>PECGKSFSQSGDLRRHQRTHTGEKPYKCPECGKSFSRNDALTEHQRTHTGKK<br>TSGQAGQASpkkkrkvGRADALDDFDLDMLGSDALDDFDLDMLGSDALDDFDL<br>DMLGSDALDDFDLDML*INYPYDVPDYAS* |
| 35 | ZFP3_Egr1_site3_antisense_VPR<br>•Zinc finger DNA recognition sequences underlined<br>•NLS lower case<br>•VP64 bold<br>•HA tag italics<br>•p65 lower case<br>•Rta italics and underlined<br>•V5 lower case and bold<br>•His tag italics and bold | MAQAALEPGEKPYKCPECGKSFSQSGDLRRHQRTHTGEKPYKCPECGKSFS<br>RSDKLVRHQRTHTGEKPYKCPECGKSFSQSGDLRRHQRTHTGEKPYKCPECG<br>KSFSRSDKLVRHQRTHTGEKPYKCPECGKSFSRNDALTEHQRTHTGEKPYKC<br>PECGKSFSQSGDLRRHQRTHTGEKPYKCPECGKSFSRNDALTEHQRTHTGKK<br>TSGQAGQASpkkkrkvGRADALDDFDLDMLGSDALDDFDLDMLGSDALDDFDL<br>DMLGSDALDDFDLDML*INYPYDVPDYAS*sGSGSGSpkkkrkvGsqylpdtddrhrieekrkrtye<br>tfksimkksgpfsgptdprpprriavtpsrssasvpkpapqpypftsslstinydefptmvfpsgqisqasalapa<br>ppqvlpgapapapamvsalaqapavpvlapgppgavappapkptqagegtlseallqlqfddedlgail<br>gnstdpavftdlasvdnsefqgllnggipvaphttepmlmeypeaitrlvtgaqrppdpapaplgapglpnglls<br>gdedfssiadmdfsallGSGSGSRDSREGMFLPKPEAGSAISDVFEGREVCQPKRIRP<br>FHPPGSPWANRPLPASLAPTPTGPVHEPVGSLTPAPVPQPLDPAPAVTPEASH<br>LLEDPDEETSQAVKALREMADTVIPGKEEAAICGQMDLSHPPPRGHLDELTTTL<br>*ESMTEDLNDSPLTPELNEILDTFLNDECLLHAMHISTGLSIFDTSLFDSSLEGPR*<br>*FEgkpipnpllgldstRTGHHHHHH* |
| 36 | ZFP4_Egr1_site1_antisense<br>•Zinc finger DNA recognition sequences underlined<br>•NLS lower case<br>•VP64 bold<br>•HA tag italics | MAQAALEPGEKPYKCPECGKSFSHTGHLLEHQRTHTGEKPYKCPECGKSFSR<br>NDTLTEHQRTHTGEKPYKCPECGKSFSRNDTLTEHQRTHTGEKPYKCPECGK<br>SFSDCRDLARHQRTHTGEKPYKCPECGKSFSHTGHLLEHQRTHTGEKPYKCP<br>ECGKSFSDCRDLARHQRTHTGKKTSGQAGQASpkkkrkvGRADALDDFDLDML<br>GSDALDDFDLDMLGSDALDDFDLDML*INYPYDVPDYAS* |
| 37 | Egr1_insert_site2<br>•Zinc finger DNA recognition sequences underlined<br>•Repressor domain bold | MAAAKAEMQLMSPLQISDPFGSFPHSPTMDNYPKLEEMMLLSNGAPQFLGAA<br>GAPEGSGSNSSSSSSGGGGGGSNSSSSSTFNPQADTGEQPYEHLTAE<br>SFPDISLNNEKVLVETSYPSQTTRLPPITVTGRFSLEPAPNSGHTLWPEPLFSLV<br>SGLVSMTNPPASSSSAPSPAASSASASASQSPPLSCAVPSNDSSPIYSAAPTFPT<br>PNTDIFPEPQSQAAFPGSAGTALQYPPPAYPAAKGGPQVPMIDYLFPQQQDL<br>GLGTFIDQKFFQGLESRTQQPSLTPLSTIKAFATQSGSGSQDLKALNTSYQSQLIK<br>PSRMRKYPNRPSKTPHERPYACPVESCDRRFSRSDELTRHIRIHTGQKPFQC<br>RICMRNFSRSDHLTTHIRTHTGEKPFACDICGRKFARSDERKRHTKIHTGQKPC<br>PVESCDRRFSQRAHLERHIRIHTGQKPFQCRICMRNFSRSDKLTEHIRTHGEK<br>PFACDICGRKFAHTGHLLEHTKIHLRQKDKKADKSVVASSATSSLSSYPSPVAT |

TABLE 3-continued

Zinc finger proteins and related sequences.

| SEQ ID NO. | Description | Sequence |
|---|---|---|
| 38 | Egr1_insert_site2_RR •Zinc finger DNA recognition sequences underlined | SYPSPVTTSYPSPATTSYPSPVPTSFSSPGSSTYPSPVHSGFPSPVATTYSSV PPAFPAQVSSFPSSAVTNSFSASTGLSDMTATFSPRTIEIC |
| | | MAAAKAEMQLMSPLQISDPFGSFPHSPTMDNYPKLEEMMLLSNGAPQFLGAA GAPEGSGSNSSSSSGGGGGGSNSSSSSSTFNPQADTGEQPYEHLTAE SFPDISLNNEKVLVETSYPSQTTRLPPITYTGRFSLEPAPNSGHTLWPEPLFSLV SGLVSMTNPPASSSSAPSPAASSASASQSPPLSCAVPSNDSSPIYSAAPTFPT PNTDIFPEPQSQAFPGSAGTALQYPPPAYPAAKGGFQVPMIPDYLFPQQQGDL GLGTPDQKPFQGLESRLIKPSRMRKYPNRPSKTPPHERPYACPVESCDRRFS RSDELTRHIRIHTGQKPFQCRICMRNFSRSDHLTTHIRTHTGEKPFACDICGRK FARSDERKRHTKIHTGQKPCPVESCDRRFSQRAHLERHIRIHTGQKPFQCRIC MRNFSRSDKLTEHIRTHTGEKPFACDICGRKFPAHTGHLLEHTKIHLRQKDKKAD KSVVASSATSSLSSYPSPVATSYPSPVTTSYPSPVPTSFSSPGSST YPSPVHSGFPSPVATTYSSVPPAFPAQVSSFPSSAVTNSFSASTGLSDMTAT FSPRTIEIC |
| 39 | Egr1_insert_site3 •Zinc finger DNA recognition sequences underlined •Repressor domain bold | MAAAKAEMQLMSPLQISDPFGSFPHSPTMDNYPKLEEMMLLSNGAPQFLGAA GAPEGSGSNSSSSSGGGGGGSNSSSSSSTFNPQADTGEQPYEHLTAE SFPDISLNNEKVLVETSYPSQTTRLPPITYTGRFSLEPAPNSGHTLWPEPLFSLV SGLVSMTNPPASSSSAPSPAASSASASQSPPLSCAVPSNDSSPIYSAAPTFPT PNTDIFPEPQSQAFPGSAGTALQYPPPAYPAAKGGFQVPMIPDYLFPQQQGDL GLGTFIDQKFFQGLESRTQQPSLTPLSTIKAFATQGSGQDLKALNTSYQSQLIK PSRMRKYPNRPSKTPHERPYACPVESCDRRFSRSDELTRHIRIHTGQKPFQC RICMRNFSRSDHLTTHIRTHTGEKPFACDICGRKFARSDERKRHTKIHCPVESC DRRFSQSGDLRRHIRIHTGQKPFQCRICMRNFSRNDALTEHIRTHTGEKPFAC DICGRKFADCRDLARHTKIHLRQKDKKADKSVVASSATSSLSSYPSPVATSYPS PVTTSYPSPATTSYPSPVPTSFSSPGSSTYPSPVHSGFPSPVATTYSSVPPAF PAQVSSFPSSAVTNSFSASTGLSDMTATFSPRTIEIC |
| 40 | Egr1_insert_site3_RR •Zinc finger DNA recognition sequences underlined | MAAAKAEMQLMSPLQISDPFGSFPHSPTMDNYPKLEEMMLLSNGAPQFLGAA GAPEGSGSNSSSSSGGGGGGSNSSSSSSTFNPQADTGEQPYEHLTAE SFPDISLNNEKVLVETSYPSQTTRLPPITYTGRFSLEPAPNSGHTLWPEPLFSLV SGLVSMTNPPASSSSAPSPAASSASASQSPPLSCAVPSNDSSPIYSAAPTFPT PNTDIFPEPQSQAFPGSAGTALQYPPPAYPAAKGGFQVPMIPDYLFPQQQGDL GLGTPDQKPFQGLESRLIKPSRMRKYPNRPSKTPPHERPYACPVESCDRRFS RSDELTRHIRIHTGQKPFQCRICMRNFSRSDHLTTHIRTHTGEKPFQCRICMRNFS RNDALTEHIRTHTGEKPFACDICGRKFADCRDLARHTKIHLRQKDKKADKSVVA SSATSSLSSYPSPVTTSYPSPATTSYPSPVPTSFSSPGSSTYPSPV HSGFPSPVATTYSSVPPAFPAQVSSFPSSAVTNSFSASTGLSDMTATFSPRTI EIC |
| 41 | ZFP1 ZF domain •N-terminal fixed region lower case bold •N-terminal backbone bold | lepgekpYKCPECGKSFSDPGHLVR*HQRTH*gekpYKCPECGKSFSSKKALTEH *QRTH*tgekpYKCPECGKSFSRNDALTEH*QRTH*tgekpYKCPECGKSFSDPGALV R*HQRTH*tgekpYKCPECGKSFSDSGHLRVH*QRTH*tgekpYKCPECGKSFSQSGH <u>LTEHQRTH</u>tgkkts |

TABLE 3-continued

Zinc finger proteins and related sequences.

| SEQ ID NO. | Description | Sequence |
|---|---|---|
| 42 | • Zinc finger DNA recognition sequences underlined<br>• C-terminal backbone italics<br>• Zinc finger linker lower case<br>• C-terminal fixed region lower case underlined<br><br>ZFP52 ZF domain<br>• N-terminal fixed region lower case bold<br>• N-terminal backbone bold<br>• Zinc finger DNA recognition sequences underlined<br>• C-terminal backbone italics<br>• Zinc finger linker lower case<br>• C-terminal fixed region lower case underlined | lepgekpYKCPECGKSFSTKNSLTEHQRTHtgekpYKCPECGKSFSDCRDLARHQRTHtgekpYKCPECGKSFSQSGDLRRH<br>QRTHtgekpYKCPECGKSFSDCRDLARHQRTHtgekpYKCPECGKSFSTKNSLT<br>EHQRTHtgekpYKCPECGKSFSRTDTLRDHQRTHtgekpYKCPECGKSFSRSDD<br>LVRHQRTHtgekpYKCPECGKSFSRSDKLTEHQRTHtgekpYKCPECGKSFSRN<br>DTLTEHQRTHtgekpYKCPECGKSFSSSRRTCRAHQRTHtgekpYKCPECGKSFS<br>QSGHLTEHQRTHgktts |
| 43 | ZFP1_Egr1_site1_sense ZF domain<br>• N-terminal fixed region lower case bold<br>• N-terminal backbone bold<br>• Zinc finger DNA recognition sequences underlined<br>• C-terminal backbone italics<br>• Zinc finger linker lower case<br>• C-terminal fixed region lower case underlined | lepgekpYKCPECGKSFSTSGHLTEHQRTHTGEKPYKCPECGKSFSRSDKLVR<br>HQRTHtgekpYKCPECGKSFSHTGHLLEHQRTHtgekpYKCPECGKSFSRSDKL<br>VRHQRTHtgekpYKCPECGKSFSRSDDLVRHQRTHtgekpYKCPECGKSFSRSD<br>DLVRHQRTHtgekpYKCPECGKSFSDPGHLVRHQRTHtgkkts |
| 44 | ZFP2_Egr1_site2_sense ZF domain<br>• N-terminal fixed region lower case bold<br>• N-terminal backbone bold | lepgekpYKCPECGKSFSRSDDLVRHQRTHtgekpYKCPECGKSFSDPGHLVRH<br>QRTHtgekpYKCPECGKSFSRSDELVRHQRTHtgekpYKCPECGKSFSRSDKLV<br>RHQRTHtgekpYKCPECGKSFSRSDDLVRHQRTHtgekpYKCPECGKSFSQRAH<br>LERHQRTHtgekpYKCPECGKSFSRSDKLTEHQRTHtgkkts |

TABLE 3-continued

Zinc finger proteins and related sequences.

| SEQ ID NO. | Description | Sequence |
|---|---|---|
| 45 | ZFP3_Egr1_site3_antisense ZF domain<br>•N-terminal fixed region lower case bold<br>•N-terminal backbone bold<br>•Zinc finger DNA recognition sequences underlined<br>•C-terminal backbone italics<br>•Zinc finger linker lower case<br>•C-terminal fixed region lower case underlined | lepgekpYKCPECGKSFSQ<u>SGDLRRH</u>QRTHtgekpYKCPECGKSFS<u>RSDKLVRH</u><br>QRTHtgekpYKCPECGKSFS<u>RSDELVRH</u>QRTHtgekpYKCPECGKSFS<u>RSDKLV</u><br>RH<u>QRTH</u>tgekpYKCPECGKSFS<u>RNDALTEH</u>QRTHtgekpYKCPECGKSFS<u>QSGD</u><br><u>LRRH</u>QRTHtgekpYKCPECGKSFS<u>RNDALTEH</u>QRTHtgkkts |
| 46 | ZFP4_Egr1_site1_antisense ZF domain<br>•N-terminal fixed region lower case bold<br>•N-terminal backbone bold<br>•Zinc finger DNA recognition sequences underlined<br>•C-terminal backbone italics<br>•Zinc finger linker lower case<br>•C-terminal fixed region lower case underlined | lepgekpYKCPECGKSFS<u>HTGHLLEH</u>QRTHgekpYKCPECGKSFS<u>RNDTLTEHQ</u><br>RTHtgekpYKCPECGKSFS<u>RNDTLTEH</u>QRTHtgekpYKCPECGKSFS<u>DCRDLAR</u><br>H<u>QRTH</u>tgekpYKCPECGKSFS<u>HTGHLLEH</u>QRTHtgekpYKCPECGKSFS<u>DCRDL</u><br><u>ARH</u>QRTHtgkkts |
| 47 | ZFP1 coding sequence | ATGGCCCAAGCTGCTTTAGAGCCCGGAGAGAAAAGCCCTATAAATGCCCGAA<br>TGCGGCAAAAGCTTTAGCGACCCCGTCATCTGGTGAGACATCAGAGAAC<br>CCACACCGGCGAAAAGCCTTATAAGTGCCCCGAGTGCGGCAAAAGCTTCA<br>GCAGCAAGAGGCTCTGACCGAACATCAAAGGACCCACACCGGCGAGAAG<br>CCCTACAAAATGCCCCGAATGCGGCAAATCCTTTCTGTAACGACGCTTTAA |

TABLE 3-continued

Zinc finger proteins and related sequences.

| SEQ ID NO. | Description | Sequence |
|---|---|---|
| | | CCGAGCACCAGAGGACCCACACCGGCGAGAAAACCCTACAAGTGTCCCGAA |
| | | TGTGGCAAGAGCTTCAGCGATCCCGGCGTTTAGTCAGACACCAAAGAACC |
| | | CACACCGGCGGAGAAAACCTATAAATGCCCGAGTGTGGCAAGTCCTTCAGC |
| | | GACAGCGGCAACCTCAGAGTGCACAGAGGACCCACACCGGCGAAAAGCC |
| | | CTATAAATGCCCCGAATGCGGCAAAAGCTTTAGCCAGAGCGACATTTAAC |
| | | AGAACACCAGAGGACCCATACCGGCGAAAAGACCTCCGGCCAAGCTGGCC |
| | | AAGCTAGCCTTAAGGAGGAAGAGGAAGAAGTCGGCAGAGCCGACGCTTTAGAT |
| | | GATTTCGATTTAGACATGCTGGGCTTCCGACGCTTTAGACGACTTTGATCTG |
| | | GATATGCTGGGCTCCGATGCTTTAGACGATTTGATCTGGATATGCTGGGC |
| | | AGCGACCCCCTCGACGACTTCGATTTAGACATGCTTAGACATGAACTACCCCTAC |
| | | GATGTGCCCGATTACGCCTCCTGA |
| 48 | ZFP1 in pcDNA3.1 TOPO vector | See sequence listing |
| 49 | ZFP52 coding sequence | ATGGCCCCAAGTGCCTTAGACCCGGCGAGAAACCCTATAAATGCCCCGAA |
| | | TGCGGAAAATCCTTCAGCACCACCAGAAACTCTTTAACCGAACACCAGAGAACA |
| | | CATACTGGTGAAAAAACCTATAAATGCCCCGAGTGCGGCAAATCCTTCAGC |
| | | CAAAGCGGCGATTTAAGGAGACATCAGAGGACCTTTAGCGACTGTCGTGATTTAGC |
| | | TCGTCACCAAAGAACCCATACCGGCGAGAAAAAACCCTATAAGTGTCCCGAGTG |
| | | CGGCAAAAGCTTCTCCCAAGAACTCTTTAACAGACACCAGAGGACCCA |
| | | TACCGGCGAGAAAACCTATAAGTGTCCCGAGTGTGGCAAGTCCTTTCCAG |
| | | AACCGACACTTTAAGGGACCCACAGAGAACCCATACCGGCGAAAAGCCTA |
| | | TAAGTGTCCCGAATGTGGACGAGAGCTTTTCCAGAAGCGACGATCTGGTGAG |
| | | ACACCAAAGGACCCATACTGGTGACAAACTGACCGAGAGTAGTGCCCGAATGTGG |
| | | CAAGTCCTTTCTCGTAGCGACAAACCTACAAGTGTCCCGAGTGTGGCAAGAGTTCTCTCGTAA |
| | | TGGTGAAAAACCTACAAGTGCCCCGAGTGTGGCAAGAGCTTCTCTCGTAA |
| | | CGACACTTAACCGAACATCGAGGACCCATACCGGCGAAAAGCCCTACAA |
| | | GTGCCCCGAATGTGAAAGAGCTTTAGCAGAGAAGAACTTGTAGAGCCCA |
| | | CCAAAGGACCCACACCAGCGAGAAGCCCTATAAATGTCCCGAATGCGGCA |
| | | AGTCCTTCAGCCAGTCCGGCCATTTAACCGAACATCAGAGAACACACCG |
| | | GCAAGAGACCAGCGGCCAAGCTGGACAAGCTAGCCCAAGAAAAAGAGA |
| | | AAGGTGGTCGTGCCGACGCTTTAGACATGCTGGATATGCTCGGCAGCGATGCTTTA |
| | | AGCGATGCTTTAGATGCTTTGATTTAGACATGCTGGGAAGCGACGCTTTAGACGACTTTGATC |
| | | TGGATATGCTGATCAATTACCCCTACGACGTGCCCGACTACGCCTCCTGA |
| 50 | ZFP1_Egr1_site1_sense CDS | ATGGCCCCAAGGCGGCCTGGAGCCGGCAGAGCCCTACAAGTGCCCCG |
| | | AGTGCGGCAAGAGCTTCAGCGACCCAGCGCAACCTGACCGAGCACCAGAGA |
| | | ACCCACACCGGCGAAGAAGCCCTACAAGTGCCCCGAGTGCGGCAAGAGCTT |
| | | CAGCAGGCGACCAAGCTGGTGAGACACCAGAGAACCCACACCGGCGAGA |
| | | AGCCCTACAAGTGCCCCGAGTGCGGCAAGAGTTCAGCCAACACCGGCCAC |
| | | CTGCTGGAGCACCAGAGAACCCACGTGCGCAAGAGCTTCAGCCCCTACAAGTGCCC |
| | | CGAGTGCGGCAAGAGCTTCAGCGAGAAGCGACAAGTGGTGAGACACCAGA |
| | | GAACCCACACCGGCGAAGAAGCCCTACAAGTGCCCCGAGTGCGGCAAGAG |
| | | CTTCAGCGAGAAGCGACACCTGTGAGACACCAGAGAACCCACCACCGGCG |

TABLE 3-continued

Zinc finger proteins and related sequences.

| SEQ ID NO. | Description | Sequence |
|---|---|---|
| | | AGAAGCCCTACAAGTGCCCGAGTGCGGCAAGAGCTTCAGCAGAAGCGAC |
| | | GACCTGGTGAGACACCAGAGAACCCACACCGGCGAGAAGCCCTACAAGTG |
| | | CCCCGAGTGCGGCAAGAGCTTCAGCGACCCCGGCCACCTGGTGAGACAC |
| | | CAGAGAACCCACACCGGCCAAGAAGAACCCAGCCGGCCAGCCCCAGGCTA |
| | | GCCTTAAGAAGAAGAGAAAGTCGGCAGGCCGAAGCGCTTTAGATGATTTC |
| | | GATTTAGACATGCTGGGCTCCGACGTTTAGACGATTTTGATCTGGATATG |
| | | CTGGGCTCCGATGCTTTAGACGATTTTGATCTGGATATGCTGGGCAGCGAC |
| | | GCCCTCGACGACTTCGATTTAGACATGCTGATCAACTACCCCTACGATGTG |
| | | CCCGATTACGCCTCCTGA |
| 51 | ZFP2_Egr1_site2 CDS | ATGGCCCAGGCGGGCCCTGGAGCCCGGCGAGAAGCCCTACAAGTGCCCG |
| | | AGTGCGGCAAGAGCTTCAGCCAGAAGCGACGACCTGGTGAGACACCAGAGA |
| | | ACCCACACCGGCGAGAAGCCCTACAAGTGCCCCGAGTGCGGCAAGAGCTT |
| | | CAGCGACCCCGGCCACCTGGTGAGACACCAGAGAACCCACACCGGCGAG |
| | | AAGCCCTACAAGTGCCCCGAGTGCGGCAAGAGAACCCAGAGAGCCTTCAGCAGAAGCGACGA |
| | | GCTGGTGAGACACCAGAGAACCCACACCGGCGAGAAGCCCTACAAGTGCC |
| | | CCGAGTGCGGCAAGAGCTTCAGCGAGGCGACAAGCTGGTGAGACACCAG |
| | | AGAACCCACACCGGCGAGAAGCCCTACAAGTGCCCCGAGTGCGGCAAGAG |
| | | CTTCAGCGAGAAGCGACGACCTGGTGAGACACCAGAGAACCCACACCGGCG |
| | | AGAAGCCCTACAAGTGCCCCGAGTGCGGCAAGAGCTTCAGCCAGAGAGCC |
| | | CACCTGAGAGACACCAGAGAACCCAGAGAAGCCCTACAAGTG |
| | | CCCCGAGTGCGCGCAAGAGCTTCAGCAGAAGACCAGCCGACAGCTGAGCCACC |
| | | AGAGAACCCACACCGGCCAAGAAGACCAGCCCGGCCAGCCCCAGGCTAG |
| | | CCCTAAGAAGAAGAGAAAGTCGGCAGGCCGAAGCGCTTTAGATGATTTCGA |
| | | TTTAGACATGCTGGGCTCCGACGTTTAGACGATTTTGATCTGGATATGCT |
| | | GGGCTCCGATGCTTTAGACGATTTTGATCTGGATATGCTGGGCAGCGACGC |
| | | CCTCGACGACTTTGATTTAGACATGCTGATCAACTACCCCTACGATGTGCC |
| | | CGATTACGCCTCCTGA |
| 52 | ZFP3_Egr1_site3_antisense CDS | ATGGCCCAGGCGGGCCCTGGAGCCCGGCGAGAAGCCCTACAAGTGCCCCG |
| | | AGTGCGGCAAGAGCTTCAGCCAGAGCGGCGACCTGAGAGTGCACCAGAGA |
| | | ACCCACACCGGCGAGAAGCCCTACAAGTGCCCCGAGTGCGGCAAGAGCTT |
| | | CAGCGAAGCGACAAGCCTGGTGAGACACCAGAGAACCCACACCGGCGAGA |
| | | AGCCCTACAAGTGCCCCGAGTGCGGCAAGAGCTTCAGCGAAGCGACGAG |
| | | CTGGTGAGACACCAGAGAACCCACACCGGCGAGAAGCCCTACAAGTGCCC |
| | | CGAGTGCGGCAAGAGCTTCAGCGAGAGCGACAAGTGCCCCGAGTGCGGCAAGAG |
| | | GAACCCACACCGGCGAGAAGCCCTACAAGTGCCCCGAGTGCGGCAAGAG |
| | | CTTCAGCGAGAAGACGACCTGACCCAGAGAACCCACACCGGCG |
| | | AGAAGCCCTACAAGTGCCCCGAGTGCGGCAAGAGCTTCAGCCAGAGCGGC |
| | | GACCTGAGAAGCGACACCCAGAGAACCCACACCGGCGAGAAGCCCTACAAGTG |
| | | CCCCGAGTGCGGCAAGAGCTTCAGCAGAAAACGACCGCCTGACCGAGCACC |
| | | AGAGAACCCACACCGGCCAGCGCCCAGCCCGGCCAGCCCCAGGCTAG |
| | | CCCAAGAAAAGAGAAAGGTCGGCAGCGATGCTTTAGATGATTTCGA |
| | | TTTAGACATGCTGGGCAGCGATGCTTTAGATGACTTCGATCTGGATATGCT |
| | | GGGCAGCGACTTTGATCTGGATATGCTGGATATATGCTGGGAAGCGACGC |
| | | TTTAGACGACTTTGATCTGGATATGCTGATCAATTACCCCTACGACGTGCCC |
| | | GACTACGCCTCCTGA |

TABLE 3-continued

Zinc finger proteins and related sequences.

| SEQ ID NO. | Description | Sequence |
|---|---|---|
| 53 | ZFP4_Egr1_site1_antisense CDS | ATGGCCCAGGCGGCCCTGGAGCCCGGCGAAGAGCCCTACAAGTGCCCCG<br>AGTGCGGCAAGAGCTTCAGCCAGCACCACCGGCCACCTGCTGGAGCACCAGAGA<br>ACCCACCCGGCGAGAAGCCCTACAAGTGCCCCGAGTGCGGCAAGAGCTT<br>CAGCAGAAACGACACCCTGACCGAGCACCAGAGAACCCACACCGGCGAGA<br>AGCCCTACAAGTGCCCCGAGTGCGGCAAGAGCTTCAGCAGAAACGACACC<br>CTGACCGAGCACCAGAGAACCCACACCGGCGAGAAGCCCTACAAGTGCCC<br>CGAGTGCGGCAAGAGCTTCAGCGACTGCAGAGACCTGGCCAGACACCAGA<br>GAACCCACACCGGCGAGAAGCCCTACAAGTGCCCCGAGTGCGGCAAGAG<br>CTTCAGCCAGCCACCTGCTGGAGCACCAGAGAACCCACACCGGCG<br>AGAAGCCCTACAAGTGCCCCGAGTGCGGCAAGAGCTTCAGCGACTGCAGA<br>GACCTGGCCAGACACCAGAGAACCCACACCGGCAAGAAGACCAGCGGCCA<br>GGCCGGCTAGCCCAAGAAAAAGAAAAGGTCGGTCGTGCCGAC<br>GCTTTAGATGATTTCGATTTAGACATGCTGGCAGCCGATGCTTTAGATGACT<br>TCGATCTGGATATGCTGGGCAGCGATGCTTTAGATGATTTGATTTAGACAT<br>GCTGGGCGACGCTTTAGACGACTTTGATCTGGATATGCTGATCAATTA<br>CCCCTACGACGTGCCCGACTACGCCTCCTGA |
| 54 | ZFP52_VPR coding sequence | ATGGCCCAAGCTGCTTAGAACCCGGCGAGAAACCCTATAAATGCCCGAA<br>TGCGGAAAATCCTTCAGCAGCACCAAAAACTCTTTAACCGAACACAGAGAACA<br>CATACTGGTGAAAAACCTTATAAATGCCCCGAGTGCGCGCAAATCCTTCAGC<br>CAAAGCGGCGATTTAAGGAGACATCAGAGGACCCACACTGGTGAGAAGCC<br>TTACAAATGCCCGAGTGTGGAAAAAGCTTTAGCGACTGCGTCGTGATTTAGC<br>TCGTCACCAAAGAACCCATACCGGAGAAAATCTTTAACAGAGCAACCAGAGACCCA<br>CGGCAAAAGCTTCTCCACCAGACACCTATAAGTGTCCCGAGTG<br>TACCGGCGAGAAACCCTATAAGTGTCCCGAGTGTGGCAAGTCTTTCCAG<br>AACCGACACTTTAAGGGACCACCAGAGAACCCATACCGGCGAAAAGCCCTA<br>TAAGTGTCCCGAATGTGGCAAGAGCTTTTCCAGAAGCGACGATCTGGTGAG<br>ACACCAAAGGACCCATACTGGTGAAAAGCCCTATAAGTGCCCCGAATGTGG<br>CAAGTCCTTTTCTGTAGCGACAAACTGACACCAGAGGACCCATAC<br>TGGTGAAAAACCCTACAAGTGCCCGAGTGTGGCAAGAGCTTCTCTCGTAA<br>CGACACTTTAACCGACAATCAGAGGACCCATACCGGCGAAAGCCCTACAA<br>GTGCCCCGAATGTGGAAAAGAGCTTTAGCAGCAGAAGAACTTGTAGAGCCCA<br>CCAAAGACACCCACCCGGAGAGAGGCCCTATAAATGTCCCGAATGCGGCA<br>AGTCCTTCAGCCAGCCAGTCCGGCCATTTAACCGACAAGCTGGACAAGCTAGCCCAAGAAAAAGAGA<br>GCAAGAAGACCAGCGGCCAAGCTGCAGCCTGGACAAGCTAGCCCAAGAAAAGAGA<br>AAGGTCCGGTCGTGCCGACGCTTCGATCTGGATATGCTGGGCGATGCTTTA<br>AGCGATGCTTTAGATGACTTCGATCTGGATATGCTGGGCGACGATGCTTTA<br>GATGATTTTGATTTAGACATGCTGGGAAGCGACGCTTTCCGACTACGCTTCTAGTTC<br>TGGATCTCGATCAATTACCCCTACGACGTTGGTAGCCAGTACGCCTCCGACAC<br>CGACGACCCGACCCGATCGAGGAAAAGCCGGACCTACGACGA<br>TTCAAGAGCATCATGAAGAAGTCCCCTTCAGCGCCTCCACCGACCCTAGA<br>CCTCCACCTAGAGAATCGCGTGCCCAGCAGATCCAGCGCCAGCCTGCC<br>AAAACCTGCCCCCCACCTACCCTTCACCCAGCAGCCTGAGCACCATCAA<br>CTACGACGAGTTCCCTACCATGGTGTTCCCCAGCGGCCAGATCTCTCAGGC<br>CTCTGCTCGGCCTCCAGCGTGCTCAGGCCTCCAGGTGCCTCCTGCTC |

TABLE 3-continued

Zinc finger proteins and related sequences.

| SEQ ID NO. | Description | Sequence |
|---|---|---|
| | | CTGCACCAGCTCCAGCCATGGTGTCTGCACTGGCTCAGGCACCAGCACCC |
| | | GTGCCTGTGCTGGCTCCTGGACCTCCACAGGCTGTGCCTGGCTCCACCAGCCC |
| | | TAAACCTACACAGGCCGGCGGAGGCACACTGTCTGAAGCTCTGCTGCAGC |
| | | TGCAGTTCGACGAGGATCTGGAGCCTGCTGGGAAACAGCACCGAT |
| | | CCTGCCGTGTTCACCGACCTGCCAGCGTGGACAACAGCGAGTTCAGCA |
| | | GCTGCTGAACCAGGGCATCCTGTGGCCCCTCACACCACCGAGCCCATGC |
| | | TGATGGAATACCCGGAGGCCATCACCCGGCTGTGACAGGCCTGCCTAATGG |
| | | CCTCCTGATCCAGCTCTGCTCCTGGGAGCCACCAGGCCTGCCTAATGG |
| | | ACTGCTGTCTGCGACGAGGACTTCAGCTCTATCGCCGATATGGATTTCTC |
| | | AGCCCTTCCTGGGCTCTCGGCAGCGCAGCCGGGATTCCAGGGAAGGGATG |
| | | TTTTTGCCGAAGCTGAGGCTCCGCTATTAGTGACGTGTTTGAGGGC |
| | | CGCGAGGTGTGCCAGCCAAAACGAATCCGGCCATTTCATCCTCCAGGAAG |
| | | TCCATGGCCAACCGCCCACTCCCCGCACCGCAGCCTGCCACCAACCACCG |
| | | GTCCAGTACATGAGCCAGTCGGGTCACTGGGCTACCCGGCCACCAGTCCCTCAG |
| | | CCACTGGATCCAGCGCCCGGAGTGACTCCCGAGGCCAGTCACCTGTTGAA |
| | | GGATCCCGATGAAGAGACGAGCCAGGCTGTCAAAGCCCTTCGGGAGATGG |
| | | CCGATACTGTGATTCCCCAGAAGGAGGCTGCAATCTGTGGCCAAATGG |
| | | ACCTTTCCATCCGCCCCAAGGGCCATCTGACTGAACCTGACCCCTGACCCTGGA |
| | | CTTGAGTCCATGACCGAGGATTCTGAACGAGTGCCTCTTGCATGC |
| | | ATTGAACGAGATTCTGATACCTTCGACACGAGTGCCTCTTGCATGC |
| | | CATGCATATCAGCACAGGAGGACTGTCCATCTTCGACACATCTGTTTGACTCG |
| | | AGTCTAGAGGGCCCGCGGTTCGAAGGTAAGCCTATCCTACCCCTCCCTC |
| | | GGTCTCGATTCTTACGCGTCATCATCACCATCACCATTGA |
| 55 | ZFP3_VPR coding sequence | ATGGCCCCAGGCGGGCCCTGGAGCCCGGCGAGAAGCCCTACAAGTGCCCG |
| | | AGTGCGGCAAGAGCTTCAGCCCAGAGCGGCGACTCGAGAAGCACCAGAGA |
| | | ACCCACCACCGGCAGCCGCGACAAGTGCCCCGAGTGCGGCAAGAGCTT |
| | | CAGCAGAAGCGACAAGCTGGTTGAGACACCAAGAGAACCCACACCGGCGAGA |
| | | AGCCCTACAAGTGCCCCGAGTGCGGCAAGAGCTTCAGCAGAAGCGACGAG |
| | | CTGGTGAGACACCAGAGAACCCACACCGGCGAGAAGCCCTACAAGTGCCC |
| | | CGAGTGCGGCAAGAGCTTCAGCGAGAAGCGACAAGTGGTGAGACACCAGA |
| | | GAACCCACACCGGCGAGAAGCCCTACAAGTGCCCCGAGTGCGGCAAGAG |
| | | CTTCAGCAGAAACGACCCCTGACCAGCAGCTGGTGAGACACCAGAGCCG |
| | | AGAAGCCCTACAAGTGCCCCGAGTGCGGCAAGAGCTTCAGCCAGAGCGGC |
| | | GACCTGAGAAGACACCAGAGAACCCACACCGGCGAGAAGCCCTACAAGTG |
| | | CCCCGAGTGCGGCAAGAGCTTCAGCAGAAGACGACGCCCTGACCGAGCACC |
| | | AGAGAACCCACACCGGCGAGAAGACCAGCCGCCAGCCGGCCAGGCTAG |
| | | CCCAAGAAAGAAAAGAAAAGGTGTGGCCGACGCTTTAGATGTATGATTTCGA |
| | | TTTAGACATGCTGGGCAGCGATGCTTTAGATGCTGGATCTGATATGCT |
| | | GGGCAGCGATGCTTTAGATGCTGGATCTGGAAGCGACGCC |
| | | TTTAGACGACTTTAGTTCCGATCGTCATCAATTACCCTACGACGTTCCG |
| | | GACTACCTGCCCGACACCGACACCGGCGATGGAAGAAGCAAAGTTGGTAGC |
| | | CAGTACCTGCCCGACACATTCAAGAGCATCATGAAGAAGAAGACCGGAA |
| | | GCGGACCTAGCAGCTCCACCTAGAAAGACTCGCCGTGCCCAGCAGG |
| | | TCCAGCCAGCCTGCCAAACCTGCCAAAACCTGACCCTGCCGTGCCCCTTCACCAG |
| | | CAGCCTGAGCAGCCATCAACTACGACGAGTTCCTACCATGGTGTTCCCCAG |

TABLE 3-continued

Zinc finger proteins and related sequences.

| SEQ ID NO. | Description | Sequence |
|---|---|---|
| | | CGGCCAGATCTCTCAGCCTCTGCTCTGGCTTCCAGCCCCTCCTCAGTGC |
| | | TGCCTCAGGCTCCTGCTCCTGCCACCAGCTCCAGCCATGGTGTCTGCACTG |
| | | GCTCAGGCACCAGCACCCGTGCCTGCCTGTCCTGGACCTCCACAGGC |
| | | TGTGGCTCCACCAGCCCCTAAACCTACACAGGCCGGCGAGGGCAACTGT |
| | | CTGAAGCTCTGCTGCAGTTGCAGCGACGAGGATCTGGGAGCCCTG |
| | | CTGGGAAACAGCACCGATCCTGCCTGTTCACCGACCTGTGGCCCTC |
| | | CAACAGCGAGTTCCAGGACTGCTGAACCAGGGCATCCTGTGGCCCCTC |
| | | ACACCACCGAGCCCATGCTGATGGAGAATACCCGAGGCCATCACCCGCTC |
| | | GTGACAGGCGCTCAGAGGCCTCTGATCCAGCCTCTGCCCCTCTGGGAGC |
| | | ACCAGGCCTGCCTAATGACTCTGTCTGCTGGCGACGAGACTTCAGCTCTAT |
| | | CGCCAGATATGGATTTCTCAGCCTTCTGCTGCTCTGGCGGCAGCCGGG |
| | | ATTCCAGGGAAGGGATGTTTTTTGCCGAAGCTGAGGCCGGCTCCGCTATTA |
| | | GTGACGTGTTTGAGGGCGCGGAGGTTCCAGCCAAAACGAATCCGGCCA |
| | | TTTCATCCTCCAGGAAGTCCATGGGCCAACCCCACTCCCGCCAGCCT |
| | | CGCACCAACACCAACCGGTCCAGTACCATGAGCCAGTCGGGTCACTGACCC |
| | | GGCACCAGTCCCTCCAGCCACTGGATCCAGCGCCCGCCAGGCTGTCAA |
| | | GCCAGTCACTGTTGGAGGATCCCGATGAAGAGACAGCCAGGCTGTCAA |
| | | AGCCCTTCGGGAGATGCCGATACTGTGATTTCCCAGAAGGAAGAGCTG |
| | | CAATCTGTGGCCAAATGGACCTTTCCATCCGCCCCAAGGGGCCATCTG |
| | | GATGAGCTGACAACCACACACTTGAGTCCATGACCGAGGATTGAACCTGGAC |
| | | TCACCCCTGACCCCGAATTGAACGAGATTCTGGATACCTTCCTGAACGAC |
| | | GAGTGCCTCTTGCATGCATGCATATCAGCACAGGACTGTCATCTTCGAC |
| | | ACATCTCTGTTTGACTCGAGTCTGAGTATCGAGGGCCCGGTTCGAAGGTAAGCCT |
| | | ATCCTAACCCTCTCCTCGGTCTCGATTCTACGCGATTCACCGGTCATCATCAC |
| | | CATCACCATTGA |
| 56 | Egr1_insert_Site2 coding sequence | ATGGCCGCGGCCAAGGCCGAGATGCAGCTGATGTCCCGCTGCAGATCTC |
| | | TGACCCGTTCGATCTTTCTCACTCGCCCACCATGGACAAACTACCCTAA |
| | | GCTGAGGAGATGATGCTGTGAGCAACGGGCTCCCAGTTCCTCGGCG |
| | | CCGCCGACCCCAGAGGCCGCCAACAGCAGCAGCAGCAG |
| | | CGGGGCGGTGAGGCCGGGGCGCAGCAACAGCAGCAGCAG |
| | | CAGCAGCTTCAACCCTCAGGCGGACAACGGCGAGCAGCCTACGAGCACC |
| | | TGACCCAGAGTCTTTCCTGACATCTCTGAACAACGAGAAGGTGCTGG |
| | | TGGAGACCAGTTACCCCAGCCAAAACCTGCCTGCCCCATCACCTATA |
| | | CTGGCCGCCTTTCCCTGAGCCTGCTGTCAGTGGCCTAGTGAGCATGACAACCTTGTGG |
| | | CCCGAGCCCTCTCCTCGTCCTCCAGCACCATCTCAGCGGCCTCTTCCGCCTCCG |
| | | CCTCCAGAGCCTCACCCCTGACCTGCCAGTGCCATCCAACGACAGCAGT |
| | | CCCATTACTCAGCCCCCACCCCGGCACCGCCCGAACACTGACATTTTC |
| | | CTGAGCCACAAAGCCAGGCCTTCCGCCGCCAAGGGTGCTTCCAGGTTCCC |
| | | ATGATCCCGACTACCTGTTTCCACAGCAGCAGGGGGATCTGGGCCTGGG |
| | | CACCCCAGACCAGAAGCCTTCAGGGCCTGAGAGCGCCGCACCAGCAG |
| | | CCTTCGCTAACCCCTCGTCTACTATTAAGGCCTTTGCCACTCAGTCGGGC |
| | | TCCCAGGACCTGAAGGCCCTCAAGTACCCCCAATACAGCAGTCCCAGCTCATCAAA |
| | | CCCAGCGCCATGCGGCAAGTACCCCCAGTAAGACGCCCCCA |
| | | CGAACGCCCTTACGCTTGCCCCGTGGAGTCCTGTGATCGCCGCTTCTCCC |

TABLE 3-continued

Zinc finger proteins and related sequences.

| SEQ ID NO. | Description | Sequence |
|---|---|---|
| | | GCTCCGACGAGCTCACCCGCCACATCCGCCATCCACACAGGCCAGAAGCCC |
| | | TTCCAGTGCCGCATCTGCATGCGCAACTTCAGCCGCAGCGACCACCTCAC |
| | | CACCCACATCCGCACCCACACAGGCGAAAAGCCCTTCGCCTGCGACATCT |
| | | GTGGAAGAAAGTTTGCCAGGAGCGATGAACGCAAGAGGCATACCAAGATC |
| | | CACACAGGCCAGAAGCCCTTCCAGTGCAGTCCTGTGATCGCCGCTTCTC |
| | | CCAGAGAGCCCACCTGGAGAGACACATCCGCCATCCACAGGCCAGAAGC |
| | | CCTTCCAGTGCCGCATCTGCATGCGCAACTTCAGCGAAGCGACAAGCTGA |
| | | CCGAGCACATCCGCACCCACACAGGCGAAAAGCCCTTCGCCTGCGACATC |
| | | TGTGGAAGAAAGTTTGCCACACGGCCACCTGCTGAGCATACCAAGATC |
| | | CACTTGCGCAGAGGACAAGAAAGCAGACAAAAGTGTTGTTGGCCTCTTCG |
| | | GCCACCTCCTCTCTCTCTTATCCATCCCGGTTGCTACCTCTTACCCG |
| | | TCCCCGGTTACTACCTCTTATCCATCCCGGTTGCTACCTCATACCCATCC |
| | | CCTGTGCCACCTCCTCTCTCTCCCCGTCCTGACCTACCCATCCCCT |
| | | GTGCACAGTGGCTTCCCCGCCCCGTCGGTGGCCACCGTACTCCTCTGTT |
| | | CCCCTGCTTTCCCGGCCCCAGTCAGCAGGGCTTTCGGACATGACAGCAGTCAACCTTTCT |
| | | AACTCCTTCAGCGCCTCCACAGGGCTTTCGGACATGACAGCAGCAACCTTTTCT |
| | | CCCAGGACAATTGAAATTTGCTAA |
| 57 | Egr1_insert_Site3 coding sequence | ATGGCCGCGGCCAAGGCCGAGATGCGAGAGCTGATGTCCCCGTGCAGATCTC |
| | | TGACCCGCTTCGATCTTCCACTCGCCCATGGACAACTACCCTAA |
| | | GCTGGAGGAGATGATGCTGCTGAGCAACGGGGCTCCCCAGTTCCTCGGCG |
| | | CCGGCGGCGGCCCCAGAGGCCGGGGGGGCCGCAGCAGCACACAGCAGCAGCAG |
| | | CGGGGCGGTGGAGGGCGGCGGGGCGGCAGCAGCAACAGCAGCAGCAGCAG |
| | | CAGCACCTTCAACCTCAGGCGGACGATCCTCTGACACGGCCGACAGCCTGAGAAGGTGCTGG |
| | | TGACCCGAGAGTCTTTTCCTGACATCTCTGAACAACAGCGAGAAGGTGCTGG |
| | | TGGAGACCAGTTACCCCAGCCAACCACTCGACTGCCCCCATCCACCTATA |
| | | CTGGCCGCCTTTCCCTGGAGCCTGCACCCCAACAGTGCAACACCTTGTGG |
| | | CCCGAGCCCTCTTCAGCTTGTCAGTGCCTAGTGAGCATGACAACCC |
| | | ACCGGCCTCTCGTCCTTCAGCACCATCTCCAGCGGCCTCTTCCGCCTCCG |
| | | CCTCCCAGAGCCCACCCTGAGCTGCAGTGCCATCCAACGACAGCAGT |
| | | CCCATTTACTCAGCGGCACCCACCTTCCCCGGCTCGGCAGGCAGCGCTCC |
| | | CCTGAGCCACAAAGCCAGGCCTTCCCGCCCTACCGCTCCGGGTGCTTCCAGGTTCCC |
| | | AGTACCCGCCTTCCTGCCTACCTGTTTCCACAGCAGGGGGATCTGGGCTGGG |
| | | ATGATCCCGACTACCCTGTTTCCACAGCAGACCAGGGGGATCTGGGCTGGG |
| | | CACCCCAGACCAGAAGCCCTTGAGAGCCTGAGAGCGCCACCAGCAG |
| | | CCTTCGCTACCCTGTCTACTATTAAGGCCTTTGCCACTCAGTCGGGC |
| | | CCCAGCCGCATGCAAGTACCCCAACCGGCCCAGTAAGACGCCCCCCA |
| | | CGAACGCCCTTACGCTTGCCCCAGTGGAGTCCGCACTTCGTGATCGCCGCTTCTCC |
| | | GCTCCGACGAGCTCACCCGCCATCCGCAACTTCAGCCGCCAGCCAGAAGCCC |
| | | CACCCACATCCGCACCCACACAGGCCGAAAAGCCCTTCGCCTGCGACATCT |
| | | GTGGAAGAAAGTTTGCCAGGAGTCCTGTGATGAACGCAAGAGGCATACCAAGATC |
| | | CACTGCGCCAGTGGAGTCCTGTGATGCCCGCTTCTCCCAGAGCGGCGACCT |
| | | GAGAAGACACATCCGCATCCACACAGGCCAGAAGCCCTTCCAGGCGGCGCA |
| | | TCTGCATGCGCAACTTCAGCAGACGACGCCCTGACCGAGCACATCCGC |
| | | ACCCACACAGGCGAAAAGCCCCTTGCCCTGCGACATCTGTGGAAGAAGTTT |

TABLE 3-continued

Zinc finger proteins and related sequences.

| SEQ ID NO. | Description | Sequence |
|---|---|---|
| | | GCCGACTGCAGAGACCTGGCCAGACATACCAAGATCCACTTGCGCAGAA |
| | | GGACAAGAAAGCAGACAAAGTGTTGGCCTCTTCGGCCACCTCCTCT |
| | | CTCTTCCTACCCGTCCCCGGTTGCTACCTCTTTACCCGTCCCCGGTTACTAC |
| | | CTCTTATCCATCCCGGCTCCCTGACCTACCCATCCCCTGTGCACACCTC |
| | | CTTCCTCCTCCGGCTCCTGACCTACCATCCCCTGTTCCCCTGCTTCC |
| | | CCCCTCCCCGTCGGTGCCACCAGTTCCCTTCCTCAGCTGTCACCAACTCCTTCAGCGC |
| | | GGCCCAGGTCAGCAGTTCCCTTCCTCAGCTGTCACCAACTCCTTCAGCGC |
| | | CTCCACAGGGCTTCGGACATGACAGCAACCTTTCTCCCAGGACAATTGA |
| | | AATTGCTAA |
| 58 | Egr1_insert_Site2_RR coding sequence | ATGGCCGCGGCCAAGGCCGAGATGCAGCTGATGTCCCGTGCAGATCTC |
| | | TGACCCGGTTCGGATCCTTTCCTCACTCGCCCACCATGGACAACTACCCTAA |
| | | GCTGGAGGAGATGATGCTGTGAGCAACGGGGCTCCCAGTTCCTCGGCG |
| | | CCGCCCGGGGCCCCAGAGGCGGCGGGGGCGGCAGCAACAGCAGCAGCAG |
| | | CGGGGCCGTGAGGCGGTGAGGGCCGCCAGCACAGCAACAGCAGCAGCAG |
| | | CAGCACCCTCAACCCTCAGGCGGACAACGGGCGAGCAGCCCTACGAGCACC |
| | | TGACCGCAGAGTCTTTTCCTGACATCTCTGAACAACGACGAAGGTGCTGG |
| | | TGGAGACCAGTTACCCGGCCAAACCACTCGACTGCCCCCATCACCTATA |
| | | CTGGCCGCTTTTCCCTGGAGCCTGCACCAACAGTGCAACACCTTGTGG |
| | | CCCGAGCCCTCTTCAGCTTGTCAGTGCCTAGTGAGCATGAGCAACCC |
| | | ACCGGCCTCCTCGTCCTCAGCACCTCCCCCAGTTCCTCCGCCTCCG |
| | | CCTCCCAGAGCCCACCCTGACTGCGCAGTGCCATCAACGACAGCAGT |
| | | CCCATTTACTCAGCGGCACCAGGCCTTCCCGGCTCGGAGGGACAGCGCTCC |
| | | TGAGCCACAAGCCAGGCCTCCCTACCCTGCCCAAGGGTGCTTCCAGGTTCCC |
| | | AGTACCCGACTACCTGTTTCCACAGCAGCAGGGGGATCTGGGCTGGG |
| | | ATGATCCCAGACCAGAGCCCTTCCAAGGCCTGGAGAGCCGCCTCATCAAAC |
| | | CACCCCCAGAGCAGAAGCCCTTCCAACGGCCAGTGAGAGGCCATACCAAGATCC |
| | | CCAGCCGCATCGCAAGTACCCCAACGGCCCAGTGAAGACGCGCCTTCTCC |
| | | GAACGCCCTTACGCTTGCCCAGTGGAGTCTGTGATCGCCGCTTCCCG |
| | | CTCCGACGAGCTCACCCGCCACATCCGCATCACACAGGCCAGAAGCCCT |
| | | TCCAGTGCCGCATCTGCATGCGCAACTTCAGCCGCAGCGACCACCTCACC |
| | | ACCCACATCCGCACCCACACAGGCGAAAAGCCCTTCGCCTGCGACATCTG |
| | | TGGAAGAAAGTTTGCCAGGAGCGATGAAGCGCAAGAGGCCATACCAAGATCC |
| | | ACACAGCCAGAAGCCCTGCCAGTGAGTCTGTGATGCGCGCTTCTCC |
| | | CAGAGAGAGCCCACCTGGAGAGACATCCGATCCACACAGGCCAGAAGCC |
| | | CTTCCAGTGCCGCATCTGCATGCGCAACTTCAGCAGAAGCGACAAGCTGAC |
| | | CGAGCACATCCGCACCCACACAGGCGAAAAGCCCTTCGCCTGCGACATCT |
| | | GTGGAAGAAAGTTTGCCACCACCGGACATACAGCACAACAGATC |
| | | CACTTGCGCAGAAGGACAAGAAAGCAGACAAAAGTGTTGCTACCTCTTACCCG |
| | | GCCACCTCCTCTCTCTTCCTTATCCATCCCGGTTCTCATACCCATCCC |
| | | CCTGTTACTACCTCTCTCCTCCCCGTCGGTGGCCACCAGTTCCTCCATCCCCT |
| | | GTGCACAGTGGCTTCCCCGCCCAGGGCCTTCCCTGGTGGCCACCAGTTCCTCACC |
| | | CCCCTGCTTTCCCCGGCCCCAGGTCAGCAGCCTTTCCTTCCTCAGCTGTCACC |
| | | AACTCCTTCAGCGCCTCCACAGGGCTTTCGGACATGACAGCAACCTTTTCT |
| | | CCCAGGACAATTGAAATTTGCTAA |

TABLE 3-continued

Zinc finger proteins and related sequences.

| SEQ ID NO. | Description | Sequence |
|---|---|---|
| 59 | Egr1_insert_Site3_RR coding sequence | ATGGCCGCGGCCAAGGCCGAGATGCAGCTGATGTCCCGCTGCAGATCTC TGACCCGTTCGGATCCTTTCCTCACTCGCCCACCATGGACAACTACCCTAA GCTGGAGGAGATGATGCTGCTGAGCAACGGGGCTCCCAGTTCCTCGGCG CCGCCGGGGCCCCAGAGGGCGAGCGGCAGCAACAGCAGCAGCAGCAG CGGGGCGGTGAGGGCGGGGGCGGCAGCAGCAACAGCAGCAGCAG CAGCACCTTCAACCCTCAGCGGAACGGAGCGGAGCAGCCCTACGAGCACC TGACCCGCAGAGTCTTTTCCTGACATCTCTGAACAACGAGAAGGTGCTGG TGGAGACCAGTTACCCCAGCCAAAACTACTGACTGCCCCCATCACCTATA CTGGCCGCTTTTCCTGGAGCCTGCACCAACAGTGGCAACACCCTTGTGG CCCGAGCCCCTTCAGCTTGTCAGTGGCCTAGTGAGCATGACCAACCC ACCGGCCTCTGTCCTCAGCACCATCTCAGCGGCCTCTCCGCCTCCG CCTCCCAGAGCCCACCCCTGACCTGCCAGTGCCATCCAACGACAGCAGT CCCATTTACTACGGGCACCACCTTCCCCGCCGAACACTGACATTTTC CCTGAGCCACAAAGCCAGGCCTTCCCGGCTTCGGCAGGGACAGCGCTCC AGTACCCGCCTCCTGCCTACCCCTGCGCCAAGGGTGGCTTCCAGGTTCCC ATGATCCCCGACTACCTGTTTCCACAGCAGCAGGGGATCTGGGCCTGGG CACCCCAGACCAGAAGCCCTTCCAGGGCCTGAGAGCCGCCTCATCAAAC CCAGCCGCATGCAAGTACCCCAACCGGCCCAGTAAGACGCCCTTCCCAC GAACGCCCTTACGCTTGCCCAGTGGAGTCTGTGATCGCCGCTTCTCCCG CTCCGACGAGCTCACCCGCCATCCGCTACCCACACCAGGCCAGAAGCCCT TCCAGTGCCGCATCTGCATGCGGAACTTCAGCCGCAGCGACCACCTCACC ACCCACATCCGCACCCACACAGGCGAAAAGCCCTTCGCCTGCGACATCTG TGGAAGAAAGTTTGCCAGGAGCGATGAACGCAAGAGGCATACCAAGATCC ACTGCCCAGTGCAGTCCTGTGATCGCCGCTTCTCCAGAGCGGCGACCTG CTGCATGCGCAACTTCAGCAGGACACGCGCCCTGACCAAGCACATCGCA CCCACACAGGCGAAAAGCCCTTCGCCTGCGACATCTGTGGAAGAAAGTTTG CCGACTGCAGAGACCTGGCCAGACATACCAAGATCCACTTCACTTGCGGCAGAAG GACAAGAAAGCAGACAAAAGTGTTGTGGCCTTCTTCGCCACCTCCTCTC TCTTCCTACCGTCCCGTCCCCGGTTGCTACCCTCTTACCCCGGTTACTACC TCTTATCCATCCCGGCCACCACTTCATACCCCATCCCTGTGCCCACCTCC TTCTCCTCCCCGGCTCCTCGACCTACCCATCCCTGTGACAGTGGCTTC CCCTCCCGTCGGTGGCCACCACGTACCTCCTGTTCCCCCTGCTTCCCG GCCCAGTGCAGCGCTTCCCTTCCCCTCACTGTCACCAACTCCTTCGCGCC TCCACAGGCTTTCGGACATGACAGCAACCTTTTCTCCCAGGACAATTGAA ATTTGCTAA |

Table 4 lists target sequences relevant to the present disclosure.

TABLE 4

Target sequences.

| SEQ ID NO. | Description | Sequence |
|---|---|---|
| 60 | Site 1 | GCGGGGCGC |
| 61 | Site 2 | GCGGGGGTG |
| 62 | Site 3 | CTGGGGGTG |
| 63 | ZFP1<br>•Position: -283 to -300 | CGAAACGTCCTGCACGGC |
| 64 | ZFP52<br>•Position: -220 to -249 | CGACGTCCGCGGGCGACGCCTGCCGCACCT |
| 65 | ZFP1_Egr1_site1<br>•Position: -45 to -65<br>•Site 1 underlined | GGCGCGGCGGGGCGCGGGCAT |
| 66 | ZFP2_Egr1_site2<br>•Position: -83 to -103<br>•Site 2 underlined | CGGGGAGCGGGGGTGGGCGCG |
| 67 | ZFP3_Egr1_site3<br>•Position: -152 to -172<br>•Site 3 underlined | CTGGCACTGGGGGTGGGGGCA |
| 68 | ZFP4_Egr1_site1_antisense<br>•Position: -47 to -64 | GCCCGCGCCCCGCCGCGC |
| 69 | Egr1_insert_site2<br>•Position: -89 to -106<br>•Site 2 underlined | CGCCGGGGAGCGGGGGTG |
| 70 | Egr1_insert_site3<br>•Position: -149 to -166<br>•Site 3 underlined | GCCCTGGCACTGGGGGTG |

Transcriptional Activation Domains

The DNA binding proteins of the present disclosure comprise or are attached to a transcriptional activation domain. A transcriptional activation domain may be a complete protein or the domain of a protein which enhances transcription of a gene. Proteins known to enhance gene expression include, for example, transcription factors, certain viral proteins and chromatin remodelling proteins.

Suitable transcriptional activation domains for use in the compositions and methods of the present disclosure may include VP16, or a plurality thereof, VP64, VP160, p65, MyoD1, HSF1, RTA, SET7/9 as well as domains from chromatin-remodelling enzymes such as DNA demethylases and histone acetyltransferases. In certain examples, the transcriptional activation domain is a TET catalytic domain such as the catalytic domain of TET1, TET2 or TET3. In other examples, the transcriptional activation domain is an acetyltransferase such as p300. In further examples, the transcriptional activation domain may be Oct 1, Oct-2A, Sp1, AP-2, CTF1, CBP, PCAF, SRC1, Pv ALF, AtHD2A, ERF-2, OsGAI, HALF-1, C1, AP1, ARF-5, -6, -8 or -8, CPRF1, CPRF4, MYC-RP/GP or TRAB1. Those skilled in the art will understand that other transcriptional activation domains may be used in connection with the DNA binding proteins of the present disclosure.

The DNA binding protein of the present disclosure may comprise a transcriptional activation domain. For example, the DNA binding protein may be fused to the transcriptional activation domain as a single polypeptide chain. Alternatively, or in addition, the DNA binding protein may attach to a transcriptional activation domain. For example, the DNA binding protein may directly attach to a protein which comprises a transcriptional activation domain. In such examples, the DNA binding protein may be engineered to comprise a binding site that is recognised by the protein comprising the transcriptional activation domain. In some examples, the transcriptional activation domain may be conjugated to an antibody or fragment thereof which specifically binds to the DNA binding protein. In a further non-limiting example, the DNA binding protein may interact with an adapter protein and the adapter protein may in turn bind to a protein which comprises a transcriptional activation domain.

Sequences

Table 5 sets forth non-limiting examples of transcriptional activation domains.

TABLE 5

Transcriptional activation domains.

| SEQ ID NO. | Description | Sequence |
|---|---|---|
| 71 | VP64 | DALDDFDLDMLGSDALDDFDLDMLGSDALDDFDLDMLGSDALDDF DLDML |
| 72 | p65 | SQYLPDTDDRHRIEEKRKRTYETFKSIMKKSPFSGPTDPRPPPRRIA VPSRSSASVPKPAPQPYPFTSSLSTINYDEFPTMVFPSGQISQASAL APAPPQVLPQAPAPAPAPAMVSALAQAPAPVPVLAPGPPQAVAPP APKPTQAGEGTLSEALLQLQFDDEDLGALLGNSTDPAVFTDLASVD NSEFQQLLNQGIPVAPHTTEPMLMEYPEAITRLVTGAQRPPDPAPA PLGAPGLPNGLLSGDEDFSSIADMDFSALL |
| 73 | Rta | RDSREGMFLPKPEAGSAISDVFEGREVCQPKRIRPFHPPGSPWAN RPLPASLAPTPTGPVHEPVGSLTPAPVPQPLDPAPAVTPEASHLLE DPDEETSQAVKALREMADTVIPQKEEAAICGQMDLSHPPPRGHLD ELTTTLESMTEDLNLDSPLTPELNEILDTFLNDECLLHAMHISTGLSIF DTSLF |
| 77 | VPR •Short 1 segment underlined •Short 2 segment in bold | DALDDFDLDMLGSDALDDFDLDMLGSDALDDFDLDMLGSDALDDF DLDMLINYPYDVPDYASSSGSPKKKRKVGSQYLPDTDDRHRIEEKR KRTYETFKSIMKKSPFSGPTDPRPPPRRIAVPSRSSASVPKPAPQP YPFTSSLSTINYDEFPTMVFPSGQISQASALAPAPPQVLPQAPAPAP APAMVSALAQAPAPVPVLAPGPPQAVAPPAPKPTQAGEGTLSEAL LQLQFDDEDLGALLGNSTDPAVFTDLASVDNSEFQQLLNQGIPVAP HTTEPMLMEYPEAITRLVTGAQRPPDPAPAPLGAPGLPNGLLSGDE DFSSIADMDFSALLGSGSGSRDSREGMFLPKPEAGSAISDVFEGRE VCQPKRIRPFHPPGSPWANRPLPASLAPTPTGPVHEPVGSLTPAP VPQPLDPAPAVTPEASHLLEDPDEETSQAVKALREMADTVIPQKEE AAICGQMDLSHPPPRGHLDELTTTLESMTEDLNLDSPLTPELNEILD TFLNDECLLHAMHISTGLSIFDTSLF |

Administration

As described herein, the DNA binding proteins of the present disclosure comprise or are attached to a transcriptional activation domain and may be administered to a cell or to a subject to increase expression of Klotho. It will be understood that the DNA binding proteins (and the transcriptional activation domains) of the present disclosure can be administered to the cell or to the subject directly as a protein or indirectly as a nucleic acid. In either case, the DNA binding protein is considered to be administered to the cell or the subject. When administered in the form of a nucleic acid, the nucleic acid may be a RNA which is translated in the cell or the subject, or the nucleic acid may be a DNA which is transcribed and then translated in the cell or the subject. Preferably, the nucleic acid is carried on a viral vector.

In some examples, activity or expression of the DNA binding and the transcriptional activation domain of the present disclosure is inducible. For example, expression of the DNA binding and the transcriptional activation domain may be controlled by an inducible promoter. In some examples, expression of the DNA binding and the transcriptional activation domain may be induced by administration of a small organic molecule such as tetracycline or doxycycline.

In some examples, the DNA binding protein is administered in the form of a DNA molecule comprising the DNA binding protein coding sequence operably connected to a promoter. A promoter can be an inducible promoter (e.g., a heat shock promoter, tetracycline-regulated promoter, steroid-regulated promoter, metal-regulated promoter, estrogen receptor-regulated promoter, etc.). The promoter can be a constitutive promoter (e.g., CMV promoter, UBC promoter). In some cases, the promoter can be a spatially restricted and/or temporally restricted promoter (e.g., a tissue specific promoter, a cell type specific promoter, etc.).

The DNA binding proteins of the present disclosure may be administered to a cell using viral or non-viral delivery vehicles known in the art. Non-viral delivery vehicles suitable for use in the methods of the present disclosure may comprise nanoparticles, positively charged peptides or liposomes. Some exemplary non-viral delivery vehicles are described in Peer and Lieberman, Gene Therapy, 18: 1127-1133 (2011). As previously noted, the DNA binding protein may be administered in the form of a nucleic acid which is transcribed (in the case of DNA) and translated. In some examples, the DNA binding protein may be administered in the form of a mRNA (Patel et al. 2019. Advanced Materials. e1805116).

Methods of delivering zinc finger proteins are also described, for example, in U.S. Pat. Nos. 6,453,242; 6,503,717; 6,534,261; 6,599,692; 6,607,882; 6,689,558; 6,824,978; 6,933,113; 6,979,539; 7,013,219; and 7,163,824.

Non-viral vector delivery systems include DNA plasmids, naked nucleic acid, and nucleic acid complexed with a delivery vehicle such as a liposome or poloxamer. Methods of non-viral delivery of nucleic acids include electroporation, lipofection, microinjection, biolistics, virosomes, liposomes, immunoliposomes, polycation or lipid:nucleic acid conjugates, naked DNA, naked RNA, artificial virions, and agent-enhanced uptake of DNA. Sonoporation using, e.g., the Sonitron 2000 system (Rich-Mar) can also be used for delivery of nucleic acids.

Additional nucleic acid delivery systems include those provided by Amaxa Biosystems (Cologne, Germany), Maxcyte, Inc. (Rockville, Maryland.), BTX Molecular Delivery Systems (Holliston, MA.) and Copernicus Therapeutics Inc, (see for example U.S. Pat. No. 6,008,336). Lipofection is described in e.g., U.S. Pat. Nos. 5,049,386;

4,946,787; and 4,897,355 and lipofection reagents are sold commercially (e.g., Transfectam™ and Lipofectin™ and Lipofectamine™ RNAiMAX). Cationic and neutral lipids that are suitable for efficient receptor recognition lipofection of polynucleotides include those of Feigner, WO 91/17424, WO 91/16024.

The preparation of lipid:nucleic acid complexes, including targeted liposomes such as immunolipid complexes, is well known to one of skill in the art (see, e.g., Crystal, 1995. Science 270:404-410; Blaese et al. 1995. Cancer Gene Ther. 2:291-297; Behr et al. 1994. Bioconjugate Chem. 5:382-389; Remy et al. 1994. Bioconjugate Chem. 5:647-654; Gao et al. 1995. Gene Therapy 2:710-722; Ahmad et al. 1992. Cancer Res. 52:4817-4820; U.S. Pat. Nos. 4,186,183, 4,217,344, 4,235,871, 4,261,975, 4,485,054, 4,501,728, 4,774,085, 4,837,028, and 4,946,787).

Additional methods of delivery include packaging the nucleic acids to be delivered into EnGeneIC delivery vehicles (EDVs). These EDVs are specifically delivered to target tissues using bispecific antibodies where one arm of the antibody has specificity for the target tissue and the other has specificity for the EDV. The antibody brings the EDVs to the target cell surface and then the EDV is brought into the cell by endocytosis. Once in the cell, the contents are released (See MacDiarmid et al. 2009. Nat. Biotech. 27(7): 643).

Several different vector systems may be used for delivery including, but not limited to, plasmid vectors, retroviral vectors, lentiviral vectors, adenovirus vectors, poxvirus vectors, herpesvirus vectors and adeno-associated virus vectors.

Viral Vectors

Viral vectors can be administered directly to a subject (in vivo) or they can be used to treat cells in vitro and the modified cells may then be administered to patients (ex vivo). Suitable viral-based delivery systems may include retroviral, lentivirus, adenoviral, adeno-associated, vaccinia and herpes simplex virus vectors. Integration in the host genome is possible with the retrovirus, lentivirus, and adeno-associated virus gene transfer methods, often resulting in long term expression of the inserted transgene.

The tropism of a retrovirus can be altered by incorporating foreign envelope proteins, expanding the potential target population of target cells. Lentiviral vectors are retroviral vectors that are able to transduce or infect non-dividing cells and typically produce high viral titres. Selection of a retroviral gene transfer system may depend on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the relevant nucleic acid into the target cell to provide transgene expression. Widely used retroviral vectors include those based upon mouse leukemia virus (MuLV), gibbon ape leukemia virus (GaLV), Simian Immunodeficiency virus (SIV), human immunodeficiency virus (HIV), and combinations thereof.

In applications in which transient expression is preferred, adenoviral based systems can be used. Adenoviral based vectors are capable of high transduction efficiency in many cell types and do not require cell division. With such vectors, high titer and high levels of expression have been obtained. This vector can be produced in large quantities in a relatively simple system. Adeno-associated virus (AAV) vectors are also used to transduce cells with target nucleic acids, e.g., in the in vitro production of nucleic acids and peptides, and for in vivo and ex vivo gene therapy procedures.

Packaging cells are used to form virus particles that are capable of infecting a host cell. Such cells include 293 cells, which package adenovirus, and ψ2 cells or PA317 cells, which package retrovirus. Viral vectors used in gene therapy are usually generated by a producer cell line that packages a nucleic acid vector into a viral particle. The vectors typically contain the minimal viral sequences required for packaging and subsequent integration into a host (if applicable), other viral sequences being replaced by an expression cassette encoding the protein to be expressed. The missing viral functions are supplied in trans by the packaging cell line. For example, AAV vectors used in gene therapy often only possess inverted terminal repeat (ITR) sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In many gene therapy applications, it is desirable that the gene therapy vector be delivered with a high degree of specificity to a particular tissue type. Accordingly, a viral vector can be modified to have specificity for a given cell type by expressing a ligand as a fusion protein with a viral coat protein on the outer surface of the virus. The ligand is chosen to have affinity for a receptor known to be present on the cell type of interest.

Gene therapy vectors can be delivered in vivo by administration to a subject, typically by systemic administration (e.g., intravenous, intraperitoneal, intramuscular, subdermal, or intracranial infusion, including direct injection into the brain) or topical application. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

In some examples, the DNA binding protein of the present disclosure is delivered directly in vivo. For example, the DNA binding protein (such as a nucleic acid encoding the DNA binding protein) may be administered directly into the central nervous system (CNS), including but not limited to direct injection into the brain or spinal cord.

In some examples, the compositions of the present disclosure are administered via a route such as, but not limited to, enteral (into the intestine), gastroenteral, epidural (into the dura matter), oral (by way of the mouth), transdermal, peridural, intracerebral (into the cerebrum), intracerebroventricular (into the cerebral ventricles), epicutaneous (application onto the skin), intradermal, (into the skin itself), subcutaneous (under the skin), nasal administration (through the nose), intravenous (into a vein), intravenous bolus, intravenous drip, intraarterial (into an artery), intramuscular (into a muscle), intracardiac (into the heart), intraosseous infusion (into the bone marrow), intrathecal (into the spinal canal), intraperitoneal, (infusion or injection into the peritoneum), intravesical infusion, intravitreal, (through the eye), intracavernous injection (into a pathologic cavity) intracavitary (into the base of the penis), intravaginal administration, intrauterine, extra-amniotic administration, transdermal (diffusion through the intact skin for systemic distribution), transmucosal (diffusion through a mucous membrane), transvaginal, insufflation (snorting), sublingual, sublabial, enema, eye drops (onto the conjunctiva), in ear drops, auricular (in or by way of the ear), buccal (directed toward the cheek), conjunctival, cutaneous, dental (to a tooth or teeth), electro-osmosis, endocervical, endosinusial, endotracheal, extracorporeal, hemodialysis, infiltration, interstitial, intra-abdominal, intra-amniotic, intra-articular, intrabiliary, intrabronchial, intrabursal, intracartilaginous (within a cartilage), intracaudal (within the cauda equine), intracisternal (within the cisterna magna cerebellomedullaris), intracorneal (within the cornea), dental intracornal, intracoronary (within the coronary arteries), intracorporus cavernosum (within the dilatable spaces of the corpus cavernosa of the penis), intradiscal (within a disc), intraductal (within a duct of a gland), intraduodenal (within the duodenum), intradural (within or beneath the dura), intraepidermal (to the epidermis), intraesophageal (to the esophagus), intragastric (within the stomach), intragingival (within the gingivae), intraileal (within the distal portion of the small intestine), intralesional (within or introduced directly to a localized lesion), intraluminal (within a lumen of a tube), intralymphatic (within the lymph), intramedullary (within the marrow cavity of a bone), intrameningeal (within the meninges), intramyocardial (within the myocardium), intraocular (within the eye), intraovarian (within the ovary), intrapericardial (within the pericardium), intrapleural (within the pleura), intraprostatic (within the prostate gland), intrapulmonary (within the lungs or its bronchi), intrasinal (within the nasal or periorbital sinuses), intraspinal (within the vertebral column), intrasynovial (within the synovial cavity of a joint), intratendinous (within a tendon), intratesticular (within the testicle), intrathecal (within the cerebrospinal fluid at any level of the cerebrospinal axis), intrathoracic (within the thorax), intratubular (within the tubules of an organ), intratumor (within a tumor), intratympanic (within the aurus media), intravascular (within a vessel or vessels), intraventricular (within a ventricle), iontophoresis (by means of electric current where ions of soluble salts migrate into the tissues of the body), irrigation (to bathe or flush open wounds or body cavities), laryngeal (directly upon the larynx), nasogastric (through the nose and into the stomach), occlusive dressing technique (topical route administration, which is then covered by a dressing that occludes the area), ophthalmic (to the external eye), oropharyngeal (directly to the mouth and pharynx), parenteral, percutaneous, periarticular, peridural, perineural, periodontal, rectal, respiratory (within the respiratory tract by inhaling orally or nasally for local or systemic effect), retrobulbar (behind the pons or behind the eyeball), intramyocardial (entering the myocardium), soft tissue, subarachnoid, subconjunctival, submucosal, topical, transplacental (through or across the placenta), transtracheal (through the wall of the trachea), transtympanic (across or through the tympanic cavity), ureteral (to the ureter), urethral (to the urethra), vaginal, caudal block, diagnostic, nerve block, biliary perfusion, cardiac perfusion, photopheresis and spinal.

Modes of administration include injection, infusion, instillation, and/or ingestion. "Injection" includes, without limitation, intravenous, intramuscular, intra-arterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In some examples, the route is intravenous. For the delivery of cells, administration by injection or infusion can be made.

Adeno-Associated Virus

A recombinant adeno-associated virus (AAV) vector can be used for delivery. Techniques to produce rAAV particles, in which an AAV genome to be packaged that includes the polynucleotide to be delivered, rep and cap genes, and helper virus functions are provided to a cell are known in the art. Production of rAAV typically prefers that the following components are present within a single cell (denoted herein as a packaging cell): a rAAV genome, AAV rep and cap genes separate from (i.e., not in) the rAAV genome, and helper virus functions. The AAV rep and cap genes can be from any AAV serotype for which recombinant virus can be derived, and can be from a different AAV serotype than the rAAV genome ITRs, including, but not limited to, AAV serotypes described herein. Production of pseudotyped rAAV is disclosed in, for example, international patent application publication number WO 01/83692.

AAV particles packaging polynucleotides encoding DNA binding proteins of the present disclosure can comprise or be derived from any natural or recombinant AAV serotype. According to the present disclosure, the AAV particles can utilize or be based on a serotype selected from any of the following serotypes, and variants thereof including but not limited to AAV1, AAV10, AAV106.1/hu.37, AAV11, AAV114.3/hu.40, AAV12, AAV127.2/hu.41, AAV127.5/hu.42, AAV128.1/hu.43, AAV128.3/hu.44, AAV130.4/hu.48, AAV145.1/hu.53, AAV145.5/hu.54, AAV145.6/hu.55, AAV16.12/hu.11, AAV16.3, AAV16.8/hu.10, AAV161.10/hu.60, AAV161.6/hu.61, AAV1-7/rh.48, AAV1-8/rh.49, AAV2, AAV2.5T, AAV2-15/rh.62, AAV223.1, AAV223.2, AAV223.4, AAV223.5, AAV223.6, AAV223.7, AAV2-3/rh.61, AAV24.1, AAV2-4/rh.50, AAV2-5/rh.51, AAV27.3, AAV29.3/bb.1, AAV29.5/bb.2, AAV2G9, AAV-2-pre-miRNA-101, AAV3, AAV3.1/hu.6, AAV3.1/hu.9, AAV3-11/rh.53, AAV3-3, AAV33.12/hu.17, AAV33.4/hu.15, AAV33.8/hu.16, AAV3-9/rh.52, AAV3a, AAV3b, AAV4, AAV4-19/rh.55, AAV42.12, AAV42-10, AAV42-11, AAV42-12, AAV42-13, AAV42-15, AAV42-1b, AAV42-2, AAV42-3a, AAV42-3b, AAV42-4, AAV42-5a, AAV42-5b, AAV42-6b, AAV42-8, AAV42-aa, AAV43-1, AAV43-12, AAV43-20, AAV43-21, AAV43-23, AAV43-25, AAV43-5, AAV4-4, AAV44.1, AAV44.2, AAV44.5, AAV46.2/hu.28, AAV46.6/hu.29, AAV4-8/r11.64, AAV4-8/rh.64, AAV4-9/rh.54, AAVS, AAV52.1/hu.20, AAV52/hu.19, AAVS-2/rh.58, AAVS-3/rh.57, AAV54.1/hu.21, AAV54.2/hu.22, AAV54.4R/hu.27, AAV54.5/hu.23, AAV54.7/hu.24, AAV58.2/hu.25, AAV6, AAV6.1, AAV6.1.2, AAV6.2, AAV7, AAV7.2, AAV7.3/hu.7, AAV8, AAV-8b, AAV-8h, AAV9, AAV9.11, AAV9.13, AAV9.16, AAV9.24, AAV9.45, AAV9.47, AAV9.61, AAV9.68, AAV9.84, AAV9.9, AAVA3.3, AAVA3.4, AAVA3.5, AAVA3.7, AAV-b, AAVC1, AAVC2, AAVC5, AAVCh.5, AAVCh.5R1, AAVcy.2, AAVcy.3, AAVcy.4, AAVcy.5, AAVCy.5R1, AAVCy.5R2, AAVCy.5R3, AAVCy.5R4, AAVcy.6, AAV-DJ, AAV-DJ8, AAVF3, AAVF5, AAV-h, AAVH-1/hu.1, AAVH2, AAVH-5/hu.3, AAVH6, AAVhE1.1, AAVhER1.14, AAVhEr1.16, AAVhEr1.18, AAVhER1.23, AAVhEr1.35, AAVhEr1.36, AAVhEr1.5, AAVhEr1.7, AAVhEr1.8, AAVhEr2.16, AAVhEr2.29, AAVhEr2.30, AAVhEr2.31, AAVhEr2.36, AAVhEr2.4, AAVhEr3.1, AAVhu.1, AAVhu.10, AAVhu.11, AAVhu.11, AAVhu.12, AAVhu.13, AAVhu.14/9, AAVhu.15, AAVhu.16, AAVhu.17, AAVhu.18, AAVhu.19, AAVhu.2, AAVhu.20, AAVhu.21, AAVhu.22, AAVhu.23.2, AAVhu.24, AAVhu.25, AAVhu.27, AAVhu.28, AAVhu.29, AAVhu.29R, AAVhu.3, AAVhu.31, AAVhu.32, AAVhu.34, AAVhu.35, AAVhu.37, AAVhu.39, AAVhu.4, AAVhu.40, AAVhu.41, AAVhu.42, AAVhu.43, AAVhu.44, AAVhu.44R1, AAVhu.44R2, AAVhu.44R3, AAVhu.45, AAVhu.46, AAVhu.47, AAVhu.48, AAVhu.48R1, AAVhu.48R2, AAVhu.48R3, AAVhu.49, AAVhu.5, AAVhu.51, AAVhu.52, AAVhu.53, AAVhu.54, AAVhu.55, AAVhu.56, AAVhu.57, AAVhu.58, AAVhu.6, AAVhu.60, AAVhu.61, AAVhu.63, AAVhu.64, AAVhu.66, AAVhu.67, AAVhu.7, AAVhu.8, AAVhu.9, AAVhu.t 19, AAVLG-10/rh.40, AAVLG-4/rh.38, AAVLG-9/hu.39, AAVLG-9/hu.39, AAV-LK01, AAV-LK02, AAVLK03, AAV-LK03, AAV-LK04, AAV-LK05, AAV-LK06, AAV-LK07, AAV-LK08, AAV-LK09, AAV-LK10, AAV-LK11, AAV-LK12, AAV-LK13, AAV-LK14, AAV-LK15, AAV-LK17, AAV-LK18, AAV-LK19, AAVN721-8/rh.43, AAV-PAEC, AAV-PAEC11, AAV-PAEC12, AAV-PAEC2, AAV-PAEC4, AAV-PAEC6, AAV-PAEC7, AAV-PAEC8, AAVpi.1, AAVpi.2, AAVpi.3, AAVrh.10, AAVrh.12, AAVrh.13, AAVrh.13R, AAVrh.14, AAVrh.17, AAVrh.18, AAVrh.19, AAVrh.2, AAVrh.20, AAVrh.21, AAVrh.22, AAVrh.23, AAVrh.24, AAVrh.25, AAVrh.2R, AAVrh.31, AAVrh.32, AAVrh.33, AAVrh.34, AAVrh.35, AAVrh.36, AAVrh.37, AAVrh.37R2, AAVrh.38, AAVrh.39, AAVrh.40, AAVrh.43, AAVrh.44, AAVrh.45, AAVrh.46, AAVrh.47, AAVrh.48, AAVrh.48, AAVrh.48.1, AAVrh.48.1.2, AAVrh.48.2, AAVrh.49, AAVrh.50, AAVrh.51, AAVrh.52, AAVrh.53, AAVrh.54, AAVrh.55, AAVrh.56, AAVrh.57, AAVrh.58, AAVrh.59, AAVrh.60, AAVrh.61, AAVrh.62, AAVrh.64, AAVrh.64R1, AAVrh.64R2, AAVrh.65, AAVrh.67, AAVrh.68, AAVrh.69, AAVrh.70, AAVrh.72, AAVrh.73, AAVrh.74, AAVrh.8, AAVrh.8R, AAVrh8R, AAVrh8R A586R mutant, AAVrh8R R533A mutant, BAAV, BNP61 AAV, BNP62 AAV, BNP63 AAV, bovine AAV, caprine AAV, Japanese AAV 10, true type AAV (ttAAV), UPENN AAV 10, AAV-LK16, AAAV, AAV Shuffle 100-1, AAV Shuffle 100-2, AAV Shuffle 100-3, AAV Shuffle 100-7, AAV Shuffle 10-2, AAV Shuffle 10-6, AAV Shuffle 10-8, AAV SM 100-10, AAV SM 100-3, AAV SM 10-1, AAV SM 10-2, and/or AAV SM 10-8.

In some examples, the AAV serotype can be, or have, a mutation in the AAV9 sequence as described by N Pulicherla et al. (Molecular Therapy 2011. 19(6):1070-1078), such as but not limited to, AAV9.9, AAV9.11, AAV9.13, AAV9.16, AAV9.24, AAV9.45, AAV9.47, AAV9.61, AAV9.68, AAV9.84.

In some examples, the AAV serotype can be, or have, a sequence as described in United States Patent No. US 6156303, such as, but not limited to, AAV3B (SEQ ID NO: 1 and 10 of US 6156303), AAV6 (SEQ ID NO: 2, 7 and 11 of US 6156303), AAV2 (SEQ ID NO: 3 and 8 of US 6156303), AAV3A (SEQ ID NO: 4 and 9, of US 6156303), or derivatives thereof.

In some examples, the serotype can be AAVDJ or a variant thereof, such as AAVDJ8 (or AAV-DJ8), as described by Grimm et al. (Journal of Virology 82(12): 5887-5911 (2008)). The amino acid sequence of AAVDJ8 can comprise two or more mutations in order to remove the heparin binding domain (HBD). As a non-limiting example, the AAV-DJ sequence described as SEQ ID NO: 1 in U.S. Pat. No. 7,588,772, can comprise two mutations: (1) R587Q where arginine (R; Arg) at amino acid 587 is changed to glutamine (Q; Gln) and (2) R590T where arginine (R; Arg) at amino acid 590 is changed to threonine (T; Thr). As another non-limiting example, the sequence may comprise three mutations: (1) K406R where lysine (K; Lys) at amino acid 406 is changed to arginine (R; Arg), (2) R587Q where arginine (R; Arg) at amino acid 587 is changed to glutamine (Q; Gln) and (3) R590T where arginine (R; Arg) at amino acid 590 is changed to threonine (T; Thr).

In some examples, the AAV serotype can be, or have, a sequence as described in International Publication No. WO2015121501, such as, but not limited to, true type AAV (ttAAV) (SEQ ID NO: 2 of WO2015121501), "UPenn AAV10" (SEQ ID NO: 8 of WO2015121501), "Japanese AAV10" (SEQ ID NO: 9 of WO2015121501), or variants thereof.

According to the present disclosure, AAV capsid serotype selection or use can be from a variety of species. In one example, the AAV can be an avian AAV (AAAV). The AAAV serotype can be, or have, a sequence as described in U.S Pat. No. 9,238,800, such as, but not limited to, AAAV (SEQ ID NO: 1, 2, 4, 6, 8, 10, 12, and 14 of U.S. Pat. No. 9,238,800), or variants thereof.

In some examples, the AAV can be a bovine AAV (BAAV). The BAAV serotype can be, or have, a sequence as described in U.S. Pat. No. 9,193,769, such as, but not limited to, BAAV (SEQ ID NO: 1 and 6 of U.S. Pat. No. 9,193,769), or variants thereof. The BAAV serotype can be or have a sequence as described in U.S. Pat. No. 7,427,396, such as, but not limited to, BAAV (SEQ ID NO: 5 and 6 of U.S. Pat. No. 7,427,396), or variants thereof.

In some examples, the AAV can be a caprine AAV. The caprine AAV serotype can be, or have, a sequence as described in U.S. Pat. No. 7,427,396, such as, but not limited to, caprine AAV (SEQ ID NO: 3 of U.S. Pat. No. 7,427,396), or variants thereof.

In other examples the AAV can be engineered as a hybrid AAV from two or more parental serotypes. In one example, the AAV can be AAV2G9 which comprises sequences from AAV2 and AAV9. The AAV2G9 AAV serotype can be, or have, a sequence as described in United States Patent Publication No. US20160017005.

In some examples, the AAV can be a serotype generated by the AAV9 capsid library with mutations in amino acids 390-627 (VP1 numbering) as described by Pulicherla et al. (Molecular Therapy. 2011. 19(6):1070-1078). The serotype and corresponding nucleotide and amino acid substitutions can be, but is not limited to, AAV9.1 (G1594C; D532H), AAV6.2 (T1418A and T1436X; V473D and 1479K), AAV9.3 (T1238A; F413Y), AAV9.4 (T1250C and A1617T; F417S), AAV9.5 (A1235G, A1314T, A1642G, C1760T; Q412R, T548A, A587V), AAV9.6 (T1231A; F411I), AAV9.9 (G1203A, G1785T; W595C), AAV9.10 (A1500G, T1676C; M559T), AAV9.11 (A1425T, A1702C, A1769T; T568P, Q590L), AAV9.13 (A1369C, A1720T; N457H, T574S), AAV9.14 (T1340A, T1362C, T1560C, G1713A; L447H), AAV9.16 (A1775T; Q592L), AAV9.24 (T1507C, T1521G; W503R), AAV9.26 (A1337G, A1769C; Y446C, Q590P), AAV9.33 (A1667C; D556A), AAV9.34 (A1534G, C1794T; N512D), AAV9.35 (A1289T, T1450A, C1494T, A1515T, C1794A, G1816A; Q430L, Y484N, N98K, V606I), AAV9.40 (A1694T, E565V), AAV9.41 (A1348T, T1362C; T450S), AAV9.44 (A1684C, A1701T, A1737G; N562H, K567N), AAV9.45 (A1492T, C1804T; N498Y, L602F), AAV9.46 (G1441C, T1525C, T1549G; G481R, W509R, L517V), 9.47 (G1241A, G1358A, A1669G, C1745T; S414N, G453D, K557E, T5821), AAV9.48 (C1445T, A1736T; P482L, Q579L), AAV9.50 (A1638T, C1683T, T1805A; Q546H, L602H), AAV9.53 (G1301A, A1405C, C1664T, G1811T; R134Q, S469R, A555V, G604V), AAV9.54 (C1531A, T1609A; L511I, L537M), AAV9.55 (T1605A; F535L), AAV9.58 (C1475T, C1579A; T492I, H527N), AAV.59 (T1336C; Y446H), AAV9.61 (A1493T; N498I), AAV9.64 (C1531A, A1617T; L511I), AAV9.65 (C1335T, T1530C, C1568A; A523D), AAV9.68 (C1510A; P504T), AAV9.80 (G1441A,;G481R), AAV9.83

(C1402A, A1500T; P468T, E500D), AAV9.87 (T1464C, T1468C; S490P), AAV9.90 (A1196T; Y399F), AAV9.91 (T1316G, A1583T, C1782G, T1806C; L439R, K528I), AAV9.93 (A1273G, A1421G, A1638C, C1712T, G1732A, A1744T, A1832T; S425G, Q474R, Q546H, P571L, G578R, T582S, D611V), AAV9.94 (A1675T; M559L) and AAV9.95 (T1605A; F535L).

In some examples, the AAV can be a serotype comprising at least one AAV capsid CD8+ T-cell epitope. As a non-limiting example, the serotype can be AAV1, AAV2 or AAV8. In some examples, the AAV can be a variant, such as PHP.A or PHP.B as described in Deverman. 2016. Nature Biotechnology. 34(2): 204-209.

A method of generating a packaging cell involves creating a cell line that stably expresses all of the necessary components for AAV particle production. For example, a plasmid (or multiple plasmids) comprising a rAAV genome lacking AAV rep and cap genes, AAV rep and cap genes separate from the rAAV genome, and a selectable marker, such as a neomycin resistance gene, are integrated into the genome of a cell. AAV genomes have been introduced into bacterial plasmids by procedures such as GC tailing (Samulski et al., 1982, Proc. Natl. Acad. S6. USA, 79:2077-2081), addition of synthetic linkers containing restriction endonuclease cleavage sites (Laughlin et al., 1983, Gene, 23:65-73) or by direct, blunt-end ligation (Senapathy & Carter, 1984, J. Biol. Chem., 259:4661-4666). The packaging cell line can then be infected with a helper virus, such as adenovirus. The advantages of this method are that the cells are selectable and are suitable for large-scale production of rAAV. Other examples of suitable methods employ adenovirus or baculovirus, rather than plasmids, to introduce rAAV genomes and/or rep and cap genes into packaging cells.

General principles of rAAV production are reviewed in, for example, Carter, 1992, Current Opinions in Biotechnology, 1533-539; and Muzyczka, 1992, Curr. Topics in Microbial. and Immunol., 158:97-129). Various approaches are described in Ratschin et al., Mol. Cell. Biol. 4:2072 (1984); Hermonat et al., Proc. Natl. Acad. Sci. USA, 81:6466 (1984); Tratschin et al., Mol. Cell. Biol. 5:3251 (1985); McLaughlin et al., J. Virol., 62:1963 (1988); and Lebkowski et al., 1988 Mol. Cell. Biol., 7:349 (1988). Samulski et al. (1989, J. Virol., 63:3822-3828); U.S. Pat. No. 5,173,414; WO 95/13365 and corresponding U.S. Pat. No. 5,658.776; WO 95/13392; WO 96/17947; PCT/US98/18600; WO 97/09441 (PCT/US96/14423); WO 97/08298 (PCT/US96/13872); WO 97/21825 (PCT/US96/20777); WO 97/06243 (PCT/FR96/01064); WO 99/11764; Perrin et al. (1995) Vaccine 13:1244-1250; Paul et al. (1993) Human Gene Therapy 4:609-615; Clark et al. (1996) Gene Therapy 3:1124-1132; U.S. Pat. No. 5,786,211; U.S. Pat. No. 5,871, 982; and U.S. Pat. No. 6,258,595.

AAV vector serotypes can be matched to target cell types. For example, the following exemplary cell types can be transduced by the indicated AAV serotypes among others:

TABLE 6

| Tissue/Cell Type | Serotype |
| --- | --- |
| Liver | AAV3, AA5, AAV8, AAV9 |
| Skeletal muscle | AAV1, AAV7, AAV6, AAV8, AAV9 |
| Central nervous system | AAV1, AAV4, AAV5, AAV8, AAV9 |
| RPE | AAV5, AAV4, AAV2, AAV8, AAV9 AAVrh8r |
| Photoreceptor cells | AAV5, AAV8, AAV9, AAVrh8R |
| Lung | AAV9, AAV5 |
| Heart | AAV8 |

TABLE 6-continued

| Tissue/Cell Type | Serotype |
| --- | --- |
| Pancreas | AAV8 |
| Kidney | AAV2, AAV8 |

In addition to adeno-associated viral vectors, other viral vectors can be used. Such viral vectors include, but are not limited to, lentivirus, alphavirus, enterovirus, pestivirus, baculovirus, herpesvirus, Epstein Barr virus, papovavirus, poxvirus, vaccinia virus, and herpes simplex virus.

Lentivirus

In some examples, lentiviral vectors or particles can be used as delivery vehicles. Lentiviruses are a subgroup of the Retroviridae family of viruses. Lentiviral particles are able to integrate their genetic material into the genome of a target/host cell. Examples of lentivirus include the Human Immunodeficiency Viruses: HIV-1 and HIV-2, Jembrana Disease Virus (JDV), equine infectious anemia virus (EIAV), equine infectious anemia virus, visna-maedi and caprine arthritis encephalitis virus (CAEV), the Simian Immunodeficiency Virus (SIV), feline immunodeficiency virus (FIV), bovine immunodeficiency virus (BIV). LVs are capable of infecting both dividing and non-dividing cells due to their ability to pass through a target cell's intact nuclear membrane (Greenberg et al., University of Berkeley, California; 2006). Lentiviral particles that form the gene delivery vehicle are generally replication defective and are generated by attenuating the HIV virulence genes. For example, the genes Vpu, Vpr, Nef, Env, and Tat are excised making the vector biologically safe. Lentiviral vehicles, for example, derived from HIV-1/HIV-2 can mediate the efficient delivery, integration and long-term expression of transgenes into non-dividing cells.

In order to produce a lentivirus that is capable of infecting host cells, three types of vectors should be co-expressed in virus producing cells: a backbone vector containing the transgene of interests and self-inactivating 3'-LTR regions, one construct expressing viral structure proteins, and one vector encoding vesicular stomatitis virus glycoprotein (VSVG) for encapsulation (Naldini, L. et al., Science 1996; 272, 263-267). Separation of the Rev gene from other structural genes further increases the biosafety by reducing the possibility of reverse recombination. Cell lines that can be used to produce high-titer lentiviral particles may include, but are not limited to 293T cells, 293FT cells, and 293SF-3F6 cells (Witting et al., Human Gene Therapy, 2012; 23: 243-249; Ansorge et al., Journal of Genetic Medicine, 2009; 11: 868-876).

Methods for generating recombinant lentiviral particles are discussed in the art, for example, WO 2013076309 (PCT/EP2012/073645); WO 2009153563 (PCT/GB2009/001527); U.S. Pat. Nos.: 7,629,153; and 6,808,905.

Treatments

The present disclosure provides methods of treating a neurological disorder in a subject the method comprising administering to the subject a therapeutically effective amount of a DNA binding protein comprising or attached to a transcriptional activation domain wherein the DNA binding protein binds to a target sequence within or near a Klotho gene in the subject and thereby increases expression of the Klotho gene. The neurological disorder may be associated with memory loss, psychological dysfunction, stress, bio-polar disorder, epilepsy, dementia (eg, post stroke dementia, post-traumatic dementia, senile dementia), Alzheimer's disease, Parkinson's disease, Huntington's disease, Creutzfeldt-Jakob disease, ataxia telangiectasia, craniocerebral trauma, amyotrophic lateral sclerosis, depression, schizophrenia, multiple sclerosis, myelin-related disease, oxidative stress, neurogenic decline or neurodegeneration. Symptoms of neurological disorders may include memory loss, anxiety, depression, insomnia, disorientation, irrational fear, decline of motor skills or locomotor activity, neophobia, apathy, agitation, tremors, loss of balance, irritability or agoraphobia.

The method may further comprise administering to the subject an active agent suitable for the treatment of a neurological disorder such as donepezil hydrochloride, memantine, rivastigmine, ligustilide, aripiprazole, asenapine, cariprazine, clozapine, lurasidone, olanzapine, quetiapine, risperidone, ziprasidone, xenazine, tetrabenazine, baclofen, lioresal, kemstro, deutetrabenazine, austedo, cannabis extract, a cannabinoid or cannabinol, an antidepressant, memantine, a cholinesterase inhibitor, an antipsychotic, antioxidants, levodopa, carbidopa, trazodone or dibenzoylmethane. Those skilled in the art will be aware of other active agents that may be suitable for treatment of neurological disorders.

The present disclosure also provides a method of enhancing cognitive ability in a subject the method comprising administering to the subject a therapeutically effective amount of a DNA binding protein comprising or attached to a transcriptional activation domain wherein the DNA binding protein binds to a target sequence within or near a Klotho gene in the subject and thereby increases expression of the Klotho gene. For example, the method may enhance memory or learning in the subject.

Klotho also plays important regulatory and protective roles in the kidney. In that regard, the present disclosure provides a method of treating renal dysfunction in a subject the method comprising administering to the subject a therapeutically effective amount of a DNA binding protein comprising or attached to a transcriptional activation domain wherein the DNA binding protein binds to a target sequence within or near a Klotho gene in the subject and thereby increases expression of the Klotho gene.

Studies have also shown that Klotho plays important roles in regulating fertility. In that regard, the present disclosure provides a method of treating infertility in a subject the method comprising administering to the subject a therapeutically effective amount of a DNA binding protein comprising or attached to a transcriptional activation domain wherein the DNA binding protein binds to a target sequence within or near a Klotho gene in the subject and thereby increases expression of the Klotho gene.

Klotho protein has been identified as a regulator of various tumorigenesis and cancer signalling pathways. In that regard, the present disclosure provides methods for treating cancer in a subject the method comprising administering to the subject a therapeutically effective amount of a DNA binding protein comprising or attached to a transcriptional activation domain wherein the DNA binding protein binds to a target sequence within or near a Klotho gene in the subject and thereby increases expression of the Klotho gene. In certain examples the cancer is mediated by IGF-1, WNT, bFGF or TGF-$\beta$. The cancer may be colon cancer, prostate cancer, lung cancer, cervical cancer, pancreatic cancer, ovarian cancer or breast cancer. Further non-limiting examples of cancer include leukemias (e.g., acute leukemia, acute lymphocytic leukemia, acute myelocytic leukemia, acute myeloblastic leukemia, acute promyelocytic leukemia, acute myclomonocytic leukemia, acute monocytic leukemia, acute erythroleukemia, chronic leukemia, chronic myelocytic leukemia, chronic lymphocytic leukemia), polycythemia vera, lymphoma (Hodgkin's disease, non-Hodgkin's disease), Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, Squamous cell carcinoma, basal cell carcinoma, adenocarcinoma, Sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, nile duct carcinoma, choriocarcinoma, seminoma, embryonal carcinoma, Wilm's tumor, cervical cancer, uterine cancer, testicular cancer, lung carcinoma, Small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodenroglioma, Schwannoma, meningioma, melanoma, neuroblastoma, and retinoblastoma). In some examples, the cancer is metastatic cancer.

The present disclosure also provides methods of suppressing tumorigenesis, such as breast tumorigenesis or pancreatic tumorigenesis in a subject the method comprising administering to the subject a therapeutically effective amount of a DNA binding protein comprising or attached to a transcriptional activation domain wherein the DNA binding protein binds to a target sequence within or near a Klotho gene in the subject and thereby increases expression of the Klotho gene.

The present disclosure also provides methods for treating an age-related condition in a subject the method comprising administering to the subject a therapeutically effective amount of a DNA binding protein comprising or attached to a transcriptional activation domain wherein the DNA binding protein binds to a target sequence within or near a Klotho gene in the subject and thereby increases expression of the Klotho gene. The age-related condition may be sarcopenia, skin atrophy, muscle wasting, brain atrophy, atherosclerosis, arteriosclerosis, pulmonary emphysema, osteoporosis, osteoarthritis, immunologic incompetence, high blood pressure, dementia, Huntington's disease, Alzheimer's disease, cataracts, age-related macular degeneration, prostate cancer, stroke, memory loss, wrinkles, impaired kidney function or hearing loss.

The present disclosure also provides methods for treating a muscular disorder such as muscle atrophy or muscular dystrophy (eg, duchene muscular dystrophy) in a subject the method comprising administering to the subject a therapeutically effective amount of a DNA binding protein comprising or attached to a transcriptional activation domain wherein the DNA binding protein binds to a target sequence within or near a Klotho gene in the subject and thereby increases expression of the Klotho gene. Muscle atrophy is associated with numerous neuromuscular, metabolic, immunological and neurological disorders and diseases as well as starvation, nutritional deficiency, metabolic stress, diabetes, aging, muscular dystrophy or myopathy. Symptoms include a decline in skeletal muscle tissue mass. In human males, muscle mass declines by one-third between the ages of 50 and 80. Some molecular features of muscle atrophy include the upregulation of ubiquitin ligases, and the loss of myofibrillar proteins (Furuno et al. 1990. J. Biol. Chem. 265:

8550-8557). The degradation of these proteins can be detected, eg, by measuring 3-methyl-histidine production, which is a specific component of actin, and in certain muscles of myosin. Release of creatine kinase can also be indicative.

The present disclosure also provides methods for treating a metabolic disorder in a subject the method comprising administering to the subject a therapeutically effective amount of a DNA binding protein comprising or attached to a transcriptional activation domain wherein the DNA binding protein binds to a target sequence within or near a Klotho gene in the subject and thereby increases expression of the Klotho gene.

Dosages may vary with the type and severity of the condition to be treated, and may include single or multiple dosses. Specific dosage regimens may be adjusted over time according to the individual need and the professional judgment of the practitioner administering the composition. When administered to a human subject, the dosage regimen may vary depending on a variety of factors including the type and severity of the condition, the age, sex, weight or medical condition of the subject and the route of administration.

The compositions described herein may be administered over a period of hours, days, weeks, or months, depending on several factors, including the severity of the condition being treated, whether a recurrence is considered likely, etc. The administration may be constant, eg, constant infusion over a period of hours, days, weeks, months, etc. Alternatively, the administration may be intermittent, eg, once per day over a period of days, once per hour over a period of hours, or any other such schedule as deemed suitable.

Compositions and Methods of the Disclosure

The present disclosure provides a composition, Composition 1, which comprises an isolated or recombinant DNA binding protein comprising or attached to a transcriptional activation domain wherein the DNA binding protein binds to a target sequence within or near a Klotho gene.

In another composition, Composition 2, there is provided the composition of Composition 1 wherein the target sequence is located within a region between the Klotho gene translation start site and 4000 nucleotides upstream of the Klotho gene translation start site.

In another composition, Composition 3, there is provided the composition of Composition 2 wherein the target sequence is located within a region between the Klotho gene translation start site and 350 nucleotides upstream of the Klotho gene translation start site.

In another composition, Composition 4, there is provided the composition of Composition 3 wherein the target sequence is located within a region between 40 nucleotides and 300 nucleotides upstream of the Klotho gene translation start site.

In another composition, Composition 5, there is provided the composition of any one of Compositions 1 to 4 wherein the target sequence comprises:
  the sequence set forth in SEQ ID NO. 60;
  the sequence set forth in SEQ ID NO. 61; or
  the sequence set forth in SEQ ID NO. 62.

In another composition, Composition 6, there is provided the composition of any one of Compositions 1 to 4 wherein the target sequence comprises at least 9 contiguous nucleotides from:
  the sequence set forth in SEQ ID NO. 63;
  the sequence set forth in SEQ ID NO. 64;
  the sequence set forth in SEQ ID NO. 65;
  the sequence set forth in SEQ ID NO. 66;
  the sequence set forth in SEQ ID NO. 67;
  the sequence set forth in SEQ ID NO. 68;
  the sequence set forth in SEQ ID NO. 69; or
  the sequence set forth in SEQ ID NO. 70

In another composition, Composition 7, there is provided the composition of Composition 6 wherein the target sequence comprises:
  the sequence set forth in SEQ ID NO. 63;
  the sequence set forth in SEQ ID NO. 64;
  the sequence set forth in SEQ ID NO. 65;
  the sequence set forth in SEQ ID NO. 66;
  the sequence set forth in SEQ ID NO. 67;
  the sequence set forth in SEQ ID NO. 68;
  the sequence set forth in SEQ ID NO. 69; or
  the sequence set forth in SEQ ID NO. 70.

In another composition, Composition 8, there is provided the composition of Composition 7 wherein the target sequence comprises:
  the sequence set forth in SEQ ID NO. 64; or
  the sequence set forth in SEQ ID NO. 62.

In another composition, Composition 9, there is provided the composition of any one of Compositions 1 to 8 wherein the DNA binding protein is a zinc finger protein.

In another composition, Composition 10, there is provided the composition of Composition 9 wherein the zinc finger protein comprises:
  a zinc finger comprising the sequence set forth in SEQ ID NO. 17, a zinc finger comprising the sequence set forth in SEQ ID NO. 16 and a zinc finger comprising the sequence set forth in SEQ ID NO. 11;
  a zinc finger comprising the sequence set forth in SEQ ID NO. 18, a zinc finger comprising the sequence set forth in SEQ ID NO. 16 and a zinc finger comprising the sequence set forth in SEQ ID NO. 11; or
  a zinc finger comprising the sequence set forth in SEQ ID NO. 18, a zinc finger comprising the sequence set forth in SEQ ID NO. 16 and a zinc finger comprising the sequence set forth in SEQ ID NO. 3.

In another composition, Composition 11, there is provided the composition of Composition 9 or Composition 10 wherein the zinc finger protein comprises:
  a ZF1 zinc finger comprising the sequence set forth in SEQ ID NO. 1, a ZF2 zinc finger comprising the sequence set forth in SEQ ID NO. 2, a ZF3 zinc finger comprising the sequence set forth in SEQ ID NO. 3, a ZF4 zinc finger comprising the sequence set forth in SEQ ID NO. 4, a ZF5 zinc finger comprising the sequence set forth in SEQ ID NO. 5 and a ZF6 zinc finger comprising the sequence set forth in SEQ ID NO. 6;
  a ZF1 zinc finger comprising the sequence set forth in SEQ ID NO. 7, a ZF2 zinc finger comprising the sequence set forth in SEQ ID NO. 8, a ZF3 zinc finger comprising the sequence set forth in SEQ ID NO. 9, a ZF4 zinc finger comprising the sequence set forth in SEQ ID NO. 7, a ZF5 zinc finger comprising the sequence set forth in SEQ ID NO. 10, a ZF6 zinc finger comprising the sequence set forth in SEQ ID NO. 11, a ZF7 zinc finger comprising the sequence set forth in SEQ ID NO. 12, a ZF8 zinc finger comprising the sequence set forth in SEQ ID NO. 13, a ZF9 zinc finger comprising the sequence set forth in SEQ ID NO. 14 and a ZF10 zinc finger comprising the sequence set forth in SEQ ID NO. 6;

a ZF1 zinc finger comprising the sequence set forth in SEQ ID NO. 15, a ZF2 zinc finger comprising the sequence set forth in SEQ ID NO. 16, a ZF3 zinc finger comprising the sequence set forth in SEQ ID NO. 17, a ZF4 zinc finger comprising the sequence set forth in SEQ ID NO. 16, a ZF5 zinc finger comprising the sequence set forth in SEQ ID NO. 11, a ZF6 zinc finger comprising the sequence set forth in SEQ ID NO. 11 and a ZF7 zinc finger comprising the sequence set forth in SEQ ID NO. 1;

a ZF1 zinc finger comprising the sequence set forth in SEQ ID NO. 11, a ZF2 zinc finger comprising the sequence set forth in SEQ ID NO. 1, a ZF3 zinc finger comprising the sequence set forth in SEQ ID NO. 18, a ZF4 zinc finger comprising the sequence set forth in SEQ ID NO. 16, a ZF5 zinc finger comprising the sequence set forth in SEQ ID NO. 11, a ZF6 zinc finger comprising the sequence set forth in SEQ ID NO. 19 and a ZF7 zinc finger comprising the sequence set forth in SEQ ID NO. 12;

a ZF1 zinc finger comprising the sequence set forth in SEQ ID NO. 8, a ZF2 zinc finger comprising the sequence set forth in SEQ ID NO. 16, a ZF3 zinc finger comprising the sequence set forth in SEQ ID NO. 18, a ZF4 zinc finger comprising the sequence set forth in SEQ ID NO. 16, a ZF5 zinc finger comprising the sequence set forth in SEQ ID NO. 3, a ZF6 zinc finger comprising the sequence set forth in SEQ ID NO. 8 and a ZF7 zinc finger comprising the sequence set forth in SEQ ID NO. 3;

a ZF1 zinc finger comprising the sequence set forth in SEQ ID NO. 17, a ZF2 zinc finger comprising the sequence set forth in SEQ ID NO. 13, a ZF3 zinc finger comprising the sequence set forth in SEQ ID NO. 13, a ZF4 zinc finger comprising the sequence set forth in SEQ ID NO. 9, a ZF5 zinc finger comprising the sequence set forth in SEQ ID NO. 17 and a ZF6 zinc finger comprising the sequence set forth in SEQ ID NO. 9;

a ZF1 zinc finger comprising the sequence set forth in SEQ ID NO. 20, a ZF2 zinc finger comprising the sequence set forth in SEQ ID NO. 21, a ZF3 zinc finger comprising the sequence set forth in SEQ ID NO. 22, a ZF4 zinc finger comprising the sequence set forth in SEQ ID NO. 19, a ZF5 zinc finger comprising the sequence set forth in SEQ ID NO. 12 and a ZF6 zinc finger comprising the sequence set forth in SEQ ID NO. 17; or a ZF1 zinc finger comprising the sequence set forth in SEQ ID NO. 20, a ZF2 zinc finger comprising the sequence set forth in SEQ ID NO. 21, a ZF3 zinc finger comprising the sequence set forth in SEQ ID NO. 22, a ZF4 zinc finger comprising the sequence set forth in SEQ ID NO. 8, a ZF5 zinc finger comprising the sequence set forth in SEQ ID NO. 3 and a ZF6 zinc finger comprising the sequence set forth in SEQ ID NO. 9.

In another composition, Composition 12, there is provided the composition of any one of Compositions 9 to 11 wherein the zinc finger protein comprises:

a ZF1 zinc finger comprising the sequence set forth in SEQ ID NO. 7, a ZF2 zinc finger comprising the sequence set forth in SEQ ID NO. 8, a ZF3 zinc finger comprising the sequence set forth in SEQ ID NO. 9, a ZF4 zinc finger comprising the sequence set forth in SEQ ID NO. 7, a ZF5 zinc finger comprising the sequence set forth in SEQ ID NO. 10, a ZF6 zinc finger comprising the sequence set forth in SEQ ID NO. 11, a ZF7 zinc finger comprising the sequence set forth in SEQ ID NO. 12, a ZF8 zinc finger comprising the sequence set forth in SEQ ID NO. 13, a ZF9 zinc finger comprising the sequence set forth in SEQ ID NO. 14 and a ZF10 zinc finger comprising the sequence set forth in SEQ ID NO. 6;

a ZF1 zinc finger comprising the sequence set forth in SEQ ID NO. 8, a ZF2 zinc finger comprising the sequence set forth in SEQ ID NO. 16, a ZF3 zinc finger comprising the sequence set forth in SEQ ID NO. 18, a ZF4 zinc finger comprising the sequence set forth in SEQ ID NO. 16, a ZF5 zinc finger comprising the sequence set forth in SEQ ID NO. 3, a ZF6 zinc finger comprising the sequence set forth in SEQ ID NO. 8 and a ZF7 zinc finger comprising the sequence set forth in SEQ ID NO. 3;

a ZF1 zinc finger comprising the sequence set forth in SEQ ID NO. 20, a ZF2 zinc finger comprising the sequence set forth in SEQ ID NO. 21, a ZF3 zinc finger comprising the sequence set forth in SEQ ID NO. 22, a ZF4 zinc finger comprising the sequence set forth in SEQ ID NO. 19, a ZF5 zinc finger comprising the sequence set forth in SEQ ID NO. 12 and a ZF6 zinc finger comprising the sequence set forth in SEQ ID NO. 17; or a ZF1 zinc finger comprising the sequence set forth in SEQ ID NO. 20, a ZF2 zinc finger comprising the sequence set forth in SEQ ID NO. 21, a ZF3 zinc finger comprising the sequence set forth in SEQ ID NO. 22, a ZF4 zinc finger comprising the sequence set forth in SEQ ID NO. 8, a ZF5 zinc finger comprising the sequence set forth in SEQ ID NO. 3 and a ZF6 zinc finger comprising the sequence set forth in SEQ ID NO. 9.

In another composition, Composition 13, there is provided the composition of any one of Compositions 9 to 12 wherein the zinc finger protein comprises:

a zinc finger domain comprising the sequence set forth in SEQ ID NO. 41, or a sequence having at least about 80% identity to SEQ ID NO. 41;

a zinc finger domain comprising the sequence set forth in SEQ ID NO. 42, or a sequence having at least about 80% identity to SEQ ID NO. 42;

a zinc finger domain comprising the sequence set forth in SEQ ID NO. 43, or a sequence having at least about 80% identity to SEQ ID NO. 43;

a zinc finger domain comprising the sequence set forth in SEQ ID NO. 44, or a sequence having at least about 80% identity to SEQ ID NO. 44;

a zinc finger domain comprising the sequence set forth in SEQ ID NO. 45, or a sequence having at least about 80% identity to SEQ ID NO. 45; or a zinc finger domain comprising the sequence set forth in SEQ ID NO. 46, or a sequence having at least about 80% identity to SEQ ID NO. 46.

In another composition, Composition 14, there is provided the composition of any one of Compositions 1 to 13 wherein the DNA binding protein competes for binding to the target sequence with a zinc finger protein comprising:

a zinc finger domain comprising the sequence set forth in SEQ ID NO. 41;

a zinc finger domain comprising the sequence set forth in SEQ ID NO. 42;

a zinc finger domain comprising the sequence set forth in SEQ ID NO. 43;

a zinc finger domain comprising the sequence set forth in SEQ ID NO. 44;
a zinc finger domain comprising the sequence set forth in SEQ ID NO. 45; or
a zinc finger domain comprising the sequence set forth in SEQ ID NO. 46.

In another composition, Composition 15, there is provided the composition of any one of Compositions 1 to 14 wherein the DNA binding protein competes for binding to the target sequence with a zinc finger protein comprising or consisting of:
the sequence set forth in SEQ ID NO. 29;
the sequence set forth in SEQ ID NO. 30;
the sequence set forth in SEQ ID NO. 32;
the sequence set forth in SEQ ID NO. 33;
the sequence set forth in SEQ ID NO. 34;
the sequence set forth in SEQ ID NO. 36;
the sequence set forth in SEQ ID NO. 37; or
the sequence set forth in SEQ ID NO. 39.

In another composition, Composition 16, there is provided the composition of any one of Compositions 1 to 15 wherein the transcriptional activation domain is selected from the group consisting of VP16, or a plurality thereof, VP64, VP160, p65, MyoD1, HSF1, RTA, TET3CD, p300 and SET7/9.

In another composition, Composition 17, there is provided the composition of any one of Compositions 1 to 16 wherein the DNA binding protein comprises or is attached to more than one transcriptional activation domain.

In another composition, Composition 18, there is provided the composition of Composition 17 wherein the more than one transcriptional activation domain comprises VP64, p65 and RTA.

In another composition, Composition 19, there is provided the composition of any one of Compositions 1 to 18 wherein the Klotho gene is a human Klotho gene.

In another composition, Composition 20, there is provided the composition of any one of Compositions 1 to 19 wherein the DNA binding protein comprises a nuclear localisation signal.

The present disclosure also provides a composition, Composition 21, comprising an isolated or recombinant nucleic acid encoding the DNA binding protein of any one of Compositions 1 to 20.

The present disclosure also provides a composition, Composition 22, comprising a vector the vector comprising the nucleic acid of Composition 21.

In another composition, Composition 23, there is provided the composition of Composition 22 wherein the vector is an adeno-associated virus (AAV) vector.

The present disclosure also provides a composition, Composition 24, comprising a cell the cell comprising the DNA binding protein of any one of Compositions 1 to 20, the nucleic acid of Composition 21 or the vector of Composition 22 or Composition 23.

In a first method, Method 1, the present disclosure provides a method of increasing expression of a Klotho gene in a cell the method comprising administering to the cell a DNA binding protein comprising or attached to a transcriptional activation domain wherein the DNA binding protein binds to a target sequence within or near the Klotho gene and thereby increases expression of the Klotho gene.

In another method, Method 2, the present disclosure provides the method of Method 1 wherein the target sequence is located within a region between the Klotho gene translation start site and 4000 nucleotides upstream of the Klotho gene translation start site.

In another method, Method 3, the present disclosure provides the method of Method 2 wherein the target sequence is located within a region between the Klotho gene translation start site and 350 nucleotides upstream of the Klotho gene translation start site.

In another method, Method 4, the present disclosure provides the method of Method 3 wherein the target sequence is located within a region between 40 nucleotides and 300 nucleotides upstream of the Klotho gene translation start site.

In another method, Method 5, the present disclosure provides the method of any one of Methods 1 to 4 wherein the target sequence comprises:
the sequence set forth in SEQ ID NO. 60;
the sequence set forth in SEQ ID NO. 61; or
the sequence set forth in SEQ ID NO. 62.

In another method, Method 6, the present disclosure provides the method of any one of Methods 1 to 4 wherein the target sequence comprises at least 9 contiguous nucleotides from:
the sequence set forth in SEQ ID NO. 63;
the sequence set forth in SEQ ID NO. 64;
the sequence set forth in SEQ ID NO. 65;
the sequence set forth in SEQ ID NO. 66;
the sequence set forth in SEQ ID NO. 67;
the sequence set forth in SEQ ID NO. 68;
the sequence set forth in SEQ ID NO. 69; or
the sequence set forth in SEQ ID NO. 70.

In another method, Method 7, the present disclosure provides the method of Method 6 wherein the target sequence comprises:
the sequence set forth in SEQ ID NO. 63;
the sequence set forth in SEQ ID NO. 64;
the sequence set forth in SEQ ID NO. 65;
the sequence set forth in SEQ ID NO. 66;
the sequence set forth in SEQ ID NO. 67;
the sequence set forth in SEQ ID NO. 68;
the sequence set forth in SEQ ID NO. 69; or
the sequence set forth in SEQ ID NO. 70.

In another method, Method 8, the present disclosure provides the method of Method 7 wherein the target sequence comprises:
the sequence set forth in SEQ ID NO. 64; or
the sequence set forth in SEQ ID NO. 62.

In another method, Method 9, the present disclosure provides the method of any one of Methods 1 to 8 wherein the DNA binding protein is a zinc finger protein.

In another method, Method 10, the present disclosure provides the method of Method 9 wherein the zinc finger protein comprises:
a zinc finger comprising the sequence set forth in SEQ ID NO. 17, a zinc finger comprising the sequence set forth in SEQ ID NO. 16 and a zinc finger comprising the sequence set forth in SEQ ID NO. 11;
a zinc finger comprising the sequence set forth in SEQ ID NO. 18, a zinc finger comprising the sequence set forth in SEQ ID NO. 16 and a zinc finger comprising the sequence set forth in SEQ ID NO. 11; or
a zinc finger comprising the sequence set forth in SEQ ID NO. 18, a zinc finger comprising the sequence set forth in SEQ ID NO. 16 and a zinc finger comprising the sequence set forth in SEQ ID NO. 3.

In another method, Method 11, the present disclosure provides the method of Method 9 or Method 10 wherein the zinc finger protein comprises:
a ZF1 zinc finger comprising the sequence set forth in SEQ ID NO. 1, a ZF2 zinc finger comprising the sequence set forth in SEQ ID NO. 2, a ZF3 zinc finger comprising the sequence set forth in SEQ ID NO. 3, a ZF4 zinc finger comprising the sequence set forth in SEQ ID NO. 4, a ZF5 zinc finger comprising the sequence set forth in SEQ ID NO. 5 and a ZF6 zinc finger comprising the sequence set forth in SEQ ID NO. 6;

a ZF1 zinc finger comprising the sequence set forth in SEQ ID NO. 7, a ZF2 zinc finger comprising the sequence set forth in SEQ ID NO. 8, a ZF3 zinc finger comprising the sequence set forth in SEQ ID NO. 9, a ZF4 zinc finger comprising the sequence set forth in SEQ ID NO. 7, a ZF5 zinc finger comprising the sequence set forth in SEQ ID NO. 10, a ZF6 zinc finger comprising the sequence set forth in SEQ ID NO. 11, a ZF7 zinc finger comprising the sequence set forth in SEQ ID NO. 12, a ZF8 zinc finger comprising the sequence set forth in SEQ ID NO. 13, a ZF9 zinc finger comprising the sequence set forth in SEQ ID NO. 14 and a ZF10 zinc finger comprising the sequence set forth in SEQ ID NO. 6;

a ZF1 zinc finger comprising the sequence set forth in SEQ ID NO. 15, a ZF2 zinc finger comprising the sequence set forth in SEQ ID NO. 16, a ZF3 zinc finger comprising the sequence set forth in SEQ ID NO. 17, a ZF4 zinc finger comprising the sequence set forth in SEQ ID NO. 16, a ZF5 zinc finger comprising the sequence set forth in SEQ ID NO. 11, a ZF6 zinc finger comprising the sequence set forth in SEQ ID NO. 11 and a ZF7 zinc finger comprising the sequence set forth in SEQ ID NO. 1;

a ZF1 zinc finger comprising the sequence set forth in SEQ ID NO. 11, a ZF2 zinc finger comprising the sequence set forth in SEQ ID NO. 1, a ZF3 zinc finger comprising the sequence set forth in SEQ ID NO. 18, a ZF4 zinc finger comprising the sequence set forth in SEQ ID NO. 16, a ZF5 zinc finger comprising the sequence set forth in SEQ ID NO. 11, a ZF6 zinc finger comprising the sequence set forth in SEQ ID NO. 19 and a ZF7 zinc finger comprising the sequence set forth in SEQ ID NO. 12;

a ZF1 zinc finger comprising the sequence set forth in SEQ ID NO. 8, a ZF2 zinc finger comprising the sequence set forth in SEQ ID NO. 16, a ZF3 zinc finger comprising the sequence set forth in SEQ ID NO. 18, a ZF4 zinc finger comprising the sequence set forth in SEQ ID NO. 16, a ZF5 zinc finger comprising the sequence set forth in SEQ ID NO. 3, a ZF6 zinc finger comprising the sequence set forth in SEQ ID NO. 8 and a ZF7 zinc finger comprising the sequence set forth in SEQ ID NO. 3;

a ZF1 zinc finger comprising the sequence set forth in SEQ ID NO. 17, a ZF2 zinc finger comprising the sequence set forth in SEQ ID NO. 13, a ZF3 zinc finger comprising the sequence set forth in SEQ ID NO. 13, a ZF4 zinc finger comprising the sequence set forth in SEQ ID NO. 9, a ZF5 zinc finger comprising the sequence set forth in SEQ ID NO. 17 and a ZF6 zinc finger comprising the sequence set forth in SEQ ID NO. 9;

a ZF1 zinc finger comprising the sequence set forth in SEQ ID NO. 20, a ZF2 zinc finger comprising the sequence set forth in SEQ ID NO. 21, a ZF3 zinc finger comprising the sequence set forth in SEQ ID NO. 22, a ZF4 zinc finger comprising the sequence set forth in SEQ ID NO. 19, a ZF5 zinc finger comprising the sequence set forth in SEQ ID NO. 12 and a ZF6 zinc finger comprising the sequence set forth in SEQ ID NO. 17; or a ZF1 zinc finger comprising the sequence set forth in SEQ ID NO. 20, a ZF2 zinc finger comprising the sequence set forth in SEQ ID NO. 21, a ZF3 zinc finger comprising the sequence set forth in SEQ ID NO. 22, a ZF4 zinc finger comprising the sequence set forth in SEQ ID NO. 8, a ZF5 zinc finger comprising the sequence set forth in SEQ ID NO. 3 and a ZF6 zinc finger comprising the sequence set forth in SEQ ID NO. 9.

In another method, Method 12, the present disclosure provides the method of any one of Methods 9 to 11 wherein the zinc finger protein comprises:

a ZF1 zinc finger comprising the sequence set forth in SEQ ID NO. 7, a ZF2 zinc finger comprising the sequence set forth in SEQ ID NO. 8, a ZF3 zinc finger comprising the sequence set forth in SEQ ID NO. 9, a ZF4 zinc finger comprising the sequence set forth in SEQ ID NO. 7, a ZF5 zinc finger comprising the sequence set forth in SEQ ID NO. 10, a ZF6 zinc finger comprising the sequence set forth in SEQ ID NO. 11, a ZF7 zinc finger comprising the sequence set forth in SEQ ID NO. 12, a ZF8 zinc finger comprising the sequence set forth in SEQ ID NO. 13, a ZF9 zinc finger comprising the sequence set forth in SEQ ID NO. 14 and a ZF10 zinc finger comprising the sequence set forth in SEQ ID NO. 6;

a ZF1 zinc finger comprising the sequence set forth in SEQ ID NO. 8, a ZF2 zinc finger comprising the sequence set forth in SEQ ID NO. 16, a ZF3 zinc finger comprising the sequence set forth in SEQ ID NO. 18, a ZF4 zinc finger comprising the sequence set forth in SEQ ID NO. 16, a ZF5 zinc finger comprising the sequence set forth in SEQ ID NO. 3, a ZF6 zinc finger comprising the sequence set forth in SEQ ID NO. 8 and a ZF7 zinc finger comprising the sequence set forth in SEQ ID NO. 3;

a ZF1 zinc finger comprising the sequence set forth in SEQ ID NO. 20, a ZF2 zinc finger comprising the sequence set forth in SEQ ID NO. 21, a ZF3 zinc finger comprising the sequence set forth in SEQ ID NO. 22, a ZF4 zinc finger comprising the sequence set forth in SEQ ID NO. 19, a ZF5 zinc finger comprising the sequence set forth in SEQ ID NO. 12 and a ZF6 zinc finger comprising the sequence set forth in SEQ ID NO. 17; or a ZF1 zinc finger comprising the sequence set forth in SEQ ID NO. 20, a ZF2 zinc finger comprising the sequence set forth in SEQ ID NO. 21, a ZF3 zinc finger comprising the sequence set forth in SEQ ID NO. 22, a ZF4 zinc finger comprising the sequence set forth in SEQ ID NO. 8, a ZF5 zinc finger comprising the sequence set forth in SEQ ID NO. 3 and a ZF6 zinc finger comprising the sequence set forth in SEQ ID NO. 9.

In another method, Method 13, the present disclosure provides the method of any one of Methods 9 to 12 wherein the zinc finger protein comprises:

a zinc finger domain comprising the sequence set forth in SEQ ID NO. 41, or a sequence having at least about 80% identity to SEQ ID NO. 41;

a zinc finger domain comprising the sequence set forth in SEQ ID NO. 42, or a sequence having at least about 80% identity to SEQ ID NO. 42;

a zinc finger domain comprising the sequence set forth in SEQ ID NO. 43, or a sequence having at least about 80% identity to SEQ ID NO. 43;
a zinc finger domain comprising the sequence set forth in SEQ ID NO. 44, or a sequence having at least about 80% identity to SEQ ID NO. 44;
a zinc finger domain comprising the sequence set forth in SEQ ID NO. 45, or a sequence having at least about 80% identity to SEQ ID NO. 45; or
a zinc finger domain comprising the sequence set forth in SEQ ID NO. 46, or a sequence having at least about 80% identity to SEQ ID NO. 46.

In another method, Method 14, the present disclosure provides the method of any one of Methods 1 to 13 wherein the DNA binding protein competes for binding to the target sequence with a zinc finger protein comprising:
a zinc finger domain comprising the sequence set forth in SEQ ID NO. 41;
a zinc finger domain comprising the sequence set forth in SEQ ID NO. 42;
a zinc finger domain comprising the sequence set forth in SEQ ID NO. 43;
a zinc finger domain comprising the sequence set forth in SEQ ID NO. 44;
a zinc finger domain comprising the sequence set forth in SEQ ID NO. 45; or
a zinc finger domain comprising the sequence set forth in SEQ ID NO. 46.

In another method, Method 15, the present disclosure provides the method of any one of Methods 1 to 14 wherein the DNA binding protein competes for binding to the target sequence with a zinc finger protein comprising or consisting of:
the sequence set forth in SEQ ID NO. 29;
the sequence set forth in SEQ ID NO. 30;
the sequence set forth in SEQ ID NO. 32;
the sequence set forth in SEQ ID NO. 33;
the sequence set forth in SEQ ID NO. 34;
the sequence set forth in SEQ ID NO. 36;
the sequence set forth in SEQ ID NO. 37; or
the sequence set forth in SEQ ID NO. 39.

In another method, Method 16, the present disclosure provides the method of any one of Methods 1 to 15 wherein the transcriptional activation domain is selected from the group consisting of VP16, or a plurality thereof, VP64, VP160, p65, MyoD1, HSF1, RTA, TET3CD, p300 and SET7/9.

In another method, Method 17, the present disclosure provides the method of any one of Methods 1 to 16 wherein the DNA binding protein comprises or is attached to more than one transcriptional activation domain.

In another method, Method 18, the present disclosure provides the method of Method 17 wherein the more than one transcriptional activation domain comprises VP64, p65 and RTA.

In another method, Method 19, the present disclosure provides the method of any one of Methods 1 to 18 wherein the DNA binding protein is administered to the cell directly as a protein.

In another method, Method 20, the present disclosure provides the method of any one of Methods 1 to 18 wherein the DNA binding protein is administered to the cell in the form of a nucleic acid.

In another method, Method 21, the present disclosure provides the method of any one of Methods 1 to 18 wherein the DNA binding protein is administered to the cell in the form of an AAV vector.

In another method, Method 22, the present disclosure provides the method of any one of Methods 1 to 21 wherein the method comprises administering to the cell more than one DNA binding protein and wherein each DNA binding protein is independently selected from the DNA binding protein defined in any one of Compositions 1 to 18.

In another method, Method 23, the present disclosure provides the method of any one of Methods 1 to 22 wherein the cell is a human cell.

In another method, Method 24, the present disclosure provides the method of any one of Methods 1 to 23 wherein the DNA binding protein comprises a nuclear localisation signal.

In another method, Method 25, there is provided a method of treating cancer in a subject the method comprising administering to the subject a therapeutically effective amount of a DNA binding protein comprising or attached to a transcriptional activation domain wherein the DNA binding protein binds to a target sequence within or near a Klotho gene in the subject and thereby increases expression of the Klotho gene.

In another method, Method 26, the present disclosure provides the method of Method 25 wherein the cancer is selected from the group consisting of colon cancer, prostate cancer, lung cancer, cervical cancer, pancreatic cancer, ovarian cancer and breast cancer.

In another method, Method 27, there is provided a method of treating a muscle disorder in a subject the method comprising administering to the subject a therapeutically effective amount of a DNA binding protein comprising or attached to a transcriptional activation domain wherein the DNA binding protein binds to a target sequence within or near a Klotho gene in the subject and thereby increases expression of the Klotho gene.

In another method, Method 28, the present disclosure provides the method of Method 27 wherein the muscle disorder is selected from the group consisting of muscle atrophy and muscular dystrophy.

In another method, Method 29, there is provided a method of treating a kidney disorder in a subject the method comprising administering to the subject a therapeutically effective amount of a DNA binding protein comprising or attached to a transcriptional activation domain wherein the DNA binding protein binds to a target sequence within or near a Klotho gene in the subject and thereby increases expression of the Klotho gene.

In another method, Method 30, the present disclosure provides the method of Method 29 wherein the kidney disorder is selected from the group consisting of renal dysfunction, acute kidney injury and kidney disease.

In another method, Method 31, there is provided a method of enhancing cognition in a subject the method comprising administering to the subject a therapeutically effective amount of a DNA binding protein comprising or attached to a transcriptional activation domain wherein the DNA binding protein binds to a target sequence within or near a Klotho gene in the subject and thereby increases expression of the Klotho gene.

In another method, Method 32, there is provided a method of treating a neurological disorder in a subject the method comprising administering to the subject a therapeutically effective amount of a DNA binding protein comprising or attached to a transcriptional activation domain wherein the DNA binding protein binds to a target sequence within or near a Klotho gene in the subject and thereby increases expression of the Klotho gene.

In another method, Method 33, the present disclosure provides the method of Method 32 wherein the neurological disorder is selected from the group consisting of memory loss, stress, biopolar disorder, epilepsy, dementia, Alzheimer's disease, Parkinson's disease, Huntington's disease, Creutzfeldt-Jakob disease, ataxia telangiectasia, craniocerebral trauma, amyotrophic lateral sclerosis, depression, schizophrenia, multiple sclerosis, myelin-related disease, oxidative stress and neurodegeneration.

In another method, Method 34, the present disclosure provides a method of promoting angiogenesis in a subject the method comprising administering to the subject a therapeutically effective amount of a DNA binding protein comprising or attached to a transcriptional activation domain wherein the DNA binding protein binds to a target sequence within or near a Klotho gene in the subject and thereby increases expression of the Klotho gene.

In another method, Method 35, the present disclosure provides a method of treating a wound or a skin disorder in a subject the method comprising administering to the subject a therapeutically effective amount of a DNA binding protein comprising or attached to a transcriptional activation domain wherein the DNA binding protein binds to a target sequence within or near a Klotho gene in the subject and thereby increases expression of the Klotho gene.

In another method, Method 36, the present disclosure provides the method of any one of Methods 25 to 35 wherein the target sequence is located within a region between the Klotho gene translation start site and 4000 nucleotides upstream of the Klotho gene translation start site.

In another method, Method 37, the present disclosure provides the method of Method 36 wherein the target sequence is located within a region between the Klotho gene translation start site and 350 nucleotides upstream of the Klotho gene translation start site.

In another method, Method 38, the present disclosure provides the method of Method 37 wherein the target sequence is located within a region between 40 nucleotides and 300 nucleotides upstream of the Klotho gene translation start site.

In another method, Method 39, the present disclosure provides the method of any one of Methods 25 to 38 wherein the target sequence comprises:
the sequence set forth in SEQ ID NO. 60;
the sequence set forth in SEQ ID NO. 61; or
the sequence set forth in SEQ ID NO. 62.

In another method, Method 40, the present disclosure provides the method of any one of Methods 25 to 38 wherein the target sequence comprises at least 9 contiguous nucleotides from:
the sequence set forth in SEQ ID NO. 63;
the sequence set forth in SEQ ID NO. 64;
the sequence set forth in SEQ ID NO. 65;
the sequence set forth in SEQ ID NO. 66;
the sequence set forth in SEQ ID NO. 67;
the sequence set forth in SEQ ID NO. 68;
the sequence set forth in SEQ ID NO. 69; or
the sequence set forth in SEQ ID NO. 70.

In another method, Method 41, the present disclosure provides the method of Method 40 wherein the target sequence comprises:
the sequence set forth in SEQ ID NO. 63;
the sequence set forth in SEQ ID NO. 64;
the sequence set forth in SEQ ID NO. 65;
the sequence set forth in SEQ ID NO. 66;
the sequence set forth in SEQ ID NO. 67;
the sequence set forth in SEQ ID NO. 68;
the sequence set forth in SEQ ID NO. 69; or
the sequence set forth in SEQ ID NO. 70.

In another method, Method 42, the present disclosure provides the method of Method 41 wherein the target sequence comprises:
the sequence set forth in SEQ ID NO. 64; or
the sequence set forth in SEQ ID NO. 62.

In another method, Method 43, the present disclosure provides the method of any one of Methods 25 to 42 wherein the DNA binding protein is a zinc finger protein.

In another method, Method 44, the present disclosure provides the method of Method 43 wherein the zinc finger protein comprises:
a zinc finger comprising the sequence set forth in SEQ ID NO. 17, a zinc finger comprising the sequence set forth in SEQ ID NO. 16 and a zinc finger comprising the sequence set forth in SEQ ID NO. 11;
a zinc finger comprising the sequence set forth in SEQ ID NO. 18, a zinc finger comprising the sequence set forth in SEQ ID NO. 16 and a zinc finger comprising the sequence set forth in SEQ ID NO. 11; or
a zinc finger comprising the sequence set forth in SEQ ID NO. 18, a zinc finger comprising the sequence set forth in SEQ ID NO. 16 and a zinc finger comprising the sequence set forth in SEQ ID NO. 3.

In another method, Method 45, the present disclosure provides the method of Method 43 or Method 44 wherein the zinc finger protein comprises:
a ZF1 zinc finger comprising the sequence set forth in SEQ ID NO. 1, a ZF2 zinc finger comprising the sequence set forth in SEQ ID NO. 2, a ZF3 zinc finger comprising the sequence set forth in SEQ ID NO. 3, a ZF4 zinc finger comprising the sequence set forth in SEQ ID NO. 4, a ZF5 zinc finger comprising the sequence set forth in SEQ ID NO. 5 and a ZF6 zinc finger comprising the sequence set forth in SEQ ID NO. 6;
a ZF1 zinc finger comprising the sequence set forth in SEQ ID NO. 7, a ZF2 zinc finger comprising the sequence set forth in SEQ ID NO. 8, a ZF3 zinc finger comprising the sequence set forth in SEQ ID NO. 9, a ZF4 zinc finger comprising the sequence set forth in SEQ ID NO. 7, a ZF5 zinc finger comprising the sequence set forth in SEQ ID NO. 10, a ZF6 zinc finger comprising the sequence set forth in SEQ ID NO. 11, a ZF7 zinc finger comprising the sequence set forth in SEQ ID NO. 12, a ZF8 zinc finger comprising the sequence set forth in SEQ ID NO. 13, a ZF9 zinc finger comprising the sequence set forth in SEQ ID NO. 14 and a ZF10 zinc finger comprising the sequence set forth in SEQ ID NO. 6;
a ZF1 zinc finger comprising the sequence set forth in SEQ ID NO. 15, a ZF2 zinc finger comprising the sequence set forth in SEQ ID NO. 16, a ZF3 zinc finger comprising the sequence set forth in SEQ ID NO. 17, a ZF4 zinc finger comprising the sequence set forth in SEQ ID NO. 16, a ZF5 zinc finger comprising the sequence set forth in SEQ ID NO. 11, a ZF6 zinc finger comprising the sequence set forth in SEQ ID NO. 11 and a ZF7 zinc finger comprising the sequence set forth in SEQ ID NO. 1;
a ZF1 zinc finger comprising the sequence set forth in SEQ ID NO. 11, a ZF2 zinc finger comprising the sequence set forth in SEQ ID NO. 1, a ZF3 zinc finger comprising the sequence set forth in SEQ ID NO. 18, a ZF4 zinc finger comprising the sequence set forth in SEQ ID NO. 16, a ZF5 zinc finger comprising the sequence set forth in SEQ ID NO. 11, a ZF6 zinc finger comprising the sequence set forth in SEQ ID NO. 19 and a ZF7 zinc finger comprising the sequence set forth in SEQ ID NO. 12;

a ZF1 zinc finger comprising the sequence set forth in SEQ ID NO. 8, a ZF2 zinc finger comprising the sequence set forth in SEQ ID NO. 16, a ZF3 zinc finger comprising the sequence set forth in SEQ ID NO. 18, a ZF4 zinc finger comprising the sequence set forth in SEQ ID NO. 16, a ZF5 zinc finger comprising the sequence set forth in SEQ ID NO. 3, a ZF6 zinc finger comprising the sequence set forth in SEQ ID NO. 8 and a ZF7 zinc finger comprising the sequence set forth in SEQ ID NO. 3;

a ZF1 zinc finger comprising the sequence set forth in SEQ ID NO. 17, a ZF2 zinc finger comprising the sequence set forth in SEQ ID NO. 13, a ZF3 zinc finger comprising the sequence set forth in SEQ ID NO. 13, a ZF4 zinc finger comprising the sequence set forth in SEQ ID NO. 9, a ZF5 zinc finger comprising the sequence set forth in SEQ ID NO. 17 and a ZF6 zinc finger comprising the sequence set forth in SEQ ID NO. 9;

a ZF1 zinc finger comprising the sequence set forth in SEQ ID NO. 20, a ZF2 zinc finger comprising the sequence set forth in SEQ ID NO. 21, a ZF3 zinc finger comprising the sequence set forth in SEQ ID NO. 22, a ZF4 zinc finger comprising the sequence set forth in SEQ ID NO. 19, a ZF5 zinc finger comprising the sequence set forth in SEQ ID NO. 12 and a ZF6 zinc finger comprising the sequence set forth in SEQ ID NO. 17; or a ZF1 zinc finger comprising the sequence set forth in SEQ ID NO. 20, a ZF2 zinc finger comprising the sequence set forth in SEQ ID NO. 21, a ZF3 zinc finger comprising the sequence set forth in SEQ ID NO. 22, a ZF4 zinc finger comprising the sequence set forth in SEQ ID NO. 8, a ZF5 zinc finger comprising the sequence set forth in SEQ ID NO. 3 and a ZF6 zinc finger comprising the sequence set forth in SEQ ID NO. 9.

In another method, Method 46, the present disclosure provides the method of any one of Methods 43 to 45 wherein the zinc finger protein comprises:

a ZF1 zinc finger comprising the sequence set forth in SEQ ID NO. 7, a ZF2 zinc finger comprising the sequence set forth in SEQ ID NO. 8, a ZF3 zinc finger comprising the sequence set forth in SEQ ID NO. 9, a ZF4 zinc finger comprising the sequence set forth in SEQ ID NO. 7, a ZF5 zinc finger comprising the sequence set forth in SEQ ID NO. 10, a ZF6 zinc finger comprising the sequence set forth in SEQ ID NO. 11, a ZF7 zinc finger comprising the sequence set forth in SEQ ID NO. 12, a ZF8 zinc finger comprising the sequence set forth in SEQ ID NO. 13, a ZF9 zinc finger comprising the sequence set forth in SEQ ID NO. 14 and a ZF10 zinc finger comprising the sequence set forth in SEQ ID NO. 6;

a ZF1 zinc finger comprising the sequence set forth in SEQ ID NO. 8, a ZF2 zinc finger comprising the sequence set forth in SEQ ID NO. 16, a ZF3 zinc finger comprising the sequence set forth in SEQ ID NO. 18, a ZF4 zinc finger comprising the sequence set forth in SEQ ID NO. 16, a ZF5 zinc finger comprising the sequence set forth in SEQ ID NO. 3, a ZF6 zinc finger comprising the sequence set forth in SEQ ID NO. 8 and a ZF7 zinc finger comprising the sequence set forth in SEQ ID NO. 3;

a ZF1 zinc finger comprising the sequence set forth in SEQ ID NO. 20, a ZF2 zinc finger comprising the sequence set forth in SEQ ID NO. 21, a ZF3 zinc finger comprising the sequence set forth in SEQ ID NO. 22, a ZF4 zinc finger comprising the sequence set forth in SEQ ID NO. 19, a ZF5 zinc finger comprising the sequence set forth in SEQ ID NO. 12 and a ZF6 zinc finger comprising the sequence set forth in SEQ ID NO. 17; or a ZF1 zinc finger comprising the sequence set forth in SEQ ID NO. 20, a ZF2 zinc finger comprising the sequence set forth in SEQ ID NO. 21, a ZF3 zinc finger comprising the sequence set forth in SEQ ID NO. 22, a ZF4 zinc finger comprising the sequence set forth in SEQ ID NO. 8, a ZF5 zinc finger comprising the sequence set forth in SEQ ID NO. 3 and a ZF6 zinc finger comprising the sequence set forth in SEQ ID NO. 9.

In another method, Method 47, the present disclosure provides the method of any one of Methods 43 to 46 wherein the zinc finger protein comprises:

a zinc finger domain comprising the sequence set forth in SEQ ID NO. 41, or a sequence having at least about 80% identity to SEQ ID NO. 41;

a zinc finger domain comprising the sequence set forth in SEQ ID NO. 42, or a sequence having at least about 80% identity to SEQ ID NO. 42;

a zinc finger domain comprising the sequence set forth in SEQ ID NO. 43, or a sequence having at least about 80% identity to SEQ ID NO. 43;

a zinc finger domain comprising the sequence set forth in SEQ ID NO. 44, or a sequence having at least about 80% identity to SEQ ID NO. 44;

a zinc finger domain comprising the sequence set forth in SEQ ID NO. 45, or a sequence having at least about 80% identity to SEQ ID NO. 45; or a zinc finger domain comprising the sequence set forth in SEQ ID NO. 46, or a sequence having at least about 80% identity to SEQ ID NO. 46.

In another method, Method 48, the present disclosure provides the method of any one of Methods 25 to 47 wherein the DNA binding protein competes for binding to the target sequence with a zinc finger protein comprising:

a zinc finger domain comprising the sequence set forth in SEQ ID NO. 41;

a zinc finger domain comprising the sequence set forth in SEQ ID NO. 42;

a zinc finger domain comprising the sequence set forth in SEQ ID NO. 43;

a zinc finger domain comprising the sequence set forth in SEQ ID NO. 44;

a zinc finger domain comprising the sequence set forth in SEQ ID NO. 45; or a zinc finger domain comprising the sequence set forth in SEQ ID NO. 46.

In another method, Method 49, the present disclosure provides the method of any one of Methods 25 to 48 wherein the DNA binding protein competes for binding to the target sequence with a zinc finger protein comprising or consisting of:

the sequence set forth in SEQ ID NO. 29;
the sequence set forth in SEQ ID NO. 30;
the sequence set forth in SEQ ID NO. 32;
the sequence set forth in SEQ ID NO. 33;

the sequence set forth in SEQ ID NO. 34;
the sequence set forth in SEQ ID NO. 36;
the sequence set forth in SEQ ID NO. 37; or
the sequence set forth in SEQ ID NO. 39.

In another method, Method 50, the present disclosure provides the method of any one of Methods 25 to 49 wherein the transcriptional activation domain is selected from the group consisting of VP16, or a plurality thereof, VP64, VP160, p65, MyoD1, HSF1, RTA, TET3CD, p300 and SET7/9.

In another method, Method 51, the present disclosure provides the method of any one of Methods 25 to 50 wherein the DNA binding protein comprises or is attached to more than one transcriptional activation domain.

In another method, Method 52, the present disclosure provides the method of Method 51 wherein the more than one transcriptional activation domain comprises VP64, p65 and RTA.

In another method, Method 53, the present disclosure provides the method of any one of Methods 25 to 52 wherein the DNA binding protein is administered to the subject directly as a protein.

In another method, Method 54, the present disclosure provides the method of any one of Methods 25 to 52 wherein the DNA binding protein is administered to the subject in the form of a nucleic acid.

In another method, Method 55, the present disclosure provides the method of any one of Methods 25 to 52 wherein the DNA binding protein is administered to the subject in the form of an AAV vector.

In another method, Method 56, the present disclosure provides the method of any one of Methods 25 to 55 wherein the method comprises administering to the subject more than one DNA binding protein and wherein each DNA binding protein is independently selected from the DNA binding protein defined in any one of Compositions 1 to 18.

In another method, Method 57, the present disclosure provides the method of any one of Methods 25 to 56 wherein the subject is a human.

In another method, Method 58, the present disclosure provides the method of any one of Methods 25 to 57 wherein the DNA binding protein comprises a nuclear localisation signal.

In a first use, Use 1, the present disclosure provides use of a DNA binding protein comprising or attached to a transcriptional activation domain in the manufacture of a medicament for increasing expression of a Klotho gene in a cell, wherein the DNA binding protein binds to a target sequence within or near the Klotho gene and thereby increases expression of the Klotho gene.

In another use, Use 2, the present disclosure provides use of a DNA binding protein comprising or attached to a transcriptional activation domain in the manufacture of a medicament for the treatment of cancer in a subject, wherein the DNA binding protein binds to a target sequence within or near a Klotho gene in the subject and thereby increases expression of the Klotho gene.

In another use, Use 3, the present disclosure provides use of a DNA binding protein comprising or attached to a transcriptional activation domain in the manufacture of a medicament for the treatment of a muscle disorder in a subject, wherein the DNA binding protein binds to a target sequence within or near a Klotho gene in the subject and thereby increases expression of the Klotho gene.

In another use, Use 4, the present disclosure provides use of a DNA binding protein comprising or attached to a transcriptional activation domain in the manufacture of a medicament for the treatment of a kidney disorder in a subject, wherein the DNA binding protein binds to a target sequence within or near a Klotho gene in the subject and thereby increases expression of the Klotho gene.

In another use, Use 5, the present disclosure provides use of a DNA binding protein comprising or attached to a transcriptional activation domain in the manufacture of a medicament for enhancing cognition in a subject, wherein the DNA binding protein binds to a target sequence within or near a Klotho gene in the subject and thereby increases expression of the Klotho gene.

In another use, Use 6, the present disclosure provides use of a DNA binding protein comprising or attached to a transcriptional activation domain in the manufacture of a medicament for the treatment of a neurological disorder in a subject, wherein the DNA binding protein binds to a target sequence within or near a Klotho gene in the subject and thereby increases expression of the Klotho gene.

In another use, Use 7, the present disclosure provides use of a DNA binding protein comprising or attached to a transcriptional activation domain in the manufacture of a medicament for promoting angiogenesis in a subject, wherein the DNA binding protein binds to a target sequence within or near a Klotho gene in the subject and thereby increases expression of the Klotho gene.

In another use, Use 8, the present disclosure provides use of a DNA binding protein comprising or attached to a transcriptional activation domain in the manufacture of a medicament for the treatment of a wound or a skin disorder in a subject, wherein the DNA binding protein binds to a target sequence within or near a Klotho gene in the subject and thereby increases expression of the Klotho gene.

EXAMPLES

Plasmid Construction

Mutations were introduced into Egr1 binding sites by amplifying DNA with ClonAmp HiFi polymerase. PCR products were self-ligated using In Fusion kit (Clontech).

ZFP1 and ZFP52 coding DNA fragments were commercially synthesized (Genewiz) and cloned into pcDNA3.1TOPO (Invitrogen). ZFP1-Egr1-site1-sense, ZFP2-Egr1-site2, ZFP3-Egr1-site3-antisense and ZFP4-Egr1-site1-antisense coding DNA fragments (BamHl-Nhel) were synthesized (Genewiz) and cloned into ZFP52/pcDNA3.1TOPO vector digested with BamHl and Nhel. To construct ZFP3-VPR and ZFP52-VPR, the VPR insert and the vector containing either ZFP3 or ZFP52 were amplified with ClonAmp HiFi polymerase according to the manufacturers protocol. The insert and vector bands (100 ng each) were ligated together using In Fusion kit (Clontech) to generate the ZFP3-VPR or ZFP52-VPR constructs.

To construct Egr1-insert-site2 and Egr1-insert-site3, the additional 3 zinc fingers were synthesized (Genewiz) and cloned into Egr1 using ClonAmp HiFi polymerase and In Fusion kit (Clontech). To construct Egr1-insert-site2-RR and Egr1-insert-site3-RR, the repressor domain was removed by amplifying DNA with ClonAmp HiFi polymerase followed by self-ligation of the PCR product using In Fusion kit (Clontech).

Cell Lines and Transfections

HEK293 and HK-2 cell lines were used in the present examples. Cell culture and transfections were performed as described by Chen et al. 2018. J. Mol. Neurosci. 64(2): 1758-184.

Luciferase Reporter Assay

FLuc expression was measured using a coincidence reporter vector under the control of the Klotho promoter and a luciferase kit (Promega) as described by Chen et al. 2018. J. Mol. Neurosci. 64(2): 1758-184.

Enzyme-Linked Immunosorbent Assay (ELISA)

ELISA components were purchased from IBL and assays were performed according to the manufacturers instructions.

Example 1

Serial deletions of the Klotho promoter have revealed a proximal 45 bp region (−90 to −45) responsible for EGF-induced promoter activity that contains an Egr1 binding element (Choi et al. 2010. Gene. 450(1-2): 121-127).

Further searching of the region upstream of the Klotho translation start site revealed two additional binding sites for Egr1; one in the region −89 bp to −97 bp (sense) and another in the region −158 bp to −166 bp (antisense). Each binding site was mutated (M1: GCGGGGGTG [SEQ ID NO. 61]→GCTGTTTTG [SEQ ID NO. 74]); (M2: CTGGGGGTGGGGGCA [SEQ ID NO. 75]→CTAAGGACAAGGACA [SEQ ID NO. 76]) and cloned into vectors comprising firefly luciferase reporters under the regulation of Klotho promoter fragments −289 bp and −1800 bp, respectively, from the translation start site (+1; ATG), in HEK293 cells. Activation of the promoter was reduced significantly, but not completely by each mutation. However, when both sites were mutated, the effect of Egr1 on promoter activation was abrogated completely (FIG. 1).

Experiments were then conducted to determine whether the Egr1 transcription factor could increase Klotho expression in brain cells. A significant increase in Klotho mRNA levels was detected in two neuronal cell lines 48 hours after transfection (FIG. 1C).

Example 2

Additional binding sites for Egr1 were identified in the Klotho promoter in addition to the binding site at −51 bp to −59 bp (GCGGGGCGC, site 1; SEQ ID NO. 60): −89 to −97 bp (GCGGGGGTG, site 2; SEQ ID NO. 61) and −158 to −166 bp (CTGGGGGTG, anti-sense orientation, site 3; SEQ ID NO. 62) upstream of the start codon. Using the ZFP design tool (Mandell and Barbas. 2006. Nucleic Acids Res. 34 (Web Server issue): W516-23) the human Klotho promoter was searched within −300 bp of the translation start site, and two target sites were identified between −300 and −200 bp; one at −300 bp (referred to as ZFP1 target) and another at about −249 bp (referred to as ZFP52 target) (FIG. 2A). The design tool was also used to design the N- and C-terminal fixed region, N- and C-terminal backbone, and 7-amino acid recognition sequences (Table 3).

Two design strategies were used to construct zinc finger proteins; one involved de novo design of the zinc finger proteins, and the other involved design based on the Egr1 protein (FIG. 2B). The de novo-designed proteins comprise the ZF domain, a nuclear localization sequence (NLS) and VP64 transcriptional activation domain as well as a HA-tag for protein detection (FIG. 2B). For the endogenous engineered method, three additional zinc fingers were inserted downstream of the existing ZF domain.

Six zinc finger proteins were designed using the de novo method; ZFP1, ZFP52, ZFP1-Egr1-site1, ZFP2-Egr1-site2, ZFP3-Egr1-site3 and ZFP4-Egr1-site1-antisense (targeting Egr1 site1 in an anti-sense orientation) (FIG. 2A). Two zinc finger proteins were designed using the endogenous engineered method; Egr1-insert-site2 (targeting Egr1 binding site 2) and Egr1-insert-site3 (targeting Egr1 binding site 3) (FIG. 2A). The zinc finger sequences, target site positions and target site sequences are provided in tables 2, 3 and 4.

Example 3

Figure 3:
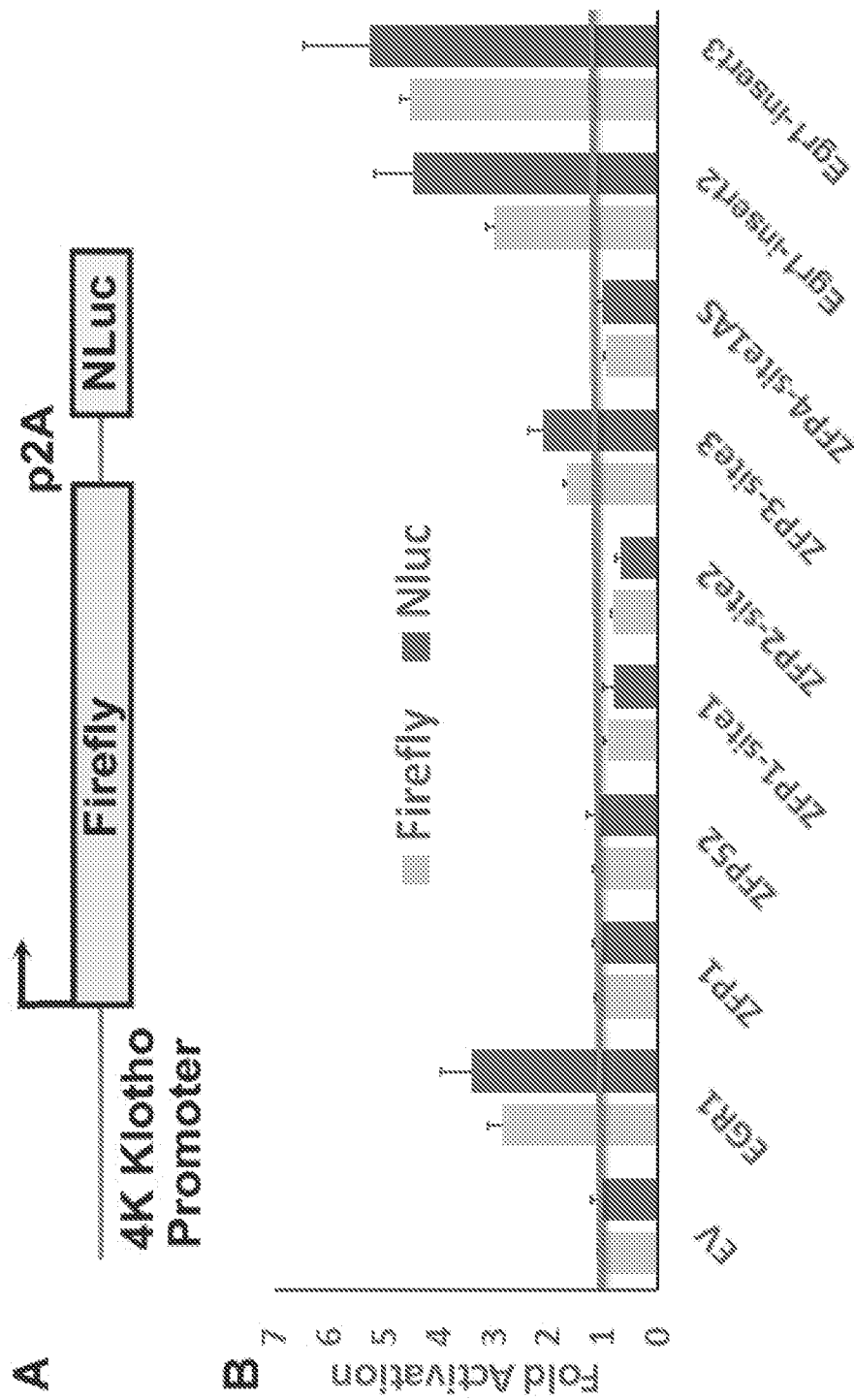
FIG. 3. Klotho gene activation in a dual luciferase coincidence reporter system. (A) Schematic representation of the firefly, NLuc coincidence reporter system under the control of a 4 kb Klotho promoter. The P2A ribosome skipping sequence is indicated. (B) Fold activation of Klotho gene expression by ZFPs evaluated using the dual luciferase coincidence reporter system in stable HEK293 cells. Cells were analyzed by the dual luciferase assay two days after transfection with ZFPs. Negative control: empty vector (EV). Positive control: Egr1-transfected cells. Data are expressed as fold over negative control. Error bars show standard deviation among 6-8 replicates.

An approximately 4 kb region of the Klotho promoter was cloned into a dual luciferase reporter system which stoichiometrically expresses two orthologous reporters, firefly luciferase (FLuc) and PEST-destabilized NLuc luciferase (NLuc) (Chen et al. 2018. J. Mol. Neurosci. 64(2): 1758-184). ZFP expression plasmids were transfected into HEK293 cells stably expressing the FLuc NLuc coincidence reporter driven by the 4 kb Klotho promoter. The results showed that ZFP3-Egr1-site3, Egr1-insert-site2 and Egr1-insert-site3 significantly increased Klotho expression (FIG. 3). The transcription factor Egr1 was used as a positive control and resulted in a 3- to 4-fold increase in Klotho expression compared to an empty vector control (FIG. 3).

Example 4

Figure 4:
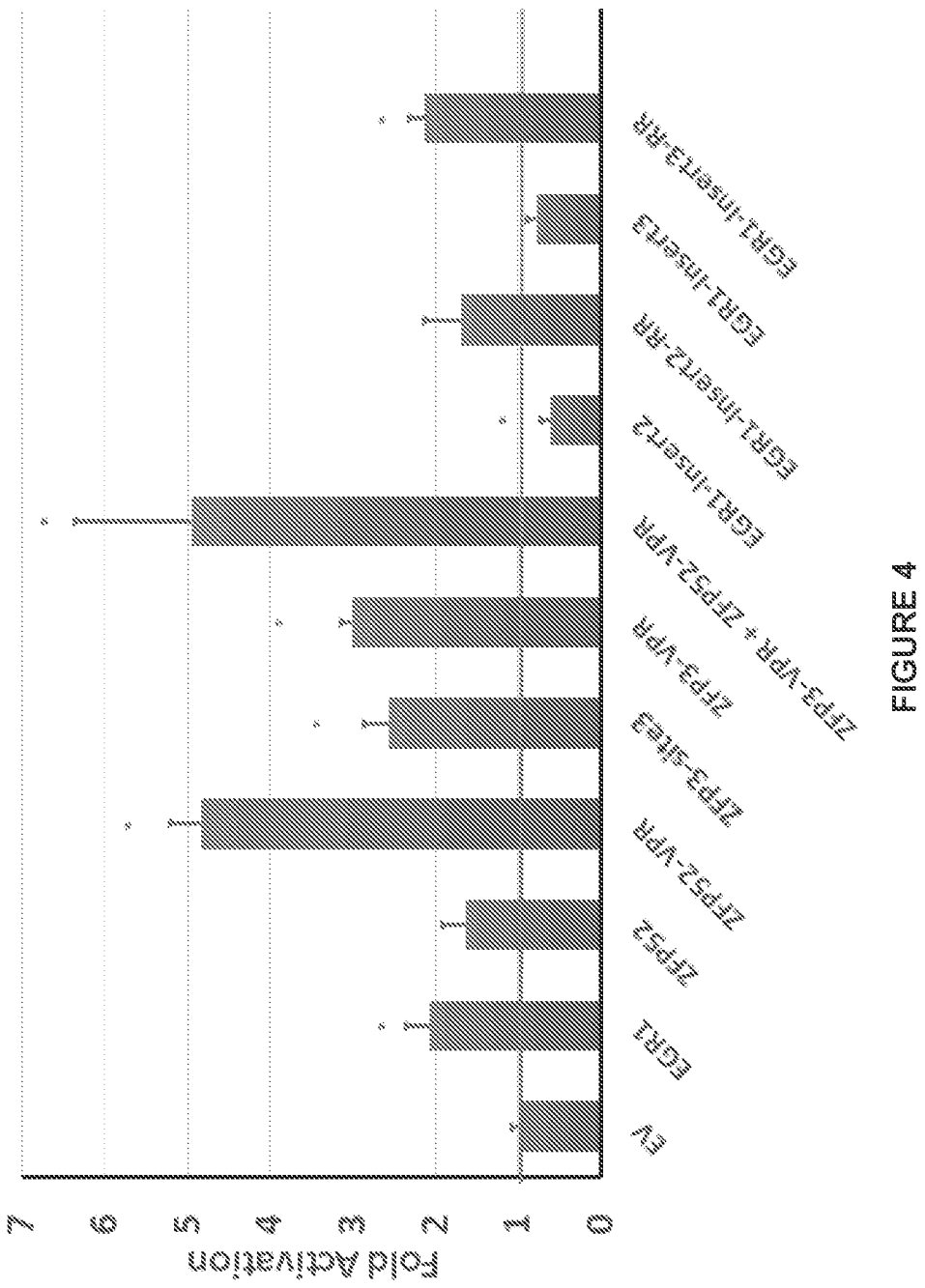
FIG. 4. Klotho fold activation in HK-2 cells using ZFP constructs measured by ELISA. *, p<0.05. Results normalized to total protein.

Klotho is largely expressed in the brain and kidney, and so further investigations were made using cell lines derived from those organs. The ZFPs were transfected into HK-2 cells and Klotho protein levels were measured. It was found that ZFP52 and ZFP3-Egr1-site3 enhanced Klotho expression about 2- and 3-fold, respectively (FIG. 4). Egr1 significantly increased Klotho gene expression compared to an empty vector control (FIG. 4).

In further experiments, ZFP52 and ZFP3_Egr1_site3 were further engineered by adding p65 and Rta transcriptional activation domains to the VP64 transcriptional activation domain. The ZFPs, denoted ZFP52_VPR and ZFP3_VPR, increased Klotho gene expression by about 5- and 3-fold, respectively (FIG. 4).

Figure 2:
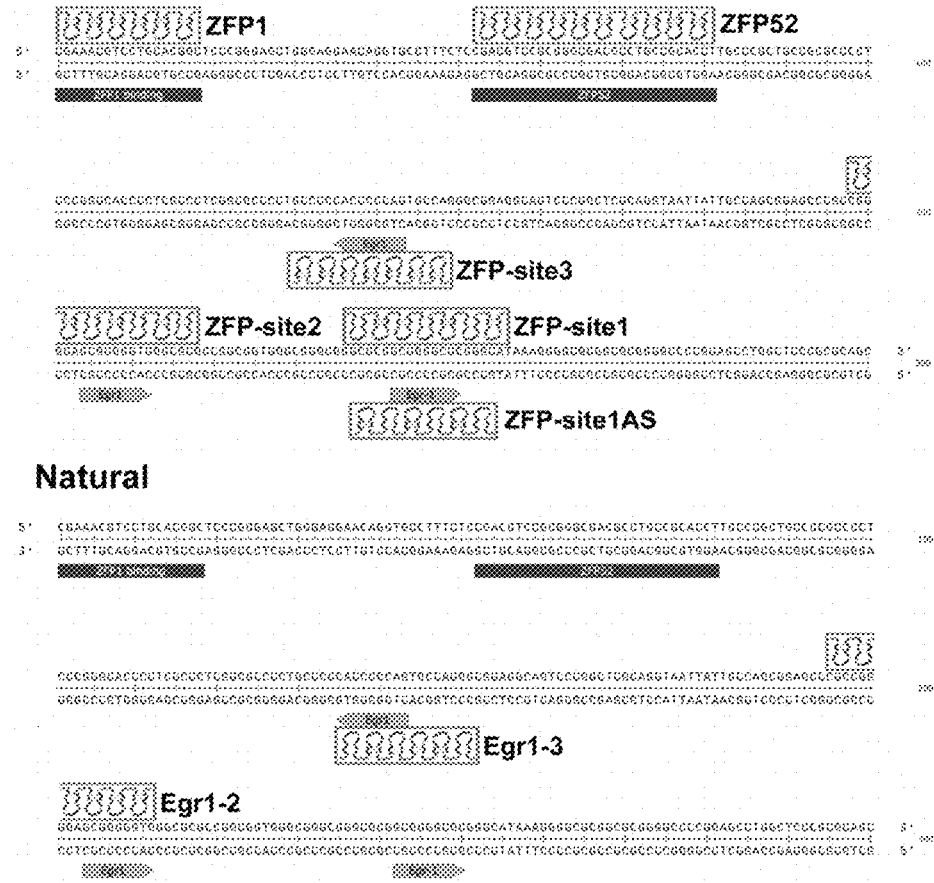
FIG. 2. (A) Schematic representation of ZFP target sites in a −300 bp Klotho promoter region. (B) Schematic representation of the de novo and endogenous engineered ZFPs. NLS: nuclear localization sequence. HA: HA epitope tag.
Figure 2:
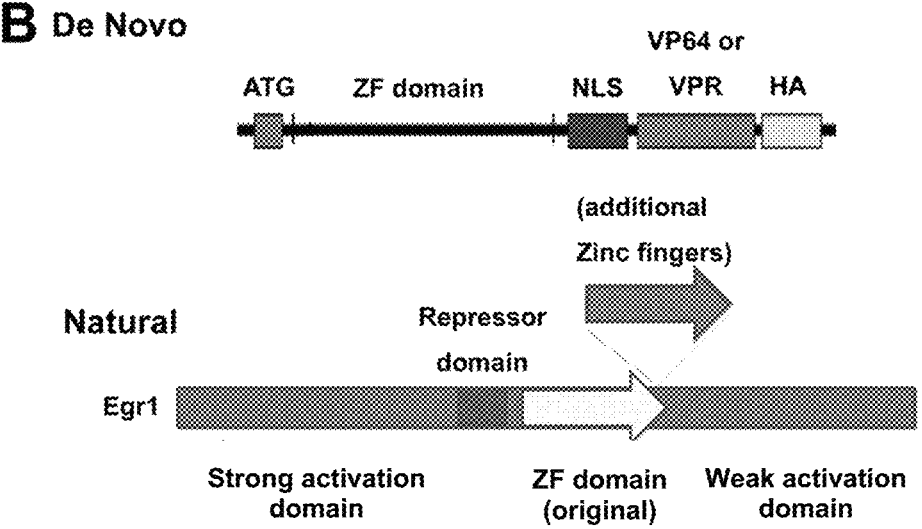

In further experiments, the engineered endogenous Egr1 constructs were further modified by removing the repressor domain (Gashler et al. 1993. Mol. Cell Biol. 13: 4556-4571; Russo et al. 1993. Mol. Cell Biol. 13: 6858-6865) (FIG. 2). Expression of Klotho was increased by these ZFPs, which are denoted Egr1-insert2-RR and Egr1-insert3-RR (FIG. 4).

Example 5

Figure 5:
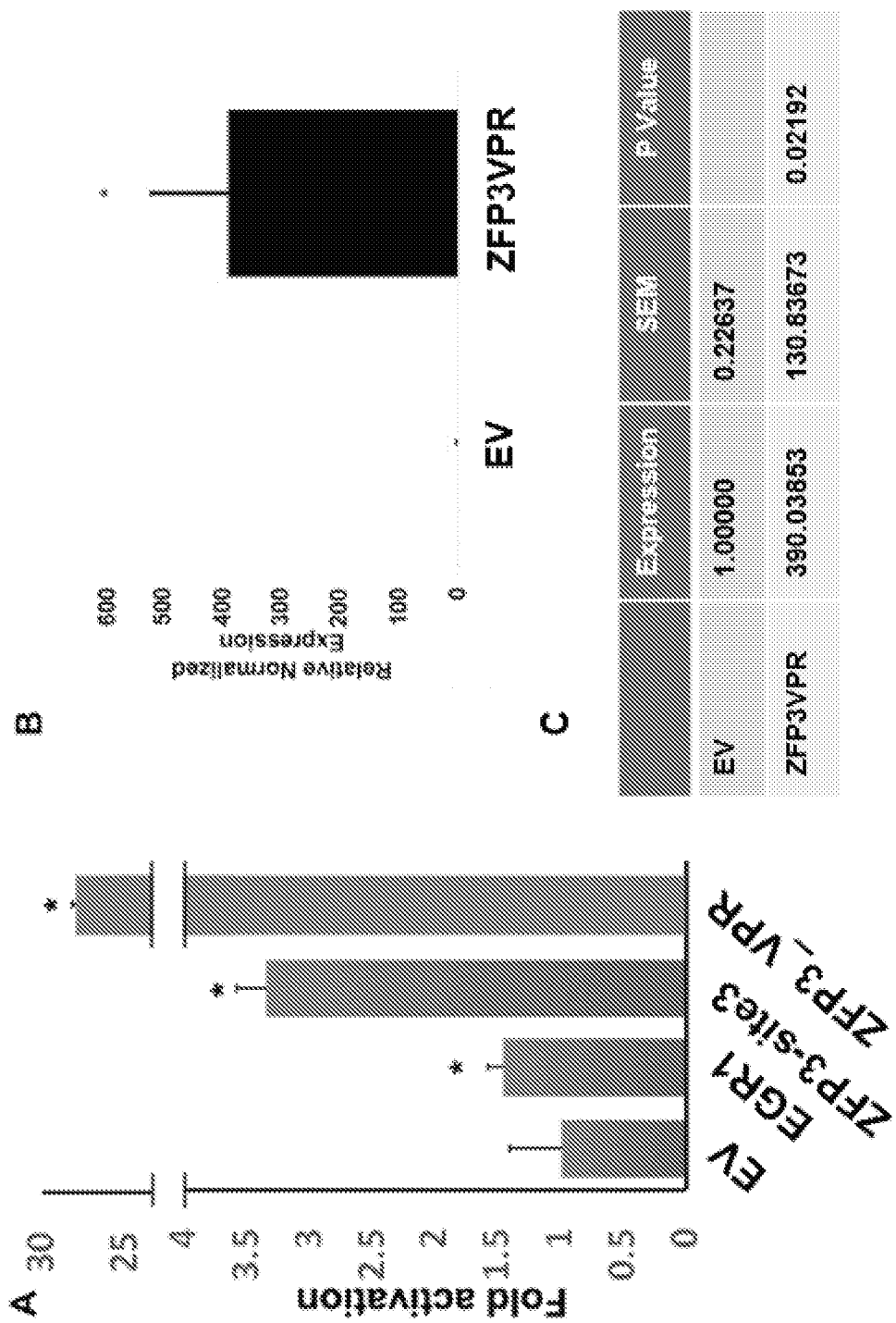
FIG. 5. (A) Klotho gene expression in N2a NLuc knock-in cells transfected with ZFP constructs measured by Nanoluc assay. Data are expressed as fold over negative control. *, p<0.05. (B, C) Expression of Klotho in mouse N2a cells measured using qPCR.

To determine whether the ZFP3 constructs increase Klotho expression in mice, the ZFP3 constructs were transfected into a N2a knock-in line which comprises NLuc inserted into 3'-UTR of the Klotho gene (Chen et al., 2018. J. Mol. Neurosci. 64(2): 175-184). Referring to FIG. 5, both ZFP3_Egr1_site3 and ZFP3 VPR increased Klotho gene expression.

Figure 6:
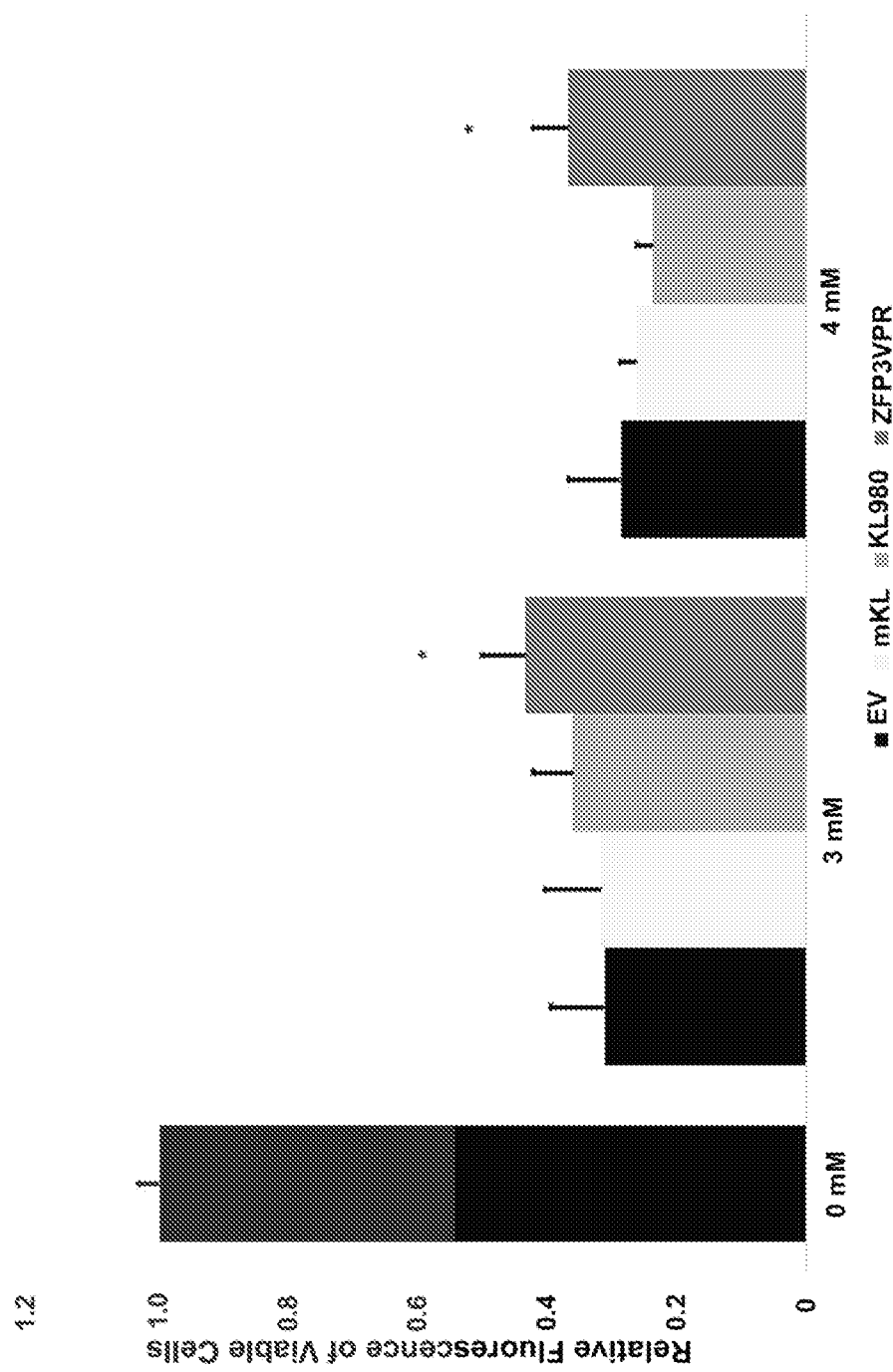
FIG. 6. HT-22 cells transfected with mouse full-length Klotho (mKL), the extracellular domain of Klotho (KL980) and ZFP3_VPR in the presence of 3 mM or 4 mM of glutamate. *, p<0.05 compared to EV control.

Next, a glutamate toxicity assay was performed using a HT-22 hippocampal cell line as a model for neuronal death by oxidative damage. Cytotoxicity was assayed as described by Zeldich et al. (2014. J. Biol. Chem. 289: 24700-15). Transfection of HT-22 cells with ZFP3_VPR significantly increased cell viability in the presence of either 3 mM or 4 mM glutamate as measured by CellTiter-Glo (FIG. 6). Over-expression of the extracellular domain of Klotho (KL980 construct) also increased cell viability, but the effects were not as substantial (FIG. 6).

Example 6

The length of the VPR transcriptional activation protein is 57 kD. To reduce the size of the transcription activation protein, efforts were made to identify and remove sequences that do not appear to contribute to transcriptional activation. To that end, the nine amino acid transactivation domain (TAD) prediction tool (https://www.med.muni.cz/9aaTAD/) was used to identify predicted TAD sequences within the VPR.

Figure 7:
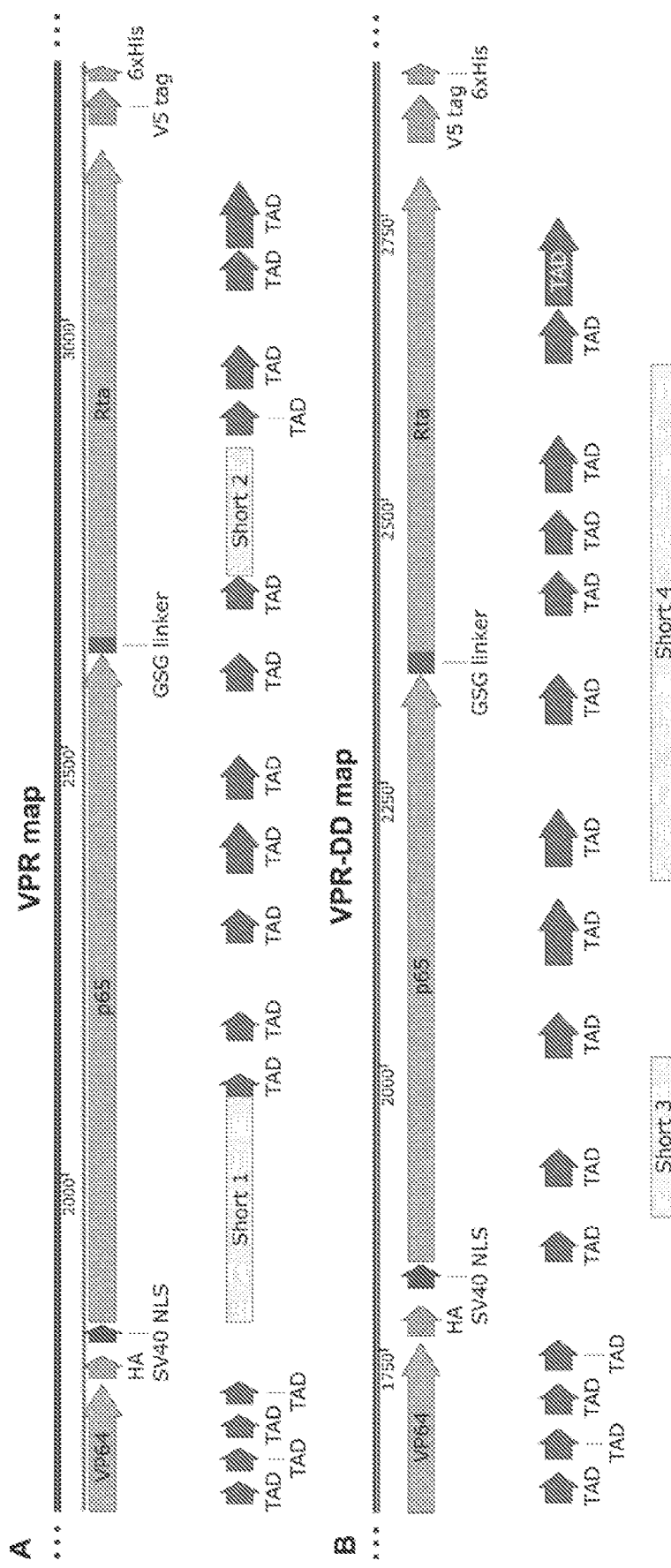
FIG. 7. Schematic representation of VPR (A) and VPR-DD (B) showing VP64, p65 and Rta transcriptional activation domains. TAD: 9-amino acid transactivation domains. Short 1, 2, 3 and 4 segments are indicated. (C) Expression of Klotho in mouse N2a and HT-22 cells and human HK-2 cells transfected with ZFP3_VPR and ZFP3_VPR deletion constructs measured using qPCR. *, p<0.05 compared to EV control. (D) Expression of Klotho in human HK-2 cells transfected with ZFP52_VPR and ZFP52_VPR deletion constructs measured using qPCR. *, p<0.05 compared to EV control.
Figure 7:
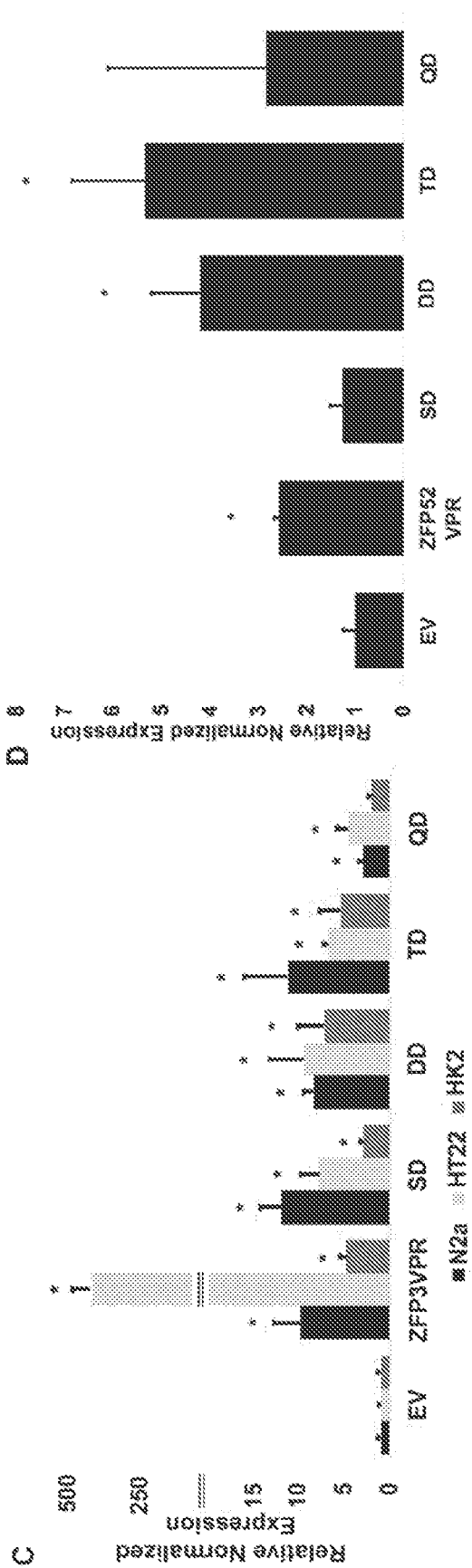

Two segments, referred to as Short 1 and Short 2, which appeared to lack TADs, were deleted from the VPR construct (see Table 5). The single deletion construct (VPR-SD) lacks Short 1, while the double deletion construct (VPR-DD) lacks both Short 1 and Short 2 (FIG. 7A). Two further segments, Short 3 and Short 4, were deleted from the VPR construct to produce a triple deletion construct (VPR-TD) and a quadruple deletion construct (VPR-QD) (FIG. 7B). The following primers were used to generate VPR-SD, VPR-DD, VPR-TD and VPR-QD:

```
Short1_FWD:
                                        (SEQ ID NO. 78)
TCTCAGGCCTCTGCTCTGGCTCCAGCC Short1_RV:
                                        (SEQ ID NO. 79)
AGCAGAGGCCTGAGAACCAACTTTGCGTTTCTTTTTCGGAG Short2_FWD:
                                        (SEQ ID NO. 80)
CCACTGGATCCAGCGCCCGCAGTG Short2_RV:
                                        (SEQ ID NO. 81)
CGCTGGATCCAGTGGGCCCTCAAACACGTCACTAATAGC Short3_FWD:
                                        (SEQ ID NO. 82)
GGCACACTGTCTGAAGCTCTGCTGC Short3_RV:
                                        (SEQ ID NO. 83)
TTCAGACAGTGTGCCCACCTGAGGAGGGGCTGGAGCCAGAG Short4_FWD:
                                        (SEQ ID NO. 84)
GATGAGCTGACAACCACACTTGAGTC Short4_RV:
                                        (SEQ ID NO. 85)
GGTTGTCAGCTCATCGGCCACAGGGATGCCCTGGTTCAGC
```

The sequence of VPR is set forth in Table 5, and the sequences of VPR-SD, VPR-DD, VPR-TD and VPR-QD are set forth in Table 7.

TABLE 7

| | | VPR deletion sequences |
|---|---|---|
| SEQ ID NO. | Description | Sequence |
| 86 | VPR-SD •Short 2 segment in bold | DALDDFDLDMLGSDALDDFDLDMLGSDALDDFDLDMLGSDALDDFDLDMLI NYPYDVPDYASSSGSPKKKRKVGSQASALAPAPPQVLPQAPAPAPAPAMV SALAQAPAPVPVLAPGPPQAVAPPAPKPTQAGEGTLSEALLQLQFDDEDLG ALLGNSTDPAVFTDLASVDNSEFQQLLNQGIPVAPHTTEPMLMEYPEAITRL VTGAQRPPDPAPAPLGAPGLPNGLLSGDEDFSSIADMDFSALLGSGSGSRD SREGMFLPKPEAGSAISDVFEGREVCQPKRIRPFHPPGSPWANRPLPASLA PTPTGPVHEPVGSLTPAPVPQPLDPAPAVTPEASHLLEDPDEETSQAVKAL REMADTVIPQKEEAAICGQMDLSHPPPRGHLDELTTTLESMTEDLNLDSPLT PELNEILDTFLNDECLLHAMHISTGLSIFDTSLF |
| 87 | VPR-DD •Short 3 segment in bold •Short 4 segment underlined | DALDDFDLDMLGSDALDDFDLDMLGSDALDDFDLDMLGSDALDDFDLDMLI NYPYDVPDYASSSGSPKKKRKVGSQASALAPAPPQVLPQAPAPAPAPAMV SALAQAPAPVPVLAPGPPQAVAPPAPKPTQAGEGTLSEALLQLQFDDEDL GALLGNSTDPAVFTDLASVDNSEFQQLLNQGIPVA<u>PHTTEPMLMEYPEAITR LVTGAQRPPDPAPAPLGAPGLPNGLLSGDEDFSSIADMDFSALLGSGSGSR DSREGMFLPKPEAGSAISDVFEGPLDPAPAVTPEASHLLEDPDEETSQAVKA LREMADTVIPQKEEAAICGQMDLSHPPPRGHLDELTTTLESMTEDLNLDSPL TPELNEILDTFLNDECLLHAMHISTGLSIFDTSLF</u> |
| 88 | VPR-TD •Short 4 segment underlined | DALDDFDLDMLGSDALDDFDLDMLGSDALDDFDLDMLGSDALDDFDLDMLI NYPYDVPDYASSSGSPKKKRKVGSQASALAPAPPQVGTLSEALLQLQFDDE DLGALLGNSTDPAVFIDLASVDNSEFQQLLNQGIPVA<u>PHTTEPMLMEYPEAI TRLVTGAQRPPDPAPAPLGAPGLPNGLLSGDEDFSSIADMDFSALLGSGSG SRDSREGMFLPKPEAGSAISDVFEGPLDPAPAVTPEASHLLEDPDEETSQA VKALREMADTVIPQKEEAAICGQMDLSHPPPRGHLDELITTLESMTEDLNLD SPLTPELNEILDTFLNDECLLHAMHISTGLSIFDTSLF</u> |
| 89 | VPR-QD | DALDDFDLDMLGSDALDDFDLDMLGSDALDDFDLDMLGSDALDDFDLDMLI NYPYDVPDYASSSGSPKKKRKVGSQASALAPAPPQVTLSEALLQLQFDDED LGALLGNSTDPAVFTDLASVDNSEFQQLLNQGIPVADELTTTLESMTEDLNL DSPLTPELNEILDTFLNDECLLHAMHISTGLSIFDTSLF |

The deletion constructs were fused to ZFP3_Egr1_site3 and ZFP52 and transfected into mouse and/or human cells. Deletion of Short 1 and Short 2 did not impair the ability of ZFP3_VPR to increase expression of Klotho in human or mouse cells. However, further deletion of Short 3 and Short 4 impaired the transcriptional activation activity of ZFP3_VPR (FIG. 7C). In the case of ZFP52, both VPR-DD and VPR-TD increased expression of Klotho in human HK-2 cells (FIG. 7D).

Example 7

In the context of gene therapy, inducible gene expression systems may enable gene expression to be triggered at specific times and in specific cell types. To develop a Tet-on system for inducing Klotho gene expression, the ZFP3_VPR construct was cloned into a doxycycline-inducible vector. The ZFP3_VPR and ZFP52_VPR sequences and the inducible vector (Lenti-iCas9-neo, Addgene #85400) were amplified using Clontech HiFi according to the manufacturers protocol and the following primers:

```
Forward primer for ZFP3_VPR:
                                        (SEQ ID NO. 90)
GACGATGACGATAAGGCCCAGGCGGCCCTGGAGCCC Reverse primer for both ZFP3_VPR and ZFP52_VPR:
                                        (SEQ ID NO. 91)
GCTGAAGTTGGTGGCATGGTGATGGTGATGATGACCGGTAC Forward primer for ZFP52_VPR:
                                        (SEQ ID NO. 92)
GACGATGACGATAAGGCCCAAGCTGCCTTAGAACCCGGCG Forward primer for inducible vector:
                                        (SEQ ID NO. 93)
GCCACCAACTTCAGCCTGCTGAAG Reverse primer for inducible vector:
                                        (SEQ ID NO. 94)
CTTATCGTCATCGTCTTTGTAATCCATGG
```

Figure 8:
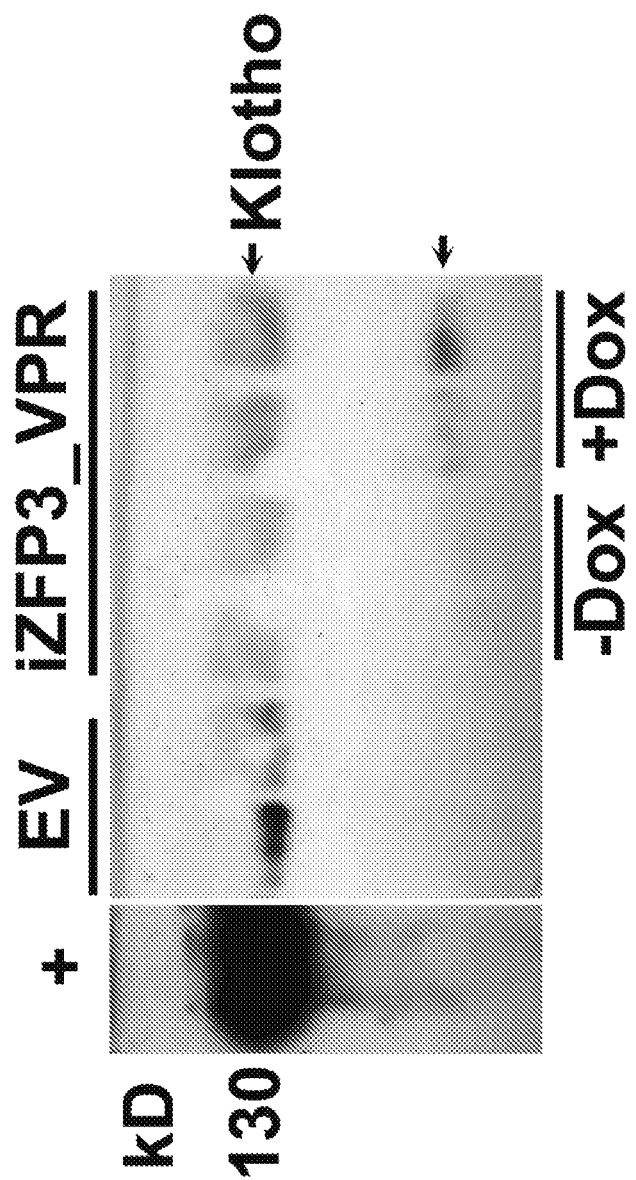
FIG. 8. Western blot analysis of Klotho protein expressed by HK-2 cells transfected with an inducible ZFP3_VPR construct with (+Dox) or without (−Dox) doxycycline treatment. Arrows indicate 130 kDa and 70 kDa Klotho isoforms.

Referring to FIG. 8, expression of Klotho by HK-22 cells transfected with the inducible ZFP3_VPR construct was increased following treatment with doxycycline.

Example 8

Klotho is expressed in human dermal fibroblasts (HDF) and has been implicated in angiogenesis of human dermal microvasculature and facilitating cell migration (Mazzotta et al. 2017. Arthritis Res. Ther. 19(1): 27). To determine whether the DNA binding proteins described herein can facilitate skin cell migration, a HDF model for skin wound healing was employed.

Figure 9:
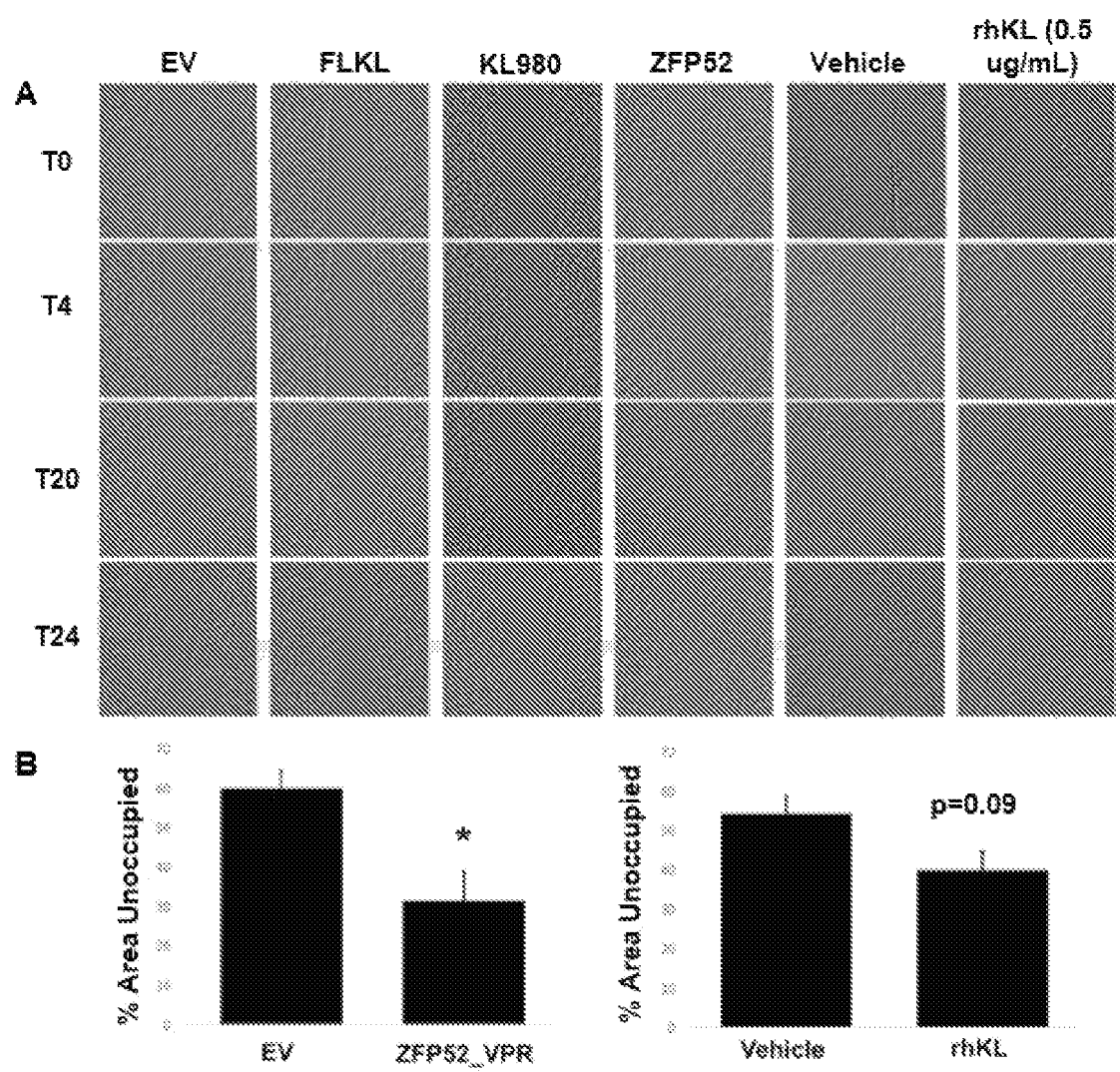
FIG. 9. ZFP52_VPR promotes migration of human dermal fibroblasts. A) Time course migration of cells transfected with either EV, FLKL, KL980 or ZFP52_VPR constructs. In another group, either vehicle control or rhKL was added in the media. T0: time 0, T4: 4 hrs time point, T20: 20 hrs time point, T24: 24 hrs time point. B) Bar graph representation of results from (A). Results normalised to total cell number after nuclear stain with DAPI. *, p<0.05 compared to EV control.

As shown in FIGS. 9A and 9B, ZFP52_VPR significantly increased cell migration (less % area unoccupied; p<0.05). Addition of recombinant human Klotho protein (rhKL) to the media also increased cell migration (FIGS. 9A and 9B). These results demonstrate that ZFP52_VPR can facilitate human dermal fibroblast migration, and may be used to facilitate wound healing.

Cell Culture

Human neonatal dermal fibroblasts were cultured on T25 flasks maintained with DMEM supplemented with 10% fetal bovine serum, 1% penicillin-streptomycin, 1% glutamax at 37° C. and 5% $CO_2$.

Cell Migration (Wound Healing) Assay

Neonatal human dermal fibroblasts were plated on uncoated twelve well plates and cultured to 80% confluence. Twenty-four hours later, cells were transfected with full length Klotho (FLKL), the extracellular domain of Klotho (KL980), ZFP52_VPR, and EV control for 4 hours. Cells treated with rhKL (0.5 μL/mL) or Vehicle control were treated for 4 hours just before seeding into culture-insert wells.

The next day, cells were re-seeded into a culture-insert well (Ibidi Culture-Insert 2 Well in μ-Dish 35 mm high). Twenty-four hours after seeding the cells in the culture-insert wells, the insert was removed and cell migration commenced. Images were captured at 4 subsequent time points in two fields of view under the microscope.

The invention claimed is:

1. A method of increasing expression of a Klotho gene in a cell the method comprising administering to the cell a DNA binding protein comprising or attached to a transcriptional activation domain wherein the DNA binding protein binds to a target sequence within or near the Klotho gene and thereby increases expression of the Klotho gene, wherein the DNA binding protein is a zinc finger protein comprising:

a ZF1 zinc finger comprising the sequence set forth in SEQ ID NO 8, a ZF2 zinc finger comprising the sequence set forth in SEQ ID NO 16, a ZF3 zinc finger comprising the sequence set forth in SEQ ID NO 18, a ZF4 zinc finger comprising the sequence set forth in SEQ ID NO. 16, a ZF5 zinc finger comprising the sequence set forth in SEQ ID NO 3, a ZF6 zinc finger comprising the sequence set forth in SEQ ID NO 8 and a ZF7 zinc finger comprising the sequence set forth in SEQ ID NO 3.

2. The method of claim 1 wherein the target sequence comprises at least 9 contiguous nucleotides from the sequence set forth in SEQ ID NO 67.

3. The method of claim 1 wherein the zinc finger protein comprises
a zinc finger domain comprising the sequence set forth in SEQ ID NO 45, or a sequence having at least about 80% identity to SEQ ID NO 45.

4. The method of claim 1 wherein the transcriptional activation domain is selected from the group consisting of VP16, or a plurality thereof, VP64, VP160, p65, MyoD1, HSF1, RTA, TET3CD, p300 and SET7/9.

5. The method of claim 1 wherein the DNA binding protein comprises or is attached to more than one transcriptional activation domain.

6. The method of claim 1 wherein the cell is a human cell.

* * * * *

SEQUENCE LISTING

```
<160> NUMBER OF SEQ ID NOS: 94

<210> SEQ ID NO 1
<211> LENGTH: 7
<212> TYPE: PRT
<213> ORGANISM: Artificial Sequence
<220> FEATURE:
<223> OTHER INFORMATION: ZFP1 - ZF1

<400> SEQUENCE: 1

Asp Pro Gly His Leu Val Arg
1               5

<210> SEQ ID NO 2
<211> LENGTH: 7
<212> TYPE: PRT
<213> ORGANISM: Artificial Sequence
<220> FEATURE:
<223> OTHER INFORMATION: ZFP1 - ZF2

<400> SEQUENCE: 2

Ser Lys Lys Ala Leu Thr Glu
1               5
```

```
<210> SEQ ID NO 3
<211> LENGTH: 7
<212> TYPE: PRT
<213> ORGANISM: Artificial Sequence
<220> FEATURE:
<223> OTHER INFORMATION: ZFP1 - ZF3

<400> SEQUENCE: 3

Arg Asn Asp Ala Leu Thr Glu
1               5

<210> SEQ ID NO 4
<211> LENGTH: 7
<212> TYPE: PRT
<213> ORGANISM: Artificial Sequence
<220> FEATURE:
<223> OTHER INFORMATION: ZFP1 - ZF4

<400> SEQUENCE: 4

Asp Pro Gly Ala Leu Val Arg
1               5

<210> SEQ ID NO 5
<211> LENGTH: 7
<212> TYPE: PRT
<213> ORGANISM: Artificial Sequence
<220> FEATURE:
<223> OTHER INFORMATION: ZFP1 - ZF5

<400> SEQUENCE: 5

Asp Ser Gly Asn Leu Arg Val
1               5

<210> SEQ ID NO 6
<211> LENGTH: 7
<212> TYPE: PRT
<213> ORGANISM: Artificial Sequence
<220> FEATURE:
<223> OTHER INFORMATION: ZFP1 - ZF6

<400> SEQUENCE: 6

Gln Ser Gly His Leu Thr Glu
1               5

<210> SEQ ID NO 7
<211> LENGTH: 7
<212> TYPE: PRT
<213> ORGANISM: Artificial Sequence
<220> FEATURE:
<223> OTHER INFORMATION: ZFP52 - ZF1

<400> SEQUENCE: 7

Thr Lys Asn Ser Leu Thr Glu
1               5

<210> SEQ ID NO 8
<211> LENGTH: 7
<212> TYPE: PRT
<213> ORGANISM: Artificial Sequence
<220> FEATURE:
<223> OTHER INFORMATION: ZFP52 - ZF2

<400> SEQUENCE: 8

Gln Ser Gly Asp Leu Arg Arg
1               5

<210> SEQ ID NO 9
```

```
<211> LENGTH: 7
<212> TYPE: PRT
<213> ORGANISM: Artificial Sequence
<220> FEATURE:
<223> OTHER INFORMATION: ZFP52 - ZF3

<400> SEQUENCE: 9

Asp Cys Arg Asp Leu Ala Arg
1               5

<210> SEQ ID NO 10
<211> LENGTH: 7
<212> TYPE: PRT
<213> ORGANISM: Artificial Sequence
<220> FEATURE:
<223> OTHER INFORMATION: ZFP52 - ZF5

<400> SEQUENCE: 10

Arg Thr Asp Thr Leu Arg Asp
1               5

<210> SEQ ID NO 11
<211> LENGTH: 7
<212> TYPE: PRT
<213> ORGANISM: Artificial Sequence
<220> FEATURE:
<223> OTHER INFORMATION: ZFP52 - ZF6

<400> SEQUENCE: 11

Arg Ser Asp Asp Leu Val Arg
1               5

<210> SEQ ID NO 12
<211> LENGTH: 7
<212> TYPE: PRT
<213> ORGANISM: Artificial Sequence
<220> FEATURE:
<223> OTHER INFORMATION: ZFP52 - ZF7

<400> SEQUENCE: 12

Arg Ser Asp Lys Leu Thr Glu
1               5

<210> SEQ ID NO 13
<211> LENGTH: 7
<212> TYPE: PRT
<213> ORGANISM: Artificial Sequence
<220> FEATURE:
<223> OTHER INFORMATION: ZFP52 - ZF8

<400> SEQUENCE: 13

Arg Asn Asp Thr Leu Thr Glu
1               5

<210> SEQ ID NO 14
<211> LENGTH: 7
<212> TYPE: PRT
<213> ORGANISM: Artificial Sequence
<220> FEATURE:
<223> OTHER INFORMATION: ZFP52 - ZF9

<400> SEQUENCE: 14

Ser Arg Arg Thr Cys Arg Ala
1               5

<210> SEQ ID NO 15
<211> LENGTH: 7
```

```
<212> TYPE: PRT
<213> ORGANISM: Artificial Sequence
<220> FEATURE:
<223> OTHER INFORMATION: ZFP1-Egr1-site1-sense - ZF1

<400> SEQUENCE: 15

Thr Ser Gly Asn Leu Thr Glu
1               5

<210> SEQ ID NO 16
<211> LENGTH: 7
<212> TYPE: PRT
<213> ORGANISM: Artificial Sequence
<220> FEATURE:
<223> OTHER INFORMATION: ZFP1-Egr1-site1-sense - ZF1

<400> SEQUENCE: 16

Arg Ser Asp Lys Leu Val Arg
1               5

<210> SEQ ID NO 17
<211> LENGTH: 7
<212> TYPE: PRT
<213> ORGANISM: Artificial Sequence
<220> FEATURE:
<223> OTHER INFORMATION: ZFP1-Egr1-site1-sense - ZF3

<400> SEQUENCE: 17

His Thr Gly His Leu Leu Glu
1               5

<210> SEQ ID NO 18
<211> LENGTH: 7
<212> TYPE: PRT
<213> ORGANISM: Artificial Sequence
<220> FEATURE:
<223> OTHER INFORMATION: ZFP2-Egr1-site2-sense - ZF3

<400> SEQUENCE: 18

Arg Ser Asp Glu Leu Val Arg
1               5

<210> SEQ ID NO 19
<211> LENGTH: 7
<212> TYPE: PRT
<213> ORGANISM: Artificial Sequence
<220> FEATURE:
<223> OTHER INFORMATION: ZFP2-Egr1-site2-sense - ZF6

<400> SEQUENCE: 19

Gln Arg Ala His Leu Glu Arg
1               5

<210> SEQ ID NO 20
<211> LENGTH: 7
<212> TYPE: PRT
<213> ORGANISM: Artificial Sequence
<220> FEATURE:
<223> OTHER INFORMATION: Egr1-insert-site2 - ZF1

<400> SEQUENCE: 20

Arg Ser Asp Glu Leu Thr Arg
1               5

<210> SEQ ID NO 21
<211> LENGTH: 7
<212> TYPE: PRT
```

<213> ORGANISM: Artificial Sequence
<220> FEATURE:
<223> OTHER INFORMATION: Egr1-insert-site2 - ZF2

<400> SEQUENCE: 21

Arg Ser Asp His Leu Thr Thr
1               5

<210> SEQ ID NO 22
<211> LENGTH: 7
<212> TYPE: PRT
<213> ORGANISM: Artificial Sequence
<220> FEATURE:
<223> OTHER INFORMATION: Egr1-insert-site2 - ZF3

<400> SEQUENCE: 22

Arg Ser Asp Glu Arg Lys Arg
1               5

<210> SEQ ID NO 23
<211> LENGTH: 4000
<212> TYPE: DNA
<213> ORGANISM: Homo sapiens

<400> SEQUENCE: 23

```
acaatatatt gtattttga  aaatctcaga  gtagatttta  agtattcttc  ttttctttc     60
ttttcttctt tctttttctt ttttctttt   tgaaacagac  tcttgctctg  ttgccaaagc    120
tggagtacag tggtgtgatc tcagctcact  gcaacctccg  cctcccgggt  tcaagtgatt   180
ctcctgcctc agcctcctga gtagctggga  ttacaggtgc  ctgccaccat  gttggtgaat   240
ttttgtattt tagtagaga  caggagtttc  accatgttgg  ccaggctggt  ctcgaactcc   300
tgaccttagg tggtccacct gcctcggcct  ctcaaagtgc  tgggattaca  ggtgtgagcc   360
accacgcccg gccagatttt aagtcttctt  accacaaaaa  aataagtat   gtgaggtaat   420
acatcgtttt attagctcaa tttagccact  ctacaaatgt  gtatatattt  taaaataaca   480
tgctgtacat gaaaatatat ataatttttt  gtctgttaaa  aattaattaa  ttaattaatt   540
ttaaaaagag gagggcaggg aatacttgtg  tattttgtta  actggacaaa  tgaaactcta   600
ctttcatttg ctcattaaac aaatacttgt  tttgtgctca  gcatgattct  aggcactggg   660
actactgcat tttggtccat tacttccttg  cgcacaaaaa  ccctttcttt  tcaccacgaa   720
tacactatga acatgttttt ttcttcagtg  ttggcatctc  ttgattcctt  ccctccaggt   780
ctttgtgcga gttttactct ttaaaccca   gatattgtca  tattttctc   tgttaaactt   840
ttccaaacaa ctcaaaatag ggtaatttct  tcttcttctg  aatttctctg  acaattattc   900
tatgggtcat ttattaacac agcataatca  aacaacttat  ttatttcat   ctttcttgat   960
cctttcttca gttggatgtt gtctttgagg  gcagaggttg  tcctctatgt  tttgaagtct  1020
ccacacagct catcgttgcc ttgcccgtag  ttgtagctca  gtgaaataaa  aatatgtccg  1080
tagaaggtga tgtctgtgac tggtgagccg  agagcttgtg  gggttggtgt  tgtatttgag  1140
tgcatgtgaa tcagtgcatc tcctgctcca  ttggtgttaa  aaggctccca  tcgtcctggg  1200
aacacaatag gaaagagaac aggtgggaag  gcactggatg  aaggaatgtg  gagaatggag  1260
gaaaagttga tcagattgtt gacaactttc  agtgttgaaa  ttgtcaccaa  atcaaagtc   1320
agtaaataaa tttacaatgt ccttttcttc  aatgcatcaa  taacttcacc  ttcctgttca  1380
aagcacagca agtaattaat ctcttatttg  catttgaaac  ccaagtttca  gatgtttgaa  1440
ggtggttgta aaaaataaaa accaaaataa  agccaaaata  aataagcagc  agcactaggc  1500
```

```
cgggcacagt gtctcacacc tgtaatccca gcattttagg agaccgaggt gggtggatca   1560
caggagatca ggagtttgag accagcctgg tcagcatggt gaaaccctgt ctctactaaa   1620
aatacaaaaa ttagccaggt gtggtggtgt gcccttataa tcccagctac tgggggctg   1680 agacaggaga attgcttgaa cctgggaggc agaggttgca gtgagcagag accatgccac   1740
tgcactccag cctgggcgac agagtgagac tccgtctcac acttgtggaa cccagaactt   1800
agtaaccatg aacagaacct aataaacag aaagttctgg aaataaagtt taatcatcat   1860
gcaatcttta tcactgggtt aaatgaacaa tcatctggga acatgtcttg gaatgcttaa   1920
agctttgaga tgcatgtgcc tatgtggcag acaaatttca aatgtgaaac gtttagttaa   1980
cttggtcttg cttttaatc actgctttaa aatttaaaaa atgctgctgg tcaagtaaaa   2040
atagcaatag ataaaatctg ccctgagcaa acagaccata catcaataaa tgaatactta   2100
gcttaagcga ttttccatga gacccatgaa gcatttctaa ttgaaactta acaagctaca   2160
acccaacaga cactccaatc ttcacttcta gaagggaaat gtgatactcc atgtagacgt   2220 agcttttaa atttagctgg aagacagcgt gacagtgaag ttgtgtgctg taatttttta   2280
aaattgctga agtgtcatgg tttgctattt cgtatttatt gaaaaaatgt aaatgctata   2340
tttaacagaa tggcagtaac tctgtttcaa tctgaagact taatcttact aatcatggta   2400
atatatgctg gctggagttg ggaatatttc ataaaatact ggataaaatt tgtgcttata   2460
tttcagggga attaataaaa gcaccttcat ctgcaacatt taaaatgtta ttgcctttaa   2520
atttgtatta ataatgcag ggaggataga tcactggggg agaatggatg cacctctgtg   2580
aggatcttgg tcattcaaca cacgtgtacg ggtgaggaaa ctaaggcacg acttactggg   2640
tagggaggta gggatattag caagatcctt cacttgtctg ggctttctgt ctttgagtca   2700
cctttgcgca gttttcact ggacttcaca agcctctgag gcggcagggc agacaggaca   2760
tccttatttt atagaggaaa aaacttaggc ttacagaggt ttcctgcccc aaatcacaaa   2820
ggtggagcct agaccttctc agtctccacc aactgtattt cggttagcca caatcctatc   2880
tacccacatc caaatggaca ccgtggctct gcaacttctg tcaaaagggc tctttggcaa   2940
caggaaaaac gtcatggctc cattgtattg tagaggatgg gaatgggtgt tccggctaaa   3000
ttctccctcc cctttccctc cacagctcag atggcaaatg tgcgacccag ggacctcccg   3060
ctccagcaga cctgtgcgca caactttgca cagattacct gctaagtcag agccgaaagg   3120
taacacagat gccaaggat aataaaggtg aatgagattt actcaaaatt ggaaacttgg   3180
tgtttggttt tcaggagaa caatcaacga ctgtgatttg aagttcacca gggtattctg   3240
agagatctaa tcaaagatag agtgctggtt tgaaattatt aaaaggtaac agtaaagggg   3300
agagcaaaac cccagtccca acgcaaccca taaatctact ttgtcttcct cgaaagaggg   3360
gcgcgggtgg gcgcgtctcc ccgcgagcat ctcacctaag ggggaatccc tttcagcgca   3420
cggcgaagtt ccccctcggc tgtcccacct ggcagtccct ctaggatttc ggccagtccc   3480
taattggctc cagcaatgtc cagccggagc ttctttgggc ctccgagtgg gagaaaagtg   3540
agagcaggtg cttccccagc ggcgcgctcc gctagggccc ggcaggatcc cgccccaag   3600 tcggggaaag ttggtcggcg cctttctcc ccgacgaagc cgctccaggg ctgctctcag   3660
aggacgcgcg gcaggcaaag agaatgaacc tgagcgtcca cgaaacgtcc tgcacggctc   3720 ccggagctg ggaggaacag gtgccttttct ccgacgtccg cgggcgacgc ctgccgcacc   3780
ttgcccgctg ccgcgcccct cccgggcacc cctcgccctc ggcgcccctg cccccacccc   3840
```

```
cagtgccagg gcggaggcag tcccggctcg caggtaatta ttgccagcgg agcccgccgg    3900
ggagcggggg tgggcgcgcc ggcggtgggc gggcgggcgc ggcggggcgc gggcataaag    3960
gggcgcggcg cggggccccg agcctggct cccgcgcagc                           4000

<210> SEQ ID NO 24
<211> LENGTH: 4000
<212> TYPE: DNA
<213> ORGANISM: Homo sapiens

<400> SEQUENCE: 24
gctgcgcggg agccaggctc cggggccccg cgccgcgccc ctttatgccc gcgcccgcc      60 gcgcccgccc gcccaccgcc ggcgcgccca ccccgctcc ccggcgggct ccgctggcaa    120
taattacctg cgagccggga ctgcctccgc cctggcactg gggtggggg caggggcgcc    180 gagggcgagg ggtgcccggg aggggcgcgg cagcgggcaa ggtgcggcag cgtcgcccg    240 cggacgtcgg agaaaggcac ctgttcctcc cagctcccgg gagccgtgca ggacgtttcg    300
tggacgctca ggttcattct ctttgcctgc cgcgcgtcct ctgagagcag ccctggagcg    360
gcttcgtcgg ggagaaaagg cgccgaccaa cttccccga cttggggcg gatcctgcc     420 gggccctagc ggagcgcgcc gctggggaag cacctgctct cacttttctc ccactcggag    480
gcccaaagaa gctccggctg acattgctg gagccaatta gggactggcc gaaatcctag    540
agggactgcc aggtgggaca gccgagggg aacttcgccg tgcgctgaaa gggattcccc    600
cttaggtgag atgctcgcgg ggagacgcgc ccaccgcgc ccctctttcg aggaagacaa    660
agtagattta tgggttgcgt tgggactggg gttttgctct cccttttact gttacctttt    720
aataatttca aaccagcact ctatctttga ttagatctct cagaataccc tggtgaactt    780
caaatcacag tcgttgattg ttctcctgaa aaaccaaaca ccaagtttcc aattttgagt    840
aaatctcatt cacctttatt atcctttggc atctgtgtta cctttcggct ctgacttagc    900
aggtaatctg tgcaaagttg tgcgcacagg tctgctggag cggaggtcc ctgggtcgca    960 catttgccat ctgagctgtg gagggaaagg ggagggagaa tttagccgga cacccattc   1020 ccatcctcta caatacaatg gagccatgac gttttttcctg ttgccaaaga gcccttttga   1080
cagaagttgc agagccacgg tgtccatttg gatgtgggta gataggattg tggctaaccg   1140
aaatacagtt ggtggagact gagaaggtct aggctccacc tttgtgattt ggggcaggaa   1200
acctctgtaa gcctaagttt tttcctctat aaaataagga tgtcctgtct gccctgccgc   1260
ctcagaggct tgtgaagtcc agtgaaaaac tgcgcaaagg tgactcaaag acagaaagcc   1320
cagacaagtg aaggatcttg ctaatatccc tacctcccta cccagtaagt cgtgccttag   1380
tttcctcacc cgtacacgtg tgttgaatga ccaagatcct cacagaggtg catccattct   1440
cccccagtga tctatcctcc ctgcattatt aatacaaat ttaaaggcaa taacatttta   1500
aatgttgcag atgaaggtgc ttttattaat tcccctgaaa ataagcaca aatttattcc   1560 agtattttat gaaatattcc caactccagc cagcatatat taccatgatt agtaagatta   1620
agtcttcaga ttgaaacaga gttactgcca ttctgttaaa tatagcattt acatttttc    1680 aataaatacg aaatagcaaa ccatgacact tcagcaattt taaaaaatta cagcacacaa   1740
cttcactgtc acgctgtctt ccagctaaat ttaaaagct acgtctacat ggagtatcac   1800
atttcccttc tagaagtgaa gattggagtg tctgttgggt tgtagcttgt aagtttcaa    1860 ttagaaatgc ttcatgggtc tcatggaaaa tcgcttaagc taagtattca tttattgatg   1920
tatggtctgt ttgctcaggg cagatttat ctattgctat ttttacttga ccagcagcat   1980
```

| | |
|---|---|
| tttttaaatt ttaaagcagt gattaaaaag caagaccaag ttaactaaac gtttcacatt | 2040 |
| tgaaatttgt ctgccacata ggcacatgca tctcaaagct ttaagcattc caagacatgt | 2100 |
| tcccagatga ttgttcattt aacccagtga taaagattgc atgatgatta aactttattt | 2160 |
| ccagaacttt ctgtttatta aggttctgtt catggttact aagttctggg ttccacaagt | 2220 |
| gtgagacgga gtctcactct gtcgcccagg ctggagtgca gtggcatggt ctctgctcac | 2280 |
| tgcaacctct gcctcccagg ttcaagcaat tctcctgtct cagcccccca gtagctggga | 2340 |
| ttataagggc acaccaccac acctggctaa ttttttgtatt tttagtagag acagggtttc | 2400 |
| accatgctga ccaggctggt ctcaaactcc tgatctcctg tgatccaccc acctcggtct | 2460 |
| cctaaaatgc tgggattaca ggtgtgagac actgtgcccg gcctagtgct gctgcttatt | 2520 |
| tattttggct ttattttggt ttttattttt tacaaccacc ttcaaacatc tgaaacttgg | 2580 |
| gtttcaaatg caaataagag attaattact tgctgtgctt tgaacaggaa ggtgaagtta | 2640 |
| ttgatgcatt gaagaaaagg acattgtaaa tttatttact gactttgatt ttggtgacaa | 2700 |
| tttcaacact gaaagttgtc aacaatctga tcaactttc ctccattctc cacattcctt | 2760 |
| catccagtgc cttcccacct gttctctttc ctattgtgtt cccaggacga tgggagcctt | 2820 |
| ttaacaccaa tggagcagga gatgcactga ttcacatgca ctcaaataca acaccaaccc | 2880 |
| cacaagctct cggctcacca gtcacagaca tcaccttcta cggacatatt tttatttcac | 2940 |
| tgagctacaa ctacgggcaa ggcaacgatg agctgtgtgg agacttcaaa acatagagga | 3000 |
| caacctctgc cctcaaagac aacatccaac tgaagaaagg atcaagaaag atgaaaataa | 3060 |
| ataagttgtt tgattatgct gtgttaataa atgacccata gaataattgt cagagaaatt | 3120 |
| cagaagaaga agaaattacc ctattttgag ttgtttggaa aagtttaaca gagaaaaata | 3180 |
| tgacaatatc tggggtttaa agagtaaaac tcgcacaaag acctggaggg aaggaatcaa | 3240 |
| gagatgccaa cactgaagaa aaaaacatgt tcatagtgta ttcgtggtga aaagaaaggg | 3300 |
| tttttgtgcg caaggaagta atggaccaaa atgcagtagt cccagtgcct agaatcatgc | 3360 |
| tgagcacaaa acaagtattt gtttaatgag caaatgaaag tagagtttca tttgtccagt | 3420 |
| taacaaaata cacaagtatt ccctgccctc ctcttttaa aattaattaa ttaattaatt | 3480 |
| tttaacagac aaaaaattat atatatttc atgtacagca tgttatttta aaatatatac | 3540 |
| acatttgtag agtggctaaa ttgagctaat aaacgtatgt attacctcac atacttattt | 3600 |
| ttttgtggt aagaagactt aaaatctggc cgggcgtggt ggctcacacc tgtaatccca | 3660 |
| gcactttgag aggccgaggc aggtggacca cctaaggtca ggagttcgag accagcctgg | 3720 |
| ccaacatggt gaaactcctg tctctactaa aaatacaaaa attcaccaac atggtggcag | 3780 |
| gcacctgtaa tccagctac tcaggaggct gaggcaggaa atcacttga acccgggagg | 3840 |
| cggaggttgc agtgagctga gatcacacca ctgtactcca gctttggcaa cagagcaaga | 3900 |
| gtctgtttca aaaagaaaa aagaaaagaa aagaagaaaa gaaagaaaaa gaagaatact | 3960 |
| taaaatctac tctgagattt tcaaaaatac aatatattgt | 4000 |

<210> SEQ ID NO 25
<211> LENGTH: 47745
<212> TYPE: DNA
<213> ORGANISM: Homo sapiens

<400> SEQUENCE: 25

| | |
|---|---|
| atgcccgcca gcgccccgcc gcgccgcccg cggccgccgc cgccgtcgct gtcgctgctg | 60 |

-continued

| | |
|---|---|
| ctggtgctgc tgggcctggg cggccgccgc ctgcgtgcgg agccgggcga cggcgcgcag | 120 |
| acctgggccc gtttctcgcg gcctcctgcc cccgaggccg cgggcctctt ccagggcacc | 180 |
| ttccccgacg gcttcctctg ggccgtgggc agcgccgcct accagaccga gggcggctgg | 240 |
| cagcagcacg gcaagggtgc gtccatctgg gatacgttca cccaccaccc cctggcaccc | 300 |
| ccgggagact cccggaacgc cagtctgccg ttgggcgccc cgtcgccgct gcagcccgcc | 360 |
| accggggacg tagccagcga cagctacaac aacgtcttcc gcgacacgga ggcgctgcgc | 420 |
| gagctcgggg tcactcacta ccgcttctcc atctcgtggg cgcgagtgct ccccaatggc | 480 |
| agcgcgggc tccccaaccg cgaggggctg cgctactacc ggcgcctgct ggagcggctg | 540 |
| cgggagctgg gcgtgcagcc cgtggtcacc ctgtaccact gggacctgcc ccagcgcctg | 600 |
| caggacgcct acggcggctg ggccaaccgc gccctggccg accacttcag ggattacgcg | 660 |
| gagctctgct tccgccactt cggcggtcag gtcaagtact ggatcaccat cgacaacccc | 720 |
| tacgtggtgg cctggcacgg ctacgccacc gggcgcctgg cccccggcat ccggggcagc | 780 |
| ccgcggctcg ggtacctggt ggcgcacaac ctcctcctgg tgagtgcgag gggccaggcg | 840 |
| gagggccacg caggggagac agagggcctc cacaggggcc aggggaagt gtgggaactg | 900 |
| agtctccccc agacgaggct tcacttggac acgtgtatgt ggtcaccggg ggaaactgag | 960 |
| cagttctgac ttcccttgga aggcgtggaa ttaggagaga aatcccttag tgggcacacg | 1020 |
| agtgagtgcc ccttggagtc catctgtgga aggaagcgg tgataggttt ccgcagtgag | 1080 |
| gaaagaaact cctttctctg ggtgtagagg aattcctaga ggtgagggcg gggaggattt | 1140 |
| gctaggagta actgcaggaa gagaatgagc agggtggatg aaagaaacac gtttgttctt | 1200 |
| aagccgcaca gatagcatta ctctctggag ctgtcacgag ttcagtgtta atccaataag | 1260 |
| atctgtcttg cttgtggcac aagttccacc tgttgtgaaa gtgtcaaaac acaactcccg | 1320 |
| gagagtcaga tttaaactgt gtttggaggt ccctctgcg gcagggcagg gaactgcatc | 1380 |
| caccaatctt attcaccggg gtgtgaagac cgctttatac aatctcaaac aaagctagtc | 1440 |
| atagaaacac agaaacaact gcagggtgat atagattgtt ctaccacatc tatatttcca | 1500 |
| cagtgctctc tacagttgaa agggttcctc acttatgaca ttgttagcct gataaaatta | 1560 |
| attgtaacac ccttgtgcaa atatttttat taattttgac agcaggaaat attgctatgc | 1620 |
| catggtaaag ttgtctcaag tatttcttcc tcctttttc tccttagtgt tcaaatttag | 1680 |
| gcaccattgt tttggggatt catttataat catgtcagtt gttagtacac tttgtacaga | 1740 |
| gttttgtatc acaataaaat attttatgta catgtataaa cattttaata aaagtgttta | 1800 |
| aatgtacaac ttttggtacc caattctgat cacttgtggg cctactggaa gacttatttt | 1860 |
| taaatttaga attcagccac atattctgaa caaagtcagt actaaaacca tttctaaaca | 1920 |
| cttttaatta aagccataga taatatgggc agagcagtac tgggttattg aggtgactta | 1980 |
| gtgctctgag ctgctggtaa tgttgtaata atggctaaat tagatttat gtcagttcca | 2040 |
| caaaacctgt ttgctgctac tggccataaa agaatgttgg atttgtttgg aaacacattg | 2100 |
| tgatttttgt gatttcatac ttatgtatgt cttttcataa ggatgtttta gagcggtgat | 2160 |
| tcttatactt tttcaatcct tttatggatc tgaaaaactc taaagaccac cagtgtatgg | 2220 |
| ctggtgatag aaaaactatg ggaagaatgg tctcactttt tgaagaaaac ataagcaagt | 2280 |
| tatcagttca tactggaagc aaataaatgg atcagctgga ggatctaata gatcatgccc | 2340 |
| ataaaatctt tactttagat ttaaatccta caagttctat ttttgagtc cctaggataa | 2400 |
| acttgcatat acaaagtagt caattgttat tatagtgact tataggatca ttttattata | 2460 |

```
agataaagac ttgcgtgctc tctggtgctc tggtgtttta aataatcaac atgttttaga    2520 tcttttttgcc cactcatggc cctctgatta acttctcagt tatatttttc aatgcttaca   2580
caaaaaattt gccaaacact aaccatcctt cctagaaatg cagtggactt tgtatttagg    2640
gaaattagta acaggtgaat gctccatttg ctgatgttgc aaacaaactg ttagttggtg    2700
taaagtatta atttgctttt cacatttctt ttggtttggt gtttagtcat tcttgtatct    2760
tatttagaag cgagttccca ttgtcaaaga aagtatcttg aattaattt gttgtatgag     2820 atactttcat tctgttttca atgacctttc tcggtgtgta tatagggggtt gggggaagcg   2880 agaatagaaa aatttgagct tacctgaaaa agataaaaca ttctgcagat tttgataaaa    2940
gggcatttta gctggggctt agatattgct gctgtacaga tatagggggcc agttgtgttc   3000 cgggatctga tgttggtgaa ggataaagac tggctagcac ccttccctca ctccctctgt    3060
gtttccacta acttacaaat gggctaagga gatccctgg gatgatggga agcttgaccc     3120
ctcctagaga gtcaagaatc attgatggcc tggaggacag gaggcagaac aaacaaacag    3180
caggacaaat aatggaggcc tgctcagaa tggaggtctt ggtgttcttt gtgggttcct     3240
catactggag tgagccttgg caaaaatggt gtgtgtgtgt gtgtgtgtgt gtgagagaga    3300
gagagagaga gagagaggag acagaagaga aggagaagag gggagagggg aggagggaca    3360
gagagagaga ggtctcctac aaagagcttg gagctcaggc tgctttgctc atttgagtgt    3420
aatccaggag gatgcacctt ttctctcgga cttgaagacc aactgctcag ccttcacagc    3480
tcttgaaaca aagttcttaa tgtcccctga aatcagcact agggactgta gttggggagt    3540
tcagccccag cagtgcctct gagtctttgt tctgtatatg ggttctaaga ggattagaat    3600
caagttggaa atacacgtgt tcccatttcc caccttcaac tcccctcacc gcctgagatt    3660
cttgcaaaca tttgtgcaag gaacctgtga aaaagacttc tttcacgtaa ggaagtaggg    3720
ctaggagata ttaatctggg cattgttgag cattagcatc agtgtgcagg tctcagccca    3780
tctgtctgca atgtttgttg aagccatcac ttcttgtccc ttgaatcctt cctcaacttg    3840
gatttcaggc cctggctctc ccttgcttct cctctcagct ccctggcgat tccctcttag    3900
tctcctttgc ttgttcctcc tcaccttgcc tgtaaatagt ggagggctca gggctctgtc    3960
tagattcact ccaggccatt gctttgaata ctgctgcatc ccgatgactg gagattttga    4020
gtctccaccc aggtttcccc gagcatcaga ctggcataga caaccgcctt ctccacgtgg    4080
atgtctaatg ggcatgtcac atcgaacaca tcccaaacca aacccctgct tccccttctc    4140
tattatgatg acttttact cttccagttg ttggaccccg aatcttaact actccccttt     4200
ttcatgtctt gtttctaatc catcaacaaa tcctgcagct ctacctacct ccaggatgtg    4260
tccagaatca aaccacttct cccttatct atgactacga tggaggtgca agacaccatc     4320
caaccttgcc tgggtaatgg gaacagcctc actgctgggg ttcttatttc tgccttgccc    4380
cctgcagtgt gccatgatgg atgctctaca gggtgacatt atgtgtggac aagacagagt    4440
ccttgctttt tcaaatccca cctgttcttc tggagccagc taacacgctc ccttgggccc    4500
catgcctgaa tgccatctct tccttctatg gcatcctgca caggacttcg ctttgctcag    4560
atgcctcctc ccgcgctctt ccctttattt aaccatttgt ctccatttta ccccttcgct    4620
atctggggta atcctgttcc cttcatctgt atctctgaaa atggcatctt gccctccctt    4680
ggtgctcaga aggtggcttc tggtttaccg aatagcctga tttcaccttt ataaactcat    4740
gctactagaa ttttctctcc ttgtcagtct ttctagccac tttccaatgg aacagagact    4800
```

| | |
|---|---|
| accaaatcct aatctgataa ggaaaaatag gtaaacataa cgtggcagac tctgacatct | 4860 |
| gcagtgaaaa tttaaggttc atcatcaaat gtatgattcc attgtgaaaa tgtccagtta | 4920 |
| aaagctatct gtagtcacca tgcagcatta tgaagaagtt ttcagaataa gggcaggtgg | 4980 |
| taaagtctcc tggccagctt taggagtata tattggaagg ggctttgtta gctgattgaa | 5040 |
| tttttattcc ccaagtaatt agtatgagcg atttgtctac tgtatatatg ctcaaattac | 5100 |
| atatactatg cacttttgag aaatacttta caagttttc tttcattaaa atgtatttgg | 5160 |
| ggccgggcgc agtggctcac acctgtaatc ccagcacttt gggaggctga ggcgggtgga | 5220 |
| tcacctgaga tcaggagttt gagaacagcc tggccaacat ggtgaaaccc cgtctctact | 5280 |
| aaaaatatgg aaaattcacc agacgtggtg gcaggtgcct gtaatcccag ctacttggga | 5340 |
| ggctgaggca ggagaatcgt ttgaacatgg gaggcagagg ttgtagtgag ctgagatcgc | 5400 |
| accattgcac tccatcctga gcaacaagag cgaaactcca tctcaaaaaa atgtatttg | 5460 |
| tacataacta gaataatcaa ctggattgaa agttaatata aattttagaa tactactgaa | 5520 |
| ttcaatagtg catttagtca gaaatagtta aaatatctcc caaacagctt gaatcactcc | 5580 |
| tttttgaaca cattgttttt tgaaggttac agtcaagtcc aagaaaaaat tttaaaatag | 5640 |
| gaaaagaatt aatcaaatca tttcaaaatc atagcagtgt tttaacaatg ccaattattt | 5700 |
| tgagttgaag aaaagaagga aaatgtaaac tatgcattca agtaatgtca atgcaccttc | 5760 |
| tcaggtgcaa aatgaatgaa caattaactg tgccagctga atatgtagca atcacggctt | 5820 |
| ttgcacatag aagccttctg aattatctta tattctcaaa aatatcattg ctctaaacta | 5880 |
| gaattttatt ataattaatt tgtgcaaaag ttgtctttct ttcaatgaat gttgtctttt | 5940 |
| tgaggcataa aggaaatttt aggtggagga ggagaataga atacatgctt actgggagga | 6000 |
| caagtaataa taggtgagta aaaacacaca gcttattgaa ttgtctcaga tccacatttt | 6060 |
| ctccagaaat gcaaagttat acttgaaatc tatatttaaa cagataagca gaatgtgact | 6120 |
| tttatatgct ctattttgat gtattctgag tatgaagata acctgaagga tgccttttc | 6180 |
| ccctctttat cttggggtaa actcttactt acccttcaga gacttgactc aaatattttc | 6240 |
| attctgcaat aaccacaggt agaatggatc atttactcag ttgtggctct cttaagagca | 6300 |
| cagactacct atcatatttta tttcaaaatt tgtagtgctt atctcagtgc ttggcacaga | 6360 |
| ggaaagaaat acaatttta ataaaggcat aagtggagag gtaaaataca tatttctggt | 6420 |
| ttcaacgtgt ccatattctt tcttgtaaat ggaatattgc gcttgcagtc tgctctcaca | 6480 |
| caatatctgg gaaggagttt taagagtgga ggaagaacag taaagatttt cctaggcaga | 6540 |
| tacgttatgt gacctttgtt gatttccaga gcacataata tcccaatttc atccagtgga | 6600 |
| caggaaaaga gaggaagagg gaaaaggtgg cctctcaagt gcctgacctg gaagctgcac | 6660 |
| ctatcactgt cccttgggca gaactcagtc acatggtcaa aaggagtctg caaataattg | 6720 |
| tccctgagg agccgggtgc tcagtgaatg attctattaa gttgaaatca gatgggaaca | 6780 |
| gatcatttag gataaccagc aggctctacc acattgccta actcccaggc atattgtgag | 6840 |
| aattaaaagc accttatata tgtcaacgtg ttttgaaaaa atacaaaaag ctctacaaaa | 6900 |
| gtgagctata aatttatcat taataataat agtaataata gcaaaatact tgagaaatgg | 6960 |
| tcctcttgag ctgtttagaa ggaatcatac aaatgcatta gacatggtag cctcacttaa | 7020 |
| ctacttaatt tgcctcttct ttgaaattat tcaatagca tttgaccaaa aactatcaaa | 7080 |
| tcatttttga aataacgtat ttttacataa aacacattat caaatatctt tctgatcca | 7140 |
| gcttggtggt aaaaagatac atactaaagt ttatgactga tataacttta tatattgact | 7200 |

```
aaaccaaaga taaatattga ttgaacttttt gtggcccag tttcaataga ttttttatt    7260
aacatttttt gtttgaagta cagatgtcac gtcatccatg aaccggtatc attatagctt    7320
gataaaatac tcaaactgaa agcagtgatg tacattaatt ttaaatataa tggttaagca    7380
aatgttattt ccatatctat aagtgcattt tatttgataa ttagaatgtt agaatcagaa    7440
ggaatttgga aaatcccagg ttacacttct ctccaggacg aactccttac agtggctctc    7500
ctggggtcag ctagcttttg cttgacccct tgaagcagga ggaactcagt tccactcaag    7560
ttgcccccct gattttctct ttcatattga acctgctgct gcacaggact cctccgtgac    7620
tgtctctttg ccttcctaaa tctcaaagaa taaagcaagt cacttttga caagacatct    7680
ttcacatatt tgaaaagaca tctttcacat atttgaaaag accagtacgt tttgttcttc    7740
ctagaattt ctccttcatg ctaatgtctg ctccaagaag acatggaggt gactggacat    7800
ttagtcagga acatttcttg agagcttacc ctgtggcagg caggtgcaat gttgaattct    7860
gagaatatga atgtaacctt tgaacaggtg gctctgtctt ctgacgtttc aggataaggt    7920
ggaggagagg agagggaaa gtcgacctat ctccccagcg ggagggttt agggttgtct    7980
gtgggacctg cctctgtctc atcatccatc accattgtcc tgctgatggg tgcagaggac    8040
tgaggacgag tggttggagt tctccctgtg ccggaccctg tagagagtcc agagccctgg    8100
ctcccaaagg aggcatattt gtagggctct tttcgtgagg gtccagagga cggctgcaaa    8160
gctgcagggg aggatggggg catgggaggc aagcccgttg ccctgtcaga gcctcttggg    8220
gatgctgctc ttccccgcct gtcctctctt ctctttgatt tctcatcatg tggtcctctt    8280
tcctctgcct tttcctctct tcggtgtccc aagttcttcc atagagacct gtgtcccctt    8340
gttcccatca ggcctttatg ccagccctgc acaggtgcgg ggacagtggt aggggcgtct    8400
cactcccgac tcaactacat tctcccagaa attgtctgca gtcaaacaca actcagcgtg    8460
gacattgctc accaaaggta tactgcttgg gctgcacgag agattcagtt ttctcctatc    8520
tatctggcat gggctgtgag ggggctccta acctagggg ccttttttact ccttcctggc    8580
cagagctgcc atttccaagt ttctgcactg tcagaaaaga gggataaggt aagattcctg    8640
ccctcatgtc acagattagt aggggagagg taattgtcaa ataattacag taaaatgtat    8700
aaatgcctta agagaaataa gtacttgctt aggaacctat ttcaagaaag gagagatagg    8760
ttagcgtttt ggggaggtag tacgggagca gtcagggaaa gcaatacttg taagatcaga    8820
ggctggcaat ctttttctgt agagggctaa gttttggact ttgcagatcc tacagtgtct    8880
gttgcaacta ttacacagtt ctgtggttgc agcatgaatg cagccatggg caatgtgtta    8940
atgaatgggc acagctgtgt ttcaataaaa ctttatttac aaaaataggt agtgggccct    9000
gctgctgggc ttggcttgct gggcacacaa agtgagaagg gcattgtgcc tttctaggaa    9060
acatcccttg caaagtcagt acaggtgaga cagtgtggcc attcccacca cagcatgagg    9120
tcttttgaat ggctgaagcg tcaggtggga aggatgagg agctgaagaa gaaagcctgg    9180
gaatttccaa ggcctctctt aacatttgct gtgcagaacc aagcagtgcc ccaggtgttc    9240
agagtaggct tcagcgatta catttcttgt tagacactga attttgttca tgccgcccaa    9300
gattgcatta acaattttgg ctgtcacctt accgcggact caaattagtt tgcagtcagc    9360
taaaacctct caggttttttt ccccccagct tgtgaattgc tgtgaagcca acatccctg    9420
tcatctcttt ggtagtttat tttcaaactt tcaatcttat taaatttcat ctccaatgtg    9480
caaagataag aggaagttta ccgctgatgg tggtttattc tttaaaactg gacatcagct    9540
```

```
aaatgtgtta aggtaatccg ttagaggaat gttggtacgc ttatacagtg gaatactaat    9600
tggttattaa aatgttgatg tatgattatt aaaaggcagc ccatgttatg tctcttctgt    9660
atgaataagt atgtaaaaag tatgtaaaga ttactgtata gttcatgggt gggactgggc    9720
tctctctagc ctctgtcctt cattctccct gccagtgcct tttcccttgc agtgtccctt    9780
ccctggctgc atactcaaga ctggatttgc ccagccaaac ccattaact cacagaagca    9840 agaggaaaaa aataaattct tattagttca attctccaaa ttggggcgg tctatttcac    9900 agcaataggt aactgacgta aaaggaaagg aaacaatgaa gtaattccag aaaatttcct    9960
atagctggag gacatgcatt ttcatattga atgggaagaa tggggtgggg gggtcatacc   10020
tctgtgttat tgcagggtcc tggctcctag ggacctaggc acctcttcag tcagtgaatt   10080
atagcttgga aaattggcta agtcggggaa ctgtacaagg ggtcatcact ttttatgtag   10140
ccatgctcta tgaaccatct ttataactcc ctggcttctg gcagttaagc accactcact   10200
atctggcctc tgtaatttca acttctgacc atccccgtgg gtggcaacaa gcccagctct   10260
gtgacacctc tgctaccagc agccctggcc tggagagcgg tgcccccact gaatgtctca   10320
gtgagattgg cacccccatg agcatattcc tgagggtgca gtgaatgctc tttctcccta   10380
cttgggactt ctgggaaaca ctgtcctctg gtgggttgtt tgacctcaca taatatactg   10440
gttcttgcat gccagcttct ctctgcttct tgattctttt atcagctgtt agggcaacaa   10500
tgtcaggcat ttccgcctgc tcagcattgg gcatcccttt ttacaggctt ctcagagcca   10560
ccctagcagc aactttaccg cgtctcctgg ggtccttgct ggatcgtgaa aacatacttc   10620
cggagaaagt gttccctaga taatgaatta tttcttgtcc tgtgttaagt tccagttcct   10680
tggtcaagga ccccagcgct actcctcagg atttgcagtg catgctcaat cttgaagcaa   10740
tgttgggata tagtatcttt tcttctctat caggcccagc tgtctccagg tgggttatac   10800
taggatttaa tcctcgttag tgccgggtca gctcctgagg ggtgcacctg ttgctttta   10860 gggacgaggc ctcttcagca taaagaagtg ctatctctta ctagggaaga atgggccacc   10920
tctgtaagct ccaaatattc ccaggtttcc ccaaccgggg ccttgacctt ggcataactg   10980
atctgccttg gctgagcatt taaacatccc taaatctctg caagtctatc aggtcctagg   11040
cctgctgcta agtttctcta ctcttccact gtaggagaga aggctgtggc tcttatattg   11100
agcctttaac tgtttgttat tggccctcag tttctcatta gctctctgta gagtctcaat   11160
acaatatatc agaaagcatt caattccatc tccttgtagg cagggaatgc ctaaatcatt   11220
gcacctacaa tgacattctc caccaggata tttcccaggt tactgctgtt gaaatattta   11280
gcaattgaag caccatttgt gcaaggggac tatctgcccc tacacaacac tcagaatggc   11340
attctctttg ctttccagaa agtgaatgag ctggttcccc aaccctctt gtgttagttt   11400 gagtcctgaa agaagtaaat gtcaagatag gattagatgt acaagaaatt tattgggaa    11460 agaattgtga aggataaagg ggaaggagct aggggaggca ttgaaccttt ggatcatgat   11520
gtgtgtccaa caactatgaa ggagagtggg cagggagaag gatgggctgg gaagagtttc   11580
agttggcact gtgggtctca gaacaaccca ggcataggct gatggggacg ccttgagcca   11640
atgttgccca ttggcggagt ccacatcttg ctgaaatggg cctgcattag ttcccctgcc   11700
atgtttagtc atctgggagt agccgatgag aatcatgatc ttaggatcaa ctgcaatggc   11760
agattcaaag gggtagcaac tgatggcctc agtcaactgt gctccttata gcaggaacac   11820
tgagcagtgc atttcttggc catcacaaag actagtgagg agtgcccttc agagaaggga   11880
atgaaaatta tttccagcct agaatttgat acttatctaa actgtcaatc attcatgaga   11940
```

```
gtcaaagtcc caaaaaataa atcttccata aacccttcct caggaagtta ttggagggta    12000
accgccacat aacatgagga agacaaggag gaagacatgg gatctatgaa agggcaggtc    12060
taacccagga aaaggatgat gaactgtaga cccatgatgt cagatgtgca gcagactaag    12120
atcagccagt gcagaatggg ggagattcca gaagtgtgtc cccccaaaat attggaggct    12180
catgtgactt ccctggggaa gtttctgctg agaggctatt ggaaattgag gaagaatta     12240 gccacagtcc caagaaaac  agagccaatc aaaaagcaat gcaattatga acttcaaaga    12300
aaacaaaaat aagaaggaaa acagtcttac ttactacatt acaaggtcca gctgtgaatg    12360
atattcatgt tggcagaata atgtcaatac caaatgtcgg ttaaacccaa aactattgta    12420
taactaaatt gcctgtgtaa gagagctaaa cccttatcta gcataatagg aagtcagtgg    12480
atacttcctg aagtgtggat gtgtggagat gtaaattcca aaagaaaacg tcttaagagt    12540
caaaagtggt tgcctctaga gagaactggg ggaattgtag ggcaatgtag gacagggaac    12600 tgtgatttt  cttgtaagtt gttctgacat tttaaaccat gaacatatat tacttgtatt    12660
tttaatttta aaaagacata atatttttt  ctatcacttt aaatattaat tttgctagtt    12720
atagcacata tttatagcat tacactctgt agagctcttt tggattcaag ttttggagaa    12780
ttttcaaagt tttagattaa tgcctttgtg agttttcatc cctttgatga taacaagtta    12840
caaagaaata gggttatgaa taaaccttgt gggatattgt tagtcacctt ctctcaagtc    12900
gatctgtccc atgaatcaat gtttcaaaca ttgaccagca tttgatactt aataagcaac    12960
gagtaagttt ttgttgaacc aatgaatact cttaaaatat attttttcaa gtggcaacag    13020
tactatctta tttgcactct acttttcttt ttgaccctaa gaatgtcaca aaaatgttta    13080
gcaactgtca agattattac atacagagat gactattgtg ttctcagata tgctgtatgt    13140
cttagttcat tttgtacagc tataagagta gctgagacta ggttatttat ttatttattt    13200
atttattttt tgagacggag tcttgctgtg ttgcccaggc tggagtgcag tggcacaatc    13260
tcggctcact ccaagctccg cctcccaggt tcacgccatt ctcctgcctc agcctcccga    13320
gtagctggga ctacaggcac ctgccgccat gcctggctaa ttttttgtat ttttagtaga    13380
gacggggttt caccgtgtta gtcgggatgg tctcgatctc ctgaccttgt gatccactca    13440
cctcggcctc ccaaagtgct gggattacag gcgtgagcca ccgcgcctgg ccctattttt    13500 tttttttta  aaggaattta tttcctcaca gttctgttgg ctgggaagtc caagggcaag    13560
tctctggcat ctggtgagag acttcttgct gctttctccc atggtggaag gtgagagggc    13620
aagagagaga caaaaggagg ctgaactcat ccttttacaa ggaacccatg cctgagatat    13680
tgaacccact tctatgataa cagcattaat tcattgatga ggacagagac ctcattgcct    13740
aattggccta aagtgagacc tcttaaaggt ctcgcttaat actattacaa tggcaattaa    13800
atttcaacat gagttttgga ggggcaagca ttcaaatcat agcaccatat aatacaataa    13860
aaattttctg agctaagttt ggtaaattta ttctaggaat ccatgttgtc tcctagttat    13920
cttcccttcc atagtactga tgcattttg  ttaaccatta cctaatttg  cttgagtcta    13980 ttatttctga aattcacatt atcttcccct ttaaagttga gaaattttc  attcttcaag    14040 cgccttattt tctataatct ctcaaagtaa ctgatggctg ttgcatgatc ataagtgcaa    14100
attattttgc tagaccacac ttggagatga tgaatttgga atggcatgca gactcccgac    14160
atcaggagtc ttgtctcctg caataatcag gaacccaggc ttaaagggga gcaggtacaa    14220
cagaagggca aggggtgaca atgctggtga aagacatttg aggaaagcta tcaacatgaa    14280
```

```
acagaataaa ataaacagaa aagcaaacca gggaaaataa attatgcagg aattaaacac   14340
atacacaaac tgaaacagga accatcagaa catataaaaa attcttgaac atcagtaaca   14400
caatagttga aacaaaatat ttagtaaaat atttgaaaag taaggtcaaa gcaatgctgt   14460
aaaagtagta caagatgata aagaaataga acacattttt gaaagggaaa agatttaaa    14520 ggatattcat aaagatccaa catcagacta atagaagttc tggaaagaga gaataaggaa   14580
atacaggtca ggaaatttgt aaagaaataa tataataaaa tgccccagaa ctgaagaaca   14640
tgagctttta actttaaaga gccgactgag ttcctagctc aatgaatgta tagacatgta   14700
agggtattga aagttcacct tcagtgtcat gtttcctaag aagctaatgg aagatatgca   14760
ccagcaaaat tgtagtaaat acataggaag aaatagtata tagaaaaagt atggtttcaa   14820
tccataagaa ataaaggaaa ctcccaggac gagagcagct cttgacagca tctagtccaa   14880
actggacttg gaggctggaa acttctagca gggaaggaag agctctgggt gaaaaagtag   14940
actcaacaga atagatacga tcatagaaaa catgatagag aatcactaac acattgaaaa   15000
aatcacatat agaatattct gcacgcttaa taatgaggtc attatttatt caagggaaaa   15060
ttaaaagctg tttagaaaag ggaaatgtta tagtgcccta tttggctcta aaatgaacat   15120
ttatatagga atcttcatgt aaatactaac aatgatttaa ataagaacag acatttcgga   15180
aaataaggga agaaaatggg gcatgtaaaa gagctaactc ctcattatcc taatgaatta   15240
ttaaatttca caatagcata gtatttagaa atatgatagt tattacgaga agaaagagct   15300
aaaaggttgc cagtggggag caggagtgag ggttagagac gggattgggg gagatgctta   15360
ctgttttcat gataagcctt tggtactatt tgattttaaa ctatataaat gcatttatta   15420
atttaaagta atttaaaaaa cccataccac tggataatgc ttgataattt ctagagtcct   15480 tttttttgt attttggggc aggtaaattc attgagagac ccagagagtt tagctgactt    15540
tcctgtgggt accaagggtc agagctgggg tcaaaactca ggttttctga accctattc    15600 ccagtgtaca ttccatgact ccaggctgcc tcccgcattg cacaggttac atctagggt    15660 gtgctagcaa atgcctagac catcctcgtc cacatcagca tctgaaatgg acaagaatgt   15720
tagtcatgac ttgccactaa cgtctttaac cttaattgac atctgagagt gtcatcatta   15780
catcattaca aaaacactaa cccagataca tctgttccca ttactatttc tgcgtaattc   15840
ccccagactt aattgcttta aataaccatt ttatttggtt tacaaactta tgggtcagga   15900
ttaggggagg gctcacccac gcagtttttc tctggtccgc agtcatctga agcttgaacg   15960
gggtggggca tgcaagacgg ctcacacatg tgatccgcgg ttgagcctgg ctgtggacca   16020
gagcatctct gttggcctcg cttacacaag tggtctcaga ttagtagcct ctgtacatgg   16080
aaactagctt ccctcccggc aagcatccca agagaactag gaggaagtgg tatgtgacttc  16140 ttttcttctt cttcttcttc ttttcactta ttcttgatat catgtagctt catttctatc   16200
agagcagtca catgcccaca gattcaaggg ggagggtcca cagatccgcc aatgggagga   16260
acagccaggt tatatcgtaa aagatcatgg ggcatgggag atacccatct attttctgta   16320
aaaaatacat tttgccacag catcactggc tttccagctc acagtgatct gcctggaatg   16380 ccttttttccg tctctccagg atctacatct ttcaatataa ggtttagaaa ctacctccta   16440
caggaagact tccttgattt ccctcagcaa gaaagaatct ttccttcctc tgaatcgcca   16500
ttgcattaaa aaaaaaatcc atcttctggc gttttcactt tcagacttat actgtaatta   16560
ttctatgtac ctatgtttga cccctcacga tgcccacgat aataatttgt ctattgagta   16620
aatatttgct taatgaaata atcattacat gataactcaa atagcagtcc tgaaaaagtg   16680
```

```
catttcaatt cagatctctc ttttttcttc cttcacaatt ctcatttccg aaaaatgaaa    16740
gaagccagag gatcctttat gaggagttac agtataactt atgcgtggct gtttcctgtg    16800
tttactgcta ctcagtgaga aatacgggag atgggagagt gaaaaaccat gtcatttaca    16860
atttgattaa aaagctttt atcttttcct ttcacgttta agccttgccg ttttaaaaat     16920
ttccctttcg tcacagggga tcaagcagca gttaacgctg cagttccctg ttctggaaac    16980
actctcaaag gtgtttcaac acattttgtc tcaactctga ctcctgcccc gctgccccac    17040
gccatccagc cacactgaag gtcttgcatt tgtgccttgg ggcattattt ttttttactc    17100
ttctccctgc ctggaaggtt cttcccaacc tgccctaccg ccatagccac agaaccaacc    17160
cttcactttc cttaagtcta tggtcacaag ctccttctca aaggaggcac acctctaacc    17220
acccccattt ggtgacttcc tgtctcctgg aggccccgg aactagtctt ctctacttcc     17280
agcaacccac tttacgagca gcggagaaga ctgactactt ctgggggcct cgaggagaca    17340
ggaagtcacc aaatttacag gtgctgtgga tgaaactgtg tgataatgaa tttattgggc    17400 ttgtttttt agcttctgaa tagaagaacc aataagatca tttttttaaa aaagataaaa     17460
acagacaaac acaaaccctc tagtataaaa gcattttttt ttaaaaaaga tgaacacaca    17520
ccctcagatt gccttctttt gaaaaggcaa tctgagattc cttatgaaat ccccagacag    17580
aagctgtttc tttgaattta atatgctgta cactgtagag ccaagaggct tatagagtgt    17640
taattaacac cccttgtcaa acatttgtaa atgaatctgg ctaaagctca aggaaaccag    17700 gttttctgt gtgataaaat ataatctttg gagattattt atgatcacaa agggagactg     17760
tacagaaaat tttcctagac ttggaaatga ggcaggatta ttggtgtcca tctggactga    17820
ggcctcaggc aggcctgcct agttaatccc attctcctat cctcattctc tgggggtgaa    17880
gaaggcagtg cacctttgtt caatttgctg cttaccatgg attagggcat tttaaattct    17940
gtaagggtag ttttaactt gtagaaaact gatagcgatg ggaaggattc ttgcctaata     18000
gggacacaaa cggattttgt tctgtagaga tgtaaatgaa aagatgaaaa tcacaacaca    18060
tttaatgaaa ggaaaataaa gactcttgtg agtgccacca aaaaaaaaaa taaataaaat    18120
gtatctcctc tccgtggcac cccaggcctt ccttacctca ctctatttct tcatagcact    18180
tattgcctta gaacattctt tataatttac atttattatg tttgttgttg gttgtcgctc    18240
ctcctgctaa aatggaatct ccgtgagggc acgggttttt ctttgatttg ttccctgttg    18300
tgccccaaag tgctagaatc atgccaggca cacaatagat gctcaataaa tacttctgga    18360
atgaaaatcc ccctccactt agaccagtga gttccaaact ttttgatct tgacccatag     18420 taagaaaggc attttccatg ttgaatatac accattgaaa caaaattttc acagaaaaaa    18480
cttaccatta ttacaggcag tgcactgtga tatttcctaa tctcttctat tttgattttc    18540
aaaattgctg aggctactca taggttgatt tcacaagtgg agtttgtgtt atgaaaaact    18600
ttgacttaac accatgtcga aactgctacc acaaaaaggc aaatgcgaaa gaaggggggaa   18660 agagcaggcc gatgactttc cgctatccac cactccataa agcatatttc attttcctgt    18720
aattgtatcc tgttcaatga tgtagaaatc ctcacacact cacatgccac tttttctttg    18780
ggtgaaaagc gttctctact gcaagatgaa ttgagttatt tcaaaagcaa agagctataa    18840
atgagcctgt taagaaaagt ctcaaggaga gtctgttggc atctgctgtt gataacttaa    18900
agcaggagaa ttagataagg aggcagaagt agaatgttta gaaaataaaa gtgaccatta    18960
tagaggaaaa actgcttgtc tcagttttgt tgatattgga gagtagctct ttcatgaggg    19020
```

```
tattgtggaa ttattggcaa ttatactaat agatgtttac tgaaaaaatc ctatttgact   19080
gatgaaccat ggaatacttt tgctgacctt gtggaaaaca tcacttatct gagttcctta   19140
tcttcttgtc tctttttct catctagcct atgcctccct acctgttccc tcatggttct    19200
cattttgttg ctattagaaa aacagagata caaaaaccag gaattggaac ccctctgtgt   19260
ctccagtaat aattctgtga ttaatgggtt agatggattc tggtcacaag ctggatattt   19320
tgttaacaac ctagcgtcaa tgacttggaa tgattttcac cgcagcatga tttagtattg   19380
aatagaatga tttaactaat gttaattagt tctgtacaga taaattaatg aagcaagaag   19440
ctcaatctct gatttattga tgtatttacc cagtgtaagt tatgaaatct tttttatttc   19500
atttgaagga agtttttatt taaatacaaa taaataagcc ctttattgtc acctactttg   19560
gaaaagtcca gataaaacaa tcttaagtaa caaaactcca aaattacaac atgattttca   19620
aaaactaccc tgacctttgt cttgcctggt tgttacagtg tacttttaac taaacggatt   19680
cttatagaat ctcaagtttg gttatatttg tattaaggaa ctctatattt gcatttgacc   19740
agccctaact aaaacaagct taaggaagaa aagggacttt acgacaagga caaggattg    19800 aagaagaact ccagggactt tagatgttaa caactgtatt tgtcactaaa gtaaccatta   19860
ctgtcaaggt gggttctcct tctccctcac taaacacatg cacacacacc acacacacat   19920
acacatacca catacatacc acacacatgc acacacacca cacacacacc acaccacaca   19980
cacagaaata cacacagaca tacacacatg cacttatgct tgggtcagtt tggcttttat   20040
catcccagag agtctcttcc catgtcagca actccagatt cacttcctct cctaatatag   20100
gacagtcaca tgtctctatt ccagcaaaac aatctcaggg aaggtatctc attggcctgg   20160
cttgggtcat tcaacttgaa gtacaagaag agaaaacagt attcttttat ttttatagat   20220
ttcctgtaaa atcagtggat aatggtaaaa atttcatgac agcaggtgtt ttaccttatt   20280
tatgtttact atctctagaa cccagtatga tagttcataa taaatgctta ctaaaacaat   20340
tatcaaactg tacacttaaa aattaaaaga gtaaattttta agttgtgtat gttttaccac   20400
agtaaaacaa aataaaataa acctattatt gatcttattg tctatttctc aaaagtagca   20460
tacgtcataa tttcatgtga tttctaaagg agatctaatc tcaaacttag ttcttagagt   20520
aaaataaaag gttttggcaa tcatatacag cagtagactt taccttgaag atttaacaaa   20580
ggtttgaaag caaaatgcta tgatactgaa tatactaatg tttgagggct tgtgaaaagg   20640
tcttaatata ggaatcatat atcttctttt agattgtgtc ttggggaaca ttgggggtca   20700
gtttttctat cagtgttagt atgtagtaag taatggcata catctaagct tgagattttg   20760
ctcatttctg tattcttagc acttatatat ccaacatata ataggtgttg gataatattt   20820
gttgaataaa tgactaaata aatgtcttgg catgagaatt atgccatcta caaaccgtc   20880 acttttaaaa aaacaacaa agattttttga acctgtagat ccagccagaa agcaagaaat   20940
atcttcacct ttccagactg acttattttt tggtctagct gtgtactatg catgagctgt   21000
caactttaat actttattttt ttaatgccta ggtctagtga gttacaatgt gatgtagact   21060
gattgaatta aaggccccaa tgttgtcctc tcttcattgt atccatgcct tttgtcatgt   21120
aactttgcag tgtcctctac tctaggtgtc cattcagctt atcctttgac tctgccttc    21180 ttctcctttg actctggctt tatccatgtg acttactta gccaacaatc ataatgctgg    21240
caaacactga gaaaatgctt attagtgtct gcttagtctc ttgcttctct gcaattgcca   21300
tgagaaaatg cccaagctag tacactggag gatgagacat gtggggcaga agcaacctgt   21360
cccatttgtc ccagccaaca ccatcctaga ttaaccagat gagaccagag cagaagacat   21420
```

```
gttcagtgga gcccaaccca gctcacgaat aatatttctt catgagcatg tgagcaatgt    21480
gtaactaatg caccatgctc tttttattct gcacttccaa acatctctca gattgccctg    21540
ttgttttgct tttcagtagt catcacctt  gtccagaacc ttaattgtat ctgcattttg    21600
gcagtatcct gccaattttc cacatccagc tgttcacatt ctaatgcatt ctgcaatgga    21660
tgattttgag catatgactg atcatcactg tctcagaaat ttatgctaat ctattgtgac    21720
ctattctgtc aaatccaaat aactttacat tcaaaacttt tcatattctg gccccatact    21780
gtctattgta atcttatttt ctaaaagcca caaactatta atcctgtagc ctaattaggt    21840
tgatatcatc attttcacaa cacgttgggt aaattcttat atctgttcct ttaatcatag    21900
tttccatgct tagacactcc attgccctcc ctaagcacca gccagagtcc actatggggg    21960
gatattttaa aggctctttt cccctaaccc atctgcccca gaggtggcac aggctagaaa    22020
agatagtcca attatttggc ttaattattt ggatcttaca gttttttttgg gagagttcca    22080 gatgatttga tgaaatgcaa catggtcaaa aacattttgg tggagaataa tttaatcaac    22140
tagaccattt ggtgaaaaat aaatcccagt tactagactt cccagtatta ataattttgg    22200
tatgccagga attttttaaaa catttctaac aaatttttttc agaaatcaga atgactgaaa    22260
ggtataacaa taggaaatta ggaaatcaat aagtaatcat tgaaaagtga gtgattgaat    22320
tagttggaac aatctatgcc atccatcctg tgggggaaaa aatgaaaaca gctaaacaag    22380
cagagcagac atcatcaact tagaaaaaca atatagtaaa taatttgaac tagaaaatttt    22440 tccaaaattg aaaattccag ttttaaaaaa tttgtgtttt cttattcaaa aagcaataca    22500
tatttcgtta cataaaagtc agaaaatcag agaagcagaa gaacataata aatgcccact    22560
gtcctactca atagagacta taactgctat ctctgtacaa atcctttaaa atcctgtctt    22620 atgtgtatttt attttacatc tgtacatatg attccaaaat taggtaatac tgtacgtggt    22680
ctatctatag ctaactatag tttgtaattt aataagctat atttgtccat ggtgatcatt    22740
tattgctcat aaaattaata aattataatt tatttatcaa cactgatcat ttgttgctaa    22800
taatttattt catttaatgt cttattcctg ggttattttta actaatccct attgttagcc    22860
ctttaggttg tttcaactaa tttaagaatt ataaatggcc catagtagtt acttaataaa    22920
tatttgagtg aaaggataaa tgaatgaata attccacatt attggatgtt caagttgttt    22980
ccattcaact ttattgttgt gggggagtat aatacaatct tggtgaagag ccaccaactt    23040
aggaagaact atgaagaagc atgttattta ctcctgcttg tgggtggggt gcattgggaa    23100
aggaatgcct aaatgcacgt ggggagccaa acaagacttc acaggggaga tgggaattga    23160
gccaaatttg gaagaagtga gaattttcag ttgataattg gggaagatag tactaagagt    23220 aagtgggggtt cattaggaac tacttcttag aagaggcaag tccagaacag aaggcagaaa    23280
gggatatgga tatgaaggaa aagtagaatg caacttcagg gctagtaggt tggcatccaa    23340
cgtaggtaca gccctggatg aggagtaatg agaaactgac ctggctgtag caaaacagct    23400
aggctgggaa gtgatgctgt ttacatttat atgcgattct actggtcttc ctgttacttt    23460
gtagaagact gtaaggcttg gtgctcagag ctagaaatgc aacttatttg atttgctaag    23520
aagtccaaag caggtagggg tgccaagctg ctgcctgttc acacatattc gtctaactgg    23580
gtgtcaggga aagcagatat gagccccctt gcattggtta aatcctgagc aacttttaag    23640
gaactgcaca cagagactac tggctatttt ttgtggataa agttgtagat agttattttt    23700
gggaaattat ttatgtgttc tattaggtgg ttgttttgtg ggaggctgtt tgaaattctg    23760
```

```
tcttaaggaa ctgcagctta taaaccatag tgctgataga aataagagaa ataatttggt    23820
ctgcgagcac aaacatcagg ctagttggca tgcttatgta aacaccacac agtagcagtg    23880
acttttaagg aagtcctcag acaatgtaat cccaatactc ttcttgaagt tgaggtaata    23940
gggtgccaga aagaaaaaga aaataaatct ctagtgcctt ctaaaatttt ttcaatcctt    24000
tgaccttttt gaaaacggtc acctttaatt cagaactaaa gtaacatctg gagggccctt    24060
ttcttagata gggagaagac ataaatgagc tatttgaatt attttctgct tatgggctgc    24120
atttcatttc ttccaccatt ggtctcagtc catttaatta agattatttg taggattaaa    24180
ttaatccttt aagaattatt ccatttcaat ttttaaaaaa tctaatgaat gatagataac    24240
aaaaagcggt ccattcagta ttacccctga aacatatttg ggtgattggt gataccatcc    24300
atgtctctcc aacttcagct tcatatactc agctgagtac caggcatctt cattgaaagc    24360
tagacttgtg acctaaatag aacttgatcc cttccttcc ccaactcctt attttttgtt    24420
ttctttgagt tccttgattc ctcttcccct cctcacatgc aacatgtaac atccaattca    24480
tcagcaggtt ctacagattc tgccttcaat aatagcctaa atctagccac ttgttactat    24540 ctttttggt ccaaaccatc atgatctttt gcctggacca ttgcaatagt tgtctaactg    24600
gtatccttgc tcccattttg tcctcctaga tcctattttc cacgtagtag ccactgattt    24660
ttggaaactt atcaatcatt acccagacac aatgagtaca tttacatagt tgtttgattc    24720
catttacata aagtcccaca atcactctat gtactgggaa tcacaacagt ggtctcctat    24780
gttgagaatt gattaagagt cacaaggaaa caaggagtaa tattccattg tattaacaga    24840
ccacactgtt catacattct cctgtaaatg gacatttatg ttgttttcag ttttttttgct    24900 attgtgatta aagctattag gttggtgcca aagtaattgc agttttttgcc attactttt    24960 aaaatggcaaa aactgcaatt actttggcac caacctaata ctgtaagtat ctttgaactt    25020
accaatcaaa cattactaca acacttgaat aagaaacact tccatagcat ttacaattct    25080
aagtgctttc catgtattga cttagttaat cctcacaagg atataaccat gaggtgctat    25140
tactatccct actttacaga tgaggaaata gaggcacaga cttcagataa tttgcccaag    25200
gtcccacagc taataagggg gcagaattag gaaagcctgg ctgagtctat gctctcatca    25260
cttgctcaac tctgcctgga atgcccttcc cgtaccctct accgcctctg cccaatcctc    25320
cgggttctct gctccttcca cacaccccca tctcaggtcc cagtcttttt tagcattctt    25380
cacttttctt gttacagatc ctcagacaat gcttccttga agaagacttg cctgtctaaa    25440
ctgccttccc atcccaatcc ctgttacctt ctatcctttc tctgctttgt ttcatttgt    25500 tatctctctt cttcccaaga atgtaagctc cataagaaca ggatcatatt ttgaatcccc    25560
tagaaaagtg cctagtgtaa tatttgttga atgaatatga tccctgcaat taaaagctaa    25620
atatatatat tttttttaact aacagattac tgtagtagtt tcaaagatga atttatgttt    25680
cggagaaaat cagtattctc ttgccacata aattgtaggt aattatattt ctatacctga    25740
atagctttgc caatgactaa gatattaatc tattatatat ttattaatct atagatcttt    25800
aaaattgatg cacatgtttt ataagcaatt tgatgaattt tgatgactac atacacctgt    25860
atgtgtatgg atatctgtaa caaatatcca agtaaagata tagaatattc tcattacccc    25920
agaaagtttc tttgtgactt ctaatcaatt ctcacctccg taggaaaccg ctgttgtgat    25980
tcccatcacc acagactgat tttgggactt tatgtaaatg gaatcaaaca actctgtgaa    26040
tgtactctgt gtctgagttc tttcaatcta cacaatcttt ttgacattaa tccatattac    26100
tgcctagaag agtagttcac tctttgcatt aatgaatagt attccattgt ataaacaaac    26160
```

```
cacactgttt atacattctc ctgtgaatgg acatttgtgt tgttttcagt tttctgctat    26220
tgcgatttaa gctactataa gcattttttt ttaattgtga tggggtttcg ctcttgttcc    26280
ccaggctgga gtgcagtggc agcgatctca gctcactgca gcttctgcca cgtgggtcca    26340
agcgattctc ctgcctcagc ctcccgagta cctgggatta caggcatgtg ccaccacacc    26400
tggctaagtt tcgtatttc agtagagacg gggtttcacc atgttggtca ggctggtctc    26460
gaagtcctga cctcaggtga tccacccacc tcggcctccc aaagtgctgg gattacagtc    26520
ttgagccact gtgcccggcc agcatctttg aacatatcaa tttgtaagtt ttatcttaat    26580
attgtacaag tcttttgggg ggcttatgtt gtcatttctc ttggtaaata cctaggtatg    26640
aacttgctag attatagaga aaatctatct ttaattttat aagaaactgt caaatagttt    26700
tccaaagtgg tggtactatt tatactccca ccatcaatgt atgaaatttc cgttgtttta    26760
cgtccttgcc agaatttgtt ggtagtcttt tttttttttt gaggcagcat ctcactgtgt    26820
tgcccaggca tacaatggtg tgatctcggc tcactgcaac ctctgcctcc caggttcaag    26880
ggattttcat gcctcagcat cccaagcagc tgggactaca gaggcgtgcc accacaccca    26940
gctaattttt gtattttag tagagatggg gtttcaccat gttgcccaag ttggtctcga    27000
actcctggct tcaagtgatt cgcccgcctc agcctcccaa attgctggga ttataggcgt    27060
gagtcactgt acccagcctg ttgccagtat ttttagttgt aggcatctta gtgggtgtga    27120
gtgctcgttg gggttttaat ttgcattttc ctgatagtgt tgatgttgag acatttcta    27180 tgtgtttact gagcattggt gaagattctc ttgtgaaata tctattcaaa tattttgctc    27240
atggtgggaa ggggagttat ttttcttta ctactgatag gtaggcttac gtatttattt    27300
cggatataat tattttgtca attatatact aatcataaac aaaaactgat aaattggacg    27360
acgtcaaaat taaaacctgc tcatcaaatg ttagcgaaat gtaaaggcaa atcacatact    27420
gaggggagat attttaatat atgtatattt atatagtgct ttctgtgttc taagaagtat    27480
tttcctactc caagataaag agactattct cttacatttt gttctataag ttttatagtt    27540
ttagctttta gctttggatc tatgatctgt ctcaaatttt tatgcaagat tggggtttaa    27600
ttttttcata cacttttcca gttgtcaagg atcatttgtt gaaacgtctt tcctgttgcc    27660
acataattgc tttgatgcat tcgttagaaa tcagttggct gtgggtttat tttggaattt    27720
tctgttctgc tcctttgatg tatttgtcta tccttatgcc aatatcaccc tatattaaat    27780
aattatagct ttataataag tcttgaaatc aggtaatgtg aatgtttcaa ctgtgttttt    27840
ccttttctta gttattttag ctgttttatg ttcttattgt atatatttta gaatcaactt    27900
attcatttct acaaaagtt tattgggatt ctggatgaga tggtgttgat tcagtaggtc    27960
aatctgggga aatctgataa caatattgac tcttccaatc catgaaaatg gtatctcatt    28020
ctttatttac atattcttta atttctgtta gcaatgtgtt ataattgtag caaacttgca    28080
catcttttgt taaattattt tctaagtatt ttacgatttt ggtaccactg taagtggcat    28140
tgtatttaaa atttattttc tgtttgtttt ctgttcatat ataaatgcaa ttgatttct    28200 tttttttttt tttttttttt tttttttgag acagaggctt actttgtcac ccaggctgga    28260
gtgcagtggc gtgatcagca ctcactgcag acttgaactc ctgggctgaa gggagcctct    28320
cacctcagcc tcccaagtag ctgggactat gggtgtgagc cagtgttcct ggccaaatgc    28380
agctgatttt tgtattgaca ttgtattctg ccaacttgct aaattaactt attcgtttta    28440 atagttttc tgtttttta aaaatcttag gatttctaca cagacaatca tgttttaat    28500
```

```
gaacaacaaa gtttgttttt ttgtttgttt gttttcccct tttcaatcaa catgccttt       28560
atgttttat ttgccttact gcactggcta ggacctccag tacaattta atagcaatgg        28620
tgagagtgtt taaatgtact cctgtgtata ttttattctt ttggaactta ttataaatgg      28680
aattgttttc ttaattttct ttttggactg ttcattgcta ttgtacagaa atacaactga      28740
ctattgtgtg ttgatcttgt accttgcaat tttgctgaaa tcgtttattt tttgcaatag      28800
attttttgtga attctttagg attttccata tgtagaatca tgttatctgt gaatagggat     28860
agttttactt cttttctaac ttggatagtt ttttccttcc taattgctct ggcaagaact      28920
tctagtacaa tgttagagag caatagtgaa agcaggcatc ttccttcaa tcctgatgtt       28980
aggggtgaag ctctcagcct ttcactgtaa tgttggctgt ggattttcat aatttttgt       29040
ttgtttgttt ttttgtttga dacggagttt ctcttgttgc ctgggctgga gtgcagtggc      29100
gtgatctcgg ctcatcacaa cctctgcctc ctgggttcaa gcgattctcc tgcctcagcc      29160
tccagagtag ctgggattac aggtgcctgc caccacaccg actaattttg tattttagt       29220
agagacgggg tttctcgatg ttggtcaggc tgctctcgaa ctcctgacct cagatgatcc      29280
gcccgcctcg gcctcccaaa gtgctgggat tacaggcatg agccaccacg cccggcccat      29340
aaatgctttt cttaatcata ttaaggaagt tccttctag tcgtagtttt ctgagtgttt       29400
ttattatgaa agactttcag attttgtaa aatgctttc ctgcgttaat tgagataatc        29460
atatgggttt tctccccctt tactctattg atgtaatgca ttacaacgat tttttaat       29520
gtttacccat ctttgcattc ctggaataaa tactagttga ttgtgctgta taattcttaa      29580
aatatgctgc tggatttgtt ttgttagtat ttggttgcat tcttttgcat ctatattcat     29640
aagggatatt gatctgtaac tattattttc ttgtggtggc tttatctggc tttggtatca     29700
agataatgct ggccacattg gctaagttag aaagtgttct ttcttctatt ttttgaagag     29760
cttgaaaaga gtcgtgttaa ttcttcttta aatatttggt acaattcact attaaagcca    29820
ctagtcctgg gcttttctta gtttgaaagt ttttgattac taattcaatc tcttttacac    29880
ctagattaga ttttgtattt tttccttagc cacttttggt aatgtgtgtg cttccgggaa    29940
tttggccagg tcatctctgt tatctaattt gctggcatcc aaatgttcat aatgttctct   30000
tgtaatcctt tttattatag aaatgatata cagaaaaggt cagttaccac tttcttttat   30060
gattgcatta atttgcttct tttctcttt tttctctagt cagtcttgct aaaggttggt   30120
ctgttttgtt gatttttttc aaagaaccaa cttttgattt tgttgattct ataattttc    30180
tgctctgtat tttgtgtata tccattctaa tttttattag ttcctttatt ctgttagctg   30240
tgagtttagt tggctcttct ttttattttt cttaaggtgg aagactaagt tattgagata   30300
tatcttgttt tttttttga tgtaggtatt taaagctata aaatttcctc tgagcattgc   30360
ttttgctgca atttataagt attggtatgt tacatattca gttagttttt tatatacaca   30420
tttaagcttt tgctaatcta ccttgtgatt tcttcattga cttattgctt gtttgagtgt   30480
gtcaacaatt tccacgtatt tgtgaatatt ctagttttcc ttttgttatt gatttctagt   30540
ttcatttcat tgtggtaaga aacaatactt tttatgatct caacagttta aaatttatta   30600
agacttattt tctggtctaa catatgatct atcctggaaa atgtatcatg tgcacttgag   30660
aaaaatgtat attctgattt ttttaggtgg gtggcatgtt ctattaatat atatgtctgt   30720
tagctctagg tgaattatag tgatgttcaa agcctccatt ttgttattaa tataaccatg   30780
ccagattttt aatgctgtcc atttgcataa tatgtctctt tccattcttt ttctttaca    30840
tgatcacttt atatttatag tatatttctt gcacacagaa tgtaattgaa acttactttt  30900
```

```
ctaaaatcta ctttcttttt ttttttttg  agatggagtc ttgctctgtt gcccaggctg   30960
gagtgcagtg gcacaatctt ggctcactgc aatctctgct tcccgggttc aagcaattct   31020
cctgtctcag cctcccgagt agctgggatt acaggcacct gtattttag  tagagacggg   31080
gtttcaccat gttggtcagg ctggtcttga actcctgacc tcgtgatcca cctgccttgg   31140
cctcccaaag tgctgggatt acaggcgtga gccactgcac ccagcccta  aaatctgctt   31200
tcatagcatc tgtcttgtac ttggaacatt tagtccatgt gtatttgaat atttattgat   31260
atgtttgggt ttatgtttac aatcctgcta tttgttttct ttttgttcca tgtgttttt   31320
gttttttatt tctgcatctt ttggaaaaat cagatttttt ggtaattcat ttttcttatt   31380
ttattggctt tttagagaaa ccttttaata tctttgtgag ttttagggat tacattattt   31440
attcttatta ttattccatt tagaattaat attgttaatc ccattcaaaa atttgtttat   31500
ttcgctttc  agttctagaa ttttcatgtt ttcttcagtt gttgtttctc tgttgttatt   31560
ctccatttgt tcattatatc tatctttct  ttgaaatcct taaaaatatt tataatagct   31620
attttaaagt cctctgctaa tcccaatgtc tgggacatct tggcttctgt tgatattgaa   31680
tacttctttt ttcccctta  attaagggtt tcattttcct gcttttcac  atatctagta   31740
gatttttatt atgctctgtg tgctatgaat gagatattat aggaagcctg tcaatattg   31800
tctcttttta aagggtgttg tatttagttc tgccaagaag ttaaattacc agatttactt   31860
gatgtggctt tagtctttgt tagagctggt ctattcctgc tttgttctta cttctcaggt   31920
aatgaccttc ctgagtttca gctggatgcc tgaagtgctc agctgcattt ttctactctg   31980
gctattctga aatgcaatat tttccagacc tacccaacct ttggtattca tctcccagac   32040
ctgtggctgc ttctctttgc tgagcctcac aaaatcttgt cctgtgcatg acagccaag   32100
gatccttggg aaatctcatg cagacttcta ggtccttcct ttgtgtagat tcttctctc   32160
cagtacgttg acctgcttca gagtcctcat cattgctttc ttcctttca  gctcagcaat   32220
actgctgtgt attgtgtggg cttcatttgc ctcagccata cctagaacac aacccaaggc   32280
agaaagctgg agtggacctg aggctcatca cctgtttcct tccacccacc atttaaaagc   32340
agcttatttg tgtgaaactt tttgttgggt tctgtggggg atacgtatag gcaaatgaca   32400
gggagcttat aatttagcca aagagaaaat gtctatatgt tctgtggaat tcagagtatt   32460
ttcctcgact tccaaaatta ttttcctcga cttccaaaat ttggggctac tagctagttg   32520
gtaggaagga attccagatc cattttctt  ctagatttt  ttcagactcc atgtttcaaa   32580
atctagatgg aaggtaagaa ggaagcaagg agggcatcac atacgagaga gacttatacc   32640
ccaaagtgga tcattagcac attatgagat aatatggtat tattctcaga ggcctgccat   32700
ataaaattcc ttctaattta tttttaatg  gtatgtgcct gaaagttttc tgtctttcat   32760
gatcttgaaa gcaaataag  aaccagagta gcttatgaga gagttttcct gcttcagccc   32820
agaaaaatgt tgcttctgtc ctagacccct tgatctggtt cttagtgcca gccttcattc   32880
ctctagatct gtttattgaa tactggctct gttgcagaga ctttgctaga atctgagaga   32940
taaaagactc aatgccttca aaacacctac aatccagaca cttaaataaa tgcaataata   33000
tatggttaag gtcttggata gaggaccatc atagaaacac atagaacaga catttagtcc   33060
atgctaggga gagggaagat gtcaaggaat gcttcctgga ggtggcgaca tctaagctga   33120
gttttaaagt gggtgtaaga gtgaaggaac tgggaatagg caaaacatac cttagagagc   33180
tgcacctcca aagcatggaa ggctagataa tcttagaact tcaagtgggg ttcaatgtgc   33240
```

```
ctgggacttg gatttcaggc agagaccata gggcaagttg gagaacaggt gggcagggtg    33300
agatgaagca gagacttta ataaccatca acaggcctg ccatccaact gctatcagcc     33360
attttcccct tttgaatttt attttttaa tctctagagc aatacatgtt tatggtagga    33420
aatgaaaaaa atatatagat gggtaaaatg aagtgaatta taccacccac aatcctgctg    33480
taaaacaggt tttaacaagt tataaatccc tccagatcaa agtgctacta aactctactt    33540 gctatttat aacctttttc tgttcagagt attttagaaa cgttttttaca tgttaattga   33600 tattcttttg cattatcctg aataatggta tttctttagt tatactatca tgtattaaaa    33660
cattcataca tggtaaacat atttgaatat tagacatttc aattgttttc aatgtttggc    33720
tattaaaaat agtatttaga tgaatgttct tggccataca gttaataact tcactgagtc    33780
cttgtcaata actttattaa atcccaatct taagacaaca agcctataag attaacatac    33840
caggaataat tagaaagcat tgcaagacta tatgtaacca tctccctgtt aatcatcctt    33900
atttgttgca acatcctaaa tagcgacctt cccacactct gcctcataat atttaatctg    33960
tcaaatgtac catccgcaaa gggagtgaac tggctcgtga agaggtggtg aagctggttc    34020
aactcagttt aacagacaat gagggcctcc gtgtgccagg gagggagtga gggaactcca    34080
cagggagctc attctgggga gggatgcccc tcattatctg cagtaaatga tattagagaa    34140
gtatgtgtga gactcttggt gtccagagga ggggcatgca gcacagtatg ggggtccatg    34200
gggttgcagc gatttcttag agacggtgcc atgcctggga tgaccaccaa gttaggatgc    34260
tgtaaagagt aatcaaataa gtttcaacag ggttttggca tgaggtgagc agttaatcca    34320
aatgatatct gaaatgcttt ctaatgctgc aagtgtattc ctctgtaaaa taatcaacta    34380
cttaaaagac actctcactt gcattatgtc atttaatcct cacagtgtcc ctacgggaca    34440
atagatgtca ttcccacttg tacagagcag taagtgaggc tcacaccggt catagttaga    34500
ggagtaggga atctaaacct aagtctcttc tactccaaac cccaagtttt atcagtatgt    34560
cacatcgcta ctgtgggctg aattccttag caggggttgt ttcctccacc tgcaatattc    34620
ttccttttgg tttgttcatc ctctagagag agaagggata cgcattcatg gagatcctac    34680
tgttgcaaac tctgcattag gagttttaca tgaattgtct catttagtcc tcacaacagt    34740
cctgtgaggc acaggaaagt tagatttacc tgcccaaatt aaggaatgtg gccaactcaa    34800
gagtgacgaa ggccaggtgc ggtggctcat gcctgtaatc tcagcacttt gggaggctga    34860
ggtgggaggc tgaggatcgc ttgagcccag gagtttaaga ccagccaggg caacacagca    34920
agatttaatc tctactagaa ataaaaaaga aattagccag gtgcctgtag tcccagttac    34980
ttgggaggtt gaagtgggac gattgcttga gcctgggagg tagaggctgc agtgagccat    35040
gatcccatca cttcactcca gtcagggtga cagagtgaga cccagtctta aaacaaaaca    35100
aaacaaaaaa gagtgatgga gcaggaactt tatctgccat cagagaccat atatgtcttt    35160
ccttatggcc caggtcattt atcatgtcct tgctaaacct cctcctctga gccttgttaa    35220
agtcctcaag gttagaagag tggtctataa ttataaaaaa ttccattgta tgacttcagc    35280
tacctgcaaa actgaccgag attaatgcat tctttgtttg ctttcactct ttcattccct    35340
gttcagcgct tattctacag aaaggtgcct ggtagattta ggacatgact gttcataggc    35400
ctcaaatgcg gtcaaattag gaaagtcccc tggttttttgg tctcaagagg ttaattgctg    35460
agtactagcc tggactgctc aatggatttt atgtttaact gttgtgttta tttgtttgtt    35520 tgttttgtt ttgtgagaca tatctttctc tgtcacctgg gctggaggtc agtggtgtga     35580
acatggctca ccgaagcctc catctcctgg gctcaagtga tcctcctgcc tcagccttcc    35640
```

```
tagtagctgg gactacaggc acacagcacc atgactggtt aagttttgga ttttttggta    35700
gaaatggggt ctcactcttt gcgcaggcta gttgtgaact cctggtatca agggattctc    35760
ccaatgtgct gggatttcgg cctcccaaag tgctgggact gcaggcatga gccatcatgc    35820
ccagcctctg tttaactgtt aacatcatga ggtttccttt caatgaggaa gggaggcctg    35880
gggaggtgtg atgggaaga tggagaaggg taggagacat cataaaactg acagaagtgt    35940
ggcacgatta agaccctggt ttcttagacc acataagcaa gtgccactat tcttttgatc    36000
aacatttgat tctctatttc cttcttagca tatagatagc tgcttcaggt cgtgaaaaaa    36060
tacatttagt gaaatgaaac atagtagata tgttcaccaa gaaactaaaa agaaaagtta    36120
gccacaaact atcttatttc attgaaatgt ttggctgaac ccataagaat gttgatgagg    36180
ccattcttgg atgcctgtac tgaaatgaac cacgagagga atatttagga tatgttgaag    36240
aggctgtttg gcttaatgaa caaggagtt tctgcaggcc cagggagtgg aatgaaaatt    36300
ggcatgatca ttttggagaa tatatggagt caaacagaga atttgaatgg agttttcaaa    36360
gaggatatgt taggggaata aaggctgata acaacactt gtatttgtag gaaaataggg    36420
agagtaaatc aaggaattca aagagaaaga gaaactcact tcaagtaggg gagaaaaaac    36480
ccctataatt ttcactcttc cttgtaaata aaaggaaac aaatgaaaat aagatattag    36540
aagtcagtaa gaatttatgg gagtataaag ttggttttat ggatgcaaag ccctttcac    36600
tgctgtacga aactcctggc tgcatgctaa caatggacaa ctgatttcct tgcagctgta    36660
ttttgctgtt ttttgctctt ggcttggacc tagcaccctg ggtctgtggg aaaccagaac    36720
tgtcccagag ttctggaggg taggccaagg ttagatgctg gagtgggttc tttaatttat    36780
tgtactgatt cttcttggga agaaagaaga ttgcttgtta gaattttagc tacgagagat    36840
gactatgaaa cagtaaatta actccaacga cctgagtcat tttgaaaact cccagtctca    36900
ggataaaaaa tataatccta tttagaaatt cctggtgtga tcacagatgt agcattggtt    36960
cttttcatga aacccgtaaa ttaaaaagta cataatccaa agtcaattaa atagtaagct    37020
attataacaa attctttat ttcattagct tttcaaaatg tggataacta cacactcaac    37080
ccaaggaatc tacatttttc cactgactgc taaagaccaa tggaaataac tctagtcccc    37140
gtagcacctc actgtggggt gacctaccttt gaaataatg tattggttct agctgatttt    37200
tatattgtta gtcattaagt taggcttgat gagaaacaga tataatctga tttggggatt    37260
caagtattat attgcatttc tcctcacaac tagagataaa tttgccatgg ttttctctt    37320
cataggctca tgccaaagtc tggcatctct acaatacttc tttccgtccc actcaggag    37380
gtcaggtgtc cattgcccta agctctcact ggatcaatcc tcgaagaatg accgaccaca    37440
gcatcaaaga atgtcaaaaa tctctggact ttgtactagg ttggtttgcc aaacccgtat    37500
ttattgatgg tgactatccc gagagcatga agaataacct ttcatctatt ctgcctgatt    37560
ttactgaatc tgagaaaaag ttcatcaaag gaactgctga cttttttgct ctttgctttg    37620
gacccacctt gagttttcaa cttttggacc ctcacatgaa gttccgccaa ttggaatctc    37680
ccaacctgag gcaactgctt tcctggattg accttgaatt taaccatcct caaatattta    37740
ttgtggaaaa tggctggttt gtctcaggga ccaccaagag agatgatgcc aaatatatgt    37800
attacctcaa aaagttcatc atggaaacct taaaggtat gattgtgggt aaagttctca    37860
tttcctgcca aaatcttctg gaaaaaaatc tctaagatta tctaacataa atgatgtgaa    37920
tttatatttt taaatcctaa tggagacatt cattttggca atagtagaat gcattcattt    37980
```

```
aacaccttc  tcatttggag  tcttgaggaa  cttgaattaa  tttttaaaaa  cccatttgta   38040
aatgagaaac  tgggttataa  tatttgtaat  tacttaactt  tcagttatta  atctagattt   38100
ttagattaaa  ttgaacataa  aacaaatccc  aggatatcta  gctctctgca  catgttttc    38160 agttcttgtt  attttggttg  aataaaacac  tttaaagaaa  aaggaatgtc  catgttttct   38220
agagaaaata  gtataaatag  atcatgcttt  taaagccttc  atttatttat  ttattgcatc   38280
agacacaaag  ctgggtgtct  aggatggaaa  gtggtacaag  acatctttcc  agccctgtag   38340
aatatctatt  ataaataagg  aactattttt  tcaaggtgct  cagaaatcca  aaaacatat    38400 tagataggcc  aattttgagg  gcatttattt  gtagagttat  ataggtttga  ttagagtctt   38460
tcgtcaagaa  gaaaaatcat  tggcttacca  aacgagaagc  attacactt   atttatttaa   38520 gtaggaaacg  ctcagctgct  cttgaaccat  gatgcaagtg  cccagcgaag  ggtcatgttg   38580
ctcttgtccc  ctcttccctt  tgcagccatc  aagctggatg  gggtggatgt  catcgggtat   38640
accgcatggt  ccctcatgga  tggtttcgag  tggcacagag  gttacagcat  caggcgtgga   38700
ctcttctatg  ttgactttct  aagccaggac  aagatgttgt  tgccaaagtc  ttcagccttg   38760
ttctaccaaa  agctgataga  gaaaaatggc  ttccctcctt  tacctgaaaa  tcagcccta    38820 gaagggacat  ttccctgtga  ctttgcttgg  ggagttgttg  acaactacat  tcaagtaagt   38880
cagctgacaa  aaccaatcag  cagtctcacc  aagccctatc  actagtaagt  agtgcttcct   38940
tcctaggctg  attgtcatgg  cacattgtcc  gttctttgag  ccaaaacaa   ttccttatga   39000 gtacactaag  ggcacaattt  ggaatgctgc  accctctct   ccaaaactct  tccaatcttc   39060
atcttgttta  agttagatcc  aaagataaat  aaatttaaag  catatcaata  tttaagatcc   39120
gattaagaca  gtaaaaagat  aaaacactct  cttttcatac  tgtggttt    gatccttttt   39180 aaggcagttg  agttttttca  tgaacaggat  ctaacacaga  actccaaagc  ctctgagttt   39240
cagtggtgct  gctgagactg  aggcaggaac  attaggcaga  gtcctccaga  ggcacaactg   39300
tgggctccac  aaatgtgcag  aaataccta   agaaagtaaa  ccctagatcc  aatgattcac   39360
tggtcagaat  gtctttttta  gcaatagtca  ttgaaatgat  acgaaatttc  ttcagaatga   39420
tcaaccaata  tttattgagc  atcttctcag  tagtaagccc  ttaacattct  ttcagacttc   39480 ctaaatttg   aaggggcttg  ttttccagca  tttgactgga  tactctagta  agcacttatt   39540
ggatgtctag  tgtgtccgaa  gccttgtgtt  agttgctcgg  gtcgcttggt  taagggag     39600 gcaggtagag  ggtatactga  gatgagtaag  ggtaacctt   gctttcaaag  gagcaaagga   39660
gtctactgag  cgaaaacaat  gtatgcacaa  atgatgcaat  ggagtgaagc  gggcatggtg   39720
gtaagtaaca  agggcggggc  tgggggattg  ctgctgatag  agtcccaagt  gtgaaaatag   39780
ccctcaagac  agagacagag  ttcagtgtcc  atagacaagc  agttggcttt  gacatgttgg   39840
gttatggtag  ccaattaatt  ggttctgcaa  atcacagctt  gaaaggaaac  acttggaaga   39900
atgtgaaatg  ggttgctgtt  ttcttgtaaa  tatccaattg  aaatctttta  tttataagga   39960
aataaattaa  caccatcctt  agtacatttt  ttgctggttg  ggattattct  tctttttcag   40020
accacccagt  tcatttaca   ggcagtctca  gacttaaacc  ctcgccttcc  atttaaaaga   40080
tgactggctc  acgcctgtaa  tcccagcact  tgggaggcc   gaggcgggcg  gatcatgagg   40140
tcaggagatc  aagaccatcc  tgaataacac  ggtgaaaccc  cgtctctact  aaaaatacaa   40200 aaaaaaaaa   aaaattatc   cgggtgtggt  ggcgggcacc  tgtagtccca  gctactctgg   40260
aggctggggc  aggagaatgg  catgaaccca  ggaggcggag  cttgcagtga  gccgagattg   40320
cgccactgca  ctccagcctg  ggtgacagag  caagagtccg  tctcttaaaa  aaaaaaatga   40380
```

```
ctggatgtgt catcttttat gccaggatat gtgagcccag gagaaaggct tctgagctcc    40440
ctcctgctcg gtgtgcaatt ttctgccctg ccccgactct ctccttctct cccagcctcc    40500
tgctatttga aatctcctta tcctaatttc cctcctcaga gtggattcca ctgtgggtt     40560
cagagaggat ctgaggtggg agaagtgagg ctggtgagga agaaggggag gagaaaggga    40620
agaagacctc cgtagccttc cttcctcctc ctctttactg gggttgggga tagatcggat    40680
ggtccctggt ccttgttcta tctcttgacc ttctgcctgc tccctgctga gcacggatct    40740
ctgatagcag cctgagtctg gcaggttcag tcctttgtat gcggcacaat ctcccagcca    40800
gcattgctgt gcagatcatg ggaacgaatg cagaacaaga gtggggtgt cggagggagc     40860
cctacttctc ctgttctatt cctcatcagg gggctgtgcg ctggctttgg gaattggtaa    40920
atagtgagaa agtcttaagg gtacatccta tttccttgag ggagaagaga aaacgctggt    40980
cagaagcaat aagtatagca gtgaatagca agggagatgg gagataattc cttttcctac    41040
tacactctag aagctattgt tttagaatct gacctaaggt cagccactaa ttggccccag    41100
aggtctctct ctcagatcac acggtccttt tttcctcatc agcttgggga ccccaccct     41160
cctcctggca gtctcctcct gtgcagaacc caacaaacac aaaattaagt cactctcaaa    41220
cccacagcag atgagagctt ctctggaagc tccctggtgg ggaaaggctg caattgctat    41280
tttcttcttc tggttttcac ctcaggcttt gtgttatatt gacagtaccc ttctcaagct    41340
aactccctaa ctgacctgac gtagtcaaaa taagttcttt gtatgtcagt tctgaggtgt    41400
gtgtgttttc acttacaaac agtactctac agctttaaga cattatatta aagtcctgag    41460
aagtgatttt taaaccactg aacttcatct tttccctcct ggctagtatt tcagactttc    41520
agtgtttgag gcatgcattt cacctgaaca acttgaaaaa taatatccta agaagcacac    41580
aacctgactt taggctcatt cacatggatt gtcactttac ttggacccac tttctcggct    41640
gagaggtttg ttttcccata accacggatg ctcatagtta atataaatat tgaactcact    41700
atgtagtgag gacatagagc ctcttttaaca ttggtccctg ttaggagaaa gtttctccca    41760
taacatacta aatacatgtt ttaatagccg ttccttctga aggtccaac ttcactattt     41820
tattttttta gtaaaatctt agttaacaaa ttaatggagg ttaggtggaa ttttgcccca    41880
aaagtcctgt atttcttttt ttttttttttc ttttttttttg acagagtctt gctctgtcgc   41940
ccaggctgga gtgcagtggc gtgatctcgg ctcactgcaa gctccgcctc ctaaggtcac    42000
gccattctcc tgcctcagcc tcctgagtag ctggggctac aggtgcccgc caccgcaccc    42060
ggctaatttt ttgtattttt agtagagacc gggtttcact gtgttagcca ggatggtctc    42120
aatctcctga cctcgggatc cacccacctc ggcctcccaa agtgctggga ttacaggcgt    42180
gagccaccat gcccggcctg tcctgtattt tcaagaaact ttttttttcc tccagaaatg    42240
atacccctagt cttttcatatt tgttttcaga tggactgaat aaaagctgtt gttttggaac   42300
aatcacggtt aaaaaaaaaa gttatgaatt tagtcaactc agagctctat aaaaataatc    42360
caaaaaattc cttcaaactc tgaacgcttc aaaagagcgt gcaaatattc tgtccttcaa    42420
agctaaggaa acatgatttg tggggtgcat cacagtggaa aaatactctg acagcattcc    42480
cacagcatta ggggaagtgc atgtgtgggt gttctgcaag ggacaattct ccagaaaagg    42540
caatttccct ttgacatgct gttttttaatg acttttcttt ataaacacac ttatctctcc    42600
agagaaatag cagtgcattt gcaacaggcc cgtaaaatgc aacaaaacct ctgctatggt    42660
ttctgacccc tgcttttata cagagcatca gaccaaggaa cctgttctaa caggattatt    42720
```

```
tcagagggga acacaggctt agggtgcaga tcttccagct ggattttca ctttgcattc    42780
cctccacagc agacacatga aggaatgatt ttgtgatttt gattttataa tttgcacact    42840
tttcctaaat actttttta aattttatt tgggaggatt ttatagcata tgattgagaa    42900
ctataatcat catcattgtt acagaagaat aatttagaaa aatttttaa ctacgttaaa    42960
aattccacta tgggtggatg acaatattgt tctttccttc cacattctcc ctccttagac    43020
tttcttttct tttttctat tttttttg agatgaagtc tcgctctgtc actcaggctg    43080
gagtgcagtg ccatgatcct ggctcactgc aacctctgcc tcccgggttc aagtgattct    43140
cccgcctcag cttcctgagt agctgggatt acaggtgtgc accaccacac ctggctactt    43200
tttgtatttt tagtagagat gggtttcac catgttggtc aggctggtct caaactcctg    43260
atctcatgat ctgcccgcct tggccccgca aagtgccggg attacaggcg tgagccactg    43320
cgcctggcct ctctctcgga ctttctacca tcagtcagat tgaatttgtt aaattctgtc    43380
actgaccta aacccaacaa aaggcaagag ttatgtttat ttagcacttc ctctacctat    43440
agcaaacctc aatttagagc gtaattttaa gcacaattta attataaata tcttttcatt    43500
ttcttactta actcactcag tttttaaat cttcttttt gagacaagat cttgctctgt    43560
cactgaggcc gatgtacagt gatgtgatca tgacttactg cagccttgac ctcccaggct    43620
taggtgatcc tcatacctca gcctcccgag caactaggac tacaggcccg tgccaccatg    43680
ccgggccaag acggggtttg gacgtgttgc cccagctggt ctccaactcc tggcctcaag    43740
tgaccctccc gcctcggcct ctcaaagtgc tgggattata ggcatgagcc accgcacctg    43800
gccaactcac tcacatttta agtttttct tttttcatc tagttttttt tctttttaaa    43860
tttgaaagcc tcatgacatt aatgatttct tacattaaaa gaaaaacacc caaaaatact    43920
ctgcttacat aacaccgaca agtagtgtgc aagactcatt agcatttgtc atctgaagtg    43980
accaaatcca gacttttggg ggtcacatta aagaaacagt tgaagagtta gaactatggg    44040
taaagcgagt gtgcatatca gaaagtggaa tattgtcttc ctcaggagct gacaatttat    44100
gaaaaatagt tcacattctc agctagaaag gcttctattt ttgctcatat tcctggctag    44160
ttttgctgaa ataattgctt tgaattactt cctcaggact gcccaggtga cgctaatgtt    44220
tactctgccc ttcacaggta gataccactc tgtctcagtt taccgacctg aatgtttacc    44280
tgtgggatgt ccaccacagt aaaaggctta ttaaagtgga tgggggttgtg accaagaaga    44340
ggaaatccta ctgtgttgac tttgctgcca tccagcccca gatcgcttta ctccaggaaa    44400
tgcacgttac acattttcgc ttctccctgg actgggccct gattctccct ctgggtaacc    44460
agtcccaggt gaaccacacc atcctgcagt actatcgctg catggccagc gagcttgtcc    44520
gtgtcaacat caccccagtg gtggcctgt ggcagcctat ggccccgaac caaggactgc    44580
cgcgcctcct ggccaggcag ggcgcctggg agaacccta cactgccctg gcctttgcag    44640
agtatgcccg actgtgcttt caagagctcg gccatcacgt caagcttgg ataacgatga    44700
atgagccgta caaggaat atgacataca gtgctggcca caaccttctg aaggcccatg    44760
ccctggcttg gcatgtgtac aatgaaaagt ttaggcatgc tcagaatggg aaaatatcca    44820
tagccttgca ggctgattgg atagaacctg cctgcccttt ctcccaaaag gacaaagagg    44880
tggctgagag agtttttggaa tttgacattg gctggctggc tgagcccatt tcggctctg    44940
gagattatcc atgggtgatg agggactggc tgaaccaaag aaacaatttt cttcttcctt    45000
atttcactga agatgaaaaa aagctaatcc agggtacctt tgactttttg gctttaagcc    45060
attataccac catccttgta gactcagaaa aagaagatcc aataaaatac aatgattacc    45120
```

```
tagaagtgca agaaatgacc gacatcacgt ggctcaactc ccccagtcag gtggcggtag    45180
tgccctgggg gttgcgcaaa gtgctgaact ggctgaagtt caagtacgga gacctcccca    45240
tgtacataat atccaatgga atcgatgacg ggctgcatgc tgaggacgac cagctgaggg    45300
tgtattatat gcagaattac ataaacgaag ctctcaaagg taaggagccc tagctgcggc    45360
tatctcctga aggttatgtc accagagggc atgacacttg attaaatctc caacatcaac    45420
acacactgcc acccttggaa tggagggcta tccattttgt gcctcactga acagtccaa     45480 gagatatcta gcatttcccc aaggataaag gagtgtagct aaaagtagaa gaccagaaat    45540
ccctagcccc tactctggat ctatgcaagc ctagattctt gtcttccatc ttggatggct    45600
ccacagcagt cttaactgtt tcatgtacat aaagcagtac ataaagattt aaccttgctg    45660
ggcatggtgg ctcacacctg taatcccagc attttggaag gccaaggcag gaggattgct    45720
tgagcctaga agtttgagac cagcctgggc aacatagtga gaccttgtct ctactaaaaa    45780
tcacaaaaat tagctgggca cggtggcata tacgcctgca gattcagtta cttgggagga    45840
gaggcgggag gattgcttga gcttgggagg tccagctgca gtgaatcatg atcacagcac    45900
tgcaatctgg cctgggtgac agagcaagac actatttcaa aaaaaaaaag accaagcatg    45960
gtggctcatg cctgtaatcc cagcactttg ggaggctgag gcaggtggat catctgaggt    46020
cagaagttca agaccagcct gaccaacatg gtgaaacccc gtctctactg aaaatacgaa    46080
aattatccag gtgtagtgat gcacacctgt aatctcagct actcgggagg ctgaggcaga    46140
agaatcactt gaactgggga cgtggaggct gcagtgagcc aagattgcac cattgcactc    46200
cagcctgggt gacagagcaa gactccatct caaaaaaaaa aaaaaaaaaa aaaggattta    46260
acccaagtat atcatagtag attgaattat gtaaaacacc catttaacaa ccaggtccag    46320
gtttgttctc tctgtgtagt aaatcaatca ctgtgacaca ggttttgcaa aagagaaaag    46380
atttatttgt aaggggacca agcgaggggg tgggagaata acttccaatc ctgcctctct    46440
gaagacaagg cttaggaata tgtatgggtt agggaatggg tggtctaagg catggtgaag    46500
agtgattggc agggggggaa aatgaagtaa caggttagac acatgcacag aaaatggtgg    46560
tgttagcatg atctgagggc agagttttgg gccctctgac gtcaaaagac cacctctcag    46620
gcacttgtgc aggcccagtg gaagggtcag tggtcttaac tagtttgaac tggacaggag    46680
ctgccccaag ttcttggaaa acaactgaa gtgaccattg ccatggtaac ctatgaatgt     46740
catcagtaaa gtagccagtg aaggttaagt ttcagcatac aatgggacaa ccttcagctt    46800
catggaaaaa ggaaaaaaaa aaaacacata cacacacgaa aagcaagtga ccaaaagcaa    46860
gcaggacagg cagacctgat ccaattaacc cctgggtttc aaccctgcta aatgcagctc    46920
aatatttgtc ttgataattt gcctatttgg ctttacataa aataaagcct tttctgatga    46980
aatctaattg agtctgaagt tgtattaaat ggtatcggaa acttcccagc aggaaggcta    47040
cgtaaaagtg gccgggcgtg gtgactcacg cctgtaatcc cagcactttg ggaggctgag    47100
gcaggcagat cacaaggtca agaaatcgag accatcctgg ccaacatggc gaaatcccat    47160
ctctactaaa aaaaaaaata caaaaatttg ccaggtgtgg tggtgctcac ctgtagtccc    47220
agctactcag gaggctgagg caggagaatc tgttgaacct gggaggcgga ggttgcagtg    47280
agtcaagatg gtgccattgc actccagcct gtgtgacaga gcaagactcc gtctcaaaaa    47340
aaaaaaaaag tgatgtgttg tgtgcaaaat acgtaataac tactctccta tccttttgtt    47400
tttccagccc acatactgga tggtatcaat ctttgcggat actttgctta ttcgtttaac    47460
```

| | |
|---|---:|
| gaccgcacag ctccgaggtt tggcctctat cgttatgctg cagatcagtt tgagcccaag | 47520 |
| gcatccatga acattacag gaaaattatt gacagcaatg gtttcccggg cccagaaact | 47580 |
| ctggaaagat tttgtccaga agaattcacc gtgtgtactg agtgcagttt ttttcacacc | 47640 |
| cgaaagtctt tactggcttt catagctttt ctattttttg cttctattat ttctctctcc | 47700 |
| cttatatttt actactcgaa gaaaggcaga agaagttaca aatag | 47745 |

<210> SEQ ID NO 26
<211> LENGTH: 47745
<212> TYPE: DNA
<213> ORGANISM: Homo sapiens

<400> SEQUENCE: 26

| | |
|---|---:|
| ctatttgtaa cttcttctgc ctttcttcga gtagtaaaat ataagggaga gagaaataat | 60 |
| agaagcaaaa aatagaaaag ctatgaaagc cagtaaagac tttcgggtgt gaaaaaaact | 120 |
| gcactcagta cacacggtga attcttctgg acaaaatctt tccagagttt ctgggcccgg | 180 |
| gaaaccattg ctgtcaataa ttttcctgta atgtttcatg gatgccttgg gctcaaactg | 240 |
| atctgcagca taacgataga ggccaaacct cggagctgtg cggtcgttaa acgaataagc | 300 |
| aaagtatccg caaagattga taccatccag tatgtgggct ggaaaaacaa aaggatagga | 360 |
| gagtagttat tacgtatttt gcacacaaca catcactttt tttttttttt gagacggagt | 420 |
| cttgctctgt cacacaggct ggagtgcaat ggcaccatct tgactcactg caacctccgc | 480 |
| ctcccaggtt caacagattc tcctgcctca gcctcctgag tagctgggac tacaggtgag | 540 |
| caccaccaca cctggcaaat ttttgtattt tttttttttag tagagatggg atttcgccat | 600 |
| gttggccagg atggtctcga tttcttgacc ttgtgatctg cctgcctcag cctcccaaag | 660 |
| tgctgggatt acaggcgtga gtcaccacgc ccggccactt ttacgtagcc ttcctgctgg | 720 |
| gaagtttccg ataccattta atacaacttc agactcaatt agatttcatc agaaaaggct | 780 |
| ttattttatg taaagccaaa taggcaaatt atcaagacaa atattgagct gcatttagca | 840 |
| gggttgaaac ccaggggtta attggatcag gtctgcctgt cctgcttgct tttggtcact | 900 |
| tgcttttcgt gtgtgtatgt gtttttttttt tttcctttttt ccatgaagct gaaggttgtc | 960 |
| ccattgtatg ctgaaactta accttcactg gctactttac tgatgacatt cataggttac | 1020 |
| catggcaatg gtcacttcag ttgttttttcc aagaacttgg ggcagctcct gtccagttca | 1080 |
| aactagttaa gaccactgac ccttccactg ggcctgcaca agtgcctgag aggtggtctt | 1140 |
| ttgacgtcag agggcccaaa actctgcccct cagatcatgc taacaccacc attttctgtg | 1200 |
| catgtgtcta acctgttact tcatttttccc ccctgccaa tcactcttca ccatgcctta | 1260 |
| gaccacccat tccctaaccc atacatattc ctaagccttg tcttcagaga ggcaggattg | 1320 |
| gaagttattc tcccaccccc tcgcttggtc cccttacaaa taaatctttt ctcttttgca | 1380 |
| aaacctgtgt cacagtgatt gatttactac acagagagaa caaacctgga cctggttgtt | 1440 |
| aaatgggtgt tttacataat tcaatctact atgatatact tgggttaaat ccttttttttt | 1500 |
| tttttttttt ttttgagatg gagtcttgct ctgtcaccca ggctggagtg caatggtgca | 1560 |
| atcttggctc actgcagcct ccacgtcccc agttcaagtg attcttctgc ctcagcctcc | 1620 |
| cgagtagctg agattacagg tgtgcatcac tacacctgga taattttcgt attttcagta | 1680 |
| gagacggggt ttcaccatgt tggtcaggct ggtcttgaac ttctgacctc agatgatcca | 1740 |
| cctgcctcag cctcccaaag tgctgggatt acaggcatga gccaccatgc ttggtctttt | 1800 |
| tttttttgaa atagtgtctt gctctgtcac ccaggccaga ttgcagtgct gtgatcatga | 1860 |

```
ttcactgcag ctggacctcc caagctcaag caatcctccc gcctctcctc ccaagtaact   1920
gaatctgcag gcgtatatgc caccgtgccc agctaatttt tgtgattttt agtagagaca   1980
aggtctcact atgttgccca ggctggtctc aaacttctag gctcaagcaa tcctcctgcc   2040
ttggccttcc aaaatgctgg gattacaggt gtgagccacc atgcccagca aggttaaatc   2100
tttatgtact gctttatgta catgaaacag ttaagactgc tgtggagcca tccaagatgg   2160
aagacaagaa tctaggcttg catagatcca gagtaggggc tagggatttc tggtcttcta   2220
cttttagcta cactcctttt tccttgggga aatgctagat atctcttgga ctgtttcagt   2280
gaggcacaaa atggatagcc ctccattcca agggtggcag tgtgtgttga tgttggagat   2340
ttaatcaagt gtcatgccct ctggtgacat aaccttcagg agatagccgc agctagggct   2400
ccttaccttt gagagcttcg tttatgtaat tctgcatata atacaccctc agctggtcgt   2460
cctcagcatg cagcccgtca tcgattccat tggatattat gtacatgggg aggtctccgt   2520
acttgaactt cagccagttc agcactttgc gcaaccccca gggcactacc gccacctgac   2580
tgggggagtt gagccacgtg atgtcggtca tttcttgcac ttctaggtaa tcattgtatt   2640
ttattggatc ttcttttttct gagtctacaa ggatggtggt ataatggctt aaagccaaaa   2700
agtcaaaggt accctggatt agcttttttt catcttcagt gaaataagga agaagaaaat   2760
tgtttctttg gttcagccag tccctcatca cccatggata atctccagag ccgaaaatgg   2820
gctcagccag ccagccaatg tcaaattcca aaactctctc agccacctct ttgtccttttt  2880
gggagaaagg gcaggcaggt tctatccaat cagcctgcaa ggctatggat attttcccat   2940
tctgagcatg cctaaacttt tcattgtaca catgccaagc cagggcatgg gccttcagaa   3000
ggttgtggcc agcactgtat gtcatattcc ttgtatacgg ctcattcatc gttatccaaa   3060
gcttgacgtg atggccgagc tcttgaaagc acagtcgggc atactctgca aaggccaggg   3120
cagtgtaggg gttctcccag gcgccctgcc tggccaggag gcgcggcagt ccttggttcg   3180
gggccatagg ctgccacagg gccaccactg gggtgatgtt gacacggaca agctcgctgg   3240
ccatgcagcg atagtactgc aggatggtgt ggttcacctg ggactggtta cccagaggga   3300
gaatcagggc ccagtccagg gagaagcgaa aatgtgtaac gtgcatttcc tggagtaaag   3360
cgatctgggg ctggatggca gcaaagtcaa cacagtagga tttcctcttc ttggtcacaa   3420
ccccatccac tttaataagc cttttactgt ggtggacatc ccacaggtaa acattcaggt   3480
cggtaaactg agacagagtg gtatctacct gtgaagggca gagtaaacat tagcgtcacc   3540
tgggcagtcc tgaggaagta attcaaagca attatttcag caaaactagc caggaatatg   3600
agcaaaaata gaagcctttc tagctgagaa tgtgaactat ttttcataaa ttgtcagctc   3660
ctgaggaaga caatattcca ctttctgata tgcacactcg ctttacccat agttctaact   3720
cttcaactgt ttctttaatg tgaccccccaa aagtctggat ttggtcactt cagatgacaa   3780
atgctaatga gtcttgcaca ctacttgtcg gtgttatgta agcagagtat ttttgggtgt   3840
ttttcttttta atgtaagaaa tcattaatgt catgaggctt tcaaatttaa aaagaaaaaa   3900
aactagatga aaaaagaaa aaacttaaaa tgtgagtgag ttggccaggt gcggtggctc   3960
atgcctataa tcccagcact tgagaggcc gaggcggag ggtcacttga ggccaggagt   4020
tggagaccag ctgggcaac acgtccaaac cccgtcttgg cccggcatgg tggcacgggc   4080
ctgtagtcct agttgctcgg gaggctgagg tatgaggatc acctaagcct gggaggtcaa   4140
ggctgcagta agtcatgatc acatcactgt acatcggcct cagtgacaga gcaagatctt   4200
```

```
gtctcaaaaa agaagattta aaaaactgag tgagttaagt aagaaaatga aaagatattt    4260
ataattaaat tgtgcttaaa attacgctct aaattgaggt ttgctatagg tagaggaagt    4320
gctaaataaa cataactctt gccttttgtt gggtttaggg tcagtgacag aatttaacaa    4380
attcaatctg actgatggta gaaagtccga gagagaggcc aggcgcagtg gctcacgcct    4440
gtaatcccgg cactttgcgg ggccaaggcg ggcagatcat gagatcagga gtttgagacc    4500
agcctgacca acatggtgaa accccatctc tactaaaaat acaaaaagta gccaggtgtg    4560
gtggtgcaca cctgtaatcc cagctactca ggaagctgag gcgggagaat cacttgaacc    4620
cgggaggcag aggttgcagt gagccaggat catggcactg cactccagcc tgagtgacag    4680
agcgagactt catctcaaaa aaaaaataga aaaaagaaa agaaagtcta aggagggaga    4740
atgtggaagg aaagaacaat attgtcatcc acccatagtg gaattttttaa cgtagttaaa    4800
aaattttttct aaattattct tctgtaacaa tgatgatgat tatagttctc aatcatatgc    4860
tataaaatcc tcccaaataa aaatttaaaa aaagtattta ggaaaagtgt gcaaattata    4920
aaatcaaaat cacaaaatca ttccttcatg tgtctgctgt ggagggaatg caaagtgaaa    4980
aatccagctg gaagatctgc accctaagcc tgtgttcccc tctgaaataa tcctgttaga    5040
acaggttcct tggtctgatg ctctgtataa agcaggggt cagaaaccat agcagaggtt    5100
ttgttgcatt ttacgggcct gttgcaaatg cactgctatt tctctggaga gataagtgtg    5160
tttataaaga aaagtcatta aaacagcat gtcaaaggga aattgccttt tctggagaat    5220
tgtcccttgc agaacaccca cacatgcact tcccctaatg ctgtgggaat gctgtcagag    5280
tatttttcca ctgtgatgca ccccacaaat catgtttcct tagcttttgaa ggacagaata    5340
tttgcacgct cttttgaagc gttcagagtt tgaaggaatt ttttggatta ttttttataga    5400
gctctgagtt gactaaattc ataacttttt tttttaaccg tgattgttcc aaaacaacag    5460
cttttattca gtccatctga aaacaaatat gaaagactag ggtatcattt ctggaggaaa    5520
aaaaagttt cttgaaaata caggacaggc cgggcatggt ggctcacgcc tgtaatccca    5580
gcactttggg aggccgaggt gggtggatcc cgaggtcagg agattgagac catcctggct    5640
aacacagtga aaccccggtct ctactaaaaa tacaaaaaat tagccgggtg cggtggcggg    5700
cacctgtagc cccagctact caggaggctg aggcaggaga atggcgtgac cttaggaggc    5760
ggagcttgca gtgagccgag atcacgccac tgcactccag cctgggcgac agagcaagac    5820
tctgtcaaaa aaaagaaaa aaaaaaaag aaaatacagg acttttgggg caaaattcca    5880
cctaacctcc attaatttgt taactaagat tttactaaaa aaataaaata gtgaagttgg    5940
acctttcaga aggaacggct attaaaacat gtatttagta tgttatggga gaaactttct    6000
cctaacaggg accaatgtta aagaggctct atgtcctcac tacatagtga gttcaatatt    6060
tatattaact atgagcatcc gtggttatgg gaaaacaaac ctctcagccg agaaagtggg    6120
tccaagtaaa gtgacaatcc atgtgaatga gcctaaagtc aggttgtgtg cttcttagga    6180
tattattttt caagttgttc aggtgaaatg catgcctcaa acactgaaag tctgaaatac    6240
tagccaggag ggaaaagatg aagttcagtg gtttaaaaat cacttctcag gactttaata    6300
taatgtctta aagctgtaga gtactgtttg taagtgaaaa cacacacacc tcagaactga    6360
catacaaaga acttatttg actacgtcag gtcagttagg gagttagctt gagaagggta    6420
ctgtcaatat aacacaaagc ctgaggtgaa aaccagaaga agaaaatagc aattgcagcc    6480
tttccccacc agggagcttc cagagaagct ctcatctgct gtgggtttga gagtgactta    6540
attttgtgtt tgttgggttc tgcacaggag gagactgcca ggaggagggg tggggtcccc    6600
```

```
aagctgatga ggaaaaaagg accgtgtgat ctgagagaga gacctctggg gccaattagt   6660
ggctgacctt aggtcagatt ctaaaacaat agcttctaga gtgtagtagg aaaaggaatt   6720
atctcccatc tcccttgcta ttcactgcta tacttattgc ttctgaccag cgttttctct   6780
tctccctcaa ggaaatagga tgtaccctta agactttctc actatttacc aattcccaaa   6840
gccagcgcac agcccctga tgaggaatag aacaggagaa gtagggctcc ctccgacacc    6900
cccactcttg ttctgcattc gttcccatga tctgcacagc aatgctggct gggagattgt   6960
gccgcataca aaggactgaa cctgccagac tcaggctgct atcagagatc cgtgctcagc   7020
agggagcagg cagaaggtca agagataaa caaggaccag ggaccatccg atctatcccc    7080
aaccccagta agaggagga ggaaggaagg ctacggaggt cttcttccct ttctcctccc    7140
cttcttcctc accagcctca cttctcccac ctcagatcct ctctgaaccc cacagtggaa   7200
tccactctga ggagggaaat taggataagg agatttcaaa tagcaggagg ctgggagaga   7260
aggagagagt cggggcaggg cagaaaattg cacaccgagc aggagggagc tcagaagcct   7320
ttctcctggg ctcacatatc ctggcataaa agatgacaca tccagtcatt tttttttta    7380 agagacggac tcttgctctg tcacccaggc tggagtgcag tggcgcaatc tcggctcact   7440
gcaagctccg cctcctgggt tcatgccatt ctcctgcccc agcctccaga gtagctggga   7500
ctacaggtgc ccgccaccac acccggataa tttttttttt ttttttttgta tttttagtag   7560 agacggggtt tcaccgtgtt attcaggatg gtcttgatct cctgacctca tgatccgccc    7620
gcctcggcct cccaaagtgc tgggattaca ggcgtgagcc agtcatcttt taaatggaag    7680
gcgagggttt aagtctgaga ctgcctgtaa aatgaactgg gtggtctgaa aaagaagaat    7740
aatcccaacc agcaaaaaat gtactaagga tggtgttaat ttatttcctt ataaataaaa    7800
gatttcaatt ggatatttac aagaaaacag caacccattt cacattcttc caagtgtttc   7860
ctttcaagct gtgatttgca gaaccaatta attggctacc ataacccaac atgtcaaagc   7920
caactgcttg tctatggaca ctgaactctg tctctgtctt gagggctatt ttcacacttg   7980
ggactctatc agcagcaatc ccccagcccc gcccttgtta cttaccacca tgcccgcttc   8040
actccattgc atcatttgtg catacattgt tttcgctcag tagactcctt tgctcctttg   8100
aaagcaaagg ttacccttac tcatctcagt ataccctcta cctgcactcc ccttaaccaa    8160
gcgacccgag caactaacac aaggcttcgg acacactaga catccaataa gtgcttacta   8220
gagtatccag tcaaatgctg gaaaacaagc cccttcaaaa tttaggaagt ctgaaagaat    8280
gttaagggct tactactgag aagatgctca ataaatattg gttgatcatt ctgaagaaat    8340
ttcgtatcat ttcaatgact attgctaaaa aagacattct gaccagtgaa tcattggatc    8400
tagggtttac tttcttaggg tatttctgca catttgtgga gcccacagtt gtgcctctgg    8460
aggactctgc ctaatgttcc tgcctcagtc tcagcagcac cactgaaact cagaggcttt   8520
ggagttctgt gttagatcct gttcatgaaa aaactcaact gccttaaaaa ggatcaaaaa    8580
ccacagtatg aaaagagagt gttttatctt tttactgtct taatcggatc ttaaatattg    8640
atatgcttta aatttattta tctttggatc taacttaaac aagatgaaga ttggaagagt    8700
tttggagaga agggtgcagc attccaaatt gtgcccttag tgtactcata aggaattgtt    8760
tttggctcaa agaacggaca atgtgccatg acaatcagcc taggaaggaa gcactactta    8820
ctagtgatag ggcttggtga gactgctgat tggttttgtc agctgactta cttgaatgta    8880
gttgtcaaca actcccccaag caaagtcaca gggaaatgtc ccttctaggg gctgattttc    8940
```

```
aggtaaagga gggaagccat ttttctctat cagcttttgg tagaacaagg ctgaagactt    9000
tggcaacaac atcttgtcct ggcttagaaa gtcaacatag aagagtccac gcctgatgct    9060
gtaacctctg tgccactcga aaccatccat gagggaccat gcggtatacc cgatgacatc    9120
caccccatcc agcttgatgg ctgcaaaggg aagaggggac aagagcaaca tgacccttcg    9180
ctgggcactt gcatcatggt tcaagagcag ctgagcgttt cctacttaaa taaataaagt    9240
gtaatgcttc tcgtttggta agccaatgat ttttcttctt gacgaaagac tctaatcaaa    9300
cctatataac tctacaaata aatgccctca aaattggcct atctaatatg tttttttggat   9360
ttctgagcac cttgaaaaaa tagttcctta tttataatag atattctaca gggctggaaa    9420
gatgtcttgt accactttcc atcctagaca cccagctttg tgtctgatgc aataaataaa    9480
taaatgaagg cttaaaaagc atgatctatt tatactattt tctctagaaa acatggacat    9540
tccttttttct ttaaagtgtt ttattcaacc aaaataacaa gaactgaaaa acatgtgcag   9600
agagctagat atcctgggat ttgttttatg ttcaatttaa tctaaaaatc tagattaata    9660
actgaaagtt aagtaattac aaatattata acccagtttc tcatttacaa atgggttttt    9720
aaaaattaat tcaagttcct caagactcca aatgagaaag gtgttaaatg aatgcattct    9780
actattgcca aaatgaatgt ctccattagg atttaaaaat ataaattcac atcatttatg    9840
ttagataatc ttagagattt ttttccagaa gattttggca ggaaatgaga actttaccca    9900
caatcatacc ttttaaggtt tccatgatga acttttttgag gtaatacata tatttggcat   9960
catctctctt ggtggtccct gagacaaacc agccattttc cacaataaat atttgaggat   10020
ggttaaattc aaggtcaatc caggaaagca gttgcctcag gttgggagat tccaattggc   10080
ggaacttcat gtgagggtcc aaaagttgaa aactcaaggt gggtccaaag caaagagcaa   10140
aaagtcagc agttcctttg atgaactttt tctcagattc agtaaaatca ggcagaatag    10200
atgaaaggtt attcttcatg ctctcgggat agtcaccatc aataaatacg ggtttggcaa   10260
accaacctag tacaaagtcc agagattttt gacattcttt gatgctgtgg tcggtcattc   10320
ttcgaggatt gatccagtga gagcttaggg caatggacac ctgacctccc tgagtgggac   10380
ggaaagaagt attgtagaga tgccagactt tggcatgagc ctatgaagag aaaaaccatg   10440
gcaaatttat ctctagttgt gaggagaaat gcaatataat acttgaatcc ccaaatcaga   10500
ttatatctgt ttctcatcaa gcctaactta atgactaaca atataaaaat cagctagaac   10560
caatacatta tttcaaaggt aggtcacccc acagtgaggt gctacgggga ctagagttat   10620
ttccattggt ctttagcagt cagtggaaaa atgtagattc cttgggttga gtgtgtagtt   10680
atccacattt tgaaaagcta atgaaataaa agaatttgtt ataatagctt actatttaat   10740
tgactttgga ttatgtactt tttaatttac gggtttcatg aaaagaacca atgctacatc   10800
tgtgatcaca ccaggaattt ctaaatagga ttatatttttt tatcctgaga ctgggagttt   10860
tcaaaatgac tcaggtcgtt ggagttaatt tactgtttca tagtcatctc tcgtagctaa   10920
aattctaaca agcaatcttc tttcttccca agaagaatca gtacaataaa ttaaagaacc   10980
cactccagca tctaaccttg gcctaccctc cagaactctg ggacagttct ggtttcccac   11040
agacccaggg tgctaggtcc aagccaagag caaaaaacag caaaatacag ctgcaaggaa   11100
atcagttgtc cattgttagc atgcagccag gagtttcgta cagcagtgaa aagggctttg   11160
catccataaa accaacttta tactcccata aattcttact gacttctaat atcttatttt   11220
catttgtttc cttttttattt acaaggaaga gtgaaaatta tagggggtttt ttctccccta   11280
cttgaagtga gtttctcttt ctctttgaat tccttgattt actctcccta ttttcctaca   11340
```

```
aatacaagtg ttgtttatca gcctttattc ccctaacata tcctctttga aaactccatt    11400
caaattctct gtttgactcc atatattctc caaaatgatc atgccaattt tcattccact    11460
ccctgggcct gcagaaactc ctttgttcat taagccaaac agcctcttca acatatccta    11520
aatattcctc tcgtggttca tttcagtaca ggcatccaag aatggcctca tcaacattct    11580
tatgggttca gccaaacatt tcaatgaaat aagatagttt gtggctaact tttctttta    11640 gtttcttggt gaacatatct actatgtttc atttcactaa atgtatttt tcacgacctg    11700 aagcagctat ctatatgcta agaaggaaat agagaatcaa atgttgatca aaagaatagt    11760
ggcacttgct tatgtggtct aagaaaccag ggtcttaatc gtgccacact tctgtcagtt    11820
ttatgatgtc tcctacccct ctccatcttc ccatcacac ctccccaggc ctcccttcct    11880
cattgaaagg aaacctcatg atgttaacag ttaaacagag gctgggcatg atggctcatg    11940
cctgcagtcc cagcactttg ggaggccgaa atcccagcac attgggagaa tcccttgata    12000
ccaggagttc acaactagcc tgcgcaaaga gtgagacccc atttctacca aaaaatccaa    12060
aacttaacca gtcatggtgc tgtgtgcctg tagtcccagc tactaggaag gctgaggcag    12120
gaggatcact tgagcccagg agatggaggc ttcggtgagc catgttcaca ccactgacct    12180
ccagcccagg tgacagagaa agatatgtct cacaaaacaa aaacaaacaa acaaataaac    12240
acaacagtta aacataaaat ccattgagca gtccaggcta gtactcagca attaacctct    12300
tgagaccaaa aaccagggga cttcctaat ttgaccgcat ttgaggccta tgaacagtca    12360
tgtcctaaat ctaccaggca cctttctgta gaataagcgc tgaacaggga atgaaagagt    12420
gaaagcaaac aaagaatgca ttaatctcgg tcagttttgc aggtagctga agtcatacaa    12480
tggaattttt tataattata gaccactctt ctaaccttga ggactttaac aaggctcaga    12540
ggaggaggtt tagcaaggac atgataaatg acctgggcca taaggaaaga catatatggt    12600
ctctgatggc agataaagtt cctgctccat cactctttt tgttttgttt tgttttaaga    12660
ctgggtctca ctctgtcacc ctgactggag tgaagtgatg ggatcatggc tcactgcagc    12720
ctctacctcc caggctcaag caatcgtccc acttcaacct cccaagtaac tgggactaca    12780
ggcacctggc taatttcttt tttatttcta gtagagatta atcttgctg tgttgccctg    12840 gctggtctta aactcctggg ctcaagcgat cctcagcctc ccacctcagc ctcccaaagt    12900
gctgagatta caggcatgag ccaccgcacc tggccttcgt cactcttgag ttggccacat    12960
tccttaattt gggcaggtaa atctaacttt cctgtgcctc acaggactgt tgtgaggact    13020 aaaatgagaca attcatgtaa aactcctaat gcagagtttg caacagtagg atctccatga    13080
atgcgtatcc cttctctctc tagaggatga acaaaccaaa aggaagaata ttgcaggtgg    13140
aggaaacaac ccctgctaag gaattcagcc cacagtagcg atgtgacata ctgataaaac    13200 ttgggggtttg gagtagaaga gacttaggtt tagattccct actcctctaa ctatgaccgg    13260
tgtgagcctc acttactgct ctgtacaagt gggaatgaca tctattgtcc cgtagggaca    13320
ctgtgaggat taaatgacat aatgcaagtg agagtgtctt ttaagtagtt gattatttta    13380
cagaggaata cacttgcagc attagaaagc atttcagata tcatttggat taactgctca    13440
cctcatgcca aaaccctgtt gaaacttatt tgattactct ttacagcatc ctaacttggt    13500
ggtcatccca ggcatggcac cgtctctaag aaatcgctgc aaccccatgg acccccatac    13560
tgtgctgcat gcccctcctc tggacaccaa gagtctcaca catacttctc taatatcatt    13620
tactgcagat aatgagggc atccctcccc agaatgagct ccctgtggag ttccctcact    13680
```

```
ccctccctgg cacacggagg ccctcattgt ctgttaaact gagttgaacc agcttcacca  13740
cctcttcacg agccagttca ctcccttgc ggatggtaca tttgacagat taaatattat    13800
gaggcagagt gtgggaaggt cgctatttag gatgttgcaa caaataagga tgattaacag    13860
ggagatggtt acatatagtc ttgcaatgct ttctaattat tcctggtatg ttaatcttat    13920
aggcttgttg tcttaagatt gggatttaat aaagttattg acaaggactc agtgaagtta    13980
ttaactgtat ggccaagaac attcatctaa atactatttt taatagccaa acattgaaaa    14040
caattgaaat gtctaatatt caaatatgtt taccatgtat gaatgtttta atacatgata    14100
gtataactaa agaaatacca ttattcagga taatgcaaaa gaatatcaat taacatgtaa    14160
aaacgtttct aaaatactct gaacagaaaa aggttataaa atagcaagta gagtttagta    14220
gcactttgat ctggagggat ttataacttg ttaaaacctg ttttacagca ggattgtggg    14280
tggtataatt cacttcattt tacccatcta tatatttttt tcatttccta ccataaacat    14340
gtattgctct agagattaaa aaaataaat tcaaaaaggg aaaatggctg atagcagttg    14400
gatggcaggc ctgtttgatg gttattaaaa gtctctgctt catctcaccc tgcccacctg    14460
ttctccaact tgccctatgg tctctgcctg aaatccaagt cccaggcaca ttgaaccca     14520 cttgaagttc taagattatc tagccttcca tgctttggag gtgcagctct ctaaggtatg    14580
ttttgcctat tcccagttcc ttcactctta cacccacttt aaaactcagc ttagatgtcg    14640
ccacctccag gaagcattcc ttgacatctt ccctctccct agcatggact aaatgtctgt    14700
tctatgtgtt tctatgatgg tcctctatcc aagaccttaa ccatatatta ttgcattat     14760 ttaagtgtct ggattgtagg tgttttgaag gcattgagtc ttttatctct cagattctag    14820
caaagtctct gcaacagagc cagtattcaa taaacagatc tagaggaatg aaggctggca    14880
ctaagaacca gatcaagggg tctaggacag aagcaacatt tttctgggct gaagcaggaa    14940
aactctctca taagctactc tggttcttat tttgctttca agatcatgaa agacagaaaa    15000 cttttcaggca cataccatta aaaaataaat tagaaggaat tttatatggc aggcctctga   15060
gaataatacc atattatctc ataatgtgct aatgatccac tttggggtat aagtctctct    15120
cgtatgtgat gccctccttg cttccttctt accttccatc tagattttga acatggagt     15180 ctgaaaaaaa tctagaagaa aaatggatct ggaattcctt cctaccaact agctagtagc    15240
cccaaatttt ggaagtcgag gaaaataatt ttggaagtcg aggaaaatac tctgaattcc    15300
acagaacata tagacatttt ctctttggct aaattataag ctccctgtca tttgcctata    15360
cgtatccccc acagaaccca acaaaaagtt tcacacaaat aagctgcttt taaatggtgg    15420
gtggaaggaa acaggtgatg agcctcaggt ccactccagc tttctgcctt gggttgtgtt    15480
ctaggtatgg ctgaggcaaa tgaagcccac acaatacaca gcagtattgc tgagctgaaa    15540
aggaagaaag caatgatgag gactctgaag caggtcaacg tactggagag aagaaatcta    15600
cacaaaggaa ggacctagaa gtctgcatga gatttcccaa ggatccttgg ctgtccatgc    15660
acaggacaag atttgtgag gctcagcaaa gagaagcagc cacaggtctg ggagatgaat    15720
accaaaggtt gggtaggtct ggaaaatatt gcatttcaga atagccagag tagaaaaatg    15780
cagctgagca cttcaggcat ccagctgaaa ctcaggaagg tcattacctg agaagtaaga    15840
acaaagcagg aatagaccag ctctaacaaa gactaaagcc acatcaagta aatctggtaa    15900
tttaacttct tggcagaact aaatacaaca ccctttaaaa agagacaata ttgaccaggc    15960
ttcctataat atctcattca tagcacacag agcataataa aaatctacta gatatgtgaa    16020
aaagcaggaa aatgaaaccc ttaattaagg ggaaaaaaag aagtattcaa tatcaacaga    16080
```

-continued

```
agccaagatg tcccagacat tgggattagc agaggacttt aaaatagcta ttataaatat   16140
ttttaaggat ttcaaagaaa agatagatat aatgaacaaa tggagaataa aacacagagaa  16200
acaacaactg aagaaaacat gaaaattcta gaactgaaaa gcgaaataaa caaattttg    16260
aatgggatta acaatattaa ttctaaatgg aataataata agaataaata atgtaatccc   16320
taaaactcac aaagatatta aaaggtttct ctaaaaagcc aataaaataa gaaaatgaa    16380
ttaccaaaaa atctgatttt tccaaaagat gcagaaataa aaaacaaaaa acacatggaa   16440
caaaagaaa acaaatagca ggattgtaaa cataaaccca aacatatcaa taaatattca    16500
aatacacatg gactaaatgt tccaagtaca agacagatgc tatgaaagca gattttaggg   16560
gctgggtgca gtggctcacg cctgtaatcc cagcactttg ggaggccaag gcaggtggat   16620
cacgaggtca ggagttcaag accagcctga ccaacatggt gaaacccgt ctctactaaa    16680
aatacaggtg cctgtaatcc cagctactcg ggaggctgag acaggagaat tgcttgaacc   16740
cgggaagcag agattgcagt gagccaagat tgtgccactg cactccagcc tgggcaacag   16800
agcaagactc catctcaaaa aaaaaaaaa gaaagtagat tttagaaaag taagtttcaa    16860
ttacattctg tgtgcaagaa atatactata aatataaagt gatcatgtaa aagaaaaaga   16920
atggaaagag acatattatg caaatggaca gcattaaaaa tctggcatgg ttatattaat   16980
aacaaaatgg aggctttgaa catcactata attcacctag agctaacaga catatatatt   17040
aatagaacat gccacccacc taaaaaaatc agaatataca ttttctcaa gtgcacatga    17100
tacattttcc aggatagatc atatgttaga ccagaaaata agtcttaata aattttaaac   17160
tgttgagatc ataaaaagta ttgtttctta ccacaatgaa atgaaactag aaatcaataa   17220
caaaaggaaa actagaatat tcacaaatac gtggaaattg ttgacacact caaacaagca   17280
ataagtcaat gaagaaatca caaggtagat tagcaaaagc ttaaatgtgt atataaaaaa   17340
ctaactgaat atgtaacata ccaatactta taaattgcag caaaagcaat gctcagagga   17400
aatttttatag ctttaaatac ctacatcaaa aaaaaaaca agatatatct caataactta   17460
gtcttccacc ttaagaaaat aaaaaagaag agccaactaa actcacagct aacagaataa   17520
aggaactaat aaaaattaga atggatatac acaaaataca gagcagaaaa attatagaat   17580
caacaaaatc aaaagttggt tctttgaaaa aaatcaacaa aacagaccaa cctttagcaa   17640
gactgactag agaaaaaaag agaaagaag caaattaatg caatcataaa agaaagtggt    17700
aactgacctt ttctgtatat catttctata ataaaagga ttacaagaga acattatgaa    17760
catttggatg ccagcaaatt agataacaga gatgacctgg ccaaattccc ggaagcacac   17820
acattaccaa aagtggctaa ggaaaaaata caaaatctaa tctaggtgta aaagagattg   17880
aattagtaat caaaactttt caaactaaga aaagcccagg actagtggct ttaatagtga   17940
attgtaccaa atatttaaag aagaattaac acgactcttt tcaagctctt caaaaaatag   18000
aagaagaac actttctaac ttagccaatg tggccagcat tatcttgata ccaaagccag    18060
ataaagccac cacaagaaaa taatagttac agatcaatat cccttatgaa tatagatgca   18120
aaagaatgca accaaatact aacaaaacaa atccagcagc atattttaag aattatacag   18180
cacaatcaac tagtatttat tccaggaatg caaagatggg taaacattaa aaaaaatcgt   18240
tgtaatgcat tacatcaata gagtaaaggg ggagaaaacc catatgatta tctcaattaa   18300
cgcaggaaaa gcattttaca aaaatctgaa agtctttcat aataaaaaca ctcagaaaac   18360
tacgactaga aaggaacttc cttaatatga ttaagaaaag catttatggg ccgggcgtgg   18420
```

-continued

```
tggctcatgc ctgtaatccc agcactttgg gaggccgagg cgggcggatc atctgaggtc    18480
aggagttcga gagcagcctg accaacatcg agaaaccccg tctctactaa aaatacaaaa    18540
ttagtcggtg tggtggcagg cacctgtaat cccagctact ctggaggctg aggcaggaga    18600
atcgcttgaa cccaggaggc agaggttgtg atgagccgag atcacgccac tgcactccag    18660
cccaggcaac aagagaaact ccgtctcaaa caaaaaaaca aacaaacaaa aaattatgaa    18720
aatccacagc caacattaca gtgaaaggct gagagcttca cccctaacat caggattgaa    18780
aggaagatgc ctgctttcac tattgctctc taacattgta ctagaagttc ttgccagagc    18840
aattaggaag gaaaaaacta tccaagttag aaaagaagta aaactatccc tattcacaga    18900
taacatgatt ctacatatgg aaaatcctaa agaattcaca aaaatctatt gcaaaaaata    18960
aacgatttca gcaaaattgc aaggtacaag atcaacacac aatagtcagt tgtatttctg    19020
tacaatagca atgaacagtc caaaagaaaa attaagaaaa caattccatt tataataagt    19080
tccaaaagaa taaatatac acaggagtac atttaaacac tctcaccatt gctattaaaa    19140
ttgtactgga ggtcctagcc agtgcagtaa ggcaaataaa acataaaag gcatgttgat    19200
tgaaaaggga aaaacaaaca aacaaaaaaa caaactttgt tgttcattaa aaacatgatt    19260
gtctgtgtag aaatcctaag atttttaaaa aaacagaaaa actattaaaa cgaataagtt    19320
aatttagcaa gttggcagaa tacaatgtca atacaaaaat cagctgcatt tggccaggaa    19380
cactggctca cacccatagt cccagctact tgggaggctg aggtgagagg ctcccttcag    19440
cccaggagtt caagtctgca gtgagtgctg atcacgccac tgcactccag cctgggtgac    19500
aaagtaagcc tctgtctcaa aaaaaaaaa aaaaaaaaaa aaaaagaaa atcaattgca    19560
tttatatatg aacagaaaac aaacagaaaa taaattttaa atacaatgcc acttacagtg    19620
gtaccaaaat cgtaaaatac ttagaaaata atttaacaaa agatgtgcaa gtttgctaca    19680
attataacac attgctaaca gaaattaaag aatatgtaaa taaagaatga gataccattt    19740
tcatggattg gaagagtcaa tattgttatc agatttcccc agattgacct actgaatcaa    19800
caccatctca tccagaatcc caataaactt tttgtagaaa tgaataagtt gattctaaaa    19860
tatatacaat aagaacataa aacagctaaa ataactagaa aaaggaaaaa cacagttgaa    19920
acattcacat tacctgattt caagacttat tataaagcta taattattta atataggtg    19980
atattggcat aaggatagac aaatacatca aaggagcaga acagaaaatt ccaaaataaa    20040
cccacagcca actgatttct aacgaatgca tcaaagcaat tatgtggcaa caggaaagac    20100
gtttcaacaa atgatccttg acaactggaa aagtgtatga aaaaattaaa ccccaatctt    20160
gcataaaaat ttgagacaga tcatagatcc aaagctaaaa gctaaaacta taaaacttat    20220
agaacaaaat gtaagagaat agtctcttta tcttggagta ggaaaatact tcttagaaca    20280
cagaaagcac tatataaata tacatatatt aaaatatctc ccctcagtat gtgatttgcc    20340
tttacatttc gctaacattt gatgagcagg ttttaatttt gacgtcgtcc aatttatcag    20400
tttttgttta tgattagtat ataattgaca aaataattat atccgaaata aatacgtaag    20460
cctacctatc agtagtaaaa gaaaaataac tccccttccc accatgagca aaatatttga    20520
atagatattt cacaagagaa tcttcaccaa tgctcagtaa acacatagaa atgtcctcaa    20580
catcaacact atcaggaaaa tgcaaattaa aaccccaacg agcactcaca cccactaaga    20640
tgcctacaac taaaaatact ggcaacaggc tgggtacagt gactcacgcc tataatccca    20700
gcaatttggg aggctgaggc gggcgaatca cttgaagcca ggagttcgag accaacttgg    20760
gcaacatggt gaaaccccat ctctactaaa aatacaaaaa ttagctgggt gtggtggcac    20820
```

```
gcctctgtag tcccagctgc ttgggatgct gaggcatgaa atcccttga acctgggagg   20880
cagaggttgc agtgagccga gatcacacca ttgtatgcct gggcaacaca gtgagatgct   20940
gcctcaaaaa aaaaaaaaga ctaccaacaa attctggcaa ggacgtaaaa caacggaaat   21000
ttcatacatt gatggtggga gtataaatag taccaccact ttggaaaact atttgacagt   21060
ttcttataaa attaaagata gattttctct ataatctagc aagttcatac ctaggtattt   21120
accaagagaa atgacaacat aagcccccca aaagacttgt acaatattaa gataaaactt   21180
acaaattgat atgttcaaag atgctggccg ggcacagtgg ctcaagactg taatcccagc   21240
actttgggag gccgaggtgg gtggatcacc tgaggtcagg acttcgagac cagcctgacc   21300
aacatggtga acccccgtct ctactgaaaa tacgaaactt agccaggtgt ggtggcacat   21360
gcctgtaatc ccaggtactc gggaggctga ggcaggagaa tcgcttggac ccacgtggca   21420
gaagctgcag tgagctgaga tcgctgccac tgcactccag cctgggaac aagagcgaaa   21480
ccccatcaca attaaaaaaa aatgcttata gtagcttaaa tcgcaatagc agaaaactga   21540
aaacaacaca aatgtccatt cacaggagaa tgtataaaca gtgtggtttg tttatacaat   21600
ggaatactat tcattaatgc aaagagtgaa ctactcttct aggcagtaat atggattaat   21660
gtcaaaaaga ttgtgtagat tgaaagaact cagacacaga gtacattcac agagttgttt   21720
gattccattt acataaagtc ccaaaatcag tctgtggtga tgggaatcac aacagcggtt   21780
tcctacggag gtgagaattg attagaagtc acaagaaac tttctggggt aatgagaata   21840
ttctatatct ttacttggat atttgttaca gatatccata cacatacagg tgtatgtagt   21900
catcaaaatt catcaaattg cttataaaac atgtgcatca attttaaaga tctatagatt   21960
aataaatata taatagatta atatcttagt cattggcaaa gctattcagg tatagaaata   22020
taattaccta caatttatgt ggcaagagaa tactgatttt ctccgaaaca taaattcatc   22080
tttgaaacta ctacagtaat ctgttagtta aaaaaatata tatatttagc ttttaattgc   22140
agggatcata ttcattcaac aaatattaca ctaggcactt ttctagggga ttcaaaatat   22200
gatcctgttc ttatggagct tacattcttg ggaagaagag agataacaaa tgaaaacaaa   22260
gcagagaaag gatagaaggt aacagggatt gggatgggaa ggcagtttag acaggcaagt   22320
cttcttcaag gaagcattgt ctgaggatct gtaacagaaa aagtgaagaa tgctaaaaaa   22380
gactgggacc tgagatgggg gtgtgtggaa ggagcagaga acccggagga ttgggcagag   22440
gcggtagagg gtacgggaag ggcattccag gcagagttga gcaagtgatg agagcataga   22500
ctcagccagg ctttcctaat tctgccccct tattagctgt gggaccttgg gcaaattatc   22560
tgaagtctgt gcctctattt cctcatctgt aaagtaggga tagtaatagc acctcatggt   22620
tatatccttg tgaggattaa ctaagtcaat acatggaaag cacttagaat tgtaaatgct   22680
atggaagtgt ttcttattca agtgttgtag taatgtttga ttggtaagtt caaagatact   22740
tacagtatta ggttggtgcc aaagtaattg cagttttttgc catttaaaaa gtaatggcaa   22800
aaactgcaat tactttggca ccaacctaat agctttaatc acaatagcaa aaaaactgaa   22860
aacaacataa atgtccattt acaggagaat gtatgaacag tgtggtctgt taatacaatg   22920
gaatattact ccttgtttcc ttgtgactct taatcaattc tcaacatagg agaccactgt   22980
tgtgattccc agtacataga gtgattgtgg gactttatgt aaatggaatc aaacaactat   23040
gtaaatgtac tcattgtgtc tgggtaatga ttgataagtt tccaaaaatc agtggctact   23100
acgtggaaaa taggatctag gaggacaaaa tgggagcaag gataccagtt agacaactat   23160
```

```
tgcaatggtc caggcaaaag atcatgatgg tttggaccaa aaaagatagt aacaagtggc   23220
tagatttagg ctattattga aggcagaatc tgtagaacct gctgatgaat tggatgttac   23280
atgttgcatg tgaggagggg aagaggaatc aaggaactca agaaaacaa aaaataagga    23340 gttggggaag ggaagggatc aagttctatt taggtcacaa gtctagcttt caatgaagat   23400
gcctggtact cagctgagta tatgaagctg aagttggaga gacatggatg gtatcaccaa   23460
tcacccaaat atgtttcagg ggtaatactg aatggaccgc ttttgttat ctatcattca    23520 ttagattttt taaaaattga atggaataa ttcttaaagg attaatttaa tcctacaaat    23580
aatcttaatt aaatggactg agaccaatgg tggaagaaat gaaatgcagc ccataagcag   23640
aaaataattc aaatagctca tttatgtctt ctccctatct aagaaaaggg ccctccagat   23700
gttactttag ttctgaatta aaggtgaccg ttttcaaaaa ggtcaaagga ttgaaaaaat   23760
tttagaaggc actagagatt tatttctttt ttctttctgg caccctatta cctcaacttc   23820
aagaagagta ttgggattac attgtctgag gacttcctta aaagtcactg ctactgtgtg   23880
gtgtttacat aagcatgcca actagcctga tgttgtgct cgcagaccaa attatttctc    23940
ttatttctat cagcactatg gtttataagc tgcagttcct taagacagaa tttcaaacag   24000
cctcccacaa aacaaccacc taatagaaca cataaataat ttcccaaaaa taactatcta   24060
caactttatc cacaaaaaat agccagtagt ctctgtgtgc agttccttaa aagttgctca   24120
ggatttaacc aatgcaaggg ggctcatatc tgctttccct gacacccagt tagacgaata   24180
tgtgtgaaca ggcagcagct tggcacccct acctgctttg gacttcttag caaatcaaat   24240
aagttgcatt tctagctctg agcaccaagc cttacagtct tctacaaagt aacaggaaga   24300
ccagtagaat cgcatataaa tgtaaacagc atcacttccc agcctagctg ttttgctaca   24360
gccaggtcag tttctcatta ctcctcatcc agggctgtac ctacgttgga tgccaaccta   24420
ctagccctga agttgcattc tacttttcct tcatatccat atcctttct gccttctgtt    24480 ctggacttgc ctcttctaag aagtagttcc taatgaaccc cacttactct tagtactatc   24540
ttccccaatt atcaactgaa aattctcact tcttccaaat ttggctcaat tcccatctcc   24600
cctgtgaagt cttgtttggc tccccacgtg catttaggca ttccttttccc aatgcaccccc  24660 acccacaagc aggagtaaat aacatgcttc ttcatagttc ttcctaagtt ggtggctctt   24720
caccaagatt gtattatact cccccacaac aataaagttg aatggaaaca acttgaacat   24780
ccaataatgt ggaattattc attcatttat cctttcactc aaatatttat taagtaacta   24840
ctatgggcca tttataattc ttaaattagt tgaaacaacc taaagggcta acaatagggga  24900 ttagttaaaa taacccagga ataagacatt aaatgaaata aattattagc aacaaatgat   24960
cagtgttgat aaaataatta taatttatta attttatgag caataaatga tcaccatgga   25020
caaatatagc ttattaaatt acaaactata gttagctata gatagaccac gtacagtatt   25080
acctaatttt ggaatcatat gtacagatgt aaaataaata cacataagac aggatttaa    25140 aggatttgta cagagatagc agttatagtc tctattgagt aggacagtgg gcatttatta   25200
tgttcttctg cttctctgat tttctgactt ttatgtaacg aaatatgtat tgcttttga    25260 ataagaaaac acaaattttt taaaactgga attttcaatt ttggaaaatt ttctagttca   25320
aattatttac tatattgttt ttctaagttg atgatgtctg ctctgcttgt ttagctgttt   25380 tcatttttc ccccacagga tggatggcat agattgttcc aactaattca atcactcact   25440
tttcaatgat tacttattga tttcctaatt tcctattgtt atacctttca gtcattctga   25500
tttctgaaaa aatttgttag aaatgtttta aaaattcctg gcataccaaa attattaata   25560
```

```
ctgggaagtc tagtaactgg gatttatttt tcaccaaatg gtctagttga ttaaattatt   25620
ctccaccaaa atgtttttga ccatgttgca tttcatcaaa tcatctggaa ctctcccaaa   25680
aaaactgtaa gatccaaata attaagccaa ataattggac tatcttttct agcctgtgcc   25740
acctctgggg cagatgggtt aggggaaaag agcctttaaa atatcccccc atagtggact   25800
ctggctggtg cttagggagg gcaatggagt gtctaagcat ggaaactatg attaaaggaa   25860
cagatataag aatttaccca acgtgttgtg aaaatgatga tatcaaccta attaggctac   25920
aggattaata gtttgtggct tttagaaaat aagattacaa tagacagtat ggggccagaa   25980
tatgaaaagt tttgaatgta aagttatttg gatttgacag aataggtcac aatagattag   26040
cataaatttc tgagacagtg atgatcagtc atatgctcaa aatcatccat tgcagaatgc   26100
attagaatgt gaacagctgg atgtggaaaa ttggcaggat actgccaaaa tgcagataca   26160
attaaggttc tggacaaagg tgatgactac tgaaaagcaa acaacaggg caatctgaga    26220 gatgtttgga agtgcagaat aaaaagagca tggtgcatta gttacacatt gctcacatgc   26280
tcatgaagaa atattattcg tgagctgggt tgggctccac tgaacatgtc ttctgctctg   26340
gtctcatctg gttaatctag gatggtgttg gctgggacaa atgggacagg ttgcttctgc   26400
cccacatgtc tcatcctcca gtgtactagc ttgggcattt tctcatggca attgcagaga   26460
agcaagagac taagcagaca ctaataagca ttttctcagt gtttgccagc attatgattg   26520
ttggctaaag taagtcacat ggataaagcc agagtcaaag gagaagaagg ccagagtcaa   26580
aggataagct gaatggacac ctagagtaga ggacactgca aagttacatg acaaaaggca   26640
tggatacaat gaagagagga caacattggg gcctttaatt caatcagtct acatcacatt   26700
gtaactcact agacctaggc attaaaaaat aaagtattaa agttgacagc tcatgcatag   26760
tacacagcta gaccaaaaaa taagtcagtc tggaaaggtg aagatatttc ttgctttctg   26820
gctggatcta caggttcaaa atctttgtt gttttttta aaagtgacgg ttttgtagat     26880
ggcataattc tcatgccaag acatttattt agtcatttat tcaacaaata ttatccaaca   26940
cctattatat gttggatata taagtgctaa gaatacagaa atgagcaaaa tctcaagctt   27000
agatgtatgc cattacttac tacatactaa cactgataga aaaactgacc cccaatgttc   27060
cccaagacac aatctaaaag aagatatatg attcctatat taagacccttt tcacaagccc   27120 tcaaacatta gtatattcag tatcatagca ttttgctttc aaacctttgt taaatcttca   27180
aggtaaagtc tactgctgta tatgattgcc aaaaccttt attttactct aagaactaag    27240
tttgagatta gatctccttt agaaatcaca tgaaattatg acgtatgcta cttttgaaaa   27300
atagacaata agatcaataa taggtttatt ttattttgtt ttactgtggt aaaacataca   27360
caacttaaaa tttactcttt taattttaa gtgtacagtt tgataattgt tttagtaagc    27420
atttattatg aactatcata ctgggttcta gagatagtaa acataaataa ggtaaaacac   27480
ctgctgtcat gaaatttta ccattatcca ctgattttac aggaaatcta taaaaataaa    27540
agaatactgt tttctcttct tgtacttcaa gttgaatgac ccaagccagg ccaatgagat   27600
accttccctg agattgtttt gctggaatag agacatgtga ctgtcctata ttaggagagg   27660
aagtgaatct ggagttgctg acatgggaag agactctctg gatgataaaa agccaaactg   27720
acccaagcat aagtgcatgt gtgtatgtct gtgtgtattt ctgtgtgtgt ggtgtggtgt   27780
gtgtgtggtg tgtgtgcatg tgtgtggtat gtatgtggta tgtgtatgtg tgtgtggtgt   27840
gtgtgcatgt gtttagtgag ggagaaggag aacccaccctt gacagtaatg gttactttag   27900
```

```
tgacaaatac agttgttaac atctaaagtc cctggagttc ttcttcaatc ctttgtcctt    27960
gtcgtaaagt ccctttttctt ccttaagctt gttttagtta gggctggtca aatgcaaata    28020
tagagttcct taatacaaat ataaccaaac ttgagattct ataagaatcc gtttagttaa    28080
aagtacactg taacaaccag gcaagacaaa ggtcagggta gttttttgaaa atcatgttgt    28140 aattttggag ttttgttact taagattgtt ttatctggac ttttccaaag taggtgacaa    28200
taaagggctt atttatttgt atttaaataa aaacttcctt caaatgaaat aaaaaagatt    28260
tcataactta cactgggtaa atacatcaat aaatcagaga ttgagcttct tgcttcatta    28320
atttatctgt acagaactaa ttaacattag ttaaatcatt ctattcaata ctaaatcatg    28380
ctgcggtgaa aatcattcca agtcattgac gctaggttgt taacaaaata tccagcttgt    28440
gaccagaatc catctaaccc attaatcaca gaattattac tggagacaca gagggggttcc    28500 aattcctggt ttttgtatct ctgttttttct aatagcaaca aaatgagaac catgagggaa    28560
caggtaggga ggcataggct agatgagaaa aaagagacaa gaagataagg aactcagata    28620
agtgatgttt tccacaaggt cagcaaaagt attccatggt tcatcagtca aataggattt    28680
tttcagtaaa catctattag tataattgcc aataattcca caataccctc atgaaagagc    28740
tactctccaa tatcaacaaa actgagacaa gcagtttttc ctctataatg gtcactttta    28800
ttttctaaac attctacttc tgcctcctta tctaattctc ctgctttaag ttatcaacag    28860
cagatgccaa cagactctcc ttgagacttt ctttaacagg ctcattata gctctttgct    28920 tttgaaataa ctcaattcat cttgcagtag agaacgcttt tcacccaaag aaaaagtggc    28980
atgtgagtgt gtgaggattt ctacatcatt gaacaggata caattacagg aaaatgaaat    29040
atgctttatg gagtggtgga tagcggaaag tcatcggcct gctctttccc ccttctttcg    29100
catttgcctt tttgtggtag cagtttcgac atggtgttaa gtcaaagttt ttcataacac    29160
aaactccact tgtgaaatca acctatgagt agcctcagca attttgaaaa tcaaaataga    29220
agagattagg aaatatcaca gtgcactgcc tgtaataatg gtaagttttt tctgtgaaaa    29280
ttttgtttca atggtgtata ttcaacatgg aaaatgcctt tcttactatg ggtcaagatc    29340
aaaaaagttt ggaactcact ggtctaagtg gagggggatt ttcattccag aagtatttat    29400
tgagcatcta ttgtgtgcct ggcatgattc tagcactttg gggcacaaca gggaacaaat    29460
caaagaaaaa cccgtgccct cacggagatt ccatttttagc aggaggagcg acaaccaaca    29520
acaaacataa taaatgtaaa ttataaagaa tgttctaagg caataagtgc tatgaagaaa    29580
tagagtgagg taaggaaggc ctggggtgcc acggagagga gatacatttt atttattttt    29640
ttttttggtg gcactcacaa gagtctttat tttcctttca ttaaatgtgt tgtgattttc    29700
atcttttcat ttcatctctc acagaacaaa atccgtttgt gtccctatta ggcaagaatc    29760
cttcccatcg ctatcagttt tctacaagtt aaaaactacc cttacagaat ttaaaatgcc    29820
ctaatccatg gtaagcagca aattgaacaa aggtgcactg ccttcttcac ccccagagaa    29880
tgaggatagg agaatgggat taactaggca ggcctgcctg aggcctcagt ccagatggac    29940
accaataatc ctgcctcatt tccaagtcta ggaaaatttt ctgtacagtc tccctttgtg    30000
atcataaata atctccaaag attatatttt atcacacaga aaaacctggt ttccttgagc    30060
tttagccaga ttcatttaca aatgtttgac aagggggtgtt aattaacact ctataagcct    30120
cttggctcta cagtgtacag catattaaat tcaaagaaac agcttctgtc tggggatttc    30180
ataaggaatc tcagattgcc ttttcaaaag aaggcaatct gagggtgtgt gttcatcttt    30240
tttaaaaaaa aatgctttta tactagaggg tttgtgtttg tctgttttta tctttttaa    30300
```

```
aaaaatgatc ttattggttc ttctattcag aagctaaaaa aacaagccca ataaattcat    30360
tatcacacag tttcatccac agcacctgta aatttggtga cttcctgtct cctcgaggcc    30420
cccagaagta gtcagtcttc tccgctgctc gtaaagtggg ttgctggaag tagagaagac    30480
tagttccggg ggcctccagg agacaggaag tcaccaaatg ggggtggtta gaggtgtgcc    30540
tcctttgaga aggagcttgt gaccatagac ttaaggaaag tgaagggttg gttctgtggc    30600
tatggcggta gggcaggttg ggaagaacct tccaggcagg gagaagagta aaaaaaaata    30660
atgccccaag gcacaaatgc aagaccttca gtgtggctgg atggcgtggg gcagcggggc    30720
aggagtcaga gttgagacaa aatgtgttga aacacctttg agagtgtttc cagaacaggg    30780
aactgcagcg ttaactgctg cttgatcccc tgtgacgaaa gggaattttt taaaacggca    30840
aggcttaaac gtgaaaggaa aagataaaaa gcttttttaat caaattgtaa atgacatggt    30900
ttttcactct cccatctccc gtatttctca ctgagtagca gtaaacacag gaaacagcca    30960
cgcataagtt atactgtaac tcctcataaa ggatcctctg gcttctttca tttttcggaa    31020
atgagaattg tgaaggaaga aaaagagag atctgaattg aaatgcactt tttcaggact     31080
gctatttgag ttatcatgta atgattattt cattaagcaa atatttactc aatagacaaa    31140
ttattatgct gggcatcgtg aggggtcaaa cataggtaca tagaataatt acagtataag    31200
tctgaaagtg aaaacgccag aagatggatt tttttttttaa tgcaatggcg attcaggaga    31260
aggaaagatt ctttcttgct gagggaaatc aaggaagtct tcctgtagga ggtagtttct    31320
aaaccttata ttgaaagatg tagatcctgg agagacggaa aaaggcattc caggcagatc    31380
actgtgagct ggaaagccag tgatgctgtg gcaaaatgta ttttttacag aaaatagatg    31440
ggtatctccc atgccccatg atcttttacg atataacctg gctgttcctc ccattggcgg    31500
atctgtggac cctcccccctt gaatctgtgg gcatgtgact gctctgatag aaatgaagct    31560
acatgatatc aagaataagt gaaagaaga agaagaagaa gaaagaagt ccataccact     31620 tcctcctagt tctcttggga tgcttgccgg gagggaagct agtttccatg tacagaggct    31680
actaatctga gaccacttgt gtaagcgagg ccaacagaga tgctctggtc cacagccagg    31740
ctcaaccgcg gatcacatgt gtgagccgtc ttgcatgccc cacccccgttc aagcttcaga    31800 tgactgcgga ccagagaaaa actgcgtggg tgagccctcc cctaatcctg acccataagt    31860
ttgtaaacca aataaaatgg ttatttaaag caattaagtc tgggggaatt acgcagaaat    31920
agtaatggga acagatgtat ctgggttagt gttttttgtaa tgatgtaatg atgacactct    31980
cagatgtcaa ttaaggttaa agacgttagt ggcaagtcat gactaacatt cttgtccatt    32040
tcagatgctg atgtggacga ggatggtcta ggcatttgct agcacacccc tagatgtaac    32100
ctgtgcaatg cggaggcag cctggagtca tggaatgtac actgggaata ggggttcaga     32160
aaacctgagt tttgacccca gctctgaccc ttggtaccca caggaaagtc agctaaactc    32220
tctgggtctc tcaatgaatt tacctgcccc aaaatacaaa aaaaaggac tctagaaatt      32280 atcaagcatt atccagtggt atgggttttt taaattactt taaattaata aatgcattta    32340
tatagtttaa aatcaaatag taccaaaggc ttatcatgaa aacagtaagc atctcccccca   32400 atcccgtctc taaccctcac tcctgctccc cactggcaac cttttagctc tttcttctcg    32460
taataactat catatttcta aatactatgc tattgtgaaa tttaataatt cattaggata    32520
atgaggagtt agctctttta catgcccccat tttcttccct tattttccga aatgtctgtt    32580
cttatttaaa tcattgttag tatttacatg aagattccta tataaatgtt cattttagag    32640
```

| | |
|---|---|
| ccaaataggg cactataaca tttcccttttt ctaaacagct tttaattttc ccttgaataa | 32700 |
| ataatgacct cattattaag cgtgcagaat attctatatg tgatttttc aatgtgttag | 32760 |
| tgattctcta tcatgttttc tatgatcgta tctattctgt tgagtctact ttttcaccca | 32820 |
| gagctcttcc ttccctgcta gaagtttcca gcctccaagt ccagtttgga ctagatgctg | 32880 |
| tcaagagctg ctctcgtcct gggagtttcc tttatttctt atggattgaa accatacttt | 32940 |
| ttctatatac tatttcttcc tatgtattta ctacaatttt gctggtgcat atcttccatt | 33000 |
| agcttcttag gaaacatgac actgaaggtg aactttcaat acccttacat gtctatacat | 33060 |
| tcattgagct aggaactcag tcggctcttt aaagttaaaa gctcatgttc ttcagttctg | 33120 |
| gggcatttta ttatattatt tctttacaaa tttcctgacc tgtatttcct tattctctct | 33180 |
| ttccagaact tctattagtc tgatgttgga tctttatgaa tatcctttaa atcttttcc | 33240 |
| cttttcaaaaa tgtgttctat ttctttatca tcttgtacta cttttacagc attgctttga | 33300 |
| ccttactttt caaatatttt actaaatatt ttgtttcaac tattgtgtta ctgatgttca | 33360 |
| agaatttttt atatgttctg atggttcctg tttcagtttg tgtatgtgtt taattcctgc | 33420 |
| ataatttatt ttccctggtt tgcttttctg tttattttat tctgtttcat gttgatagct | 33480 |
| ttcctcaaat gtctttcacc agcattgtca cccttgccc ttctgttgta cctgctccct | 33540 |
| tttaagcctg ggttcctgat tattgcagga gacaagactc ctgatgtcgg gagtctgcat | 33600 |
| gccattccaa attcatcatc tccaagtgtg gtctagcaaa ataatttgca cttatgatca | 33660 |
| tgcaacagcc atcagttact ttgagagatt atagaaaata aggcgcttga agaatgaaaa | 33720 |
| ttttctcaac tttaaaaggg aagataatgt gaatttcaga aataatagac tcaagcaaaa | 33780 |
| ttaggtaatg gttaacaaaa atgcatcagt actatggaag ggaagataac taggagacaa | 33840 |
| catggattcc tagaataaat ttaccaaact tagctcagaa aatttttatt gtattatatg | 33900 |
| gtgctatgat ttgaatgctt gccctccaa aactcatgtt gaaatttaat tgccattgta | 33960 |
| atagtattaa gcgagacctt taagaggtct cactttaggc caattaggca atgaggtctc | 34020 |
| tgtcctcatc aatgaattaa tgctgttatc atagaagtgg gttcaatatc tcaggcatgg | 34080 |
| gttccttgta aaaggatgag ttcagcctcc ttttgtctct ctcttgccct ctcaccttcc | 34140 |
| accatgggag aaagcagcaa gaagtctctc accagatgcc agagacttgc ccttggactt | 34200 |
| cccagccaac agaactgtga ggaaataaat tcctttaaaa aaaaaaaaaa tagggccagg | 34260 |
| cgcggtggct cacgcctgta atcccagcac tttgggaggc cgaggtgagt ggatcacaag | 34320 |
| gtcaggagat cgagaccatc ccgactaaca cggtgaaacc ccgtctctac taaaaataca | 34380 |
| aaaaattagc caggcatggc ggcaggtgcc tgtagtccca gctactcggg aggctgaggc | 34440 |
| aggagaatgg cgtgaacctg ggaggcggag cttggagtga ccgagattg tgccactgca | 34500 |
| ctccagcctg ggcaacacag caagactccg tctcaaaaaa taaataaata aataaataaa | 34560 |
| taacctagtc tcagctactc ttatagctgt acaaaatgaa ctaagacata cagcatatct | 34620 |
| gagaacacaa tagtcatctc tgtatgtaat aatcttgaca gttgctaaac atttttgtga | 34680 |
| cattcttagg gtcaaaaaga aagtagagt gcaaataaga tagtactgtt gccacttgaa | 34740 |
| aaaatatatt ttaagagtat tcattggttc aacaaaaact tactcgttgc ttattaagta | 34800 |
| tcaaatgctg gtcaatgttt gaaacattga ttcatgggac agatcgactt gagagaaggt | 34860 |
| gactaacaat atcccacaag gtttattcat aaccctattt ctttgtaact tgttatcatc | 34920 |
| aaagggatga aaactcacaa aggcattaat ctaaactttt gaaaattctc caaaacttga | 34980 |
| atccaaaaga gctctacaga gtgtaatgct ataaatatgt gctataacta gcaaaattaa | 35040 |

```
tatttaaagt gatagaaaaa atatttatgt cttttaaaa ttaaaaatac aagtaatata   35100
tgttcatggt ttaaaatgtc agaacaactt acaagaaaaa tcacagttcc ctgtcctaca   35160
ttgccctaca attcccccag ttctctctag aggcaaccac ttttgactct taagacgttt   35220
tcttttggaa tttacatctc cacacatcca cacttcagga agtatccact gacttcctat   35280
tatgctagat aagggtttag ctctcttaca caggcaattt agttatacaa tagttttggg   35340
tttaaccgac atttggtatt gacattattc tgccaacatg aatatcattc acagctggac   35400
cttgtaatgt agtaagtaag actgttttcc ttcttatttt tgttttcttt gaagttcata   35460
attgcattgc ttttgattg gctctgtttt ctttgggact gtggctaatt cttccctcaa    35520
tttccaatag cctctcagca gaaacttccc cagggaagtc acatgagcct ccaatatttt   35580
gggggacac acttctggaa tctcccccat tctgcactgg ctgatcttag tctgctgcac    35640
atctgacatc atgggtctac agttcatcat ccttttcctg ggttagacct gccctttcat   35700
agatcccatg tcttcctcct tgtcttcctc atgttatgtg gcggttaccc tccaataact   35760
tcctgagaaa gggtttatgg aagatttatt ttttgggact ttgactctca tgaatgattg   35820
acagtttaga taagtatcaa attctaggct ggaaataatt ttcattccct tctctgaagg   35880
gcactcctca ctagtctttg tgatggccaa gaaatgcact gctcagtgtt cctgctataa   35940
ggagcacagt tgactgaggc catcagttgc tacccctttg aatctgccat tgcagttgat   36000
cctaagatca tgattctcat cggctactcc cagatgacta aacatggcag gggaactaat   36060
gcaggcccat ttcagcaaga tgtggactcc gccaatgggc aacattggct caaggcgtcc   36120
ccatcagcct atgcctgggt tgttctgaga cccacagtgc caactgaaac tcttcccagc   36180
ccatccttct ccctgcccac tctccttcat agttgttgga cacacatcat gatccaaagg   36240
ttcaatgcct cccctagctc cttcccctttt atccttcaca attctttccc caataaattt   36300
cttgtacatc taatcctatc ttgacattta cttctttcag gactcaaact aacacaagag   36360
gggttgggga accagctcat tcactttctg gaaagcaaag agaatgccat tctgagtgtt   36420
gtgtagggc agatagtccc cttgcacaaa tggtgcttca attgctaaat atttcaacag    36480
cagtaacctg ggaaatatcc tggtggagaa tgtcattgta ggtgcaatga tttaggcatt   36540
ccctgcctac aaggagatgg aattgaatgc tttctgatat attgtattga gactctacag   36600
agagctaatg agaaactgag ggccaataac aaacagttaa aggctcaata taagagccac   36660
agccttctct cctacagtgg aagagtagag aaacttagca gcaggcctag gacctgatag   36720
acttgcagag atttagggat gtttaaatgc tcagccaagg cagatcagtt atgccaaggt   36780
caaggccccg gttggggaaa cctgggaata tttggagctt acagaggtgg cccattcttc   36840
cctagtaaga gatagcactt ctttatgctg aagaggcctc gtccctaaaa agcaacaggt   36900
gcacccctca ggagctgacc cggcactaac gaggattaaa tcctagtata acccacctgg   36960
agacagctgg gcctgataga aagaaaaga tactatatcc caacattgct tcaagattga    37020
gcatgcactg caaatcctga ggagtagcgc tggggtcctt gaccaaggaa ctggaactta   37080
acacaggaca agaaataatt cattatctag ggaacacttt ctccggaagt atgttttcac   37140
gatccagcaa ggaccccagg agacgcggta agttgctgc tagggtggct ctgagaagcc    37200
tgtaaaaagg gatgcccaat gctgagcagg cggaaatgcc tgacattgtt gccctaacag   37260
ctgataaaag aatcaagaag cagagagaag ctggcatgca agaaccagta tattatgtga   37320
ggtcaaacaa cccaccagag gacagtgttt cccagaagtc ccaagtaggg agaaagagca   37380
```

```
ttcactgcac cctcaggaat atgctcatgg gggtgccaat ctcactgaga cattcagtgg   37440
gggcaccgct ctccaggcca gggctgctgg tagcagaggt gtcacagagc tgggcttgtt   37500
gccacccacg gggatggtca gaagttgaaa ttacagaggc cagatagtga gtggtgctta   37560
actgccagaa gccagggagt tataaagatg gttcatagag catggctaca taaaaagtga   37620
tgacccttg tacagttccc cgacttagcc aattttccaa gctataattc actgactgaa    37680
gaggtgccta ggtccctagg agccaggacc ctgcaataac acagaggtat gaccccccca   37740
ccccattctt cccattcaat atgaaaatgc atgtcctcca gctataggaa attttctgga   37800
attacttcat tgtttccttt ccttttacgt cagttaccta ttgctgtgaa atagaccgcc   37860
cccaatttgg agaattgaac taataagaat ttatttttt cctcttgctt ctgtgagtta    37920
atggggtttg gctgggcaaa tccagtcttg agtatgcagc cagggaaggg acactgcaag   37980
ggaaaaggca ctggcaggga gaatgaagga cagaggctag agagagccca gtcccaccca   38040
tgaactatac agtaatcttt acatactttt tacatactta ttcatacaga agagacataa   38100
catgggctgc cttttaataa tcatacatca acattttaat aaccaattag tattccactg   38160
tataagcgta ccaacattcc tctaacggat taccttaaca catttagctg atgtccagtt   38220
ttaaagaata aaccaccatc agcggtaaac ttcctcttat ctttgcacat tggagatgaa   38280
atttaataag attgaaagtt tgaaaataaa ctaccaaaga gatgacaggg atgtttggct   38340
tcacagcaat tcacaagctg gggggaaaaa acctgagagg ttttagctga ctgcaaacta   38400
atttgagtcc gcggtaaggt gacagccaaa attgttaatg caatcttggg cggcatgaac   38460
aaaattcagt gtctaacaag aaatgtaatc gctgaagcct actctgaaca cctggggcac   38520
tgcttggttc tgcacagcaa atgttaagag aggccttgga aattcccagg ctttcttctt   38580
cagctcctca tcctttccca cctgacgctt cagccattca aaagacctca tgctgtggtg   38640
ggaatggcca cactgtctca cctgtactga ctttgcaagg gatgtttcct agaaaggcac   38700
aatgcccttc tcactttgtg tgcccagcaa gccaagccca gcagcagggc ccactaccta   38760
tttttgtaaa taaagttta ttgaaacaca gctgtgccca ttcattaaca cattgcccat    38820
ggctgcattc atgctgcaac cacagaactg tgtaatagtt gcaacagaca ctgtaggatc   38880
tgcaaagtcc aaaacttagc cctctacaga aaaagattgc cagcctctga tcttacaagt   38940
attgctttcc ctgactgctc ccgtactacc tccccaaaac gctaacctat ctctcctttc   39000
ttgaaatagg ttcctaagca agtacttatt tctcttaagg catttataca ttttactgta   39060
attatttgac aattacctct cccctactaa tctgtgacat gagggcagga atcttacctt   39120
atccctcttt tctgacagtg cagaaacttg gaaatggcag ctctggccag gaaggagtaa   39180
aaaggccccc taggttagga gcccctcac agcccatgcc agatagatag gagaaaactg    39240
aatctctcgt gcagcccaag cagtatacct ttggtgagca atgtccacgc tgagttgtgt   39300
ttgactgcag acaatttctg ggagaatgta gttgagtcgg gagtgagacg cccctaccac   39360
tgtccccgca cctgtgcagg gctggcataa aggcctgatg ggaacaaggg gacacaggtc   39420
tctatggaag aacttgggac accgaagaga ggaaaaggca gaggaaagag gaccacatga   39480
tgagaaatca aagagaagag aggacaggcg gggaagagca gcatcccaa gaggctctga    39540
cagggcaacg ggcttgcctc ccatgccccc atcctcccct gcagctttgc agccgtcctc   39600
tggacccctca cgaaaagagc cctacaaata tgcctccttt gggagccagg gctctggact   39660
ctctacaggg tccggcacag ggagaactcc aaccactcgt cctcagtcct ctgcacccat   39720
cagcaggaca atggtgatgg atgatgagac agaggcaggt cccacagaca accctaaacc   39780
```

```
ctccccgctg gggagatagg tcgactttcc cctctcctct cctccacctt atcctgaaac    39840
gtcagaagac agagccacct gttcaaaggt tacattcata ttctcagaat tcaacattgc    39900
acctgcctgc cacagggtaa gctctcaaga aatgttcctg actaaatgtc cagtcacctc    39960
catgtcttct tggagcagac attagcatga aggagaaaat tctaggaaga acaaaacgta    40020
ctggtctttt caaatatgtg aaagatgtct tttcaaatat gtgaaagatg tcttgtcaaa    40080
aagtgacttg ctttattctt tgagatttag gaaggcaaag agacagtcac ggaggagtcc    40140
tgtgcagcag caggttcaat atgaaagaga aaatcaaggg ggcaacttga gtggaactga    40200
gttcctcctg cttcaaaggg tcaagcaaaa gctagctgac cccaggagag ccactgtaag    40260
gagttcgtcc tggagagaag tgtaacctgg gattttccaa attccttctg attctaacat    40320
tctaattatc aaataaaatg cacttataga tatggaaata acatttgctt aaccattata    40380
tttaaaatta atgtacatca ctgctttcag tttgagtatt ttatcaagct ataatgatac    40440
cggttcatgg atgacgtgac atctgtactt caaacaaaaa atgttaataa aaaaatctat    40500
tgaaactggg gccacaaaag ttcaatcaat atttatcttt ggtttagtca atatataaag    40560
ttatatcagt cataaacttt agtatgtatc tttttaccac caagctggat ccagaaagat    40620
atttgataat gtgttttatg taaaaatacg ttatttcaaa aatgatttga tagttttttgg   40680 tcaaatgcta ttgaaataat ttcaagaag aggcaaatta agtagttaag tgaggctacc     40740
atgtctaatg catttgtatg attccttcta aacagctcaa gaggaccatt tctcaagtat    40800
tttgctatta ttactattat tattaatgat aaatttatag ctcacttttg tagagctttt    40860
tgtatttttt caaaacacgt tgacatatat aaggtgcttt taattctcac aatatgcctg    40920
ggagttaggc aatgtggtag agcctgctgg ttatcctaaa tgatctgttc ccatctgatt    40980
tcaacttaat agaatcattc actgagcacc cggctcctca ggggacaatt atttgcagac    41040
tccttttgac catgtgactg agttctgccc aagggacagt gataggtgca gcttccaggt    41100
caggcacttg agaggccacc ttttccctct tcctctcttt tcctgtccac tggatgaaat    41160
tgggatatta tgtgctctgg aaatcaacaa aggtcacata acgtatctgc ctaggaaaat    41220
ctttactgtt cttcctcact cttttaaaact ccttcccaga tattgtgtga gagcagactg   41280
caagcgcaat attccattta caagaaagaa tatggacacg ttgaaaccag aaatatgtat    41340
tttacctctc cacttatgcc tttattaaaa attgtatttc tttcctctgt gccaagcact    41400
gagataagca ctacaaattt tgaaataaat atgataggta gtctgtgctc ttaagagagc    41460
cacaactgag taaatgatcc attctacctg tggttattgc agaatgaaaa tatttgagtc    41520
aagtctctga agggtaagta agagtttacc ccaagataaa gaggggaaaa aggcatcctt    41580
caggttatct tcatactcag aatacatcaa aatagagcat ataaaagtca cattctgctt    41640
atctgtttaa atatagattt caagtataac tttgcatttc tggagaaaat gtggatctga    41700
gacaattcaa taagctgtgt gttttttactc acctattatt acttgtcctc ccagtaagca   41760
tgtattctat tctcctcctc cacctaaaat ttcctttatg cctcaaaaag acaacattca    41820
ttgaaagaaa gacaactttt gcacaaatta attataataa aattctagtt tagagcaatg    41880
atatttttga gaatataaga taattcagaa ggcttctatg tgcaaaagcc gtgattgcta    41940
catattcagc tggcacagtt aattgttcat tcattttgca cctgagaagg tgcattgaca    42000
ttacttgaat gcatagttta catttttcctt cttttcttca actcaaaata attggcattg    42060
ttaaaacact gctatgattt tgaaatgatt tgattaattc ttttcctatt ttaaaatttt    42120
```

```
ttcttggact tgactgtaac cttcaaaaaa caatgtgttc aaaaaggagt gattcaagct    42180
gtttgggaga tattttaact atttctgact aaatgcacta ttgaattcag tagtattcta    42240
aaatttatat taactttcaa tccagttgat tattctagtt atgtacaaaa tacatttttt    42300
tgagatggag tttcgctctt gttgctcagg atggagtgca atggtgcgat ctcagctcac    42360
tacaacctct gcctcccatg ttcaaacgat tctcctgcct cagcctccca agtagctggg    42420
attacaggca cctgccacca cgtctggtga attttccata tttttagtag agacggggtt    42480
tcaccatgtt ggccaggctg ttctcaaact cctgatctca ggtgatccac ccgcctcagc    42540
ctcccaaagt gctgggatta caggtgtgag ccactgcgcc cggccccaaa tacattttaa    42600
tgaaagaaaa acttgtaaag tatttctcaa aagtgcatag tatatgtaat ttgagcatat    42660
atacagtaga caaatcgctc atactaatta cttggggaat aaaaattcaa tcagctaaca    42720
aagccccttc aatatatac tcctaaagct ggccaggaga ctttaccacc tgcccttatt    42780
ctgaaaactt cttcataatg ctgcatggtg actacagata gcttttaact ggacattttc    42840
acaatggaat catacatttg atgatgaacc ttaaattttc actgcagatg tcagagtctg    42900
ccacgttatg tttacctatt tttccttatc agattaggat ttggtagtct ctgttccatt    42960
ggaaagtggc tagaaagact gacaaggaga gaaaattcta gtagcatgag tttataaagg    43020
tgaaatcagg ctattcggta aaccagaagc caccttctga gcaccaaggg agggcaagat    43080
gccattttca gagatacaga tgaagggaac aggattaccc cagatagcga aggggtaaaa    43140
tggagacaaa tggttaaata aagggaagag cgcgggagga ggcatctgag caaagcgaag    43200
tcctgtgcag gatgccatag aaggaagaga tggcattcag gcatgggcc caagggagcg    43260 tgttagctgg ctccagaaga acaggtggga tttgaaaaag caaggactct gtcttgtcca    43320
cacataatgt caccctgtag agcatccatc atggcacact gcaggggca aggcagaaat    43380 aagaaccca gcagtgaggc tgttcccatt acccaggcaa ggttggatgg tgtcttgcac    43440
ctccatcgta gtcatagata aggggagaag tggtttgatt ctggacacat cctggaggta    43500
ggtagagctg caggatttgt tgatggatta gaaacaagac atgaaaaagg ggagtagtta    43560
agattcgggg tccaacaact ggaagagtaa aaagtcatca taatagagaa ggggaagcag    43620
gggtttggtt tgggatgtgt tcgatgtgac atgcccatta gacatccacg tggagaaggc    43680
ggttgtctat gccagtctga tgctcgggga aacctgggtg gagactcaaa atctccagtc    43740
atcgggatgc agcagtattc aaagcaatgg cctggagtga atctagacag agccctgagc    43800
cctccactat ttacaggcaa ggtgaggagg aacaagcaaa ggagactaag agggaatcgc    43860
cagggagctg agaggagaag caagggagag ccagggcctg aaatccaagt tgaggaagga    43920
ttcaagggac aagaagtgat ggcttcaaca acattgcag acagatgggc tgagacctgc    43980
acactgatgc taatgctcaa caatgcccag attaatatct cctagcccta cttccttacg    44040
tgaaagaagt ctttttcaca ggttccttgc acaaatgttt gcaagaatct caggcggtga    44100
ggggagttga aggtgggaaa tgggaacacg tgtatttcca acttgattct aatcctctta    44160
gaacccatat acagaacaaa gactcagagg cactgctggg gctgaactcc ccaactacag    44220
tccctagtgc tgatttcagg ggacattaag aactttgttt caagagctgt gaaggctgag    44280
cagttggtct tcaagtccga gagaaaaggt gcatcctcct ggattacact caaatgagca    44340
aagcagcctg agctccaagc tctttgtagg agacctctct ctctctgtcc ctcctcccct    44400
ctcccctctt ctccttctct tctgtctcct ctctctctct ctctctctct ctcacacaca    44460
cacacacaca cacacaccat ttttgccaag gctcactcca gtatgaggaa cccacaaaga    44520
```

```
acaccaagac ctccattctg agcagggcct ccattatttg tcctgctgtt tgtttgttct    44580
gcctcctgtc ctccaggcca tcaatgattc ttgactctct aggaggggtc aagcttccca    44640
tcatcccagg ggatctcctt agcccatttg taagttagtg gaaacacaga gggagtgagg    44700
gaagggtgct agccagtctt tatccttcac caacatcaga tcccggaaca caactggccc    44760
ctatatctgt acagcagcaa tatctaagcc ccagctaaaa tgcccttttta tcaaaatctg    44820
cagaatgttt tatctttttc aggtaagctc aaattttttct attctcgctt cccccaaccc    44880
ctatatacac accgagaaag gtcattgaaa acagaatgaa agtatctcat acaacaaaat    44940
taattcaaga tactttcttt gacaatggga actcgcttct aaataagata caagaatgac    45000
taaacaccaa accaaaagaa atgtgaaagc aaaattaata ctttacacca actaacagtt    45060
tgtttgcaac atcagcaaat ggagcattca cctgttacta atttccctaa atacaaagtc    45120
cactgcattt ctaggaagga tggttagtgt ttggcaaatt ttttgtgtaa gcattgaaaa    45180
atataactga gaagttaatc agagggccat gagtgggcaa aaagatctaa aacatgttga    45240
ttatttaaaa caccagagca ccagagagca cgcaagtctt tatcttataa taaaatgatc    45300
ctataagtca ctataataac aattgactac tttgtatatg caagtttatc ctagggactc    45360
taaaaataga acttgtagga tttaaatcta aagtaaagat tttatgggca tgatctatta    45420
gatcctccag ctgatccatt tatttgcttc cagtatgaac tgataacttg cttatgtttt    45480
cttcaaaaag tgagaccatt cttcccatag tttttctatc accagccata cactggtggt    45540
ctttagagtt tttcagatcc ataaaaggat tgaaaaagta taagaatcac cgctctaaaa    45600
catccttatg aaaagacata cataagtatg aaatcacaaa aatcacaatg tgtttccaaa    45660
caaatccaac attcttttat ggccagtagc agcaaacagg ttttgtggaa ctgacataaa    45720
atctaattta gccattatta caacattacc agcagctcag agcactaagt cacctcaata    45780
acccagtact gctctgccca tattatctat ggctttaatt aaaagtgttt agaaatggtt    45840
ttagtactga ctttgttcag aatatgtggc tgaattctaa atttaaaaat aagtcttcca    45900
gtaggcccac aagtgatcag aattgggtac caaaagttgt acatttaaac acttttatta    45960
aaatgtttat acatgtacat aaaatatttt attgtgatac aaaactctgt acaaagtgta    46020
ctaacaactg acatgattat aaatgaatcc ccaaaacaat ggtgcctaaa tttgaacact    46080
aaggagaaaa aaggaggaag aaatacttga gacaacttta ccatggcata gcaatatttc    46140
ctgctgtcaa aattaataaa atattttgca caagggtgtt acaattaatt ttatcaggct    46200
aacaatgtca taagtgagga acccttcaa ctgtagagag cactgtggaa atatagatgt    46260
ggtagaacaa tctatatcac cctgcagttg tttctgtgtt tctatgacta gctttgtttg    46320
agattgtata aagcggtctt cacaccccgg tgaataagat tggtggatgc agttccctgc    46380
cctgccgcag aagggacctc caaacacagt ttaaatctga ctctccggga gttgtgtttt    46440
gacactttca caacagtgtg aacttgtgcc acaagcaaga cagatcttat tggattaaca    46500
ctgaactcgt gacagctcca gagagtaatg ctatctgtgc ggcttaagaa caaacgtgtt    46560
tctttcatcc accctgctca ttctcttcct gcagttactc ctagcaaatc ctccccgccc    46620
tcacctctag gaattcctct acacccagag aaaggagttt ctttcctcac tgcggaaacc    46680
tatcaccgct tcctttccac agatggactc caaggggcac tcactcgtgt gcccactaag    46740
ggatttctct cctaattcca cgccttccaa gggaagtcag aactgctcag tttccccgg    46800
tgaccacata cacgtgtcca agtgaagcct cgtctggggg agactcagtt cccacacttc    46860
```

| | |
|---|---|
| ccctggccc ctgtggaggc cctctgtctc ccctgcgtgg ccctccgcct ggcccctcgc | 46920 |
| actcaccagg aggaggttgt gcgccaccag gtacccgagc cgcgggctgc ccggatgcc | 46980 |
| ggggccagg cgcccggtgg cgtagccgtg ccaggccacc acgtagggt tgtcgatggt | 47040 |
| gatccagtac ttgacctgac cgccgaagtg gcggaagcag agctccgcgt aatccctgaa | 47100 |
| gtggtcggcc agggcgcggt tggcccagcc gccgtaggcg tcctgcaggc gctggggcag | 47160 |
| gtcccagtgg tacagggtga ccacgggctg cacgcccagc tcccgcagcc gctccagcag | 47220 |
| gcgccggtag tagcgcagcc cctcgcggtt ggggacgccc gcgctgccat tggggagcac | 47280 |
| tcgcgcccac gagatggaga gcggtagtg agtgaccccg agctcgcgca gcgcctccgt | 47340 |
| gtcgcggaag acgttgttgt agctgtcgct ggctacgtcc ccggtggcgg gctgcagcgg | 47400 |
| cgacggggcg cccaacggca gactggcgtt ccgggagtct cccggggtg ccaggggtg | 47460 |
| gtgggtgaac gtatcccaga tggacgcacc cttgccgtgc tgctgccagc cgccctcggt | 47520 |
| ctggtaggcg gcgctgccca cggcccgag gaagccgtcg ggaaggtgc cctggaagag | 47580 |
| gcccgcggcc tcggggcag gaggccgcga gaaacgggcc caggtctgcg cgccgtcgcc | 47640 |
| cggctccgca cgcaggcggc ggccgcccag gcccagcagc accagcagca gcgacagcga | 47700 |
| cggcggcggc ggccgcgggc ggcgcggcgg ggcgctggcg ggcat | 47745 |

<210> SEQ ID NO 27
<211> LENGTH: 51745
<212> TYPE: DNA
<213> ORGANISM: Homo sapiens

<400> SEQUENCE: 27

| | |
|---|---|
| acaatatatt gtattttga aaatctcaga gtagattta agtattcttc tttttctttc | 60 |
| ttttcttctt ttctttttctt ttttctttt tgaaacagac tcttgctctg ttgccaaagc | 120 |
| tggagtacag tggtgtgatc tcagctcact gcaacctccg cctcccgggt tcaagtgatt | 180 |
| ctcctgcctc agcctcctga gtagctggga ttacaggtgc ctgccaccat gttggtgaat | 240 |
| ttttgtatttt ttagtagaga caggagtttc accatgttgg ccaggctggt ctcgaactcc | 300 |
| tgaccttagg tggtccacct gcctcggcct ctcaaagtgc tgggattaca ggtgtgagcc | 360 |
| accacgcccg gccagatttt aagtcttctt accacaaaaa aaataagtat gtgaggtaat | 420 |
| acatcgtttt attagctcaa tttagccact ctacaaatgt gtatatattt taaaataaca | 480 |
| tgctgtacat gaaaatatat ataattttttt gtctgttaaa aattaattaa ttaattaatt | 540 |
| ttaaaagag gagggcaggg aatacttgtg tattttgtta actggacaaa tgaaactcta | 600 |
| ctttcatttg ctcattaaac aaatacttgt tttgtgctca gcatgattct aggcactggg | 660 |
| actactgcat tttggtccat tacttccttg cgcacaaaaa ccctttctttt tcaccacgaa | 720 |
| tacactatga acatgttttt ttcttcagtg ttggcatctc ttgattcctt ccctccaggt | 780 |
| ctttgtgcga gttttactct ttaaacccca gatattgtca tattttctc tgttaaactt | 840 |
| ttccaaacaa ctcaaaatag ggtaatttct tcttcttctg aatttctctg acaattattc | 900 |
| tatgggtcat ttattaacac agcataatca acaacttat ttattttcat ctttcttgat | 960 |
| cctttcttca gttggatgtt gtctttgagg gcagaggtt tcctctatgt tttgaagtct | 1020 |
| ccacacagct catcgttgcc ttgcccgtag ttgtagctca gtgaaataaa aatatgtccg | 1080 |
| tagaaggtga tgtctgtgac tggtgagccg agagcttgtg gggttggtgt tgtatttgag | 1140 |
| tgcatgtgaa tcagtgcatc tcctgctcca ttggtgttaa aaggctccca tcgtcctggg | 1200 |
| aacacaatag gaaagagaac aggtgggaag gcactggatg aaggaatgtg gagaatggag | 1260 |

-continued

```
gaaaagttga tcagattgtt gacaactttc agtgttgaaa ttgtcaccaa aatcaaagtc    1320
agtaaataaa tttacaatgt ccttttcttc aatgcatcaa taacttcacc ttcctgttca    1380
aagcacagca agtaattaat ctcttatttg catttgaaac ccaagtttca gatgtttgaa    1440
ggtggttgta aaaaataaaa accaaaataa agccaaaata aataagcagc agcactaggc    1500
cgggcacagt gtctcacacc tgtaatccca gcattttagg agaccgaggt gggtggatca    1560
caggagatca ggagtttgag accagcctgg tcagcatggt gaaaccctgt ctctactaaa    1620
aatacaaaaa ttagccaggt gtggtggtgt gcccttataa tcccagctac tgggggggctg   1680
agacaggaga attgcttgaa cctgggaggc agaggttgca gtgagcagag accatgccac    1740
tgcactccag cctgggcgac agagtgagac tccgtctcac acttgtggaa cccagaactt    1800
agtaaccatg aacagaacct aataaacag aaagttctgg aaataaagtt taatcatcat     1860
gcaatcttta tcactgggtt aaatgaacaa tcatctggga acatgtcttg gaatgcttaa    1920
agctttgaga tgcatgtgcc tatgtggcag acaaatttca aatgtgaaac gtttagttaa    1980
cttggtcttg cttttaatc actgctttaa aatttaaaaa atgctgctgg tcaagtaaaa      2040
atagcaatag ataaaatctg ccctgagcaa acagaccata catcaataaa tgaatactta    2100
gcttaagcga ttttccatga gacccatgaa gcatttctaa ttgaaactta acaagctaca    2160
acccaacaga cactccaatc ttcacttcta gaagggaaat gtgatactcc atgtagacgt    2220
agcttttaa atttagctgg aagacagcgt gacagtgaag ttgtgtgctg taattttta      2280
aaattgctga agtgtcatgg tttgctattt cgtatttatt gaaaaaatgt aaatgctata    2340
tttaacagaa tggcagtaac tctgtttcaa tctgaagact taatcttact aatcatggta    2400
atatatgctg gctggagttg ggaatatttc ataaaatact ggaataaatt tgtgcttata    2460
tttcagggga attaataaaa gcaccttcat ctgcaacatt taaaatgtta ttgcctttaa    2520
atttgtatta ataatgcag ggaggataga tcactggggg agaatggatg cacctctgtg     2580
aggatcttgg tcattcaaca cacgtgtacg ggtgaggaaa ctaaggcacg acttactggg    2640
tagggaggta gggatattag caagatcctt cacttgtctg ggctttctgt cttttgagtca   2700
cctttgcgca gttttttcact ggacttcaca agcctctgag gcggcagggc agacaggaca   2760
tccttatttt atagaggaaa aaacttaggc ttacagaggt ttcctgcccc aaatcacaaa    2820
ggtggagcct agaccttctc agtctccacc aactgtattt cggttagcca caatcctatc    2880
tacccacatc caaatggaca ccgtggctct gcaacttctg tcaaagggc tcttggcaa      2940
caggaaaaac gtcatggctc cattgtattg tagaggatgg gaatgggtgt tccggctaaa    3000
ttctccctcc cctttccctc cacagctcag atggcaaatg tgcgacccag ggacctcccg    3060
ctccagcaga cctgtgcgca caactttgca cagattacct gctaagtcag agccgaaagg    3120
taacacagat gccaaaggat aataaaggtg aatgagattt actcaaaatt ggaaacttgg    3180
tgtttggttt ttcaggagaa caatcaacga ctgtgatttg aagttcacca gggtattctg    3240
agagatctaa tcaaagatag agtgctggtt tgaaattatt aaaaggtaac agtaaaaggg    3300
agagcaaaac cccagtccca acgcaaccca taaatctact ttgtcttcct cgaaagaggg    3360
gcgcgggtgg gcgcgtctcc ccgcgagcat ctcacctaag ggggaatccc tttcagcgca    3420
cggcgaagtt ccccctcggc tgtcccacct ggcagtccct ctaggatttc ggccagtccc    3480
taattggctc cagcaatgtc cagccggagc ttctttgggc ctccgagtgg gagaaaagtg    3540
agagcaggtg cttccccagc ggcgcgctcc gctagggccc ggcaggatcc cgcccccaag    3600
```

```
tcggggaaag ttggtcggcg cctttctcc  ccgacgaagc cgctccaggg ctgctctcag   3660
aggacgcgcg gcaggcaaag agaatgaacc tgagcgtcca cgaaacgtcc tgcacggctc   3720
ccgggagctg ggaggaacag gtgcctttct ccgacgtccg cgggcgacgc ctgccgcacc   3780
ttgcccgctg ccgcgcccct cccgggcacc cctcgccctc ggcgcccctg ccccacccc   3840
cagtgccagg gcggaggcag tcccggctcg caggtaatta ttgccagcgg agcccgccgg   3900
ggagcggggg tgggcgcgcc ggcggtgggc gggcgggcgc ggcggggcgc gggcataaag   3960
gggcgcggcg cggggccccg gagcctggct cccgcgcagc atgcccgcca gcgccccgcc   4020
gcgccgcccg cggccgccgc cgccgtcgct gtcgctgctg ctggtgctgc tgggcctggg   4080
cggccgccgc ctgcgtgcgg agccgggcga cggcgcgcag acctgggccc gtttctcgcg   4140
gcctcctgcc cccgaggccg cgggcctctt ccagggcacc ttccccgacg gcttcctctg   4200
ggccgtgggc agcgccgcct accagaccga gggcggctgg cagcagcacg gcaagggtgc   4260
gtccatctgg gatacgttca cccaccaccc cctggcaccc cgggagact cccggaacgc    4320
cagtctgccg ttgggcgccc cgtcgccgct gcagcccgcc accggggacg tagccagcga   4380
cagctacaac aacgtcttcc gacacggaa  ggcgctgcgc gagctcgggg tcactcacta   4440
ccgcttctcc atctcgtggg cgcgagtgct ccccaatggc agcgcgggcg tccccaaccg   4500
cgaggggctg cgctactacc ggcgcctgct ggagcggctg cgggagctgg gcgtgcagcc   4560
cgtggtcacc ctgtaccact gggacctgcc ccagcgcctg caggacgcct acggcggctg   4620
ggccaaccgc gccctggccg accacttcag ggattacgcg gagctctgct ccgccactt   4680
cggcggtcag gtcaagtact ggatcaccat cgacaacccc tacgtggtgg cctggcacgg   4740
ctacgccacc gggcgcctgg ccccggcat ccggggcagc ccgcggctcg ggtacctggt    4800
ggcgcacaac ctcctcctgg tgagtgcgag gggccaggcg gagggccacg caggggagac   4860
agagggcctc cacaggggcc aggggaagt  gtgggaactg agtctccccc agacgaggct   4920
tcacttggac acgtgtatgt ggtcaccggg ggaaactgag cagttctgac ttcccttgga   4980
aggcgtggaa ttaggagaga aatcccttag tgggcacacg agtgagtgcc ccttggagtc   5040
catctgtgga aaggaagcgg tgataggttt ccgcagtgag gaaagaaact cctttctctg   5100
ggtgtagagg aattcctaga ggtgagggcg gggaggattt gctaggagta actgcaggaa   5160
gagaatgagc agggtggatg aaagaaacac gtttgttctt aagccgcaca gatagcatta   5220
ctctctggag ctgtcacgag ttcagtgtta atccaataag atctgtcttg cttgtggcac   5280
aagttcacac tgttgtgaaa gtgtcaaaac acaactcccg gagagtcaga tttaaactgt   5340
gtttggaggt cccttctgcg gcagggcagg gaactgcatc caccaatctt attcaccggg   5400
gtgtgaagac cgctttatac aatctcaaac aaagctagtc atagaaacac agaaacaact   5460
gcagggtgat atagattgtt ctaccacatc tatatttcca cagtgctctc tacagttgaa   5520
agggttcctc acttatgaca ttgttagcct gataaaatta attgtaacac ccttgtgcaa   5580
aatatttat  taatttgac  agcaggaaat attgctatgc catggtaaag ttgtctcaag   5640
tatttcttcc tccttttttc tccttagtgt tcaaatttag gcaccattgt tttggggatt   5700
catttataat catgtcagtt gttagtacac tttgtacaga gttttgtatc acaataaat    5760
attttatgta catgtataaa cattttaata aaagtgttta aatgtacaac ttttggtacc   5820
caattctgat cacttgtggg cctactggaa gacttatttt taaatttaga attcagccac   5880
atattctgaa caaagtcagt actaaaacca tttctaaaca cttttaatta aagccataga   5940
taatatgggc agagcagtac tgggttattg aggtgactta gtgctctgag ctgctggtaa   6000
```

```
tgttgtaata atggctaaat tagattttat gtcagttcca caaaacctgt ttgctgctac   6060
tggccataaa agaatgttgg atttgtttgg aaacacattg tgattttgt gatttcatac    6120
ttatgtatgt cttttcataa ggatgtttta gagcggtgat tcttatactt tttcaatcct   6180
tttatggatc tgaaaaactc taaagaccac cagtgtatgg ctggtgatag aaaaactatg   6240
ggaagaatgg tctcactttt tgaagaaaac ataagcaagt tatcagttca tactggaagc   6300
aaataaatgg atcagctgga ggatctaata gatcatgccc ataaaatctt tactttagat   6360
ttaaatccta caagttctat ttttagagtc cctaggataa acttgcatat acaaagtagt   6420
caattgttat tatagtgact tataggatca ttttattata agataaagac ttgcgtgctc   6480
tctggtgctc tggtgtttta aataatcaac atgttttaga tcttttttgcc cactcatggc   6540
cctctgatta acttctcagt tatattttc aatgcttaca caaaaatttt gccaaacact   6600
aaccatcctt cctagaaatg cagtggactt tgtatttagg gaaattagta acaggtgaat   6660
gctccatttg ctgatgttgc aaacaaactg ttagttggtg taaagtatta attttgcttt   6720
cacatttctt ttggtttggt gtttagtcat tcttgtatct tatttagaag cgagttccca   6780
ttgtcaaaga aagtatcttg aattaatttt gttgtatgag atactttcat tctgttttca   6840
atgacctttc tcggtgtgta tataggggtt gggggaagcg agaatagaaa aatttgagct   6900
tacctgaaaa agataaaaca ttctgcagat tttgataaaa gggcatttta gctgggcctt   6960
agatattgct gctgtacaga tataggggcc agttgtgttc cgggatctga tgttggtgaa   7020
ggataaaagac tggctagcac ccttccctca ctccctctgt gtttccacta acttacaaat   7080
gggctaagga gatcccctgg gatgatggga agcttgaccc ctcctagaga gtcaagaatc   7140
attgatggcc tggaggacag gaggcagaac aaacaaacag caggacaaat aatggaggcc   7200
ctgctcagaa tggaggtctt ggtgttcttt gtgggttcct catactggag tgagccttgg   7260
caaaaatggt gtgtgtgtgt gtgtgtgtgt gtgagagaga gagagagaga gagagaggag   7320
acagaagaga aggagaagag gggagagggg aggagggaca gagagagaga ggtctcctac   7380
aaagagcttg gagctcaggc tgctttgctc atttgagtgt aatccaggag gatgcacctt   7440
ttctctcgga cttgaagacc aactgctcag ccttcacagc tcttgaaaca aagttcttaa   7500
tgtcccctga aatcagcact agggactgta gttgggagt tcagcccag cagtgcctct    7560
gagtctttgt tctgtatatg ggttctaaga ggattagaat caagttggaa atacacgtgt   7620
tcccatttcc caccttcaac tccccctcacc gcctgagatt cttgcaaaca tttgtgcaag   7680
gaacctgtga aaaagacttc tttcacgtaa ggaagtaggg ctaggagata ttaatctggg   7740
cattgttgag cattagcatc agtgtgcagg tctcagccca tctgtctgca atgtttgttg   7800
aagccatcac ttcttgtccc ttgaatcctt cctcaacttg gatttcaggc cctggctctc   7860
ccttgcttct cctctcagct ccctggcgat tccctcttag tctcctttgc ttgttcctcc   7920
tcaccttgcc tgtaaatagt ggagggctca gggctctgtc tagattcact ccaggccatt   7980
gctttgaata ctgctgcatc ccgatgactg gagattttga gtctccaccc aggtttcccc   8040
gagcatcaga ctggcataga caaccgcctt ctccacgtgg atgtctaatg gcatgtcac    8100
atcgaacaca tcccaaacca aaccctgct tccccttctc tattatgatg actttttact   8160
cttccagttg ttggaccccg aatcttaact actccccttt ttcatgtctt gtttctaatc   8220
catcaacaaa tcctgcagct ctacctacct ccaggatgtg tccagaatca aaccacttct   8280
ccccttatct atgactacga tggaggtgca agacaccatc caaccttgcc tgggtaatgg   8340
```

```
gaacagcctc actgctgggg ttcttatttc tgccttgccc cctgcagtgt gccatgatgg   8400
atgctctaca gggtgacatt atgtgtggac aagacagagt ccttgctttt tcaaatccca   8460
cctgttcttc tggagccagc taacacgctc ccttgggccc catgcctgaa tgccatctct   8520
tccttctatg gcatcctgca caggacttcg ctttgctcag atgcctcctc ccgcgctctt   8580
ccctttattt aaccatttgt ctccatttta ccccttcgct atctggggta atcctgttcc   8640
cttcatctgt atctctgaaa atggcatctt gccctccctt ggtgctcaga aggtggcttc   8700
tggtttaccg aatagcctga tttcaccttt ataaactcat gctactagaa ttttctctcc   8760
ttgtcagtct ttctagccac tttccaatgg aacagagact accaaatcct aatctgataa   8820
ggaaaaatag gtaaacataa cgtggcagac tctgacatct gcagtgaaaa tttaaggttc   8880
atcatcaaat gtatgattcc attgtgaaaa tgtccagtta aaagctatct gtagtcacca   8940
tgcagcatta tgaagaagtt ttcagaataa gggcaggtgg taaagtctcc tggccagctt   9000
taggagtata tattggaagg ggctttgtta gctgattgaa tttttattcc ccaagtaatt   9060
agtatgagcg atttgtctac tgtatatatg ctcaaattac atatactatg cacttttgag   9120
aaatacttta caagtttttc tttcattaaa atgtatttgg ggccgggcgc agtggctcac   9180
acctgtaatc ccagcacttt gggaggctga ggcgggtgga tcacctgaga tcaggagttt   9240
gagaacagcc tggccaacat ggtgaaaccc cgtctctact aaaaatatgg aaaattcacc   9300
agacgtggtg gcaggtgcct gtaatcccag ctacttggga ggctgaggca ggagaatcgt   9360
ttgaacatgg gaggcagagg ttgtagtgag ctgagatcgc accattgcac tccatcctga   9420
gcaacaagag cgaaactcca tctcaaaaaa atgtattttg tacataacta gaataatcaa   9480
ctggattgaa agttaatata aattttagaa tactactgaa ttcaatagtg catttagtca   9540
gaaatagtta aaatatctcc caaacagctt gaatcactcc tttttgaaca cattgttttt   9600
tgaaggttac agtcaagtcc aagaaaaaat tttaaaatag gaaagaatt aatcaaatca   9660
tttcaaaatc atagcagtgt tttaacaatg ccaattattt tgagttgaag aaaagaagga   9720
aaatgtaaac tatgcattca agtaatgtca atgcaccttc tcaggtgcaa aatgaatgaa   9780
caattaactg tgccagctga atatgtagca atcacggctt ttgcacatag aagccttctg   9840
aattatctta tattctcaaa aatatcattg ctctaaacta gaattttatt ataattaatt   9900
tgtgcaaaag ttgtctttct ttcaatgaat gttgtctttt tgaggcataa aggaaatttt   9960
aggtggagga ggagaataga atacatgctt actgggagga caagtaataa taggtgagta  10020
aaaacacaca gcttattgaa ttgtctcaga tccacatttt ctccagaaat gcaaagttat  10080
acttgaaatc tatatttaaa cagataagca gaatgtgact tttatatgct ctattttgat  10140
gtattctgag tatgaagata acctgaagga tgccttttc ccctctttat cttggggtaa  10200
actcttactt acccttcaga gacttgactc aaatattttc attctgcaat aaccacaggt  10260
agaatggatc atttactcag ttgtggctct cttaagagca cagactacct atcatattta  10320
tttcaaaatt tgtagtgctt atctcagtgc ttggcacaga ggaaagaaat acaattttta  10380
ataaaggcat aagtggagag gtaaaataca tatttctggt ttcaacgtgt ccatattctt  10440
tcttgtaaat ggaatattgc gcttgcagtc tgctctcaca caatatctgg gaaggagttt  10500
taaagagtga ggaagaacag taaagatttt cctaggcaga tacgttatgt gaccttgtt   10560
gatttccaga gcacataata tcccaatttc atccagtgga caggaaaaga gaggaagagg  10620
gaaaaggtgg cctctcaagt gcctgacctg gaagctgcac ctatcactgt cccttgggca  10680
gaactcagtc acatggtcaa aaggagtctg caaataattg tccccctgagg agccgggtgc  10740
```

```
tcagtgaatg attctattaa gttgaaatca gatgggaaca gatcatttag gataaccagc  10800
aggctctacc acattgccta actcccaggc atattgtgag aattaaaagc accttatata  10860
tgtcaacgtg ttttgaaaaa atacaaaaag ctctacaaaa gtgagctata aatttatcat  10920
taataataat agtaataata gcaaaatact tgagaaatgg tcctcttgag ctgtttagaa  10980
ggaatcatac aaatgcatta gacatggtag cctcacttaa ctacttaatt tgcctcttct  11040
ttgaaattat ttcaatagca tttgaccaaa aactatcaaa tcattttga aataacgtat   11100 ttttacataa aacacattat caaatatctt tctggatcca gcttggtggt aaaaagatac  11160
atactaaagt ttatgactga tataacttta tatattgact aaaccaaaga taaatattga  11220
ttgaactttt gtggccccag tttcaataga ttttttttatt aacatttttt gtttgaagta  11280
cagatgtcac gtcatccatg aaccggtatc attatagctt gataaaatac tcaaactgaa  11340
agcagtgatg tacattaatt ttaaatataa tggttaagca aatgttattt ccatatctat  11400
aagtgcattt tatttgataa ttagaatgtt agaatcagaa ggaatttgga aaatcccagg  11460
ttacacttct ctccaggacg aactccttac agtggctctc ctggggtcag ctagcttttg  11520
cttgacccct tgaagcagga ggaactcagt tccactcaag ttgccccctt gatttttctct  11580 ttcatattga acctgctgct gcacaggact cctccgtgac tgtctctttg ccttcctaaa  11640
tctcaaagaa taaagcaagt cacttttga caagacatct ttcacatatt tgaaaagaca  11700
tctttcacat atttgaaaag accagtacgt tttgttcttc ctagaatttt ctccttcatg  11760
ctaatgtctg ctccaagaag acatggaggt gactggacat ttagtcagga acatttcttg  11820
agagcttacc ctgtggcagg caggtgcaat gttgaattct gagaatatga atgtaacctt  11880
tgaacaggtg gctctgtctt ctgacgtttc aggataaggt ggaggagagg agagggaaa   11940 gtcgacctat ctccccagcg gggagggttt agggttgtct gtgggacctg cctctgtctc  12000
atcatccatc accattgtcc tgctgatggg tgcagaggac tgaggacgag tggttggagt  12060
tctccctgtg ccggaccctg tagagagtcc agagccctgg ctcccaaagg aggcatattt  12120
gtagggctct tttcgtgagg gtccagagga cggctgcaaa gctgcagggg aggatggggg  12180
catgggaggc aagcccgttg ccctgtcaga gcctcttggg gatgctgctc ttccccgcct  12240
gtcctctctt ctctttgatt tctcatcatg tggtcctctt tcctctgcct tttcctctct  12300
tcggtgtccc aagttcttcc atagagacct gtgtccccctt gttcccatca ggcctttatg  12360
ccagccctgc acaggtgcgg ggacagtggt aggggcgtct cactcccgac tcaactacat  12420
tctcccagaa attgtctgca gtcaaacaca actcagcgtg gacattgctc accaaaggta  12480
tactgcttgg gctgcacgag agattcagtt ttctcctatc tatctggcat gggctgtgag  12540
ggggctccta acctaggggg cctttttact ccttcctggc cagagctgcc atttccaagt  12600
ttctgcactg tcagaaaaga gggataaggt aagattcctg ccctcatgtc acagattagt  12660
aggggagagg taattgtcaa ataattacag taaaatgtat aaatgcctta agagaaataa  12720
gtacttgctt aggaacctat ttcaagaaag gagagatagg ttagcgtttt ggggaggtag  12780
tacgggagca gtcagggaaa gcaatacttg taagatcaga ggctggcaat cttttttctgt  12840 agagggctaa gttttggact ttgcagatcc tacagtgtct gttgcaacta ttacacagtt  12900
ctgtggttgc agcatgaatg cagccatggg caatgtgtta atgaatgggc acagctgtgt  12960
ttcaataaaa cttatttac aaaaataggt agtgggccct gctgctgggc ttggcttgct   13020
gggcacacaa agtgagaagg gcattgtgcc tttctaggaa acatcccttg caaagtcagt  13080
```

```
acaggtgaga cagtgtggcc attcccacca cagcatgagg tcttttgaat ggctgaagcg    13140
tcaggtggga aaggatgagg agctgaagaa gaaagcctgg gaatttccaa ggcctctctt    13200
aacatttgct gtgcagaacc aagcagtgcc ccaggtgttc agagtaggct tcagcgatta    13260
catttcttgt tagacactga attttgttca tgccgcccaa gattgcatta acaattttgg    13320
ctgtcacctt accgcggact caaattagtt tgcagtcagc taaaacctct caggtttttt    13380
ccccccagct tgtgaattgc tgtgaagcca aacatccctg tcatctcttt ggtagtttat    13440
tttcaaactt tcaatcttat taaatttcat ctccaatgtg caaagataag aggaagttta    13500
ccgctgatgg tggtttattc tttaaaactg gacatcagct aaatgtgtta aggtaatccg    13560
ttagaggaat gttggtacgc ttatacagtg gaatactaat tggttattaa aatgttgatg    13620
tatgattatt aaaaggcagc ccatgttatg tctcttctgt atgaataagt atgtaaaaag    13680
tatgtaaaga ttactgtata gttcatgggt gggactgggc tctctctagc ctctgtcctt    13740
cattctccct gccagtgcct tttcccttgc agtgtcccct ccctggctgc atactcaaga    13800
ctggatttgc ccagccaaac cccattaact cacagaagca agaggaaaaa aataaattct    13860
tattagttca attctccaaa ttggggggcgg tctatttcac agcaataggt aactgacgta    13920
aaaggaaagg aaacaatgaa gtaattccag aaaatttcct atagctggag gacatgcatt    13980
ttcatattga atgggaagaa tgggtgggg gggtcatacc tctgtgttat tgcagggtcc    14040
tggctcctag ggacctaggc acctcttcag tcagtgaatt atagcttgga aaattggcta    14100
agtcggggaa ctgtacaagg ggtcatcact ttttatgtag ccatgctcta tgaaccatct    14160
ttataactcc ctggcttctg gcagttaagc accactcact atctggcctc tgtaatttca    14220
acttctgacc atccccgtgg gtggcaacaa gcccagctct gtgacacctc tgctaccagc    14280
agccctggcc tggagagcgg tgccccact gaatgtctca gtgagattgg cacccccatg    14340
agcatattcc tgagggtgca gtgaatgctc tttctcccta cttgggactt ctgggaaaca    14400
ctgtcctctg gtgggttgtt tgacctcaca taatatactg gttcttgcat gccagcttct    14460
ctctgcttct tgattctttt atcagctgtt agggcaacaa tgtcaggcat ttccgcctgc    14520
tcagcattgg gcatcccttt ttacaggctt ctcagagcca ccctagcagc aactttaccg    14580
cgtctcctgg ggtccttgct ggatcgtgaa acatacttc cggagaaagt gttccctaga    14640
taatgaatta tttcttgtcc tgtgttaagt tccagttcct tggtcaagga ccccagcgct    14700
actcctcagg atttgcagtg catgctcaat cttgaagcaa tgttgggata tagtatcttt    14760
tcttctctat caggcccagc tgtctccagg tgggttatac taggatttaa tcctcgttag    14820
tgccgggtca gctcctgagg ggtgcacctg ttgcttttta gggacgaggc ctcttcagca    14880
taaagaagtg ctatctctta ctagggaaga atgggccacc tctgtaagct ccaaatattc    14940
ccaggtttcc ccaaccgggg ccttgacctt ggcataactg atctgccttg gctgagcatt    15000
taaacatccc taaatctctg caagtctatc aggtcctagg cctgctgcta agttctctca    15060
ctcttccact gtaggagaga aggctgtggc tcttatattg agcctttaac tgtttgttat    15120
tggccctcag tttctcatta gctctctgta gagtctcaat acaatatatc agaaagcatt    15180
caattccatc tccttgtagg cagggaatgc ctaaatcatt gcacctacaa tgacattctc    15240
caccaggata tttcccaggt tactgctgtt gaaatattta gcaattgaag caccatttgt    15300
gcaaggggac tatctgcccc tacacaacac tcagaatggc attctctttg ctttccagaa    15360
agtgaatgag ctggttcccc aacccctctt gtgttagttt gagtcctgaa agaagtaaat    15420
gtcaagatag gattagatgt acaagaaatt tattgggaa agaattgtga aggataaagg    15480
```

```
ggaaggagct  aggggaggca  ttgaaccttt  ggatcatgat  gtgtgtccaa  caactatgaa   15540
ggagagtggg  cagggagaag  gatgggctgg  gaagagtttc  agttggcact  gtgggtctca   15600
gaacaaccca  ggcataggct  gatggggacg  ccttgagcca  atgttgccca  ttggcggagt   15660
ccacatcttg  ctgaaatggg  cctgcattag  ttcccctgcc  atgtttagtc  atctgggagt   15720
agccgatgag  aatcatgatc  ttaggatcaa  ctgcaatggc  agattcaaag  gggtagcaac   15780
tgatggcctc  agtcaactgt  gctccttata  gcaggaacac  tgagcagtgc  atttcttggc   15840
catcacaaag  actagtgagg  agtgcccttc  agagaaggga  atgaaaatta  tttccagcct   15900
agaatttgat  acttatctaa  actgtcaatc  attcatgaga  gtcaaagtcc  caaaaaataa   15960
atcttccata  aacccttcct  caggaagtta  ttggagggta  accgccacat  aacatgagga   16020
agacaaggag  gaagacatgg  gatctatgaa  agggcaggtc  taacccagga  aaaggatgat   16080
gaactgtaga  cccatgatgt  cagatgtgca  gcagactaag  atcagccagt  gcagaatggg   16140
ggagattcca  gaagtgtgtc  cccccaaaat  attggaggct  catgtgactt  ccctggggaa   16200
gtttctgctg  agaggctatt  ggaaattgag  ggaagaatta  gccacagtcc  caaagaaaac   16260
agagccaatc  aaaaagcaat  gcaattatga  acttcaaaga  aaacaaaaat  aagaaggaaa   16320
acagtcttac  ttactacatt  acaaggtcca  gctgtgaatg  atattcatgt  tggcagaata   16380
atgtcaatac  caaatgtcgg  ttaaacccaa  aactattgta  taactaaatt  gcctgtgtaa   16440
gagagctaaa  cccttatcta  gcataatagg  aagtcagtgg  atacttcctg  aagtgtggat   16500
gtgtggagat  gtaaattcca  aaagaaaacg  tcttaagagt  caaaagtggt  tgcctctaga   16560
gagaactggg  ggaattgtag  ggcaatgtag  gacagggaac  tgtgattttt  cttgtaagtt   16620
gttctgacat  tttaaaccat  gaacatatat  tacttgtatt  tttaatttta  aaaagacata   16680
aatatttttt  ctatcacttt  aaatattaat  tttgctagtt  atagcacata  tttatagcat   16740
tacactctgt  agagctcttt  tggattcaag  ttttggagaa  ttttcaaagt  tttagattaa   16800
tgcctttgtg  agttttcatc  cctttgatga  taacaagtta  caaagaaata  gggttatgaa   16860
taaaccttgt  gggatattgt  tagtcacctt  ctctcaagtc  gatctgtccc  atgaatcaat   16920
gtttcaaaca  ttgaccagca  tttgatactt  aataagcaac  gagtaagttt  ttgttgaacc   16980
aatgaatact  cttaaaatat  attttttcaa  gtggcaacag  tactatctta  tttgcactct   17040
acttttcttt  ttgaccctaa  gaatgtcaca  aaaatgttta  gcaactgtca  agattattac   17100
atacagagat  gactattgtg  ttctcagata  tgctgtatgt  cttagttcat  tttgtacagc   17160
tataagagta  gctgagacta  ggttatttat  ttatttattt  atttattttt  tgagacggag   17220
tcttgctgtg  ttgcccaggc  tggagtgcag  tggcacaatc  tcggctcact  ccaagctccg   17280
cctcccaggt  tcacgccatt  ctcctgcctc  agcctcccga  gtagctggga  ctacaggcac   17340
ctgccgccat  gcctggctaa  ttttttgtat  ttttagtaga  gacggggttt  caccgtgtta   17400
gtcgggatgt  tctcgatctc  ctgaccttgt  gatccactca  cctcggcctc  caaagtgct   17460
gggattacag  gcgtgagcca  ccgcgcctgg  ccctattttt  ttttttttta  aggaattta   17520
tttcctcaca  gttctgttgg  ctgggaagtc  caagggcaag  tctctggcat  ctggtgagag   17580
acttcttgct  gctttctccc  atggtggaag  gtgagagggc  aagagagaga  caaaggagg   17640
ctgaactcat  cctttacaa  ggaacccatg  cctgagatat  tgaacccact  tctatgataa   17700
cagcattaat  tcattgatga  ggacagagac  ctcattgcct  aattggccta  aagtgagacc   17760
tcttaaaggt  ctcgcttaat  actattacaa  tggcaattaa  atttcaacat  gagttttgga   17820
```

-continued

| | |
|---|---|
| ggggcaagca ttcaaatcat agcaccatat aatacaataa aaattttctg agctaagttt | 17880 |
| ggtaaattta ttctaggaat ccatgttgtc tcctagttat cttcccttcc atagtactga | 17940 |
| tgcattttg ttaaccatta cctaattttg cttgagtcta ttatttctga aattcacatt | 18000 |
| atcttcccctt ttaaagttga gaaaattttc attcttcaag cgccttattt tctataatct | 18060 |
| ctcaaagtaa ctgatggctg ttgcatgatc ataagtgcaa attattttgc tagaccacac | 18120 |
| ttggagatga tgaatttgga atggcatgca gactcccgac atcaggagtc ttgtctcctg | 18180 |
| caataatcag gaacccaggc ttaaaaggga gcaggtacaa cagaagggca aggggtgaca | 18240 |
| atgctggtga aagacatttg aggaaagcta tcaacatgaa acagaataaa ataaacagaa | 18300 |
| aagcaaacca gggaaaataa attatgcagg aattaaacac atacacaaac tgaaacagga | 18360 |
| accatcagaa catataaaaa attcttgaac atcagtaaca caatagttga aacaaaatat | 18420 |
| ttagtaaaat atttgaaaag taaggtcaaa gcaatgctgt aaaagtagta caagatgata | 18480 |
| aagaaataga acacattttt gaaagggaaa aagatttaaa ggatattcat aaagatccaa | 18540 |
| catcagacta atagaagttc tggaaagaga gaataaggaa atacaggtca ggaaatttgt | 18600 |
| aaagaaataa tataataaaa tgccccagaa ctgaagaaca tgagctttta actttaaaga | 18660 |
| gccgactgag ttcctagctc aatgaatgta tagacatgta agggtattga aagttcacct | 18720 |
| tcagtgtcat gtttcctaag aagctaatgg aagatatgca ccagcaaaat tgtagtaaat | 18780 |
| acataggaag aaatagtata tagaaaaagt atggtttcaa tccataagaa ataaggaaa | 18840 |
| ctcccaggac gagagcagct cttgacagca tctagtccaa actggacttg gaggctggaa | 18900 |
| acttctagca gggaaggaag agctctgggt gaaaaagtag actcaacaga atagatcga | 18960 |
| tcatagaaaa catgatagag aatcactaac acattgaaaa aatcacatat agaatattct | 19020 |
| gcacgcttaa taatgaggtc attatttatt caagggaaaa ttaaaagctg tttagaaaag | 19080 |
| ggaaatgtta tagtgcccta tttggctcta aaatgaacat ttatatagga atcttcatgt | 19140 |
| aaatactaac aatgatttaa ataagaacag acatttcgga aaataaggga agaaaatggg | 19200 |
| gcatgtaaaa gagctaactc ctcattatcc taatgaatta ttaaatttca caatagcata | 19260 |
| gtatttagaa atatgatagt tattacgaga agaaagagct aaaaggttgc cagtggggag | 19320 |
| caggagtgag ggttagagac gggattgggg gagatgctta ctgttttcat gataagcctt | 19380 |
| tggtactatt tgatttaaaa ctatataaat gcatttatta atttaaagta atttaaaaaa | 19440 |
| cccataccac tggataatgc ttgataattt ctagagtcct ttttttttgt attttggggc | 19500 |
| aggtaaattc attgagagac ccagagagtt tagctgactt tcctgtgggt accaagggtc | 19560 |
| agagctgggg tcaaaactca ggttttctga acccctattc ccagtgtaca ttccatgact | 19620 |
| ccaggctgcc tcccgcattg cacaggttac atctaggggt gtgctagcaa atgcctagac | 19680 |
| catcctcgtc cacatcagca tctgaaatgg acaagaatgt tagtcatgac ttgccactaa | 19740 |
| cgtcttttaac cttaattgac atctgagagt gtcatcatta catcattaca aaacactaa | 19800 |
| cccagataca tctgttccca ttactatttc tgcgtaattc ccccagactt aattgcttta | 19860 |
| aataaccatt ttatttggtt tacaaactta tgggtcagga ttaggggagg gctcacccac | 19920 |
| gcagttttc tctggtccgc agtcatctga agcttgaacg gggtggggca tgcaagacgg | 19980 |
| ctcacacatg tgatccgcgg ttgagcctgg ctgtggacca gagcatctct gttggcctcg | 20040 |
| cttacacaag tggtctcaga ttagtagcct ctgtacatgg aaactagctt ccctcccggc | 20100 |
| aagcatccca agagaactag gaggaagtgg tatggacttc ttttcttctt cttcttcttc | 20160 |
| ttttcactta ttcttgatat catgtagctt catttctatc agagcagtca catgcccaca | 20220 |

```
gattcaaggg ggagggtcca cagatccgcc aatgggagga acagccaggt tatatcgtaa   20280
aagatcatgg ggcatgggag atacccatct attttctgta aaaaatacat tttgccacag   20340
catcactggc tttccagctc acagtgatct gcctggaatg ccttttttccg tctctccagg   20400 atctacatct ttcaatataa ggtttagaaa ctacctccta caggaagact tccttgattt   20460
ccctcagcaa gaaagaatct ttccttcctc tgaatcgcca ttgcattaaa aaaaaaatcc   20520
atcttctggc gttttcactt tcagacttat actgtaatta ttctatgtac ctatgtttga   20580
cccctcacga tgcccagcat aataatttgt ctattgagta aatatttgct taatgaaata   20640
atcattacat gataactcaa atagcagtcc tgaaaaagtg catttcaatt cagatctctc   20700 tttttttcttc cttcacaatt ctcatttccg aaaaatgaaa gaagccagag gatcctttat   20760
gaggagttac agtataactt atgcgtggct gtttcctgtg tttactgcta ctcagtgaga   20820
aatacgggag atgggagagt gaaaaaccat gtcatttaca atttgattaa aaagcttttt   20880
atcttttcct ttcacgttta agccttgccg ttttaaaaat ttcccttttcg tcacaggggga   20940 tcaagcagca gttaacgctg cagttccctg ttctggaaac actctcaaag gtgtttcaac   21000
acattttgtc tcaactctga ctcctgcccc gctgccccac gccatccagc cacactgaag   21060
gtcttgcatt tgtgccttgg ggcattattt ttttttactc ttctccctgc ctggaaggtt   21120
cttcccaacc tgccctaccg ccatagccac agaaccaacc cttcactttc cttaagtcta   21180
tggtcacaag ctccttctca aaggaggcac acctctaacc cccccatttt ggtgacttcc   21240
tgtctcctgg aggccccccgg aactagtctt ctctacttcc agcaacccac tttacgagca   21300
gcggagaaga ctgactactt ctgggggcct cgaggagaca ggaagtcacc aaatttacag   21360
gtgctgtgga tgaaactgtg tgataatgaa tttattgggc ttgtttttttt agcttctgaa   21420 tagaagaacc aataagatca tttttttaaa aaagataaaa acagacaaac acaaaccctc   21480
tagtataaaa gcattttttt ttaaaaaaga tgaacacaca ccctcagatt gccttctttt   21540
gaaaaggcaa tctgagattc cttatgaaat ccccagacag aagctgtttc tttgaattta   21600
atatgctgta cactgtagag ccaagaggct tatagagtgt taattaacac cccttgtcaa   21660
acatttgtaa atgaatctgg ctaaagctca aggaaaccag gttttttctgt gtgataaaat   21720 ataatctttg gagattattt atgatcacaa agggagactg tacagaaaat tttcctagac   21780
ttggaaatga ggcaggatta ttggtgtcca tctggactga ggcctcaggc aggcctgcct   21840
agttaatccc attctcctat cctcattctc tgggggtgaa gaaggcagtg cacctttgtt   21900
caatttgctg cttaccatgg attagggcat tttaaattct gtaagggtag tttttaactt   21960
gtagaaaact gatagcgatg ggaaggattc ttgcctaata gggacacaaa cggattttgt   22020
tctgtagaga tgtaaatgaa aagatgaaaa tcacaacaca tttaatgaaa ggaaaataaa   22080
gactcttgtg agtgccacca aaaaaaaaaa taaataaaat gtatctcctc tccgtggcac   22140
cccaggcctt ccttacctca ctctatttct tcatagcact tattgcctta gaacattctt   22200
tataatttac atttattatg tttgttgttg gttgtcgctc ctcctgctaa aatggaatct   22260
ccgtgagggc acgggttttt ctttgatttg ttccctgttg tgccccaaag tgctagaatc   22320
atgccaggca cacaatagat gctcaataaa tacttctgga atgaaaatcc ccctccactt   22380
agaccagtga gttccaaact ttttgatct tgacccatag taagaaaggc attttccatg   22440
ttgaatatac accattgaaa caaaattttc acagaaaaaa cttaccatta ttacaggcag   22500
tgcactgtga tatttcctaa tctcttctat tttgattttc aaaattgctg aggctactca   22560
```

```
taggttgatt tcacaagtgg agtttgtgtt atgaaaaact ttgacttaac accatgtcga   22620
aactgctacc acaaaaaggc aaatgcgaaa gaagggggaa agagcaggcc gatgactttc   22680
cgctatccac cactccataa agcatatttc attttcctgt aattgtatcc tgttcaatga   22740
tgtagaaatc ctcacacact cacatgccac ttttctcttg ggtgaaaagc gttctctact   22800
gcaagatgaa ttgagttatt tcaaaagcaa agagctataa atgagcctgt taagaaagt    22860 ctcaaggaga gtctgttggc atctgctgtt gataacttaa agcaggagaa ttagataagg   22920
aggcagaagt agaatgttta gaaaataaaa gtgaccatta tagaggaaaa actgcttgtc   22980
tcagttttgt tgatattgga gagtagctct ttcatgaggg tattgtggaa ttattggcaa   23040
ttatactaat agatgtttac tgaaaaaatc ctatttgact gatgaaccat ggaatacttt   23100
tgctgacctt gtggaaaaca tcacttatct gagttcctta tcttcttgtc tcttttttct   23160
catctagcct atgcctccct acctgttccc tcatggttct cattttgttg ctattagaaa   23220
aacagagata caaaaaccag gaattggaac ccctctgtgt ctccagtaat aattctgtga   23280
ttaatgggtt agatggattc tggtcacaag ctggatattt tgttaacaac ctagcgtcaa   23340
tgacttggaa tgattttcac cgcagcatga tttagtattg aatagaatga tttaactaat   23400
gttaattagt tctgtacaga taaattaatg aagcaagaag ctcaatctct gatttattga   23460
tgtatttacc cagtgtaagt tatgaaatct ttttatttc atttgaagga agttttatt    23520 taaatacaaa taaataagcc ctttattgtc acctactttg gaaagtcca gataaaacaa    23580 tcttaagtaa caaaactcca aaattacaac atgatttca aaactacccc tgaccttgt    23640 cttgcctggt tgttacagtg tacttttaac taaacggatt cttatagaat ctcaagtttg   23700
gttatatttg tattaaggaa ctctatattt gcatttgacc agccctaact aaaacaagct   23760
taaggaagaa aagggacttt acgacaagga caaaggattg aagaagaact ccagggactt   23820
tagatgttaa caactgtatt tgtcactaaa gtaaccatta ctgtcaaggt gggttctcct   23880
tctccctcac taaacacatg cacacacacc acacacacat acacatacca catacatacc   23940
acacacatgc acacacacca cacacacacc acaccacaca cacagaaata cacacagaca   24000
tacacacatg cacttatgct tgggtcagtt tggcttttat catcccagag agtctcttcc   24060
catgtcagca actccagatt cacttcctct cctaatatag gacagtcaca tgtctctatt   24120
ccagcaaaac aatctcaggg aaggtatctc attggcctgg cttgggtcat tcaacttgaa   24180
gtacaagaag agaaaacagt attctttat ttttatagat ttcctgtaaa atcagtggat    24240
aatggtaaaa atttcatgac agcaggtgtt ttaccttatt tatgtttact atctctagaa   24300
cccagtatga tagttcataa taaatgctta ctaaaacaat tatcaaactg tacacttaaa   24360
aattaaaaga gtaaattta agttgtgtat gttttaccac agtaaaacaa aataaaataa    24420
acctattatt gatcttattg tctatttctc aaaagtagca tacgtcataa tttcatgtga   24480
tttctaaagg agatctaatc tcaaacttag ttcttagagt aaaataaaag gttttggcaa   24540
tcatatacag cagtagactt taccttgaag atttaacaaa ggtttgaaag caaaatgcta   24600
tgatactgaa tatactaatg tttgagggct tgtgaaaagg tcttaatata ggaatcatat   24660
atcttctttt agattgtgtc ttggggaaca ttggggggtca gttttctat cagtgttagt    24720 atgtagtaag taatggcata catctaagct tgagattttg ctcatttctg tattcttagc   24780
acttatatat ccaacatata ataggtgttg gataatattt gttgaataaa tgactaaata   24840
aatgtcttgg catgagaatt atgccatcta caaaaccgtc acttttaaaa aaacaacaa    24900 agattttga acctgtagat ccagccagaa agcaagaaat atcttcacct ttccagactg    24960
```

| | | | | | |
|---|---|---|---|---|---|
| acttattttt | tggtctagct | gtgtactatg | catgagctgt | caactttaat | actttatttt | 25020
| ttaatgccta | ggtctagtga | gttacaatgt | gatgtagact | gattgaatta | aaggcccaa | 25080
| tgttgtcctc | tcttcattgt | atccatgcct | tttgtcatgt | aactttgcag | tgtcctctac | 25140
| tctaggtgtc | cattcagctt | atcctttgac | tctggcctc | ttctcctttg | actctggctt | 25200
| tatccatgtg | acttacttta | gccaacaatc | ataatgctgg | caaacactga | gaaaatgctt | 25260
| attagtgtct | gcttagtctc | ttgcttctct | gcaattgcca | tgagaaaatg | cccaagctag | 25320
| tacactggag | gatgagacat | gtggggcaga | agcaacctgt | cccatttgtc | ccagccaaca | 25380
| ccatcctaga | ttaaccagat | gagaccagag | cagaagacat | gttcagtgga | gcccaaccca | 25440
| gctcacgaat | aatatttctt | catgagcatg | tgagcaatgt | gtaactaatg | caccatgctc | 25500
| tttttattct | gcacttccaa | acatctctca | gattgccctg | ttgttttgct | tttcagtagt | 25560
| catcaccttt | gtccagaacc | ttaattgtat | ctgcattttg | gcagtatcct | gccaattttc | 25620
| cacatccagc | tgttcacatt | ctaatgcatt | ctgcaatgga | tgattttgag | catatgactg | 25680
| atcatcactg | tctcagaaat | ttatgctaat | ctattgtgac | ctattctgtc | aaatccaaat | 25740
| aactttacat | tcaaaacttt | tcatattctg | gccccatact | gtctattgta | atcttatttt | 25800
| ctaaaagcca | caaactatta | atcctgtagc | ctaattaggt | tgatatcatc | attttcacaa | 25860
| cacgttgggt | aaattcttat | atctgttcct | ttaatcatag | tttccatgct | tagacactcc | 25920
| attgccctcc | ctaagcacca | gccagagtcc | actatggggg | gatattttaa | aggctctttt | 25980
| cccctaaccc | atctgcccca | gaggtggcac | aggctagaaa | agatagtcca | attatttggc | 26040
| ttaattattt | ggatcttaca | gttttttgg | gagagttcca | gatgatttga | tgaaatgcaa | 26100
| catggtcaaa | aacattttgg | tggagaataa | tttaatcaac | tagaccattt | ggtgaaaaat | 26160
| aaatcccagt | tactagactt | cccagtatta | ataattttgg | tatgccagga | attttaaaa | 26220
| catttctaac | aaattttttc | agaaatcaga | atgactgaaa | ggtataacaa | taggaaatta | 26280
| ggaaatcaat | aagtaatcat | tgaaagtga | gtgattgaat | tagttggaac | aatctatgcc | 26340
| atccatcctg | tgggggaaaa | aatgaaaaca | gctaaacaag | cagagcagac | atcatcaact | 26400
| tagaaaaaca | atatagtaaa | taatttgaac | tagaaaattt | tccaaaattg | aaaattccag | 26460
| ttttaaaaaa | tttgtgtttt | cttattcaaa | aagcaataca | tatttcgtta | cataaaagtc | 26520
| agaaaatcag | agaagcagaa | gaacataata | aatgcccact | gtcctactca | atagagacta | 26580
| taactgctat | ctctgtacaa | atcctttaaa | atcctgtctt | atgtgtattt | attttacatc | 26640
| tgtacatatg | attccaaaat | taggtaatac | tgtacgtggt | ctatctatag | ctaactatag | 26700
| tttgtaattt | aataagctat | atttgtccat | ggtgatcatt | tattgctcat | aaaattaata | 26760
| aattataatt | tatttatcaa | cactgatcat | ttgttgctaa | taatttatttt | catttaatgt | 26820
| cttattcctg | ggttatttta | actaatccct | attgttagcc | ctttaggttg | tttcaactaa | 26880
| tttaagaatt | ataaatggcc | catagtagtt | acttaataaa | tatttgagtg | aaaggataaa | 26940
| tgaatgaata | attccacatt | attggatgtt | caagttgttt | ccattcaact | ttattgttgt | 27000
| ggggagtat | aatacaatct | tggtgaagag | ccaccaactt | aggaagaact | atgaagaagc | 27060
| atgttatta | ctcctgcttg | tgggtgggt | gcattggaa | aggaatgcct | aaatgcacgt | 27120
| ggggagccaa | acaagacttc | acaggggaga | tgggaattga | gccaaatttg | gaagaagtga | 27180
| gaattttcag | ttgataattg | gggaagatag | tactaagagt | aagtgggtt | cattaggaac | 27240
| tacttcttag | aagaggcaag | tccagaacag | aaggcagaaa | gggatatgga | tatgaaggaa | 27300

```
aagtagaatg caacttcagg gctagtaggt tggcatccaa cgtaggtaca gccctggatg   27360
aggagtaatg agaaactgac ctggctgtag caaaacagct aggctgggaa gtgatgctgt   27420
ttacatttat atgcgattct actggtcttc ctgttacttt gtagaagact gtaaggcttg   27480
gtgctcagag ctagaaatgc aacttatttg atttgctaag aagtccaaag caggtagggg   27540
tgccaagctg ctgcctgttc acacatattc gtctaactgg gtgtcaggga aagcagatat   27600 gagcccctt gcattggtta aatcctgagc aacttttaag gaactgcaca cagagactac   27660
tggctatttt ttgtggataa agttgtagat agttattttt gggaaattat ttatgtgttc   27720
tattaggtgg ttgttttgtg ggaggctgtt tgaaattctg tcttaaggaa ctgcagctta   27780
taaaccatag tgctgataga aataagagaa ataatttggt ctgcgagcac aaacatcagg   27840
ctagttggca tgcttatgta aacaccacac agtagcagtg acttttaagg aagtcctcag   27900
acaatgtaat cccaatactc ttcttgaagt tgaggtaata gggtgccaga aagaaaaaga   27960
aaataaatct ctagtgcctt ctaaaatttt ttcaatcctt tgacctttt gaaaacggtc   28020 acctttaatt cagaactaaa gtaacatctg gagggcccct tcttagata gggagaagac   28080 ataaatgagc tatttgaatt attttctgct tatgggctgc atttcatttc ttccaccatt   28140
ggtctcagtc catttaatta agattatttg taggattaaa ttaatccttt aagaattatt   28200
ccatttcaat ttttaaaaaa tctaatgaat gatagataac aaaaagcggt ccattcagta   28260 ttaccctga acatatttg ggtgattggt gataccatcc atgtctctcc aacttcagct   28320
tcatatactc agctgagtac caggcatctt cattgaaagc tagacttgtg acctaaatag   28380
aacttgatcc cttcccttcc ccaactcctt atttttgtt ttctttgagt tccttgattc   28440
ctcttcccct cctcacatgc aacatgtaac atccaattca tcagcaggtt ctacagattc   28500
tgccttcaat aatagcctaa atctagccac ttgttactat cttttttggt ccaaaccatc   28560
atgatctttt gcctggacca ttgcaatagt tgtctaactg gtatccttgc tcccattttg   28620
tcctcctaga tcctatttc cacgtagtag ccactgattt ttggaaactt atcaatcatt   28680
acccagacac aatgagtaca tttacatagt tgtttgattc catttacata aagtcccaca   28740
atcactctat gtactgggaa tcacaacagt ggtctcctat gttgagaatt gattaagagt   28800
cacaaggaaa caaggagtaa tattccattg tattaacaga ccacactgtt catacattct   28860
cctgtaaatg gacatttatg ttgttttcag ttttttttgct attgtgatta aagctattag   28920
gttggtgcca aagtaattgc agttttttgcc attactttt aaatggcaaa aactgcaatt   28980
actttggcac caacctaata ctgtaagtat ctttgaactt accaatcaaa cattactaca   29040
acacttgaat aagaaacact tccatagcat ttacaattct aagtgctttc catgtattga   29100
cttagttaat cctcacaagg atataaccat gaggtgctat tactatccct actttacaga   29160
tgaggaaata gaggcacaga cttcagataa tttgcccaag gtcccacagc taataagggg   29220
gcagaattag gaaagcctgg ctgagtctat gctctcatca cttgctcaac tctgcctgga   29280
atgcccttcc cgtaccctct accgcctctg cccaatcctc cgggttctct gctccttcca   29340
cacaccccca tctcaggtcc cagtcttttt tagcattctt cacttttttct gttacagatc   29400 ctcagacaat gcttccttga agaagacttg cctgtctaaa ctgccttccc atcccaatcc   29460
ctgttacctt ctatccttc tctgctttgt tttcatttgt tatctctctt cttcccaaga   29520
atgtaagctc cataagaaca ggatcatatt ttgaatcccc tagaaaagtg cctagtgtaa   29580
tatttgttga atgaatatga tccctgcaat taaaagctaa atatatatat tttttaact   29640 aacagattac tgtagtagtt tcaaagatga atttatgttt cggagaaaat cagtattctc   29700
```

```
ttgccacata aattgtaggt aattatattt ctatacctga atagctttgc caatgactaa   29760
gatattaatc tattatatat ttattaatct atagatcttt aaaattgatg cacatgtttt   29820
ataagcaatt tgatgaattt tgatgactac atacacctgt atgtgtatgg atatctgtaa   29880
caaatatcca agtaaagata tagaatattc tcattacccc agaaagtttc tttgtgactt   29940
ctaatcaatt ctcacctccg taggaaaccg ctgttgtgat tcccatcacc acagactgat   30000
tttgggactt tatgtaaatg gaatcaaaca actctgtgaa tgtactctgt gtctgagttc   30060
tttcaatcta cacaatcttt ttgacattaa tccatattac tgcctagaag agtagttcac   30120
tctttgcatt aatgaatagt attccattgt ataaacaaac cacactgttt atacattctc   30180
ctgtgaatgg acatttgtgt tgttttcagt tttctgctat tgcgatttaa gctactataa   30240 gcatttttt ttaattgtga tggggttcg ctcttgttcc ccaggctgga gtgcagtggc   30300
agcgatctca gctcactgca gcttctgcca cgtgggtcca agcgattctc ctgcctcagc   30360
ctcccgagta cctgggatta caggcatgtg ccaccacacc tggctaagtt tcgtattttc   30420
agtagagacg gggtttcacc atgttggtca ggctggtctc gaagtcctga cctcaggtga   30480
tccacccacc tcggcctccc aaagtgctgg gattacagtc ttgagccact gtgcccggcc   30540
agcatctttg aacatatcaa tttgtaagtt ttatcttaat attgtacaag tcttttgggg   30600
ggcttatgtt gtcatttctc ttggtaaata cctaggtatg aacttgctag attatagaga   30660
aaatctatct ttaattttat aagaaactgt caaatagttt tccaaagtgg tggtactatt   30720
tatactccca ccatcaatgt atgaaatttc cgttgtttta cgtccttgcc agaatttgtt   30780
ggtagtcttt ttttttttt gaggcagcat ctcactgtgt tgcccaggca tacaatggtg   30840
tgatctcggc tcactgcaac ctctgcctcc caggttcaag ggattttcat gcctcagcat   30900
cccaagcagc tgggactaca gaggcgtgcc accacaccca gctaattttt gtatttttag   30960
tagagatggg gtttcaccat gttgcccaag ttggtctcga actcctggct tcaagtgatt   31020
cgcccgcctc agcctcccaa attgctggga ttataggcgt gagtcactgt acccagcctg   31080
ttgccagtat ttttagttgt aggcatctta gtgggtgtga gtgctcgttg gggttttaat   31140
ttgcattttc ctgatagtgt tgatgttgag acatttcta tgtgtttact gagcattggt   31200
gaagattctc ttgtgaaata tctattcaaa tattttgctc atggtgggaa ggggagttat   31260
ttttctttta ctactgatag gtaggcttac gtatttattt cggatataat tattttgtca   31320
attatatact aatcataaac aaaaactgat aaattggacg acgtcaaaat taaaacctgc   31380
tcatcaaatg ttagcgaaat gtaaaggcaa atcacatact gagggagat atttaatat   31440 atgtatattt atatagtgct ttctgtgttc taagaagtat tttcctactc caagataaag   31500
agactattct cttacatttt gttctataag ttttatagtt ttagctttta gctttggatc   31560
tatgatctgt ctcaaatttt tatgcaagat tggggtttaa ttttttcata cacttttcca   31620
gttgtcaagg atcatttgtt gaaacgtctt tcctgttgcc acataattgc tttgatgcat   31680
tcgttagaaa tcagttggct gtgggtttat tttggaattt tctgttctgc tcctttgatg   31740
tatttgtcta tccttatgcc aatatcaccc tatattaaat aattatagct ttataataag   31800
tcttgaaatc aggtaatgtg aatgtttcaa ctgtgttttt cctttttcta gttattttag   31860
ctgttttatg ttcttattgt atatatttta gaatcaactt attcatttct acaaaaagtt   31920
tattgggatt ctggatgaga tggtgttgat tcagtaggtc aatctgggga aatctgataa   31980
caatattgac tcttccaatc catgaaaatg gtatctcatt ctttatttac atattcttta   32040
```

```
atttctgtta gcaatgtgtt ataattgtag caaacttgca catcttttgt taaattattt    32100
tctaagtatt ttacgatttt ggtaccactg taagtggcat tgtatttaaa atttattttc    32160
tgtttgtttt ctgttcatat ataaatgcaa ttgattttct tttttttttt tttttttttt    32220
tttttttgag acagaggctt actttgtcac ccaggctgga gtgcagtggc gtgatcagca    32280
ctcactgcag acttgaactc ctgggctgaa gggagcctct cacctcagcc tcccaagtag    32340 ctggactat gggtgtgagc cagtgttcct ggccaaatgc agctgatttt tgtattgaca     32400
ttgtattctg ccaacttgct aaattaactt attcgtttta atagtttttc tgttttttta    32460
aaaatcttag gatttctaca cagacaatca tgttttttaat gaacaacaaa gtttgttttt   32520
ttgtttgttt gttttttccct tttcaatcaa catgcctttt atgtttttat ttgccttact   32580
gcactggcta ggacctccag tacaatttta atagcaatgg tgagagtgtt taaatgtact    32640
cctgtgtata ttttattctt ttggaactta ttataaatgg aattgttttc ttaattttct    32700
ttttggactg ttcattgcta ttgtacagaa atacaactga ctattgtgtg ttgatcttgt    32760
accttgcaat tttgctgaaa tcgtttattt tttgcaatag attttttgtga attctttagg   32820 attttccata tgtagaatca tgttatctgt gaatagggat agttttactt cttttctaac    32880
ttggatagtt ttttccttcc taattgctct ggcaagaact tctagtacaa tgttagagag    32940
caatagtgaa agcaggcatc ttccttcaa tcctgatgtt aggggtgaag ctctcagcct     33000
ttcactgtaa tgttggctgt ggattttcat aattttttgt ttgtttgttt tttgtttga    33060 gacggagttt ctcttgttgc ctgggctgga gtgcagtggc gtgatctcgg ctcatcacaa    33120
cctctgcctc ctgggttcaa gcgattctcc tgcctcagcc tccagagtag ctgggattac    33180
aggtgcctgc caccacaccg actaattttg tattttttagt agagacgggg tttctcgatg   33240
ttggtcaggc tgctctcgaa ctcctgacct cagatgatcc gcccgcctcg gcctcccaaa    33300
gtgctgggat tacaggcatg agccaccacg cccggcccat aaatgctttt cttaatcata    33360
ttaaggaagt tcctttctag tcgtagtttt ctgagtgttt ttattatgaa agactttcag    33420 attttttgtaa aatgcttttc ctgcgttaat tgagataatc atatgggttt tctcccccctt  33480 tactctattg atgtaatgca ttacaacgat tttttttaat gtttacccat cttttgcattc   33540 ctggaataaa tactagttga ttgtgctgta taattcttaa aatatgctgc tggatttgtt    33600
ttgttagtat ttggttgcat tcttttgcat ctatattcat aagggatatt gatctgtaac    33660 tattatttc ttgtggtggc tttatctggc tttggtatca agataatgct ggccacattg     33720
gctaagttag aaagtgttct ttcttctatt ttttgaagag cttgaaaaga gtcgtgttaa    33780 ttcttctta aatatttggt acaattcact attaaagcca ctagtcctgg gcttttctta     33840
gtttgaaagt ttttgattac taattcaatc tcttttacac ctagattaga ttttgtattt    33900
tttccttagc cacttttggt aatgtgtgtg cttccgggaa tttggccagg tcatctctgt    33960
tatctaattt gctggcatcc aaatgttcat aatgttctct tgtaatccctt tttattatag   34020 aaatgatata cagaaaaggt cagttaccac tttcttttat gattgcatta atttgcttct    34080
tttctctttt tttctctagt cagtcttgct aaaggttggt ctgttttgtt gatttttttc    34140
aaagaaccaa cttttgattt tgttgattct ataatttttc tgctctgtat tttgtgtata    34200
tccattctaa ttttttattag ttcctttatt ctgttagctg tgagtttagt tggctcttct   34260
tttttatttt cttaaggtgg aagactaagt tattgagata tatcttgttt ttttttttga   34320
tgtaggtatt taaagctata aaatttcctc tgagcattgc ttttgctgca atttataagt    34380
attggtatgt tacatattca gttagttttt tatatacaca tttaagcttt tgctaatcta    34440
```

```
ccttgtgatt tcttcattga cttattgctt gtttgagtgt gtcaacaatt tccacgtatt   34500
tgtgaatatt ctagttttcc ttttgttatt gatttctagt ttcatttcat tgtggtaaga   34560
aacaatactt tttatgatct caacagttta aaatttatta agacttattt tctggtctaa   34620
catatgatct atcctggaaa atgtatcatg tgcacttgag aaaaatgtat attctgattt   34680
ttttaggtgg gtggcatgtt ctattaatat atatgtctgt tagctctagg tgaattatag   34740
tgatgttcaa agcctccatt ttgttattaa tataaccatg ccagatttt aatgctgtcc     34800 atttgcataa tatgtctctt tccattcttt ttcttttaca tgatcacttt atatttatag   34860
tatatttctt gcacacagaa tgtaattgaa acttactttt ctaaaatcta ctttcttttt   34920 ttttttttg agatggagtc ttgctctgtt gcccaggctg gagtgcagtg gcacaatctt    34980
ggctcactgc aatctctgct tcccgggttc aagcaattct cctgtctcag cctcccgagt   35040
agctgggatt acaggcacct gtatttttag tagagacggg gtttcaccat gttggtcagg   35100
ctggtcttga actcctgacc tcgtgatcca cctgccttgg cctcccaaag tgctgggatt   35160
acaggcgtga gccactgcac ccagccccta aaatctgctt tcatagcatc tgtcttgtac   35220
ttggaacatt tagtccatgt gtatttgaat atttattgat atgtttgggt ttatgtttac    35280
aatcctgcta tttgttttct ttttgttcca tgtgtttttt gttttttatt tctgcatctt   35340
ttggaaaaat cagattttt ggtaattcat ttttcttatt ttattggctt tttagagaaa    35400 cctttaata tctttgtgag ttttagggat tacattattt attcttatta ttattccatt     35460
tagaattaat attgttaatc ccattcaaaa atttgtttat ttcgcttttc agttctagaa   35520
ttttcatgtt ttcttcagtt gttgtttctc tgttgttatt ctccatttgt tcattatatc   35580 tatctttct ttgaaatcct taaaatatt tataatagct attttaaagt cctctgctaa     35640
tcccaatgtc tgggacatct tggcttctgt tgatattgaa tacttctttt tttcccctta   35700
attaagggtt tcattttcct gcttttcac atatctagta gatttttatt atgctctgtg    35760
tgctatgaat gagatattat aggaagcctg gtcaatattg tctcttttta aagggtgttg   35820
tatttagttc tgccaagaag ttaaattacc agatttactt gatgtggctt tagtcttgt    35880 tagagctggt ctattcctgc tttgttctta cttctcaggt aatgaccttc ctgagtttca   35940
gctggatgcc tgaagtgctc agctgcattt ttctactctg gctattctga aatgcaatat   36000
tttccagacc tacccaacct ttggtattca tctcccagac ctgtggctgc ttctctttgc   36060
tgagcctcac aaaatcttgt cctgtgcatg gacagccaag gatccttggg aaatctcatg   36120
cagacttcta ggtccttcct ttgtgtagat ttcttctctc cagtacgttg acctgcttca   36180
gagtcctcat cattgctttc ttcctttttca gctcagcaat actgctgtgt attgtgtggg   36240
cttcatttgc ctcagccata cctagaacac aacccaaggc agaaagctgg agtggacctg   36300
aggctcatca cctgtttcct tccacccacc atttaaaagc agcttatttg tgtgaaactt   36360
tttgttgggt tctgtggggg atacgtatag gcaaatgaca gggagcttat aatttagcca   36420
aagagaaaat gtctatatgt tctgtggaat tcagagtatt ttcctcgact tccaaaatta   36480
ttttcctcga cttccaaaat tgggggctac tagctagttg gtaggaagga attccagatc   36540
catttttctt ctagattttt ttcagactcc atgtttcaaa atctagatgg aaggtaagaa   36600
ggaagcaagg agggcatcac atacgagaga gacttatacc ccaaagtgga tcattagcac   36660
attatgagat aatatggtat tattctcaga ggcctgccat ataaaattcc ttctaattta   36720 tttttttaatg gtatgtgcct gaaagttttc tgtctttcat gatcttgaaa gcaaaataag   36780
```

```
aaccagagta gcttatgaga gagttttcct gcttcagccc agaaaaatgt tgcttctgtc    36840 ctagacccctt tgatctggtt cttagtgcca gccttcattc ctctagatct gtttattgaa   36900
tactggctct gttgcagaga ctttgctaga atctgagaga taaaagactc aatgccttca    36960
aaacacctac aatccagaca cttaaataaa tgcaataata tatggttaag gtcttggata    37020
gaggaccatc atagaaacac atagaacaga catttagtcc atgctaggga gagggaagat    37080
gtcaaggaat gcttcctgga ggtggcgaca tctaagctga gttttaaagt gggtgtaaga    37140
gtgaaggaac tgggaatagg caaaacatac cttagagagc tgcacctcca aagcatggaa    37200
ggctagataa tcttagaact tcaagtgggg ttcaatgtgc ctgggacttg gatttcaggc    37260
agagaccata gggcaagttg gagaacaggt gggcagggtg agatgaagca gagactttta    37320
ataaccatca aacaggcctg ccatccaact gctatcagcc attttccctt tttgaatttt    37380
atttttttaa tctctagagc aatacatgtt tatggtagga aatgaaaaaa atatatagat    37440
gggtaaaatg aagtgaatta taccacccac aatcctgctg taaaacaggt tttaacaagt    37500
tataaatccc tccagatcaa agtgctacta aactctactt gctatttat aaccttttc      37560 tgttcagagt attttagaaa cgttttaca tgttaattga tattcttttg cattatcctg     37620
aataatggta tttctttagt tatactatca tgtattaaaa cattcataca tggtaaacat    37680
atttgaatat tagacatttc aattgttttc aatgtttggc tattaaaaat agtatttaga    37740
tgaatgttct tggccataca gttaataact tcactgagtc cttgtcaata actttattaa    37800
atcccaatct taagacaaca agcctataag attaacatac caggaataat tagaaagcat    37860
tgcaagacta tatgtaacca tctccctgtt aatcatcctt atttgttgca acatcctaaa   37920
tagcgacctt cccacactct gcctcataat atttaatctg tcaaatgtac catccgcaaa   37980
gggagtgaac tggctcgtga agaggtggtg aagctggttc aactcagttt aacagacaat   38040
gagggcctcc gtgtgccagg gagggagtga gggaactcca cagggagctc attctgggga   38100
gggatgcccc tcattatctg cagtaaatga tattagagaa gtatgtgtga gactcttggt    38160
gtccagagga ggggcatgca gcacagtatg ggggtccatg gggttgcagc gatttcttag   38220
agacggtgcc atgcctggga tgaccaccaa gttaggatgc tgtaaagagt aatcaaataa    38280
gtttcaacag ggttttggca tgaggtgagc agttaatcca aatgatatct gaaatgcttt    38340
ctaatgctgc aagtgtattc ctctgtaaaa taatcaacta cttaaaagac actctcactt    38400
gcattatgtc atttaatcct cacagtgtcc ctacgggaca atagatgtca ttcccacttg    38460
tacagagcag taagtgaggc tcacaccggt catagttaga ggagtaggga atctaaacct    38520
aagtctcttc tactccaaac cccaagtttt atcagtatgt cacatcgcta ctgtgggctg    38580
aattccttag cagggttgt ttcctccacc tgcaatattc ttccttttgg tttgttcatc     38640
ctctagagag agaagggata cgcattcatg gagatcctac tgttgcaaac tctgcattag    38700
gagttttaca tgaattgtct catttagtcc tcacaacagt cctgtgaggc acaggaaagt    38760
tagatttacc tgcccaaatt aaggaatgtg gccaactcaa gagtgacgaa ggccaggtgc    38820
ggtggctcat gcctgtaatc tcagcacttt gggaggctga ggtgggaggc tgaggatcgc    38880
ttgagcccag gagtttaaga ccagccaggg caacacagca gatttaatc tctactagaa     38940 ataaaaaga aattagccag gtgcctgtag tcccagttac ttgggaggtt gaagtgggac     39000
gattgcttga gcctggggagg tagaggctgc agtgagccat gatcccatca cttcactcca   39060
gtcagggtga cagagtgaga cccagtctta aaacaaaaca aaacaaaaaa gagtgatgga    39120
gcaggaactt tatctgccat cagagaccat atatgtcttt ccttatggcc caggtcattt    39180
```

```
atcatgtcct tgctaaacct cctcctctga gccttgttaa agtcctcaag gttagaagag    39240
tggtctataa ttataaaaaa ttccattgta tgacttcagc tacctgcaaa actgaccgag    39300
attaatgcat tctttgtttg ctttcactct ttcattccct gttcagcgct tattctacag    39360
aaaggtgcct ggtagattta ggacatgact gttcataggc ctcaaatgcg gtcaaattag    39420
gaaagtcccc tggttttttgg tctcaagagg ttaattgctg agtactagcc tggactgctc    39480
aatggatttt atgtttaact gttgtgttta tttgtttgtt tgttttttgtt ttgtgagaca    39540 tatctttctc tgtcacctgg gctggaggtc agtggtgtga acatggctca ccgaagcctc    39600
catctcctgg gctcaagtga tcctcctgcc tcagccttcc tagtagctgg gactacaggc    39660
acacagcacc atgactggtt aagttttgga ttttttggta gaaatggggt ctcactcttt    39720
gcgcaggcta gttgtgaact cctggtatca agggattctc ccaatgtgct gggatttcgg    39780
cctcccaaag tgctgggact gcaggcatga gccatcatgc ccagcctctg tttaactgtt    39840
aacatcatga ggtttccttt caatgaggaa gggaggcctg ggggaggtgtg atggggaaga    39900 tggagaaggg taggagacat cataaaactg acagaagtgt ggcacgatta agaccctggt    39960
ttcttagacc acataagcaa gtgccactat tcttttgatc aacatttgat tctctatttc    40020
cttcttagca tatagatagc tgcttcaggt cgtgaaaaaa tacatttagt gaaatgaaac    40080
atagtagata tgttcaccaa gaaactaaaa agaaaagtta gccacaaact atcttatttc    40140
attgaaatgt ttggctgaac ccataagaat gttgatgagg ccattcttgg atgcctgtac    40200
tgaaatgaac cacgagagga atatttagga tatgttgaag aggctgtttg gcttaatgaa    40260
caaaggagtt tctgcaggcc cagggagtgg aatgaaaatt ggcatgatca ttttggagaa    40320
tatatggagt caaacagaga atttgaatgg agttttcaaa gaggatatgt tagggggaata    40380 aaggctgata acaacacttt gtatttgtag gaaaataggg agagtaaatc aaggaattca    40440
aagagaaaga gaaactcact tcaagtaggg gagaaaaaac ccctataatt ttcactcttc    40500
cttgtaaata aaaaggaaac aaatgaaaat aagatattag aagtcagtaa gaatttatgg    40560
gagtataaag ttggtttat ggatgcaaag ccctttttcac tgctgtacga aactcctggc    40620
tgcatgctaa caatggacaa ctgatttcct tgcagctgta ttttgctgtt ttttgctctt    40680
ggcttggacc tagcaccctg ggtctgtggg aaaccagaac tgtcccagag ttctggaggg    40740
taggccaagg ttagatgctg gagtgggttc tttaatttat tgtactgatt cttcttggga    40800
agaaagaaga ttgcttgtta gaattttagc tacgagagat gactatgaaa cagtaaatta    40860
actccaacga cctgagtcat tttgaaaact cccagtctca ggataaaaaaa tataatccta    40920 tttagaaatt cctggtgtga tcacagatgt agcattggtt cttttcatga aacccgtaaa    40980
ttaaaaagta cataatccaa agtcaattaa atagtaagct attataacaa attcttttat    41040
ttcattagct tttcaaaatg tggataacta cacactcaac ccaaggaatc tacatttttc    41100
cactgactgc taaagaccaa tggaaataac tctagtcccc gtagcacctc actgtggggt    41160
gacctacctt tgaaataatg tattggttct agctgatttt tatattgtta gtcattaagt    41220
taggcttgat gagaaacaga tataatctga tttggggatt caagtattat attgcatttc    41280
tcctcacaac tagagataaa tttgccatgg ttttttctctt cataggctca tgccaaagtc    41340
tggcatctct acaatacttc tttccgtccc actcagggag gtcaggtgtc cattgcccta    41400
agctctcact ggatcaatcc tcgaagaatg accgaccaca gcatcaaaga atgtcaaaaa    41460
tctctggact ttgtactagg ttggtttgcc aaacccgtat ttattgatgg tgactatccc    41520
```

```
gagagcatga agaataacct ttcatctatt ctgcctgatt ttactgaatc tgagaaaaag    41580
ttcatcaaag gaactgctga cttttttgct ctttgctttg gacccacctt gagttttcaa    41640
cttttggacc ctcacatgaa gttccgccaa ttggaatctc ccaacctgag caactgctt     41700 tcctggattg accttgaatt taaccatcct caaatattta ttgtggaaaa tggctggttt    41760
gtctcaggga ccaccaagag agatgatgcc aaatatatgt attacctcaa aaagttcatc    41820
atggaaacct taaaaggtat gattgtgggt aaagttctca tttcctgcca aaatcttctg    41880
gaaaaaaatc tctaagatta tctaacataa atgatgtgaa tttatatttt taaatcctaa    41940
tggagacatt cattttggca atagtagaat gcattcattt aacacctttc tcatttggag    42000
tcttgaggaa cttgaattaa tttttaaaaa cccatttgta aatgagaaac tgggttataa    42060
tatttgtaat tacttaactt tcagttatta atctagattt ttagattaaa ttgaacataa    42120
aacaaatccc aggatatcta gctctctgca catgttttc  agttcttgtt attttggttg    42180
aataaaacac tttaaagaaa aaggaatgtc catgttttct agagaaaata gtataaatag    42240
atcatgcttt taaagccttc atttatttat ttattgcatc agacacaaag ctgggtgtct    42300
aggatggaaa gtggtacaag acatctttcc agccctgtag aatatctatt ataaataagg    42360 aactatttt  tcaaggtgct cagaaatcca aaaaacatat tagataggcc aattttgagg    42420
gcatttattt gtagagttat ataggtttga ttagagtctt tcgtcaagaa gaaaaatcat    42480
tggcttacca aacgagaagc attacacttt atttatttaa gtaggaaacg ctcagctgct    42540
cttgaaccat gatgcaagtg cccagcgaag ggtcatgttg ctcttgtccc ctcttcccct    42600
tgcagccatc aagctggatg gggtggatgt catcgggtat accgcatggt ccctcatgga    42660
tggtttcgag tggcacagag gttacagcat caggcgtgga ctcttctatg ttgactttct    42720
aagccaggac aagatgttgt tgccaaagtc ttcagccttg ttctaccaaa agctgataga    42780
gaaaaatggc ttccctcctt tacctgaaaa tcagccccta aagggacat  ttccctgtga    42840 ctttgcttgg ggagttgttg acaactacat tcaagtaagt cagctgacaa aaccaatcag    42900
cagtctcacc aagccctatc actagtaagt agtgcttcct tcctaggctg attgtcatgg    42960
cacattgtcc gttctttgag ccaaaaacaa ttccttatga gtacactaag ggcacaattt    43020
ggaatgctgc acccttctct ccaaaactct tccaatcttc atcttgttta agttagatcc    43080
aaagataaat aaatttaaag catatcaata tttaagatcc gattaagaca gtaaaaagat    43140
aaaacactct cttttcatac tgtggttttt gatccttttt aaggcagttg agttttttca    43200
tgaacaggat ctaacacaga actccaaagc ctctgagttt cagtggtgct gctgagactg    43260
aggcaggaac attaggcaga gtcctccaga ggcacaactg tgggctccac aaatgtgcag    43320
aaatacccta agaaagtaaa ccctagatcc aatgattcac tggtcagaat gtctttttta    43380
gcaatagtca ttgaaatgat acgaaatttc ttcagaatga tcaaccaata tttattgagc    43440
atcttctcag tagtaagccc ttaacattct ttcagacttc ctaaattttg aaggggcttg    43500
ttttccagca tttgactgga tactctagta agcacttatt ggatgtctag tgtgtccgaa    43560
gccttgtgtt agttgctcgg gtcgcttggt taagggagt  gcaggtagag ggtatactga    43620
gatgagtaag ggtaaccttt gctttcaaag gagcaaagga gtctactgag cgaaaacaat    43680
gtatgcacaa atgatgcaat ggagtgaagc gggcatggtg gtaagtaaca agggcgggc     43740 tgggggattg ctgctgatag agtcccaagt gtgaaaatag ccctcaagac agagacagag    43800
ttcagtgtcc atagacaagc agttggcttt gacatgttgg gttatggtag ccaattaatt    43860
ggttctgcaa atcacagctt gaaaggaaac acttggaaga atgtgaaatg ggttgctgtt    43920
```

```
ttcttgtaaa tatccaattg aaatctttta tttataagga aataaattaa caccatcctt    43980
agtacatttt ttgctggttg ggattattct tcttttccag accacccagt tcattttaca    44040
ggcagtctca gacttaaacc ctcgccttcc atttaaaaga tgactggctc acgcctgtaa    44100
tcccagcact ttgggaggcc gaggcgggcg gatcatgagg tcaggagatc aagaccatcc    44160
tgaataacac ggtgaaaccc cgtctctact aaaaatacaa aaaaaaaaaa aaaattatc    44220 cgggtgtggt ggcgggcacc tgtagtccca gctactctgg aggctgggc aggagaatgg    44280 catgaaccca ggaggcggag cttgcagtga gccgagattg cgccactgca ctccagcctg    44340
ggtgacagag caagagtccg tctcttaaaa aaaaaaatga ctggatgtgt catcttttat    44400
gccaggatat gtgagcccag gagaaaggct tctgagctcc ctcctgctcg gtgtgcaatt    44460
ttctgccctg ccccgactct ctccttctct cccagcctcc tgctatttga aatctcctta    44520
tcctaatttc cctcctcaga gtggattcca ctgtggggtt cagagaggat ctgaggtggg    44580
agaagtgagg ctggtgagga agaaggggag gagaaaggga agaagacctc cgtagccttc    44640
cttcctcctc ctctttactg gggttgggga tagatcggat ggtccctggt ccttgttcta    44700
tctcttgacc ttctgcctgc tccctgctga gcacggatct ctgatagcag cctgagtctg    44760
gcaggttcag tcctttgtat gcggcacaat ctcccagcca gcattgctgt gcagatcatg    44820
ggaacgaatg cagaacaaga gtgggggtgt cggagggagc cctacttctc ctgttctatt    44880
cctcatcagg gggctgtgcg ctggctttgg gaattggtaa atagtgagaa agtcttaagg    44940
gtacatccta tttccttgag ggagaagaga aaacgctggt cagaagcaat aagtatagca    45000
gtgaatagca agggagatgg gagataaattc cttttcctac tacactctag aagctattgt    45060
tttagaatct gacctaaggt cagccactaa ttggccccag aggtctctct ctcagatcac    45120
acggtccttt tttcctcatc agcttgggga ccccaccccct cctcctggca gtctcctcct    45180
gtgcagaacc caacaaacac aaaattaagt cactctcaaa cccacagcag atgagagctt    45240
ctctggaagc tccctggtgg ggaaaggctg caattgctat tttcttcttc tggttttcac    45300
ctcaggcttt gtgttatatt gacagtaccc ttctcaagct aactccctaa ctgacctgac    45360
gtagtcaaaa taagttcttt gtatgtcagt tctgaggtgt gtgtgttttc acttacaaac    45420
agtactctac agcttaaaga cattatatta aagtcctgag aagtgatttt taaaccactg    45480
aacttcatct tttccctcct ggctagtatt tcagactttc agtgtttgag gcatgcattt    45540
cacctgaaca acttgaaaaa taatatccta agaagcacac aacctgactt taggctcatt    45600
cacatggatt gtcactttac ttggacccac tttctcggct gagaggtttg ttttcccata    45660
accacggatg ctcatagtta atataaatat tgaactcact atgtagtgag gacatagagc    45720
ctctttaaca ttggtccctg ttaggagaaa gtttctccca taacatacta aatacatgtt    45780
ttaatagccg ttccttctga aaggtccaac ttcactattt tattttttta gtaaaatctt    45840
agttaacaaa ttaatggagg ttaggtggaa ttttgcccca aaagtcctgt attttctttt    45900
tttttttttc tttttttttg acagagtctt gctctgtcgc ccaggctgga gtgcagtggc    45960
gtgatctcgg ctcactgcaa gctccgcctc ctaaggtcac gccattctcc tgcctcagcc    46020
tcctgagtag ctggggctac aggtgcccgc caccgcaccc ggctaatttt ttgtattttt    46080
agtagagacc gggtttcact gtgttagcca ggatggtctc aatctcctga cctcgggatc    46140
cacccacctc ggcctcccaa agtgctggga ttacaggcgt gagccaccat gcccggcctg    46200
tcctgtattt tcaagaaact tttttttttcc tccagaaatg atacccctagt ctttcatatt    46260
```

```
tgttttcaga tggactgaat aaaagctgtt gttttggaac aatcacggtt aaaaaaaaaa    46320
gttatgaatt tagtcaactc agagctctat aaaaataatc caaaaaattc cttcaaactc    46380
tgaacgcttc aaaagagcgt gcaaatattc tgtccttcaa agctaaggaa acatgatttg    46440
tggggtgcat cacagtggaa aaatactctg acagcattcc cacagcatta ggggaagtgc    46500
atgtgtgggt gttctgcaag ggacaattct ccagaaaagg caatttccct ttgacatgct    46560 gttttaatg acttttcttt ataaacacac ttatctctcc agagaaatag cagtgcattt    46620
gcaacaggcc cgtaaaatgc aacaaaacct ctgctatggt ttctgacccc tgcttttata    46680
cagagcatca gaccaaggaa cctgttctaa caggattatt tcagagggga acacaggctt    46740
agggtgcaga tcttccagct ggattttttca ctttgcattc cctccacagc agacacatga    46800
aggaatgatt ttgtgatttt gatttttataa tttgcacact tttcctaaat acttttttta    46860
aatttttatt tgggaggatt ttatagcata tgattgagaa ctataatcat catcattgtt    46920
acagaagaat aatttagaaa aattttttaa ctacgttaaa aattccacta tgggtggatg    46980
acaatattgt tctttccttc cacattctcc ctccttagac tttcttttct tttttctat     47040 ttttttttg agatgaagtc tcgctctgtc actcaggctg gagtgcagtg ccatgatcct    47100
ggctcactgc aacctctgcc tcccgggttc aagtgattct cccgcctcag cttcctgagt    47160
agctgggatt acaggtgtgc accaccacac ctggctactt tttgtatttt tagtagagat    47220
ggggtttcac catgttggtc aggctggtct caaactcctg atctcatgat ctgcccgcct    47280
tggccccgca aagtgccggg attacaggcg tgagccactg cgcctggcct ctctctcgga    47340 cttctacca tcagtcagat tgaatttgtt aaattctgtc actgaccta aacccaacaa     47400 aaggcaagag ttatgtttat ttagcacttc ctctaccatat agcaaacctc aatttagagc    47460
gtaattttaa gcacaattta attataaata tcttttcatt ttcttactta actcactcag    47520 tttttaaat cttcttttttt gagacaagat cttgctctgt cactgaggcc gatgtacagt    47580
gatgtgatca tgacttactg cagccttgac ctcccaggct taggtgatcc tcatacctca    47640
gcctcccgag caactaggac tacaggcccg tgccaccatg ccgggccaag acggggtttg    47700
gacgtgttgc cccagctggt ctccaactcc tggcctcaag tgaccctccc gcctcggcct    47760
ctcaaagtgc tgggattata ggcatgagcc accgcacctg ccaactcac tcacatttta     47820 agttttttct ttttttcatc tagttttttt tcttttttaaa tttgaaagcc tcatgacatt    47880
aatgatttct tacattaaaa gaaaaacacc caaaaatact ctgcttacat aacaccgaca    47940
agtagtgtgc aagactcatt agcatttgtc atctgaagtg accaaatcca gactttttggg    48000 ggtcacatta agaaacagt tgaagagtta gaactatggg taaagcgagt gtgcatatca     48060
gaaagtggaa tattgtcttc ctcaggagct gacaatttat gaaaaatagt tcacattctc    48120
agctagaaag gcttctatttt ttgctcatat tcctggctag ttttgctgaa ataattgctt    48180
tgaattactt cctcaggact gcccaggtga cgctaatgtt tactctgccc ttcacaggta    48240
gataccactc tgtctcagtt taccgacctg aatgtttacc tgtgggatgt ccaccacagt    48300
aaaaggctta ttaaagtgga tggggttgtg accaagaaga ggaaatccta ctgtgttgac    48360
tttgctgcca tccagcccca gatcgcttta ctccaggaaa tgcacgttac acattttcgc    48420
ttctccctgg actgggccct gattctccct ctgggtaacc agtcccaggt gaaccacacc    48480
atcctgcagt actatcgctg catggccagc gagcttgtcc gtgtcaacat caccccagtg    48540
gtggccctgt ggcagcctat ggccccgaac caaggactgc cgcgcctcct ggccaggcag    48600
ggcgcctggg agaaccccta cactgccctg gcctttgcag agtatgcccg actgtgcttt    48660
```

```
caagagctcg gccatcacgt caagctttgg ataacgatga atgagccgta tacaaggaat   48720
atgacataca gtgctggcca caaccttctg aaggcccatg ccctggcttg gcatgtgtac   48780
aatgaaaagt ttaggcatgc tcagaatggg aaaatatcca tagccttgca ggctgattgg   48840
atagaacctg cctgcccttt ctcccaaaag gacaaagagg tggctgagag agttttggaa   48900
tttgacattg gctggctggc tgagcccatt ttcggctctg gagattatcc atgggtgatg   48960
agggactggc tgaaccaaag aaacaatttt cttcttcctt atttcactga agatgaaaaa   49020
aagctaatcc agggtaccct tgactttttg gctttaagcc attataccac catccttgta   49080
gactcagaaa aagaagatcc aataaaatac aatgattacc tagaagtgca agaaatgacc   49140
gacatcacgt ggctcaactc ccccagtcag gtggcggtag tgccctgggg gttgcgcaaa   49200
gtgctgaact ggctgaagtt caagtacgga gacctcccca tgtacataat atccaatgga   49260
atcgatgacg ggctgcatgc tgaggacgac cagctgaggg tgtattatat gcagaattac   49320
ataaacgaag ctctcaaagg taaggagccc tagctgcggc tatctcctga aggttatgtc   49380
accagagggc atgacacttg attaaatctc caacatcaac acacactgcc accttggaa    49440
tggagggcta tccattttgt gcctcactga aacagtccaa gagatatcta gcatttcccc   49500
aaggataaag gagtgtagct aaaagtagaa gaccagaaat ccctagcccc tactctggat   49560
ctatgcaagc ctagattctt gtcttccatc ttggatggct ccacagcagt cttaactgtt   49620
tcatgtacat aaagcagtac ataagattt  aaccttgctg gcatggtgg  ctcacacctg   49680
taatcccagc atttggaag  gccaaggcag gaggattgct tgagcctaga agtttgagac   49740
cagcctgggc aacatagtga gaccttgtct ctactaaaaa tcacaaaaat tagctgggca   49800
cggtggcata tacgcctgca gattcagtta cttgggagga gaggcgggag gattgcttga   49860
gcttgggagg tccagctgca gtgaatcatg atcacagcac tgcaatctgg cctgggtgac   49920
agagcaagac actatttcaa aaaaaaaaag accaagcatg gtggctcatg cctgtaatcc   49980
cagcactttg ggaggctgag gcaggtggat catctgaggt cagaagttca agaccagcct   50040
gaccaacatg gtgaaacccc gtctctactg aaaatacgaa aattatccag gtgtagtgat   50100
gcacacctgt aatctcagct actcgggagg ctgaggcaga gaatcactt  gaactgggga   50160
cgtggaggct gcagtgagcc aagattgcac cattgcactc cagcctgggt gacagagcaa   50220
gactccatct caaaaaaaaa aaaaaaaaaa aaaggattta acccaagtat atcatagtag   50280
attgaattat gtaaaacacc catttaacaa ccaggtccag gtttgttctc tctgtgtagt   50340
aaatcaatca ctgtgacaca ggttttgcaa agagaaaag  atttatttgt aaggggacca   50400
agcgaggggg tgggagaata acttccaatc ctgcctctct gaagacaagg cttaggaata   50460
tgtatgggtt agggaatggg tggtctaagg catggtgaag agtgattggc aggggggaa    50520
aatgaagtaa caggttagac acatgcacag aaaatggtgg tgttagcatg atctgagggc   50580
agagttttgg gccctctgac gtcaaaagac cacctctcag gcacttgtgc aggcccagtg   50640
gaagggtcag tggtcttaac tagtttgaac tggacaggag ctgccccaag ttcttggaaa   50700
aacaactgaa gtgaccattg ccatggtaac ctatgaatgt catcagtaaa gtagccagtg   50760
aaggttaagt ttcagcatac aatgggacaa ccttcagctt catggaaaaa ggaaaaaaaa   50820
aaaacacata cacacacgaa agcaagtga  ccaaaagcaa gcaggacagg cagacctgat   50880
ccaattaacc cctgggtttc aaccctgcta aatgcagctc aatatttgtc ttgataattt   50940
gcctatttgg ctttacataa aataaagcct tttctgatga aatctaattg agtctgaagt   51000
```

```
tgtattaaat ggtatcggaa acttcccagc aggaaggcta cgtaaaagtg gccgggcgtg   51060
gtgactcacg cctgtaatcc cagcactttg ggaggctgag gcaggcagat cacaaggtca   51120
agaaatcgag accatcctgg ccaacatggc gaaatcccat ctctactaaa aaaaaaaata   51180
caaaaatttg ccaggtgtgg tggtgctcac ctgtagtccc agctactcag gaggctgagg   51240
caggagaatc tgttgaacct gggaggcgga ggttgcagtg agtcaagatg gtgccattgc   51300
actccagcct gtgtgacaga gcaagactcc gtctcaaaaa aaaaaaaaag tgatgtgttg   51360
tgtgcaaaat acgtaataac tactctccta tccttttgtt tttccagccc acatactgga   51420
tggtatcaat ctttgcggat actttgctta ttcgtttaac gaccgcacag ctccgaggtt   51480
tggcctctat cgttatgctg cagatcagtt tgagcccaag gcatccatga acattacag    51540 gaaaattatt gacagcaatg gtttcccggg cccagaaact ctggaaagat tttgtccaga   51600
agaattcacc gtgtgtactg agtgcagttt ttttcacacc cgaaagtctt tactggcttt   51660
catagctttt ctattttttg cttctattat ttctctctcc cttatatttt actactcgaa   51720
gaaaggcaga agaagttaca aatag                                         51745

<210> SEQ ID NO 28
<211> LENGTH: 51745
<212> TYPE: DNA
<213> ORGANISM: Homo sapiens

<400> SEQUENCE: 28
ctatttgtaa cttcttctgc ctttcttcga gtagtaaaat ataagggaga gagaaataat     60
agaagcaaaa aatagaaaag ctatgaaagc cagtaaagac tttcgggtgt gaaaaaaact    120
gcactcagta cacacggtga attcttctgg acaaatcttt tccagagttt ctgggcccgg    180
gaaaccattg ctgtcaataa ttttcctgta atgtttcatg gatgccttgg gctcaaactg    240
atctgcagca taacgataga ggccaaacct cggagctgtg cggtcgttaa acgaataagc    300
aaagtatccg caaagattga taccatccag tatgtgggct ggaaaaacaa aaggatagga    360
gagtagttat tacgtatttt gcacacaaca catcactttt ttttttttt gagacggagt     420 cttgctctgt cacacaggct ggagtgcaat ggcaccatct tgactcactg caacctccgc    480
ctcccaggtt caacagattc tcctgcctca gcctcctgag tagctgggac tacaggtgag    540
caccaccaca cctggcaaat ttttgtattt tttttttag tagagatggg atttcgccat     600
gttggccagg atggtctcga tttcttgacc ttgtgatctg cctgcctcag cctcccaaag    660
tgctgggatt acaggcgtga gtcaccacgc ccggccactt ttacgtagcc ttcctgctgg    720
gaagtttccg ataccattta atacaacttc agactcaatt agatttcatc agaaaaggct    780
ttattttatg taaagccaaa taggcaaatt atcaagacaa atattgagct gcatttagca    840
gggttgaaac ccaggggtta attggatcag gtctgcctgt cctgcttgct tttggtcact    900
tgcttttcgt gtgtgtatgt gttttttttt tttcctttt ccatgaagct gaaggttgtc    960
ccattgtatg ctgaaactta accttcactg gctactttac tgatgacatt cataggttac   1020
catggcaatg gtcacttcag ttgttttttcc aagaacttgg ggcagctcct gtccagttca   1080
aactagttaa gaccactgac ccttccactg ggcctgcaca agtgcctgag aggtggtctt   1140
ttgacgtcag agggcccaaa actctgccct cagatcatgc taacaccacc attttctgtg   1200
catgtgtcta acctgttact tcatttttccc ccctgccaa tcactcttca ccatgcctta   1260
gaccacccat tccctaaccc atacatattc ctaagccttg tcttcagaga ggcaggattg   1320
gaagttattc tcccaccccc tcgcttggtc cccttacaaa taaatctttt ctcttttgca   1380
```

```
aaacctgtgt cacagtgatt gatttactac acagagagaa caaacctgga cctggttgtt    1440
aaatgggtgt tttacataat tcaatctact atgatatact tgggttaaat ccttttttt    1500 ttttttttt ttttgagatg gagtcttgct ctgtcaccca ggctggagtg caatggtgca    1560
atcttggctc actgcagcct ccacgtcccc agttcaagtg attcttctgc ctcagcctcc    1620
cgagtagctg agattacagg tgtgcatcac tacacctgga taattttcgt attttcagta    1680
gagacggggt ttcaccatgt tggtcaggct ggtcttgaac ttctgacctc agatgatcca    1740
cctgcctcag cctcccaaag tgctgggatt acaggcatga gccaccatgc ttggtctttt    1800 ttttttgaa atagtgtctt gctctgtcac ccaggccaga ttgcagtgct gtgatcatga    1860
ttcactgcag ctggacctcc caagctcaag caatcctccc gcctctcctc ccaagtaact    1920
gaatctgcag gcgtatatgc caccgtgccc agctaatttt tgtgattttt agtagagaca    1980
aggtctcact atgttgccca ggctggtctc aaacttctag gctcaagcaa tcctcctgcc    2040
ttggccttcc aaaatgctgg gattacaggt gtgagccacc atgccagca aggttaaatc    2100 tttatgtact gctttatgta catgaaacag ttaagactgc tgtggagcca tccaagatgg    2160
aagacaagaa tctaggcttg catagatcca gagtaggggc tagggatttc tggtcttcta    2220
cttttagcta cactcctttta tccttgggga aatgctagat atctcttgga ctgtttcagt    2280
gaggcacaaa atggatagcc ctccattcca agggtggcag tgtgtgttga tgttggagat    2340
ttaatcaagt gtcatgccct ctggtgacat aaccttcagg agatagccgc agctagggct    2400
ccttaccttt gagagcttcg tttatgtaat tctgcatata atacaccctc agctggtcgt    2460
cctcagcatg cagcccgtca tcgattccat tggatattat gtacatgggg aggtctccgt    2520
acttgaactt cagccagttc agcactttgc gcaaccccca gggcactacc gccacctgac    2580
tgggggagtt gagccacgtg atgtcggtca tttcttgcac ttctaggtaa tcattgtatt    2640
ttattggatc ttcttttttct gagtctacaa ggatggtggt ataatggctt aaagccaaaa    2700
agtcaaaggt accctggatt agcttttttt catcttcagt gaaataagga agaagaaaat    2760
tgtttctttg gttcagccag tccctcatca cccatggata atctccagag ccgaaaatgg    2820
gctcagccag ccagccaatg tcaaattcca aaactctctc agccacctct ttgtccttt    2880 gggagaaagg gcaggcaggt tctatccaat cagcctgcaa ggctatggat attttcccat    2940
tctgagcatg cctaaacttt tcattgtaca catgccaagc cagggcatgg gccttcagaa    3000
ggttgtggcc agcactgtat gtcatattcc ttgtatacgg ctcattcatc gttatccaaa    3060
gcttgacgtg atggccgagc tcttgaaagc acagtcgggc atactctgca aaggccaggg    3120
cagtgtaggg gttctcccag gcgccctgcc tggccaggag gcgcggcagt ccttggttcg    3180
gggccatagg ctgccacagg gccaccactg gggtgatgtt gacacggaca agctcgctgg    3240
ccatgcagcg atagtactgc aggatggtgt ggttcacctg ggactggtta cccagaggga    3300
gaatcagggc ccagtccagg gagaagcgaa aatgtgtaac gtgcatttcc tggagtaaag    3360
cgatctgggg ctggatggca gcaaagtcaa cacagtagga tttcctcttc ttggtcacaa    3420
ccccatccac tttaataagc cttttactgt ggtggacatc ccacaggtaa acattcaggt    3480
cggtaaactg agacagagtg gtatctacct gtgaagggca gagtaaacat tagcgtcacc    3540
tgggcagtcc tgaggaagta attcaaagca attatttcag caaaactagc caggaatatg    3600
agcaaaaata gaagcctttc tagctgagaa tgtgaactat ttttcataaa ttgtcagctc    3660
ctgaggaaga caatattcca ctttctgata tgcacactcg ctttacccat agttctaact    3720
```

```
cttcaactgt tctttaatg tgaccccaa aagtctggat ttggtcactt cagatgacaa    3780
atgctaatga gtcttgcaca ctacttgtcg gtgttatgta agcagagtat ttttgggtgt    3840
ttttctttta atgtaagaaa tcattaatgt catgaggctt tcaaatttaa aagaaaaaa    3900
aactagatga aaaaagaaa aaacttaaaa tgtgagtgag ttggccaggt gcggtggctc    3960
atgcctataa tcccagcact ttgagaggcc gaggcgggag ggtcacttga ggccaggagt    4020
tggagaccag ctggggcaac acgtccaaac cccgtcttgg cccggcatgg tggcacgggc    4080
ctgtagtcct agttgctcgg gaggctgagg tatgaggatc acctaagcct gggaggtcaa    4140
ggctgcagta agtcatgatc acatcactgt acatcggcct cagtgacaga gcaagatctt    4200
gtctcaaaaa agaagattta aaaaactgag tgagttaagt aagaaaatga aagatatt    4260
ataattaaat tgtgcttaaa attacgctct aaattgaggt ttgctatagg tagaggaagt    4320
gctaaataaa cataactctt gccttttgtt gggtttaggg tcagtgacag aatttaacaa    4380
attcaatctg actgatggta gaaagtccga gagagaggcc aggcgcagtg gctcacgcct    4440
gtaatcccgg cactttgcgg ggccaaggcg ggcagatcat gagatcagga gtttgagacc    4500
agcctgacca acatggtgaa accccatctc tactaaaaat acaaaaagta gccaggtgtg    4560
gtggtgcaca cctgtaatcc cagctactca ggaagctgag gcgggagaat cacttgaacc    4620
cgggaggcag aggttgcagt gagccaggat catggcactg cactccagcc tgagtgacag    4680
agcgagactt catctcaaaa aaaaaataga aaaaagaaa agaaagtcta aggagggaga    4740
atgtggaagg aaagaacaat attgtcatcc acccatagtg gaattttaa cgtagttaaa    4800
aaattttct aaattattct tctgtaacaa tgatgatgat tatagttctc aatcatatgc    4860
tataaaatcc tcccaaataa aaatttaaaa aagtatttta ggaaaagtgt gcaaattata    4920
aaatcaaaat cacaaaatca ttccttcatg tgtctgctgt ggagggaatg caaagtgaaa    4980
aatccagctg gaagatctgc accctaagcc tgtgttcccc tctgaaataa tcctgttaga    5040
acaggttcct tggtctgatg ctctgtataa agcaggggt cagaaaccat agcagaggtt    5100
ttgttgcatt ttacgggcct gttgcaaatg cactgctatt tctctggaga gataagtgtg    5160
tttataaga aaagtcatta aaaacagcat gtcaaaggga aattgccttt tctggagaat    5220
tgtcccttgc agaacaccca cacatgcact tcccctaatg ctgtgggaat gctgtcagag    5280
tatttttcca ctgtgatgca ccccacaaat catgtttcct tagctttgaa ggacagaata    5340
tttgcacgct cttttgaagc gttcagagtt tgaaggaatt ttttggatta tttttataga    5400
gctctgagtt gactaaattc ataacttttt tttttaaccg tgattgttcc aaaacaacag    5460
cttttattca gtccatctga aaacaaatat gaaagactag ggtatcattt ctggaggaaa    5520
aaaaagttt cttgaaaata caggacaggc cgggcatggt ggctcacgcc tgtaatccca    5580
gcactttggg aggccgaggt gggtggatcc cgaggtcagg agattgagac catcctggct    5640
aacacagtga acccggtct ctactaaaaa tacaaaaaat tagccgggtg cggtggcggg    5700
cacctgtagc cccagctact caggaggctg aggcaggaga atggcgtgac cttaggaggc    5760
ggagcttgca gtgagccgag atcacgccac tgcactccag cctgggcgac agagcaagac    5820
tctgtcaaaa aaaagaaaa aaaaaaaag aaaatacagg acttttgggg caaaattcca    5880
cctaacctcc attaatttgt taactaagat tttactaaaa aaataaaata gtgaagttgg    5940
acctttcaga aggaacggct attaaaacat gtatttagta tgttatggga gaaacttct    6000
cctaacaggg accaatgtta aagaggctct atgtcctcac tacatagtga gttcaatatt    6060
tatattaact atgagcatcc gtggttatgg gaaaacaaac ctctcagccg agaaagtggg    6120
```

-continued

```
tccaagtaaa gtgacaatcc atgtgaatga gcctaaagtc aggttgtgtg cttcttagga    6180
tattattttt caagttgttc aggtgaaatg catgcctcaa acactgaaag tctgaaatac    6240
tagccaggag ggaaaagatg aagttcagtg gtttaaaaat cacttctcag gactttaata    6300
taatgtctta aagctgtaga gtactgtttg taagtgaaaa cacacacacc tcagaactga    6360
catacaaaga acttattttg actacgtcag gtcagttagg gagttagctt gagaagggta    6420
ctgtcaatat aacacaaagc ctgaggtgaa aaccagaaga agaaaatagc aattgcagcc    6480
tttccccacc agggagcttc cagagaagct ctcatctgct gtgggtttga gagtgactta    6540
attttgtgtt tgttgggttc tgcacaggag gagactgcca ggaggagggg tggggtcccc    6600
aagctgatga ggaaaaaagg accgtgtgat ctgagagaga gacctctggg gccaattagt    6660
ggctgacctt aggtcagatt ctaaaacaat agcttctaga gtgtagtagg aaaaggaatt    6720
atctcccatc tcccttgcta ttcactgcta tacttattgc ttctgaccag cgttttctct    6780
tctccctcaa ggaaatagga tgtacccttt agactttctc actatttacc aattcccaaa    6840
gccagcgcac agccccctga tgaggaatag aacaggagaa gtagggctcc ctccgacacc    6900
cccactcttg ttctgcattc gttcccatga tctgcacagc aatgctggct gggagattgt    6960
gccgcataca aaggactgaa cctgccagac tcaggctgct atcagagatc cgtgctcagc    7020
agggagcagg cagaaggtca agagatagaa caaggaccag ggaccatccg atctatcccc    7080
aaccccagta agaggagga ggaaggaagg ctacggaggt cttcttccct ttctcctccc    7140
cttcttcctc accagcctca cttctcccac ctcagatcct ctctgaaccc cacagtggaa    7200
tccactctga ggagggaaat taggataagg agatttcaaa tagcaggagg ctgggagaga    7260
aggagagagt cggggcaggg cagaaaattg cacaccgagc aggagggagc tcagaagcct    7320
ttctcctggg ctcacatatc ctggcataaa agatgacaca tccagtcatt tttttttta    7380 agagacggac tcttgctctg tcacccaggc tggagtgcag tggcgcaatc tcggctcact    7440
gcaagctccg cctcctgggt tcatgccatt ctcctgcccc agcctccaga gtagctggga    7500
ctacaggtgc ccgccaccac acccggataa tttttttttt tttttttgta ttttagtag    7560 agacggggtt tcaccgtgtt attcaggatg gtcttgatct cctgacctca tgatccgccc    7620
gcctcggcct cccaaagtgc tgggattaca ggcgtgagcc agtcatcttt taaatggaag    7680
gcgagggttt aagtctgaga ctgcctgtaa aatgaactgg gtggtctgaa aaagaagaat    7740
aatcccaacc agcaaaaaat gtactaagga tggtgttaat ttatttcctt ataaataaaa    7800
gatttcaatt ggatatttac aagaaaacag caacccattt cacattcttc caagtgtttc    7860
ctttcaagct gtgatttgca gaaccaatta attggctacc ataacccaac atgtcaaagc    7920
caactgcttg tctatggaca ctgaactctg tctctgtctt gagggctatt ttcacacttg    7980
ggactctatc agcagcaatc ccccagcccc gcccttgtta cttaccacca tgcccgcttc    8040
actccattgc atcatttgtg catacattgt tttcgctcag tagactcctt tgctcctttg    8100
aaagcaaagg ttacccttac tcatctcagt ataccctcta cctgcactcc ccttaaccaa    8160
gcgacccgag caactaacac aaggcttcgg acacactaga catccaataa gtgcttacta    8220
gagtatccag tcaaatgctg gaaaacaagc cccttcaaaa tttaggaagt ctgaaagaat    8280
gttaagggct tactactgag aagatgctca ataaatattg gttgatcatt ctgaagaaat    8340
ttcgtatcat ttcaatgact attgctaaaa aagacattct gaccagtgaa tcattggatc    8400
tagggtttac tttcttaggg tatttctgca catttgtgga gcccacagtt gtgcctctgg    8460
```

```
aggactctgc ctaatgttcc tgcctcagtc tcagcagcac cactgaaact cagaggcttt    8520
ggagttctgt gttagatcct gttcatgaaa aaactcaact gccttaaaaa ggatcaaaaa    8580
ccacagtatg aaagagagt gttttatctt tttactgtct taatcggatc ttaaatattg    8640
atatgcttta aatttattta tctttggatc taacttaaac aagatgaaga ttggaagagt    8700
tttggagaga agggtgcagc attccaaatt gtgcccttag tgtactcata aggaattgtt    8760
tttggctcaa agaacggaca atgtgccatg acaatcagcc taggaaggaa gcactactta    8820
ctagtgatag ggcttggtga gactgctgat tggttttgtc agctgactta cttgaatgta    8880
gttgtcaaca actccccaag caaagtcaca gggaaatgtc ccttctaggg gctgattttc    8940
aggtaaagga gggaagccat ttttctctat cagcttttgg tagaacaagg ctgaagactt    9000
tggcaacaac atcttgtcct ggcttagaaa gtcaacatag aagagtccac gcctgatgct    9060
gtaacctctg tgccactcga aaccatccat gagggaccat gcggtatacc cgatgacatc    9120
caccccatcc agcttgatgg ctgcaaaggg aagaggggac aagagcaaca tgacccttcg    9180
ctgggcactt gcatcatggt tcaagagcag ctgacgtttt cctacttaaa taaataaagt    9240
gtaatgcttc tcgtttggta agccaatgat ttttcttctt gacgaaagac tctaatcaaa    9300
cctatataac tctacaaata aatgccctca aaattggcct atctaatatg ttttttggat    9360
ttctgagcac cttgaaaaaa tagttcctta tttataatag atattctaca gggctggaaa    9420
gatgtcttgt accactttcc atcctagaca cccagctttg tgtctgatgc aataaataaa    9480
taaatgaagg ctttaaaagc atgatctatt tatactattt tctctagaaa acatggacat    9540 tccttttttct ttaaagtgtt ttattcaacc aaaataacaa gaactgaaaa acatgtgcag    9600
agagctagat atcctgggat ttgttttatg ttcaatttaa tctaaaaatc tagattaata    9660
actgaaagtt aagtaattac aaatattata acccagtttc tcatttacaa atgggttttt    9720
aaaaattaat tcaagttcct caagactcca aatgagaaag gtgttaaatg aatgcattct    9780
actattgcca aaatgaatgt ctccattagg atttaaaaat ataaattcac atcatttatg    9840
ttagataatc ttagagattt ttttccagaa gatttggca ggaaatgaga actttaccca    9900
caatcatacc ttttaaggtt tccatgatga acttttttgag gtaatacata tatttggcat    9960
catctctctt ggtggtccct gagacaaacc agccattttc cacaataaat atttgaggat    10020
ggttaaattc aaggtcaatc caggaaagca gttgcctcag gttgggagat tccaattggc    10080
ggaacttcat gtgagggtcc aaaagttgaa aactcaaggt gggtccaaag caaagagcaa    10140
aaaagtcagc agttcctttg atgaactttt tctcagattc agtaaaatca ggcagaatag    10200
atgaaaggtt attcttcatg ctctcgggat agtcaccatc aataaatacg ggtttggcaa    10260
accaacctag tacaaagtcc agagattttt gacattcttt gatgctgtgg tcggtcattc    10320
ttcgaggatt gatccagtga gagcttaggg caatggacac ctgacctccc tgagtgggac    10380
ggaaagaagt attgtagaga tgccagactt tggcatgagc ctatgaagag aaaaaccatg    10440
gcaaatttat ctctagttgt gaggagaaat gcaatataat acttgaatcc ccaaatcaga    10500
ttatatctgt ttctcatcaa gcctaactta atgactaaca atataaaaat cagctagaac    10560
caatacatta tttcaaaggt aggtcacccc acagtgaggt gctacgggga ctagagttat    10620
ttccattggt ctttagcagt cagtggaaaa atgtagattc cttgggttga gtgtgtagtt    10680
atccacattt tgaaaagcta atgaaataaa agaatttgtt ataatagctt actatttaat    10740
tgactttgga ttatgtactt tttaatttac ggggtttcatg aaaagaacca atgctacatc    10800
tgtgatcaca ccaggaattt ctaaatagga ttatattttt tatcctgaga ctgggagttt    10860
```

```
tcaaaatgac tcaggtcgtt ggagttaatt tactgtttca tagtcatctc tcgtagctaa   10920
aattctaaca agcaatcttc tttcttccca agaagaatca gtacaataaa ttaaagaacc   10980
cactccagca tctaaccttg gcctaccctc cagaactctg ggacagttct ggtttcccac   11040
agacccaggg tgctaggtcc aagccaagag caaaaaacag caaaatacag ctgcaaggaa   11100
atcagttgtc cattgttagc atgcagccag gagtttcgta cagcagtgaa aagggctttg   11160
catccataaa accaacttta tactcccata aattcttact gacttctaat atcttatttt   11220
catttgtttc cttttattt acaaggaaga gtgaaaatta taggggtttt ttctccccta   11280
cttgaagtga gtttctcttt ctctttgaat tccttgattt actctcccta ttttcctaca   11340
aatacaagtg ttgtttatca gcctttattc ccctaacata tcctctttga aaactccatt   11400
caaattctct gtttgactcc atatattctc caaaatgatc atgccaattt tcattccact   11460
ccctgggcct gcagaaactc ctttgttcat taagccaaac agcctcttca acatatccta   11520
aatattcctc tcgtggttca tttcagtaca ggcatccaag aatggcctca tcaacattct   11580
tatgggttca gccaaacatt tcaatgaaat aagatagttt gtggctaact tttcttttta   11640
gtttcttggt gaacatatct actatgtttc atttcactaa atgtattttt tcacgacctg   11700
aagcagctat ctatatgcta agaaggaaat agagaatcaa atgttgatca aaagaatagt   11760
ggcacttgct tatgtggtct aagaaaccag ggtcttaatc gtgccacact tctgtcagtt   11820
ttatgatgtc tcctacccct tccatcttc cccatcacac ctccccaggc ctcccttcct   11880
cattgaaagg aaacctcatg atgttaacag ttaaacagag gctgggcatg atggctcatg   11940
cctgcagtcc cagcactttg ggaggccgaa atcccagcac attgggagaa tcccttgata   12000
ccaggagttc acaactagcc tgcgcaaaga gtgagacccc atttctacca aaaaatccaa   12060
aacttaacca gtcatggtgc tgtgtgcctg tagtcccagc tactaggaag gctgaggcag   12120
gaggatcact tgagcccagg agatggaggc ttcggtgagc catgttcaca ccactgacct   12180
ccagcccagg tgacagagaa agatatgtct cacaaaacaa aaacaaacaa acaaataaac   12240
acaacagtta aacataaaat ccattgagca gtccaggcta gtactcagca attaacctct   12300
tgagaccaaa aaccagggga cttttcctaat ttgaccgcat ttgaggccta tgaacagtca   12360
tgtcctaaat ctaccaggca cctttctgta gaataagcgc tgaacaggga atgaaagagt   12420
gaaagcaaac aaagaatgca ttaatctcgg tcagttttgc aggtagctga agtcatacaa   12480
tggaattttt tataattata gaccactctt ctaaccttga ggactttaac aaggctcaga   12540
ggaggaggtt tagcaaggac atgataaatg acctgggcca taaggaaaga catatatggt   12600
ctctgatggc agataaagtt cctgctccat cactctttt tgttttgttt tgttttaaga   12660
ctgggtctca ctctgtcacc ctgactggag tgaagtgatg ggatcatggc tcactgcagc   12720
ctctacctcc caggctcaag caatcgtccc acttcaacct cccaagtaac tgggactaca   12780
ggcacctggc taatttcttt tttatttcta gtagagatta atcttgctg tgttgccctg   12840 gctggtctta aactcctggg ctcaagcgat cctcagcctc ccacctcagc ctcccaaagt   12900
gctgagatta caggcatgag ccaccgcacc tggccttcgt cactcttgag ttggccacat   12960
tccttaattt gggcaggtaa atctaacttt cctgtgcctc acaggactgt tgtgaggact   13020
aaatgagaca attcatgtaa aactcctaat gcagagtttg caacagtagg atctccatga   13080
atgcgtatcc cttctctctc tagaggatga acaaaccaaa aggaagaata ttgcaggtgg   13140
aggaaacaac ccctgctaag gaattcagcc cacagtagcg atgtgacata ctgataaaac   13200
```

```
ttggggtttg gagtagaaga gacttaggtt tagattccct actcctctaa ctatgaccgg   13260
tgtgagcctc acttactgct ctgtacaagt gggaatgaca tctattgtcc cgtagggaca   13320
ctgtgaggat taaatgacat aatgcaagtg agagtgtctt ttaagtagtt gattatttta   13380
cagaggaata cacttgcagc attagaaagc atttcagata tcatttggat taactgctca   13440
cctcatgcca aaaccctgtt gaaacttatt tgattactct ttacagcatc ctaacttggt   13500
ggtcatccca ggcatggcac cgtctctaag aaatcgctgc aaccccatgg accccatac    13560 tgtgctgcat gcccctcctc tggacaccaa gagtctcaca catacttctc taatatcatt   13620
tactgcagat aatgaggggc atccctcccc agaatgagct ccctgtggag ttccctcact   13680
ccctccctgg cacacggagg ccctcattgt ctgttaaact gagttgaacc agcttcacca   13740
cctcttcacg agccagttca ctcccttttgc ggatggtaca tttgacagat taaatattat   13800
gaggcagagt gtgggaaggt cgctatttag gatgttgcaa caaataagga tgattaacag   13860
ggagatggtt acatatagtc ttgcaatgct ttctaattat tcctggtatg ttaatcttat   13920
aggcttgttg tcttaagatt gggatttaat aaagttattg acaaggactc agtgaagtta   13980
ttaactgtat ggccaagaac attcatctaa atactatttt taatagccaa acattgaaaa   14040
caattgaaat gtctaatatt caaatatgtt taccatgtat gaatgtttta atacatgata   14100
gtataactaa agaaatacca ttattcagga taatgcaaaa gaatatcaat taacatgtaa   14160
aaacgtttct aaaatactct gaacagaaaa aggttataaa atagcaagta gagtttagta   14220
gcactttgat ctggagggat ttataacttg ttaaaacctg ttttacagca ggattgtggg   14280
tggtataatt cacttcattt tacccatcta tatatttttt tcatttccta ccataaacat   14340
gtattgctct agagattaaa aaaataaaat tcaaaagggg aaaatggctg atagcagttg   14400
gatggcaggc ctgtttgatg gttattaaaa gtctctgctt catctcaccc tgcccacctg   14460
ttctccaact tgccctatgg tctctgcctg aaatccaagt cccaggcaca ttgaacccca   14520
cttgaagttc taagattatc tagccttcca tgctttggag gtgcagctct ctaaggtatg   14580
ttttgcctat tcccagttcc ttcactctta cacccacttt aaaactcagc ttagatgtcg   14640
ccacctccag gaagcattcc ttgacatctt ccctctccct agcatggact aaatgtctgt   14700
tctatgtgtt tctatgatgg tcctctatcc aagaccttaa ccatatatta ttgcatttat   14760
ttaagtgtct ggattgtagg tgtttttgaag gcattgagtc ttttatctct cagattctag   14820
caaagtctct gcaacagagc cagtattcaa taaacagatc tagaggaatg aaggctggca   14880
ctaagaacca gatcaaaggg tctaggacag aagcaacatt tttctgggct gaagcaggaa   14940
aactctctca taagctactc tggttcttat tttgctttca agatcatgaa agacagaaaa   15000 cttttcaggca cataccatta aaaaataaat tagaaggaat tttatatggc aggcctctga   15060
gaataatacc atattatctc ataatgtgct aatgatccac tttggggtat aagtctctct   15120
cgtatgtgat gccctccttg cttccttctt accttccatc tagattttga aacatggagt   15180
ctgaaaaaaa tctagaagaa aaatggatct ggaattcctt cctaccaact agctagtagc   15240
cccaaatttt ggaagtcgag gaaaataatt ttggaagtcg aggaaaatac tctgaattcc   15300
acagaacata tagacatttt ctctttggct aaattataag ctccctgtca tttgcctata   15360
cgtatccccc acagaaccca acaaaaagtt tcacacaaat aagctgcttt taaatggtgg   15420
gtggaaggaa acaggtgatg agcctcaggt ccactccagc tttctgcctt gggttgtgtt   15480
ctaggtatgg ctgaggcaaa tgaagcccac acaatacaca gcagtattgc tgagctgaaa   15540
aggaagaaag caatgatgag gactctgaag caggtcaacg tactggagag aagaaatcta   15600
```

```
cacaaaggaa ggacctagaa gtctgcatga gatttcccaa ggatccttgg ctgtccatgc   15660
acaggacaag attttgtgag gctcagcaaa gagaagcagc cacaggtctg ggagatgaat   15720
accaaaggtt gggtaggtct ggaaaatatt gcatttcaga atagccagag tagaaaaatg   15780
cagctgagca cttcaggcat ccagctgaaa ctcaggaagg tcattacctg agaagtaaga   15840
acaaagcagg aatagaccag ctctaacaaa gactaaagcc acatcaagta aatctggtaa   15900
tttaacttct tggcagaact aaatacaaca ccctttaaaa agagacaata ttgaccaggc   15960
ttcctataat atctcattca tagcacacag agcataataa aaatctacta gatatgtgaa   16020
aaagcaggaa aatgaaaccc ttaattaagg ggaaaaaaag aagtattcaa tatcaacaga   16080
agccaagatg tcccagacat tgggattagc agaggacttt aaaatagcta ttataaatat   16140
ttttaaggat ttcaaagaaa agatagatat aatgaacaaa tggagaataa caacagagaa   16200
acaacaactg aagaaaacat gaaaattcta gaactgaaaa gcgaaataaa caaattttg    16260 aatgggatta caatattaa ttctaaatgg aataataata agaataaata atgtaatccc    16320
taaaactcac aaagatatta aaaggtttct ctaaaaagcc aataaaataa gaaaatgaa    16380 ttaccaaaaa atctgatttt tccaaaagat gcagaaataa aaacaaaaa acacatggaa    16440 caaaagaaa acaaatagca ggattgtaaa cataaaccca aacatatcaa taaatattca    16500
aatacacatg gactaaatgt tccaagtaca agacagatgc tatgaaagca gattttaggg   16560
gctgggtgca gtggctcacg cctgtaatcc cagcactttg ggaggccaag gcaggtggat   16620
cacgaggtca ggagttcaag accagcctga ccaacatggt gaaaccccgt ctctactaaa   16680
aatacaggtg cctgtaatcc cagctactcg ggaggctgag acaggagaat tgcttgaacc   16740
cgggaagcag agattgcagt gagccaagat tgtgccactg cactccagcc tgggcaacag   16800
agcaagactc catctcaaaa aaaaaaaaaa gaaagtagat tttagaaaag taagtttcaa   16860
ttacattctg tgtgcaagaa atatactata aatataaagt gatcatgtaa aagaaaaaga   16920
atggaaagag acatattatg caaatggaca gcattaaaaa tctggcatgg ttatattaat   16980
aacaaaatgg aggctttgaa catcactata attcacctag agctaacaga catatatatt   17040
aatagaacat gccacccacc taaaaaaatc agaatataca tttttctcaa gtgcacatga   17100 tacatttttcc aggatagatc atatgttaga ccagaaaata agtcttaata aattttaaac   17160
tgttgagatc ataaaaagta ttgtttctta ccacaatgaa atgaaactag aaatcaataa   17220
caaaaggaaa actagaatat tcacaaatac gtggaaattg ttgacacact caaacaagca   17280
ataagtcaat gaagaaatca caaggtagat tagcaaaagc ttaaatgtgt atataaaaaa   17340
ctaactgaat atgtaacata ccaatactta taaattgcag caaaagcaat gctcagagga   17400
aattttatag ctttaaatac ctacatcaaa aaaaaaaaca agatatatct caataactta   17460
gtcttccacc ttaagaaaat aaaaagaag agccaactaa actcacagct aacagaataa    17520
aggaactaat aaaaattaga atggatatac acaaaataca gagcagaaaa attatagaat   17580
caacaaaatc aaaagttggt tctttgaaaa aaatcaacaa aacagaccaa cctttagcaa   17640
gactgactag agaaaaaaag agaaagaag caaattaatg caatcataaa agaaagtggt    17700
aactgacctt ttctgtatat catttctata ataaaagga ttacaagaga acattatgaa    17760
catttggatg ccagcaaatt agataacaga gatgacctgg ccaaattccc ggaagcacac   17820
acattaccaa aagtggctaa ggaaaaaata caaaatctaa tctaggtgta aaagagattg   17880
aattagtaat caaaaacttt caaactaaga aaagcccagg actagtggct ttaatagtga   17940
```

```
attgtaccaa atatttaaag aagaattaac acgactcttt tcaagctctt caaaaaatag    18000
aagaaagaac actttctaac ttagccaatg tggccagcat tatcttgata ccaaagccag    18060
ataaagccac cacaagaaaa taatagttac agatcaatat cccttatgaa tatagatgca    18120
aaagaatgca accaaatact aacaaaacaa atccagcagc atattttaag aattatacag    18180
cacaatcaac tagtatttat tccaggaatg caaagatggg taaacattaa aaaaaatcgt    18240
tgtaatgcat tacatcaata gagtaaaggg ggagaaaacc catatgatta tctcaattaa    18300
cgcaggaaaa gcattttaca aaaatctgaa agtctttcat aataaaaaca ctcagaaaac    18360
tacgactaga aaggaacttc cttaatatga ttaagaaaag catttatggg ccgggcgtgg    18420
tggctcatgc ctgtaatccc agcactttgg gaggccgagg cgggcggatc atctgaggtc    18480
aggagttcga gagcagcctg accaacatcg agaaaccccg tctctactaa aaatacaaaa    18540
ttagtcggtg tggtggcagg cacctgtaat cccagctact ctggaggctg aggcaggaga    18600
atcgcttgaa cccaggaggc agaggttgtg atgagccgag atcacgccac tgcactccag    18660
cccaggcaac aagagaaact ccgtctcaaa caaaaaaaca aacaaacaaa aaattatgaa    18720
aatccacagc caacattaca gtgaaaggct gagagcttca cccctaacat caggattgaa    18780
aggaagatgc ctgctttcac tattgctctc taacattgta ctagaagttc ttgccagagc    18840
aattaggaag gaaaaaacta tccaagttag aaaagaagta aaactatccc tattcacaga    18900
taacatgatt ctacatatgg aaaatcctaa agaattcaca aaaatctatt gcaaaaaata    18960
aacgatttca gcaaaattgc aaggtacaag atcaacacac aatagtcagt tgtatttctg    19020
tacaatagca atgaacagtc caaaagaaa attaagaaaa caattccatt tataataagt    19080
tccaaaagaa taaaatatac acaggagtac atttaaacac tctcaccatt gctattaaaa    19140
ttgtactgga ggtcctagcc agtgcagtaa ggcaaataaa aacataaaag gcatgttgat    19200
tgaaaaggga aaaacaaaca aacaaaaaaa caaactttgt tgttcattaa aaacatgatt    19260
gtctgtgtag aaatcctaag attttttaaaa aaacagaaaa actattaaaa cgaataagtt    19320
aatttagcaa gttggcagaa tacaatgtca atacaaaaat cagctgcatt tggccaggaa    19380
cactggctca cacccatagt cccagctact tgggaggctg aggtgagagg ctcccttcag    19440
cccaggagtt caagtctgca gtgagtgctg atcacgccac tgcactccag cctgggtgac    19500
aaagtaagcc tctgtctcaa aaaaaaaaa aaaaaaaaa aaaaaagaaa atcaattgca    19560
tttatatatg aacagaaaac aaacagaaaa taaattttaa atacaatgcc acttacagtg    19620
gtaccaaaat cgtaaaatac ttagaaaata atttaacaaa agatgtgcaa gtttgctaca    19680
attataacac attgctaaca gaaattaaag aatatgtaaa taaagaatga gataccatttt   19740 tcatggattg gaagagtcaa tattgttatc agatttcccc agattgacct actgaatcaa    19800
caccatctca tccagaatcc caataaactt tttgtagaaa tgaataagtt gattctaaaa    19860 tatatcaat aagaacataa aacagctaaa ataactagaa aaaggaaaaa cacagttgaa    19920
acattcacat tacctgatt caagacttat tataaagcta taattattta atatagggtg    19980
atattggcat aaggatagac aaatacatca aaggagcaga acagaaaatt ccaaaataaa    20040
cccacagcca actgatttct aacgaatgca tcaaagcaat tatgtggcaa caggaaagac    20100
gtttcaacaa atgatccttg acaactggaa aagtgtatga aaaaattaaa ccccaatctt    20160
gcataaaaat ttgagacaga tcatagatcc aaagctaaaa gctaaaacta taaaacttat    20220
agaacaaaat gtaagagaat agtctcttta tcttggagta ggaaaatact tcttagaaca    20280
cagaaagcac tatataaata tacatatatt aaaatatctc ccctcagtat gtgatttgcc    20340
```

```
tttacatttc gctaacattt gatgagcagg ttttaatttt gacgtcgtcc aatttatcag   20400
tttttgttta tgattagtat ataattgaca aataattat atccgaaata aatacgtaag    20460
cctacctatc agtagtaaaa gaaaaataac tcccttccc accatgagca aaatatttga    20520
atagatattt cacaagagaa tcttcaccaa tgctcagtaa acacatagaa atgtcctcaa   20580
catcaacact atcaggaaaa tgcaaattaa aaccccaacg agcactcaca cccactaaga   20640
tgcctacaac taaaaatact ggcaacaggc tgggtacagt gactcacgcc tataatccca   20700
gcaatttggg aggctgaggc gggcgaatca cttgaagcca ggagttcgag accaacttgg   20760
gcaacatggt gaaaccccat ctctactaaa aatacaaaaa ttagctgggt gtggtggcac   20820
gcctctgtag tcccagctgc ttgggatgct gaggcatgaa aatcccttga acctgggagg   20880
cagaggttgc agtgagccga gatcacacca ttgtatgcct gggcaacaca gtgagatgct   20940
gcctcaaaaa aaaaaaaaga ctaccaacaa attctggcaa ggacgtaaaa caacggaaat   21000
ttcatacatt gatggtggga gtataaatag taccaccact ttggaaaact atttgacagt   21060
ttcttataaa attaaagata gattttctct ataatctagc aagttcatac ctaggtattt   21120
accaagagaa atgacaacat aagcccccca aaagacttgt acaatattaa gataaaactt   21180
acaaattgat atgttcaaag atgctggccg ggcacagtgg ctcaagactg taatcccagc   21240
actttgggag gccgaggtgg gtggatcacc tgaggtcagg acttcgagac cagcctgacc   21300
aacatggtga aaccccgtct ctactgaaaa tacgaaactt agccaggtgt ggtggcacat   21360
gcctgtaatc ccaggtactc gggaggctga ggcaggagaa tcgcttggac ccacgtggca   21420
gaagctgcag tgagctgaga tcgctgccac tgcactccag cctggggaac aagagcgaaa   21480
ccccatcaca attaaaaaaa aatgcttata gtagcttaaa tcgcaatagc agaaaactga   21540
aaacaacaca aatgtccatt cacaggagaa tgtataaaca gtgtggtttg tttatacaat   21600
ggaatactat tcattaatgc aaagagtgaa ctactcttct aggcagtaat atggattaat   21660
gtcaaaaaga ttgtgtagat tgaaagaact cagacacaga gtacattcac agagttgttt   21720
gattccattt acataaagtc ccaaaatcag tctgtggtga tgggaatcac aacagcggtt   21780
tcctacggag gtgagaattg attagaagtc acaaagaaac tttctggggt aatgagaata   21840
ttctatatct ttacttggat atttgttaca gatatccata cacatacagg tgtatgtagt   21900
catcaaaatt catcaaattg cttataaaac atgtgcatca atttttaaaga tctatagatt   21960 aataaatata taatagatta atatcttagt cattggcaaa gctattcagg tatagaaata   22020
taattaccta caatttatgt ggcaagagaa tactgatttt ctccgaaaca taaattcatc   22080
tttgaaacta ctacagtaat ctgttagtta aaaaaatata tatatttagc ttttaattgc   22140
agggatcata ttcattcaac aaatattaca ctaggcactt ttctagggga ttcaaaatat   22200
gatcctgttc ttatggagct tacattcttg ggaagaagag agataacaaa tgaaaacaaa   22260
gcagagaaag gatagaaggt aacagggatt gggatgggaa ggcagtttag acaggcaagt   22320
cttcttcaag gaagcattgt ctgaggatct gtaacagaaa aagtgaagaa tgctaaaaaa   22380
gactgggacc tgagatgggg gtgtgtggaa ggagcagaga acccggagga ttgggcagag   22440
gcggtagagg gtacgggaag ggcattccag gcagagttga gcaagtgatg agagcataga   22500
ctcagccagg cttccctaat tctgccccct tattagctgt gggaccttgg gcaaattatc   22560
tgaagtctgt gcctctattt cctcatctgt aaagtaggga tagtaatagc acctcatggt   22620
tatatccttg tgaggattaa ctaagtcaat acatggaaag cacttagaat tgtaaatgct   22680
```

```
atggaagtgt tccttattca agtgttgtag taatgtttga ttggtaagtt caaagatact    22740
tacagtatta ggttggtgcc aaagtaattg cagtttttgc catttaaaaa gtaatggcaa    22800
aaactgcaat tactttggca ccaacctaat agctttaatc acaatagcaa aaaaactgaa    22860
aacaacataa atgtccattt acaggagaat gtatgaacag tgtggtctgt taatacaatg    22920
gaatattact ccttgtttcc ttgtgactct taatcaattc tcaacatagg agaccactgt    22980
tgtgattccc agtacataga gtgattgtgg gactttatgt aaatggaatc aaacaactat    23040
gtaaatgtac tcattgtgtc tgggtaatga ttgataagtt tccaaaaatc agtggctact    23100
acgtggaaaa taggatctag gaggacaaaa tgggagcaag gataccagtt agacaactat    23160
tgcaatggtc caggcaaaag atcatgatgg tttggaccaa aaaagatagt aacaagtggc    23220
tagatttagg ctattattga aggcagaatc tgtagaacct gctgatgaat tggatgttac    23280
atgttgcatg tgaggagggg aagaggaatc aaggaactca agaaaacaa aaataagga    23340 gttggggaag ggaagggatc aagttctatt taggtcacaa gtctagcttt caatgaagat    23400
gcctggtact cagctgagta tatgaagctg aagttggaga gacatggatg gtatcaccaa    23460
tcacccaaat atgtttcagg ggtaatactg aatggaccgc ttttgttat ctatcattca    23520 ttagattttt taaaaattga atggaataa ttcttaaagg attaatttaa tcctacaaat    23580
aatcttaatt aaatgactg agaccaatgg tggaagaaat gaaatgcagc ccataagcag    23640
aaaataattc aaatagctca tttatgtctt ctccctatct aagaaaaggg ccctccagat    23700
gttactttag ttctgaatta aaggtgaccg ttttcaaaaa ggtcaaagga ttgaaaaaat    23760
tttagaaggc actagagatt tatttctttt tcctttctgg caccctatta cctcaacttc    23820
aagaagagta ttgggattac attgtctgag gacttcctta aaagtcactg ctactgtgtg    23880
gtgtttacat aagcatgcca actagcctga tgtttgtgct cgcagaccaa attatttctc    23940
ttatttctat cagcactatg gtttataagc tgcagttcct taagacagaa tttcaaacag    24000
cctcccacaa aacaaccacc taatagaaca cataaataat ttcccaaaaa taactatcta    24060
caactttatc cacaaaaaat agccagtagt ctctgtgtgc agttccttaa aagttgctca    24120
ggatttaacc aatgcaaggg ggctcatatc tgctttccct gacacccagt tagacgaata    24180
tgtgtgaaca ggcagcagct tggcacccct acctgctttg gacttcttag caaatcaaat    24240
aagttgcatt tctagctctg agcaccaagc cttacagtct tctacaaagt aacaggaaga    24300
ccagtagaat cgcatataaa tgtaaacagc atcacttccc agcctagctg ttttgctaca    24360
gccaggtcag tttctcatta ctcctcatcc agggctgtac ctacgttgga tgccaaccta    24420
ctagccctga agttgcattc tacttttcct tcatatccat atccctttct gccttctgtt    24480
ctggacttgc ctcttctaag aagtagttcc taatgaaccc cacttactct tagtactatc    24540
ttccccaatt atcaactgaa aattctcact tcttccaaat ttggctcaat tcccatctcc    24600
cctgtgaagt cttgtttggc tccccacgtg catttaggca ttccttccc aatgcaccc    24660 acccacaagc aggagtaaat aacatgcttc ttcatagttc ttcctaagtt ggtggctctt    24720
caccaagatt gtattatact cccccacaac aataaagttg aatggaaaca acttgaacat    24780
ccaataatgt ggaattattc attcatttat cctttcactc aaatatttat taagtaacta    24840
ctatgggcca tttataattc ttaaattagt tgaaacaacc taagggcta acaatagga    24900 ttagttaaaa taacccagga ataagacatt aaatgaaata aattattagc acaaatgat    24960 cagtgttgat aaataaatta taatttatta atttttatgag caataaatga tcaccatgga    25020
caaatatagc ttattaaatt acaaactata gttagctata gatagaccac gtacagtatt    25080
```

```
acctaattttt ggaatcatat gtacagatgt aaaataaata cacataagac aggattttaa    25140
aggatttgta cagagatagc agttatagtc tctattgagt aggacagtgg gcatttatta    25200
tgttcttctg cttctctgat tttctgactt ttatgtaacg aaatatgtat tgcttttga     25260 ataagaaaac acaaattttt taaaactgga atttttcaatt ttggaaaatt ttctagttca   25320
aattatttac tatattgttt ttctaagttg atgatgtctg ctctgcttgt ttagctgttt    25380
tcattttttc ccccacagga tggatggcat agattgttcc aactaattca atcactcact    25440
tttcaatgat tacttattga tttcctaatt tcctattgtt ataccttttca gtcattctga   25500 tttctgaaaa aatttgttag aaatgtttta aaaattcctg gcataccaaa attattaata    25560
ctgggaagtc tagtaactgg gatttatttt tcaccaaatg gtctagttga ttaaattatt    25620
ctccaccaaa atgtttttga ccatgttgca tttcatcaaa tcatctggaa ctctcccaaa    25680
aaaactgtaa gatccaaata attaagccaa ataattggac tatcttttct agcctgtgcc    25740
acctctgggg cagatgggtt aggggaaaag agcctttaaa atatcccccc atagtggact    25800
ctggctggtg cttagggagg gcaatggagt gtctaagcat ggaaactatg attaaaggaa    25860
cagatataag aatttaccca acgtgttgtg aaaatgatga tatcaaccta attaggctac    25920
aggattaata gtttgtggct tttagaaaat aagattacaa tagacagtat ggggccagaa    25980
tatgaaaagt tttgaatgta aagttatttg gatttgacag aataggtcac aatagattag    26040
cataaatttc tgagacagtg atgatcagtc atatgctcaa aatcatccat tgcagaatgc    26100
attagaatgt gaacagctgg atgtggaaaa ttggcaggat actgccaaaa tgcagataca    26160
attaaggttc tggacaaagg tgatgactac tgaaaagcaa aacaacaggg caatctgaga    26220
gatgtttgga agtgcagaat aaaaagagca tggtgcatta gttacacatt gctcacatgc    26280
tcatgaagaa atattattcg tgagctgggt tgggctccac tgaacatgtc ttctgctctg    26340
gtctcatctg gttaatctag gatggtgttg gctgggacaa atgggacagg ttgcttctgc    26400
cccacatgtc tcatcctcca gtgtactagc ttgggcattt tctcatggca attgcagaga    26460
agcaagagac taagcagaca ctaataagca ttttctcagt gtttgccagc attatgattg    26520
ttggctaaag taagtcacat ggataaagcc agagtcaaag gagaagaagg ccagagtcaa    26580
aggataagct gaatggacac ctagagtaga ggacactgca aagttacatg acaaaaggca    26640
tggatacaat gaagagagga caacattggg gcctttaatt caatcagtct acatcacatt    26700
gtaactcact agacctaggc attaaaaaat aaagtattaa agttgacagc tcatgcatag    26760
tacacagcta gaccaaaaaa taagtcagtc tggaaaggtg aagatatttc ttgctttctg    26820
gctggatcta caggttcaaa atctttgtt gttttttta aaagtgacgg ttttgtagat      26880
ggcataattc tcatgccaag acatttattt agtcatttat tcaacaaata ttatccaaca   26940
cctattatat gttggatata taagtgctaa gaatacagaa atgagcaaaa tctcaagctt    27000
agatgtatgc cattacttac tacatactaa cactgataga aaaactgacc cccaatgttc    27060
cccaagacac aatctaaaag aagatatatg attcctatat taagaccttt tcacaagccc    27120
tcaaacatta gtatattcag tatcatagca ttttgctttc aaaccttttgt taaatcttca   27180 aggtaaagtc tactgctgta tatgattgcc aaaacctttt attttactct aagaactaag    27240
tttgagatta gatctccttt agaaatcaca tgaaattatg acgtatgcta cttttgagaa    27300
atagacaata agatcaataa taggtttatt ttattttgtt ttactgtggt aaaacataca    27360
caacttaaaa tttactcttt taattttaa gtgtacagtt tgataattgt tttagtaagc     27420
```

```
atttattatg aactatcata ctgggttcta gagatagtaa acataaataa ggtaaaacac    27480
ctgctgtcat gaaatttta ccattatcca ctgattttac aggaaatcta taaaaataaa     27540
agaatactgt tttctcttct tgtacttcaa gttgaatgac ccaagccagg ccaatgagat    27600
accttccctg agattgtttt gctggaatag agacatgtga ctgtcctata ttaggagagg    27660
aagtgaatct ggagttgctg acatgggaag agactctctg ggatgataaa agccaaactg    27720
acccaagcat aagtgcatgt gtgtatgtct gtgtgtattt ctgtgtgtgt ggtgtggtgt    27780
gtgtgtggtg tgtgtgcatg tgtgtggtat gtatgtggta tgtgtatgtg tgtgtggtgt    27840
gtgtgcatgt gtttagtgag ggagaaggag aacccaccttt gacagtaatg gttacttag    27900 tgacaaatac agttgttaac atctaaagtc cctggagttc ttcttcaatc ctttgtcctt    27960
gtcgtaaagt ccctttttctt ccttaagctt gttttagtta gggctggtca aatgcaaata    28020
tagagttcct taatacaaat ataaccaaac ttgagattct ataagaatcc gtttagttaa    28080
aagtacactg taacaaccag gcaagacaaa ggtcagggta gttttgaaa atcatgttgt     28140 aattttggag ttttgttact taagattgtt ttatctggac ttttccaaag taggtgacaa    28200
taaagggctt atttattgt atttaaataa aaacttcctt caaatgaaat aaaaaagatt     28260
tcataactta cactgggtaa atacatcaat aaatcagaga ttgagcttct tgcttcatta    28320
atttatctgt acagaactaa ttaacattag ttaaatcatt ctattcaata ctaaatcatg    28380
ctgcggtgaa aatcattcca agtcattgac gctaggttgt taacaaaata tccagcttgt    28440
gaccagaatc catctaaccc attaatcaca gaattattac tggagacaca gagggggttcc   28500 aattcctggt ttttgtatct ctgttttct aatagcaaca aaatgagaac catgagggaa     28560
caggtaggga ggcataggct agatgagaaa aaagagacaa gaagataagg aactcagata    28620
agtgatgttt tccacaaggt cagcaaaagt attccatggt tcatcagtca aataggattt    28680
tttcagtaaa catctattag tataattgcc aataattcca caatacctc atgaaagagc     28740 tactctccaa tatcaacaaa actgagacaa gcagttttc ctctataatg gtcacttta     28800 ttttctaaac attctacttc tgcctcctta tctaattctc ctgctttaag ttatcaacag    28860
cagatgccaa cagactctcc ttgagacttt cttaacagg ctcatttata gctctttgct    28920
tttgaaataa ctcaattcat cttgcagtag agaacgcttt tcacccaaag aaaaagtggc    28980
atgtgagtgt gtgaggattt ctacatcatt gaacaggata caattacagg aaaatgaaat    29040
atgctttatg gagtggtgga tagcggaaag tcatcggcct gctctttccc ccttctttcg    29100
catttgcctt tttgtggtag cagtttcgac atggtgttaa gtcaaagttt ttcataacac    29160
aaactccact tgtgaaatca acctatgagt agcctcagca atttttgaaaa tcaaaataga   29220 agagattagg aaatatcaca gtgcactgcc tgtaataatg gtaagttttt tctgtgaaaa    29280
ttttgtttca atggtgtata ttcaacatgg aaaatgcctt tcttactatg ggtcaagatc    29340
aaaaaagttt ggaactcact ggtctaagtg gaggggatt tcattccag aagtatttat      29400 tgagcatcta ttgtgtgcct ggcatgattc tagcactttg gggcacaaca gggaacaaat    29460
caaagaaaaa cccgtgccct cacggagatt ccattttagc aggaggagcg acaaccaaca    29520
acaaacataa taaatgtaaa ttataaagaa tgttctaagg caataagtgc tatgaagaaa    29580
tagagtgagg taaggaaggc ctggggtgcc acggagagga gatacatttt atttattttt    29640
ttttttggtg gcactcacaa gagtcttat ttttcctttca ttaaatgtgt tgtgattttc    29700 atctttcat ttcatctct acagaacaaa atccgtttgt gtccctatta ggcaagaatc      29760
cttcccatcg ctatcagttt tctacaagtt aaaaactacc cttacagaat ttaaaatgcc    29820
```

```
ctaatccatg gtaagcagca aattgaacaa aggtgcactg ccttcttcac ccccagagaa    29880
tgaggatagg agaatgggat taactaggca ggcctgcctg aggcctcagt ccagatggac    29940
accaataatc ctgcctcatt tccaagtcta ggaaaatttt ctgtacagtc tcctttgtg     30000 atcataaata atctccaaag attatatttt atcacacaga aaaacctggt ttccttgagc    30060
tttagccaga ttcatttaca aatgtttgac aagggg tgtt aattaacact ctataagcct    30120
cttggctcta cagtgtacag catattaaat tcaaagaaac agcttctgtc tgggga tttc    30180 ataaggaatc tcagattgcc ttttcaaaag aaggcaatct gagggtgtgt gttcatcttt    30240
tttaaaaaaa aatgctttta tactagaggg tttgtgtttg tctgttttta tcttttttaa    30300
aaaaatgatc ttattggttc ttctattcag aagctaaaaa aacaagccca ataaattcat    30360
tatcacacag tttcatccac agcacctgta aatttggtga cttcctgtct cctcgaggcc    30420
cccagaagta gtcagtcttc tccgctgctc gtaaagtggg ttgctggaag tagagaagac    30480
tagttccggg ggcctccagg agacaggaag tcaccaaatg ggggtggtta gaggtgtgcc    30540
tcctttgaga aggagcttgt gaccatagac ttaaggaaag tgaagggttg gttctgtggc    30600
tatggcggta gggcaggttg ggaagaacct tccaggcagg gagaagagta aaaaaaaata    30660
atgccccaag gcacaaatgc aagaccttca gtgtggctgg atggcgtggg gcagcggggc    30720
aggagtcaga gttgagacaa aatgtgttga aacacctttg agagtgtttc cagaacaggg    30780
aactgcagcg ttaactgctg cttgatcccc tgtgacgaaa gggaaatttt taaaacggca    30840
aggcttaaac gtgaaaggaa aagataaaaa gcttttttaat caaattgtaa atgacatggt    30900
ttttcactct cccatctccc gtatttctca ctgagtagca gtaaacacag gaaacagcca    30960
cgcataagtt atactgtaac tcctcataaa ggatcctctg gcttctttca tttttcggaa    31020
atgagaattg tgaaggaaga aaaagagag atctgaattg aaatgcactt tttcaggact    31080
gctatttgag ttatcatgta atgattattt cattaagcaa atatttactc aatagacaaa    31140
ttattatgct gggcatcgtg aggggtcaaa cataggtaca tagaataatt acagtataag    31200
tctgaaagtg aaaacgccag aagatggatt ttttttttaa tgcaatggcg attcagagga    31260
aggaaagatt ctttcttgct gagggaaatc aaggaagtct tcctgtagga ggtagtttct    31320
aaaccttata ttgaaagatg tagatcctgg agagacggaa aaaggcattc caggcagatc    31380
actgtgagct ggaagccagt gatgctgtg gcaaaatgta ttttttacag aaaatagatg    31440
ggtatctccc atgccccatg atcttttacg atataacctg gctgttcctc ccattggcgg    31500
atctgtggac cctcccccctt gaatctgtgg gcatgtgact gctctgatag aaatgaagct    31560
acatgatatc aagaataagt gaaaagaaga agaagaagaa gaaaagaagt ccataccact    31620
tcctcctagt tctcttggga tgcttgccgg gagggaagct agtttccatg tacagaggct    31680
actaatctga gaccacttgt gtaagcgagg ccaacagaga tgctctggtc cacagccagg    31740
ctcaaccgcg gatcacatgt gtgagccgtc ttgcatgccc cacccgttc aagcttcaga    31800 tgactgcgga ccagagaaaa actgcgtggg tgagccctcc cctaatcctg acccataagt    31860
ttgtaaacca aataaatgg ttatttaaag caattaagtc tgggggaatt acgcagaaat    31920
agtaatggga acagatgtat ctgggttagt gttttt gtaa tgatgtaatg atgacactct    31980
cagatgtcaa ttaaggttaa agacgttagt ggcaagtcat gactaacatt cttgtccatt    32040
tcagatgctg atgtggacga ggatggtcta ggcatttgct agcacacccc tagatgtaac    32100
ctgtgcaatg cgggaggcag cctggagtca tggaatgtac actgggaata ggggttcaga    32160
```

```
aaacctgagt tttgaccoca gctctgaccc ttggtaccca caggaaagtc agctaaactc    32220
tctgggtctc tcaatgaatt tacctgcccc aaaatacaaa aaaaaaggac tctagaaatt    32280
atcaagcatt atccagtggt atgggttttt taaattactt taaattaata aatgcattta    32340
tatagtttaa aatcaaatag taccaaaggc ttatcatgaa aacagtaagc atctccccca    32400
atcccgtctc taaccctcac tcctgctccc cactggcaac cttttagctc tttcttctcg    32460
taataactat catatttcta aatactatgc tattgtgaaa tttaataatt cattaggata    32520
atgaggagtt agctctttta catgccccat tttcttccct tattttccga aatgtctgtt    32580
cttatttaaa tcattgttag tatttacatg aagattccta tataaatgtt cattttagag    32640
ccaaataggg cactataaca tttcccttt ctaaacagct tttaattttc ccttgaataa    32700
ataatgacct cattattaag cgtgcagaat attctatatg tgattttttc aatgtgttag    32760
tgattctcta tcatgttttc tatgatcgta tctattctgt tgagtctact ttttcaccca    32820
gagctcttcc ttccctgcta gaagtttcca gcctccaagt ccagtttgga ctagatgctg    32880
tcaagagctg ctctcgtcct gggagtttcc tttatttctt atggattgaa accatacttt    32940
ttctatatac tatttcttcc tatgtattta ctacaatttt gctggtgcat atcttccatt    33000
agcttcttag gaaacatgac actgaaggtg aactttcaat acccttacat gtctatacat    33060
tcattgagct aggaactcag tcggctcttt aaagttaaaa gctcatgttc ttcagttctg    33120 gggcattta ttatattatt tctttacaaa tttcctgacc tgtatttcct tattctctct    33180
ttccagaact tctattagtc tgatgttgga tctttatgaa tatcctttaa atcttttcc    33240 cttttcaaaa tgtgttctat ttctttatca tcttgtacta cttttacagc attgctttga    33300
ccttactttt caaatatttt actaaatatt ttgtttcaac tattgtgtta ctgatgttca    33360 agaattttt tatatgttctg atggttcctg tttcagtttg tgtatgtgtt taattcctgc    33420
ataatttatt ttccctggtt tgcttttctg tttattttat tctgtttcat gttgatagct    33480
ttcctcaaat gtctttcacc agcattgtca ccccttgccc ttctgttgta cctgctccct    33540
tttaagcctg ggttcctgat tattgcagga gacaagactc ctgatgtcgg gagtctgcat    33600
gccattccaa attcatcatc tccaagtgtg gtctagcaaa ataatttgca cttatgatca    33660
tgcaacagcc atcagttact ttgagagatt atagaaaata aggcgcttga agaatgaaaa    33720
ttttctcaac tttaaaaggg aagataatgt gaatttcaga aataatagac tcaagcaaaa    33780
ttaggtaatg gttaacaaaa atgcatcagt actatggaag ggaagataac taggagacaa    33840
catggattcc tagaataaat ttaccaaact tagctcagaa aatttttatt gtattatatg    33900
gtgctatgat ttgaatgctt gcccctccaa aactcatgtt gaaatttaat tgccattgta    33960
atagtattaa gcgagacctt taagaggtct cactttaggc caattaggca atgaggtctc    34020
tgtcctcatc aatgaattaa tgctgttatc atagaagtgg gttcaatatc tcaggcatgg    34080
gttccttgta aaaggatgag ttcagcctcc ttttgtctct ctcttgccct ctcaccttcc    34140
accatgggag aaagcagcaa gaagtctctc accagatgcc agagacttgc ccttggactt    34200
cccagccaac agaactgtga ggaaataaat tcctttaaaa aaaaaaaaaa tagggccagg    34260
cgcggtggct cacgcctgta atcccagcac tttgggaggc cgaggtgagt ggatcacaag    34320
gtcaggagat cgagaccatc ccgactaaca cggtgaaacc ccgtctctac taaaaataca    34380
aaaaattagc caggcatggc ggcaggtgcc tgtagtccca gctactcggg aggctgaggc    34440
aggagaatgg cgtgaacctg ggaggcggag cttgagtgag ccgagattg tgccactgca    34500 ctccagcctg ggcaacacag caagactccg tctcaaaaaa taaataaata aataaataaa    34560
```

```
taacctagtc tcagctactc ttatagctgt acaaaatgaa ctaagacata cagcatatct   34620
gagaacacaa tagtcatctc tgtatgtaat aatcttgaca gttgctaaac attttttgtga  34680 cattcttagg gtcaaaaaga aaagtagagt gcaaataaga tagtactgtt gccacttgaa   34740
aaaatatatt ttaagagtat tcattggttc aacaaaaact tactcgttgc ttattaagta   34800
tcaaatgctg gtcaatgttt gaaacattga ttcatgggac agatcgactt gagagaaggt   34860
gactaacaat atcccacaag gtttattcat aaccctattt ctttgtaact tgttatcatc   34920
aaagggatga aaactcacaa aggcattaat ctaaactttt gaaaattctc caaaacttga   34980
atccaaaaga gctctacaga gtgtaatgct ataaatatgt gctataacta gcaaaattaa   35040
tatttaaagt gatagaaaaa atatttatgt cttttaaaa ttaaaaatac aagtaatata    35100
tgttcatggt ttaaaatgtc agaacaactt acaagaaaaa tcacagttcc ctgtcctaca   35160
ttgccctaca attcccccag ttctctctag aggcaaccac ttttgactct taagacgttt   35220
tcttttggaa tttacatctc cacacatcca cacttcagga agtatccact gacttcctat   35280
tatgctagat aagggtttag ctctcttaca caggcaattt agttatacaa tagttttggg   35340
tttaaccgac atttggtatt gacattattc tgccaacatg aatatcattc acagctggac   35400
cttgtaatgt agtaagtaag actgttttcc ttcttatttt tgttttcttt gaagttcata   35460
attgcattgc ttttgattg gctctgtttt ctttgggact gtggctaatt cttccctcaa    35520
tttccaatag cctctcagca gaaacttccc cagggaagtc acatgagcct ccaatatttt   35580 gggggggacac acttctggaa tctcccccat tctgcactgg ctgatcttag tctgctgcac   35640
atctgacatc atgggtctac agttcatcat cctttcctg ggttagaccct gcccttcat    35700 agatcccatg tcttcctcct tgtcttcctc atgttatgtg gcggttaccc tccaataact   35760
tcctgagaaa gggtttatgg aagatttatt ttttgggact ttgactctca tgaatgattg   35820
acagtttaga taagtatcaa attctaggct ggaaataatt ttcattccct tctctgaagg   35880
gcactcctca ctagtctttg tgatggccaa gaaatgcact gctcagtgtt cctgctataa   35940
ggagcacagt tgactgaggc catcagttgc tacccctttg aatctgccat tgcagttgat   36000
cctaagatca tgattctcat cggctactcc cagatgacta acatggcag  gggaactaat    36060 gcaggcccat ttcagcaaga tgtggactcc gccaatgggc aacattggct caaggcgtcc   36120
ccatcagcct atgcctgggt tgttctgaga cccacagtgc caactgaaac tcttcccagc   36180
ccatccttct ccctgcccac tctccttcat agttgttgga cacacatcat gatccaaagg   36240
ttcaatgcct cccctagctc cttccccttt atccttcaca attctttccc caataaattt    36300
cttgtacatc taatcctatc ttgacattta cttctttcag gactcaaact aacacaagag   36360
gggttgggga accagctcat tcactttctg gaaagcaaag agaatgccat tctgagtgtt   36420
gtgtaggggc agatagtccc cttgcacaaa tggtgcttca attgctaaat atttcaacag   36480
cagtaacctg ggaaatatcc tggtggagaa tgtcattgta ggtgcaatga tttaggcatt   36540
ccctgcctac aaggagatgg aattgaatgc tttctgatat attgtattga gactctacag   36600
agagctaatg agaaactgag ggccaataac aaacagttaa aggctcaata taagagccac   36660
agccttctct cctacagtgg aagagtagag aaacttagca gcaggcctag gacctgatag   36720
acttgcagag atttagggat gtttaaatgc tcagccaagg cagatcagtt atgccaaggt   36780
caaggccccg gttggggaaa cctgggaata tttggagctt acagaggtgg cccattcttc   36840
cctagtaaga gatagcactt ctttatgctg aagaggcctc gtccctaaaa agcaacaggt   36900
```

```
gcacccctca ggagctgacc cggcactaac gaggattaaa tcctagtata acccacctgg    36960
agacagctgg gcctgataga gaagaaaaga tactatatcc caacattgct tcaagattga    37020
gcatgcactg caaatcctga ggagtagcgc tggggtcctt gaccaaggaa ctggaactta    37080
acacaggaca agaaataatt cattatctag ggaacacttt ctccggaagt atgttttcac    37140
gatccagcaa ggaccccagg agacgcggta aagttgctgc tagggtggct ctgagaagcc    37200
tgtaaaaagg gatgcccaat gctgagcagg cggaaatgcc tgacattgtt gccctaacag    37260
ctgataaaag aatcaagaag cagagagaag ctggcatgca agaaccagta tattatgtga    37320
ggtcaaacaa cccaccagag gacagtgttt cccagaagtc ccaagtaggg agaaagagca    37380
ttcactgcac cctcaggaat atgctcatgg gggtgccaat ctcactgaga cattcagtgg    37440
gggcaccgct ctccaggcca gggctgctgg tagcagaggt gtcacagagc tgggcttgtt    37500
gccacccacg gggatggtca gaagttgaaa ttacagaggc cagatagtga gtggtgctta    37560
actgccagaa gccagggagt tataaagatg gttcatagag catggctaca taaaagtga    37620 tgacccttg tacagttccc cgacttagcc aattttccaa gctataattc actgactgaa    37680
gaggtgccta ggtccctagg agccaggacc ctgcaataac acagaggtat gacccccca    37740 ccccattctt cccattcaat atgaaaatgc atgtcctcca gctataggaa attttctgga    37800
attacttcat tgtttccttt ccttttacgt cagttaccta ttgctgtgaa atagaccgcc    37860
cccaatttgg agaattgaac taataagaat ttattttttt cctcttgctt ctgtgagtta    37920
atggggtttg gctgggcaaa tccagtcttg agtatgcagc cagggaaggg acactgcaag    37980
ggaaaaggca ctggcaggga gaatgaagga cagaggctag agagagccca gtcccaccca    38040
tgaactatac agtaatcttt acatactttt tacatactta ttcatacaga agagacataa    38100
catgggctgc cttttaataa tcatacatca acattttaat aaccaattag tattccactg    38160
tataagcgta ccaacattcc tctaacggat taccttaaca catttagctg atgtccagtt    38220
ttaaagaata aaccaccatc agcggtaaac ttcctcttat cttttgcacat tggagatgaa    38280 atttaataag attgaaagtt tgaaaataaa ctaccaaaga gatgacaggg atgtttggct    38340
tcacagcaat tcacaagctg gggggaaaaa acctgagagg ttttagctga ctgcaaaacta    38400 atttgagtcc gcggtaaggt gacagccaaa attgttaatg caatcttggg cggcatgaac    38460
aaaattcagt gtctaacaag aaatgtaatc gctgaagcct actctgaaca cctggggcac    38520
tgcttggttc tgcacagcaa atgttaagag aggccttgga aattcccagg cttttcttctt    38580 cagctcctca tcctttccca cctgacgctt cagccattca aaagacctca tgctgtggtg    38640
ggaatggcca cactgtctca cctgtactga cttttgcaagg gatgtttcct agaaaggcac    38700
aatgcccttc tcactttgtg tgcccagcaa gccaagccca gcagcagggc ccactaccta    38760
tttttgtaaa taaagttta ttgaaacaca gctgtgccca ttcattaaca cattgcccat    38820
ggctgcattc atgctgcaac cacagaactg tgtaatagtt gcaacagaca ctgtaggatc    38880
tgcaaagtcc aaaacttagc cctctacaga aaaagattgc cagcctctga tcttacaagt    38940
attgctttcc ctgactgctc ccgtactacc tccccaaaac gctaacctat ctctcctttc    39000
ttgaaatagg ttcctaagca agtacttatt tctcttaagg catttataca ttttactgta    39060
attatttgac aattacctct cccctactaa tctgtgacat gagggcagga atcttacctt    39120
atccctcttt tctgacagtg cagaaacttg gaaatggcag ctctggccag gaaggagtaa    39180
aaaggccccc taggttagga gcccctcac agcccatgcc agatagatag gagaaaactg    39240
aatctctcgt gcagcccaag cagtatacct ttggtgagca atgtccacgc tgagttgtgt    39300
```

```
ttgactgcag acaatttctg ggagaatgta gttgagtcgg gagtgagacg cccctaccac   39360
tgtccccgca cctgtgcagg gctggcataa aggcctgatg ggaacaaggg gacacaggtc   39420
tctatggaag aacttgggac accgaagaga ggaaaaggca gaggaaagag gaccacatga   39480
tgagaaatca aagagaagag aggacaggcg gggaagagca gcatcccaa gaggctctga    39540 cagggcaacg ggcttgcctc ccatgccccc atcctcccct gcagctttgc agccgtcctc   39600
tggaccctca cgaaaagagc cctacaaata tgcctccttt gggagccagg gctctggact   39660
ctctacaggg tccggcacag ggagaactcc aaccactcgt cctcagtcct ctgcacccat   39720
cagcaggaca atggtgatgg atgatgagac agaggcaggt cccacagaca accctaaacc   39780
ctccccgctg gggagatagg tcgactttcc cctctcctct cctccacctt atcctgaaac   39840
gtcagaagac agagccacct gttcaaaggt tacattcata ttctcagaat tcaacattgc   39900
acctgcctgc cacagggtaa gctctcaaga aatgttcctg actaaatgtc cagtcacctc   39960
catgtcttct tggagcagac attagcatga aggagaaaat tctaggaaga acaaaacgta   40020
ctggtctttt caaatatgtg aaagatgtct tttcaaatat gtgaaagatg tcttgtcaaa   40080
aagtgacttg cttttattctt tgagatttag gaaggcaaag agacagtcac ggaggagtcc   40140
tgtgcagcag caggttcaat atgaaagaga aaatcaaggg ggcaacttga gtggaactga   40200
gttcctcctg cttcaaaggg tcaagcaaaa gctagctgac cccaggagag ccactgtaag   40260
gagttcgtcc tggagagaag tgtaacctgg gatttccaa attccttctg attctaacat     40320
tctaattatc aaataaaatg cacttataga tatggaaata acatttgctt aaccattata   40380
tttaaaatta atgtacatca ctgctttcag tttgagtatt ttatcaagct ataatgatac   40440
cggttcatgg atgacgtgac atctgtactt caaacaaaaa atgttaataa aaaaatctat   40500
tgaaactggg gccacaaaag ttcaatcaat atttatcttt ggtttagtca atatataaag   40560
ttatatcagt cataaacttt agtatgtatc ttttttaccac caagctggat ccagaaagat   40620
atttgataat gtgttttatg taaaaatacg ttatttcaaa aatgatttga tagttttttgg   40680 tcaaatgcta ttgaaataat ttcaaagaag aggcaaatta agtagttaag tgaggctacc   40740
atgtctaatg catttgtatg attccttcta aacagctcaa gaggaccatt tctcaagtat   40800
tttgctatta ttactattat tattaatgat aaatttatag ctcacttttg tagagctttt   40860 tgtattttt caaaacacgt tgacatatat aaggtgcttt taattctcac aatatgcctg     40920
ggagttaggc aatgtggtag agcctgctgg ttatcctaaa tgatctgttc ccatctgatt   40980
tcaacttaat agaatcattc actgagcacc cggctcctca ggggacaatt atttgcagac   41040
tccttttgac catgtgactg agttctgccc aagggacagt gataggtgca gcttccaggt   41100
caggcacttg agaggccacc ttttccctct tcctctcttt tcctgtccac tggatgaaat   41160
tgggatatta tgtgctctgg aaatcaacaa aggtcacata acgtatctgc ctaggaaaat   41220
ctttactgtt cttcctcact cttttaaaact ccttcccaga tattgtgtga gagcagactg  41280
caagcgcaat attccattta caagaaagaa tatggacacg ttgaaaccag aaatatgtat   41340
tttacctctc cacttatgcc tttattaaaa attgtatttc tttcctctgt gccaagcact   41400
gagataagca ctacaaattt tgaaataaat atgataggta gtctgtgctc ttaagagagc   41460
cacaactgag taaatgatcc attctacctg tggttattgc agaatgaaaa tatttgagtc   41520
aagtctctga agggtaagta agagtttacc ccaagataaa gagggggaaaa aggcatcctt  41580 caggttatct tcatactcag aatacatcaa aatagagcat ataaaagtca cattctgctt   41640
```

```
atctgtttaa atatagattt caagtataac tttgcatttc tggagaaaat gtggatctga   41700
gacaattcaa taagctgtgt gtttttactc acctattatt acttgtcctc ccagtaagca   41760
tgtattctat tctcctcctc cacctaaaat ttcctttatg cctcaaaaag acaacattca   41820
ttgaaagaaa gacaacttt gcacaaatta attataataa aattctagtt tagagcaatg    41880
atatttttga gaatataaga taattcagaa ggcttctatg tgcaaaagcc gtgattgcta   41940
catattcagc tggcacagtt aattgttcat tcattttgca cctgagaagg tgcattgaca   42000
ttacttgaat gcatagttta cattttcctt cttttcttca actcaaaata attggcattg   42060
ttaaaacact gctatgattt tgaaatgatt tgattaattc ttttcctatt ttaaaatttt   42120
ttcttggact tgactgtaac cttcaaaaaa caatgtgttc aaaaaggagt gattcaagct   42180
gtttgggaga tattttaact atttctgact aaatgcacta ttgaattcag tagtattcta   42240
aaatttatat taactttcaa tccagttgat tattctagtt atgtacaaaa tacatttttt   42300
tgagatggag tttcgctctt gttgctcagg atggagtgca atggtgcgat ctcagctcac   42360
tacaacctct gcctcccatg ttcaaacgat tctcctgcct cagcctccca agtagctggg   42420
attacaggca cctgccacca cgtctggtga attttccata ttttagtag agacgggggt    42480 tcaccatgtt ggccaggctg ttctcaaact cctgatctca ggtgatccac ccgcctcagc   42540
ctcccaaagt gctgggatta caggtgtgag ccactgcgcc cggccccaaa tacattttaa   42600
tgaaagaaaa acttgtaaag tatttctcaa aagtgcatag tatatgtaat ttgagcatat   42660
atacagtaga caaatcgctc atactaatta cttggggaat aaaaattcaa tcagctaaca   42720 aagcccttc caatatatac tcctaaagct ggccaggaga ctttaccacc tgcccttatt    42780
ctgaaaactt cttcataatg ctgcatggtg actacagata gcttttaact ggacattttc   42840
acaatggaat catacatttg atgatgaacc ttaaattttc actgcagatg tcagagtctg   42900
ccacgttatg tttacctatt tttccttatc agattaggat ttggtagtct ctgttccatt   42960
ggaaagtggc tagaaagact gacaaggaga gaaaattcta gtagcatgag tttataaagg   43020
tgaaatcagg ctattcggta aaccagaagc caccttctga gcaccaaggg agggcaagat   43080
gccattttca gagatacaga tgaagggaac aggattaccc cagatagcga aggggtaaaa   43140
tggagacaaa tggttaaata aagggaagag cgcgggagga ggcatctgag caaagcgaag   43200
tcctgtgcag gatgccatag aaggaagaga tggcattcag gcatgggcc caagggagcg    43260 tgttagctgg ctccagaaga acaggtggga tttgaaaaag caaggactct gtcttgtcca   43320
cacataatgt caccctgtag agcatccatc atggcacact gcaggggca aggcagaaat    43380 aagaaccca gcagtgaggc tgttcccatt acccaggcaa ggttggatgg tgtcttgcac    43440
ctccatcgta gtcatagata aggggagaag tggtttgatt ctggacacat cctggaggta   43500
ggtagagctg caggatttgt tgatggatta gaaacaagac atgaaaagg ggagtagtta    43560 agattcgggg tccaacaact ggaagagtaa aaagtcatca taatagagaa ggggaagcag   43620
gggtttggtt tgggatgtgt tcgatgtgac atgcccatta gacatccacg tggagaaggc   43680
ggttgtctat gccagtctga tgctcgggga aacctgggtg gagactcaaa atctccagtc   43740
atcgggatgc agcagtattc aaagcaatgg cctggagtga atctagacag agccctgagc   43800
cctccactat ttacaggcaa ggtgaggagg aacaagcaaa ggagactaag agggaatcgc   43860
cagggagctg agaggagaag caagggagag ccagggcctg aaatccaagt tgaggaagga   43920 ttcaaggac aagaagtgat ggcttcaaca acattgcag acagatgggc tgagacctgc    43980
acactgatgc taatgctcaa caatgcccag attaatatct cctagcccta cttccttacg   44040
```

```
tgaaagaagt cttttcaca ggttccttgc acaaatgttt gcaagaatct caggcggtga   44100
ggggagttga aggtgggaaa tgggaacacg tgtatttcca acttgattct aatcctctta   44160
gaacccatat acagaacaaa gactcagagg cactgctggg gctgaactcc ccaactacag   44220
tccctagtgc tgatttcagg ggacattaag aactttgttt caagagctgt gaaggctgag   44280
cagttggtct tcaagtccga gagaaaaggt gcatcctcct ggattacact caaatgagca   44340
aagcagcctg agctccaagc tctttgtagg agacctctct ctctctgtcc ctcctcccct   44400
ctcccctctt ctccttctct tctgtctcct ctctctctct ctctctctct ctcacacaca   44460
cacacacaca cacacaccat ttttgccaag gctcactcca gtatgaggaa cccacaaaga   44520
acaccaagac ctccattctg agcagggcct ccattatttg tcctgctgtt tgtttgttct   44580
gcctcctgtc ctccaggcca tcaatgattc ttgactctct aggaggggtc aagcttccca   44640
tcatcccagg ggatctcctt agcccatttg taagttagtg gaaacacaga gggagtgagg   44700
gaagggtgct agccagtctt tatccttcac caacatcaga tcccggaaca caactggccc   44760
ctatatctgt acagcagcaa tatctaagcc ccagctaaaa tgcccttta tcaaaatctg   44820
cagaatgttt tatctttttc aggtaagctc aaatttttct attctcgctt cccccaaccc   44880
ctatatacac accgagaaag gtcattgaaa acagaatgaa agtatctcat acaacaaaat   44940
taattcaaga tactttcttt gacaatggga actcgcttct aaataagata caagaatgac   45000
taaacaccaa accaaaagaa atgtgaaagc aaaattaata ctttacacca actaacagtt   45060
tgtttgcaac atcagcaaat ggagcattca cctgttacta atttccctaa atacaaagtc   45120
cactgcattt ctaggaagga tggttagtgt ttggcaaatt ttttgtgtaa gcattgaaaa   45180
atataactga gaagttaatc agagggccat gagtgggcaa aaagatctaa acatgttga   45240
ttatttaaaa caccagagca ccagagagca cgcaagtctt tatcttataa taaaatgatc   45300
ctataagtca ctataataac aattgactac tttgtatatg caagtttatc ctagggactc   45360
taaaaataga acttgtagga tttaaatcta agtaaagat tttatgggca tgatctatta   45420
gatcctccag ctgatccatt tatttgcttc cagtatgaac tgataacttg cttatgtttt   45480
cttcaaaaag tgagaccatt cttcccatag tttttctatc accagccata cactggtggt   45540
ctttagagtt tttcagatcc ataaaaggat tgaaaagta taagaatcac cgctctaaaa   45600
catccttatg aaaagacata cataagtatg aaatcacaaa atcacaatg tgtttccaaa   45660
caaatccaac attctttat ggccagtagc agcaaacagg ttttgtggaa ctgacataaa   45720
atctaattta gccattatta caacattacc agcagctcag agcactaagt cacctcaata   45780
acccagtact gctctgccca tattatctat ggctttaatt aaaagtgttt agaaatggtt   45840
ttagtactga ctttgttcag aatatgtggc tgaattctaa atttaaaaat aagtcttcca   45900
gtaggcccac aagtgatcag aattgggtac caaaagttgt acatttaaac acttttatta   45960
aaatgtttat acatgtacat aaaatatttt attgtgatac aaaactctgt acaaagtgta   46020
ctaacaactg acatgattat aaatgaatcc ccaaaacaat ggtgcctaaa tttgaacact   46080
aaggagaaaa aaggaggaag aaatacttga gacaactta ccatggcata gcaatatttc   46140
ctgctgtcaa aattaataaa atattttgca caagggtgtt acaattaatt ttatcaggct   46200
aacaatgtca taagtgagga acccttcaa ctgtagagag cactgtggaa atatagatgt   46260
ggtagaacaa tctatatcac cctgcagttg tttctgtgtt tctatgacta gctttgtttg   46320
agattgtata aagcggtctt cacacccccgg tgaataagat tggtggatgc agttccctgc   46380
```

```
cctgccgcag aagggacctc caaacacagt ttaaatctga ctctccggga gttgtgtttt     46440
gacactttca caacagtgtg aacttgtgcc acaagcaaga cagatcttat tggattaaca     46500
ctgaactcgt gacagctcca gagagtaatg ctatctgtgc ggcttaagaa caaacgtgtt     46560
tctttcatcc accctgctca ttctcttcct gcagttactc ctagcaaatc ctccccgccc     46620
tcacctctag gaattcctct acacccagag aaaggagttt ctttcctcac tgcggaaacc     46680
tatcaccgct tcctttccac agatggactc caaggggcac tcactcgtgt gcccactaag     46740
ggatttctct cctaattcca cgccttccaa gggaagtcag aactgctcag tttcccccgg     46800
tgaccacata cacgtgtcca agtgaagcct cgtctggggg agactcagtt cccacacttc     46860
cccctggccc ctgtggaggc cctctgtctc ccctgcgtgg ccctccgcct ggcccctcgc     46920
actcaccagg aggaggttgt gcgccaccag gtacccgagc cgcgggctgc cccggatgcc     46980
gggggccagg cgcccggtgg cgtagccgtg ccaggccacc acgtagggg  tgtcgatggt     47040 gatccagtac ttgacctgac cgccgaagtg gcggaagcag agctccgcgt aatccctgaa     47100
gtggtcggcc agggcgcggt tggcccagcc gccgtaggcg tcctgcaggc gctggggcag     47160
gtcccagtgg tacagggtga ccacgggctg cacgcccagc tcccgcagcc gctccagcag     47220
gcgccggtag tagccgcagcc cctcgcgtt ggggacgccc gcgctgccat ggggagcac     47280 tcgcgcccac gagatggaga agcggtagtg agtgaccccg agctcgcgca gcgcctccgt     47340
gtcgcggaag acgttgttgt agctgtcgct ggctacgtcc ccggtggcgg gctgcagcgg     47400
cgacggggcg cccaacggca gactggcgtt ccggagtct  cccggggggtg ccaggggggtg    47460 gtgggtgaac gtatcccaga tggacgcacc cttgccgtgc tgctgccagc cgccctcggt     47520
ctggtaggcg gcgctgccca cggcccagag gaagccgtcg gggaaggtgc cctggaagag     47580
gcccgcggcc tcgggggcag gaggccgcga gaaacgggcc caggtctgcg cgccgtcgcc     47640
cggctccgca cgcaggcggc ggccgcccag gcccagcagc accagcagca gcgacagcga     47700
cggcggcggc ggccgcgggc ggcgcggcgg ggcgctggcg gcatgctgc gcgggagcca     47760 ggctccgggg ccccgcgccg cgccccttta tgcccgcgcc ccgccgcgcc cgcccgccca     47820
ccgccggcgc gcccaccccc gctccccggc gggctccgct ggcaataatt acctgcgagc     47880
cgggactgcc tccgccctgg cactgggggt ggggcaggg gcgccgaggg cgagggtgc      47940 ccgggagggg cgcggcagcg ggcaaggtgc ggcaggcgtc gcccgcggac gtcggagaaa     48000
ggcacctgtt cctcccagct cccgggagcc gtgcaggacg tttcgtggac gctcaggttc     48060
attctctttg cctgccgcgc gtcctctgag agcagccctg gagcggcttc gtcggggaga     48120
aaaggcgccg accaactttc cccgacttgg gggcgggatc ctgccgggcc ctagcggagc     48180
gcgccgctgg ggaagcacct gctctcactt ttctcccact cggaggccca agaagctcc      48240 ggctggacat tgctggagcc aattagggac tggccgaaat cctagaggga ctgccaggtg     48300
ggacagccga gggggaactt cgccgtgcgc tgaaagggat tccccttag gtgagatgct      48360 cgcggggaga cgcgcccacc cgcgcccctc tttcgaggaa gacaaagtag atttatgggt     48420
tgcgttggga ctgggtttt gctctcctt  ttactgttac cttttaataa tttcaaacca     48480
gcactctatc tttgattaga tctctcagaa taccctggtg aacttcaaat cacagtcgtt     48540
gattgttctc ctgaaaaacc aaacaccaag tttccaattt tgagtaaatc tcattcacct     48600
ttattatcct ttggcatctg tgttaccttt cggctctgac ttagcaggta atctgtgcaa     48660
agttgtgcgc acaggtctgc tggagcggga ggtccctggg tcgcacattt gccatctgag     48720
ctgtggaggg aaaggggagg gagaatttag ccggaacacc cattcccatc ctctacaata     48780
```

```
caatggagcc atgacgtttt tcctgttgcc aaagagccct tttgacagaa gttgcagagc    48840
cacggtgtcc atttggatgt gggtagatag gattgtggct aaccgaaata cagttggtgg    48900
agactgagaa ggtctaggct ccacctttgt gatttggggc aggaaacctc tgtaagccta    48960
agttttttcc tctataaaat aaggatgtcc tgtctgccct gccgcctcag aggcttgtga    49020
agtccagtga aaaactgcgc aaaggtgact caaagacaga aagcccagac aagtgaagga    49080
tcttgctaat atccctacct ccctacccag taagtcgtgc cttagtttcc tcacccgtac    49140
acgtgtgttg aatgaccaag atcctcacag aggtgcatcc attctccccc agtgatctat    49200
cctccctgca ttatttaata caaatttaaa ggcaataaca ttttaaatgt tgcagatgaa    49260
ggtgctttta ttaattcccc tgaaatataa gcacaaattt attccagtat tttatgaaat    49320
attcccaact ccagccagca tatattacca tgattagtaa gattaagtct tcagattgaa    49380
acagagttac tgccattctg ttaaatatag catttacatt ttttcaataa atacgaaata    49440
gcaaaccatg acacttcagc aattttaaaa aattacagca cacaacttca ctgtcacgct    49500
gtcttccagc taaatttaaa aagctacgtc tacatggagt atcacatttc ccttctagaa    49560
gtgaagattg gagtgtctgt tggttgtag cttgttaagt ttcaattaga aatgcttcat     49620
gggtctcatg gaaaatcgct taagctaagt attcatttat tgatgtatgg tctgtttgct    49680
cagggcagat tttatctatt gctatttta cttgaccagc agcatttttt aaatttaaa      49740 gcagtgatta aaaagcaaga ccaagttaac taaacgtttc acatttgaaa tttgtctgcc    49800
acataggcac atgcatctca aagctttaag cattccaaga catgttccca gatgattgtt    49860
catttaaccc agtgataaag attgcatgat gattaaactt tatttccaga actttctgtt    49920
tattaaggtt ctgttcatgg ttactaagtt ctggttcca caagtgtgag acggagtctc     49980
actctgtcgc ccaggctgga gtgcagtggc atggtctctg ctcactgcaa cctctgcctc    50040
ccaggttcaa gcaattctcc tgtctcagcc ccccagtagc tgggattata agggcacacc    50100
accacacctg gctaatttt gtatttttag tagagacagg gtttcaccat gctgaccagg     50160
ctggtctcaa actcctgatc tcctgtgatc cacccacctc ggtctcctaa aatgctggga    50220
ttacaggtgt gagacactgt gcccggccta gtgctgctgc ttatttattt tggctttatt    50280 ttggtttta tttttacaa ccaccttcaa acatctgaaa cttgggtttc aaatgcaaat      50340
aagagattaa ttacttgctg tgcttttgaac aggaaggtga agttattgat gcattgaaga   50400
aaaggacatt gtaaatttat ttactgactt tgattttggt gacaatttca acactgaaag    50460
ttgtcaacaa tctgatcaac ttttcctcca ttctccacat tccttcatcc agtgccttcc    50520
cacctgttct ctttcctatt gtgttcccag gacgatggga gcctttaac accaatggag     50580 caggagatgc actgattcac atgcactcaa atacaacacc aacccacaa gctctcggct     50640 caccagtcac agacatcacc ttctacggac atatttttat ttcactgagc tacaactacg    50700
ggcaaggcaa cgatgagctg tgtggagact tcaaaacata gaggacaacc tctgccctca    50760
aagacaacat ccaactgaag aaaggatcaa gaaagatgaa aataaataag ttgtttgatt    50820
atgctgtgtt aataaatgac ccatagaata attgtcagag aaattcagaa gaagaagaaa    50880
ttaccctatt ttgagttgtt tggaaaagtt taacagagaa aaatatgaca atatctgggg    50940
tttaaagagt aaaactcgca caaagacctg gagggaagga atcaagagat gccaacactg    51000
aagaaaaaaa catgttcata gtgtattcgt ggtgaaaaga aagggttttt gtgcgcaagg    51060
aagtaatgga ccaaaatgca gtagtcccag tgcctagaat catgctgagc acaaaacaag    51120
```

```
tatttgttta atgagcaaat gaaagtagag tttcatttgt ccagttaaca aaatacacaa    51180
gtattccctg ccctcctctt tttaaaatta attaattaat taattttaa cagacaaaaa     51240 attatatata ttttcatgta cagcatgtta ttttaaaata tatacacatt tgtagagtgg    51300
ctaaattgag ctaataaacg tatgtattac ctcacatact tatttttttt gtggtaagaa    51360
gacttaaaat ctggccgggc gtggtggctc acacctgtaa tcccagcact ttgagaggcc    51420
gaggcaggtg gaccacctaa ggtcaggagt tcgagaccag cctggccaac atggtgaaac    51480
tcctgtctct actaaaaata caaaaattca ccaacatggt ggcaggcacc tgtaatccca    51540
gctactcagg aggctgaggc aggagaatca cttgaacccg ggaggcggag gttgcagtga    51600
gctgagatca caccactgta ctccagcttt ggcaacagag caagagtctg tttcaaaaaa    51660 gaaaaagaa aagaaaagaa gaaaagaaag aaaaagaaga atacttaaaa tctactctga    51720
gattttcaaa aatacaatat attgt                                         51745
```

<210> SEQ ID NO 29
<211> LENGTH: 260
<212> TYPE: PRT
<213> ORGANISM: Artificial Sequence
<220> FEATURE:
<223> OTHER INFORMATION: ZFP1

<400> SEQUENCE: 29

```
Met Ala Gln Ala Ala Leu Glu Pro Gly Glu Lys Pro Tyr Lys Cys Pro
1               5                   10                  15

Glu Cys Gly Lys Ser Phe Ser Asp Pro Gly His Leu Val Arg His Gln
            20                  25                  30

Arg Thr His Thr Gly Glu Lys Pro Tyr Lys Cys Pro Glu Cys Gly Lys
        35                  40                  45

Ser Phe Ser Ser Lys Lys Ala Leu Thr Glu His Gln Arg Thr His Thr
    50                  55                  60

Gly Glu Lys Pro Tyr Lys Cys Pro Glu Cys Gly Lys Ser Phe Ser Arg
65                  70                  75                  80

Asn Asp Ala Leu Thr Glu His Gln Arg Thr His Thr Gly Glu Lys Pro
                85                  90                  95

Tyr Lys Cys Pro Glu Cys Gly Lys Ser Phe Ser Asp Pro Gly Ala Leu
            100                 105                 110

Val Arg His Gln Arg Thr His Thr Gly Glu Lys Pro Tyr Lys Cys Pro
        115                 120                 125

Glu Cys Gly Lys Ser Phe Ser Asp Ser Gly Asn Leu Arg Val His Gln
    130                 135                 140

Arg Thr His Thr Gly Glu Lys Pro Tyr Lys Cys Pro Glu Cys Gly Lys
145                 150                 155                 160

Ser Phe Ser Gln Ser Gly His Leu Thr Glu His Gln Arg Thr His Thr
                165                 170                 175

Gly Lys Lys Thr Ser Gly Gln Ala Gly Gln Ala Ser Pro Lys Lys Lys
            180                 185                 190

Arg Lys Val Gly Arg Ala Asp Ala Leu Asp Asp Phe Asp Leu Asp Met
        195                 200                 205

Leu Gly Ser Asp Ala Leu Asp Asp Phe Asp Leu Asp Met Leu Gly Ser
    210                 215                 220

Asp Ala Leu Asp Asp Phe Asp Leu Asp Met Leu Gly Ser Asp Ala Leu
225                 230                 235                 240

Asp Asp Phe Asp Leu Asp Met Leu Ile Asn Tyr Pro Tyr Asp Val Pro
                245                 250                 255
```

Asp Tyr Ala Ser
            260

<210> SEQ ID NO 30
<211> LENGTH: 372
<212> TYPE: PRT
<213> ORGANISM: Artificial Sequence
<220> FEATURE:
<223> OTHER INFORMATION: ZFP52

<400> SEQUENCE: 30

Met Ala Gln Ala Ala Leu Glu Pro Gly Glu Lys Pro Tyr Lys Cys Pro
1               5                   10                  15

Glu Cys Gly Lys Ser Phe Ser Thr Lys Asn Ser Leu Thr Glu His Gln
            20                  25                  30

Arg Thr His Thr Gly Glu Lys Pro Tyr Lys Cys Pro Glu Cys Gly Lys
        35                  40                  45

Ser Phe Ser Gln Ser Gly Asp Leu Arg Arg His Gln Arg Thr His Thr
    50                  55                  60

Gly Glu Lys Pro Tyr Lys Cys Pro Glu Cys Gly Lys Ser Phe Ser Asp
65                  70                  75                  80

Cys Arg Asp Leu Ala Arg His Gln Arg Thr His Thr Gly Glu Lys Pro
                85                  90                  95

Tyr Lys Cys Pro Glu Cys Gly Lys Ser Phe Ser Thr Lys Asn Ser Leu
            100                 105                 110

Thr Glu His Gln Arg Thr His Thr Gly Glu Lys Pro Tyr Lys Cys Pro
        115                 120                 125

Glu Cys Gly Lys Ser Phe Ser Arg Thr Asp Thr Leu Arg Asp His Gln
    130                 135                 140

Arg Thr His Thr Gly Glu Lys Pro Tyr Lys Cys Pro Glu Cys Gly Lys
145                 150                 155                 160

Ser Phe Ser Arg Ser Asp Asp Leu Val Arg His Gln Arg Thr His Thr
                165                 170                 175

Gly Glu Lys Pro Tyr Lys Cys Pro Glu Cys Gly Lys Ser Phe Ser Arg
            180                 185                 190

Ser Asp Lys Leu Thr Glu His Gln Arg Thr His Thr Gly Glu Lys Pro
        195                 200                 205

Tyr Lys Cys Pro Glu Cys Gly Lys Ser Phe Ser Arg Asn Asp Thr Leu
    210                 215                 220

Thr Glu His Gln Arg Thr His Thr Gly Glu Lys Pro Tyr Lys Cys Pro
225                 230                 235                 240

Glu Cys Gly Lys Ser Phe Ser Arg Arg Thr Cys Arg Ala His Gln
                245                 250                 255

Arg Thr His Thr Gly Glu Lys Pro Tyr Lys Cys Pro Glu Cys Gly Lys
            260                 265                 270

Ser Phe Ser Gln Ser Gly His Leu Thr Glu His Gln Arg Thr His Thr
        275                 280                 285

Gly Lys Lys Thr Ser Gly Gln Ala Gly Gln Ala Ser Pro Lys Lys Lys
    290                 295                 300

Arg Lys Val Gly Arg Ala Asp Ala Leu Asp Asp Phe Asp Leu Asp Met
305                 310                 315                 320

Leu Gly Ser Asp Ala Leu Asp Asp Phe Asp Leu Asp Met Leu Gly Ser
                325                 330                 335

Asp Ala Leu Asp Asp Phe Asp Leu Asp Met Leu Gly Ser Asp Ala Leu
            340                 345                 350

```
Asp Asp Phe Asp Leu Asp Met Leu Ile Asn Tyr Pro Tyr Asp Val Pro
        355                 360                 365

Asp Tyr Ala Ser
    370

<210> SEQ ID NO 31
<211> LENGTH: 874
<212> TYPE: PRT
<213> ORGANISM: Artificial Sequence
<220> FEATURE:
<223> OTHER INFORMATION: ZFP52_VPR

<400> SEQUENCE: 31

Met Ala Gln Ala Ala Leu Glu Pro Gly Glu Lys Pro Tyr Lys Cys Pro
1               5                   10                  15

Glu Cys Gly Lys Ser Phe Ser Thr Lys Asn Ser Leu Thr Glu His Gln
            20                  25                  30

Arg Thr His Thr Gly Glu Lys Pro Tyr Lys Cys Pro Glu Cys Gly Lys
        35                  40                  45

Ser Phe Ser Gln Ser Gly Asp Leu Arg Arg His Gln Arg Thr His Thr
    50                  55                  60

Gly Glu Lys Pro Tyr Lys Cys Pro Glu Cys Gly Lys Ser Phe Ser Asp
65                  70                  75                  80

Cys Arg Asp Leu Ala Arg His Gln Arg Thr His Thr Gly Glu Lys Pro
                85                  90                  95

Tyr Lys Cys Pro Glu Cys Gly Lys Ser Phe Ser Thr Lys Asn Ser Leu
            100                 105                 110

Thr Glu His Gln Arg Thr His Thr Gly Glu Lys Pro Tyr Lys Cys Pro
        115                 120                 125

Glu Cys Gly Lys Ser Phe Ser Arg Thr Asp Thr Leu Arg Asp His Gln
    130                 135                 140

Arg Thr His Thr Gly Glu Lys Pro Tyr Lys Cys Pro Glu Cys Gly Lys
145                 150                 155                 160

Ser Phe Ser Arg Ser Asp Asp Leu Val Arg His Gln Arg Thr His Thr
                165                 170                 175

Gly Glu Lys Pro Tyr Lys Cys Pro Glu Cys Gly Lys Ser Phe Ser Arg
            180                 185                 190

Ser Asp Lys Leu Thr Glu His Gln Arg Thr His Thr Gly Glu Lys Pro
        195                 200                 205

Tyr Lys Cys Pro Glu Cys Gly Lys Ser Phe Ser Arg Asn Asp Thr Leu
    210                 215                 220

Thr Glu His Gln Arg Thr His Thr Gly Glu Lys Pro Tyr Lys Cys Pro
225                 230                 235                 240

Glu Cys Gly Lys Ser Phe Ser Ser Arg Thr Cys Arg Ala His Gln
                245                 250                 255

Arg Thr His Thr Gly Glu Lys Pro Tyr Lys Cys Pro Glu Cys Gly Lys
            260                 265                 270

Ser Phe Ser Gln Ser Gly His Leu Thr Glu His Gln Arg Thr His Thr
        275                 280                 285

Gly Lys Lys Thr Ser Gly Gln Ala Gly Gln Ala Ser Pro Lys Lys Lys
    290                 295                 300

Arg Lys Val Gly Arg Ala Asp Ala Leu Asp Asp Phe Asp Leu Asp Met
305                 310                 315                 320

Leu Gly Ser Asp Ala Leu Asp Asp Phe Asp Leu Asp Met Leu Gly Ser
                325                 330                 335
```

```
Asp Ala Leu Asp Asp Phe Asp Leu Asp Met Leu Gly Ser Asp Ala Leu
            340                 345                 350

Asp Asp Phe Asp Leu Asp Met Leu Ile Asn Tyr Pro Tyr Asp Val Pro
        355                 360                 365

Asp Tyr Ala Ser Ser Gly Ser Pro Lys Lys Arg Lys Val Gly
370                 375                 380

Ser Gln Tyr Leu Pro Asp Thr Asp Arg His Arg Ile Glu Glu Lys
385                 390                 395                 400

Arg Lys Arg Thr Tyr Glu Thr Phe Lys Ser Ile Met Lys Lys Ser Pro
                405                 410                 415

Phe Ser Gly Pro Thr Asp Pro Arg Pro Pro Arg Arg Ile Ala Val
            420                 425                 430

Pro Ser Arg Ser Ser Ala Ser Val Pro Lys Pro Ala Pro Gln Pro Tyr
            435                 440                 445

Pro Phe Thr Ser Ser Leu Ser Thr Ile Asn Tyr Asp Glu Phe Pro Thr
            450                 455                 460

Met Val Phe Pro Ser Gly Gln Ile Ser Gln Ala Ser Ala Leu Ala Pro
465                 470                 475                 480

Ala Pro Pro Gln Val Leu Pro Gln Ala Pro Ala Pro Ala Pro
                485                 490                 495

Ala Met Val Ser Ala Leu Ala Gln Ala Pro Ala Pro Val Pro Val Leu
            500                 505                 510

Ala Pro Gly Pro Pro Gln Ala Val Ala Pro Pro Ala Pro Lys Pro Thr
            515                 520                 525

Gln Ala Gly Glu Gly Thr Leu Ser Glu Ala Leu Leu Gln Leu Gln Phe
            530                 535                 540

Asp Asp Glu Asp Leu Gly Ala Leu Leu Gly Asn Ser Thr Asp Pro Ala
545                 550                 555                 560

Val Phe Thr Asp Leu Ala Ser Val Asp Asn Ser Glu Phe Gln Gln Leu
                565                 570                 575

Leu Asn Gln Gly Ile Pro Val Ala Pro His Thr Thr Glu Pro Met Leu
            580                 585                 590

Met Glu Tyr Pro Glu Ala Ile Thr Arg Leu Val Thr Gly Ala Gln Arg
            595                 600                 605

Pro Pro Asp Pro Ala Pro Ala Pro Leu Gly Ala Pro Gly Leu Pro Asn
610                 615                 620

Gly Leu Leu Ser Gly Asp Glu Asp Phe Ser Ser Ile Ala Asp Met Asp
625                 630                 635                 640

Phe Ser Ala Leu Leu Gly Ser Gly Ser Gly Ser Arg Asp Ser Arg Glu
                645                 650                 655

Gly Met Phe Leu Pro Lys Pro Glu Ala Gly Ser Ala Ile Ser Asp Val
            660                 665                 670

Phe Glu Gly Arg Glu Val Cys Gln Pro Lys Arg Ile Arg Pro Phe His
            675                 680                 685

Pro Pro Gly Ser Pro Trp Ala Asn Arg Pro Leu Pro Ala Ser Leu Ala
            690                 695                 700

Pro Thr Pro Thr Gly Pro Val His Glu Pro Val Gly Ser Leu Thr Pro
705                 710                 715                 720

Ala Pro Val Pro Gln Pro Leu Asp Pro Ala Pro Ala Val Thr Pro Glu
                725                 730                 735

Ala Ser His Leu Leu Glu Asp Pro Asp Glu Glu Thr Ser Gln Ala Val
            740                 745                 750
```

```
Lys Ala Leu Arg Glu Met Ala Asp Thr Val Ile Pro Gln Lys Glu Glu
                755                 760                 765

Ala Ala Ile Cys Gly Gln Met Asp Leu Ser His Pro Pro Arg Gly
770                 775                 780

His Leu Asp Glu Leu Thr Thr Thr Leu Glu Ser Met Thr Glu Asp Leu
785                 790                 795                 800

Asn Leu Asp Ser Pro Leu Thr Pro Glu Leu Asn Glu Ile Leu Asp Thr
                805                 810                 815

Phe Leu Asn Asp Glu Cys Leu Leu His Ala Met His Ile Ser Thr Gly
                820                 825                 830

Leu Ser Ile Phe Asp Thr Ser Leu Phe Asp Ser Ser Leu Glu Gly Pro
                835                 840                 845

Arg Phe Glu Gly Lys Pro Ile Pro Asn Pro Leu Leu Gly Leu Asp Ser
                850                 855                 860

Thr Arg Thr Gly His His His His His His
865                 870

<210> SEQ ID NO 32
<211> LENGTH: 288
<212> TYPE: PRT
<213> ORGANISM: Artificial Sequence
<220> FEATURE:
<223> OTHER INFORMATION: ZFP1_Egr1_site1_sense

<400> SEQUENCE: 32

Met Ala Gln Ala Ala Leu Glu Pro Gly Glu Lys Pro Tyr Lys Cys Pro
1               5                   10                  15

Glu Cys Gly Lys Ser Phe Ser Thr Ser Gly Asn Leu Thr Glu His Gln
                20                  25                  30

Arg Thr His Thr Gly Glu Lys Pro Tyr Lys Cys Pro Glu Cys Gly Lys
            35                  40                  45

Ser Phe Ser Arg Ser Asp Lys Leu Val Arg His Gln Arg Thr His Thr
    50                  55                  60

Gly Glu Lys Pro Tyr Lys Cys Pro Glu Cys Gly Lys Ser Phe Ser His
65                  70                  75                  80

Thr Gly His Leu Leu Glu His Gln Arg Thr His Thr Gly Glu Lys Pro
                85                  90                  95

Tyr Lys Cys Pro Glu Cys Gly Lys Ser Phe Ser Arg Ser Asp Lys Leu
                100                 105                 110

Val Arg His Gln Arg Thr His Thr Gly Glu Lys Pro Tyr Lys Cys Pro
            115                 120                 125

Glu Cys Gly Lys Ser Phe Ser Arg Ser Asp Asp Leu Val Arg His Gln
        130                 135                 140

Arg Thr His Thr Gly Glu Lys Pro Tyr Lys Cys Pro Glu Cys Gly Lys
145                 150                 155                 160

Ser Phe Ser Arg Ser Asp Asp Leu Val Arg His Gln Arg Thr His Thr
                165                 170                 175

Gly Glu Lys Pro Tyr Lys Cys Pro Glu Cys Gly Lys Ser Phe Ser Asp
            180                 185                 190

Pro Gly His Leu Val Arg His Gln Arg Thr His Thr Gly Lys Lys Thr
            195                 200                 205

Ser Gly Gln Ala Gly Gln Ala Ser Pro Lys Lys Lys Arg Lys Val Gly
        210                 215                 220

Arg Ala Asp Ala Leu Asp Asp Phe Asp Leu Asp Met Leu Gly Ser Asp
225                 230                 235                 240
```

Ala Leu Asp Asp Phe Asp Leu Asp Met Leu Gly Ser Asp Ala Leu Asp
            245                 250                 255

Asp Phe Asp Leu Asp Met Leu Gly Ser Asp Ala Leu Asp Phe Asp
        260                 265                 270

Leu Asp Met Leu Ile Asn Tyr Pro Tyr Asp Val Pro Asp Tyr Ala Ser
        275                 280                 285

<210> SEQ ID NO 33
<211> LENGTH: 288
<212> TYPE: PRT
<213> ORGANISM: Artificial Sequence
<220> FEATURE:
<223> OTHER INFORMATION: ZFP2_Egr1_site2_sense

<400> SEQUENCE: 33

Met Ala Gln Ala Ala Leu Glu Pro Gly Glu Lys Pro Tyr Lys Cys Pro
1               5                   10                  15

Glu Cys Gly Lys Ser Phe Ser Arg Ser Asp Asp Leu Val Arg His Gln
            20                  25                  30

Arg Thr His Thr Gly Glu Lys Pro Tyr Lys Cys Pro Glu Cys Gly Lys
        35                  40                  45

Ser Phe Ser Asp Pro Gly His Leu Val Arg His Gln Arg Thr His Thr
    50                  55                  60

Gly Glu Lys Pro Tyr Lys Cys Pro Glu Cys Gly Lys Ser Phe Ser Arg
65                  70                  75                  80

Ser Asp Glu Leu Val Arg His Gln Arg Thr His Thr Gly Glu Lys Pro
                85                  90                  95

Tyr Lys Cys Pro Glu Cys Gly Lys Ser Phe Ser Arg Ser Asp Lys Leu
            100                 105                 110

Val Arg His Gln Arg Thr His Thr Gly Glu Lys Pro Tyr Lys Cys Pro
        115                 120                 125

Glu Cys Gly Lys Ser Phe Ser Arg Ser Asp Asp Leu Val Arg His Gln
    130                 135                 140

Arg Thr His Thr Gly Glu Lys Pro Tyr Lys Cys Pro Glu Cys Gly Lys
145                 150                 155                 160

Ser Phe Ser Gln Arg Ala His Leu Glu Arg His Gln Arg Thr His Thr
                165                 170                 175

Gly Glu Lys Pro Tyr Lys Cys Pro Glu Cys Gly Lys Ser Phe Ser Arg
            180                 185                 190

Ser Asp Lys Leu Thr Glu His Gln Arg Thr His Thr Gly Lys Lys Thr
        195                 200                 205

Ser Gly Gln Ala Gly Gln Ala Ser Pro Lys Lys Lys Arg Lys Val Gly
    210                 215                 220

Arg Ala Asp Ala Leu Asp Asp Phe Asp Leu Asp Met Leu Gly Ser Asp
225                 230                 235                 240

Ala Leu Asp Asp Phe Asp Leu Asp Met Leu Gly Ser Asp Ala Leu Asp
            245                 250                 255

Asp Phe Asp Leu Asp Met Leu Gly Ser Asp Ala Leu Asp Phe Asp
        260                 265                 270

Leu Asp Met Leu Ile Asn Tyr Pro Tyr Asp Val Pro Asp Tyr Ala Ser
        275                 280                 285

<210> SEQ ID NO 34
<211> LENGTH: 288
<212> TYPE: PRT
<213> ORGANISM: Artificial Sequence
<220> FEATURE:

<223> OTHER INFORMATION: ZFP3_Egr1_site3_antisense

<400> SEQUENCE: 34

```
Met Ala Gln Ala Ala Leu Glu Pro Gly Glu Lys Pro Tyr Lys Cys Pro
1               5                   10                  15
Glu Cys Gly Lys Ser Phe Ser Gln Ser Gly Asp Leu Arg Arg His Gln
            20                  25                  30
Arg Thr His Thr Gly Glu Lys Pro Tyr Lys Cys Pro Glu Cys Gly Lys
        35                  40                  45
Ser Phe Ser Arg Ser Asp Lys Leu Val Arg His Gln Arg Thr His Thr
    50                  55                  60
Gly Glu Lys Pro Tyr Lys Cys Pro Glu Cys Gly Lys Ser Phe Ser Arg
65                  70                  75                  80
Ser Asp Glu Leu Val Arg His Gln Arg Thr His Thr Gly Glu Lys Pro
                85                  90                  95
Tyr Lys Cys Pro Glu Cys Gly Lys Ser Phe Ser Arg Ser Asp Lys Leu
            100                 105                 110
Val Arg His Gln Arg Thr His Thr Gly Glu Lys Pro Tyr Lys Cys Pro
        115                 120                 125
Glu Cys Gly Lys Ser Phe Ser Arg Asn Asp Ala Leu Thr Glu His Gln
    130                 135                 140
Arg Thr His Thr Gly Glu Lys Pro Tyr Lys Cys Pro Glu Cys Gly Lys
145                 150                 155                 160
Ser Phe Ser Gln Ser Gly Asp Leu Arg Arg His Gln Arg Thr His Thr
                165                 170                 175
Gly Glu Lys Pro Tyr Lys Cys Pro Glu Cys Gly Lys Ser Phe Ser Arg
            180                 185                 190
Asn Asp Ala Leu Thr Glu His Gln Arg Thr His Thr Gly Lys Lys Thr
        195                 200                 205
Ser Gly Gln Ala Gly Gln Ala Ser Pro Lys Lys Lys Arg Lys Val Gly
    210                 215                 220
Arg Ala Asp Ala Leu Asp Asp Phe Asp Leu Asp Met Leu Gly Ser Asp
225                 230                 235                 240
Ala Leu Asp Asp Phe Asp Leu Asp Met Leu Gly Ser Asp Ala Leu Asp
                245                 250                 255
Asp Phe Asp Leu Asp Met Leu Gly Ser Asp Ala Leu Asp Asp Phe Asp
            260                 265                 270
Leu Asp Met Leu Ile Asn Tyr Pro Tyr Asp Val Pro Asp Tyr Ala Ser
        275                 280                 285
```

<210> SEQ ID NO 35
<211> LENGTH: 790
<212> TYPE: PRT
<213> ORGANISM: Artificial Sequence
<220> FEATURE:
<223> OTHER INFORMATION: ZFP3_Egr1_site3_antisense_VPR

<400> SEQUENCE: 35

```
Met Ala Gln Ala Ala Leu Glu Pro Gly Glu Lys Pro Tyr Lys Cys Pro
1               5                   10                  15
Glu Cys Gly Lys Ser Phe Ser Gln Ser Gly Asp Leu Arg Arg His Gln
            20                  25                  30
Arg Thr His Thr Gly Glu Lys Pro Tyr Lys Cys Pro Glu Cys Gly Lys
        35                  40                  45
Ser Phe Ser Arg Ser Asp Lys Leu Val Arg His Gln Arg Thr His Thr
    50                  55                  60
```

```
Gly Glu Lys Pro Tyr Lys Cys Pro Glu Cys Gly Lys Ser Phe Ser Arg
 65                  70                  75                  80

Ser Asp Glu Leu Val Arg His Gln Arg Thr His Thr Gly Glu Lys Pro
                 85                  90                  95

Tyr Lys Cys Pro Glu Cys Gly Lys Ser Phe Ser Arg Ser Asp Lys Leu
            100                 105                 110

Val Arg His Gln Arg Thr His Thr Gly Glu Lys Pro Tyr Lys Cys Pro
        115                 120                 125

Glu Cys Gly Lys Ser Phe Ser Arg Asn Asp Ala Leu Thr Glu His Gln
    130                 135                 140

Arg Thr His Thr Gly Lys Pro Tyr Lys Cys Pro Glu Cys Gly Lys
145                 150                 155                 160

Ser Phe Ser Gln Ser Gly Asp Leu Arg Arg His Gln Arg Thr His Thr
                165                 170                 175

Gly Glu Lys Pro Tyr Lys Cys Pro Glu Cys Gly Lys Ser Phe Ser Arg
            180                 185                 190

Asn Asp Ala Leu Thr Glu His Gln Arg Thr His Thr Gly Lys Lys Thr
        195                 200                 205

Ser Gly Gln Ala Gly Gln Ala Ser Pro Lys Lys Arg Lys Val Gly
    210                 215                 220

Arg Ala Asp Ala Leu Asp Asp Phe Asp Leu Asp Met Leu Gly Ser Asp
225                 230                 235                 240

Ala Leu Asp Asp Phe Asp Leu Asp Met Leu Gly Ser Asp Ala Leu Asp
                245                 250                 255

Asp Phe Asp Leu Asp Met Leu Gly Ser Asp Ala Leu Asp Asp Phe Asp
            260                 265                 270

Leu Asp Met Leu Ile Asn Tyr Pro Tyr Asp Val Pro Asp Tyr Ala Ser
        275                 280                 285

Ser Ser Gly Ser Pro Lys Lys Lys Arg Lys Val Gly Ser Gln Tyr Leu
    290                 295                 300

Pro Asp Thr Asp Asp Arg His Arg Ile Glu Glu Lys Arg Lys Arg Thr
305                 310                 315                 320

Tyr Glu Thr Phe Lys Ser Ile Met Lys Lys Ser Pro Phe Ser Gly Pro
                325                 330                 335

Thr Asp Pro Arg Pro Pro Arg Arg Ile Ala Val Pro Ser Arg Ser
            340                 345                 350

Ser Ala Ser Val Pro Lys Pro Ala Pro Gln Pro Tyr Pro Phe Thr Ser
        355                 360                 365

Ser Leu Ser Thr Ile Asn Tyr Asp Glu Phe Pro Thr Met Val Phe Pro
    370                 375                 380

Ser Gly Gln Ile Ser Gln Ala Ser Ala Leu Ala Pro Ala Pro Pro Gln
385                 390                 395                 400

Val Leu Pro Gln Ala Pro Ala Pro Ala Pro Ala Pro Ala Met Val Ser
                405                 410                 415

Ala Leu Ala Gln Ala Pro Ala Pro Val Pro Val Leu Ala Pro Gly Pro
            420                 425                 430

Pro Gln Ala Val Ala Pro Pro Ala Pro Lys Pro Thr Gln Ala Gly Glu
        435                 440                 445

Gly Thr Leu Ser Glu Ala Leu Leu Gln Leu Gln Phe Asp Asp Glu Asp
    450                 455                 460

Leu Gly Ala Leu Leu Gly Asn Ser Thr Asp Pro Ala Val Phe Thr Asp
465                 470                 475                 480
```

Leu Ala Ser Val Asp Asn Ser Glu Phe Gln Gln Leu Leu Asn Gln Gly
                485                 490                 495

Ile Pro Val Ala Pro His Thr Thr Glu Pro Met Leu Met Glu Tyr Pro
            500                 505                 510

Glu Ala Ile Thr Arg Leu Val Thr Gly Ala Gln Arg Pro Pro Asp Pro
        515                 520                 525

Ala Pro Ala Pro Leu Gly Ala Pro Gly Leu Pro Asn Gly Leu Leu Ser
    530                 535                 540

Gly Asp Glu Asp Phe Ser Ser Ile Ala Asp Met Asp Phe Ser Ala Leu
545                 550                 555                 560

Leu Gly Ser Gly Ser Gly Ser Arg Asp Ser Arg Glu Gly Met Phe Leu
                565                 570                 575

Pro Lys Pro Glu Ala Gly Ser Ala Ile Ser Asp Val Phe Glu Gly Arg
            580                 585                 590

Glu Val Cys Gln Pro Lys Arg Ile Arg Pro Phe His Pro Pro Gly Ser
        595                 600                 605

Pro Trp Ala Asn Arg Pro Leu Pro Ala Ser Leu Ala Pro Thr Pro Thr
    610                 615                 620

Gly Pro Val His Glu Pro Val Gly Ser Leu Thr Pro Ala Pro Val Pro
625                 630                 635                 640

Gln Pro Leu Asp Pro Ala Pro Ala Val Thr Pro Glu Ala Ser His Leu
                645                 650                 655

Leu Glu Asp Pro Asp Glu Glu Thr Ser Gln Ala Val Lys Ala Leu Arg
            660                 665                 670

Glu Met Ala Asp Thr Val Ile Pro Gln Lys Glu Glu Ala Ala Ile Cys
        675                 680                 685

Gly Gln Met Asp Leu Ser His Pro Pro Pro Arg Gly His Leu Asp Glu
    690                 695                 700

Leu Thr Thr Thr Leu Glu Ser Met Thr Glu Asp Leu Asn Leu Asp Ser
705                 710                 715                 720

Pro Leu Thr Pro Glu Leu Asn Glu Ile Leu Asp Thr Phe Leu Asn Asp
                725                 730                 735

Glu Cys Leu Leu His Ala Met His Ile Ser Thr Gly Leu Ser Ile Phe
            740                 745                 750

Asp Thr Ser Leu Phe Asp Ser Ser Leu Glu Gly Pro Arg Phe Glu Gly
        755                 760                 765

Lys Pro Ile Pro Asn Pro Leu Leu Gly Leu Asp Ser Thr Arg Thr Gly
    770                 775                 780

His His His His His His
785                 790

<210> SEQ ID NO 36
<211> LENGTH: 260
<212> TYPE: PRT
<213> ORGANISM: Artificial Sequence
<220> FEATURE:
<223> OTHER INFORMATION: ZFP4_Egr1_site1_antisense

<400> SEQUENCE: 36

Met Ala Gln Ala Ala Leu Glu Pro Gly Glu Lys Pro Tyr Lys Cys Pro
1               5                   10                  15

Glu Cys Gly Lys Ser Phe Ser His Thr Gly His Leu Glu His Gln
            20                  25                  30

Arg Thr His Thr Gly Glu Lys Pro Tyr Lys Cys Pro Glu Cys Gly Lys
        35                  40                  45

```
Ser Phe Ser Arg Asn Asp Thr Leu Thr Glu His Gln Arg Thr His Thr
    50                  55                  60

Gly Glu Lys Pro Tyr Lys Cys Pro Glu Cys Gly Lys Ser Phe Ser Arg
 65                  70                  75                  80

Asn Asp Thr Leu Thr Glu His Gln Arg Thr His Thr Gly Glu Lys Pro
                 85                  90                  95

Tyr Lys Cys Pro Glu Cys Gly Lys Ser Phe Ser Asp Cys Arg Asp Leu
                100                 105                 110

Ala Arg His Gln Arg Thr His Thr Gly Glu Lys Pro Tyr Lys Cys Pro
            115                 120                 125

Glu Cys Gly Lys Ser Phe Ser His Thr Gly His Leu Leu Glu His Gln
130                 135                 140

Arg Thr His Thr Gly Glu Lys Pro Tyr Lys Cys Pro Glu Cys Gly Lys
145                 150                 155                 160

Ser Phe Ser Asp Cys Arg Asp Leu Ala Arg His Gln Arg Thr His Thr
                165                 170                 175

Gly Lys Lys Thr Ser Gly Gln Ala Gly Gln Ala Ser Pro Lys Lys Lys
                180                 185                 190

Arg Lys Val Gly Arg Ala Asp Ala Leu Asp Asp Phe Asp Leu Asp Met
            195                 200                 205

Leu Gly Ser Asp Ala Leu Asp Asp Phe Asp Leu Asp Met Leu Gly Ser
    210                 215                 220

Asp Ala Leu Asp Asp Phe Asp Leu Asp Met Leu Gly Ser Asp Ala Leu
225                 230                 235                 240

Asp Asp Phe Asp Leu Asp Met Leu Ile Asn Tyr Pro Tyr Asp Val Pro
                245                 250                 255

Asp Tyr Ala Ser
            260

<210> SEQ ID NO 37
<211> LENGTH: 627
<212> TYPE: PRT
<213> ORGANISM: Artificial Sequence
<220> FEATURE:
<223> OTHER INFORMATION: Egr1_insert_site2

<400> SEQUENCE: 37

Met Ala Ala Lys Ala Glu Met Gln Leu Met Ser Pro Leu Gln Ile
 1               5                  10                  15

Ser Asp Pro Phe Gly Ser Phe Pro His Ser Pro Thr Met Asp Asn Tyr
                20                  25                  30

Pro Lys Leu Glu Glu Met Met Leu Leu Ser Asn Gly Ala Pro Gln Phe
            35                  40                  45

Leu Gly Ala Ala Gly Ala Pro Glu Gly Ser Gly Ser Asn Ser Ser Ser
    50                  55                  60

Ser Ser Ser Gly Gly Gly Gly Gly Gly Gly Ser Asn Ser Ser
 65                  70                  75                  80

Ser Ser Ser Ser Thr Phe Asn Pro Gln Ala Asp Thr Gly Glu Gln Pro
                 85                  90                  95

Tyr Glu His Leu Thr Ala Glu Ser Phe Pro Asp Ile Ser Leu Asn Asn
                100                 105                 110

Glu Lys Val Leu Val Glu Thr Ser Tyr Pro Ser Gln Thr Thr Arg Leu
            115                 120                 125

Pro Pro Ile Thr Tyr Thr Gly Arg Phe Ser Leu Glu Pro Ala Pro Asn
        130                 135                 140
```

```
Ser Gly Asn Thr Leu Trp Pro Glu Pro Leu Phe Ser Leu Val Ser Gly
145                 150                 155                 160

Leu Val Ser Met Thr Asn Pro Pro Ala Ser Ser Ser Ala Pro Ser
            165                 170                 175

Pro Ala Ala Ser Ser Ala Ser Ala Ser Gln Ser Pro Leu Ser Cys
                180                 185                 190

Ala Val Pro Ser Asn Asp Ser Ser Pro Ile Tyr Ser Ala Pro Thr
        195                 200                 205

Phe Pro Thr Pro Asn Thr Asp Ile Phe Pro Glu Pro Gln Ser Gln Ala
    210                 215                 220

Phe Pro Gly Ser Ala Gly Thr Ala Leu Gln Tyr Pro Pro Ala Tyr
225                 230                 235                 240

Pro Ala Ala Lys Gly Gly Phe Gln Val Pro Met Ile Pro Asp Tyr Leu
            245                 250                 255

Phe Pro Gln Gln Gln Gly Asp Leu Gly Leu Gly Thr Pro Asp Gln Lys
            260                 265                 270

Pro Phe Gln Gly Leu Glu Ser Arg Thr Gln Gln Pro Ser Leu Thr Pro
        275                 280                 285

Leu Ser Thr Ile Lys Ala Phe Ala Thr Gln Ser Gly Ser Gln Asp Leu
290                 295                 300

Lys Ala Leu Asn Thr Ser Tyr Gln Ser Gln Leu Ile Lys Pro Ser Arg
305                 310                 315                 320

Met Arg Lys Tyr Pro Asn Arg Pro Ser Lys Thr Pro Pro His Glu Arg
                325                 330                 335

Pro Tyr Ala Cys Pro Val Glu Ser Cys Asp Arg Arg Phe Ser Arg Ser
            340                 345                 350

Asp Glu Leu Thr Arg His Ile Arg Ile His Thr Gly Gln Lys Pro Phe
            355                 360                 365

Gln Cys Arg Ile Cys Met Arg Asn Phe Ser Arg Ser Asp His Leu Thr
370                 375                 380

Thr His Ile Arg Thr His Thr Gly Glu Lys Pro Phe Ala Cys Asp Ile
385                 390                 395                 400

Cys Gly Arg Lys Phe Ala Arg Ser Asp Glu Arg Lys Arg His Thr Lys
            405                 410                 415

Ile His Thr Gly Gln Lys Pro Cys Pro Val Glu Ser Cys Asp Arg Arg
            420                 425                 430

Phe Ser Gln Arg Ala His Leu Glu Arg His Ile Arg Ile His Thr Gly
            435                 440                 445

Gln Lys Pro Phe Gln Cys Arg Ile Cys Met Arg Asn Phe Ser Arg Ser
    450                 455                 460

Asp Lys Leu Thr Glu His Ile Arg Thr His Thr Gly Glu Lys Pro Phe
465                 470                 475                 480

Ala Cys Asp Ile Cys Gly Arg Lys Phe Ala His Thr Gly His Leu Leu
            485                 490                 495

Glu His Thr Lys Ile His Leu Arg Gln Lys Asp Lys Ala Asp Lys
                500                 505                 510

Ser Val Val Ala Ser Ser Ala Thr Ser Ser Leu Ser Ser Tyr Pro Ser
        515                 520                 525

Pro Val Ala Thr Ser Tyr Pro Ser Pro Val Thr Thr Ser Tyr Pro Ser
        530                 535                 540

Pro Ala Thr Thr Ser Tyr Pro Ser Pro Val Pro Thr Ser Phe Ser Ser
545                 550                 555                 560

Pro Gly Ser Ser Thr Tyr Pro Ser Pro Val His Ser Gly Phe Pro Ser
```

-continued

```
                565                 570                 575

Pro Ser Val Ala Thr Thr Tyr Ser Ser Val Pro Pro Ala Phe Pro Ala
            580                 585                 590

Gln Val Ser Ser Phe Pro Ser Ser Ala Val Thr Asn Ser Phe Ser Ala
            595                 600                 605

Ser Thr Gly Leu Ser Asp Met Thr Ala Thr Phe Ser Pro Arg Thr Ile
    610                 615                 620

Glu Ile Cys
625

<210> SEQ ID NO 38
<211> LENGTH: 593
<212> TYPE: PRT
<213> ORGANISM: Artificial Sequence
<220> FEATURE:
<223> OTHER INFORMATION: Egr1_insert_site2_RR

<400> SEQUENCE: 38

Met Ala Ala Ala Lys Ala Glu Met Gln Leu Met Ser Pro Leu Gln Ile
1               5                   10                  15

Ser Asp Pro Phe Gly Ser Phe Pro His Ser Pro Thr Met Asp Asn Tyr
            20                  25                  30

Pro Lys Leu Glu Glu Met Met Leu Leu Ser Asn Gly Ala Pro Gln Phe
        35                  40                  45

Leu Gly Ala Ala Gly Ala Pro Glu Gly Ser Gly Ser Asn Ser Ser Ser
    50                  55                  60

Ser Ser Ser Gly Gly Gly Gly Gly Gly Gly Ser Asn Ser Ser
65                  70                  75                  80

Ser Ser Ser Ser Thr Phe Asn Pro Gln Ala Asp Thr Gly Glu Gln Pro
                85                  90                  95

Tyr Glu His Leu Thr Ala Glu Ser Phe Pro Asp Ile Ser Leu Asn Asn
            100                 105                 110

Glu Lys Val Leu Val Glu Thr Ser Tyr Pro Ser Gln Thr Thr Arg Leu
        115                 120                 125

Pro Pro Ile Thr Tyr Thr Gly Arg Phe Ser Leu Glu Pro Ala Pro Asn
    130                 135                 140

Ser Gly Asn Thr Leu Trp Pro Glu Pro Leu Phe Ser Leu Val Ser Gly
145                 150                 155                 160

Leu Val Ser Met Thr Asn Pro Pro Ala Ser Ser Ser Ala Pro Ser
                165                 170                 175

Pro Ala Ala Ser Ser Ala Ser Ala Ser Gln Ser Pro Leu Ser Cys
            180                 185                 190

Ala Val Pro Ser Asn Asp Ser Ser Pro Ile Tyr Ser Ala Ala Pro Thr
            195                 200                 205

Phe Pro Thr Pro Asn Thr Asp Ile Phe Pro Glu Pro Gln Ser Gln Ala
    210                 215                 220

Phe Pro Gly Ser Ala Gly Thr Ala Leu Gln Tyr Pro Pro Pro Ala Tyr
225                 230                 235                 240

Pro Ala Ala Lys Gly Gly Phe Gln Val Pro Met Ile Pro Asp Tyr Leu
                245                 250                 255

Phe Pro Gln Gln Gln Gly Asp Leu Gly Leu Gly Thr Pro Asp Gln Lys
            260                 265                 270

Pro Phe Gln Gly Leu Glu Ser Arg Leu Ile Lys Pro Ser Arg Met Arg
        275                 280                 285

Lys Tyr Pro Asn Arg Pro Ser Lys Thr Pro Pro His Glu Arg Pro Tyr
```

```
                290                 295                 300
Ala Cys Pro Val Glu Ser Cys Asp Arg Arg Phe Ser Arg Ser Asp Glu
305                 310                 315                 320

Leu Thr Arg His Ile Arg Ile His Thr Gly Gln Lys Pro Phe Gln Cys
                325                 330                 335

Arg Ile Cys Met Arg Asn Phe Ser Arg Ser Asp His Leu Thr Thr His
                340                 345                 350

Ile Arg Thr His Thr Gly Glu Lys Pro Phe Ala Cys Asp Ile Cys Gly
                355                 360                 365

Arg Lys Phe Ala Arg Ser Asp Glu Arg Lys Arg His Thr Lys Ile His
                370                 375                 380

Thr Gly Gln Lys Pro Cys Pro Val Glu Ser Cys Asp Arg Arg Phe Ser
385                 390                 395                 400

Gln Arg Ala His Leu Glu Arg His Ile Arg Ile His Thr Gly Gln Lys
                405                 410                 415

Pro Phe Gln Cys Arg Ile Cys Met Arg Asn Phe Ser Arg Ser Asp Lys
                420                 425                 430

Leu Thr Glu His Ile Arg Thr His Thr Gly Glu Lys Pro Phe Ala Cys
                435                 440                 445

Asp Ile Cys Gly Arg Lys Phe Ala His Thr Gly His Leu Leu Glu His
                450                 455                 460

Thr Lys Ile His Leu Arg Gln Lys Asp Lys Lys Ala Asp Lys Ser Val
465                 470                 475                 480

Val Ala Ser Ser Ala Thr Ser Ser Leu Ser Ser Tyr Pro Ser Pro Val
                485                 490                 495

Ala Thr Ser Tyr Pro Ser Pro Val Thr Thr Ser Tyr Pro Ser Pro Ala
                500                 505                 510

Thr Thr Ser Tyr Pro Ser Pro Val Pro Thr Ser Phe Ser Ser Pro Gly
                515                 520                 525

Ser Ser Thr Tyr Pro Ser Pro Val His Ser Gly Phe Pro Ser Pro Ser
                530                 535                 540

Val Ala Thr Thr Tyr Ser Ser Val Pro Ala Phe Pro Ala Gln Val
545                 550                 555                 560

Ser Ser Phe Pro Ser Ser Ala Val Thr Asn Ser Phe Ser Ala Ser Thr
                565                 570                 575

Gly Leu Ser Asp Met Thr Ala Thr Phe Ser Pro Arg Thr Ile Glu Ile
                580                 585                 590

Cys

<210> SEQ ID NO 39
<211> LENGTH: 622
<212> TYPE: PRT
<213> ORGANISM: Artificial Sequence
<220> FEATURE:
<223> OTHER INFORMATION: Egr1_insert_site3

<400> SEQUENCE: 39

Met Ala Ala Ala Lys Ala Glu Met Gln Leu Met Ser Pro Leu Gln Ile
1               5                   10                  15

Ser Asp Pro Phe Gly Ser Phe Pro His Ser Pro Thr Met Asp Asn Tyr
                20                  25                  30

Pro Lys Leu Glu Glu Met Met Leu Leu Ser Asn Gly Ala Pro Gln Phe
                35                  40                  45

Leu Gly Ala Ala Gly Ala Pro Glu Gly Ser Gly Ser Asn Ser Ser Ser
                50                  55                  60
```

```
Ser Ser Ser Gly Gly Gly Gly Gly Gly Gly Ser Asn Ser Ser
65              70              75              80

Ser Ser Ser Ser Thr Phe Asn Pro Gln Ala Asp Thr Gly Glu Gln Pro
            85              90              95

Tyr Glu His Leu Thr Ala Glu Ser Phe Pro Asp Ile Ser Leu Asn Asn
        100             105             110

Glu Lys Val Leu Val Glu Thr Ser Tyr Pro Ser Gln Thr Thr Arg Leu
        115             120             125

Pro Pro Ile Thr Tyr Thr Gly Arg Phe Ser Leu Glu Pro Ala Pro Asn
        130             135             140

Ser Gly Asn Thr Leu Trp Pro Glu Pro Leu Phe Ser Leu Val Ser Gly
145             150             155             160

Leu Val Ser Met Thr Asn Pro Pro Ala Ser Ser Ser Ala Pro Ser
                165             170             175

Pro Ala Ala Ser Ser Ala Ser Ala Ser Gln Ser Pro Leu Ser Cys
            180             185             190

Ala Val Pro Ser Asn Asp Ser Ser Pro Ile Tyr Ser Ala Ala Pro Thr
        195             200             205

Phe Pro Thr Pro Asn Thr Asp Ile Phe Pro Glu Pro Gln Ser Gln Ala
210             215             220

Phe Pro Gly Ser Ala Gly Thr Ala Leu Gln Tyr Pro Pro Ala Tyr
225             230             235             240

Pro Ala Ala Lys Gly Gly Phe Gln Val Pro Met Ile Pro Asp Tyr Leu
            245             250             255

Phe Pro Gln Gln Gln Gly Asp Leu Gly Leu Gly Thr Pro Asp Gln Lys
            260             265             270

Pro Phe Gln Gly Leu Glu Ser Arg Thr Gln Gln Pro Ser Leu Thr Pro
        275             280             285

Leu Ser Thr Ile Lys Ala Phe Ala Thr Gln Ser Gly Ser Gln Asp Leu
        290             295             300

Lys Ala Leu Asn Thr Ser Tyr Gln Ser Gln Leu Ile Lys Pro Ser Arg
305             310             315             320

Met Arg Lys Tyr Pro Asn Arg Pro Ser Lys Thr Pro Pro His Glu Arg
            325             330             335

Pro Tyr Ala Cys Pro Val Glu Ser Cys Asp Arg Arg Phe Ser Arg Ser
            340             345             350

Asp Glu Leu Thr Arg His Ile Arg Ile His Thr Gly Gln Lys Pro Phe
            355             360             365

Gln Cys Arg Ile Cys Met Arg Asn Phe Ser Arg Ser Asp His Leu Thr
    370             375             380

Thr His Ile Arg Thr His Thr Gly Glu Lys Pro Phe Ala Cys Asp Ile
385             390             395             400

Cys Gly Arg Lys Phe Ala Arg Ser Asp Glu Arg Lys Arg His Thr Lys
            405             410             415

Ile His Cys Pro Val Glu Ser Cys Asp Arg Arg Phe Ser Gln Ser Gly
            420             425             430

Asp Leu Arg Arg His Ile Arg Ile His Thr Gly Gln Lys Pro Phe Gln
            435             440             445

Cys Arg Ile Cys Met Arg Asn Phe Ser Arg Asn Asp Ala Leu Thr Glu
    450             455             460

His Ile Arg Thr His Thr Gly Glu Lys Pro Phe Ala Cys Asp Ile Cys
465             470             475             480
```

```
Gly Arg Lys Phe Ala Asp Cys Arg Asp Leu Ala Arg His Thr Lys Ile
                485                 490                 495

His Leu Arg Gln Lys Asp Lys Lys Ala Asp Lys Ser Val Val Ala Ser
            500                 505                 510

Ser Ala Thr Ser Ser Leu Ser Ser Tyr Pro Ser Pro Val Ala Thr Ser
        515                 520                 525

Tyr Pro Ser Pro Val Thr Thr Ser Tyr Pro Ser Pro Ala Thr Thr Ser
    530                 535                 540

Tyr Pro Ser Pro Val Pro Thr Ser Phe Ser Ser Pro Gly Ser Ser Thr
545                 550                 555                 560

Tyr Pro Ser Pro Val His Ser Gly Phe Pro Ser Pro Val Ala Thr
                565                 570                 575

Thr Tyr Ser Ser Val Pro Pro Ala Phe Pro Ala Gln Val Ser Ser Phe
                580                 585                 590

Pro Ser Ser Ala Val Thr Asn Ser Phe Ser Ala Ser Thr Gly Leu Ser
            595                 600                 605

Asp Met Thr Ala Thr Phe Ser Pro Arg Thr Ile Glu Ile Cys
            610                 615                 620

<210> SEQ ID NO 40
<211> LENGTH: 588
<212> TYPE: PRT
<213> ORGANISM: Artificial Sequence
<220> FEATURE:
<223> OTHER INFORMATION: Egr1_insert_site3_RR

<400> SEQUENCE: 40

Met Ala Ala Ala Lys Ala Glu Met Gln Leu Met Ser Pro Leu Gln Ile
1               5                   10                  15

Ser Asp Pro Phe Gly Ser Phe Pro His Ser Pro Thr Met Asp Asn Tyr
                20                  25                  30

Pro Lys Leu Glu Glu Met Met Leu Leu Ser Asn Gly Ala Pro Gln Phe
            35                  40                  45

Leu Gly Ala Ala Gly Ala Pro Glu Gly Ser Gly Ser Asn Ser Ser Ser
    50                  55                  60

Ser Ser Ser Gly Gly Gly Gly Gly Gly Gly Ser Asn Ser Ser
65                  70                  75                  80

Ser Ser Ser Ser Thr Phe Asn Pro Gln Ala Asp Thr Gly Glu Gln Pro
                85                  90                  95

Tyr Glu His Leu Thr Ala Glu Ser Phe Pro Asp Ile Ser Leu Asn Asn
            100                 105                 110

Glu Lys Val Leu Val Glu Thr Ser Tyr Pro Ser Gln Thr Thr Arg Leu
        115                 120                 125

Pro Pro Ile Thr Tyr Thr Gly Arg Phe Ser Leu Glu Pro Ala Pro Asn
    130                 135                 140

Ser Gly Asn Thr Leu Trp Pro Glu Pro Leu Phe Ser Leu Val Ser Gly
145                 150                 155                 160

Leu Val Ser Met Thr Asn Pro Ala Ser Ser Ser Ala Pro Ser
                165                 170                 175

Pro Ala Ala Ser Ser Ala Ser Ala Ser Gln Ser Pro Pro Leu Ser Cys
            180                 185                 190

Ala Val Pro Ser Asn Asp Ser Ser Pro Ile Tyr Ser Ala Ala Pro Thr
        195                 200                 205

Phe Pro Thr Pro Asn Thr Asp Ile Phe Pro Glu Pro Gln Ser Gln Ala
    210                 215                 220
```

```
Phe Pro Gly Ser Ala Gly Thr Ala Leu Gln Tyr Pro Pro Ala Tyr
225                 230                 235                 240

Pro Ala Ala Lys Gly Gly Phe Gln Val Pro Met Ile Pro Asp Tyr Leu
                245                 250                 255

Phe Pro Gln Gln Gln Gly Asp Leu Gly Leu Gly Thr Pro Asp Gln Lys
            260                 265                 270

Pro Phe Gln Gly Leu Glu Ser Arg Leu Ile Lys Pro Ser Arg Met Arg
        275                 280                 285

Lys Tyr Pro Asn Arg Pro Ser Lys Thr Pro Pro His Glu Arg Pro Tyr
    290                 295                 300

Ala Cys Pro Val Glu Ser Cys Asp Arg Arg Phe Ser Arg Ser Asp Glu
305                 310                 315                 320

Leu Thr Arg His Ile Arg Ile His Thr Gly Gln Lys Pro Phe Gln Cys
                325                 330                 335

Arg Ile Cys Met Arg Asn Phe Ser Arg Ser Asp His Leu Thr Thr His
                340                 345                 350

Ile Arg Thr His Thr Gly Glu Lys Pro Phe Ala Cys Asp Ile Cys Gly
                355                 360                 365

Arg Lys Phe Ala Arg Ser Asp Glu Arg Lys Arg His Thr Lys Ile His
    370                 375                 380

Cys Pro Val Glu Ser Cys Asp Arg Arg Phe Ser Gln Ser Gly Asp Leu
385                 390                 395                 400

Arg Arg His Ile Arg Ile His Thr Gly Gln Lys Pro Phe Gln Cys Arg
                405                 410                 415

Ile Cys Met Arg Asn Phe Ser Arg Asn Asp Ala Leu Thr Glu His Ile
                420                 425                 430

Arg Thr His Thr Gly Glu Lys Pro Phe Ala Cys Asp Ile Cys Gly Arg
                435                 440                 445

Lys Phe Ala Asp Cys Arg Asp Leu Ala Arg His Thr Lys Ile His Leu
    450                 455                 460

Arg Gln Lys Asp Lys Lys Ala Asp Lys Ser Val Val Ala Ser Ser Ala
465                 470                 475                 480

Thr Ser Ser Leu Ser Ser Tyr Pro Ser Pro Val Ala Thr Ser Tyr Pro
                485                 490                 495

Ser Pro Val Thr Thr Ser Tyr Pro Ser Pro Ala Thr Thr Ser Tyr Pro
                500                 505                 510

Ser Pro Val Pro Thr Ser Phe Ser Ser Pro Gly Ser Ser Thr Tyr Pro
                515                 520                 525

Ser Pro Val His Ser Gly Phe Pro Ser Pro Ser Val Ala Thr Thr Tyr
                530                 535                 540

Ser Ser Val Pro Pro Ala Phe Pro Ala Gln Val Ser Ser Phe Pro Ser
545                 550                 555                 560

Ser Ala Val Thr Asn Ser Phe Ser Ala Ser Thr Gly Leu Ser Asp Met
                565                 570                 575

Thr Ala Thr Phe Ser Pro Arg Thr Ile Glu Ile Cys
                580                 585

<210> SEQ ID NO 41
<211> LENGTH: 176
<212> TYPE: PRT
<213> ORGANISM: Artificial Sequence
<220> FEATURE:
<223> OTHER INFORMATION: ZFP1 ZF domain

<400> SEQUENCE: 41
```

```
Leu Glu Pro Gly Glu Lys Pro Tyr Lys Cys Pro Glu Cys Gly Lys Ser
1               5                   10                  15

Phe Ser Asp Pro Gly His Leu Val Arg His Gln Arg Thr His Thr Gly
            20                  25                  30

Glu Lys Pro Tyr Lys Cys Pro Glu Cys Gly Lys Ser Phe Ser Ser Lys
        35                  40                  45

Lys Ala Leu Thr Glu His Gln Arg Thr His Thr Gly Glu Lys Pro Tyr
    50                  55                  60

Lys Cys Pro Glu Cys Gly Lys Ser Phe Ser Arg Asn Asp Ala Leu Thr
65                  70                  75                  80

Glu His Gln Arg Thr His Thr Gly Glu Lys Pro Tyr Lys Cys Pro Glu
                85                  90                  95

Cys Gly Lys Ser Phe Ser Asp Pro Gly Ala Leu Val Arg His Gln Arg
            100                 105                 110

Thr His Thr Gly Glu Lys Pro Tyr Lys Cys Pro Glu Cys Gly Lys Ser
        115                 120                 125

Phe Ser Asp Ser Gly Asn Leu Arg Val His Gln Arg Thr His Thr Gly
    130                 135                 140

Glu Lys Pro Tyr Lys Cys Pro Glu Cys Gly Lys Ser Phe Ser Gln Ser
145                 150                 155                 160

Gly His Leu Thr Glu His Gln Arg Thr His Thr Gly Lys Lys Thr Ser
                165                 170                 175

<210> SEQ ID NO 42
<211> LENGTH: 288
<212> TYPE: PRT
<213> ORGANISM: Artificial Sequence
<220> FEATURE:
<223> OTHER INFORMATION: ZFP52 ZF domain

<400> SEQUENCE: 42

Leu Glu Pro Gly Glu Lys Pro Tyr Lys Cys Pro Glu Cys Gly Lys Ser
1               5                   10                  15

Phe Ser Thr Lys Asn Ser Leu Thr Glu His Gln Arg Thr His Thr Gly
            20                  25                  30

Glu Lys Pro Tyr Lys Cys Pro Glu Cys Gly Lys Ser Phe Ser Gln Ser
        35                  40                  45

Gly Asp Leu Arg Arg His Gln Arg Thr His Thr Gly Glu Lys Pro Tyr
    50                  55                  60

Lys Cys Pro Glu Cys Gly Lys Ser Phe Ser Asp Cys Arg Asp Leu Ala
65                  70                  75                  80

Arg His Gln Arg Thr His Thr Gly Glu Lys Pro Tyr Lys Cys Pro Glu
                85                  90                  95

Cys Gly Lys Ser Phe Ser Thr Lys Asn Ser Leu Thr Glu His Gln Arg
            100                 105                 110

Thr His Thr Gly Glu Lys Pro Tyr Lys Cys Pro Glu Cys Gly Lys Ser
        115                 120                 125

Phe Ser Arg Thr Asp Thr Leu Arg Asp His Gln Arg Thr His Thr Gly
    130                 135                 140

Glu Lys Pro Tyr Lys Cys Pro Glu Cys Gly Lys Ser Phe Ser Arg Ser
145                 150                 155                 160

Asp Asp Leu Val Arg His Gln Arg Thr His Thr Gly Glu Lys Pro Tyr
                165                 170                 175

Lys Cys Pro Glu Cys Gly Lys Ser Phe Ser Arg Ser Asp Lys Leu Thr
            180                 185                 190
```

Glu His Gln Arg Thr His Thr Gly Glu Lys Pro Tyr Lys Cys Pro Glu
            195                 200                 205

Cys Gly Lys Ser Phe Ser Arg Asn Asp Thr Leu Thr Glu His Gln Arg
        210                 215                 220

Thr His Thr Gly Glu Lys Pro Tyr Lys Cys Pro Glu Cys Gly Lys Ser
225                 230                 235                 240

Phe Ser Ser Arg Arg Thr Cys Arg Ala His Gln Arg Thr His Thr Gly
                245                 250                 255

Glu Lys Pro Tyr Lys Cys Pro Glu Cys Gly Lys Ser Phe Ser Gln Ser
            260                 265                 270

Gly His Leu Thr Glu His Gln Arg Thr His Thr Gly Lys Lys Thr Ser
        275                 280                 285

<210> SEQ ID NO 43
<211> LENGTH: 204
<212> TYPE: PRT
<213> ORGANISM: Artificial Sequence
<220> FEATURE:
<223> OTHER INFORMATION: ZFP1_Egr1_site1_sense ZF domain

<400> SEQUENCE: 43

Leu Glu Pro Gly Glu Lys Pro Tyr Lys Cys Pro Glu Cys Gly Lys Ser
1               5                   10                  15

Phe Ser Thr Ser Gly Asn Leu Thr Glu His Gln Arg Thr His Thr Gly
            20                  25                  30

Glu Lys Pro Tyr Lys Cys Pro Glu Cys Gly Lys Ser Phe Ser Arg Ser
        35                  40                  45

Asp Lys Leu Val Arg His Gln Arg Thr His Thr Gly Glu Lys Pro Tyr
    50                  55                  60

Lys Cys Pro Glu Cys Gly Lys Ser Phe Ser His Thr Gly His Leu Leu
65                  70                  75                  80

Glu His Gln Arg Thr His Thr Gly Glu Lys Pro Tyr Lys Cys Pro Glu
                85                  90                  95

Cys Gly Lys Ser Phe Ser Arg Ser Asp Lys Leu Val Arg His Gln Arg
            100                 105                 110

Thr His Thr Gly Glu Lys Pro Tyr Lys Cys Pro Glu Cys Gly Lys Ser
        115                 120                 125

Phe Ser Arg Ser Asp Asp Leu Val Arg His Gln Arg Thr His Thr Gly
    130                 135                 140

Glu Lys Pro Tyr Lys Cys Pro Glu Cys Gly Lys Ser Phe Ser Arg Ser
145                 150                 155                 160

Asp Asp Leu Val Arg His Gln Arg Thr His Thr Gly Glu Lys Pro Tyr
                165                 170                 175

Lys Cys Pro Glu Cys Gly Lys Ser Phe Ser Asp Pro Gly His Leu Val
            180                 185                 190

Arg His Gln Arg Thr His Thr Gly Lys Lys Thr Ser
        195                 200

<210> SEQ ID NO 44
<211> LENGTH: 204
<212> TYPE: PRT
<213> ORGANISM: Artificial Sequence
<220> FEATURE:
<223> OTHER INFORMATION: ZFP2_Egr1_site2_sense ZF domain

<400> SEQUENCE: 44

Leu Glu Pro Gly Glu Lys Pro Tyr Lys Cys Pro Glu Cys Gly Lys Ser
1               5                   10                  15

Phe Ser Arg Ser Asp Asp Leu Val Arg His Gln Arg Thr His Thr Gly
            20                  25                  30

Glu Lys Pro Tyr Lys Cys Pro Glu Cys Gly Lys Ser Phe Ser Asp Pro
        35                  40                  45

Gly His Leu Val Arg His Gln Arg Thr His Thr Gly Glu Lys Pro Tyr
    50                  55                  60

Lys Cys Pro Glu Cys Gly Lys Ser Phe Ser Arg Ser Asp Glu Leu Val
65                  70                  75                  80

Arg His Gln Arg Thr His Thr Gly Glu Lys Pro Tyr Lys Cys Pro Glu
                85                  90                  95

Cys Gly Lys Ser Phe Ser Arg Ser Asp Lys Leu Val Arg His Gln Arg
            100                 105                 110

Thr His Thr Gly Glu Lys Pro Tyr Lys Cys Pro Glu Cys Gly Lys Ser
        115                 120                 125

Phe Ser Arg Ser Asp Asp Leu Val Arg His Gln Arg Thr His Thr Gly
    130                 135                 140

Glu Lys Pro Tyr Lys Cys Pro Glu Cys Gly Lys Ser Phe Ser Gln Arg
145                 150                 155                 160

Ala His Leu Glu Arg His Gln Arg Thr His Thr Gly Glu Lys Pro Tyr
                165                 170                 175

Lys Cys Pro Glu Cys Gly Lys Ser Phe Ser Arg Ser Asp Lys Leu Thr
            180                 185                 190

Glu His Gln Arg Thr His Thr Gly Lys Lys Thr Ser
        195                 200

<210> SEQ ID NO 45
<211> LENGTH: 204
<212> TYPE: PRT
<213> ORGANISM: Artificial Sequence
<220> FEATURE:
<223> OTHER INFORMATION: ZFP3_Egr1_site3_antisense ZF domain

<400> SEQUENCE: 45

Leu Glu Pro Gly Glu Lys Pro Tyr Lys Cys Pro Glu Cys Gly Lys Ser
1               5                   10                  15

Phe Ser Gln Ser Gly Asp Leu Arg Arg His Gln Arg Thr His Thr Gly
            20                  25                  30

Glu Lys Pro Tyr Lys Cys Pro Glu Cys Gly Lys Ser Phe Ser Arg Ser
        35                  40                  45

Asp Lys Leu Val Arg His Gln Arg Thr His Thr Gly Glu Lys Pro Tyr
    50                  55                  60

Lys Cys Pro Glu Cys Gly Lys Ser Phe Ser Arg Ser Asp Glu Leu Val
65                  70                  75                  80

Arg His Gln Arg Thr His Thr Gly Glu Lys Pro Tyr Lys Cys Pro Glu
                85                  90                  95

Cys Gly Lys Ser Phe Ser Arg Ser Asp Lys Leu Val Arg His Gln Arg
            100                 105                 110

Thr His Thr Gly Glu Lys Pro Tyr Lys Cys Pro Glu Cys Gly Lys Ser
        115                 120                 125

Phe Ser Arg Asn Asp Ala Leu Thr Glu His Gln Arg Thr His Thr Gly
    130                 135                 140

Glu Lys Pro Tyr Lys Cys Pro Glu Cys Gly Lys Ser Phe Ser Gln Ser
145                 150                 155                 160

Gly Asp Leu Arg Arg His Gln Arg Thr His Thr Gly Glu Lys Pro Tyr
                165                 170                 175

```
Lys Cys Pro Glu Cys Gly Lys Ser Phe Ser Arg Asn Asp Ala Leu Thr
            180                 185                 190

Glu His Gln Arg Thr His Thr Gly Lys Lys Thr Ser
            195                 200

<210> SEQ ID NO 46
<211> LENGTH: 176
<212> TYPE: PRT
<213> ORGANISM: Artificial Sequence
<220> FEATURE:
<223> OTHER INFORMATION: ZFP4_Egr1_site1_antisense ZF domain

<400> SEQUENCE: 46

Leu Glu Pro Gly Glu Lys Pro Tyr Lys Cys Pro Glu Cys Gly Lys Ser
1               5                   10                  15

Phe Ser His Thr Gly His Leu Leu Glu His Gln Arg Thr His Thr Gly
            20                  25                  30

Glu Lys Pro Tyr Lys Cys Pro Glu Cys Gly Lys Ser Phe Ser Arg Asn
        35                  40                  45

Asp Thr Leu Thr Glu His Gln Arg Thr His Thr Gly Glu Lys Pro Tyr
    50                  55                  60

Lys Cys Pro Glu Cys Gly Lys Ser Phe Ser Arg Asn Asp Thr Leu Thr
65                  70                  75                  80

Glu His Gln Arg Thr His Thr Gly Glu Lys Pro Tyr Lys Cys Pro Glu
                85                  90                  95

Cys Gly Lys Ser Phe Ser Asp Cys Arg Asp Leu Ala Arg His Gln Arg
            100                 105                 110

Thr His Thr Gly Glu Lys Pro Tyr Lys Cys Pro Glu Cys Gly Lys Ser
        115                 120                 125

Phe Ser His Thr Gly His Leu Leu Glu His Gln Arg Thr His Thr Gly
    130                 135                 140

Glu Lys Pro Tyr Lys Cys Pro Glu Cys Gly Lys Ser Phe Ser Asp Cys
145                 150                 155                 160

Arg Asp Leu Ala Arg His Gln Arg Thr His Thr Gly Lys Lys Thr Ser
                165                 170                 175

<210> SEQ ID NO 47
<211> LENGTH: 783
<212> TYPE: DNA
<213> ORGANISM: Artificial Sequence
<220> FEATURE:
<223> OTHER INFORMATION: ZFP1 coding sequence

<400> SEQUENCE: 47
atggcccaag ctgctttaga gcccggagaa aagcccctata atgccccga atgcggcaaa      60 agctttagcg accccggtca tctggtgaga catcagagaa cccacaccgg cgaaaagcct     120
tataagtgcc ccgagtgcgg caaaagcttc agcagcaaga aggctctgac cgaacatcaa     180
aggacccaca ccgcgagaa gccctacaaa tgccccgaat gcggcaaatc cttttctcgt     240
aacgacgctt taaccgagca ccagaggacc cacaccggcg aaaaccccta caagtgtccc     300
gaatgtggca agagcttcag cgatcccggc gctttagtca gacaccaaag aacccacacc     360
ggcgagaaac cctataaatg tcccgagtgt ggcaagtcct tcagcgacag cggcaacctc     420
agagtgcacc agaggaccca caccggcgaa agccctata atgccccga atgcggcaaa      480 agctttagcc agagcggaca tttaacagaa caccaggaga cccataccgg caaaaagacc     540
tccggccaag ctggccaagc tagccctaag aagaagagga agtcggcag agccgacgct     600
```

| | | |
|---|---|---|
| ttagatgatt tcgatttaga catgctgggc tccgacgctt tagacgactt tgatctggat | 660 | |
| atgctgggct ccgatgcttt agacgatttt gatctggata tgctgggcag cgacgccctc | 720 | |
| gacgacttcg atttagacat gctgatcaac taccectacg atgtgcccga ttacgcctcc | 780 | |
| tga | 783 | |

<210> SEQ ID NO 48
<211> LENGTH: 6243
<212> TYPE: DNA
<213> ORGANISM: Artificial Sequence
<220> FEATURE:
<223> OTHER INFORMATION: ZFP1 in pcDNA3.1 TOPO vector

<400> SEQUENCE: 48

| | |
|---|---|
| gacggatcgg gagatctccc gatccectat ggtcgactct cagtacaatc tgctctgatg | 60 |
| ccgcatagtt aagccagtat ctgctccctg cttgtgtgtt ggaggtcgct gagtagtgcg | 120 |
| cgagcaaaat ttaagctaca acaaggcaag gcttgaccga caattgcatg aagaatctgc | 180 |
| ttagggttag gcgttttgcg ctgcttcgcg atgtacgggc cagatatacg cgttgacatt | 240 |
| gattattgac tagttattaa tagtaatcaa ttacggggtc attagttcat agcccatata | 300 |
| tggagttccg cgttacataa cttacggtaa atggcccgcc tggctgaccg cccaacgacc | 360 |
| cccgcccatt gacgtcaata atgacgtatg ttcccatagt aacgccaata gggactttcc | 420 |
| attgacgtca atgggtggac tatttacggt aaactgccca cttggcagta catcaagtgt | 480 |
| atcatatgcc aagtacgccc cctattgacg tcaatgacgg taaatggccc gcctggcatt | 540 |
| atgcccagta catgacctta tgggactttc ctacttggca gtacatctac gtattagtca | 600 |
| tcgctattac catggtgatg cggttttggc agtacatcaa tgggcgtgga tagcggtttg | 660 |
| actcacgggg atttccaagt ctccacccca ttgacgtcaa tgggagtttg ttttggcacc | 720 |
| aaaatcaacg ggactttcca aaatgtcgta caactccgc cccattgacg caaatgggcg | 780 |
| gtaggcgtgt acggtgggag gtctatataa gcagagctct ctggctaact agagaaccca | 840 |
| ctgcttactg gcttatcgaa attaatacga ctcactatag ggagacccaa gctggctagt | 900 |
| taagcttggt accgagctcg gatccacaat ggcccaagct gctttagagc ccggagaaaa | 960 |
| gccctataaa tgccccgaat gcggcaaaag ctttagcgac cccggtcatc tggtgagaca | 1020 |
| tcagagaacc cacaccggcg aaaagcctta taagtgcccc gagtgcggca aaagcttcag | 1080 |
| cagcaagaag gctctgaccg aacatcaaag gacccacacc ggcgagaagc ctacaaatg | 1140 |
| ccccgaatgc ggcaaatcct tttctcgtaa cgacgcttta ccgagcacc agaggaccca | 1200 |
| caccggcgaa aaaccctaca gtgtcccga atgtggcaag agcttcagcg atcccggcgc | 1260 |
| tttagtcaga caccaaagaa cccacaccgg cgagaaaccc tataaatgtc cgagtgtgg | 1320 |
| caagtccttc agcgacagcg gcaacctcag agtgcaccag aggacccaca ccggcgaaaa | 1380 |
| gccctataaa tgccccgaat gcggcaaaag ctttagccag agcggacatt aacagaaca | 1440 |
| ccagaggacc cataccggca aaaagacctc cggccaagct ggccaagcta gccctaagaa | 1500 |
| gaagaggaaa gtcggcagag ccgacgcttt agatgatttc gatttagaca tgctgggctc | 1560 |
| cgacgcttta gacgactttg atctggatat gctgggctcc gatgctttag acgattttga | 1620 |
| tctggatatg ctgggcagcg acgccctcga cgacttcgat ttagacatgc tgatcaacta | 1680 |
| cccctacgat gtgcccgatt acgcctcctg actcgagtct agagggcccg cggttcgaag | 1740 |
| gtaagcctat ccctaaccct ctcctcggtc tcgattctac gcgtaccggt catcatcacc | 1800 |

```
atcaccattg agtttaaacc cgctgatcag cctcgactgt gccttctagt tgccagccat    1860
ctgttgtttg cccctccccc gtgccttcct tgaccctgga aggtgccact cccactgtcc    1920
tttcctaata aaatgaggaa attgcatcgc attgtctgag taggtgtcat tctattctgg    1980
gggtggggt ggggcaggac agcaaggggg aggattggga agacaatagc aggcatgctg    2040
gggatgcggt gggctctatg gcttctgagg cggaaagaac cagctggggc tctaggggt    2100
atccccacgc gccctgtagc ggcgcattaa gcgcggcggg tgtggtggtt acgcgcagcg    2160
tgaccgctac acttgccagc gccctagcgc ccgctccttt cgctttcttc ccttcctttc    2220
tcgccacgtt cgccggcttt ccccgtcaag ctctaaatcg gggcatccct ttagggttcc    2280
gatttagtgc tttacggcac ctcgacccca aaaaacttga ttagggtgat ggttcacgta    2340
gtgggccatc gccctgatag acggtttttc gccctttgac gttggagtcc acgttcttta    2400
atagtggact cttgttccaa actggaacaa cactcaaccc tatctcggtc tattcttttg    2460
atttataagg gattttgggg atttcggcct attggttaaa aaatgagctg atttaacaaa    2520
aatttaacgc gaattaattc tgtggaatgt gtgtcagtta gggtgtggaa agtccccagg    2580
ctccccaggc aggcagaagt atgcaaagca tgcatctcaa ttagtcagca accaggtgtg    2640
gaaagtcccc aggctcccca gcaggcagaa gtatgcaaag catgcatctc aattagtcag    2700
caaccatagt cccgccccta actccgccca tcccgcccct aactccgccc agttccgccc    2760
attctccgcc ccatggctga ctaattttt ttatttatgc agaggccgag gccgcctctg    2820
cctctgagct attccagaag tagtgaggag gcttttttgg aggcctaggc ttttgcaaaa    2880
agctcccggg agcttgtata tccatttcg gatctgatca agagacagga tgaggatcgt    2940
ttcgcatgat tgaacaagat ggattgcacg caggttctcc ggccgcttgg gtggagaggc    3000
tattcggcta tgactgggca acagacaa tcggctgctc tgatgccgcc gtgttccggc    3060
tgtcagcgca ggggcgcccg gttcttttg tcaagaccga cctgtccggt gccctgaatg    3120
aactgcagga cgaggcagcg cggctatcgt ggctggccac gacgggcgtt ccttgcgcag    3180
ctgtgctcga cgttgtcact gaagcgggaa gggactggct gctattgggc gaagtgccgg    3240
ggcaggatct cctgtcatct caccttgctc ctgccgagaa agtatccatc atggctgatg    3300
caatgcggcg gctgcatacg cttgatccgg ctacctgccc attcgaccac caagcgaaac    3360
atcgcatcga gcgagcacgt actcggatgg aagccggtct tgtcgatcag gatgatctgg    3420
acgaagagca tcaggggctc gcgccagccg aactgttcgc caggctcaag gcgcgcatgc    3480
ccgacggcga ggatctcgtc gtgacccatg gcgatgcctg cttgccgaat atcatggtgg    3540
aaaatggccg cttttctgga ttcatcgact gtggccggct gggtgtggcg gaccgctatc    3600
aggacatagc gttggctacc cgtgatattg ctgaagagct tggcggcgaa tgggctgacc    3660
gcttcctcgt gctttacggt atcgccgctc ccgattcgca gcgcatcgcc ttctatcgcc    3720
ttcttgacga gttcttctga gcgggactct ggggttcgcg aaatgaccga ccaagcgacg    3780
cccaacctgc catcacgaga tttcgattcc accgccgcct tctatgaaag gttgggcttc    3840
ggaatcgttt tccgggacgc cggctggatg atcctccagc gcgggatct catgctggag    3900
ttcttcgccc accccaactt gtttattgca gcttataatg gttacaaata aagcaatagc    3960
atcacaaatt tcacaaataa agcattttt tcactgcatt ctagttgtgg tttgtccaaa    4020
ctcatcaatg tatcttatca tgtctgtata ccgtcgacct ctagctagag cttggcgtaa    4080
tcatggtcat agctgtttcc tgtgtgaaat tgttatccgc tcacaattcc acacaacata    4140
cgagccggaa gcataaagtg taaagcctgg ggtgcctaat gagtgagcta actcacatta    4200
```

```
attgcgttgc gctcactgcc cgctttccag tcgggaaacc tgtcgtgcca gctgcattaa    4260
tgaatcggcc aacgcgcggg gagaggcggt ttgcgtattg ggcgctcttc cgcttcctcg    4320
ctcactgact cgctgcgctc ggtcgttcgg ctgcggcgag cggtatcagc tcactcaaag    4380
gcggtaatac ggttatccac agaatcaggg gataacgcag gaaagaacat gtgagcaaaa    4440
ggccagcaaa aggccaggaa ccgtaaaaag gccgcgttgc tggcgttttt ccataggctc    4500
cgcccccctg acgagcatca caaaaatcga cgctcaagtc agaggtggcg aaacccgaca    4560
ggactataaa gataccaggc gtttccccct ggaagctccc tcgtgcgctc tcctgttccg    4620
accctgccgc ttaccggata cctgtccgcc tttctccctt cgggaagcgt ggcgctttct    4680
caatgctcac gctgtaggta tctcagttcg gtgtaggtcg ttcgctccaa gctgggctgt    4740
gtgcacgaac ccccgttca gcccgaccgc tgcgccttat ccggtaacta tcgtcttgag    4800
tccaacccgg taagacacga cttatcgcca ctggcagcag ccactggtaa caggattagc    4860
agagcgaggt atgtaggcgg tgctacagag ttcttgaagt ggtggcctaa ctacggctac    4920
actagaagga cagtatttgg tatctgcgct ctgctgaagc cagttacctt cggaaaaaga    4980
gttggtagct cttgatccgg caaacaaacc accgctggta gcggtggttt ttttgtttgc    5040
aagcagcaga ttacgcgcag aaaaaaagga tctcaagaag atcctttgat cttttctacg    5100
gggtctgacg ctcagtggaa cgaaaactca cgttaaggga ttttggtcat gagattatca    5160
aaaaggatct tcacctagat ccttttaaat taaaaatgaa gttttaaatc aatctaaagt    5220
atatatgagt aaacttggtc tgacagttac caatgcttaa tcagtgaggc acctatctca    5280
gcgatctgtc tatttcgttc atccatagtt gcctgactcc ccgtcgtgta gataactacg    5340
atacgggagg gcttaccatc tggccccagt gctgcaatga taccgcgaga cccacgctca    5400
ccggctccag atttatcagc aataaaccag ccagccggaa gggccgagcg cagaagtggt    5460
cctgcaactt tatccgcctc catccagtct attaattgtt gccgggaagc tagagtaagt    5520
agttcgccag ttaatagttt gcgcaacgtt gttgccattg ctacaggcat cgtggtgtca    5580
cgctcgtcgt ttggtatggc ttcattcagc tccggttccc aacgatcaag gcgagttaca    5640
tgatccccca tgttgtgcaa aaaagcggtt agctccttcg gtcctccgat cgttgtcaga    5700
agtaagttgg ccgcagtgtt atcactcatg gttatggcag cactgcataa ttctcttact    5760
gtcatgccat ccgtaagatg cttttctgtg actggtgagt actcaaccaa gtcattctga    5820
gaatagtgta tgcggcgacc gagttgctct tgcccggcgt caatacggga taataccgcg    5880
ccacatagca gaactttaaa agtgctcatc attggaaaac gttcttcggg gcgaaaactc    5940
tcaaggatct taccgctgtt gagatccagt tcgatgtaac ccactcgtgc acccaactga    6000
tcttcagcat cttttacttt caccagcgtt tctgggtgag caaaaacagg aaggcaaaat    6060
gccgcaaaaa agggaataag ggcgacacgg aaatgttgaa tactcatact cttccttttt    6120
caatattatt gaagcattta tcagggttat tgtctcatga gcggatacat atttgaatgt    6180
atttagaaaa ataaacaaat aggggttccg cgcacatttc cccgaaaagt gccacctgac    6240
gtc                                                                6243
```

<210> SEQ ID NO 49
<211> LENGTH: 1119
<212> TYPE: DNA
<213> ORGANISM: Artificial Sequence
<220> FEATURE:
<223> OTHER INFORMATION: ZFP52 coding sequence

```
<400> SEQUENCE: 49
atggcccaag ctgccttaga acccggcgag aaaccctata atgcccccga atgcggaaaa      60
tccttcagca ccaaaaactc tttaaccgaa caccagagaa cacatactgg tgaaaaacct     120
tataaatgcc ccgagtgcgg caaatccttc agccaaagcg gcgatttaag gagacatcag     180
aggacccaca ctggtgagaa gccttacaaa tgccccgagt gtggaaaaag ctttagcgac     240
tgtcgtgatt tagctcgtca ccaaagaacc cataccggag aaaaacccta taagtgtccc     300
gagtgcggca aaagcttctc caccaagaat tctttaacag agcaccagag gacccatacc     360
ggcgagaaac cctataagtg tcccgagtgt ggcaagtcct tttccagaac cgacacttta     420
agggaccacc agagaaccca taccggcgaa aagcccctata gtgtcccga atgtggcaag     480
agcttttcca gaagcgacga tctggtgaga caccaaagga cccatactgg tgaaaagccc     540
tataagtgcc ccgaatgtgg caagtccttt tctcgtagcg acaaactgac cgagcaccag     600
aggacccata ctggtgaaaa ccctacaag tgtcccgagt gtggcaagag cttctctcgt     660
aacgacactt taaccgaaca tcagaggacc cataccggag aaaagcccta caagtgcccc     720
gaatgtggaa agagctttag cagcagaaga acttgtagag cccaccaaag gacccacacc     780
ggagagaagc cctataaatg tcccgaatgc ggcaagtcct tcagccagtc cggccatttta    840
accgaacatc agagaacaca caccggcaag aagaccagcg gccaagctgg acaagctagc     900
cccaagaaaa agaaaaggt cggtcgtgcc gacgctttag atgatttcga tttagacatg     960
ctgggcagcg atgctttaga tgacttcgat ctggatatgc tgggcagcga tgctttagat    1020
gattttgatt tagacatgct gggaagcgac gctttagacg actttgatct ggatatgctg    1080
atcaattacc cctacgacgt gcccgactac gcctcctga                           1119

<210> SEQ ID NO 50
<211> LENGTH: 867
<212> TYPE: DNA
<213> ORGANISM: Artificial Sequence
<220> FEATURE:
<223> OTHER INFORMATION: ZFP1_Egr1_site1_sense CDS

<400> SEQUENCE: 50 atgcccagg cggccctgga gccggcgag aagccctaca gtgccccga gtgcggcaag       60
agcttcagca ccagcggcaa cctgaccgag caccagagaa cccacaccgg cgagaagccc     120
tacaagtgcc ccgagtgcgg caagagcttc agcagaagcg acaagctggt gagacaccag     180
agaacccaca ccggcgagaa gccctacaag tgccccgagt gcggcaagag cttcagccac     240
accggccacc tgctggagca cagagaacc cacaccggcg agaagcccta caagtgcccc     300
gagtgcggca gagcttcag cagaagcgac aagctggtga gacaccagag aacccacacc     360
ggcgagaagc cctacaagtg ccccgagtgc ggcaagagct tcagcagaag cgacgacctg     420
gtgagacacc agagaaccca caccggcgag aagccctaca gtgccccga gtgcggcaag     480
agcttcagca gaagcgacga cctggtgaga caccagagaa cccacaccgg cgagaagccc     540
tacaagtgcc ccgagtgcgg caagagcttc agcgaccccg ccacctggt gagacaccag     600
agaacccaca ccggcaagaa gaccagcggc caggccggcc aggctagccc taagaagaag     660
aggaaagtcg gcagagccga cgctttagat gatttcgatt tagacatgct gggctccgac     720
gctttagacg actttgatct ggatatgctg gctccgatg ctttagacga ttttgatctg     780
gatatgctgg gcagcgacgc cctcgacgac ttcgatttag acatgctgat caactacccc     840
tacgatgtgc ccgattacgc ctcctga                                         867
```

<210> SEQ ID NO 51
<211> LENGTH: 867
<212> TYPE: DNA
<213> ORGANISM: Artificial Sequence
<220> FEATURE:
<223> OTHER INFORMATION: ZFP2_Egr1_site2 CDS

<400> SEQUENCE: 51

| | | |
|---|---|---|
| atggcccagg cggccctgga gcccggcgag aagccctaca agtgccccga gtgcggcaag | 60 |
| agcttcagca gaagcgacga cctggtgaga caccagagaa cccacaccgg cgagaagccc | 120 |
| tacaagtgcc ccgagtgcgg caagagcttc agcgaccccg ccacctggt gagacaccag | 180 |
| agaacccaca ccggcgagaa gccctacaag tgccccgagt gcggcaagag cttcagcaga | 240 |
| agcgacgagc tggtgagaca ccagagaacc cacaccggcg agaagcccta caagtgcccc | 300 |
| gagtgcggca gagcttcag cagaagcgac aagctggtga gacaccagag aacccacacc | 360 |
| ggcgagaagc cctacaagtg ccccgagtgc ggcaagagct tcagcagaag cgacgacctg | 420 |
| gtgagacacc agagaaccca caccggcgag aagccctaca agtgccccga gtgcggcaag | 480 |
| agcttcagcc agagagccca cctggagaga caccagagaa cccacaccgg cgagaagccc | 540 |
| tacaagtgcc ccgagtgcgg caagagcttc agcagaagcg acaagctgac cgagcaccag | 600 |
| agaacccaca ccggcaagaa gaccagcggc caggccggcc aggctagccc taagaagaag | 660 |
| aggaaagtcg gcagagccga cgctttagat gatttcgatt tagacatgct gggctccgac | 720 |
| gctttagacg actttgatct ggatatgctg ggctccgatg ctttagacga ttttgatctg | 780 |
| gatatgctgg gcagcgacgc cctcgacgac ttcgatttag acatgctgat caactacccc | 840 |
| tacgatgtgc ccgattacgc ctcctga | 867 |

<210> SEQ ID NO 52
<211> LENGTH: 867
<212> TYPE: DNA
<213> ORGANISM: Artificial Sequence
<220> FEATURE:
<223> OTHER INFORMATION: ZFP3_Egr1_site3_antisense CDS

<400> SEQUENCE: 52

| | | |
|---|---|---|
| atggcccagg cggccctgga gcccggcgag aagccctaca agtgccccga gtgcggcaag | 60 |
| agcttcagcc agagcggcga cctgagaaga caccagagaa cccacaccgg cgagaagccc | 120 |
| tacaagtgcc ccgagtgcgg caagagcttc agcagaagcg acaagctggt gagacaccag | 180 |
| agaacccaca ccggcgagaa gccctacaag tgccccgagt gcggcaagag cttcagcaga | 240 |
| agcgacgagc tggtgagaca ccagagaacc cacaccggcg agaagcccta caagtgcccc | 300 |
| gagtgcggca gagcttcag cagaagcgac aagctggtga gacaccagag aacccacacc | 360 |
| ggcgagaagc cctacaagtg ccccgagtgc ggcaagagct tcagcagaaa cgacgccctg | 420 |
| accgagcacc agagaaccca caccggcgag aagccctaca agtgccccga gtgcggcaag | 480 |
| agcttcagcc agagcggcga cctgagaaga caccagagaa cccacaccgg cgagaagccc | 540 |
| tacaagtgcc ccgagtgcgg caagagcttc agcagaaacg acgccctgac cgagcaccag | 600 |
| agaacccaca ccggcaagaa gaccagcggc caggccggcc aggctagccc caagaaaaag | 660 |
| agaaaggtcg gtcgtgccga cgctttagat gatttcgatt tagacatgct gggcagcgat | 720 |
| gctttagatg acttcgatct ggatatgctg ggcagcgatc tttagatga ttttgatttta | 780 |
| gacatgctgg gaagcgacgc tttagacgac tttgatctgg atatgctgat caattacccc | 840 |

```
tacgacgtgc cgactacgc ctcctga                                    867
```

<210> SEQ ID NO 53
<211> LENGTH: 783
<212> TYPE: DNA
<213> ORGANISM: Artificial Sequence
<220> FEATURE:
<223> OTHER INFORMATION: ZFP4_Egr1_site1_antisense CDS

<400> SEQUENCE: 53

```
atggcccagg cggccctgga gcccggcgag aagccctaca agtgccccga gtgcggcaag    60
agcttcagcc acaccggcca cctgctggag caccagagaa cccacaccgg cgagaagccc   120
tacaagtgcc ccgagtgcgg caagagcttc agcagaaacg acaccctgac cgagcaccag   180
agaacccaca ccggcgagaa gccctacaag tgccccgagt gcggcaagag cttcagcaga   240
aacgacaccc tgaccgagca ccagagaacc cacaccggcg agaagcccta caagtgcccc   300
gagtgcggca agagcttcag cgactgcaga gacctggcca gacaccagag aacccacacc   360
ggcgagaagc cctacaagtg ccccgagtgc ggcaagagct tcagcacacc ggccacctg   420
ctggagcacc agagaaccca caccggcgag aagccctaca agtgccccga gtgcggcaag   480
agcttcagcg actgcagaga cctggccaga caccagagaa cccacaccgg caagaagacc   540
agcggccagg ccggccaggc tagccccaag aaaaagagaa aggtcggtcg tgccgacgct   600
ttagatgatt tcgatttaga catgctgggc agcgatgctt tagatgactt cgatctggat   660
atgctgggca gcgatgcttt agatgatttt gatttagaca tgctgggaag cgacgcttta   720
gacgactttg atctggatat gctgatcaat taccctacg acgtgccga ctacgcctcc   780
tga                                                                783
```

<210> SEQ ID NO 54
<211> LENGTH: 2625
<212> TYPE: DNA
<213> ORGANISM: Artificial Sequence
<220> FEATURE:
<223> OTHER INFORMATION: ZFP52_VPR coding sequence

<400> SEQUENCE: 54

```
atggcccaag ctgccttaga acccggcgag aaaccctata atgccccga atgcggaaaa    60
tccttcagca ccaaaaactc tttaaccgaa caccagagaa cacatactgg tgaaaaacct   120
tataaatgcc ccgagtgcgg caaatccttc agccaaagcg cgatttaag agacatcag   180
aggacccaca ctggtgagaa gccttacaaa tgccccgagt gtggaaaaag ctttagcgac   240
tgtcgtgatt tagctcgtca ccaaagaacc cataccggag aaaaaccta aagtgtccc   300
gagtgcggca aaagcttctc caccaagaat tcttttaacag agcaccagag gacccatacc   360
ggcgagaaac cctataagtg tcccgagtgt ggcaagtcct tttccagaac cgacactta   420
agggaccacc agagaaccca taccggcgaa aagccctata gtgtcccga atgtggcaag   480
agcttttcca aagcgacga tctggtgaga caccaaagga cccatactgg tgaaaagccc   540
tataagtgcc ccgaatgtgg caagtccttt tctcgtagcg acaaactgac cgagcaccag   600
aggacccata ctggtgaaaa accctacaag tgtcccgagt gtggcaagag cttctctcgt   660
aacgacactt taaccgaaca tcagaggacc cataccggcg aaaagcccta caagtgcccc   720
gaatgtggaa agagctttag cagcagaaga acttgtagag cccaccaaag gacccacacc   780
ggagagaagc cctataaatg tcccgaatgc ggcaagtcct tcagccagtc cggccattta   840
accgaacatc agagaacaca caccggcaag aagaccagcg ccaagctgg acaagctagc   900
```

```
cccaagaaaa agagaaaggt cggtcgtgcc gacgctttag atgatttcga tttagacatg    960
ctgggcagcg atgctttaga tgacttcgat ctggatatgc tgggcagcga tgctttagat   1020
gattttgatt tagacatgct gggaagcgac gctttagacg actttgatct ggatatgctg   1080
atcaattacc cctacgacgt tccggactac gcttctagtt ccggatctcc gaaaaagaaa   1140
cgcaaagttg gtagccagta cctgcccgac accgacgacc ggcaccggat cgaggaaaag   1200
cggaagcgga cctacgagac attcaagagc atcatgaaga gtccccctt cagcggcccc    1260
accgacccta gacctccacc tagaagaatc gccgtgccca gcagatccag cgccagcgtg   1320
ccaaaacctg ccccccagcc ttaccccttc accagcagcc tgagcaccat caactacgac   1380
gagttcccta ccatggtgtt ccccagcggc cagatctctc aggcctctgc tctggctcca   1440
gcccctcctc aggtgctgcc tcaggctcct gctcctgcac cagctccagc catggtgtct   1500
gcactggctc aggcaccagc acccgtgcct gtgctggctc ctggacctcc acaggctgtg   1560
gctccaccag cccctaaacc tacacaggcc ggcgagggca cactgtctga agctctgctg   1620
cagctgcagt tcgacgacga ggatctggga gccctgctgg aaacagcac cgatcctgcc    1680
gtgttcaccg acctggccag cgtggacaac agcgagttcc agcagctgct gaaccagggc   1740
atccctgtgg cccctcacac caccgagccc atgctgatgg ataccccga ggccatcacc    1800
cggctcgtga caggcgctca gaggcctcct gatccagctc ctgcccctct gggagcacca   1860
ggcctgccta atggactgct gtctggcgac gaggacttca gctctatcgc cgatatggat   1920
ttctcagcct tgctgggctc tggcagcggc agccggggatt ccaggggaagg atgttttttg  1980
ccgaagcctg aggccggctc cgctattagt gacgtgtttg agggccgcga ggtgtgccag   2040
ccaaaacgaa tccggccatt tcatcctcca ggaagtccat gggccaaccg cccactcccc   2100
gccagcctcg caccaacacc aaccggtcca gtacatgagc cagtcgggtc actgaccccg   2160
gcaccagtcc ctcagccact ggatccagcg cccgcagtga ctcccgaggc cagtcacctg   2220
ttggaggatc ccgatgaaga gacgagccag gctgtcaaag cccttcggga gatggccgat   2280
actgtgattc cccagaagga agaggctgca atctgtggcc aaatggacct ttcccatccg   2340
cccccaaggg gccatctgga tgagctgaca accacacttg agtccatgac cgaggatctg   2400
aacctggact caccccctgac ccggaattg aacgagattc tggataccct cctgaacgac   2460
gagtgcctct tgcatgccat gcatatcagc acaggactgt ccatcttcga cacatctctg   2520
tttgactcga gtctagaggg cccgcggttc gaaggtaagc ctatccctaa ccctctcctc   2580
ggtctcgatt ctacgcgtac cggtcatcat caccatcacc attga                   2625
```

<210> SEQ ID NO 55
<211> LENGTH: 2373
<212> TYPE: DNA
<213> ORGANISM: Artificial Sequence
<220> FEATURE:
<223> OTHER INFORMATION: ZFP3_VPR coding sequence

<400> SEQUENCE: 55

```
atggcccagg cggccctgga gcccggcgag aagccctaca gtgcccccga gtgcggcaag     60
agcttcagcc agagcggcga cctgagaaga caccagagaa cccacaccgg cgagaagccc    120
tacaagtgcc ccgagtgcgg caagagcttc agcagaagcg acaagctggt gagacaccag    180
agaacccaca ccggcgagaa gccctacaag tgccccgagt gcggcaagag cttcagcaga    240
agcgacgagc tggtgagaca ccagagaacc cacaccggcg agaagcccta caagtgcccc    300
```

```
gagtgcggca agagcttcag cagaagcgac aagctggtga gacaccagag aacccacacc    360
ggcgagaagc cctacaagtg ccccgagtgc ggcaagagct tcagcagaaa cgacgccctg    420
accgagcacc agagaaccca caccggcgag aagccctaca agtgccccga gtgcggcaag    480
agcttcagcc agagcggcga cctgagaaga caccagagaa cccacaccgg cgagaagccc    540
tacaagtgcc ccgagtgcgg caagagcttc agcagaaacg acgccctgac cgagcaccag    600
agaacccaca ccggcaagaa gaccagcggc caggccggcc aggctagccc caagaaaaag    660
agaaaggtcg gtcgtgccga cgctttagat gatttcgatt tagacatgct gggcagcgat    720
gctttagatg acttcgatct ggatatgctg ggcagcgatg ctttagatga ttttgattta    780
gacatgctgg aagcgacgc tttagacgac tttgatctgg atatgctgat caattacccc    840
tacgacgttc cggactacgc ttctagttcc ggatctccga aaaagaaacg caaagttggt    900
agccagtacc tgcccgacac cgacgaccgg caccggatca ggaaaagcg aagcggacc    960
tacgagacat tcaagagcat catgaagaag tcccccttca gcggcccac cgaccctaga    1020
cctccaccta gaagaatcgc cgtgcccagc agatccagcg ccagcgtgcc aaaacctgcc    1080
ccccagcctt accccttcac cagcagcctg agcaccatca actacgacga gttccctacc    1140
atggtgttcc ccagcggcca gatctctcag gcctctgctc tggctccagc ccctcctcag    1200
gtgctgcctc aggctcctgc tcctgcacca gctccagcca tggtgtctgc actggctcag    1260
gcaccagcac ccgtgcctgt gctggctcct ggacctccac aggctgtggc tccaccagcc    1320
cctaaaccta cacaggccgg cgagggcaca ctgtctgaag ctctgctgca gctgcagttc    1380
gacgacgagg atctgggagc cctgctggga acagcaccg atcctgccgt gttcaccgac    1440
ctggccagcg tggacaacag cgagttccag cagctgctga accagggcat ccctgtggcc    1500
cctcacacca ccgagcccat gctgatggaa taccccgagg ccatcacccg gctcgtgaca    1560
ggcgctcaga ggcctcctga tccagctcct gcccctctgg agcaccagg cctgcctaat    1620
ggactgctgt ctggcgacga ggacttcagc tctatcgccg atatggattt ctcagccttg    1680
ctgggctctg gcagcggcag ccgggattcc agggaaggga tgttttgcc gaagcctgag    1740
gccggctccg ctattagtga cgtgtttgag ggccgcgagg tgtgccagcc aaaacgaatc    1800
cggccatttc atcctccagg aagtccatgg gccaaccgcc cactccccgc cagcctcgca    1860
ccaacaccaa ccggtccagt acatgagcca gtcgggtcac tgaccccggc accagtccct    1920
cagccactgg atccagcgcc cgcagtgact cccgaggcca gtcacctgtt ggaggatccc    1980
gatgaagaga cgagccaggc tgtcaaagcc cttcgggaga tggccgatac tgtgattccc    2040
cagaaggaag aggctgcaat ctgtggccaa atggacctttt ccatccgcc cccaagggc    2100
catctggatg agctgacaac cacacttgag tccatgaccg aggatctgaa cctggactca    2160
cccctgaccc cggaattgaa cgagattctg gataccttcc tgaacgacga gtgcctcttg    2220
catgccatgc atatcagcac aggactgtcc atcttcgaca catctctgtt tgactcgagt    2280
ctagagggcc cgcggttcga aggtaagcct atccctaacc ctctcctcgg tctcgattct    2340
acgcgtaccg gtcatcatca ccatcaccat tga                                 2373
```

<210> SEQ ID NO 56
<211> LENGTH: 1884
<212> TYPE: DNA
<213> ORGANISM: Artificial Sequence
<220> FEATURE:
<223> OTHER INFORMATION: Egr1_insert_site2 coding sequence

<400> SEQUENCE: 56

```
atggccgcgg ccaaggccga gatgcagctg atgtccccgc tgcagatctc tgacccgttc      60
ggatcctttc ctcactcgcc caccatggac aactaccccta agctggagga gatgatgctg    120
ctgagcaacg gggctcccca gttcctcggc gccgccgggg ccccagaggg cagcggcagc    180
aacagcagca gcagcagcag cgggggcggt ggaggcggcg ggggcggcag caacagcagc    240
agcagcagca gcaccttcaa ccctcaggcg gacacgggcg agcagcccta cgagcacctg    300
accgcagagt cttttcctga catctctctg aacaacgaga aggtgctggt ggagaccagt    360
tacccccagcc aaaccactcg actgccccccc atcacctata ctggccgctt ttccctggag    420
cctgcaccca cagtggcaa caccttgtgg cccgagcccc tcttcagctt ggtcagtggc    480
ctagtgagca tgaccaaccc accggcctcc tcgtcctcag caccatctcc agcggcctcc    540
tccgcctccg cctcccagag cccacccctg agctgcgcag tgccatccaa cgacagcagt    600
cccatttact cagcggcacc caccttcccc acgccgaaca ctgacatttt ccctgagcca    660
caaagccagg cctttcccggg ctcggcaggg acagcgctcc agtacccgcc tcctgcctac    720
cctgccgcca agggtggctt ccaggttccc atgatccccg actacctgtt tccacagcag    780
caggggggatc tgggcctggg caccccagac cagaagccct tccagggcct ggagagccgc    840
acccagcagc cttcgctaac ccctctgtct actattaagg cctttgccac tcagtcgggc    900
tcccaggacc tgaaggccct caataccagc taccagtccc agctcatcaa cccagccgc    960
atgcgcaagt accccaaccg gcccagtaag acgcccccc acgaacgccc ttacgcttgc   1020
ccagtggagt cctgtgatcg ccgcttctcc cgctccgacg agctcacccg ccacatccgc   1080
atccacacag gccagaagcc cttccagtgc cgcatctgca tgcgcaactt cagccgcagc   1140
gaccacctca ccacccacat ccgcacccac acaggcgaaa agcccttcgc ctgcgacatc   1200
tgtggaagaa agtttgccag gagcgatgaa cgcaagaggc ataccaagat ccacacaggc   1260
cagaagccct gccagtgga gtcctgtgat cgccgcttct cccagagagc ccacctggag   1320
agacacatcc gcatccacac aggccagaag cccttccagt gccgcatctg catgcgcaac   1380
ttcagcagaa gcgacaagct gaccgagcac atccgcaccc acacaggcga aaagcccttc   1440
gcctgcgaca tctgtggaag aaagtttgcc cacaccggcc acctgctgga gcataccaag   1500
atccacttgc ggcagaagga caagaaagca gacaaaagtg ttgtggcctc ttcggccacc   1560
tcctctctct cttcctaccc gtccccggtt gctacctctt acccgtcccc ggttactacc   1620
tcttatccat ccccggccac cacctcatac ccatcccctg tgcccaccte cttctcctct   1680
cccggctcct cgacctaccc atccctgtg cacagtggct tccccctccc gtcggtggcc   1740
accacgtact cctctgttcc ccctgctttc ccggcccagg tcagcagctt cccttcctca   1800
gctgtcacca actccttcag cgcctccaca gggctttcgg acatgacagc aaccttttct   1860
cccaggacaa ttgaaatttg ctaa                                            1884
```

<210> SEQ ID NO 57
<211> LENGTH: 1869
<212> TYPE: DNA
<213> ORGANISM: Artificial Sequence
<220> FEATURE:
<223> OTHER INFORMATION: Egr1_insert_site3 coding sequence

<400> SEQUENCE: 57

```
atggccgcgg ccaaggccga gatgcagctg atgtccccgc tgcagatctc tgacccgttc      60
ggatcctttc ctcactcgcc caccatggac aactaccccta agctggagga gatgatgctg    120
```

| | |
|---|---|
| ctgagcaacg gggctcccca gttcctcggc gccgccgggg ccccagaggg cagcggcagc | 180 |
| aacagcagca gcagcagcag cggggcggt ggaggcggcg ggggcggcag caacagcagc | 240 |
| agcagcagca gcaccttcaa ccctcaggcg gacacgggcg agcagcccta cgagcacctg | 300 |
| accgcagagt cttttcctga catctctctg aacaacgaga aggtgctggt ggagaccagt | 360 |
| taccccagcc aaaccactcg actgcccccc atcacctata ctggccgctt ttccctggag | 420 |
| cctgcaccca cagtggcaa caccttgtgg cccgagcccc tcttcagctt ggtcagtggc | 480 |
| ctagtgagca tgaccaaccc accggcctcc tcgtcctcag caccatctcc agcggcctcc | 540 |
| tccgcctccg cctcccagag cccacccctg agctgcgcag tgccatccaa cgacagcagt | 600 |
| cccatttact cagcggcacc caccttcccc acgccgaaca ctgacatttt ccctgagcca | 660 |
| caaagccagg ccttcccggg ctcggcaggg acagcgctcc agtacccgcc tcctgcctac | 720 |
| cctgccgcca agggtggctt ccaggttccc atgatccccg actacctgtt tccacagcag | 780 |
| caggggatc tgggcctggg caccccgac cagaagccct tccagggcct ggagagccgc | 840 |
| acccagcagc cttcgctaac ccctctgtct actattaagg cctttgccac tcagtcgggc | 900 |
| tcccaggacc tgaaggccct caataccagc taccagtccc agctcatcaa acccagccgc | 960 |
| atgcgcaagt accccaaccg gcccagtaag acgccccccc acgaacgccc ttacgcttgc | 1020 |
| ccagtggagt cctgtgatcg ccgcttctcc cgctccgacg agctcacccg ccacatccgc | 1080 |
| atccacacag gccagaagcc cttccagtgc cgcatctgca tgcgcaactt cagccgcagc | 1140 |
| gaccacctca ccacccacat ccgcacccac acaggcgaaa agccttcgc ctgcgacatc | 1200 |
| tgtggaagaa agtttgccag gagcgatgaa cgcaagaggc ataccaagat ccactgccca | 1260 |
| gtggagtcct gtgatcgccg cttctcccag agcggcgacc tgagaagaca catccgcatc | 1320 |
| cacacaggcc agaagccctt ccagtgccgc atctgcatgc gcaacttcag cagaaacgac | 1380 |
| gccctgaccg agcacatccg cacccacaca ggcgaaaagc ccttcgcctg cgacatctgt | 1440 |
| ggaagaaagt tgccgactg cagagacctg gccagacata ccaagatcca cttgcggcag | 1500 |
| aaggacaaga aagcagacaa aagtgttgtg gcctcttcgg ccacctcctc tctctcttcc | 1560 |
| tacccgtccc cggttgctac ctcttaccg tccccggtta ctacctctta tccatccccg | 1620 |
| gccaccacct catacccatc cctgtgccc acctccttct cctctcccgg ctcctcgacc | 1680 |
| tacccatccc ctgtgcacag tggcttcccc tcccgtcgg tggccaccac gtactcctct | 1740 |
| gttccccctg cttcccggc ccaggtcagc agcttccctt cctcagctgt caccaactcc | 1800 |
| ttcagcgcct ccacagggct ttcggacatg acagcaacct tttctcccag gacaattgaa | 1860 |
| atttgctaa | 1869 |

<210> SEQ ID NO 58
<211> LENGTH: 1782
<212> TYPE: DNA
<213> ORGANISM: Artificial Sequence
<220> FEATURE:
<223> OTHER INFORMATION: Egr1_insert_site2_RR coding sequence

<400> SEQUENCE: 58

| | |
|---|---|
| atggccgcgg ccaaggccga gatgcagctg atgtccccgc tgcagatctc tgacccgttc | 60 |
| ggatcctttc ctcactcgcc caccatggac aactacccta gctggaggga gatgatgctg | 120 |
| ctgagcaacg gggctcccca gttcctcggc gccgccgggg ccccagaggg cagcggcagc | 180 |
| aacagcagca gcagcagcag cggggcggt ggaggcggcg ggggcggcag caacagcagc | 240 |
| agcagcagca gcaccttcaa ccctcaggcg gacacgggcg agcagcccta cgagcacctg | 300 |

```
accgcagagt cttttcctga catctctctg aacaacgaga aggtgctggt ggagaccagt    360
tacccccagcc aaaccactcg actgcccccc atcacctata ctggccgctt ttccctggag   420
cctgcaccca acagtggcaa caccttgtgg cccgagcccc tcttcagctt ggtcagtggc    480
ctagtgagca tgaccaaccc accggcctcc tcgtcctcag caccatctcc agcggcctcc    540
tccgcctccg cctcccagag cccacccctg agctgcgcag tgccatccaa cgacagcagt    600
cccatttact cagcggcacc caccttcccc acgccgaaca ctgacatttt ccctgagcca    660
caaagccagg ccttcccggg ctcggcaggg acagcgctcc agtacccgcc tcctgcctac    720
cctgccgcca agggtggctt ccaggttccc atgatcccccg actacctgtt tccacagcag   780
caggggatc tgggcctggg caccccagac cagaagccct tccagggcct ggagagccgc     840
ctcatcaaac ccagccgcat gcgcaagtac cccaaccggc cagtaagac gccccccac       900
gaacgccctt acgcttgccc agtggagtcc tgtgatcgcc gcttctcccg ctccgacgag    960
ctcacccgcc acatccgcat ccacacaggc cagaagccct tccagtgccg catctgcatg    1020
cgcaacttca gccgcagcga ccacctcacc acccacatcc gcacccacac aggcgaaaag   1080
cccttcgcct gcgacatctg tggaagaaag tttgccagga gcgatgaacg caagaggcat   1140
accaagatcc acacaggcca aagccctgc ccagtggagt cctgtgatcg ccgcttctcc    1200
cagagagccc acctggagag acacatccgc atccacacag gccagaagcc cttccagtgc  1260
cgcatctgca tgcgcaactt cagcagaagc gacaagctga ccgagcacat ccgcacccac   1320
acaggcgaaa agcccttcgc ctgcgacatc tgtggaagaa agtttgccca caccggccac  1380
ctgctggagc ataccaagat ccacttgcgg cagaaggaca agaaagcaga caaaagtgtt   1440
gtggcctctt cggccacctc ctctctctct tcctacccgt ccccggttgc tacctcttac   1500
ccgtccccgg ttactacctc ttatccatcc ccggccacca cctcataccc atcccctgtg   1560
cccacctcct tctcctctcc cggctcctcg acctacccat ccctgtgca cagtggcttc    1620
cctccccgt cggtggccac cacgtactcc tctgttcccc ctgctttccc ggcccaggtc    1680
agcagcttcc cttcctcagc tgtcaccaac tccttcagcg cctccacagg gctttcggac   1740
atgacagcaa cctttctcc caggacaatt gaaatttgct aa                       1782
```

<210> SEQ ID NO 59  
<211> LENGTH: 1767  
<212> TYPE: DNA  
<213> ORGANISM: Artificial Sequence  
<220> FEATURE:  
<223> OTHER INFORMATION: Egr1_insert_site3_RR coding sequence

<400> SEQUENCE: 59

```
atggccgcgg ccaaggccga gatgcagctg atgtccccgc tgcagatctc tgacccgttc      60
ggatcctttc ctcactcgcc caccatggac aactacccta agctggagga gatgatgctg    120
ctgagcaacg gggctcccca gttcctcggc gccgccgggg cccagagggg cagcggcagc    180
aacagcagca gcagcagcag cggggcggt ggaggcggcg gggcggcag caacagcagc      240
agcagcagca gcaccttcaa ccctcaggcg gacacgggcg agcagcccta cgagcacctg   300
accgcagagt cttttcctga catctctctg aacaacgaga aggtgctggt ggagaccagt   360
tacccccagcc aaaccactcg actgcccccc atcacctata ctggccgctt ttccctggag  420
cctgcaccca acagtggcaa caccttgtgg cccgagcccc tcttcagctt ggtcagtggc   480
ctagtgagca tgaccaaccc accggcctcc tcgtcctcag caccatctcc agcggcctcc    540
```

```
tccgcctccg cctcccagag cccacccctg agctgcgcag tgccatccaa cgacagcagt    600
cccatttact cagcggcacc caccttcccc acgccgaaca ctgacatttt ccctgagcca    660
caaagccagg ccttcccggg ctcggcaggg acagcgctcc agtacccgcc tcctgcctac    720
cctgccgcca agggtggctt ccaggttccc atgatcccg  actacctgtt tccacagcag    780 caggggatc  tgggcctggg caccccagac cagaagccct tccagggcct ggagagccgc    840
ctcatcaaac ccagccgcat gcgcaagtac cccaaccggc cagtaagac  gccccccac     900 gaacgccctt acgcttgccc agtggagtcc tgtgatcgcc gcttctcccg ctccgacgag    960
ctcacccgcc acatccgcat ccacacaggc cagaagccct tccagtgccg catctgcatg   1020
cgcaacttca gccgcagcga ccacctcacc acccacatcc gcacccacac aggcgaaaag   1080
cccttcgcct gcgacatctg tggaagaaag tttgccagga gcgatgaacg caagaggcat   1140
accaagatcc actgcccagt ggagtcctgt gatcgccgct ctcccagag  cggcgacctg   1200 agaagacaca tccgcatcca cacaggccag aagcccttcc agtgccgcat ctgcatgcgc   1260
aacttcagca gaaacgacgc cctgaccgag cacatccgca cccacacagg cgaaaagccc   1320
ttcgcctgcg acatctgtgg aagaaagttt gccgactgca gagacctggc cagacatacc   1380
aagatccact gcggcagaa  ggacaagaaa gcagacaaaa gtgttgtggc ctcttcggcc   1440
acctcctctc tctcttccta cccgtccccg gttgctacct cttaccgtc  cccggttact   1500 acctcttatc catccccggc caccacctca tacccatccc ctgtgcccac ctccttctcc   1560
tctcccggct cctcgaccta cccatcccct gtgcacagtg gcttccctc  cccgtcggtg   1620 gccaccacgt actcctctgt tccccctgct ttccggccc  aggtcagcag cttcccttcc   1680
tcagctgtca ccaactcctt cagcgcctcc acagggcttt cggacatgac agcaaccttt   1740
tctcccagga caattgaaat ttgctaa                                       1767
```

<210> SEQ ID NO 60
<211> LENGTH: 9
<212> TYPE: DNA
<213> ORGANISM: Homo sapiens

<400> SEQUENCE: 60 gcggggcgc                                                                      9

<210> SEQ ID NO 61
<211> LENGTH: 9
<212> TYPE: DNA
<213> ORGANISM: Homo sapiens

<400> SEQUENCE: 61 gcggggtg                                                                       9

<210> SEQ ID NO 62
<211> LENGTH: 9
<212> TYPE: DNA
<213> ORGANISM: Homo sapiens

<400> SEQUENCE: 62 ctggggtg                                                                       9

<210> SEQ ID NO 63
<211> LENGTH: 18
<212> TYPE: DNA
<213> ORGANISM: Homo sapiens

<400> SEQUENCE: 63

```
cgaaacgtcc tgcacggc                                                   18

<210> SEQ ID NO 64
<211> LENGTH: 30
<212> TYPE: DNA
<213> ORGANISM: Homo sapiens

<400> SEQUENCE: 64
cgacgtccgc gggcgacgcc tgccgcacct                                      30

<210> SEQ ID NO 65
<211> LENGTH: 21
<212> TYPE: DNA
<213> ORGANISM: Homo sapiens

<400> SEQUENCE: 65
ggcgcggcgg ggcgcgggca t                                               21

<210> SEQ ID NO 66
<211> LENGTH: 21
<212> TYPE: DNA
<213> ORGANISM: Homo sapiens

<400> SEQUENCE: 66
cggggagcgg gggtgggcgc g                                               21

<210> SEQ ID NO 67
<211> LENGTH: 21
<212> TYPE: DNA
<213> ORGANISM: Homo sapiens

<400> SEQUENCE: 67
ctggcactgg gggtgggggc a                                               21

<210> SEQ ID NO 68
<211> LENGTH: 18
<212> TYPE: DNA
<213> ORGANISM: Homo sapiens

<400> SEQUENCE: 68
gcccgcgccc cgccgcgc                                                   18

<210> SEQ ID NO 69
<211> LENGTH: 18
<212> TYPE: DNA
<213> ORGANISM: Homo sapiens

<400> SEQUENCE: 69
cgccggggag cggggtg                                                    18

<210> SEQ ID NO 70
<211> LENGTH: 18
<212> TYPE: DNA
<213> ORGANISM: Homo sapiens

<400> SEQUENCE: 70
gccctggcac tggggtg                                                    18

<210> SEQ ID NO 71
<211> LENGTH: 50
<212> TYPE: PRT
<213> ORGANISM: Artificial Sequence
<220> FEATURE:
```

-continued

<223> OTHER INFORMATION: VP64

<400> SEQUENCE: 71

Asp Ala Leu Asp Asp Phe Asp Leu Asp Met Leu Gly Ser Asp Ala Leu
1               5                   10                  15

Asp Asp Phe Asp Leu Asp Met Leu Gly Ser Asp Ala Leu Asp Asp Phe
            20                  25                  30

Asp Leu Asp Met Leu Gly Ser Asp Ala Leu Asp Asp Phe Asp Leu Asp
        35                  40                  45

Met Leu
    50

<210> SEQ ID NO 72
<211> LENGTH: 261
<212> TYPE: PRT
<213> ORGANISM: Artificial Sequence
<220> FEATURE:
<223> OTHER INFORMATION: p65

<400> SEQUENCE: 72

Ser Gln Tyr Leu Pro Asp Thr Asp Asp Arg His Arg Ile Glu Glu Lys
1               5                   10                  15

Arg Lys Arg Thr Tyr Glu Thr Phe Lys Ser Ile Met Lys Lys Ser Pro
            20                  25                  30

Phe Ser Gly Pro Thr Asp Pro Arg Pro Pro Pro Arg Arg Ile Ala Val
        35                  40                  45

Pro Ser Arg Ser Ser Ala Ser Val Pro Lys Pro Ala Pro Gln Pro Tyr
    50                  55                  60

Pro Phe Thr Ser Ser Leu Ser Thr Ile Asn Tyr Asp Glu Phe Pro Thr
65                  70                  75                  80

Met Val Phe Pro Ser Gly Gln Ile Ser Gln Ala Ser Ala Leu Ala Pro
                85                  90                  95

Ala Pro Pro Gln Val Leu Pro Gln Ala Pro Ala Pro Ala Pro Ala Pro
            100                 105                 110

Ala Met Val Ser Ala Leu Ala Gln Ala Pro Ala Pro Val Pro Val Leu
        115                 120                 125

Ala Pro Gly Pro Pro Gln Ala Val Ala Pro Pro Ala Pro Lys Pro Thr
    130                 135                 140

Gln Ala Gly Glu Gly Thr Leu Ser Glu Ala Leu Leu Gln Leu Gln Phe
145                 150                 155                 160

Asp Asp Glu Asp Leu Gly Ala Leu Leu Gly Asn Ser Thr Asp Pro Ala
                165                 170                 175

Val Phe Thr Asp Leu Ala Ser Val Asp Asn Ser Glu Phe Gln Gln Leu
            180                 185                 190

Leu Asn Gln Gly Ile Pro Val Ala Pro His Thr Thr Glu Pro Met Leu
        195                 200                 205

Met Glu Tyr Pro Glu Ala Ile Thr Arg Leu Val Thr Gly Ala Gln Arg
    210                 215                 220

Pro Pro Asp Pro Ala Pro Ala Pro Leu Gly Ala Pro Gly Leu Pro Asn
225                 230                 235                 240

Gly Leu Leu Ser Gly Asp Glu Asp Phe Ser Ser Ile Ala Asp Met Asp
                245                 250                 255

Phe Ser Ala Leu Leu
            260

<210> SEQ ID NO 73

```
<211> LENGTH: 190
<212> TYPE: PRT
<213> ORGANISM: Artificial Sequence
<220> FEATURE:
<223> OTHER INFORMATION: Rta

<400> SEQUENCE: 73

Arg Asp Ser Arg Glu Gly Met Phe Leu Pro Lys Pro Glu Ala Gly Ser
1               5                   10                  15

Ala Ile Ser Asp Val Phe Glu Gly Arg Glu Val Cys Gln Pro Lys Arg
            20                  25                  30

Ile Arg Pro Phe His Pro Pro Gly Ser Pro Trp Ala Asn Arg Pro Leu
        35                  40                  45

Pro Ala Ser Leu Ala Pro Thr Pro Thr Gly Pro Val His Glu Pro Val
50                  55                  60

Gly Ser Leu Thr Pro Ala Pro Val Pro Gln Pro Leu Asp Pro Ala Pro
65                  70                  75                  80

Ala Val Thr Pro Glu Ala Ser His Leu Leu Glu Asp Pro Asp Glu Glu
                85                  90                  95

Thr Ser Gln Ala Val Lys Ala Leu Arg Glu Met Ala Asp Thr Val Ile
            100                 105                 110

Pro Gln Lys Glu Glu Ala Ala Ile Cys Gly Gln Met Asp Leu Ser His
        115                 120                 125

Pro Pro Pro Arg Gly His Leu Asp Glu Leu Thr Thr Thr Leu Glu Ser
    130                 135                 140

Met Thr Glu Asp Leu Asn Leu Asp Ser Pro Leu Thr Pro Glu Leu Asn
145                 150                 155                 160

Glu Ile Leu Asp Thr Phe Leu Asn Asp Glu Cys Leu Leu His Ala Met
                165                 170                 175

His Ile Ser Thr Gly Leu Ser Ile Phe Asp Thr Ser Leu Phe
            180                 185                 190

<210> SEQ ID NO 74
<211> LENGTH: 9
<212> TYPE: DNA
<213> ORGANISM: Artificial Sequence
<220> FEATURE:
<223> OTHER INFORMATION: M1 mutant

<400> SEQUENCE: 74 gctgttttg                                                                9

<210> SEQ ID NO 75
<211> LENGTH: 15
<212> TYPE: DNA
<213> ORGANISM: Artificial Sequence
<220> FEATURE:
<223> OTHER INFORMATION: M2 wild type

<400> SEQUENCE: 75
ctgggggtgg gggca                                                        15

<210> SEQ ID NO 76
<211> LENGTH: 15
<212> TYPE: DNA
<213> ORGANISM: Artificial Sequence
<220> FEATURE:
<223> OTHER INFORMATION: M2 mutant

<400> SEQUENCE: 76
ctaaggacaa ggaca                                                        15
```

```
<210> SEQ ID NO 77
<211> LENGTH: 531
<212> TYPE: PRT
<213> ORGANISM: Artificial Sequence
<220> FEATURE:
<223> OTHER INFORMATION: VPR

<400> SEQUENCE: 77

Asp Ala Leu Asp Asp Phe Asp Leu Asp Met Leu Gly Ser Asp Ala Leu
1               5                   10                  15

Asp Asp Phe Asp Leu Asp Met Leu Gly Ser Asp Ala Leu Asp Asp Phe
            20                  25                  30

Asp Leu Asp Met Leu Gly Ser Asp Ala Leu Asp Asp Phe Asp Leu Asp
        35                  40                  45

Met Leu Ile Asn Tyr Pro Tyr Asp Val Pro Asp Tyr Ala Ser Ser Ser
50                  55                  60

Gly Ser Pro Lys Lys Lys Arg Lys Val Gly Ser Gln Tyr Leu Pro Asp
65                  70                  75                  80

Thr Asp Asp Arg His Arg Ile Glu Glu Lys Arg Lys Arg Thr Tyr Glu
                85                  90                  95

Thr Phe Lys Ser Ile Met Lys Lys Ser Pro Phe Ser Gly Pro Thr Asp
            100                 105                 110

Pro Arg Pro Pro Pro Arg Arg Ile Ala Val Pro Ser Arg Ser Ser Ala
        115                 120                 125

Ser Val Pro Lys Pro Ala Pro Gln Pro Tyr Pro Phe Thr Ser Ser Leu
130                 135                 140

Ser Thr Ile Asn Tyr Asp Glu Phe Pro Thr Met Val Phe Pro Ser Gly
145                 150                 155                 160

Gln Ile Ser Gln Ala Ser Ala Leu Ala Pro Ala Pro Pro Gln Val Leu
                165                 170                 175

Pro Gln Ala Pro Ala Pro Ala Pro Ala Pro Ala Met Val Ser Ala Leu
            180                 185                 190

Ala Gln Ala Pro Ala Pro Val Pro Val Leu Ala Pro Gly Pro Pro Gln
        195                 200                 205

Ala Val Ala Pro Pro Ala Pro Lys Pro Thr Gln Ala Gly Glu Gly Thr
210                 215                 220

Leu Ser Glu Ala Leu Leu Gln Leu Gln Phe Asp Asp Glu Asp Leu Gly
225                 230                 235                 240

Ala Leu Leu Gly Asn Ser Thr Asp Pro Ala Val Phe Thr Asp Leu Ala
                245                 250                 255

Ser Val Asp Asn Ser Glu Phe Gln Gln Leu Leu Asn Gln Gly Ile Pro
            260                 265                 270

Val Ala Pro His Thr Thr Glu Pro Met Leu Met Glu Tyr Pro Glu Ala
        275                 280                 285

Ile Thr Arg Leu Val Thr Gly Ala Gln Arg Pro Pro Asp Pro Ala Pro
290                 295                 300

Ala Pro Leu Gly Ala Pro Gly Leu Pro Asn Gly Leu Leu Ser Gly Asp
305                 310                 315                 320

Glu Asp Phe Ser Ser Ile Ala Asp Met Asp Phe Ser Ala Leu Leu Gly
                325                 330                 335

Ser Gly Ser Gly Ser Arg Asp Ser Arg Glu Gly Met Phe Leu Pro Lys
            340                 345                 350

Pro Glu Ala Gly Ser Ala Ile Ser Asp Val Phe Glu Gly Arg Glu Val
        355                 360                 365
```

Cys Gln Pro Lys Arg Ile Arg Pro Phe His Pro Pro Gly Ser Pro Trp
    370                 375                 380

Ala Asn Arg Pro Leu Pro Ala Ser Leu Ala Pro Thr Pro Thr Gly Pro
385                 390                 395                 400

Val His Glu Pro Val Gly Ser Leu Thr Pro Ala Pro Val Pro Gln Pro
                405                 410                 415

Leu Asp Pro Ala Pro Ala Val Thr Pro Glu Ala Ser His Leu Leu Glu
                420                 425                 430

Asp Pro Asp Glu Glu Thr Ser Gln Ala Val Lys Ala Leu Arg Glu Met
            435                 440                 445

Ala Asp Thr Val Ile Pro Gln Lys Glu Glu Ala Ala Ile Cys Gly Gln
    450                 455                 460

Met Asp Leu Ser His Pro Pro Arg Gly His Leu Asp Glu Leu Thr
465                 470                 475                 480

Thr Thr Leu Glu Ser Met Thr Glu Asp Leu Asn Leu Asp Ser Pro Leu
                485                 490                 495

Thr Pro Glu Leu Asn Glu Ile Leu Asp Thr Phe Leu Asn Asp Glu Cys
                500                 505                 510

Leu Leu His Ala Met His Ile Ser Thr Gly Leu Ser Ile Phe Asp Thr
            515                 520                 525

Ser Leu Phe
    530

<210> SEQ ID NO 78
<211> LENGTH: 27
<212> TYPE: DNA
<213> ORGANISM: Artificial Sequence
<220> FEATURE:
<223> OTHER INFORMATION: Short1_FWD

<400> SEQUENCE: 78
tctcaggcct ctgctctggc tccagcc                                          27

<210> SEQ ID NO 79
<211> LENGTH: 41
<212> TYPE: DNA
<213> ORGANISM: Artificial Sequence
<220> FEATURE:
<223> OTHER INFORMATION: Short1_RV

<400> SEQUENCE: 79
agcagaggcc tgagaaccaa ctttgcgttt cttttcgga g                           41

<210> SEQ ID NO 80
<211> LENGTH: 24
<212> TYPE: DNA
<213> ORGANISM: Artificial Sequence
<220> FEATURE:
<223> OTHER INFORMATION: Short2_FWD

<400> SEQUENCE: 80
ccactggatc cagcgcccgc agtg                                             24

<210> SEQ ID NO 81
<211> LENGTH: 39
<212> TYPE: DNA
<213> ORGANISM: Artificial Sequence
<220> FEATURE:
<223> OTHER INFORMATION: Short2_RV

<400> SEQUENCE: 81

-continued

```
cgctggatcc agtgggccct caaacacgtc actaatagc                              39
```

<210> SEQ ID NO 82
<211> LENGTH: 25
<212> TYPE: DNA
<213> ORGANISM: Artificial Sequence
<220> FEATURE:
<223> OTHER INFORMATION: Short3_FWD

<400> SEQUENCE: 82

```
ggcacactgt ctgaagctct gctgc                                             25
```

<210> SEQ ID NO 83
<211> LENGTH: 41
<212> TYPE: DNA
<213> ORGANISM: Artificial Sequence
<220> FEATURE:
<223> OTHER INFORMATION: Short3_RV

<400> SEQUENCE: 83

```
ttcagacagt gtgcccacct gaggaggggc tggagccaga g                           41
```

<210> SEQ ID NO 84
<211> LENGTH: 26
<212> TYPE: DNA
<213> ORGANISM: Artificial Sequence
<220> FEATURE:
<223> OTHER INFORMATION: Short4_FWD

<400> SEQUENCE: 84

```
gatgagctga caaccacact tgagtc                                            26
```

<210> SEQ ID NO 85
<211> LENGTH: 40
<212> TYPE: DNA
<213> ORGANISM: Artificial Sequence
<220> FEATURE:
<223> OTHER INFORMATION: Short4_RV

<400> SEQUENCE: 85

```
ggttgtcagc tcatcggcca cagggatgcc ctggttcagc                             40
```

<210> SEQ ID NO 86
<211> LENGTH: 443
<212> TYPE: PRT
<213> ORGANISM: Artificial Sequence
<220> FEATURE:
<223> OTHER INFORMATION: VPR-SD

<400> SEQUENCE: 86

```
Asp Ala Leu Asp Asp Phe Asp Leu Asp Met Leu Gly Ser Asp Ala Leu
1               5                   10                  15

Asp Asp Phe Asp Leu Asp Met Leu Gly Ser Asp Ala Leu Asp Asp Phe
            20                  25                  30

Asp Leu Asp Met Leu Gly Ser Asp Ala Leu Asp Asp Phe Asp Leu Asp
        35                  40                  45

Met Leu Ile Asn Tyr Pro Tyr Asp Val Pro Asp Tyr Ala Ser Ser Ser
    50                  55                  60

Gly Ser Pro Lys Lys Lys Arg Lys Val Gly Ser Gln Ala Ser Ala Leu
65                  70                  75                  80

Ala Pro Ala Pro Pro Gln Val Leu Pro Gln Ala Pro Ala Pro Ala Pro
                85                  90                  95
```

```
Ala Pro Ala Met Val Ser Ala Leu Ala Gln Ala Pro Ala Pro Val Pro
            100                 105                 110

Val Leu Ala Pro Gly Pro Pro Gln Ala Val Ala Pro Pro Ala Pro Lys
        115                 120                 125

Pro Thr Gln Ala Gly Glu Gly Thr Leu Ser Glu Ala Leu Leu Gln Leu
    130                 135                 140

Gln Phe Asp Asp Glu Asp Leu Gly Ala Leu Leu Gly Asn Ser Thr Asp
145                 150                 155                 160

Pro Ala Val Phe Thr Asp Leu Ala Ser Val Asp Asn Ser Glu Phe Gln
                165                 170                 175

Gln Leu Leu Asn Gln Gly Ile Pro Val Ala Pro His Thr Thr Glu Pro
            180                 185                 190

Met Leu Met Glu Tyr Pro Glu Ala Ile Thr Arg Leu Val Thr Gly Ala
        195                 200                 205

Gln Arg Pro Pro Asp Pro Ala Pro Ala Pro Leu Gly Ala Pro Gly Leu
    210                 215                 220

Pro Asn Gly Leu Leu Ser Gly Asp Glu Asp Phe Ser Ser Ile Ala Asp
225                 230                 235                 240

Met Asp Phe Ser Ala Leu Leu Gly Ser Gly Ser Gly Ser Arg Asp Ser
                245                 250                 255

Arg Glu Gly Met Phe Leu Pro Lys Pro Glu Ala Gly Ser Ala Ile Ser
            260                 265                 270

Asp Val Phe Glu Gly Arg Glu Val Cys Gln Pro Lys Arg Ile Arg Pro
        275                 280                 285

Phe His Pro Pro Gly Ser Pro Trp Ala Asn Arg Pro Leu Pro Ala Ser
    290                 295                 300

Leu Ala Pro Thr Pro Thr Gly Pro Val His Glu Pro Val Gly Ser Leu
305                 310                 315                 320

Thr Pro Ala Pro Val Pro Gln Pro Leu Asp Pro Ala Pro Ala Val Thr
                325                 330                 335

Pro Glu Ala Ser His Leu Leu Glu Asp Pro Asp Glu Glu Thr Ser Gln
            340                 345                 350

Ala Val Lys Ala Leu Arg Glu Met Ala Asp Thr Val Ile Pro Gln Lys
        355                 360                 365

Glu Glu Ala Ala Ile Cys Gly Gln Met Asp Leu Ser His Pro Pro Pro
    370                 375                 380

Arg Gly His Leu Asp Glu Leu Thr Thr Thr Leu Glu Ser Met Thr Glu
385                 390                 395                 400

Asp Leu Asn Leu Asp Ser Pro Leu Thr Pro Glu Leu Asn Glu Ile Leu
                405                 410                 415

Asp Thr Phe Leu Asn Asp Glu Cys Leu Leu His Ala Met His Ile Ser
            420                 425                 430

Thr Gly Leu Ser Ile Phe Asp Thr Ser Leu Phe
        435                 440

<210> SEQ ID NO 87
<211> LENGTH: 393
<212> TYPE: PRT
<213> ORGANISM: Artificial Sequence
<220> FEATURE:
<223> OTHER INFORMATION: VPR-DD

<400> SEQUENCE: 87

Asp Ala Leu Asp Asp Phe Asp Leu Asp Met Leu Gly Ser Asp Ala Leu
1               5                   10                  15
```

Asp Asp Phe Asp Leu Asp Met Leu Gly Ser Asp Ala Leu Asp Asp Phe
            20                  25                  30

Asp Leu Asp Met Leu Gly Ser Asp Ala Leu Asp Asp Phe Asp Leu Asp
        35                  40                  45

Met Leu Ile Asn Tyr Pro Tyr Asp Val Pro Asp Tyr Ala Ser Ser Ser
 50                  55                  60

Gly Ser Pro Lys Lys Lys Arg Lys Val Gly Ser Gln Ala Ser Ala Leu
 65                  70                  75                  80

Ala Pro Ala Pro Pro Gln Val Leu Pro Gln Ala Pro Ala Pro Ala Pro
                85                  90                  95

Ala Pro Ala Met Val Ser Ala Leu Ala Gln Ala Pro Ala Pro Val Pro
            100                 105                 110

Val Leu Ala Pro Gly Pro Pro Gln Ala Val Ala Pro Pro Ala Pro Lys
            115                 120                 125

Pro Thr Gln Ala Gly Glu Gly Thr Leu Ser Glu Ala Leu Leu Gln Leu
130                 135                 140

Gln Phe Asp Asp Glu Asp Leu Gly Ala Leu Leu Gly Asn Ser Thr Asp
145                 150                 155                 160

Pro Ala Val Phe Thr Asp Leu Ala Ser Val Asp Asn Ser Glu Phe Gln
                165                 170                 175

Gln Leu Leu Asn Gln Gly Ile Pro Val Ala Pro His Thr Thr Glu Pro
            180                 185                 190

Met Leu Met Glu Tyr Pro Glu Ala Ile Thr Arg Leu Val Thr Gly Ala
            195                 200                 205

Gln Arg Pro Pro Asp Pro Ala Pro Ala Pro Leu Gly Ala Pro Gly Leu
210                 215                 220

Pro Asn Gly Leu Leu Ser Gly Asp Glu Asp Phe Ser Ser Ile Ala Asp
225                 230                 235                 240

Met Asp Phe Ser Ala Leu Leu Gly Ser Gly Ser Gly Ser Arg Asp Ser
                245                 250                 255

Arg Glu Gly Met Phe Leu Pro Lys Pro Glu Ala Gly Ser Ala Ile Ser
            260                 265                 270

Asp Val Phe Glu Gly Pro Leu Asp Pro Ala Pro Ala Val Thr Pro Glu
            275                 280                 285

Ala Ser His Leu Leu Glu Asp Pro Asp Glu Glu Thr Ser Gln Ala Val
290                 295                 300

Lys Ala Leu Arg Glu Met Ala Asp Thr Val Ile Pro Gln Lys Glu Glu
305                 310                 315                 320

Ala Ala Ile Cys Gly Gln Met Asp Leu Ser His Pro Pro Pro Arg Gly
                325                 330                 335

His Leu Asp Glu Leu Thr Thr Thr Leu Glu Ser Met Thr Glu Asp Leu
            340                 345                 350

Asn Leu Asp Ser Pro Leu Thr Pro Glu Leu Asn Glu Ile Leu Asp Thr
            355                 360                 365

Phe Leu Asn Asp Glu Cys Leu Leu His Ala Met His Ile Ser Thr Gly
            370                 375                 380

Leu Ser Ile Phe Asp Thr Ser Leu Phe
385                 390

<210> SEQ ID NO 88
<211> LENGTH: 346
<212> TYPE: PRT
<213> ORGANISM: Artificial Sequence
<220> FEATURE:
<223> OTHER INFORMATION: VPR-TD

<400> SEQUENCE: 88

```
Asp Ala Leu Asp Asp Phe Asp Leu Asp Met Leu Gly Ser Asp Ala Leu
1               5                   10                  15
Asp Asp Phe Asp Leu Asp Met Leu Gly Ser Asp Ala Leu Asp Asp Phe
            20                  25                  30
Asp Leu Asp Met Leu Gly Ser Asp Ala Leu Asp Phe Asp Leu Asp
        35                  40                  45
Met Leu Ile Asn Tyr Pro Tyr Asp Val Pro Asp Tyr Ala Ser Ser Ser
50                  55                  60
Gly Ser Pro Lys Lys Lys Arg Lys Val Gly Ser Gln Ala Ser Ala Leu
65                  70                  75                  80
Ala Pro Ala Pro Pro Gln Val Gly Thr Leu Ser Glu Ala Leu Leu Gln
                85                  90                  95
Leu Gln Phe Asp Asp Glu Asp Leu Gly Ala Leu Leu Gly Asn Ser Thr
            100                 105                 110
Asp Pro Ala Val Phe Thr Asp Leu Ala Ser Val Asp Asn Ser Glu Phe
        115                 120                 125
Gln Gln Leu Leu Asn Gln Gly Ile Pro Val Ala Pro His Thr Thr Glu
130                 135                 140
Pro Met Leu Met Glu Tyr Pro Glu Ala Ile Thr Arg Leu Val Thr Gly
145                 150                 155                 160
Ala Gln Arg Pro Pro Asp Pro Ala Pro Ala Pro Leu Gly Ala Pro Gly
                165                 170                 175
Leu Pro Asn Gly Leu Leu Ser Gly Asp Glu Asp Phe Ser Ser Ile Ala
            180                 185                 190
Asp Met Asp Phe Ser Ala Leu Leu Gly Ser Gly Ser Gly Ser Arg Asp
        195                 200                 205
Ser Arg Glu Gly Met Phe Leu Pro Lys Pro Glu Ala Gly Ser Ala Ile
210                 215                 220
Ser Asp Val Phe Glu Gly Pro Leu Asp Pro Ala Pro Ala Val Thr Pro
225                 230                 235                 240
Glu Ala Ser His Leu Leu Glu Asp Pro Asp Glu Glu Thr Ser Gln Ala
                245                 250                 255
Val Lys Ala Leu Arg Glu Met Ala Asp Thr Val Ile Pro Gln Lys Glu
            260                 265                 270
Glu Ala Ala Ile Cys Gly Gln Met Asp Leu Ser His Pro Pro Pro Arg
        275                 280                 285
Gly His Leu Asp Glu Leu Thr Thr Thr Leu Glu Ser Met Thr Glu Asp
290                 295                 300
Leu Asn Leu Asp Ser Pro Leu Thr Pro Glu Leu Asn Glu Ile Leu Asp
305                 310                 315                 320
Thr Phe Leu Asn Asp Glu Cys Leu Leu His Ala Met His Ile Ser Thr
                325                 330                 335
Gly Leu Ser Ile Phe Asp Thr Ser Leu Phe
            340                 345
```

<210> SEQ ID NO 89
<211> LENGTH: 193
<212> TYPE: PRT
<213> ORGANISM: Artificial Sequence
<220> FEATURE:
<223> OTHER INFORMATION: VPR-QD

<400> SEQUENCE: 89

Asp Ala Leu Asp Asp Phe Asp Leu Asp Met Leu Gly Ser Asp Ala Leu
1               5                   10                  15

Asp Asp Phe Asp Leu Asp Met Leu Gly Ser Asp Ala Leu Asp Asp Phe
            20                  25                  30

Asp Leu Asp Met Leu Gly Ser Asp Ala Leu Asp Phe Asp Leu Asp
        35                  40                  45

Met Leu Ile Asn Tyr Pro Tyr Asp Val Pro Asp Tyr Ala Ser Ser Ser
50                  55                  60

Gly Ser Pro Lys Lys Arg Lys Val Gly Ser Gln Ala Ser Ala Leu
65              70                  75                  80

Ala Pro Ala Pro Pro Gln Val Thr Leu Ser Glu Ala Leu Leu Gln Leu
            85                  90                  95

Gln Phe Asp Asp Glu Asp Leu Gly Ala Leu Leu Gly Asn Ser Thr Asp
            100                 105                 110

Pro Ala Val Phe Thr Asp Leu Ala Ser Val Asp Asn Ser Glu Phe Gln
            115                 120                 125

Gln Leu Leu Asn Gln Gly Ile Pro Val Ala Asp Glu Leu Thr Thr Thr
130                 135                 140

Leu Glu Ser Met Thr Glu Asp Leu Asn Leu Asp Ser Pro Leu Thr Pro
145                 150                 155                 160

Glu Leu Asn Glu Ile Leu Asp Thr Phe Leu Asn Asp Glu Cys Leu Leu
                165                 170                 175

His Ala Met His Ile Ser Thr Gly Leu Ser Ile Phe Asp Thr Ser Leu
            180                 185                 190

Phe

<210> SEQ ID NO 90
<211> LENGTH: 36
<212> TYPE: DNA
<213> ORGANISM: Artificial Sequence
<220> FEATURE:
<223> OTHER INFORMATION: Forward primer for ZFP3_VPR

<400> SEQUENCE: 90
gacgatgacg ataaggccca ggcggccctg gagccc                36

<210> SEQ ID NO 91
<211> LENGTH: 41
<212> TYPE: DNA
<213> ORGANISM: Artificial Sequence
<220> FEATURE:
<223> OTHER INFORMATION: Reverse primer for both ZFP3_VPR and ZFP52_VPR

<400> SEQUENCE: 91
gctgaagttg gtggcatggt gatggtgatg atgaccggta c          41

<210> SEQ ID NO 92
<211> LENGTH: 40
<212> TYPE: DNA
<213> ORGANISM: Artificial Sequence
<220> FEATURE:
<223> OTHER INFORMATION: Forward primer for ZFP52_VPR

<400> SEQUENCE: 92
gacgatgacg ataaggccca agctgcctta gaacccggcg            40

<210> SEQ ID NO 93
<211> LENGTH: 24
<212> TYPE: DNA
<213> ORGANISM: Artificial Sequence -continued

```
<220> FEATURE:
<223> OTHER INFORMATION: Forward primer for inducible vector

<400> SEQUENCE: 93
gccaccaact tcagcctgct gaag                                          24

<210> SEQ ID NO 94
<211> LENGTH: 29
<212> TYPE: DNA
<213> ORGANISM: Artificial Sequence
<220> FEATURE:
<223> OTHER INFORMATION: Reverse primer for inducible vector

<400> SEQUENCE: 94
cttatcgtca tcgtctttgt aatccatgg                                     29
```